(12) United States Patent
Frisch et al.

(10) Patent No.: US 10,208,298 B2
(45) Date of Patent: Feb. 19, 2019

(54) PEPTIDE-MEDIATED DELIVERY OF RNA-GUIDED ENDONUCLEASE INTO CELLS

(71) Applicant: E I DU PONT DE NEMOURS AND COMPANY, Wilmington, DE (US)

(72) Inventors: Ryan L. Frisch, Newark, DE (US); Xiaochun Fan, West Chester, PA (US); Seung-Pyo Hong, Hockessin, DE (US); Ethel Noland Jackson, Greenville, DE (US)

(73) Assignee: E.I. DU PONT DE NEMOURS AND COMPANY, Wilmington, DE (US)

( * ) Notice: Subject to any disclaimer, the term of this patent is extended or adjusted under 35 U.S.C. 154(b) by 64 days.

(21) Appl. No.: 15/523,741

(22) PCT Filed: Nov. 3, 2015

(86) PCT No.: PCT/US2015/058760
§ 371 (c)(1),
(2) Date: May 2, 2017

(87) PCT Pub. No.: WO2016/073433
PCT Pub. Date: May 12, 2016

(65) Prior Publication Data
US 2017/0335300 A1   Nov. 23, 2017

Related U.S. Application Data

(60) Provisional application No. 62/075,999, filed on Nov. 6, 2014.

(51) Int. Cl.
| | |
|---|---|
| *C12N 9/22* | (2006.01) |
| *C12N 9/96* | (2006.01) |
| *C12N 15/10* | (2006.01) |
| *C12N 15/62* | (2006.01) |
| *C12N 15/86* | (2006.01) |
| *C12N 15/90* | (2006.01) |

(52) U.S. Cl.
CPC .......... *C12N 9/22* (2013.01); *C12N 9/96* (2013.01); *C12N 15/102* (2013.01); *C12N 15/62* (2013.01); *C12N 15/86* (2013.01); *C12N 15/907* (2013.01); *C07K 2319/09* (2013.01); *C07K 2319/10* (2013.01); *C12N 2310/3513* (2013.01); *C12N 2750/14141* (2013.01)

(58) Field of Classification Search
CPC .............................. C12N 9/22; C12N 2310/20
See application file for complete search history.

(56) References Cited

U.S. PATENT DOCUMENTS

| | | | |
|---|---|---|---|
| 5,990,275 A | 11/1999 | Whitlow et al. | |
| 8,580,922 B2 | 11/2013 | Martini et al. | |
| 8,642,744 B2 | 2/2014 | Smart et al. | |
| 8,828,690 B2 | 9/2014 | Damude et al. | |
| 9,526,784 B2 * | 12/2016 | Liu | ............ A61K 38/465 |
| 2010/0192262 A1 | 7/2010 | Krichevsky | |
| 2011/0190813 A1 | 8/2011 | Brownlee et al. | |
| 2012/0042412 A1 | 2/2012 | Albert et al. | |
| 2014/0068797 A1 | 3/2014 | Doudna et al. | |
| 2014/0189896 A1 | 7/2014 | Zhang et al. | |

FOREIGN PATENT DOCUMENTS

| | | |
|---|---|---|
| WO | 2013/176772 A1 | 11/2013 |
| WO | 2014/065596 A1 | 5/2014 |
| WO | 2014/089290 A1 | 6/2014 |
| WO | 2014/165825 A1 | 10/2014 |
| WO | 2015/026883 A1 | 2/2015 |
| WO | 2015/086795 A1 | 6/2015 |
| WO | 2016/025131 A1 | 2/2016 |
| WO | 2016/186946 A1 | 11/2016 |
| WO | 2016/186953 A1 | 11/2016 |

OTHER PUBLICATIONS

Jiang et al. 2013; RNA-guided editing of bacterial genomes using CRISPR-Cas systems. Nature Biotechnology. 31(3): 233-239.*
DiCarlo et al. 2013; Genome engineering in Saccharomyces cerevisiae using CRISPR-Cas systems. Nucleic Acids Research. 41(7) : 4336-4343.*
Ramakrishna et al. Apr. 2, 2014 online; Gene disruption by cell-penetrating peptide-mediated delivery of Cas9 protein and guide RNA. Genome Research. 24(6): 1020-1027.*
Aguilera, Todd A. et al., Systemic in vivo distribution of activatable cell penetrating peptides is superior to cell penetrating peptides, Integr Biol, Jun. 2009, pp. 371-381, 1(5-6).
Anko, Maja et al. Influence of stearyl and triflouromethylquinoline modifications of the cell penetrating peptide TP10 on its interaction with a lipid membrane, Biochimica et Biophysica Acta 1818, 2012, pp. 915-924.
Austin, Christopher P. et al., The Knockout Mouse Project, Nat Genet, Sep. 2004, pp. 921-924, 36(9).
Bhaya, Devaki et al., CRISPR-Cas Systems in Bacteria and Archaea: Versatile Small RNAs for Adaptive Defense and Regulation, Annu. Rev. Genet., 2011, pp. 273-297, 45.

(Continued)

*Primary Examiner* — Karen Cochrane Carlson

(57) ABSTRACT

A composition is disclosed that comprises at least one protein component of an RNA-guided endonuclease (RGEN) and at least one cell-penetrating peptide (CPP), wherein the RGEN protein component and CPP are covalently or non-covalently linked to each other in an RGEN protein-CPP complex. The RGEN protein-CPP complex can traverse (i) a cell membrane, or (ii) a cell wall and cell membrane, of a cell. The RGEN protein component of an RGEN protein-CPP complex in certain embodiments can be associated with a suitable RNA component to provide an RGEN capable of specific DNA targeting. Further disclosed are compositions comprising at least one protein component of a guide polynucleotide/Cas endonuclease complex and at least one CPP, as well as methods of delivering RGEN proteins into microbial cells, as well as methods of targeting DNA with RGENs.

4 Claims, 10 Drawing Sheets

Figure 1:
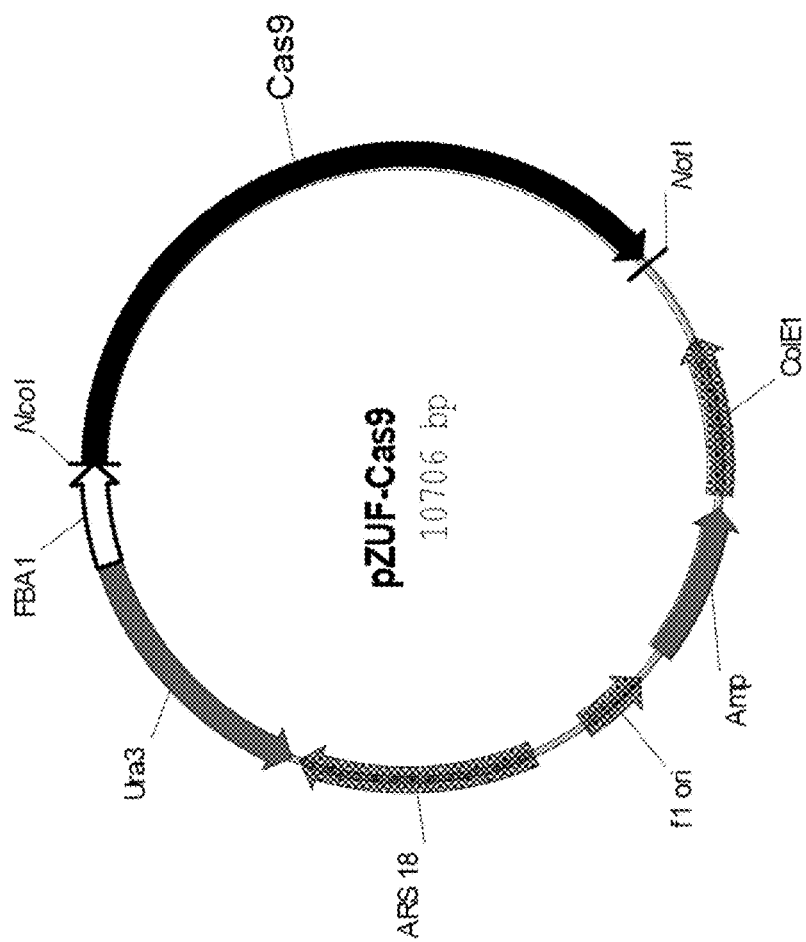

Specification includes a Sequence Listing.

(56) References Cited

OTHER PUBLICATIONS

Bibikova, Marina et al., Stimulation of Homologous Recombination through Targeted Cleavage by Chimeric Nucleases, Molecular and Cellular Biology, Jan. 2001, pp. 289-297, vol. 21, No. 1.

Bibikova, Marina et al., Enhancing Gene Targeting with Designed Zinc Finger Nucleases, Science, May 2, 2003, p. 764, vol. 300.

Database WPI, Thomson Scientific, XP002753224, Shanghai Dida Biological Technology, Co., Feb. 4, 2015—Reference Not Included.

Deltcheva, Elitza et al., CRISPR RNA maturation by trans-encoded small RNA and host factor RNase III, Nature, Mar. 31, 2011, pp. 602-607, vol. 471 (7340).

Dicarlo, James E. et al., Genome engineering in *Saccharomyces cerevisiae*, Nucleic Acids Research, 2013, pp. 4336-4343—vol. 41, No. 7.

Epinat, Jean-Charles et al., A novel engineered meganuclease induces homologous recombination in yeast and mammalian cells, Nucleic Acids Research, 2003, pp. 2952-2962, vol. 31, No. 11.

Gasiunas, Giedrius et al., Cas9-crRNA ribonucleoprotein complex mediates specific DNA cleavage for adaptive immunity in bacteria, PNAS, Sep. 4, 2012, E2579-E2586, 109.

Holm, Tina et al., Studying the uptake of cell-penetrating peptides, Nature Protocols, 2006, pp. 1001-1005, vol. 1, No. 2.

Horvath, Philippe et al., CRISPR/Cas, the Immune System of Bacteria and Archaea, Science, Jan. 8, 2010, pp. 167-170, vol. 327.

Hsu, Patrick D. et al., Development and Applications of CRISPR-Cas9 for Genome Engineering, Cell, Jun. 5, 2014, pp. 1262-1278, vol. 157.

Jiang, Wenyan et al., RNA-guided editing of bacterial genomes using CRISPR-Cas systems, Nature Biotechnology, Mar. 2013, pp. 233-239, vol. 31, No. 3.

Jinek, Martin et al., A Programmable Dual-RNA-Guided DNA Endonuclease in Adaptive Bacterial Immunity, Science, Aug. 17, 2012, pp. 816-821, vol. 337.

Karginov, Fedor V. et al., The CRISPR System: Small RNA-Guided Defense in Bacteria and Archaea, Molecular Cell, Jan. 15, 2010, pp. 7-19, vol. 37.

Liu, Min-Jie et al., A Gene Delivery Method Mediated by Three Arginine-rich Cell-penetrating Peptides in Plant Cells, Advanced Studies in Biology, 2013, pp. 71-88, vol. 5, No. 2.

Ma, Hongming et al., Pol III Promoters to Express Small RNAs: Delineation of Transcription Initiation, Molecular Therapy—Nucleic Acids, 2014, e161, 3.

Marchione, Roberta et al., ZEBRA cell-penetrating peptide as an efficient delivery system in Candida albicans, Biotechnol. J., 2014, pp. 1088-1094, vol. 9.

Miller, Jeffrey C. et al., A TALE nuclease architecture for efficient genome editing, Nature Biotechnology, Feb. 2011, pp. 143-148, vol. 29, No. 2.

Morris, May C. et al., A peptide carrier for the delivery of biologically active proteins into mammalian cells, Nat. Biotechnol, Dec. 2001, pp. 1173-1176, vol. 19.

Nekhotiaeva, Natalia et al., Cell entry and antimicrobial properties of eukaryotic cell-penetrating peptides, FASEB Journal, Feb. 1, 2004, pp. 394-396, vol. 18.

Ramakrishna, Suresh et al., Gene disruption by cell-penetrating peptide-mediated delivery of Cas9 protein and guide RNA, Genome Research, Apr. 2, 2014, pp. 1020-1027, vol. 24, No. 6.

Regberg, Jakob et al., Rational design of a series of novel amphipathic cell-penetrating peptides, International Journal of Pharmaceutics, 2014, pp. 111-116, vol. 464.

Rudin, Norah et al., Genetic and Physical Analysis of Double-Strand Break Repair and Recombination in *Saccharomyces cerevisiae*, Genetics, Jul. 1989, pp. 519-534, vol. 122.

Sapranauskas, Rimantas et al., The *Streptococcus thermophilus* CRISPR/Cas system provides immunity in *Escherichia coli*, Nucleic Acids Research, Aug. 3, 2011, pp. 9275-9282, vol. 39, No. 21.

Schmidt, Nathan et al., Arginine-rich cell-penetrating peptides, FEBS Letter, 2010, pp. 1806-1813, vol. 584.

Smith, Fatima et al., Nucleic Acids Research, 1995, pp. 5012-5019, vol. 23, No. 24.

Sternberg, Samuel H. et al., DNA interrogation by the CRISPR RNA-guided endonuclease Cas9, Nature, Mar. 6, 2014, pp. 62-67, vol. 507 (7490).

Wender, Paul A., The design, synthesis, and evaluation of molecules that enable or enhance cellular uptake: Peptoid molecular transporters, PNAS, Nov. 21, 2000, pp. 13003-13008, vol. 97, No. 24.

Yandek, Lindsay E., Mechanism of the Cell-Penetrating Peptide Transportan 10 Permeation of Lipid Bilayers, Biophysical Journal, Apr. 2007, p. 2434-2444, vol. 92.

Zetsche, Bernd et al., Cpf1 Is a Single RNA-Guided Endonuclease of a Class 2 CRISPR-Cas System, Cell, Oct. 22, 2015, pp. 759-771, vol. 163.

International Search Report and Written Opinion—PCT/US2015/058760—dated Feb. 1, 2016.

\* cited by examiner

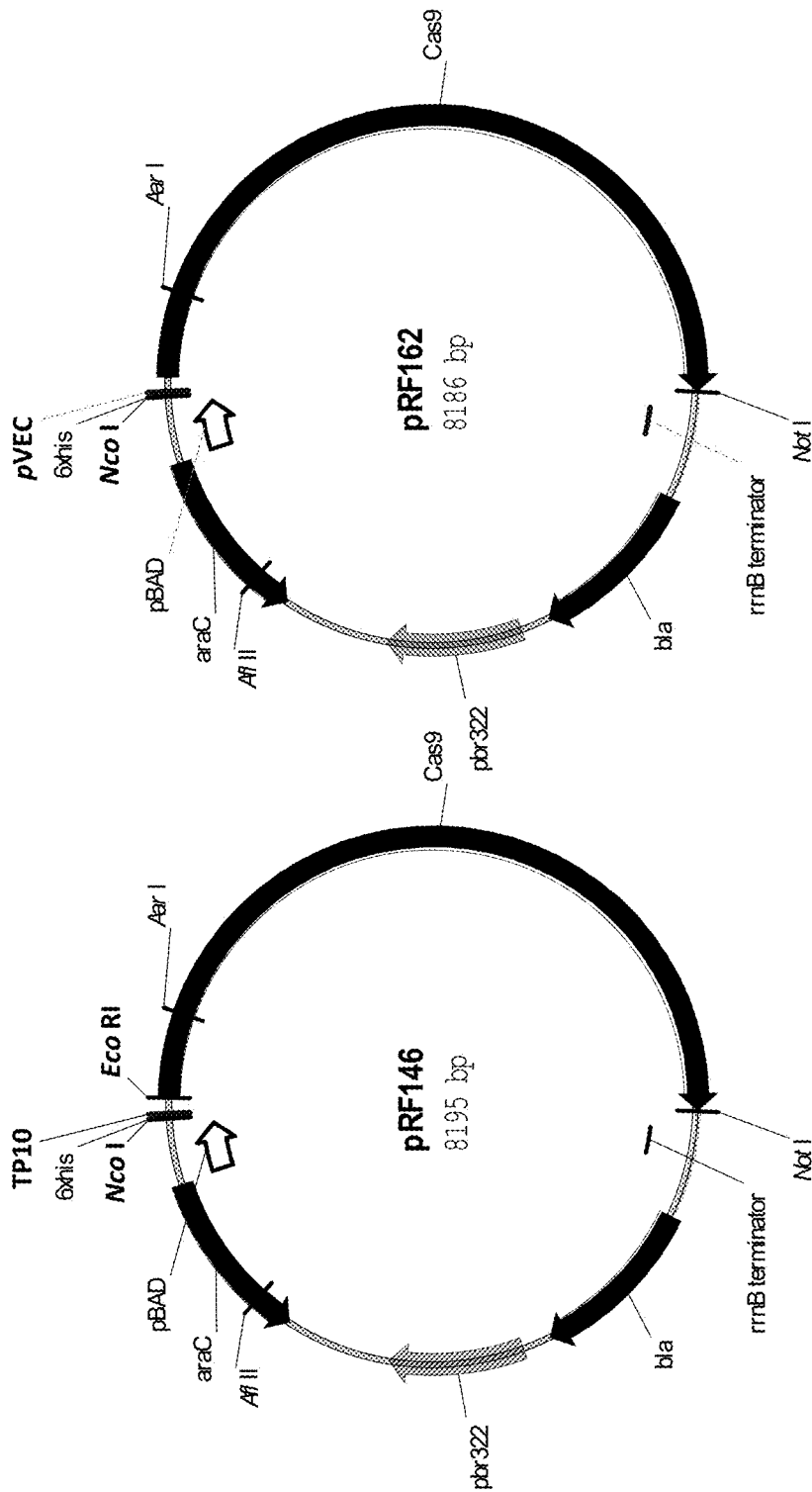

SEQUENCE LISTING

```
<160> NUMBER OF SEQ ID NOS: 144

<210> SEQ ID NO 1
<211> LENGTH: 4107
<212> TYPE: DNA
<213> ORGANISM: artificial sequence
<220> FEATURE:
<223> OTHER INFORMATION: S. pyogenes Cas9

<400> SEQUENCE: 1
atggacaaga aatactccat cggcctggac attggaacca actctgtcgg ctgggctgtc      60
atcaccgacg agtacaaggt gccctccaag aaattcaagg tcctcggaaa caccgatcga     120
cactccatca agaaaaacct cattggtgcc ctgttgttcg attctggcga gactgccgaa     180 gctaccgac tcaagcgaac tgctcggcga cgttacaccc gacggaagaa ccgaatctgc      240
tacctgcagg agatcttttc caacgagatg gccaaggtgg acgattcgtt ctttcatcga     300
ctggaggaat ccttcctcgt cgaggaagac aagaaacacg agcgtcatcc catctttggc     360
aacattgtgg acgaggttgc ttaccacgag aagtatccta ccatctacca cctgcgaaag     420
aaactcgtcg attccaccga caaggcggat ctcagactta tctacctcgc tctggcacac     480
atgatcaagt tcgaggtca tttcctcatc gagggcgatc tcaatcccga caacagcgat     540
gtggacaagc tgttcattca gctcgttcag acctacaacc agctgttcga ggaaaacccc     600
atcaatgcct ccggagtcga tgcaaaggcc atcttgtctg ctcgactctc gaagagcaga     660
cgactggaga acctcattgc ccaacttcct ggcgagaaaa agaacggact gtttggcaac     720
ctcattgccc tttctcttgg tctcacaccc aacttcaagt ccaacttcga tctggcggag     780
gacgccaagc tccagctgtc caaggacacc tacgacgatg acctcgacaa cctgcttgca     840
```

```
cagattggcg atcagtacgc cgacctgttt ctcgctgcca agaacctttc ggatgctatt      900
ctcttgtctg acattctgcg agtcaacacc gagatcacaa aggctcccct ttctgcctcc      960
atgatcaagc gatacgacga gcaccatcag gatctcacac tgctcaaggc tcttgtccga     1020
cagcaactgc ccgagaagta caaggagatc tttttcgatc agtcgaagaa cggctacgct     1080
ggatacatcg acggcggagc ctctcaggaa gagttctaca agttcatcaa gccaattctc     1140
gagaagatgg acgaaccgga gaactgctt gtcaagctca atcgagagga tctgcttcgg      1200
aagcaacgaa ccttcgacaa cggcagcatt cctcatcaga tccacctcgg tgagctgcac     1260
gccattcttc gacgtcagga agacttctac ccctttctca aggacaaccg agagaagatc     1320
gagaagattc ttacctttcg aatcccctac tatgttggtc ctcttgccag aggaaactct     1380
cgatttgctt ggatgactcg aaagtccgag gaaaccatca ctcccctggaa cttcgaggaa    1440
gtcgtggaca agggtgcctc tgcacagtcc ttcatcgagc gaatgaccaa cttcgacaag     1500
aatctgccca cgagaaggt tcttcccaag cattcgctgc tctacgagta ctttacagtc      1560
tacaacgaac tcaccaaagt caagtacgtt accgagggaa tgcgaaagcc tgccttcttg     1620
tctggcgaac agaagaaagc cattgtcgat ctccctgttca agaccaaccg aaaggtcact    1680
gttaagcagc tcaaggagga ctacttcaag aaaatcgagt gtttcgacag cgtcgagatt     1740
tccggagttg aggaccgatt caacgcctct ttgggcacct atcacgatct gctcaagatt     1800
atcaaggaca aggattttct cgacaacgag gaaaacgagg acattctgga ggacatcgtg     1860
ctcactctta ccctgttcga agatcgggag atgatcgagg aacgactcaa gacatacgct     1920
cacctgttcg acgacaaggt catgaaacaa ctcaagcgac gtagatacac cggctgggga     1980
agactttcgc gaaagctcat caacggcatc agagacaagc agtccggaaa gaccattctg     2040
gactttctca gtccgatgg ctttgccaac cgaaacttca tgcagctcat tcacgacgat     2100
tctcttacct tcaaggagga catccagaag gcacaagtgt ccggtcaggg cgacagcttg     2160
cacgaacata ttgccaacct ggctggttcg ccagccatca gaaaaggcat tctccagact     2220
gtcaaggttg tcgacgagct ggtgaaggtc atgggacgtc acaagcccga gaacattgtg     2280
atcgagatgg ccagagagaa ccagacaact caaaagggtc agaaaaactc gcgagagcgg     2340
atgaagcgaa tcgaggaagg catcaaggag ctgggatccc agattctcaa ggagcatccc     2400
gtcgagaaca ctcaactgca gaacgagaag ctgtatctct actatctgca gaatggtcga     2460
gacatgtacg tggatcagga actggacatc aatcgtctca gcgactacga tgtggaccac     2520
attgtccctc aatcctttct caaggacgat tctatcgaca caaggtcct tacacgatcc      2580
gacaagaaca gaggcaagtc ggacaacgtt cccagcgaag aggtggtcaa aaagatgaag     2640
aactactggc gacagctgct caacgccaag ctcattaccc agcgaaagtt cgacaatctt     2700
accaaggccg agcgaggcgg tctgtccgag ctcgacaagg ctggcttcat caagcgtcaa     2760
ctcgtcgaga ccagacagat cacaaagcac gtcgcacaga ttctcgattc tcggatgaac     2820
accaagtacg acgagaacga caagctcatc cgagaggtca aggtgattac tctcaagtcc     2880
aaactggtct ccgatttccg aaaggacttt cagttctaca aggtgcgaga gatcaacaat     2940
taccaccatg cccacgatgc ttacctcaac gccgtcgttg gcactgcgct catcaagaaa     3000
tacccccaagc tcgaaagcga gttcgtttac ggcgattaca aggtctacga cgttcgaaag    3060
atgattgcca agtccgaaca ggagattggc aaggctactg ccaagtactt cttttactcc     3120
aacatcatga acttttttcaa gaccgagatc accttggcca acgagagat tcgaaagaga     3180
ccacttatcg agaccaacgg cgaaactgga gagatcgtgt gggacaaggg tcgagacttt     3240
```

```
gcaaccgtgc gaaaggttct gtcgatgcct caggtcaaca tcgtcaagaa aaccgaggtt    3300
cagactggcg gattctccaa ggagtcgatt ctgcccaagc gaaactccga caagctcatc    3360
gctcgaaaga aagactggga tcccaagaaa tacggtggct tcgattctcc taccgtcgcc    3420
tattccgtgc ttgtcgttgc gaaggtcgag aagggcaagt ccaaaaagct caagtccgtc    3480
aaggagctgc tcggaattac catcatggag cgatcgagct tcgagaagaa tcccatcgac    3540
ttcttggaag ccaagggtta caaggaggtc aagaaagacc tcattatcaa gctgcccaag    3600
tactctctgt tcgaactgga gaacggtcga aagcgtatgc tcgcctccgc tggcgagctg    3660
cagaagggaa acgagcttgc cttgccttcg aagtacgtca actttctcta tctggcttct    3720
cactacgaga agctcaaggg ttctcccgag acaacgaac agaagcaact cttcgttgag    3780
cagcacaaac attcctcga cgagattatc gagcagattt ccgagttttc gaagcgagtc    3840
atcctggctg atgccaactt ggacaaggtg ctctctgcct acaacaagca tcgggacaaa    3900
cccattcgag aacaggcgga gaacatcatt cacctgttta ctcttaccaa cctgggtgct    3960
cctgcagctt tcaagtactt cgataccact atcgaccgaa agcggtacac atccaccaag    4020
gaggttctcg atgccaccct gattcaccag tccatcactg gcctgtacga gacccgaatc    4080
gacctgtctc agcttggtgg cgactaa                                         4107
```

<210> SEQ ID NO 2
<211> LENGTH: 4140
<212> TYPE: DNA
<213> ORGANISM: artificial sequence
<220> FEATURE:
<223> OTHER INFORMATION: S. pyogenes Cas9 with NLS

<400> SEQUENCE: 2

```
atggacaaga aatactccat cggcctggac attggaacca actctgtcgg ctgggctgtc      60
atcaccgacg agtacaaggt gcctccaag aaattcaagg tcctcggaaa caccgatcga     120
cactccatca agaaaaacct cattggtgcc ctgttgttcg attctggcga gactgccgaa     180
gctaccagac tcaagcgaac tgctcggcga cgttacaccc cgacgaagaa ccgaatctgc     240
tacctgcagg agatctttc caacgagatg gccaaggtgg acgattcgtt ctttcatcga     300
ctggaggaat ccttcctcgt cgaggaagac aagaaacacg agcgtcatcc catctttggc     360
aacattgtgg acgaggttgc ttaccacgag aagtatccta ccatctacca cctgcgaaag     420
aaactcgtcg attccaccga caaggcggat ctcagactta tctacctcgc tctggcacac     480
atgatcaagt tcgaggtca tttcctcatc gagggcgatc tcaatcccga caacagcgat     540
gtggacaagc tgttcattca gctcgttcag acctacaacc agctgttcga ggaaaaccc     600 atcaatgcct ccgagtcga tgcaaaggcc atcttgtctg ctcgactctc gaagagcaga     660
cgactggaga acctcattgc ccaacttcct ggcgagaaaa agaacggact gtttggcaac     720
ctcattgccc tttctcttgg tctcacaccc aacttcaagt ccaacttcga tctggcggag     780
gacgccaagc tccagctgtc caaggacacc tacgacgatg acctcgacaa cctgcttgca     840
cagattggcg atcagtacgc cgacctgttt ctcgctgcca agaacctttc ggatgctatt     900
ctcttgtctg acattctgcg agtcaacacc gagatcacaa aggctcccct ttctgcctcc     960
atgatcaagc gatacgacga gcaccatcag gatctcacac tgctcaaggc tcttgtccga    1020
cagcaactgc ccgagaagta caaggagatc tttttcgatc agtcgaagaa cggctacgct    1080
ggatacatcg acggcggagc ctctcaggaa gagttctaca gttcatcaa gccaattctc    1140
```

```
gagaagatgg acggaaccga ggaactgctt gtcaagctca atcgagagga tctgcttcgg    1200
aagcaacgaa ccttcgacaa cggcagcatt cctcatcaga tccacctcgg tgagctgcac    1260
gccattcttc gacgtcagga agacttctac cccttttctca aggacaaccg agagaagatc   1320
gagaagattc ttacctttcg aatccctac tatgttggtc ctcttgccag aggaaactct     1380
cgatttgctt ggatgactcg aaagtccgag gaaaccatca ctccctggaa cttcgaggaa    1440
gtcgtggaca agggtgcctc tgcacagtcc ttcatcgagc gaatgaccaa cttcgacaag    1500
aatctgccca acgagaaggt tcttcccaag cattcgctgc tctacgagta ctttacagtc    1560
tacaacgaac tcaccaaagt caagtacgtt accgagggaa tgcgaaagcc tgccttcttg    1620
tctggcgaac agaagaaagc cattgtcgat ctcctgttca agaccaaccg aaaggtcact    1680
gttaagcagc tcaaggagga ctacttcaag aaaatcgagt gtttcgacag cgtcgagatt    1740
tccggagttg aggaccgatt caacgcctct ttgggcacct atcacgatct gctcaagatt    1800
atcaaggaca aggatttttct cgacaacgag gaaaacgagg acattctgga ggacatcgtg   1860
ctcactctta ccctgttcga agatcggag atgatcgagg aacgactcaa gacatacgct     1920
cacctgttcg acgacaaggt catgaaacaa ctcaagcgac gtagatacac cggctgggga    1980
agactttcgc gaaagctcat caacggcatc agagacaagc agtccggaaa gaccattctg    2040
gactttctca gtccgatgg ctttgccaac cgaaacttca tgcagctcat tcacgacgat     2100
tctcttacct tcaaggagga catccagaag gcacaagtgt ccggtcaggg cgacagcttg    2160
cacgaacata ttgccaacct ggctggttcg ccagccatca agaaaggcat tctccagact    2220
gtcaaggttg tcgacgagct ggtgaaggtc atgggacgtc acaagcccga gaacattgtg    2280
atcgagatgg ccagagagaa ccagacaact caaaagggtc agaaaaactc gcgagagcgg    2340
atgaagcgaa tcgaggaagg catcaaggag ctgggatccc agattctcaa ggagcatccc    2400
gtcgagaaca ctcaactgca gaacgagaag ctgtatctct actatctgca gaatggtcga    2460
gacatgtacg tggatcagga actggacatc aatcgtctca gcgactacga tgtgaccac    2520 attgtccctc aatcctttct caaggacgat tctatcgaca caaggtcct tacacgatcc     2580 gacaagaaca gaggcaagtc ggacaacgtt cccagcgaag aggtggtcaa aaagatgaag    2640
aactactggc gacagctgct caacgccaag ctcattaccc agcgaaagtt cgacaatctt    2700
accaaggccg agcgaggcgg tctgtccgag ctcgacaagg ctggcttcat caagcgtcaa    2760
ctcgtcgaga ccagacagat cacaaagcac gtcgcacaga ttctcgattc tcggatgaac    2820
accaagtacg acgagaacga caagctcatc cgagaggtca aggtgattac tctcaagtcc    2880
aaactggtct ccgatttccg aaaggacttt cagttctaca aggtgcgaga gatcaacaat    2940
taccaccatg cccacgatgc ttacctcaac gccgtcgttg gcactgcgct catcaagaaa    3000
taccccaagc tcgaaagcga gttcgtttac ggcgattaca aggtctacga cgttcgaaag    3060
atgattgcca gtccgaaca ggagattggc aaggctactg ccaagtactt cttttactcc     3120
aacatcatga ctttttcaa gaccgagatc accttggcca acgagagat tcgaaagaga      3180 ccacttatcg agaccaacgg cgaaactgga gagatcgtgt gggacaaggg tcgagacttt    3240
gcaaccgtgc gaaaggttct gtcgatgcct caggtcaaca tcgtcaagaa aaccgaggtt    3300
cagactggcg gattctccaa ggagtcgatt ctgcccaagc gaaactccga caagctcatc    3360
gctcgaaaga aagactggga tcccaagaaa tacggtggct tcgattctcc taccgtcgcc    3420
tattccgtgc ttgtcgttgc gaaggtcgag aagggcaagt ccaaaaagct caagtccgtc    3480
aaggagctgc tcggaattac catcatggag cgatcgagct tcgagaagaa tcccatcgac    3540
```

```
ttcttggaag ccaagggtta caaggaggtc aagaaagacc tcattatcaa gctgcccaag    3600
tactctctgt tcgaactgga gaacggtcga aagcgtatgc tcgcctccgc tggcgagctg    3660
cagaagggaa acgagcttgc cttgccttcg aagtacgtca actttctcta tctggcttct    3720
cactacgaga agctcaaggg ttctcccgag acaacgaac agaagcaact cttcgttgag    3780
cagcacaaac attacctcga cgagattatc gagcagattt ccgagttttc gaagcgagtc    3840
atcctggctg atgccaactt ggacaaggtg ctctctgcct acaacaagca tcgggacaaa    3900
cccattcgag aacaggcgga gaacatcatt cacctgttta ctcttaccaa cctgggtgct    3960
cctgcagctt tcaagtactt cgataccact atcgaccgaa agcggtacac atccaccaag    4020
gaggttctcg atgccaccct gattcaccag tccatcactg gcctgtacga acccgaatc     4080 gacctgtctc agcttggtgg cgactccaga gccgatccca agaaaaagcg aaaggtctaa    4140
```

<210> SEQ ID NO 3
<211> LENGTH: 1379
<212> TYPE: PRT
<213> ORGANISM: artificial sequence
<220> FEATURE:
<223> OTHER INFORMATION: S. pyogenes Cas9 with NLS

<400> SEQUENCE: 3

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255
```

```
Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
```

```
            675                 680                 685
Ala Asn Arg Asn Phe Met Gln Leu Ile His Asp Asp Ser Leu Thr Phe
690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
                740                 745                 750
Arg His Lys Pro Glu Asn Ile Val Ile Glu Met Ala Arg Glu Asn Gln
                755                 760                 765
Thr Thr Gln Lys Gly Gln Lys Asn Ser Arg Glu Arg Met Lys Arg Ile
770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
                820                 825                 830
Leu Ser Asp Tyr Asp Val Asp His Ile Val Pro Gln Ser Phe Leu Lys
                835                 840                 845
Asp Asp Ser Ile Asp Asn Lys Val Leu Thr Arg Ser Asp Lys Asn Arg
850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
                915                 920                 925
Lys His Val Ala Gln Ile Leu Asp Ser Arg Met Asn Thr Lys Tyr Asp
                930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
                995                 1000                1005
Val Tyr Gly Asp Tyr Lys Val Tyr Asp Val Arg Lys Met Ile Ala
                1010                1015                1020
Lys Ser Glu Gln Glu Ile Gly Lys Ala Thr Ala Lys Tyr Phe Phe
                1025                1030                1035
Tyr Ser Asn Ile Met Asn Phe Phe Lys Thr Glu Ile Thr Leu Ala
                1040                1045                1050
Asn Gly Glu Ile Arg Lys Arg Pro Leu Ile Glu Thr Asn Gly Glu
                1055                1060                1065
Thr Gly Glu Ile Val Trp Asp Lys Gly Arg Asp Phe Ala Thr Val
                1070                1075                1080
Arg Lys Val Leu Ser Met Pro Gln Val Asn Ile Val Lys Lys Thr
                1085                1090                1095
```

```
Glu Val Gln Thr Gly Gly Phe Ser Lys Glu Ser Ile Leu Pro Lys
    1100            1105                1110

Arg Asn Ser Asp Lys Leu Ile Ala Arg Lys Lys Asp Trp Asp Pro
    1115            1120                1125

Lys Lys Tyr Gly Gly Phe Asp Ser Pro Thr Val Ala Tyr Ser Val
    1130            1135                1140

Leu Val Val Ala Lys Val Glu Lys Gly Lys Ser Lys Lys Leu Lys
    1145            1150                1155

Ser Val Lys Glu Leu Leu Gly Ile Thr Ile Met Glu Arg Ser Ser
    1160            1165                1170

Phe Glu Lys Asn Pro Ile Asp Phe Leu Glu Ala Lys Gly Tyr Lys
    1175            1180                1185

Glu Val Lys Lys Asp Leu Ile Ile Lys Leu Pro Lys Tyr Ser Leu
    1190            1195                1200

Phe Glu Leu Glu Asn Gly Arg Lys Arg Met Leu Ala Ser Ala Gly
    1205            1210                1215

Glu Leu Gln Lys Gly Asn Glu Leu Ala Leu Pro Ser Lys Tyr Val
    1220            1225                1230

Asn Phe Leu Tyr Leu Ala Ser His Tyr Glu Lys Leu Lys Gly Ser
    1235            1240                1245

Pro Glu Asp Asn Glu Gln Lys Gln Leu Phe Val Glu Gln His Lys
    1250            1255                1260

His Tyr Leu Asp Glu Ile Ile Glu Gln Ile Ser Glu Phe Ser Lys
    1265            1270                1275

Arg Val Ile Leu Ala Asp Ala Asn Leu Asp Lys Val Leu Ser Ala
    1280            1285                1290

Tyr Asn Lys His Arg Asp Lys Pro Ile Arg Glu Gln Ala Glu Asn
    1295            1300                1305

Ile Ile His Leu Phe Thr Leu Thr Asn Leu Gly Ala Pro Ala Ala
    1310            1315                1320

Phe Lys Tyr Phe Asp Thr Thr Ile Asp Arg Lys Arg Tyr Thr Ser
    1325            1330                1335

Thr Lys Glu Val Leu Asp Ala Thr Leu Ile His Gln Ser Ile Thr
    1340            1345                1350

Gly Leu Tyr Glu Thr Arg Ile Asp Leu Ser Gln Leu Gly Gly Asp
    1355            1360                1365

Ser Arg Ala Asp Pro Lys Lys Lys Arg Lys Val
    1370            1375

<210> SEQ ID NO 4
<211> LENGTH: 543
<212> TYPE: DNA
<213> ORGANISM: Yarrowia lipolytica

<400> SEQUENCE: 4
tcgacgttta aaccatcatc taagggcctc aaaactacct cggaactgct gcgctgatct      60
ggacaccaca gaggttccga gcactttagg ttgcaccaaa tgtcccacca ggtgcaggca     120
gaaaacgctg aacagcgtg tacagtttgt cttaacaaaa agtgagggcg ctgaggtcga     180
gcagggtggt gtgacttgtt atagccttta gagctgcgaa agcgcgtatg gatttggctc     240
atcaggccag attgagggtc tgtggacaca tgtcatgtta gtgtacttca atcgcccct     300 ggatatagcc ccgacaatag gccgtggcct cattttttg ccttccgcac atttccattg     360
ctcggtaccc acaccttgct tctcctgcac ttgccaacct taatactggt ttacattgac     420
```

```
caacatctta caagcggggg gcttgtctag ggtatatata aacagtggct ctcccaatcg      480
gttgccagtc tctttttcc tttctttccc cacagattcg aaatctaaac tacacatcac      540
acc                                                                   543
```

<210> SEQ ID NO 5
<211> LENGTH: 4683
<212> TYPE: DNA
<213> ORGANISM: artificial sequence
<220> FEATURE:
<223> OTHER INFORMATION: Cas9-NLS expression cassette (FBA1 promoter and Cas9-NLS open reading frame)

<400> SEQUENCE: 5

```
tcgacgttta aaccatcatc taagggcctc aaaactacct cggaactgct gcgctgatct       60
ggacaccaca gaggttccga gcactttagg ttgcaccaaa tgtcccacca ggtgcaggca      120
gaaaacgctg aacagcgtg  tacagtttgt cttaacaaaa agtgagggcg ctgaggtcga      180
gcagggtggt gtgacttgtt atagccttta gagctgcgaa agcgcgtatg gatttggctc      240
atcaggccag attgagggtc tgtggacaca tgtcatgtta gtgtacttca atcgccccct      300
ggatatagcc ccgacaatag gccgtggcct cattttttg ccttccgcac atttccattg      360
ctcggtaccc acaccttgct tctcctgcac ttgccaacct taatactggt ttacattgac      420
caacatctta caagcggggg gcttgtctag ggtatatata aacagtggct ctcccaatcg      480
gttgccagtc tctttttcc tttctttccc cacagattcg aaatctaaac tacacatcac      540
accatggaca gaaatactc catcggcctg acattggaa ccaactctgt cggctgggct      600
gtcatcaccg acgagtacaa ggtgccctcc aagaaattca aggtcctcgg aaacaccgat      660
cgacactcca tcaagaaaaa cctcattggt gccctgttgt tcgattctgg cgagactgcc      720
gaagctacca gactcaagcg aactgctcgg cgacgttaca cccgacggaa gaaccgaatc      780
tgctacctgc aggagatctt ttccaacgag atggccaagg tggacgattc gttctttcat      840
cgactggagg aatccttcct cgtcgaggaa gacaagaaac acgagcgtca tcccatcttt      900
ggcaacattg tggacgaggt tgcttaccac gagaagtatc ctaccatcta ccacctgcga      960
aagaaactcg tcgattccac cgacaaggcg gatctcagac ttatctacct cgctctggca     1020
cacatgatca gtttcgagg tcatttcctc atcgagggcg atctcaatcc cgacaacagc     1080
gatgtggaca gctgttcat tcagctcgtt cagacctaca accagctgtt cgaggaaaac     1140
cccatcaatg cctccggagt cgatgcaaag gccatcttgt ctgctcgact ctcgaagagc     1200
agacgactgg agaacctcat tgcccaactt cctggcgaga aaagaacgg actgtttggc     1260 aacctcattg ccctttctct tggtctcaca cccaacttca gtccaacttc gatctggcg     1320 gaggacgcca agctccagct gtccaaggac acctacgacg atgacctcga caacctgctt     1380
gcacagattg cgatcagta cgccgacctg tttctcgctg ccaagaacct ttcggatgct     1440
attctcttgt ctgacattct gcgagtcaac accgagatca caaggctcc ctttctgcc     1500 tccatgatca agcgatacga cgagcaccat caggatctca cactgctcaa ggctcttgtc     1560
cgacagcaac tgcccgagaa gtacaaggag atcttttcg atcagtcgaa gaacggctac     1620
gctggataca tcgacggcgg agcctctcag gaagagttct acaagttcat caagccaatt     1680
ctcgagaaga tggacggaac cgaggaactg cttgtcaagc tcaatcgaga ggatctgctt     1740
cggaagcaac gaaccttcga caacggcagc attcctcatc agatccacct cggtgagctg     1800
cacgccattc ttcgacgtca ggaagacttc tacccctttc tcaaggacaa ccgagagaag     1860
```

```
atcgagaaga ttcttacctt tcgaatcccc tactatgttg gtcctcttgc cagaggaaac    1920
tctcgatttg cttggatgac tcgaaagtcc gaggaaacca tcactccctg gaacttcgag    1980
gaagtcgtgg acaagggtgc ctctgcacag tccttcatcg agcgaatgac caacttcgac    2040
aagaatctgc ccaacgagaa ggttcttccc aagcattcgc tgctctacga gtactttaca    2100
gtctacaacg aactcaccaa agtcaagtac gttaccgagg aatgcgaaa gcctgccttc    2160 ttgtctggcg aacagaagaa agccattgtc gatctcctgt tcaagaccaa ccgaaaggtc    2220
actgttaagc agctcaagga ggactacttc aagaaaatcg agtgtttcga cagcgtcgag    2280
atttccggag ttgaggaccg attcaacgcc tctttgggca cctatcacga tctgctcaag    2340
attatcaagg acaaggattt tctcgacaac gaggaaaacg aggacattct ggaggacatc    2400
gtgctcactc ttaccctgtt cgaagatcgg gagatgatcg aggaacgact caagacatac    2460
gctcacctgt tcgacgacaa ggtcatgaaa caactcaagc gacgtagata caccggctgg    2520
ggaagacttt cgcgaaagct catcaacggc atcagagaca agcagtccgg aaagaccatt    2580
ctggactttc tcaagtccga tggctttgcc aaccgaaact tcatgcagct cattcacgac    2640
gattctctta ccttcaagga ggacatccag aaggcacaag tgtccggtca gggcgacagc    2700
ttgcacgaac atattgccaa cctggctggt tcgccagcca tcaagaaagg cattctccag    2760
actgtcaagg ttgtcgacga gctggtgaag gtcatgggac gtcacaagcc cgagaacatt    2820
gtgatcgaga tggccagaga gaaccagaca actcaaaagg gtcagaaaaa ctcgcgagag    2880
cggatgaagc gaatcgagga aggcatcaag gagctgggat cccagattct caaggagcat    2940
cccgtcgaga acactcaact gcagaacgag aagctgtatc tctactatct gcagaatggt    3000
cgagacatgt acgtggatca ggaactggac atcaatcgtc tcagcgacta cgatgtggac    3060
cacattgtcc ctcaatcctt tctcaaggac gattctatcg acaacaaggt ccttacacga    3120
tccgacaaga acagaggcaa gtcggacaac gttcccagcg aagaggtggt caaaaagatg    3180
aagaactact ggcgacagct gctcaacgcc aagctcatta cccagcgaaa gttcgacaat    3240
cttaccaagg ccgagcgagg cggtctgtcc gagctcgaca aggctggctt catcaagcgt    3300
caactcgtcg agaccagaca gatcacaaag cacgtcgcac agattctcga ttctcggatg    3360
aacaccaagt acgacgagaa cgacaagctc atccgagagg tcaaggtgat tactctcaag    3420
tccaaactgg tctccgattt ccgaaaggac tttcagttct acaaggtgcg agagatcaac    3480
aattaccacc atgcccacga tgcttacctc aacgccgtcg ttggcactgc gctcatcaag    3540
aaatacccca agctcgaaag cgagttcgtt tacggcgatt acaaggtcta cgacgttcga    3600
aagatgattg ccaagtccga acaggagatt ggcaaggcta ctgccaagta cttctttac    3660 tccaacatca tgaacttttt caagaccgag atcaccttgg ccaacggaga gattcgaaag    3720
agaccactta tcgagaccaa cggcgaaact ggagagatcg tgtgggacaa gggtcgagac    3780
tttgcaaccg tgcgaaaggt tctgtcgatg cctcaggtca acatcgtcaa gaaaaccgag    3840
gttcagactg gcggattctc caaggagtcg attctgccca agcgaaactc gacaagctc    3900 atcgctcgaa agaaagactg ggatcccaag aaatacggtg gcttcgattc tcctaccgtc    3960
gcctattccg tgcttgtcgt tgcgaaggtc gagaagggca agtccaaaaa gctcaagtcc    4020
gtcaaggagc tgctcggaat taccatcatg gagcgatcga gcttcgagaa gaatcccatc    4080
gacttcttgg aagccaaggg ttacaaggag gtcaagaaag acctcattat caagctgccc    4140
aagtactctc tgttcgaact ggagaacggt cgaaagcgta tgctcgcctc cgctggcgag    4200
```

| | |
|---|---|
| ctgcagaagg gaaacgagct tgccttgcct tcgaagtacg tcaactttct ctatctggct | 4260 |
| tctcactacg agaagctcaa gggttctccc gaggacaacg aacagaagca actcttcgtt | 4320 |
| gagcagcaca acattacct cgacgagatt atcgagcaga tttccgagtt ttcgaagcga | 4380 |
| gtcatcctgg ctgatgccaa cttggacaag gtgctctctg cctacaacaa gcatcgggac | 4440 |
| aaacccattc gagaacaggc ggagaacatc attcacctgt ttactcttac caacctgggt | 4500 |
| gctcctgcag ctttcaagta cttcgatacc actatcgacc gaaagcggta cacatccacc | 4560 |
| aaggaggttc tcgatgccac cctgattcac cagtccatca ctggcctgta cgagacccga | 4620 |
| atcgacctgt ctcagcttgg tggcgactcc agagccgatc caagaaaaaa gcgaaaggtc | 4680 |
| taa | 4683 |

<210> SEQ ID NO 6
<211> LENGTH: 10706
<212> TYPE: DNA
<213> ORGANISM: artificial sequence
<220> FEATURE:
<223> OTHER INFORMATION: pZUFCas9 plasmid

<400> SEQUENCE: 6

| | |
|---|---|
| catggacaag aaatactcca tcggcctgga cattggaacc aactctgtcg gctgggctgt | 60 |
| catcaccgac gagtacaagg tgccctccaa gaaattcaag gtcctcggaa acaccgatcg | 120 |
| acactccatc aagaaaaacc tcattggtgc cctgttgttc gattctggcg agactgccga | 180 |
| agctaccaga ctcaagcgaa ctgctcggcg acgttacacc cgacggaaga accgaatctg | 240 |
| ctacctgcag gagatctttt ccaacgagat ggccaaggtg gacgattcgt tctttcatcg | 300 |
| actggaggaa tccttcctcg tcgaggaaga caagaaacac gagcgtcatc ccatctttgg | 360 |
| caacattgtg gacgaggttg cttaccacga gaagtatcct accatctacc acctgcgaaa | 420 |
| gaaactcgtc gattccaccg acaaggcgga tctcagactt atctacctcg ctctggcaca | 480 |
| catgatcaag tttcgaggtc atttcctcat cgagggcgat ctcaatcccg acaacagcga | 540 |
| tgtggacaag ctgttcattc agctcgttca gacctacaac cagctgttcg aggaaaaccc | 600 |
| catcaatgcc tccggagtcg atgcaaaggc catcttgtct gctcgactct cgaagagcag | 660 |
| acgactggag aacctcattg cccaacttcc tggcgagaaa agaacggac tgtttggcaa | 720 |
| cctcattgcc ctttctcttg gtctcacacc caacttcaag tccaacttcg atctggcgga | 780 |
| ggacgccaag ctccagctgt ccaaggacac ctacgacgat gacctcgaca acctgcttgc | 840 |
| acagattggc gatcagtacg ccgacctgtt tctcgctgcc aagaaccttt cggatgctat | 900 |
| tctcttgtct gacattctgc gagtcaacac cgagatcaca aaggctcccc tttctgcctc | 960 |
| catgatcaag cgatacgacg agcaccatca ggatctcaca ctgctcaagg ctcttgtccg | 1020 |
| acagcaactg cccgagaagt acaaggagat ctttttcgat cagtcgaaga acggctacgc | 1080 |
| tggatacatc gacggcggag cctctcagga gagttctac aagttcatca agccaattct | 1140 |
| cgagaagatg gacggaaccg aggaactgct tgtcaagctc aatcgagagg atctgcttcg | 1200 |
| gaagcaacga accttcgaca acggcagcat tcctcatcag atccacctcg gtgagctgca | 1260 |
| cgccattctt cgacgtcagg aagacttcta ccccttttctc aaggacaacc gagagaagat | 1320 |
| cgagaagatt cttacctttc gaatccccta ctatgttggt cctcttgcca gaggaaactc | 1380 |
| tcgatttgct tggatgactc gaaagtccga ggaaaccatc actccctgga acttcgagga | 1440 |
| agtcgtggac aagggtgcct ctgcacagtc cttcatcgag cgaatgacca acttcgacaa | 1500 |
| gaatctgccc aacgagaagg ttcttcccaa gcattcgctg ctctacgagt actttacagt | 1560 |

```
ctacaacgaa ctcaccaaag tcaagtacgt taccgaggga atgcgaaagc ctgccttctt    1620
gtctggcgaa cagaagaaag ccattgtcga tctcctgttc aagaccaacc gaaaggtcac    1680
tgttaagcag ctcaaggagg actacttcaa gaaaatcgag tgtttcgaca gcgtcgagat    1740
ttccggagtt gaggaccgat tcaacgcctc tttgggcacc tatcacgatc tgctcaagat    1800
tatcaaggac aaggattttc tcgacaacga ggaaaacgag gacattctgg aggacatcgt    1860
gctcactctt accctgttcg aagatcggga gatgatcgag gaacgactca agacatacgc    1920
tcacctgttc gacgacaagg tcatgaaaca actcaagcga cgtagataca ccggctgggg    1980
aagactttcg cgaaagctca tcaacggcat cagagacaag cagtccggaa agaccattct    2040
ggactttctc aagtccgatg ctttgccaa ccgaaacttc atgcagctca ttcacgacga    2100
ttctcttacc ttcaaggagg acatccagaa ggcacaagtg tccggtcagg cgacagctt     2160
gcacgaacat attgccaacc tggctggttc gccagccatc aagaaaggca ttctccagac    2220
tgtcaaggtt gtcgacgagc tggtgaaggt catgggacgt cacaagcccg agaacattgt    2280
gatcgagatg gccagagaga accagacaac tcaaaagggt cagaaaaact cgcgagagcg    2340
gatgaagcga atcgaggaag gcatcaagga gctgggatcc cagattctca aggagcatcc    2400
cgtcgagaac actcaactgc agaacgagaa gctgtatctc tactatctgc agaatggtcg    2460
agacatgtac gtggatcagg aactggacat caatcgtctc agcgactacg atgtggacca    2520
cattgtccct caatcctttc tcaaggacga ttctatcgac aacaaggtcc ttacacgatc    2580
cgacaagaac agaggcaagt cggacaacgt tcccagcgaa gaggtggtca aaaagatgaa    2640
gaactactgg cgacagctgc tcaacgccaa gctcattacc cagcgaaagt cgacaatct     2700
taccaaggcc gagcgaggcg gtctgtccga gctcgacaag gctggcttca tcaagcgtca    2760
actcgtcgag accagacaga tcacaaagca cgtcgcacag attctcgatt ctcggatgaa    2820
caccaagtac gacgagaacg acaagctcat ccgagaggtc aaggtgatta ctctcaagtc    2880
caaactggtc tccgatttcc gaaaggactt tcagttctac aaggtgcgag agatcaacaa    2940
ttaccaccat gcccacgatg cttacctcaa cgccgtcgtt ggcactgcgc tcatcaagaa    3000
ataccccaag ctcgaaagcg agttcgttta cggcgattac aaggtctacg acgttcgaaa    3060
gatgattgcc aagtccgaac aggagattgg caaggctact gccaagtact tcttttactc    3120
caacatcatg aacttttca agaccgagat caccttggcc aacggagaga ttcgaaagag    3180
accacttatc gagaccaacg gcgaaactgg agagatcgtg tgggacaagg tcgagacttt    3240
tgcaaccgtg cgaaaggttc tgtcgatgcc tcaggtcaac atcgtcaaga aaaccgaggt    3300
tcagactggc ggattctcca aggagtcgat tctgcccaag cgaaactccg acaagctcat    3360
cgctcgaaag aaagactggg atcccaagaa atacggtggc ttcgattctc taccgtcgc     3420
ctattccgtg cttgtcgttg cgaaggtcga gaagggcaag tccaaaaagc tcaagtccgt    3480
caaggagctg ctcggaatta ccatcatgga gcgatcgagc ttcgagaaga tcccatcga    3540
cttcttggaa gccaagggtt acaaggaggt caagaaagac ctcattatca gctgcccaa     3600
gtactctctg ttcgaactgg agaacggtcg aaagcgtatg ctcgcctccg ctggcgagct    3660
gcagaaggga aacgagcttg ccttgccttc gaagtacgtc aactttctct atctggcttc    3720
tcactacgag aagctcaagg gttctcccga ggacaacgaa cagaagcaac tcttcgttga    3780
gcagcacaaa cattacctcg acgagattat cgagcagatt tccgagtttt cgaagcgagt    3840
catcctggct gatgccaact tggacaaggt gctctctgcc tacaacaagc atcgggacaa    3900
```

```
acccattcga gaacaggcgg agaacatcat tcacctgttt actcttacca acctgggtgc    3960
tcctgcagct ttcaagtact tcgataccac tatcgaccga aagcggtaca catccaccaa    4020
ggaggttctc gatgccaccc tgattcacca gtccatcact ggcctgtacg agacccgaat    4080
cgacctgtct cagcttggtg gcgactccag agccgatccc aagaaaaagc gaaaggtcta    4140
agcggccgca agtgtggatg gggaagtgag tgcccggttc tgtgtgcaca attggcaatc    4200
caagatggat ggattcaaca cagggatata gcgagctacg tggtggtgcg aggatatagc    4260
aacggatatt tatgtttgac acttgagaat gtacgataca agcactgtcc aagtacaata    4320
ctaaacatac tgtacatact catactcgta cccgggcaac ggtttcactt gagtgcagtg    4380
gctagtgctc ttactcgtac agtgtgcaat actgcgtatc atagtctttg atgtatatcg    4440
tattcattca tgttagttgc gtacgagccg aagcataaa gtgtaaagcc tggggtgcct     4500
aatgagtgag ctaactcaca ttaattgcgt tgcgctcact gcccgctttc cagtcgggaa    4560
acctgtcgtg ccagctgcat taatgaatcg gccaacgcgc ggggagaggc ggtttgcgta    4620
ttgggcgctc ttccgcttcc tcgctcactg actcgctgcg ctcggtcgtt cggctgcggc    4680
gagcggtatc agctcactca aaggcggtaa tacggttatc cacagaatca ggggataacg    4740
caggaaagaa catgtgagca aaaggccagc aaaaggccag gaaccgtaaa aaggccgcgt    4800
tgctggcgtt tttccatagg ctccgccccc ctgacgagca tcacaaaaat cgacgctcaa    4860
gtcagaggtg gcgaaacccg acaggactat aaagatacca ggcgtttccc cctggaagct    4920
ccctcgtgcg ctctcctgtt ccgaccctgc cgcttaccgg atacctgtcc gcctttctcc    4980
cttcgggaag cgtggcgctt tctcatagct cacgctgtag gtatctcagt tcggtgtagg    5040
tcgttcgctc caagctgggc tgtgtgcacg aaccccccgt tcagcccgac cgctgcgcct    5100
tatccggtaa ctatcgtctt gagtccaacc cggtaagaca cgacttatcg ccactggcag    5160
cagccactgg taacaggatt agcagagcga ggtatgtagg cggtgctaca gagttcttga    5220
agtggtggcc taactacggc tacactagaa ggacagtatt tggtatctgc gctctgctga    5280
agccagttac cttcggaaaa agagttggta gctcttgatc cggcaaacaa accaccgctg    5340
gtagcggtgg tttttttgtt tgcaagcagc agattacgcg cagaaaaaaa ggatctcaag    5400
aagatccttt gatcttttct acggggtctg acgctcagtg gaacgaaaac tcacgttaag    5460
ggattttggt catgagatta tcaaaaagga tcttcaccta gatcctttta aattaaaaat    5520
gaagttttaa atcaatctaa agtatatatg agtaaacttg gtctgacagt taccaatgct    5580
taatcagtga ggcacctatc tcagcgatct gtctatttcg ttcatccata gttgcctgac    5640
tccccgtcgt gtagataact acgatacggg agggcttacc atctggcccc agtgctgcaa    5700
tgataccgcg agacccacgc tcaccggctc cagatttatc agcaataaac cagccagccg    5760
gaagggccga gcgcagaagt ggtcctgcaa ctttatccgc ctccatccag tctattaatt    5820
gttgccggga agctagagta agtagttcgc cagttaatag tttgcgcaac gttgttgcca    5880
ttgctacagg catcgtggtg tcacgctcgt cgtttggtat ggcttcattc agctccggtt    5940
cccaacgatc aaggcgagtt acatgatccc ccatgttgtg caaaaaagcg gttagctcct    6000
tcggtcctcc gatcgttgtc agaagtaagt tggccgcagt gttatcactc atggttatgg    6060
cagcactgca taattctctt actgtcatgc catccgtaag atgcttttct gtgactggtg    6120
agtactcaac caagtcattc tgagaatagt gtatgcggcg accgagttgc tcttgcccgg    6180
cgtcaatacg ggataatacc gcgccacata gcagaacttt aaaagtgctc atcattggaa    6240
aacgttcttc ggggcgaaaa ctctcaagga tcttaccgct gttgagatcc agttcgatgt    6300
```

```
aacccactcg tgcacccaac tgatcttcag catcttttac tttcaccagc gtttctgggt    6360
gagcaaaaac aggaaggcaa aatgccgcaa aaaagggaat aagggcgaca cggaaatgtt    6420
gaatactcat actcttcctt tttcaatatt attgaagcat ttatcagggt tattgtctca    6480
tgagcggata catatttgaa tgtatttaga aaaataaaca aataggggtt ccgcgcacat    6540
ttccccgaaa agtgccacct gacgcgccct gtagcggcgc attaagcgcg gcgggtgtgg    6600
tggttacgcg cagcgtgacc gctacacttg ccagcgccct agcgcccgct cctttcgctt    6660
tcttcccttc ctttctcgcc acgttcgccg gctttccccg tcaagctcta atcgggggc    6720 tccctttagg gttccgattt agtgctttac ggcacctcga ccccaaaaaa cttgattagg    6780
gtgatggttc acgtagtggg ccatcgccct gatagacggt ttttcgccct tgacgttgg    6840 agtccacgtt ctttaatagt ggactcttgt tccaaactgg aacaacactc aaccctatct    6900
cggtctattc ttttgattta aagggatttt gccgatttc ggcctattgg ttaaaaaatg    6960
agctgattta caaaaatttt aacgcgaatt ttaacaaaat attaacgctt acaatttcca    7020
ttcgccattc aggctgcgca actgttggga agggcgatcg gtgcgggcct cttcgctatt    7080
acgccagctg gcgaaagggg gatgtgctgc aaggcgatta agttgggtaa cgccagggtt    7140
ttcccagtca cgacgttgta aaacgacggc cagtgaattg taatacgact cactataggg    7200
cgaattgggt accgggcccc ccctcgaggt cgatggtgtc gataagcttg atatcgaatt    7260
catgtcacac aaaccgatct cgcctcaag gaaacctaat tctacatccg agagactgcc    7320
gagatccagt ctacactgat taattttcgg gccataatt taaaaaaatc gtgttatata    7380
atattatatg tattatatat atacatcatg atgatactga cagtcatgtc ccattgctaa    7440
atagacagac tccatctgcc gcctccaact gatgttctca atatttaagg ggtcatctcg    7500
cattgtttaa taataaacag actccatcta ccgcctccaa atgatgttct caaaatatat    7560
tgtatgaact tattttttat acttagtatt attagacaac ttacttgctt tatgaaaaac    7620
acttcctatt taggaaacaa tttataatgg cagttcgttc atttaacaat ttatgtagaa    7680
taaatgttat aaatgcgtat gggaaatctt aaatatggat agcataaatg atatctgcat    7740
tgcctaattc gaaatcaaca gcaacgaaaa aaatcccttg tacaacataa atagtcatcg    7800
agaaatatca actatcaaag aacagctatt cacacgttac tattgagatt attattggac    7860
gagaatcaca cactcaactg tctttctctc ttctagaaat acaggtacaa gtatgtacta    7920
ttctcattgt tcatacttct agtcatttca tcccacatat tccttggatt tctctccaat    7980
gaatgacatt ctatccttgca aattcaacaa ttataataag atataccaaa gtagcggtat    8040
agtggcaatc aaaaagcttc tctggtgtgc ttctcgtatt tatttttatt ctaatgatcc    8100
attaaaggta tatatttatt tcttgttata taatcctttt gtttattaca tgggctggat    8160
acataaaggt attttgattt aattttttgc ttaaattcaa tcccccctcg ttcagtgtca    8220
actgtaatgg taggaaatta ccatactttt gaagaagcaa aaaaaatgaa agaaaaaaaa    8280 aatcgtatt ccaggttaga cgttccgcag aatctagaat gcggtatgcg gtacattgtt    8340
cttcgaacgt aaaagttgcg ctccctgaga tattgtacat ttttgctttt acaagtacaa    8400
gtacatcgta caactatgta ctactgttga tgcatccaca acagtttgtt ttgttttttt    8460 ttgtttttt ttttctaat gattcattac cgctatgtat acctacttgt acttgtagta    8520
agccgggtta ttggcgttca attaatcata gacttatgaa tctgcacggt gtgcgctgcg    8580
agttactttt agcttatgca tgctacttgg gtgtaatatt gggatctgtt cggaaatcaa    8640
```

```
cggatgctca atcgatttcg acagtaatta attaagtcat acacaagtca gctttcttcg    8700
agcctcatat aagtataagt agttcaacgt attagcactg tacccagcat ctccgtatcg    8760
agaaacacaa caacatgccc cattggacag atcatgcgga tacacaggtt gtgcagtatc    8820
atacatactc gatcagacag gtcgtctgac catcatacaa gctgaacaag cgctccatac    8880
ttgcacgctc tctatataca cagttaaatt acatatccat agtctaacct ctaacagtta    8940
atcttctggt aagcctccca gccagccttc tggtatcgct tggcctcctc aataggatct    9000
cggttctggc cgtacagacc tcggccgaca attatgatat ccgttccggt agacatgaca    9060
tcctcaacag ttcggtactg ctgtccgaga gcgtctccct tgtcgtcaag acccaccccg    9120
ggggtcagaa taagccagtc ctcagagtcg cccttaggtc ggttctgggc aatgaagcca    9180
accacaaact cggggtcgga tcgggcaagc tcaatggtct gcttggagta ctcgccagtg    9240
gccagagagc ccttgcaaga cagctcggcc agcatgagca gacctctggc cagcttctcg    9300 ttggagagg ggactaggaa ctccttgtac tgggagttct cgtagtcaga gacgtcctcc       9360
ttcttctgtt cagagacagt ttcctcggca ccagctcgca ggccagcaat gattccggtt    9420
ccgggtacac cgtgggcgtt ggtgatatcg gaccactcgg cgattcggtg acaccggtac    9480
tggtgcttga cagtgttgcc aatatctgcg aactttctgt cctcgaacag gaagaaaccg    9540
tgcttaagag caagttcctt gaggggagc acagtgccgg cgtaggtgaa gtcgtcaatg      9600
atgtcgatat gggttttgat catgcacaca taaggtccga ccttatcggc aagctcaatg    9660
agctccttgg tggtggtaac atccagagaa gcacacaggt tggttttctt ggctgccacg    9720
agcttgagca ctcgagcggc aaaggcggac ttgtggacgt tagctcgagc ttcgtaggag    9780
ggcattttgg tggtgaagag gagactgaaa taaatttagt ctgcagaact ttttatcgga    9840
accttatctg gggcagtgaa gtatatgtta tggtaatagt tacgagttag ttgaacttat    9900
agatagactg gactatacgg ctatcggtcc aaattagaaa gaacgtcaat ggctctctgg    9960
gcgtcgcctt tgccgacaaa aatgtgatca tgatgaaagc cagcaatgac gttgcagctg   10020
atattgttgt cggccaaccg cgccgaaaac gcagctgtca gacccacagc ctccaacgaa    10080
gaatgtatcg tcaaagtgat ccaagcacac tcatagttgg agtcgtactc caaaggcggc    10140
aatgacgagt cagacagata ctcgtcgacg tttaaaccat catctaaggg cctcaaaact    10200
acctcggaac tgctgcgctg atctggacac cacagaggtt ccgagcactt taggttgcac    10260
caaatgtccc accaggtgca ggcagaaaac gctggaacag cgtgtacagt ttgtcttaac    10320
aaaaagtgag ggcgctgagg tcgagcaggg tggtgtgact tgtttatagcc tttagagctg    10380 cgaaagcgcg tatggatttg gctcatcagg ccagattgag ggtctgtgga cacatgtcat    10440
gttagtgtac ttcaatcgcc ccctggatat agccccgaca ataggccgtg gcctcattt     10500 tttgccttcc gcacatttcc attgctcggt acccacacct tgcttctcct gcacttgcca    10560
accttaatac tggtttacat tgaccaacat cttacaagcg gggggcttgt ctagggtata    10620
tataaacagt ggctctccca atcggttgcc agtctctttt ttcctttctt tccccacaga    10680
ttcgaaatct aaactacaca tcacac                                         10706
```

<210> SEQ ID NO 7
<211> LENGTH: 35
<212> TYPE: DNA
<213> ORGANISM: artificial sequence
<220> FEATURE:
<223> OTHER INFORMATION: Cas9-NLS forward PCR primer

<400> SEQUENCE: 7

```
gggggaattc gacaagaaat actccatcgg cctgg                          35
```

<210> SEQ ID NO 8
<211> LENGTH: 31
<212> TYPE: DNA
<213> ORGANISM: artificial sequence
<220> FEATURE:
<223> OTHER INFORMATION: Cas9-NLS reverse PCR primer

<400> SEQUENCE: 8

```
ccccaagctt agcggccgct tagacctttc g                              31
```

<210> SEQ ID NO 9
<211> LENGTH: 4166
<212> TYPE: DNA
<213> ORGANISM: artificial sequence
<220> FEATURE:
<223> OTHER INFORMATION: EcoRI-Cas9-NLS-HinDIII PCR product

<400> SEQUENCE: 9

```
gggggaattc gacaagaaat actccatcgg cctggacatt ggaaccaact ctgtcggctg      60
ggctgtcatc accgacgagt acaaggtgcc ctccaagaaa ttcaaggtcc tcggaaacac     120
cgatcgacac tccatcaaga aaaacctcat tggtgccctg ttgttcgatt ctggcgagac     180
tgccgaagct accagactca gcgaactgc tcggcgacgt acacccgac ggaagaaccg      240
aatctgctac ctgcaggaga tcttttccaa cgagatggcc aaggtggacg attcgttctt     300
tcatcgactg gaggaatcct tcctcgtcga ggaagacaag aaaacgagc gtcatcccat     360
ctttggcaac attgtggacg aggttgctta ccacgagaag tatcctacca tctaccacct     420
gcgaaagaaa ctcgtcgatt ccaccgacaa ggcggatctc agacttatct acctcgctct     480
ggcacacatg atcaagtttc gaggtcattt cctcatcgag ggcgatctca atcccgacaa     540
cagcgatgtg gacaagctgt tcattcagct cgttcagacc tacaaccagc tgttcgagga     600
aaaccccatc aatgcctccg agtcgatgc aaaggccatc ttgtctgctc gactctcgaa     660
gagcagacga ctggagaacc tcattgccca acttcctggc gagaaaaaga cggactgtt    720
tggcaaccctc attgcccttt ctcttggtct cacacccaac ttcaagtcca acttcgatct    780
ggcggaggac gccaagctcc agctgtccaa ggacacctac gacgatgacc tcgacaacct    840
gcttgcacag attggcgatc agtacgccga cctgtttctc gctgccaaga acctttcgga    900
tgctattctc ttgtctgaca ttctgcgagt caacaccgag atcacaaagg ctcccctttc    960
tgcctccatg atcaagcgat acgacgagca ccatcaggat ctcacactgc tcaaggctct   1020
tgtccgacag caactgcccg agaagtacaa ggagatcttt ttcgatcagt cgaagaacgg   1080
ctacgctgga tacatcgacg gcggagcctc tcaggaagag ttctacaagt catcaagcc    1140
aattctcgag aagatggacg gaaccgagga actgcttgtc aagctcaatc gagaggatct   1200
gcttcggaag caacgaacct tcgacaacgg cagcattcct catcagatcc acctcggtga   1260
gctgcacgcc attcttcgac gtcaggaaga cttctacccc tttctcaagg acaaccgaga   1320
gaagatcgag aagattctta ccttccgaat cccctactat gttggtcctc ttgccagagg   1380
aaactctcga tttgcttgga tgactcgaaa gtccgaggaa accatcactc cctgaactt    1440
cgaggaagtc gtggacaagg gtgcctctgc acagtccttc atcgagcgaa tgaccaactt   1500
cgacaagaat ctgcccaacg agaaggttct tcccaagcat tcgctgctct acgagtactt   1560
tacagtctac aacgaactca ccaaagtcaa gtacgttacc gagggaatgc gaaagcctgc   1620
```

```
cttcttgtct ggcgaacaga agaaagccat tgtcgatctc ctgttcaaga ccaaccgaaa    1680
ggtcactgtt aagcagctca aggaggacta cttcaagaaa atcgagtgtt tcgacagcgt    1740
cgagatttcc ggagttgagg accgattcaa cgcctctttg ggcacctatc acgatctgct    1800
caagattatc aaggacaagg attttctcga caacgaggaa aacgaggaca ttctggagga    1860
catcgtgctc actcttaccc tgttcgaaga tcgggagatg atcgaggaac gactcaagac    1920
atacgctcac ctgttcgacg acaaggtcat gaaacaactc aagcgacgta gatacaccgg    1980
ctggggaaga ctttcgcgaa agctcatcaa cggcatcaga gacaagcagt ccggaaagac    2040
cattctggac tttctcaagt ccgatggctt tgccaaccga aacttcatgc agctcattca    2100
cgacgattct cttaccttca aggaggacat ccagaaggca caagtgtccg gtcagggcga    2160
cagcttgcac gaacatattg ccaacctggc tggttcgcca gccatcaaga aaggcattct    2220
ccagactgtc aaggttgtcg acgagctggt gaaggtcatg gacgtcaca agcccgagaa     2280 cattgtgatc gagatggcca gagagaacca gacaactcaa aagggtcaga aaaactcgcg    2340
agagcggatg aagcgaatcg aggaaggcat caaggagctg ggatcccaga ttctcaagga    2400
gcatcccgtc gagaacactc aactgcagaa cgagaagctg tatctctact atctgcagaa    2460
tggtcgagac atgtacgtgg atcaggaact ggacatcaat cgtctcagcg actacgatgt    2520
ggaccacatt gtccctcaat cctttctcaa ggacgattct atcgacaaca aggtccttac    2580
acgatccgac aagaacagag gcaagtcgga caacgttccc agcgaagagg tggtcaaaaa    2640
gatgaagaac tactggcgac agctgctcaa cgccaagctc attcccagc gaaagttcga    2700 caatcttacc aaggccgagc gaggcggtct gtccgagctc gacaaggctg gcttcatcaa    2760
gcgtcaactc gtcgagacca gacagatcac aaagcacgtc gcacagattc tcgattctcg    2820
gatgaacacc aagtacgacg agaacgacaa gctcatccga gaggtcaagg tgattactct    2880
caagtccaaa ctggtctccg atttccgaaa ggactttcag ttctacaagg tgcgagagat    2940
caacaattac caccatgccc acgatgctta cctcaacgcc gtcgttggca ctgcgctcat    3000
caagaaatac cccaagctcg aaagcgagtt cgtttacggc gattacaagg tctacgacgt    3060
tcgaaagatg attgccaagt ccgaacagga gattggcaag gctactgcca agtacttctt    3120
ttactccaac atcatgaact ttttcaagac cgagatcacc ttggccaacg gagagattcg    3180
aaagagacca cttatcgaga ccaacggcga aactggagag atcgtgtggg acaagggtcg    3240
agactttgca accgtgcgaa aggttctgtc gatgcctcag gtcaacatcg tcaagaaaac    3300
cgaggttcag actggcggat tctccaagga gtcgattctg cccaagcgaa actccgacaa    3360
gctcatcgct cgaaagaaag actgggatcc caagaaatac ggtggcttcg attctcctac    3420
cgtcgcctat tccgtgcttg tcgttgcgaa ggtcgagaag ggcaagtcca aaaagctcaa    3480
gtccgtcaag gagctgctcg gaattaccat catggagcga tcgagcttcg agaagaatcc    3540
catcgacttc ttggaagcca agggttacaa ggaggtcaag aaagacctca ttatcaagct    3600
gcccaagtac tctctgttcg aactggagaa cggtcgaaag cgtatgctcg cctccgctgg    3660
cgagctgcag aagggaaacg agcttgcctt gccttcgaag tacgtcaact ttctctatct    3720
ggcttctcac tacgagaagc tcaagggttc tcccggagac aacgaacaga gcaactctt    3780 cgttgagcag cacaaacatt acctcgacga gattatcgag cagatttccg agttttcgaa    3840
gcgagtcatc ctggctgatg ccaacttgga caaggtgctc tctgcctaca acaagcatcg    3900
ggacaaaccc attcgagaac aggcggagaa catcattcac ctgttactc ttaccaacct     3960 gggtgctcct gcagctttca agtacttcga taccactatc gaccgaaagc ggtacacatc    4020
```

```
caccaaggag gttctcgatg ccaccctgat tcaccagtcc atcactggcc tgtacgagac    4080
ccgaatcgac ctgtctcagc ttggtggcga ctccagagcc gatcccaaga aaaagcgaaa    4140
ggtctaagcg gccgctaagc ttgggg                                         4166
```

<210> SEQ ID NO 10
<211> LENGTH: 4092
<212> TYPE: DNA
<213> ORGANISM: artificial sequence
<220> FEATURE:
<223> OTHER INFORMATION: pBAD/HisB plasmid

<400> SEQUENCE: 10

```
aagaaaccaa ttgtccatat tgcatcagac attgccgtca ctgcgtcttt tactggctct      60
tctcgctaac caaaccggta accccgctta ttaaaagcat tctgtaacaa agcgggacca     120
aagccatgac aaaaacgcgt aacaaaagtg tctataatca cggcagaaaa gtccacattg     180
attatttgca cggcgtcaca ctttgctatg ccatagcatt tttatccata agattagcgg     240
atcctacctg acgcttttta tcgcaactct ctactgtttc tccatacccg ttttttgggc     300
taacaggagg aattaaccat ggggggttct catcatcatc atcatcatgg tatggctagc     360
atgactggtg gacagcaaat gggtcgggat ctgtacgacg atgacgataa ggatccgagc     420
tcgagatctg cagctggtac catatgggaa ttcgaagctt ggctgttttg gcggatgaga     480
gaagattttc agcctgatac agattaaatc agaacgcaga agcggtctga taaaacagaa     540
tttgcctggc ggcagtagcg cggtggtccc acctgacccc atgccgaact cagaagtgaa     600
acgccgtagc gccgatggta gtgtggggtc tccccatgcg agagtaggga actgccaggc     660
atcaaataaa acgaaaggct cagtcgaaag actgggcctt tcgttttatc tgttgtttgt     720
cggtgaacgc tctcctgagt aggacaaatc cgccgggagc ggatttgaac gttgcgaagc     780
aacggcccgg agggtggcgg gcaggacgcc cgccataaac tgccaggcat caaattaagc     840
agaaggccat cctgacggat ggcctttttg cgtttctaca actcttttg tttatttttc      900 taaatacatt caaatatgta tccgctcatg agacaataac cctgataaat gcttcaataa     960
tattgaaaaa ggaagagtat gagtattcaa catttccgtg tcgcccttat tcccttttt     1020 gcggcatttt gccttcctgt ttttgctcac ccagaaacgc tggtgaaagt aaaagatgct     1080
gaagatcagt tgggtgcacg agtgggttac atcgaactgg atctcaacag cggtaagatc     1140
cttgagagtt ttcgccccga agaacgtttt ccaatgatga gcacttttaa agttctgcta     1200
tgtggcgcgg tattatcccg tgttgacgcc gggcaagagc aactcggtcg ccgcatacac     1260
tattctcaga atgacttggt tgagtactca ccagtcacag aaaagcatct tacggatggc     1320
atgacagtaa gagaattatg cagtgctgcc ataaccatga gtgataacac tgcggccaac     1380
ttacttctga caacgatcgg aggaccgaag gagctaaccg cttttttgca acatgggg      1440 gatcatgtaa ctcgccttga tcgttgggaa ccggagctga atgaagccat accaaacgac     1500
gagcgtgaca ccacgatgcc tgtagcaatg gcaacaacgt tgcgcaaact attaactggc     1560
gaactactta ctctagcttc ccggcaacaa ttaatagact ggatggaggc ggataaagtt     1620
gcaggaccac ttctgcgctc ggcccttccg gctggctggt ttattgctga taaatctgga     1680
gccggtgagc gtgggtctcg cggtatcatt gcagcactgg ggccagatgg taagccctcc     1740
cgtatcgtag ttatctacac gacggggagt caggcaacta tggatgaacg aaatagacag     1800
atcgctgaga taggtgcctc actgattaag cattggtaac tgtcagacca agtttactca     1860
```

```
tatatacttt agattgattt aaaacttcat ttttaattta aaaggatcta ggtgaagatc    1920 cttttgata atctcatgac caaaatccct taacgtgagt tttcgttcca ctgagcgtca    1980
gaccccgtag aaaagatcaa aggatcttct tgagatcctt ttttctgcg cgtaatctgc    2040 tgcttgcaaa caaaaaaacc accgctacca gcggtggttt gtttgccgga tcaagagcta    2100
ccaactcttt ttccgaaggt aactggcttc agcagagcgc agataccaaa tactgtcctt    2160
ctagtgtagc cgtagttagg ccaccacttc aagaactctg tagcaccgcc tacatacctc    2220
gctctgctaa tcctgttacc agtggctgct gccagtggcg ataagtcgtg tcttaccggg    2280
ttggactcaa gacgatagtt accggataag gcgcagcggt cgggctgaac ggggggttcg    2340
tgcacacagc ccagcttgga gcgaacgacc tacaccgaac tgagatacct acagcgtgag    2400
ctatgagaaa gcgccacgct tcccgaaggg agaaaggcgg acaggtatcc ggtaagcggc    2460
agggtcggaa caggagagcg cacgagggag cttccagggg gaaacgcctg gtatctttat    2520
agtcctgtcg ggtttcgcca cctctgactt gagcgtcgat ttttgtgatg ctcgtcaggg    2580
gggcggagcc tatggaaaaa cgccagcaac gcggcctttt tacggttcct ggccttttgc    2640
tggccttttg ctcacatgtt ctttcctgcg ttatcccctg attctgtgga taaccgtatt    2700
accgcctttg agtgagctga taccgctcgc cgcagccgaa cgaccgagcg cagcgagtca    2760
gtgagcgagg aagcggaaga gcgcctgatg cggtattttc tccttacgca tctgtgcggt    2820
atttcacacc gcatatggtg cactctcagt acaatctgct ctgatgccgc atagttaagc    2880
cagtatacac tccgctatcg ctacgtgact gggtcatggc tgcgcccga cacccgccaa    2940 cacccgctga cgcgccctga cgggcttgtc tgctcccggc atccgcttac agacaagctg    3000
tgaccgtctc cgggagctgc atgtgtcaga ggttttcacc gtcatcaccg aaacgcgcga    3060
ggcagcagat caattcgcgc gcgaaggcga agcggcatgc ataatgtgcc tgtcaaatgg    3120
acgaagcagg gattctgcaa accctatgct actccgtcaa gccgtcaatt gtctgattcg    3180
ttaccaatta tgacaacttg acggctacat cattcacttt ttcttcacaa ccggcacgga    3240
actcgctcgg gctggccccg gtgcattttt taaatacccg cgagaaatag agttgatcgt    3300
caaaaccaac attgcgaccg acggtggcga taggcatccg ggtggtgctc aaaagcagct    3360
tcgcctggct gatacgttgg tcctcgcgcc agcttaagac gctaatccct aactgctggc    3420
ggaaaagatg tgacagacgc gacggcgaca agcaaacatg ctgtgcgacg ctggcgatat    3480
caaaattgct gtctgccagg tgatcgctga tgtactgaca agcctcgcgt acccgattat    3540
ccatcggtgg atggagcgac tcgttaatcg cttccatgcg ccgcagtaac aattgctcaa    3600
gcagatttat cgccagcagc tccgaatagc gcccttcccc ttgcccggcg ttaatgattt    3660
gcccaaacag gtcgctgaaa tgcggctggt gcgcttcatc cgggcgaaag aaccccgtat    3720
tggcaaatat tgacggccag ttaagccatt catgccagta ggcgcgcgga cgaaagtaaa    3780
cccactggtg ataccattcg cgagcctccg gatgacgacc gtagtgatga atctctcctg    3840
gcgggaacag caaaatatca cccggtcggc aaacaaattc tcgtccctga tttttcacca    3900 cccctgacc gcgaatggtg agattgagaa tataaccttt cattcccagc ggtcggtcga    3960
taaaaaaatc gagataaccg ttggcctcaa tcggcgttaa acccgccacc agatgggcat    4020
taaacgagta tcccggcagc aggggatcat tttgcgcttc agccatactt ttcatactcc    4080
cgccattcag ag                                                      4092
```

<210> SEQ ID NO 11
<211> LENGTH: 8237

<212> TYPE: DNA
<213> ORGANISM: artificial sequence
<220> FEATURE:
<223> OTHER INFORMATION: pRF48 plasmid

<400> SEQUENCE: 11

```
aattcgacaa gaaatactcc atcggcctgg acattggaac caactctgtc ggctgggctg      60
tcatcaccga cgagtacaag gtgccctcca agaaattcaa ggtcctcgga acaccgatc     120
gacactccat caagaaaaac ctcattggtg ccctgttgtt cgattctggc gagactgccg    180
aagctaccag actcaagcga actgctcggc gacgttacac ccgacggaag aaccgaatct    240
gctacctgca ggagatcttt ccaacgaga tggccaaggt ggacgattcg ttctttcatc     300
gactggagga atccttcctc gtcgaggaag acaagaaaca cgagcgtcat cccatctttg    360
gcaacattgt ggacgaggtt gcttaccacg agaagtatcc taccatctac cacctgcgaa    420
agaaactcgt cgattccacc gacaaggcgg atctcagact tatctacctc gctctggcac    480
acatgatcaa gtttcgaggt catttcctca tcgaggggcga tctcaatccc gacaacagcg   540
atgtggacaa gctgttcatt cagctcgttc agacctacaa ccagctgttc gaggaaaacc    600
ccatcaatgc ctccggagtc gatgcaaagg ccatcttgtc tgctcgactc tcgaagagca    660
gacgactgga gaacctcatt gcccaacttc ctggcgagaa aaagaacgga ctgtttggca    720
acctcattgc cctttctctt ggtctcacac ccaacttcaa gtccaacttc gatctggcgg    780
aggacgccaa gctccagctg tccaaggaca cctacgacga tgacctcgac aacctgcttg    840
cacagattgg cgatcagtac gccgaccctgt ttctcgctgc caagaacctt tcggatgcta   900
ttctcttgtc tgacattctg cgagtcaaca ccgagatcac aaaggctccc ctttctgcct    960
ccatgatcaa gcgatacgac gagcaccatc aggatctcac actgctcaag gctcttgtcc   1020
gacagcaact gcccgagaag tacaaggaga tctttttcga tcagtcgaag aacggctacg   1080
ctggatacat cgacggcgga gcctctcagg aagagttcta caagttcatc aagccaattc   1140
tcgagaagat ggacggaacc gaggaactgc ttgtcaagct caatcgagag gatctgcttc   1200
ggaagcaacg aaccttcgac aacggcagca ttcctcatca gatccacctc ggtgagctgc   1260
acgccattct tcgacgtcag gaagacttct accccttcct caaggacaac cgagagaaga   1320
tcgagaagat tcttaccttt cgaatccccc actatgttgg tcctcttgcc agaggaaact   1380
ctcgatttgc ttggatgact cgaaagtccg aggaaaccat cactccctgg aacttcgagg   1440
aagtcgtgga caagggtgcc tctgcacagt ccttcatcga gcgaatgacc aacttcgaca   1500
agaatctgcc caacgagaag gttcttccca gcattcgct gctctacgag tactttacag   1560
tctacaacga actcaccaaa gtcaagtacg ttaccgaggg aatgcgaaag cctgccttct   1620
tgtctggcga acagaagaaa gccattgtcg atctcctgtt caagaccaac cgaaaggtca   1680
ctgttaagca gctcaaggag gactacttca gaaaatcga gtgtttcgac agcgtcgaga   1740
tttccggagt tgaggaccga ttcaacgcct ctttgggcac ctatcacgat ctgctcaaga   1800
ttatcaagga caaggatttt ctcgacaacg aggaaaacga ggacattctg gaggacatcg   1860
tgctcactct taccctgttc gaagatcggg agatgatcga ggaacgactc aagacatacg   1920
ctcacctgtt cgacgacaag gtcatgaaac aactcaagcg acgtagatac accggctggg   1980
gaagactttc gcgaaagctc atcaacggca tcagagacaa gcagtccgga aagaccattc   2040
tggactttct caagtccgat ggctttgcca ccgaaaactt catgcagctc attcacgacg   2100
attctcttac cttcaaggag gacatccaga aggcacaagt gtccggtcag ggcgacagct   2160
```

```
tgcacgaaca tattgccaac ctggctggtt cgccagccat caagaaaggc attctccaga    2220
ctgtcaaggt tgtcgacgag ctggtgaagg tcatgggacg tcacaagccc gagaacattg    2280
tgatcgagat ggccagagag aaccagacaa ctcaaaaggg tcagaaaaac tcgcgagagc    2340
ggatgaagcg aatcgaggaa ggcatcaagg agctgggatc ccagattctc aaggagcatc    2400
ccgtcgagaa cactcaactg cagaacgaga agctgtatct ctactatctg cagaatggtc    2460
gagacatgta cgtggatcag gaactggaca tcaatcgtct cagcgactac gatgtggacc    2520
acattgtccc tcaatccttt ctcaaggacg attctatcga caacaaggtc cttacacgat    2580
ccgacaagaa cagaggcaag tcggacaacg ttcccagcga agaggtggtc aaaaagatga    2640
agaactactg gcgacagctg ctcaacgcca agctcattac ccagcgaaag ttcgacaatc    2700
ttaccaaggc cgagcgaggc ggtctgtccg agctcgacaa ggctggcttc atcaagcgtc    2760
aactcgtcga gaccagacag atcacaaagc acgtcgcaca gattctcgat ctcggatga     2820
acaccaagta cgacgagaac gacaagctca tccgagaggt caaggtgatt actctcaagt    2880
ccaaactggt ctccgatttc cgaaaggact ttcagttcta caaggtgcga gagatcaaca    2940
attaccacca tgcccacgat gcttacctca acgccgtcgt tggcactgcg ctcatcaaga    3000
aatacccaa gctcgaaagc gagttcgttt acggcgatta caaggtctac gacgttcgaa    3060
agatgattgc caagtccgaa caggagattg gcaaggctac tgccaagtac ttctttttact    3120
ccaacatcat gaacttttc aagaccgaga tcaccttggc caacgagag attcgaaaaga    3180
gaccacttat cgagaccaac ggcgaaactg gagagatcgt gtgggacaag ggtcgagact    3240
ttgcaaccgt gcgaaaggtt ctgtcgatgc tcaggtcaa catcgtcaag aaaaccgagg    3300
ttcagactgg cggattctcc aaggagtcga ttctgcccaa gcgaaactcc gacaagctca    3360
tcgctcgaaa gaaagactgg gatcccaaga aatacggtgg cttcgattct cctaccgtcg    3420
cctattccgt gcttgtcgtt gcgaaggtcg agaagggcaa gtccaaaaag ctcaagtccg    3480
tcaaggagct gctcggaatt accatcatgg agcgatcgag cttcgagaag aatcccatcg    3540
acttcttgga agccaagggt tacaaggagg tcaagaaaga cctcattatc aagctgccca    3600
agtactctct gttcgaactg gagaacggtc gaaagcgtat gctcgcctcc gctggcgagc    3660
tgcagaaggg aaacgagctt gccttgcctt cgaagtacgt caactttctc tatctggctt    3720
ctcactacga gaagctcaag ggttctcccg aggacaacga acagaagcaa ctcttcgttg    3780
agcagcacaa acattacctc gacgagatta tcgagcagat ttccgagttt tcgaagcgag    3840
tcatcctggc tgatgccaac ttggacaagg tgctctctgc ctacaacaag catcgggaca    3900
aacccattcg agaacaggcg gagaacatca ttcacctgtt tactcttacc aacctgggtg    3960
ctcctgcagc tttcaagtac ttcgatacca ctatcgaccg aaagcggtac acatccacca    4020
aggaggttct cgatgccacc ctgattcacc agtccatcac tggcctgtac gagacccgaa    4080
tcgacctgtc tcagcttggt ggcgactcca gagccgatcc caagaaaaag cgaaaggtct    4140
aagcggccgc taagcttggc tgttttggcg gatgagagaa gattttcagc ctgatacaga    4200
ttaaatcaga acgcagaagc ggtctgataa aacagaattt gcctggcggc agtagcgcgg    4260
tggtcccacc tgaccccatg ccgaactcag aagtgaaacg ccgtagcgcc gatggtagtg    4320
tggggtctcc ccatgcgaga gtagggaact gccaggcatc aaataaaacg aaaggctcag    4380
tcgaaagact gggcctttcg ttttatctgt tgtttgtcgg tgaacgctct cctgagtagg    4440
acaaatccgc cgggagcgga tttgaacgtt gcgaagcaac ggcccggagg gtggcgggca    4500
ggacgcccgc cataaactgc caggcatcaa attaagcaga aggccatcct gacggatggc    4560
```

```
cttttttgcgt ttctacaaac tcttttgttt attttctaa atacattcaa atatgtatcc    4620
gctcatgaga caataaccct gataaatgct tcaataatat tgaaaaagga agagtatgag    4680
tattcaacat ttccgtgtcg cccttattcc cttttttgcg gcattttgcc ttcctgtttt    4740
tgctcaccca gaaacgctgg tgaaagtaaa agatgctgaa gatcagttgg gtgcacgagt    4800
gggttacatc gaactggatc tcaacagcgg taagatcctt gagagttttc gccccgaaga    4860
acgttttcca atgatgagca cttttaaagt tctgctatgt ggcgcggtat tatcccgtgt    4920
tgacgccggg caagagcaac tcggtcgccg catacactat tctcagaatg acttggttga    4980
gtactcacca gtcacagaaa agcatcttac ggatggcatg acagtaagag aattatgcag    5040
tgctgccata accatgagtg ataacactgc ggccaactta cttctgacaa cgatcggagg    5100
accgaaggag ctaaccgctt ttttgcacaa catgggggat catgtaactc gccttgatcg    5160
ttgggaaccg gagctgaatg aagccatacc aaacgacgag cgtgacacca cgatgcctgt    5220
agcaatggca acaacgttgc gcaaactatt aactggcgaa ctacttactc tagcttcccg    5280
gcaacaatta atagactgga tggaggcgga taaagttgca ggaccacttc tgcgctcggc    5340
ccttccggct ggctggttta ttgctgataa atctggagcc ggtgagcgtg gtctcgcgg    5400
tatcattgca gcactggggc cagatggtaa gccctcccgt atcgtagtta tctacacgac    5460
ggggagtcag gcaactatgg atgaacgaaa tagacagatc gctgagatag gtgcctcact    5520
gattaagcat tggtaactgt cagaccaagt ttactcatat atactttaga ttgatttaaa    5580
acttcatttt taatttaaaa ggatctaggt gaagatcctt tttgataatc tcatgaccaa    5640
aatcccttaa cgtgagtttt cgttccactg agcgtcagac cccgtagaaa agatcaaagg    5700
atcttcttga tccttttttt ttctgcgcgt aatctgctgc ttgcaaacaa aaaaaccacc    5760
gctaccagcg gtggtttgtt tgccggatca agagctacca actcttttc cgaaggtaac    5820
tggcttcagc agagcgcaga taccaaatac tgtccttcta gtgtagccgt agttaggcca    5880
ccacttcaag aactctgtag caccgcctac atacctcgct ctgctaatcc tgttaccagt    5940
ggctgctgcc agtggcgata agtcgtgtct taccgggttg gactcaagac gatagttacc    6000
ggataaggcg cagcggtcgg gctgaacggg ggttcgtgc acacagccca gcttggagcg    6060
aacgacctac accgaactga gatacctaca gcgtgagcta tgagaaagcg ccacgcttcc    6120
cgaagggaga aaggcggaca ggtatccggt aagcggcagg gtcggaacag gagagcgcac    6180
gagggagctt ccagggggaa acgcctggta tctttatagt cctgtcgggt ttcgccacct    6240
ctgacttgag cgtcgatttt tgtgatgctc gtcaggggg cggagcctat ggaaaaacgc    6300
cagcaacgcg gcctttttac ggttcctggc cttttgctgg ccttttgctc acatgttctt    6360
tcctgcgtta tccctgatt ctgtggataa ccgtattac gcctttgagt gagctgatac    6420
cgctcgccgc agccgaacga ccgagcgcag cgagtcagtg agcgaggaag cggaagagcg    6480
cctgatgcgg tattttctcc ttacgcatct gtgcggtatt tcacaccgca tatggtgcac    6540
tctcagtaca atctgctctg atgccgcata gttaagccag tatacactcc gctatcgcta    6600
cgtgactggg tcatggctgc gccccgacac ccgccaacac ccgctgacgc gccctgacgg    6660
gcttgtctgc tcccggcatc cgcttacaga caagctgtga ccgtctccgg gagctgcatg    6720
tgtcagaggt tttcaccgtc atcaccgaaa cgcgcgaggc agcagatcaa ttcgcgcgcg    6780
aaggcgaagc ggcatgcata atgtgcctgt caaatggacg aagcagggat tctgcaaacc    6840
ctatgctact ccgtcaagcc gtcaattgtc tgattcgtta ccaattatga caacttgacg    6900
```

-continued

```
gctacatcat tcacttttc ttcacaaccg gcacggaact cgctcgggct ggccccggtg    6960
cattttttaa atacccgcga gaaatagagt tgatcgtcaa aaccaacatt gcgaccgacg   7020
gtggcgatag gcatccgggt ggtgctcaaa agcagcttcg cctggctgat acgttggtcc   7080
tcgcgccagc ttaagacgct aatccctaac tgctggcgga aaagatgtga cagacgcgac   7140
ggcgacaagc aaacatgctg tgcgacgctg gcgatatcaa aattgctgtc tgccaggtga   7200
tcgctgatgt actgacaagc ctcgcgtacc cgattatcca tcggtggatg gagcgactcg   7260
ttaatcgctt ccatgcgccg cagtaacaat tgctcaagca gatttatcgc cagcagctcc   7320
gaatagcgcc cttccccttg cccggcgtta atgatttgcc caaacaggtc gctgaaatgc   7380
ggctggtgcg cttcatccgg gcgaaagaac cccgtattgg caaatattga cggccagtta   7440
agccattcat gccagtaggc gcgcggacga aagtaaaccc actggtgata ccattcgcga   7500
gcctccggat gacgaccgta gtgatgaatc tctcctggcg ggaacagcaa aatatcaccc   7560
ggtcggcaaa caaattctcg tccctgattt ttcaccaccc cctgaccgcg aatggtgaga   7620
ttgagaatat aacctttcat tcccagcggt cggtcgataa aaaaatcgag ataaccgttg   7680
gcctcaatcg gcgttaaacc cgccaccaga tgggcattaa acgagtatcc cggcagcagg   7740
ggatcatttt gcgcttcagc catactttc atactcccgc cattcagaga agaaaccaat   7800
tgtccatatt gcatcagaca ttgccgtcac tgcgtctttt actggctctt ctcgctaacc   7860
aaaccggtaa ccccgcttat taaaagcatt ctgtaacaaa gcgggaccaa agccatgaca   7920
aaaacgcgta acaaaagtgt ctataatcac ggcagaaaag tccacattga ttatttgcac   7980
ggcgtcacac tttgctatgc catagcattt ttatccataa gattagcgga tcctacctga   8040
cgcttttat cgcaactctc tactgtttct ccatacccgt ttttttgggct aacaggagga   8100
attaaccatg gggggttctc atcatcatca tcatcatggt atggctagca tgactggtgg   8160
acagcaaatg ggtcgggatc tgtacgacga tgacgataag gatccgagct cgagatctgc   8220
agctggtacc atatggg                                                 8237
```

<210> SEQ ID NO 12
<211> LENGTH: 54
<212> TYPE: PRT
<213> ORGANISM: Epstein-Barr virus

<400> SEQUENCE: 12

Glu Cys Asp Ser Glu Leu Glu Ile Lys Arg Tyr Lys Arg Val Arg Val
1               5                   10                  15

Ala Ser Arg Lys Cys Arg Ala Lys Phe Lys Gln Leu Leu Gln His Tyr
            20                  25                  30

Arg Glu Val Ala Ala Ala Lys Ser Ser Glu Asn Asp Arg Leu Arg Leu
        35                  40                  45

Leu Leu Lys Gln Met Cys
    50

<210> SEQ ID NO 13
<211> LENGTH: 18
<212> TYPE: PRT
<213> ORGANISM: mus musculus

<400> SEQUENCE: 13

Leu Leu Ile Ile Leu Arg Arg Arg Ile Arg Lys Gln Ala His Ala His
1               5                   10                  15

Ser Lys

<210> SEQ ID NO 14
<211> LENGTH: 21
<212> TYPE: PRT
<213> ORGANISM: unknown
<220> FEATURE:
<223> OTHER INFORMATION: TP10 CPP

<400> SEQUENCE: 14

Ala Gly Tyr Leu Leu Gly Lys Ile Asn Leu Lys Ala Cys Ala Ala Cys
1               5                   10                  15

Ala Lys Lys Ile Leu
            20

<210> SEQ ID NO 15
<211> LENGTH: 17
<212> TYPE: PRT
<213> ORGANISM: artificial sequence
<220> FEATURE:
<223> OTHER INFORMATION: PolyR CPP

<400> SEQUENCE: 15

Gly Gly Gly Gly Arg Arg Arg Arg Arg Arg Arg Arg Leu Leu Leu
1               5                   10                  15

Leu

<210> SEQ ID NO 16
<211> LENGTH: 194
<212> TYPE: DNA
<213> ORGANISM: artificial sequence
<220> FEATURE:
<223> OTHER INFORMATION: NcoI-6xHis-ZEBRA CPP-EcoRI

<400> SEQUENCE: 16
ccatggggca tcaccaccat caccacgaat gcgactcaga actggaaatc aaacgctata      60
aacgtgtgcg tgtggcatcc cgtaaatgtc gcgcaaagtt taaacagctg ctgcaacatt     120
atcgtgaagt agcggctgcg aaaagctccg aaaacgaccg tttacgcctc ctcctgaagc     180
aaatgtgcga attc                                                      194

<210> SEQ ID NO 17
<211> LENGTH: 86
<212> TYPE: DNA
<213> ORGANISM: artificial sequence
<220> FEATURE:
<223> OTHER INFORMATION: NcoI-6xHis-pVEC CPP-EcoRI

<400> SEQUENCE: 17
ccatggggca tcaccaccat caccacttat tgattatctt gcgtcgtcgc atccgcaaac      60
aggcgcacgc acatagcaag gaattc                                          86

<210> SEQ ID NO 18
<211> LENGTH: 95
<212> TYPE: DNA
<213> ORGANISM: artificial sequence
<220> FEATURE:
<223> OTHER INFORMATION: NcoI-6xHis-TP10 CPP-EcoRI

<400> SEQUENCE: 18
ccatggggca tcaccaccat caccacgcgg ttacctgctg ggcaagatt aatcttaaag       60 cctgcgccgc gtgtgctaag aaaattttgg aattc                                95

<210> SEQ ID NO 19

```
<211> LENGTH: 83
<212> TYPE: DNA
<213> ORGANISM: artificial sequence
<220> FEATURE:
<223> OTHER INFORMATION: NcoI-6xHis-PolyR CPP-EcoRI

<400> SEQUENCE: 19
ccatggggca tcaccaccat caccacggcg ggggtggtcg tcgtcgccgt cgccgccgtc    60
gtcgcctcct gctgctggaa ttc                                           83

<210> SEQ ID NO 20
<211> LENGTH: 8294
<212> TYPE: DNA
<213> ORGANISM: artificial sequence
<220> FEATURE:
<223> OTHER INFORMATION: pRF144 plasmid

<400> SEQUENCE: 20
ccatggggca tcaccaccat caccacgaat gcgactcaga actggaaatc aaacgctata    60
aacgtgtgcg tgtggcatcc cgtaaatgtc gcgcaaagtt taaacagctg ctgcaacatt   120
atcgtgaagt agcggctgcg aaaagctccg aaaacgaccg tttacgcctc ctcctgaagc   180
aaatgtgcga attcgacaag aaatactcca tcggcctgga cattggaacc aactctgtcg   240
gctgggctgt catcaccgac gagtacaagg tgccctccaa gaaattcaag gtcctcggaa   300
acaccgatcg acactccatc aagaaaaacc tcattggtgc cctgttgttc gattctggcg   360
agactgccga agctaccaga ctcaagcgaa ctgctcggcg acgttacacc cgacggaaga   420
accgaatctg ctacctgcag agatcttttt ccaacgagat ggccaaggtg gacgattcgt   480
tctttcatcg actggaggaa tccttcctcg tcgaggaaga caagaaacac gagcgtcatc   540
ccatctttgg caacattgtg gacgaggttg cttaccacga agtatcctac catctaccc   600 acctgcgaaa gaaactcgtc gattccaccg acaaggcgga tctcagactt atctacctcg   660
ctctggcaca catgatcaag tttcgaggtc atttcctcat cgagggcgat ctcaatcccg   720
acaacagcga tgtggacaag ctgttcattc agctcgttca gacctacaac cagctgttcg   780
aggaaaaccc catcaatgcc tccggagtcg atgcaaaggc catcttgtct gctcgactct   840
cgaagagcag acgactggag aacctcattg cccaacttcc tggcgagaaa aagaacggac   900
tgtttggcaa cctcattgcc cttctcttg gtctcacacc caacttcaag tccaacttcg   960
atctggcgga ggacgccaag ctccagctgt ccaaggacac ctacgacgat gacctcgaca  1020
acctgcttgc acagattggc gatcagtacg ccgacctgtt tctcgctgcc aagaaccttt  1080
cggatgctat tctcttgtct gacattctgc gagtcaacac cgagatcaca aaggctcccc  1140
tttctgcctc catgatcaag cgatacgacg agcaccatca ggatctcaca ctgctcaagg  1200
ctcttgtccg acagcaactg cccgagaagt acaaggagat ctttttcgat cagtcgaaga  1260
acggctacgc tggatacatc gacggcgag cctctcagga agttctac aagttcatca  1320 agccaattct cgagaagatg gacggaaccg aggaactgct tgtcaagctc aatcgagagg  1380
atctgcttcg gaagcaacga accttcgaca cggcagcat tcctcatcag atccacctcg  1440
gtgagctgca cgccattctt cgacgtcagg aagacttcta ccccttctc aaggacaacc  1500 gagagaagat cgagaagatt cttaccttc gaatccccta ctatgttggt cctcttgcca  1560
gaggaaactc tcgatttgct tggatgactc gaaagtccga ggaaaccatc actccctgga  1620
acttcgagga agtcgtggac aagggtgcct ctgcacagtc cttcatcgag cgaatgacca  1680
acttcgacaa gaatctgccc aacgagaagg ttcttcccaa gcattcgctg ctctacgagt  1740
```

```
actttacagt ctacaacgaa ctcaccaaag tcaagtacgt taccgaggga atgcgaaagc    1800
ctgccttctt gtctggcgaa cagaagaaag ccattgtcga tctcctgttc aagaccaacc    1860
gaaaggtcac tgttaagcag ctcaaggagg actacttcaa gaaaatcgag tgtttcgaca    1920
gcgtcgagat ttccggagtt gaggaccgat tcaacgcctc tttgggcacc tatcacgatc    1980
tgctcaagat tatcaaggac aaggattttc tcgacaacga ggaaaacgag gacattctgg    2040
aggacatcgt gctcactctt accctgttcg aagatcggga gatgatcgag aacgactca     2100
agacatacgc tcacctgttc gacgacaagg tcatgaaaca actcaagcga cgtagataca    2160
ccggctgggg aagactttcg cgaaagctca tcaacggcat cagagacaag cagtccggaa    2220
agaccattct ggactttctc aagtccgatg gctttgccaa ccgaaacttc atgcagctca    2280
ttcacgacga ttctcttacc ttcaaggagg acatccagaa ggcacaagtg tccggtcagg    2340
gcgacagctt gcacgaacat attgccaacc tggctggttc gccagccatc aagaaaggca    2400
ttctccagac tgtcaaggtt gtcgacgagc tggtgaaggt catgggacgt cacaagcccg    2460
agaacattgt gatcgagatg gccagagaga accagacaac tcaaaagggt cagaaaaact    2520
cgcgagagcg gatgaagcga atcgaggaag gcatcaagga gctgggatcc cagattctca    2580
aggagcatcc cgtcgagaac actcaactgc agaacgagaa gctgtatctc tactatctgc    2640
agaatggtcg agacatgtac gtggatcagg aactggacat caatcgtctc agcgactacg    2700
atgtggacca cattgtccct caatcctttc tcaaggacga ttctatcgac aacaaggtcc    2760
ttacacgatc cgacaagaac agaggcaagt cggacaacgt tcccagcgaa gaggtggtca    2820
aaaagatgaa gaactactgg cgacagctgc tcaacgccaa gctcattacc cagcgaaagt    2880
tcgacaatct taccaaggcc gagcgaggcg gtctgtccga gctcgacaag gctggcttca    2940
tcaagcgtca actcgtcgag accagacaga tcacaaagca cgtcgcacag attctcgatt    3000
ctcggatgaa caccaagtac gacgagaacg acaagctcat ccgagaggtc aaggtgatta    3060
ctctcaagtc caaactggtc tccgatttcc gaaaggactt tcagttctac aaggtgcgag    3120
agatcaacaa ttaccaccat gcccacgatg cttacctcaa cgccgtcgtt ggcactgcgc    3180
tcatcaagaa ataccccaag ctcgaaagcg agttcgttta cggcgattac aaggtctacg    3240
acgttcgaaa gatgattgcc aagtccgaac aggagattgg caaggctact gccaagtact    3300
tctttttactc caacatcatg aacttttttca agaccgagat caccttggcc aacgagaga    3360
ttcgaaagag accacttatc gagaccaacg gcgaaactgg agagatcgtg tgggacaagg    3420
gtcgagactt tgcaaccgtg cgaaaggttc tgtcgatgcc tcaggtcaac atcgtcaaga    3480
aaaccgaggt tcagactggc ggattctcca aggagtcgat tctgcccaag cgaaactccg    3540
acaagctcat cgctcgaaag aaagactggg atcccaagaa atacggtggc ttcgattctc    3600
ctaccgtcgc ctattccgtg cttgtcgttg cgaaggtcga gaagggcaag tccaaaaagc    3660
tcaagtccgt caaggagctg ctcggaatta ccatcatgga gcgatcgagc ttcgagaaga    3720
atcccatcga cttcttggaa gccaagggtt acaaggaggt caagaaagac ctcattatca    3780
agctgcccaa gtactctctg ttcgaactgg agaacggtcg aaagcgtatg ctcgcctccg    3840
ctggcgagct gcagaaggga aacgagcttg ccttgccttc gaagtacgtc aactttctct    3900
atctggcttc tcactacgag aagctcaagg gttctcccga ggacaacgaa cagaagcaac    3960
tcttcgttga gcagcacaaa cattacctcg acgagattat cgagcagatt tccgagtttt    4020
cgaagcgagt catcctggct gatgccaact tggacaaggt gctctctgcc tacaacaagc    4080
```

```
atcgggacaa acccattcga gaacaggcgg agaacatcat tcacctgttt actcttacca    4140
acctgggtgc tcctgcagct ttcaagtact tcgataccac tatcgaccga aagcggtaca    4200
catccaccaa ggaggttctc gatgccaccc tgattcacca gtccatcact ggcctgtacg    4260
agacccgaat cgacctgtct cagcttggtg gcgactccag agccgatccc aagaaaaagc    4320
gaaaggtcta agcggccgct aagcttggct gttttggcgg atgagagaag attttcagcc    4380
tgatacagat taaatcagaa cgcagaagcg gtctgataaa acagaatttg cctggcggca    4440
gtagcgcggt ggtcccacct gacccccatgc cgaactcaga agtgaaacgc cgtagcgccg    4500
atggtagtgt ggggtctccc catgcgagag tagggaactg ccaggcatca ataaaaacga    4560
aaggctcagt cgaaagactg ggcctttcgt tttatctgtt gtttgtcggt gaacgctctc    4620
ctgagtagga caaatccgcc gggagcggat ttgaacgttg cgaagcaacg gcccggaggg    4680
tggcgggcag gacgcccgcc ataaactgcc aggcatcaaa ttaagcagaa ggccatcctg    4740
acggatggcc ttttttgcgtt tctacaaact cttttgttta ttttttctaaa tacattcaaa    4800
tatgtatccg ctcatgagac aataaccctg ataaatgctt caataatatt gaaaaggaa     4860
gagtatgagt attcaacatt tccgtgtcgc ccttattccc ttttttgcgg cattttgcct    4920
tcctgttttt gctcacccag aaacgctggt gaaagtaaaa gatgctgaag atcagttggg    4980
tgcacgagtg ggttacatcg aactggatct caacagcggt aagatccttg agagttttcg    5040
ccccgaagaa cgttttccaa tgatgagcac ttttaaagtt ctgctatgtg gcgcggtatt    5100
atcccgtgtt gacgccgggc aagagcaact cggtcgccgc atacactatt ctcagaatga    5160
cttggttgag tactcaccag tcacagaaaa gcatcttacg gatggcatga cagtaagaga    5220
attatgcagt gctgccataa ccatgagtga taacactgcg gccaacttac ttctgacaac    5280
gatcggagga ccgaaggagc taaccgcttt tttgcacaac atgggggatc atgtaactcg    5340
ccttgatcgt tgggaaccgg agctgaatga agccatacca aacgacgagc gtgacaccac    5400
gatgcctgta gcaatggcaa caacgttgcg caaactatta actggcgaac tacttactct    5460
agcttcccgg caacaattaa tagactggat ggaggcggat aaagttgcag gaccacttct    5520
gcgctcggcc cttccggctg ctggttttat tgctgataaa tctggagccg gtgagcgtgg    5580
gtctcgcggt atcattgcag cactggggcc agatggtaag ccctcccgta tcgtagttat    5640
ctacacgacg gggagtcagg caactatgga tgaacgaaat agacagatcg ctgagatagg    5700
tgcctcactg attaagcatt ggtaactgtc agaccaagtt tactcatata ctttagat      5760
tgatttaaaa cttcattttt aatttaaaag gatctaggtg aagatccttt ttgataatct    5820
catgaccaaa atcccttaac gtgagttttc gttccactga gcgtcagacc ccgtagaaaa    5880
gatcaaagga tcttcttgag atccttttt tctgcgcgta atctgctgct tgcaaacaaa     5940
aaaaccaccg ctaccagcgg tggtttgttt gccggatcaa gagctaccaa ctcttttcc     6000
gaaggtaact ggcttcagca gagcgcagat accaaatact gtccttctag tgtagccgta    6060
gttaggccac cacttcaaga actctgtagc accgcctaca tacctcgctc tgctaatcct    6120
gttaccagtg gctgctgcca gtggcgataa gtcgtgtctt accgggttgg actcaagacg    6180
atagttaccg gataaggcgc agcggtcggg ctgaacgggg ggttcgtgca cacagcccag    6240
cttggagcga acgacctaca ccgaactgag atacctacag cgtgagctat gagaaagcgc    6300
cacgcttccc gaagggagaa aggcggacag gtatccggta agcggcaggg tcggaacagg    6360
agagcgcacg agggagcttc caggggggaaa cgcctggtat ctttatagtc ctgtcgggtt    6420
tcgccaccte tgacttgagc gtcgattttt gtgatgctcg tcagggggc ggagcctatg      6480
```

```
gaaaaacgcc agcaacgcgg ccttttttacg gttcctggcc ttttgctggc cttttgctca    6540 catgttctttt cctgcgttat ccctgattc tgtggataac cgtattaccg cctttgagtg    6600
agctgatacc gctcgccgca gccgaacgac cgagcgcagc gagtcagtga gcgaggaagc    6660
ggaagagcgc ctgatgcggt attttctcct tacgcatctg tgcggtattt cacaccgcat    6720
atggtgcact ctcagtacaa tctgctctga tgccgcatag ttaagccagt atacactccg    6780
ctatcgctac gtgactgggt catggctgcg ccccgacacc cgccaacacc cgctgacgcg    6840
ccctgacggg cttgtctgct cccggcatcc gcttacagac aagctgtgac cgtctccggg    6900
agctgcatgt gtcagaggtt ttcaccgtca tcaccgaaac gcgcgaggca gcagatcaat    6960
tcgcgcgcga aggcgaagcg gcatgcataa tgtgcctgtc aaatggacga agcagggatt    7020
ctgcaaaccc tatgctactc cgtcaagccg tcaattgtct gattcgttac caattatgac    7080
aacttgacgg ctacatcatt cactttttct tcacaaccgg cacggaactc gctcgggctg    7140
gccccggtgc attttttaaa tacccgcgag aaatagagtt gatcgtcaaa accaacattg    7200
cgaccgacgg tggcgatagg catccgggtg gtgctcaaaa gcagcttcgc ctggctgata    7260
cgttggtcct cgcgccagct taagacgcta atccctaact gctggcggaa agatgtgac    7320 agacgcgacg gcgacaagca aacatgctgt gcgacgctgg cgatatcaaa attgctgtct    7380
gccaggtgat cgctgatgta ctgacaagcc tcgcgtaccc gattatccat cggtggatgg    7440
agcgactcgt taatcgcttc catgcgccgc agtaacaatt gctcaagcag atttatcgcc    7500
agcagctccg aatagcgccc ttccccttgc ccggcgttaa tgatttgccc aaacaggtcg    7560
ctgaaatgcg gctggtgcgc ttcatccggg cgaaagaacc ccgtattggc aaatattgac    7620
ggccagttaa gccattcatg ccagtaggcg cgcggacgaa agtaaaccca ctggtgatac    7680
cattcgcgag cctccggatg acgaccgtag tgatgaatct ctcctggcgg aacagcaaa    7740 atatcacccg gtcggcaaac aaattctcgt ccctgatttt tcaccacccc ctgaccgcga    7800
atggtgagat tgagaatata accttttcatt cccagcggtc ggtcgataaa aaaatcgaga    7860
taaccgttgg cctcaatcgg cgttaaaccc gccaccagat gggcattaaa cgagtatccc    7920
ggcagcaggg gatcattttg cgcttcagcc atacttttca tactcccgcc attcagagaa    7980
gaaaccaatt gtccatattg catcagacat tgccgtcact gcgtcttttta ctggctcttc    8040 tcgctaacca aaccggtaac cccgcttatt aaaagcattc tgtaacaaag cgggaccaaa    8100
gccatgacaa aaacgcgtaa caaaagtgtc tataatcacg gcagaaaagt ccacattgat    8160
tatttgcacg gcgtcacact ttgctatgcc atagcatttt tatccataag attagcggat    8220
cctacctgac gctttttatc gcaactctct actgtttctc catacccgtt ttttgggcta    8280
acaggaggaa ttaa                                                      8294
```

<210> SEQ ID NO 21
<211> LENGTH: 8183
<212> TYPE: DNA
<213> ORGANISM: artificial sequence
<220> FEATURE:
<223> OTHER INFORMATION: pRF145 plasmid

<400> SEQUENCE: 21

```
aattcgacaa gaaatactcc atcggcctgg acattggaac caactctgtc ggctgggctg     60
tcatcaccga cgagtacaag gtgccctcca agaaattcaa ggtcctcgga acaccgatc     120 gacactccat caagaaaaac ctcattggtg ccctgttgtt cgattctggc gagactgccg    180
```

```
aagctaccag actcaagcga actgctcggc gacgttacac ccgacggaag aaccgaatct    240
gctacctgca ggagatcttt tccaacgaga tggccaaggt ggacgattcg ttctttcatc    300
gactggagga atccttcctc gtcgaggaag acaagaaaca cgagcgtcat cccatctttg    360
gcaacattgt ggacgaggtt gcttaccacg agaagtatcc taccatctac cacctgcgaa    420
agaaactcgt cgattccacc gacaaggcgg atctcagact tatctacctc gctctggcac    480
acatgatcaa gtttcgaggt catttcctca tcgagggcga tctcaatccc gacaacagcg    540
atgtggacaa gctgttcatt cagctcgttc agacctacaa ccagctgttc gaggaaaacc    600
ccatcaatgc ctccggagtc gatgcaaagg ccatcttgtc tgctcgactc tcgaagagca    660
gacgactgga gaacctcatt gcccaacttc ctggcgagaa aaagaacgga ctgtttggca    720
acctcattgc cctttctctt ggtctcacac ccaacttcaa gtccaacttc gatctggcgg    780
aggacgccaa gctccagctg tccaaggaca cctacgacga tgacctcgac aacctgcttg    840
cacagattgg cgatcagtac gccgacctgt ttctcgctgc caagaacctt cggatgctat    900
ttctcttgtc tgacattctg cgagtcaaca ccgagatcac aaaggctccc ctttctgcct    960
ccatgatcaa gcgatacgac gagcaccatc aggatctcac actgctcaag gctcttgtcc   1020
gacagcaact gcccgagaag tacaaggaga tcttttttcga tcagtcgaag aacggctacg   1080
ctggatacat cgacggcgga gcctctcagg aagagttcta caagttcatc aagccaattc   1140
tcgagaagat ggacggaacc gaggaactgc ttgtcaagct caatcgagag gatctgcttc   1200
ggaagcaacg aaccttcgac aacggcagca ttcctcatca gatccacctc ggtgagctgc   1260
acgccattct tcgacgtcag gaagacttct accccttttct caaggacaac cgagagaaga   1320
tcgagaagat tcttaccttt cgaatcccct actatgttgg tcctcttgcc agaggaaact   1380
ctcgatttgc ttggatgact cgaaagtccg aggaaaccat cactccctgg aacttcgagg   1440
aagtcgtgga caagggtgcc tctgcacagt ccttcatcga gcgaatgacc aacttcgaca   1500
agaatctgcc caacgagaag gttcttccca agcattcgct gctctacgag tactttacag   1560
tctacaacga actcaccaaa gtcaagtacg ttaccgaggg aatgcgaaag cctgccttct   1620
tgtctggcga acagaagaaa gccattgtcg atctcctgtt caagaccaac cgaaaggtca   1680
ctgttaagca gctcaaggag gactacttca agaaaatcga gtgtttcgac agcgtcgaga   1740
tttccggagt tgaggaccga ttcaacgcct ctttgggcac ctatcacgat ctgctcaaga   1800
ttatcaagga caaggatttt ctcgacaacg aggaaaacga ggacattctg gaggacatcg   1860
tgctcactct tacccctgttc gaagatcggg agatgatcga ggaacgactc aagacatacg   1920
ctcacctgtt cgacgacaag gtcatgaaac aactcaagcg acgtagatac accggctggg   1980
gaagactttc gcgaaagctc atcaacggca tcagagacaa gcagtccgga agaccattc    2040 tggactttct caagtccgat ggctttgcca accgaaactt catgcagctc attcacgacg   2100
attctcttac cttcaaggag gacatccaga aggcacaagt gtccggtcag gcgacagct    2160 tgcacgaaca tattgccaac ctggctggtt cgccagccat caagaaaggc attctccaga   2220
ctgtcaaggt tgtcgacgag ctggtgaagg tcatgggacg tcacaagccc gagaacattg   2280
tgatcgagat ggcagagag aaccagacaa ctcaaaaggg tcagaaaaac tcgcgagagc   2340
ggatgaagcg aatcgaggaa ggcatcaagg agctgggatc ccagattctc aaggagcatc   2400
ccgtcgagaa cactcaactg cagaacgaga agctgtatct ctactatctg cagaatggtc   2460
gagacatgta cgtggatcag gaactggaca tcaatcgtct cagcgactac gatgtggacc   2520
acattgtccc tcaatccttt ctcaaggacg attctatcga caacaaggtc cttacacgat   2580
```

```
ccgacaagaa cagaggcaag tcggacaacg ttcccagcga agaggtggtc aaaaagatga    2640
agaactactg gcgacagctg ctcaacgcca agctcattac ccagcgaaag ttcgacaatc    2700
ttaccaaggc cgagcgaggc ggtctgtccg agctcgacaa ggctggcttc atcaagcgtc    2760
aactcgtcga gaccagacag atcacaaagc acgtcgcaca gattctcgat tctcggatga    2820
acaccaagta cgacgagaac gacaagctca tccgagaggt caaggtgatt actctcaagt    2880
ccaaactggt ctccgatttc cgaaaggact ttcagttcta caaggtgcga gagatcaaca    2940
attaccacca tgcccacgat gcttacctca acgccgtcgt tggcactgcg ctcatcaaga    3000 aatacccccaa gctcgaaagc gagttcgttt acggcgatta caaggtctac gacgttcgaa    3060
agatgattgc caagtccgaa caggagattg gcaaggctac tgccaagtac ttcttttact    3120
ccaacatcat gaacttttc aagaccgaga tcaccttggc caacggagag attcgaaaga    3180
gaccacttat cgagaccaac ggcgaaactg gagagatcgt gtgggacaag ggtcgagact    3240
ttgcaaccgt gcgaaaggtt ctgtcgatgc ctcaggtcaa catcgtcaag aaaaccgagg    3300
ttcagactgg cggattctcc aaggagtcga ttctgcccaa gcgaaactcc gacaagctca    3360
tcgctcgaaa gaaagactgg gatcccaaga aatacggtgg cttcgattct cctaccgtcg    3420
cctattccgt gcttgtcgtt gcgaaggtcg agaagggcaa gtccaaaaag ctcaagtccg    3480
tcaaggagct gctcggaatt accatcatgg agcgatcgag cttcgagaag aatcccatcg    3540
acttcttgga agccaagggt tacaaggagg tcaagaaaga cctcattatc aagctgccca    3600
agtactctct gttcgaactg gagaacggtc gaaagcgtat gctcgcctcc gctggcgagc    3660
tgcagaaggg aaacgagctt gccttgcctt cgaagtacgt caactttctc tatctggctt    3720
ctcactacga gaagctcaag ggttctcccg aggacaacga acagaagcaa ctcttcgttg    3780
agcagcacaa acattacctc gacgagatta tcgagcagat ttccgagttt tcgaagcgag    3840
tcatcctggc tgatgccaac ttggacaagg tgctctctgc ctacaacaag catcgggaca    3900
aacccattcg agaacaggcg gagaacatca ttcacctgtt tactcttacc aacctgggtg    3960
ctcctgcagc tttcaagtac ttcgatacca ctatcgaccg aaagcggtac acatccacca    4020
aggaggttct cgatgccacc ctgattcacc agtccatcac tggcctgtac gagacccgaa    4080
tcgacctgtc tcagcttggt ggcgactcca gagccgatcc caagaaaaag cgaaaggtct    4140
aagcggccgc taagcttggc tgttttggcg gatgagagaa gattttcagc ctgatacaga    4200
ttaaatcaga acgcagaagc ggtctgataa aacagaattt gcctggcggc agtagcgcgg    4260
tggtcccacc tgaccccatg ccgaactcag aagtgaaacg ccgtagcgcc gatggtagtg    4320
tggggtctcc ccatgcgaga gtagggaact gccaggcatc aaataaaacg aaaggctcag    4380
tcgaaagact gggcctttcg ttttatctgt tgtttgtcgg tgaacgctct cctgagtagg    4440
acaaatccgc cgggagcgga tttgaacgtt gcgaagcaac ggcccggagg gtggcgggca    4500
ggacgcccgc cataaactgc caggcatcaa attaagcaga aggccatcct gacgcatggc    4560
ctttttgcgt ttctacaaac tcttttgttt atttttctaa atacattcaa atatgtatcc    4620
gctcatgaga caataaccct gataaatgct tcaataatat tgaaaaagga agagtatgag    4680
tattcaacat ttccgtgtcg cccttattcc cttttttgcg gcattttgcc ttcctgtttt    4740
tgctcaccca gaaacgctgg tgaaagtaaa agatgctgaa gatcagttgg gtgcacgagt    4800
gggttacatc gaactggatc tcaacagcgg taagatcctt gagagttttc gccccgaaga    4860
acgttttcca atgatgagca cttttaaagt tctgctatgt ggcgcggtat tatcccgtgt    4920
```

```
tgacgccggg caagagcaac tcggtcgccg catacactat tctcagaatg acttggttga    4980
gtactcacca gtcacagaaa agcatcttac ggatggcatg acagtaagag aattatgcag    5040
tgctgccata accatgagtg ataacactgc ggccaactta cttctgacaa cgatcggagg    5100
accgaaggag ctaaccgctt ttttgcacaa catgggggat catgtaactc gccttgatcg    5160
ttgggaaccg gagctgaatg aagccatacc aaacgacgag cgtgacacca cgatgcctgt    5220
agcaatggca acaacgttgc gcaaactatt aactggcgaa ctacttactc tagcttcccg    5280
gcaacaatta atagactgga tggaggcgga taaagttgca ggaccacttc tgcgctcggc    5340
ccttccggct ggctggttta ttgctgataa atctggagcc ggtgagcgtg gtctcgcgg    5400
tatcattgca gcactggggc cagatggtaa gccctcccgt atcgtagtta tctacacgac    5460
ggggagtcag gcaactatgg atgaacgaaa tagacagatc gctgagatag gtgcctcact    5520
gattaagcat tggtaactgt cagaccaagt ttactcatat atactttaga ttgatttaaa    5580
acttcatttt taatttaaaa ggatctaggt gaagatcctt tttgataatc tcatgaccaa    5640
aatcccttaa cgtgagtttt cgttccactg agcgtcagac cccgtagaaa agatcaaagg    5700
atcttcttga tccttttttt tctgcgcgt aatctgctgc ttgcaaacaa aaaaaccacc    5760
gctaccagcg gtggtttgtt tgccggatca agagctacca actctttttc cgaaggtaac    5820
tggcttcagc agagcgcaga taccaaatac tgtccttcta gtgtagccgt agttaggcca    5880
ccacttcaag aactctgtag caccgcctac atacctcgct ctgctaatcc tgttaccagt    5940
ggctgctgcc agtggcgata agtcgtgtct taccgggttg gactcaagac gatagttacc    6000
ggataaggcg cagcggtcgg gctgaacggg ggttcgtgc acacagccca gcttggagcg    6060
aacgacctac accgaactga gatacctaca gcgtgagcta tgagaaagcg ccacgcttcc    6120
cgaagggaga aaggcggaca ggtatccggt aagcggcagg gtcggaacag gagagcgcac    6180
gagggagctt ccagggggaa acgcctggta tctttatagt cctgtcgggt ttcgccacct    6240
ctgacttgag cgtcgatttt tgtgatgctc gtcaggggg cggagcctat ggaaaaacgc    6300
cagcaacgcg gccttttac ggttcctggc cttttgctgg ccttttgctc acatgttctt    6360
tcctgcgtta tccccctgatt ctgtggataa ccgtattacc gcctttgagt gagctgatac    6420
cgctcgccgc agccgaacga ccgagcgcag cgagtcagtg agcgaggaag cggaagagcg    6480
cctgatgcgg tattttctcc ttacgcatct gtgcggtatt tcacaccgca tatggtgcac    6540
tctcagtaca atctgctctg atgccgcata gttaagccag tatacactcc gctatcgcta    6600
cgtgactggg tcatggctgc gccccgacac ccgccaacac ccgctgacgc gccctgacgg    6660
gcttgtctgc tcccggcatc cgcttacaga caagctgtga ccgtctccgg agctgcatg    6720
tgtcagaggt tttcaccgtc atcaccgaaa cgcgcgaggc agcagatcaa ttcgcgcgcg    6780
aaggcgaagc ggcatgcata atgtgcctgt caaatggacg aagcagggat tctgcaaacc    6840
ctatgctact ccgtcaagcc gtcaattgtc tgattcgtta ccaattatga caacttgacg    6900
gctacatcat tcactttttc ttcacaaccg gcacggaact cgctcgggct ggccccggtg    6960
cattttttaa atacccgcga gaaatagagt tgatcgtcaa accaacatt gcgaccgacg    7020
gtggcgatag gcatccgggt ggtgctcaaa agcagcttcg cctggctgat acgttggtcc    7080
tcgcgccagc ttaagacgct aatccctaac tgctggcgga aaagatgtga cagacgcgac    7140
ggcgacaagc aaacatgctg tgcgacgctg gcgatatcaa aattgctgtc tgccaggtga    7200
tcgctgatgt actgacaagc ctcgcgtacc cgattccca tcggtggatg gagcgactcg    7260
ttaatcgctt ccatgcgccg cagtaacaat tgctcaagca gatttatcgc cagcagctcc    7320
```

```
gaatagcgcc cttccccttg cccggcgtta atgatttgcc caaacaggtc gctgaaatgc      7380
ggctggtgcg cttcatccgg gcgaaagaac cccgtattgg caaatattga cggccagtta      7440
agccattcat gccagtaggc gcgcggacga agtaaaccc  actggtgata ccattcgcga      7500
gcctccggat gacgaccgta gtgatgaatc tctcctggcg ggaacagcaa aatatcaccc      7560
ggtcggcaaa caaattctcg tccctgattt ttcaccaccc cctgaccgcg aatggtgaga      7620
ttgagaatat aaccttcat tcccagcggt cggtcgataa aaaaatcgag ataaccgttg       7680
gcctcaatcg gcgttaaacc cgccaccaga tgggcattaa acgagtatcc cggcagcagg     7740
ggatcatttt gcgcttcagc catactttc  atactcccgc cattcagaga agaaaccaat     7800
tgtccatatt gcatcagaca ttgccgtcac tgcgtctttt actggctctt ctcgctaacc     7860
aaaccggtaa ccccgcttat taaaagcatt ctgtaacaaa gcgggaccaa agccatgaca     7920
aaaacgcgta acaaaagtgt ctataatcac ggcagaaaag tccacattga ttatttgcac     7980
ggcgtcacac tttgctatgc catagcattt ttatccataa gattagcgga tcctacctga     8040 cgcttttat  cgcaactctc tactgtttct ccatacccgt tttttgggct aacaggagga     8100
attaaccatg gggcatcacc accatcacca cggcgggggt ggtcgtcgtc gccgtcgccg     8160
ccgtcgtcgc ctcctgctgc tgg                                            8183
```

<210> SEQ ID NO 22
<211> LENGTH: 8195
<212> TYPE: DNA
<213> ORGANISM: artificial sequence
<220> FEATURE:
<223> OTHER INFORMATION: pRF146 plasmid

<400> SEQUENCE: 22

```
aattcgacaa gaaatactcc atcggcctgg acattggaac caactctgtc ggctgggctg       60
tcatcaccga cgagtacaag gtgccctcca agaaattcaa ggtcctcgga aacaccgatc      120
gacactccat caagaaaaac ctcattggtg ccctgttgtt cgattctggc gagactgccg      180
aagctaccag actcaagcga actgctcggc gacgttacac ccgacggaag aaccgaatct      240
gctacctgca ggagatcttt tccaacgaga tggccaaggt ggacgattcg ttctttcatc      300
gactggagga atccttcctc gtcgaggaag acaagaaaca cgagcgtcat cccatctttg      360
gcaacattgt ggacgaggtt gcttaccacg agaagtatcc taccatctac cacctgcgaa      420
agaaactcgt cgattccacc gacaaggcgg atctcagact tatctacctc gctctggcac      480
acatgatcaa gtttcgaggt catttcctca tcgagggcga tctcaatccc gacaacagcg      540
atgtggacaa gctgttcatt cagctcgttc agacctacaa ccagctgttc gaggaaaacc      600
ccatcaatgc ctccggagtc gatgcaaagg ccatcttgtc tgctcgactc tcgaagagca      660
gacgactgga gaacctcatt gcccaacttc ctggcgagaa aaagaacgga ctgtttggca      720
acctcattgc cctttctctt ggtctcacac ccaacttcaa gtccaacttc gatctggcgg      780
aggacgccaa gctccagctg tccaaggaca cctacgacga tgacctcgac aacctgcttg      840
cacagattgg cgatcagtac gccgacctgt ttcgctgc  caagaacctt tcggatgcta      900
ttctcttgtc tgacattctg cgagtcaaca ccgagatcac aaaggctccc ctttctgcct      960
ccatgatcaa gcgatacgac gagcaccatc aggatctcac actgctcaag gctcttgtcc     1020
gacagcaact gcccgagaag tacaaggaga tctttttcga tcagtcgaag aacggctacg     1080
ctggatacat cgacggcgga gcctctcagg aagagttcta caagttcatc aagccaattc     1140
```

```
tcgagaagat ggacggaacc gaggaactgc ttgtcaagct caatcgagag gatctgcttc    1200
ggaagcaacg aaccttcgac aacggcagca ttcctcatca gatccacctc ggtgagctgc    1260
acgccattct tcgacgtcag gaagacttct accccttct caaggacaac cgagagaaga     1320
tcgagaagat tcttaccttt cgaatcccct actatgttgg tcctcttgcc agaggaaact    1380
ctcgatttgc ttggatgact cgaaagtccg aggaaaccat cactccctgg aacttcgagg    1440
aagtcgtgga caagggtgcc tctgcacagt ccttcatcga gcgaatgacc aacttcgaca    1500
agaatctgcc caacgagaag gttcttccca agcattcgct gctctacgag tactttacag    1560
tctacaacga actcaccaaa gtcaagtacg ttaccgaggg aatgcgaaag cctgccttct    1620
tgtctggcga acagaagaaa gccattgtcg atctcctgtt caagaccaac cgaaaggtca    1680
ctgttaagca gctcaaggag gactacttca agaaaatcga gtgtttcgac agcgtcgaga    1740
tttccggagt tgaggaccga ttcaacgcct ctttgggcac ctatcacgat ctgctcaaga    1800
ttatcaagga caaggatttt ctcgacaacg aggaaaacga ggacattctg gaggacatcg    1860
tgctcactct taccctgttc gaagatcggg agatgatcga ggaacgactc aagacatacg    1920
ctcacctgtt cgacgacaag gtcatgaaac aactcaagcg acgtagatac accggctggg    1980
gaagactttc gcgaaagctc atcaacgca tcagagacaa gcagtccgga aagaccattc     2040
tggactttct caagtccgat ggctttgcca ccgaaactt catgcagctc attcacgacg     2100
attctcttac cttcaaggag gacatccaga aggcacaagt gtccggtcag ggcgacagct    2160
tgcacgaaca tattgccaac ctggctggtt cgccagccat caagaaaggc attctccaga    2220
ctgtcaaggt tgtcgacgag ctggtgaagg tcatgggacg tcacaagccc gagaacattg    2280
tgatcgagat ggccagagag aaccagacaa ctcaaaaggg tcagaaaaac tcgcgagagc    2340
ggatgaagcg aatcgaggaa ggcatcaagg agctgggatc ccagattctc aaggagcatc    2400
ccgtcgagaa cactcaactg cagaacgaga agctgtatct ctactatctg cagaatggtc    2460
gagacatgta cgtggatcag gaactggaca tcaatcgtct cagcgactac gatgtggacc    2520
acattgtccc tcaatccttt tcaaggacg attctatcga caacaaggtc cttacacgat     2580
ccgacaagaa cagaggcaag tcggacaacg ttcccagcga agaggtggtc aaaaagatga    2640
agaactactg gcgacagctg ctcaacgcca agctcattac ccagcgaaag ttcgacaatc    2700
ttaccaaggc cgagcgaggc ggtctgtccg agctcgacaa ggctggcttc atcaagcgtc    2760
aactcgtcga gaccagacag atcacaaagc acgtcgcaca gattctcgat ctcggatga    2820 acaccaagta cgacgagaac gacaagctca tccgagaggt caaggtgatt actctcaagt    2880
ccaaactggt ctccgatttc cgaaaggact ttcagttcta caaggtgcga gagatcaaca    2940
attaccacca tgcccacgat gcttacctca acgccgtcgt tggcactgcg ctcatcaaga    3000
aataccccaa gctcgaaagc gagttcgttt acggcgatta caaggtctac gacgttcgaa    3060
agatgattgc caagtccgaa caggagattg caaggctac tgccaagtac ttctttttact    3120 ccaacatcat gaacttttc aagaccgaga tcaccttggc caacgagag attcgaaaga     3180 gaccacttat cgagaccaac ggcgaaactg gagagatcgt gtgggacaag ggtcgagact    3240 tgcaaccgt gcgaaaggtt ctgtcgatgc ctcaggtcaa catcgtcaag aaaaccgagg     3300
ttcagactgg cggattctcc aaggagtcga ttctgcccaa gcgaaactcc gacaagctca    3360
tcgctcgaaa gaaagactgg gatcccaaga aatacggtgg cttcgattct cctaccgtcg    3420
cctattccgt gcttgtcgtt gcgaaggtcg agaagggcaa gtccaaaaag ctcaagtccg    3480
tcaaggagct gctcggaatt accatcatgg agcgatcgag cttcgagaag aatcccatcg    3540
```

```
acttcttgga agccaagggt tacaaggagg tcaagaaaga cctcattatc aagctgccca   3600
agtactctct gttcgaactg gagaacggtc gaaagcgtat gctcgcctcc gctggcgagc   3660
tgcagaaggg aaacgagctt gccttgcctt cgaagtacgt caactttctc tatctggctt   3720
ctcactacga gaagctcaag ggttctcccg aggacaacga acagaagcaa ctcttcgttg   3780
agcagcacaa acattacctc gacgagatta tcgagcagat ttccgagttt tcgaagcgag   3840
tcatcctggc tgatgccaac ttggacaagg tgctctctgc ctacaacaag catcgggaca   3900
aacccattcg agaacaggcg gagaacatca ttcacctgtt tactcttacc aacctgggtg   3960
ctcctgcagc tttcaagtac ttcgatacca ctatcgaccg aaagcggtac acatccacca   4020
aggaggttct cgatgccacc ctgattcacc agtccatcac tggcctgtac gagacccgaa   4080
tcgacctgtc tcagcttggt ggcgactcca gagccgatcc caagaaaaag cgaaaggtct   4140
aagcggccgc taagcttggc tgttttggcg gatgagagaa gattttcagc ctgatacaga   4200
ttaaatcaga acgcagaagc ggtctgataa aacagaattt gcctggcggc agtagcgcgg   4260
tggtcccacc tgaccccatg ccgaactcag aagtgaaacg ccgtagcgcc gatggtagtg   4320
tggggtctcc ccatgcgaga gtagggaact gccaggcatc aaataaaacg aaaggctcag   4380
tcgaaagact gggcctttcg ttttatctgt tgtttgtcgg tgaacgctct cctgagtagg   4440
acaaatccgc cgggagcgga tttgaacgtt gcgaagcaac ggcccggagg gtggcgggca   4500
ggacgcccgc cataaactgc caggcatcaa attaagcaga aggccatcct gacggatggc   4560
cttttttgcgt ttctacaaac tcttttgttt attttttctaa atacattcaa atatgtatcc   4620
gctcatgaga caataaccct gataaatgct tcaataatat tgaaaaagga agagtatgag   4680
tattcaacat ttccgtgtcg cccttattcc cttttttgcg cattttgcc ttcctgttttt   4740
tgctcaccca gaaacgctgg tgaaagtaaa agatgctgaa gatcagttgg gtgcacgagt   4800
gggttacatc gaactggatc tcaacagcgg taagatcctt gagagttttc gccccgaaga   4860
acgttttcca atgatgagca cttttaaagt tctgctatgt ggcgcggtat tatcccgtgt   4920
tgacgccggg caagagcaac tcggtcgccg catacactat tctcagaatg acttggttga   4980
gtactcacca gtcacagaaa agcatcttac ggatggcatg acagtaagag aattatgcag   5040
tgctgccata accatgagtg ataacactgc ggccaactta cttctgacaa cgatcggagg   5100
accgaaggag ctaaccgctt ttttgcacaa catgggggat catgtaactc gccttgatcg   5160
ttgggaaccg gagctgaatg aagccatacc aaacgacgag cgtgacacca cgatgcctgt   5220
agcaatggca acaacgttgc gcaaactatt aactggcgaa ctacttactc tagcttcccg   5280
gcaacaatta atagactgga tggaggcgga taaagttgca ggaccacttc tgcgctcggc   5340
ccttccggct ggctggttta ttgctgataa atctggagcc ggtgagcgtg gtctcgcgg   5400
tatcattgca gcactggggc cagatggtaa gccctcccgt atcgtagtta tctacacgac   5460
ggggagtcag gcaactatgg atgaacgaaa tagacagatc gctgagatag gtgcctcact   5520
gattaagcat tggtaactgt cagaccaagt ttactcatat atactttaga ttgatttaaa   5580
acttcatttt taatttaaaa ggatctaggt gaagatcctt tttgataatc tcatgaccaa   5640
aatcccttaa cgtgagtttt cgttccactg agcgtcagac cccgtagaaa agatcaaagg   5700
atcttcttga tccttttttt ttctgcgcgt aatctgctgc ttgcaaacaa aaaaaccacc   5760
gctaccagcg gtggtttgtt tgccggatca agagctacca actctttttc cgaaggtaac   5820
tggcttcagc agagcgcaga taccaaatac tgtccttcta gtgtagccgt agttaggcca   5880
```

```
ccacttcaag aactctgtag caccgcctac atacctcgct ctgctaatcc tgttaccagt   5940
ggctgctgcc agtggcgata agtcgtgtct taccggggttg gactcaagac gatagttacc   6000
ggataaggcg cagcggtcgg gctgaacggg gggttcgtgc acacagccca gcttggagcg   6060
aacgacctac accgaactga gatacctaca gcgtgagcta tgagaaagcg ccacgcttcc   6120
cgaagggaga aaggcggaca ggtatccggt aagcggcagg gtcggaacag gagagcgcac   6180
gagggagctt ccaggggaa acgcctggta tctttatagt cctgtcgggt ttcgccacct   6240
ctgacttgag cgtcgatttt tgtgatgctc gtcagggggg cggagcctat ggaaaaacgc   6300
cagcaacgcg gccttttac ggttcctggc cttttgctgg ccttttgctc acatgttctt   6360
tcctgcgtta tcccctgatt ctgtggataa ccgtattacc gcctttgagt gagctgatac   6420
cgctcgccgc agccgaacga ccgagcgcag cgagtcagtg agcgaggaag cggaagagcg   6480
cctgatgcgg tattttctcc ttacgcatct gtgcggtatt tcacaccgca tatggtgcac   6540
tctcagtaca atctgctctg atgccgcata gttaagccag tatacactcc gctatcgcta   6600
cgtgactggg tcatggctgc gccccgacac ccgccaacac ccgctgacgc gccctgacgg   6660
gcttgtctgc tcccggcatc cgcttacaga caagctgtga ccgtctccgg gagctgcatg   6720
tgtcagaggt tttcaccgtc atcaccgaaa cgcgcgaggc agcagatcaa ttcgcgcgcg   6780
aaggcgaagc ggcatgcata atgtgcctgt caaatggacg aagcagggat tctgcaaacc   6840
ctatgctact ccgtcaagcc gtcaattgtc tgattcgtta ccaattatga aacttgacg   6900
gctacatcat tcacttttc ttcacaaccg gcacggaact cgctcgggct ggccccggtg   6960
catttttaa atacccgcga gaatagagt tgatcgtcaa aaccaacatt gcgaccgacg   7020
gtggcgatag gcatccgggt ggtgctcaaa agcagcttcg cctggctgat acgttggtcc   7080
tcgcgccagc ttaagacgct aatccctaac tgctggcgga aaagatgtga cagacgcgac   7140
ggcgacaagc aaacatgctg tgcgacgctg gcgatatcaa aattgctgtc tgccaggtga   7200
tcgctgatgt actgacaagc ctcgcgtacc cgattatcca tcggtggatg gagcgactcg   7260
ttaatcgctt ccatgcgccg cagtaacaat tgctcaagca gatttatcgc cagcagctcc   7320
gaatagcgcc cttccccttg cccggcgtta atgatttgcc caaacaggtc gctgaaatgc   7380
ggctggtgcg cttcatccgg gcgaaagaac cccgtattgg caaatattga cggccagtta   7440
agccattcat gccagtaggc gcgcggacga aagtaaaccc actggtgata ccattcgcga   7500
gcctccggat gacgaccgta gtgatgaatc tctcctggcg ggaacagcaa aatatcaccc   7560
ggtcggcaaa caaattctcg tccctgattt ttcaccaccc cctgaccgcg aatggtgaga   7620
ttgagaatat aacctttcat tcccagcggt cggtcgataa aaaaatcgag ataaccgttg   7680
gcctcaatcg gcgttaaacc cgccaccaga tgggcattaa acgagtatcc cggcagcagg   7740
ggatcatttt gcgcttcagc catactttc atactcccgc cattcagaga agaaaccaat   7800
tgtccatatt gcatcagaca ttgccgtcac tgcgtctttt actggctctt ctcgctaacc   7860
aaaccggtaa ccccgcttat taaaagcatt ctgtaacaaa gcgggaccaa agccatgaca   7920
aaaacgcgta acaaaagtgt ctataatcac ggcagaaaag tccacattga ttatttgcac   7980
ggcgtcacac tttgctatgc catagcattt ttatccataa gattagcgga tcctacctga   8040
cgctttttat cgcaactctc tactgtttct ccatacccgt ttttttgggct aacaggagga   8100
attaaccatg gggcatcacc accatcacca cgcgggttac ctgctgggca agattaatct   8160
taaagcctgc gccgcgtgtg ctaagaaaat tttgg                              8195
```

<210> SEQ ID NO 23
<211> LENGTH: 8186
<212> TYPE: DNA
<213> ORGANISM: artificial sequence
<220> FEATURE:
<223> OTHER INFORMATION: pRF162 plasmid

<400> SEQUENCE: 23

| | | | | | |
|---|---|---|---|---|---|
| aattcgacaa | gaaatactcc | atcggcctgg | acattggaac | caactctgtc | ggctgggctg | 60 |
| tcatcaccga | cgagtacaag | gtgccctcca | agaaattcaa | ggtcctcgga | aacaccgatc | 120 |
| gacactccat | caagaaaaac | ctcattggtg | ccctgttgtt | cgattctggc | gagactgccg | 180 |
| aagctaccag | actcaagcga | actgctcggc | gacgttacac | ccgacggaag | aaccgaatct | 240 |
| gctacctgca | ggagatcttt | tccaacgaga | tggccaaggt | ggacgattcg | ttctttcatc | 300 |
| gactggagga | atccttcctc | gtcgaggaag | acaagaaaca | cgagcgtcat | cccatctttg | 360 |
| gcaacattgt | ggacgaggtt | gcttaccacg | agaagtatcc | taccatctac | cacctgcgaa | 420 |
| agaaactcgt | cgattccacc | gacaaggcgg | atctcagact | tatctacctc | gctctggcac | 480 |
| acatgatcaa | gtttcgaggt | catttcctca | tcgagggcga | tctcaatccc | gacaacagcg | 540 |
| atgtggacaa | gctgttcatt | cagctcgttc | agacctacaa | ccagctgttc | gaggaaaacc | 600 |
| ccatcaatgc | ctccggagtc | gatgcaaagg | ccatcttgtc | tgctcgactc | tcgaagagca | 660 |
| gacgactgga | gaacctcatt | gcccaacttc | ctggcgagaa | aaagaacgga | ctgtttggca | 720 |
| acctcattgc | cctttctctt | ggtctcacac | ccaacttcaa | gtccaacttc | gatctggcgg | 780 |
| aggacgccaa | gctccagctg | tccaaggaca | cctacgacga | tgacctcgac | aacctgcttg | 840 |
| cacagattgg | cgatcagtac | gccgacctgt | ttctcgctgc | caagaacctt | tcggatgcta | 900 |
| ttctcttgtc | tgacattctg | cgagtcaaca | ccgagatcac | aaaggctccc | ctttctgcct | 960 |
| ccatgatcaa | gcgatacgac | gagcaccatc | aggatctcac | actgctcaag | gctcttgtcc | 1020 |
| gacagcaact | gcccgagaag | tacaaggaga | tcttttttcga | tcagtcgaag | aacggctacg | 1080 |
| ctggatacat | cgacggcgga | gcctctcagg | aagagttcta | caagttcatc | aagccaattc | 1140 |
| tcgagaagat | ggacggaacc | gaggaactgc | ttgtcaagct | caatcgagag | gatctgcttc | 1200 |
| ggaagcaacg | aaccttcgac | aacggcagca | ttcctcatca | gatccacctc | ggtgagctgc | 1260 |
| acgccattct | tcgacgtcag | gaagacttct | acccctttct | caaggacaac | cgagagaaga | 1320 |
| tcgagaagat | tcttaccttt | cgaatcccct | actatgttgg | tcctcttgcc | agaggaaact | 1380 |
| ctcgatttgc | ttggatgact | cgaaagtccg | aggaaaccat | cactccctgg | aacttcgagg | 1440 |
| aagtcgtgga | caagggtgcc | tctgcacagt | ccttcatcga | gcgaatgacc | aacttcgaca | 1500 |
| agaatctgcc | caacgagaag | gttcttccca | agcattcgct | gctctacgag | tactttacag | 1560 |
| tctacaacga | actcaccaaa | gtcaagtacg | ttaccgaggg | aatgcgaaag | cctgccttct | 1620 |
| tgtctggcga | acagaagaaa | gccattgtcg | atctcctgtt | caagaccaac | cgaaaggtca | 1680 |
| ctgttaagca | gctcaaggag | gactacttca | agaaaatcga | gtgtttcgac | agcgtcgaga | 1740 |
| tttccggagt | tgaggaccga | ttcaacgcct | ctttgggcac | ctatcacgat | ctgctcaaga | 1800 |
| ttatcaagga | caaggatttt | ctcgacaacg | aggaaaacga | ggacattctg | gaggacatcg | 1860 |
| tgctcactct | taccctgttc | gaagatcggg | agatgatcga | ggaacgactc | aagacatacg | 1920 |
| ctcacctgtt | cgacgacaag | gtcatgaaac | aactcaagcg | acgtagatac | accggctggg | 1980 |
| gaagactttc | gcgaaagctc | atcaacggca | tcagagacaa | gcagtccgga | aagaccattc | 2040 |
| tggactttct | caagtccgat | ggctttgcca | accgaaactt | catgcagctc | attcacgacg | 2100 |

```
attctcttac cttcaaggag gacatccaga aggcacaagt gtccggtcag ggcgacagct   2160
tgcacgaaca tattgccaac ctggctggtt cgccagccat caagaaaggc attctccaga   2220
ctgtcaaggt tgtcgacgag ctggtgaagg tcatgggacg tcacaagccc gagaacattg   2280
tgatcgagat ggccagagag aaccagacaa ctcaaaaggg tcagaaaaac tcgcgagagc   2340
ggatgaagcg aatcgaggaa ggcatcaagg agctgggatc ccagattctc aaggagcatc   2400
ccgtcgagaa cactcaactg cagaacgaga agctgtatct ctactatctg cagaatggtc   2460
gagacatgta cgtggatcag gaactggaca tcaatcgtct cagcgactac gatgtggacc   2520
acattgtccc tcaatccttt ctcaaggacg attctatcga caacaaggtc cttacacgat   2580
ccgacaagaa cagaggcaag tcggacaacg ttcccagcga agaggtggtc aaaaagatga   2640
agaactactg cgcgacagct gctcaacgcc aagctcattac ccagcgaaag ttcgacaatc   2700
ttaccaaggc cgagcgaggc ggtctgtccg agctcgacaa ggctggcttc atcaagcgtc   2760
aactcgtcga gaccagacag atcacaaagc acgtcgcaca gattctcgat tctcggatga   2820
acaccaagta cgacgagaac gacaagctca tccgagaggt caaggtgatt actctcaagt   2880
ccaaactggt ctccgatttc cgaaaggact ttcagttcta caaggtgcga gagatcaaca   2940
attaccacca tgcccacgat gcttacctca acgccgtcgt tggcactgcg ctcatcaaga   3000
aatacccaa gctcgaaagc gagttcgttt acggcgatta caaggtctac gacgttcgaa   3060
agatgattgc caagtccgaa caggagattg gcaaggctac tgccaagtac ttcttttact   3120
ccaacatcat gaacttttc aagaccgaga tcaccttggc caacggagag attcgaaaga   3180
gaccacttat cgagaccaac ggcgaaactg gagagatcgt gtgggacaag ggtcgagact   3240
tgcaaccgt gcgaaaggtt ctgtcgatgc ctcaggtcaa catcgtcaag aaaaccgagg   3300
ttcagactgg cggattctcc aaggagtcga ttctgcccaa gcgaaactcc gacaagctca   3360
tcgctcgaaa gaaagactgg gatcccaaga aatacggtgg cttcgattct cctaccgtcg   3420
cctattccgt gcttgtcgtt gcgaaggtcg agaagggcaa gtccaaaaag ctcaagtccg   3480
tcaaggagct gctcggaatt accatcatgg agcgatcgag cttcgagaag aatcccatcg   3540
acttcttgga agccaagggt tacaaggagg tcaagaaaga cctcattatc aagctgccca   3600
agtactctct gttcgaactg gagaacggtc gaaagcgtat gctcgcctcc gctggcgagc   3660
tgcagaaggg aaacgagctt gccttgcctt cgaagtacgt caactttctc tatctggctt   3720
ctcactacga gaagctcaag ggttctcccg aggacaacga acagaagcaa ctcttcgttg   3780
agcagcacaa acattacctc gacgagatta tcgagcagat ttccgagttt tcgaagcgag   3840
tcatcctggc tgatgccaac ttggacaagg tgctctctgc ctacaacaag catcgggaca   3900
aacccattcg agaacaggcg gagaacatca ttcacctgtt tactcttacc aacctgggtg   3960
ctcctgcagc tttcaagtac ttcgatacca ctatcgaccg aaagcggtac acatccacca   4020
aggaggttct cgatgccacc ctgattcacc agtccatcac tggcctgtac gagacccgaa   4080
tcgacctgtc tcagcttggt ggcgactcca gagccgatcc caagaaaaag cgaaaggtct   4140
aagcggccgc taagcttggc tgtttttggcg gatgagagaa gattttcagc ctgatacaga   4200
ttaaatcaga acgcagaagc ggtctgataa aacagaattt gcctggcggc agtagcgcgg   4260
tggtcccacc tgacccatg ccgaactcag aagtgaaacg ccgtagcgcc gatggtagtg   4320
tggggtctcc ccatgcgaga gtagggaact gccaggcatc aaataaaacg aaaggctcag   4380
tcgaaagact gggcctttcg ttttatctgt tgtttgtcgg tgaacgctct cctgagtagg   4440
acaaatccgc cgggagcgga tttgaacgtt gcgaagcaac ggcccggagg gtggcgggca   4500
```

```
ggacgcccgc cataaactgc caggcatcaa attaagcaga aggccatcct gacggatggc    4560 cttttttgcgt ttctacaaac tcttttgttt atttttctaa atacattcaa atatgtatcc    4620
gctcatgaga caataaccct gataaatgct tcaataatat tgaaaaagga agagtatgag    4680
tattcaacat ttccgtgtcg cccttattcc ctttttttgcg gcattttgcc ttcctgttttt    4740 tgctcaccca gaaacgctgg tgaaagtaaa agatgctgaa gatcagttgg gtgcacgagt    4800
gggttacatc gaactggatc tcaacagcgg taagatcctt gagagttttc gccccgaaga    4860
acgttttcca atgatgagca cttttaaagt tctgctatgt ggcgcggtat tatcccgtgt    4920
tgacgccggg caagagcaac tcggtcgccg catacactat tctcagaatg acttggttga    4980
gtactcacca gtcacagaaa agcatcttac ggatggcatg acagtaagag aattatgcag    5040
tgctgccata accatgagtg ataacactgc ggccaactta cttctgacaa cgatcggagg    5100
accgaaggag ctaaccgctt ttttgcacaa catgggggat catgtaactc gccttgatcg    5160
ttgggaaccg gagctgaatg aagccatacc aaacgacgag cgtgacacca cgatgcctgt    5220
agcaatggca acaacgttgc gcaaactatt aactggcgaa ctacttactc tagcttcccg    5280
gcaacaatta atagactgga tggaggcgga taaagttgca ggaccacttc tgcgctcggc    5340
ccttccggct ggctggttta ttgctgataa atctggagcc ggtgagcgtg gtctcgcgg    5400 tatcattgca gcactggggc cagatggtaa gccctcccgt atcgtagtta tctacacgac    5460
ggggagtcag gcaactatgg atgaacgaaa tagacagatc gctgagatag gtgcctcact    5520
gattaagcat tggtaactgt cagaccaagt ttactcatat atactttaga ttgatttaaa    5580
acttcatttt taatttaaaa ggatctaggt gaagatcctt tttgataatc tcatgaccaa    5640
aatcccttaa cgtgagtttt cgttccactg agcgtcagac cccgtagaaa agatcaaagg    5700
atcttcttga gatccttttt ttctgcgcgt aatctgctgc ttgcaaacaa aaaaaccacc    5760
gctaccagcg gtggtttgtt tgccggatca agagctacca actctttttc cgaaggtaac    5820
tggcttcagc agagcgcaga taccaaatac tgtccttcta gtgtagccgt agttaggcca    5880
ccacttcaag aactctgtag caccgcctac atacctcgct ctgctaatcc tgttaccagt    5940
ggctgctgcc agtggcgata agtcgtgtct taccgggttg gactcaagac gatagttacc    6000
ggataaggcg cagcggtcgg gctgaacggg gggttcgtgc acacagccca gcttggagcg    6060
aacgacctac accgaactga gatacctaca gcgtgagcta tgagaaagcg ccacgcttcc    6120
cgaagggaga aaggcggaca ggtatccggt aagcggcagg gtcggaacag gagagcgcac    6180
gagggagctt ccagggggaa acgcctggta tctttatagt cctgtcgggt ttcgccacct    6240
ctgacttgag cgtcgatttt tgtgatgctc gtcagggggg cggagcctat ggaaaaacgc    6300
cagcaacgcg gcctttttac ggttcctggc cttttgctgg ccttttgctc acatgttctt    6360
tcctgcgtta tcccctgatt ctgtggataa ccgtattacc gcctttgagt gagctgatac    6420
cgctcgccgc agccgaacga ccgagcgcag cgagtcagtg agcgaggaag cggaagagcg    6480
cctgatgcgg tattttctcc ttacgcatct gtgcggtatt tcacaccgca tatggtgcac    6540
tctcagtaca atctgctctg atgccgcata gttaagccag tatacactcc gctatcgcta    6600
cgtgactggg tcatggctgc gccccgacac ccgccaacac ccgctgacgc gccctgacgg    6660
gcttgtctgc tcccggcatc cgcttacaga caagctgtga ccgtctccgg gagctgcatg    6720
tgtcagaggt tttcaccgtc atcaccgaaa cgcgcgaggc agcagatcaa ttcgcgcgcg    6780
aaggcgaagc ggcatgcata atgtgcctgt caaatggacg aagcagggat tctgcaaacc    6840
```

```
ctatgctact ccgtcaagcc gtcaattgtc tgattcgtta ccaattatga caacttgacg    6900
gctacatcat tcactttttc ttcacaaccg gcacggaact cgctcgggct ggccccggtg    6960
cattttttaa atacccgcga gaaatagagt tgatcgtcaa aaccaacatt gcgaccgacg    7020
gtggcgatag gcatccgggt ggtgctcaaa agcagcttcg cctggctgat acgttggtcc    7080
tcgcgccagc ttaagacgct aatccctaac tgctggcgga aaagatgtga cagacgcgac    7140
ggcgacaagc aaacatgctg tgcgacgctg gcgatatcaa aattgctgtc tgccaggtga    7200
tcgctgatgt actgacaagc ctcgcgtacc cgattatcca tcggtggatg gagcgactcg    7260
ttaatcgctt ccatgcgccg cagtaacaat tgctcaagca gatttatcgc cagcagctcc    7320
gaatagcgcc cttccccttg cccggcgtta atgatttgcc caaacaggtc gctgaaatgc    7380
ggctggtgcg cttcatccgg gcgaaagaac cccgtattgg caaatattga cggccagtta    7440
agccattcat gccagtaggc gcgcggacga agtaaaccc actggtgata ccattcgcga    7500
gcctccggat gacgaccgta gtgatgaatc tctcctggcg ggaacagcaa atatcaccc     7560 ggtcggcaaa caaattctcg tccctgattt ttcaccaccc cctgaccgcg aatggtgaga    7620
ttgagaatat aacctttcat tcccagcggt cggtcgataa aaaaatcgag ataaccgttg    7680
gcctcaatcg gcgttaaacc cgccaccaga tgggcattaa acgagtatcc cggcagcagg    7740
ggatcatttt gcgcttcagc catactttc atactcccgc cattcagaga agaaaccaat     7800
tgtccatatt gcatcagaca ttgccgtcac tgcgtctttt actggctctt ctcgctaacc    7860
aaaccggtaa ccccgcttat taaaagcatt ctgtaacaaa gcgggaccaa agccatgaca    7920
aaaacgcgta acaaaagtgt ctataatcac ggcagaaaag tccacattga ttatttgcac    7980
ggcgtcacac tttgctatgc catagcattt ttatccataa gattagcgga tcctacctga    8040
cgctttttat cgcaactctc tactgtttct ccatacccgt ttttttgggct aacaggagga    8100 attaaccatg gggcatcacc accatcacca cttattgatt atcttgcgtc gtcgcatccg    8160
caaacaggcg cacgcacata gcaagg                                        8186

<210> SEQ ID NO 24
<211> LENGTH: 80
<212> TYPE: RNA
<213> ORGANISM: artificial sequence
<220> FEATURE:
<223> OTHER INFORMATION: Cas9 endonuclease recognition (CER) domain

<400> SEQUENCE: 24
guuuuagagc uagaaauagc aaguuaaaau aaggcuaguc cguuaucaac uugaaaaagu    60
ggcaccgagu cggugcuuuu                                                80

<210> SEQ ID NO 25
<211> LENGTH: 20
<212> TYPE: DNA
<213> ORGANISM: Yarrowia lipolytica

<400> SEQUENCE: 25
tcaaacgatt acccaccctc                                                20

<210> SEQ ID NO 26
<211> LENGTH: 43
<212> TYPE: RNA
<213> ORGANISM: artificial sequence
<220> FEATURE:
<223> OTHER INFORMATION: Hammerhead (HH) ribozyme
<220> FEATURE:
<221> NAME/KEY: misc_feature
```

```
<222> LOCATION: (1)..(6)
<223> OTHER INFORMATION: n is a, c, g, or u

<400> SEQUENCE: 26
nnnnnncuga ugaguccgug aggacgaaac gaguaagcuc guc                    43

<210> SEQ ID NO 27
<211> LENGTH: 68
<212> TYPE: RNA
<213> ORGANISM: hepatitis delta virus

<400> SEQUENCE: 27
ggccggcaug gucccagccu ccucgcuggc gccggcuggg caacaugcuu cggcauggcg   60
aaugggac                                                           68

<210> SEQ ID NO 28
<211> LENGTH: 211
<212> TYPE: DNA
<213> ORGANISM: artificial sequence
<220> FEATURE:
<223> OTHER INFORMATION: HH-sgRNA-HDV (RGR) pre-sgRNA expression
      cassette

<400> SEQUENCE: 28
gtttgactga tgagtccgtg aggacgaaac gagtaagctc gtctcaaacg attacccacc   60
ctcgttttag agctagaaat agcaagttaa ataaggcta gtccgttatc aacttgaaaa  120
agtggcaccg agtcggtgct tttggccggc atggtcccag cctcctcgct ggcgccggct  180
gggcaacatg cttcggcatg gcgaatggga c                                211

<210> SEQ ID NO 29
<211> LENGTH: 20
<212> TYPE: DNA
<213> ORGANISM: Bacteriophage T7

<400> SEQUENCE: 29
taatacgact cactataggg                                              20

<210> SEQ ID NO 30
<211> LENGTH: 2875
<212> TYPE: DNA
<213> ORGANISM: artificial sequence
<220> FEATURE:
<223> OTHER INFORMATION: pRF46 plasmid

<400> SEQUENCE: 30
agcttgtccc attcgccatg ccgaagcatg ttgcccagcc ggcgccagcg aggaggctgg   60
gaccatgccg gccaaaagca ccaccgactc ggtgccactt tttcaagttg ataacggact  120
agccttattt taacttgcta tttctagctc taaaacgagg gtgggtaatc gtttgagacg  180
agcttactcg tttcgtcctc acggactcat cagtcaaacc cctatagtga gtcgtattag  240
aattcgtaat catggtcata gctgtttcct gtgtgaaatt gttatccgct cacaattcca  300
cacaacatac gagccggaag cataaagtgt aaagcctggg gtgcctaatg agtgagctaa  360
ctcacattaa ttgcgttgcg ctcactgccc gctttccagt cgggaaacct gtcgtgccag  420
ctgcattaat gaatcggcca acgcgcgggg agaggcggtt tgcgtattgg gcgctcttcc  480
gcttcctcgc tcactgactc gctgcgctcg gtcgttcggc tgcggcgagc ggtatcagct  540
cactcaaagg cggtaatacg gttatccaca gaatcagggg ataacgcagg aaagaacatg  600
tgagcaaaag gccagcaaaa ggccaggaac cgtaaaaagg ccgcgttgct ggcgtttttc  660
```

```
cataggctcc gccccctga cgagcatcac aaaaatcgac gctcaagtca gaggtggcga    720
aacccgacag gactataaag ataccaggcg tttccccctg gaagctccct cgtgcgctct    780
cctgttccga ccctgccgct taccggatac ctgtccgcct ttctcccttc gggaagcgtg    840
gcgctttctc atagctcacg ctgtaggtat ctcagttcgg tgtaggtcgt tcgctccaag    900
ctgggctgtg tgcacgaacc ccccgttcag cccgaccgct gcgccttatc cggtaactat    960
cgtcttgagt ccaacccggt aagacacgac ttatcgccac tggcagcagc cactggtaac   1020
aggattagca gagcgaggta tgtaggcggt gctacagagt tcttgaagtg gtggcctaac   1080
tacggctaca ctagaaggac agtatttggt atctgcgctc tgctgaagcc agttaccttc   1140 ggaaaagag ttggtagctc ttgatccggc aaacaaacca ccgctggtag cggtggtttt   1200
tttgtttgca agcagcagat tacgcgcaga aaaaaaggat ctcaagaaga tcctttgatc   1260
ttttctacgg ggtctgacgc tcagtggaac gaaaactcac gttaagggat tttggtcatg   1320
agattatcaa aaaggatctt cacctagatc cttttaaatt aaaaatgaag ttttaaatca   1380
atctaaagta tatatgagta aacttggtct gacagttacc aatgcttaat cagtgaggca   1440
cctatctcag cgatctgtct atttcgttca tccatagttg cctgactccc cgtcgtgtag   1500
ataactacga tacgggaggg cttaccatct ggccccagtg ctgcaatgat accgcgagac   1560
ccacgctcac cggctccaga tttatcagca ataaaccagc cagccggaag ggccgagcgc   1620
agaagtggtc ctgcaacttt atccgcctcc atccagtcta ttaattgttg ccgggaagct   1680
agagtaagta gttcgccagt taatagtttg cgcaacgttg ttgccattgc tacaggcatc   1740
gtggtgtcac gctcgtcgtt tggtatggct tcattcagct ccggttccca acgatcaagg   1800
cgagttacat gatcccccat gttgtgcaaa aaagcggtta gctccttcgg tcctccgatc   1860
gttgtcagaa gtaagttggc cgcagtgtta tcactcatgg ttatggcagc actgcataat   1920
tctcttactg tcatgccatc cgtaagatgc ttttctgtga ctggtgagta ctcaaccaag   1980
tcattctgag aatagtgtat gcggcgaccg agttgctctt gcccggcgtc aatacgggat   2040
aataccgcgc cacatagcag aactttaaaa gtgctcatca ttggaaaacg ttcttcgggg   2100
cgaaaactct caaggatctt accgctgttg agatccagtt cgatgtaacc cactcgtgca   2160
cccaactgat cttcagcatc ttttactttc accagcgttt ctgggtgagc aaaaacagga   2220
aggcaaaatg ccgcaaaaaa gggaataagg gcgacacgga aatgttgaat actcatactc   2280
ttcctttttc aatattattg aagcatttat cagggttatt gtctcatgag cggatacata   2340
tttgaatgta tttagaaaaa taaacaaata ggggttccgc gcacatttcc ccgaaaagtg   2400
ccacctgacg tctaagaaac cattattatc atgacattaa cctataaaaa taggcgtatc   2460
acgaggccct ttcgtctcgc gcgtttcggt gatgacggtg aaaacctctg acacatgcag   2520
ctcccggaga cggtcacagc ttgtctgtaa gcggatgccg ggagcagaca agcccgtcag   2580
ggcgcgtcag cgggtgttgg cgggtgtcgg gctggctta actatgcggc atcagagcag   2640
attgtactga gagtgcacca tatgcggtgt gaaataccgc acagatgcgt aaggagaaaa   2700
taccgcatca ggcgccattc gccattcagg ctgcgcaact gttgggaagg gcgatcggtg   2760
cgggcctctt cgctattacg ccagctggcg aaagggggat gtgctgcaag gcgattaagt   2820
tgggtaacgc cagggttttc ccagtcacga cgttgtaaaa cgacggccag tgcca        2875
```

<210> SEQ ID NO 31
<211> LENGTH: 20
<212> TYPE: DNA

```
<213> ORGANISM: artificial sequence
<220> FEATURE:
<223> OTHER INFORMATION: T7 forward PCR primer

<400> SEQUENCE: 31
ccggctcgta tgttgtgtgg                                                      20

<210> SEQ ID NO 32
<211> LENGTH: 20
<212> TYPE: DNA
<213> ORGANISM: artificial sequence
<220> FEATURE:
<223> OTHER INFORMATION: gRNArev1 reverse primer

<400> SEQUENCE: 32
aaaagcaccg actcggtgcc                                                      20

<210> SEQ ID NO 33
<211> LENGTH: 21
<212> TYPE: DNA
<213> ORGANISM: artificial sequence
<220> FEATURE:
<223> OTHER INFORMATION: IV-up forward primer

<400> SEQUENCE: 33
ccacgaaacg acgtttcgac c                                                    21

<210> SEQ ID NO 34
<211> LENGTH: 20
<212> TYPE: DNA
<213> ORGANISM: artificial sequence
<220> FEATURE:
<223> OTHER INFORMATION: IV-down reverse primer

<400> SEQUENCE: 34
gcaaagactc ggttgatggc                                                      20

<210> SEQ ID NO 35
<211> LENGTH: 982
<212> TYPE: DNA
<213> ORGANISM: Yarrowia lipolytica

<400> SEQUENCE: 35
ccacgaaacg acgtttcgac cttaacgacc ctgccgtctc catccatccg accacaatgg          60
aaaagacatt ttcaaacgat tacccaccct ccgggactga ggcccacatc cacatcaacc         120
acacggccca ctcggatgac tcagaggagg tgccctcgca caggaaaaat tacaacacca         180
gtggccacga cctggaggag tccgacccgg ataaccatgt cggtgagacc ctcgaggtca         240
agcgaggtct caagatgcga cacatctcca tgatctcgct tggaggaacc attggtaccg         300
gtctcttcat tggtaccgga ggagctctcc agcaggccgg tcctgtggc gccctcgtcg          360
cctacgtgtt catggccacc attgtctact ctgttgccga gtctcttgga gaactggcta         420
cgtacattcc catcaccggc tcctttgccg tctttactac ccgatatctg tcacagtcgt         480
ttggtgcctc catgggctgg ctatactggt tctcgtgggc gatcaccttc gccatcgagc         540
tcaacaccat tggtcccgtg attgagtact ggactgacgc cgttcctact gctgcctgga         600
ttgccatctt cttcgtcatc ctcactacca tcaacttctt ccccgtgggc ttctatggcg         660
aagtcgagtt ctgggtggcc tccgtgaagg tcattgccat cattggatgg ctcatctacg         720
cgctctgcat gacgtgtgga gcaggtgtaa caggtcctgt gggattcaga tactggaacc         780
acccccggacc catgggagac ggaatctgga ccgacggcgt gcccattgtg cgaaacgcgc        840
```

```
ccggtcgacg attcatggga tggctcaatt cgctcgttaa cgccgccttc acctaccagg    900
gctgtgagct ggtcggagtc actgccggtg aggcccagaa ccccagaaag tccgtccctc    960
gagccatcaa ccgagtcttt gc                                             982
```

<210> SEQ ID NO 36
<211> LENGTH: 4
<212> TYPE: RNA
<213> ORGANISM: unknown
<220> FEATURE:
<223> OTHER INFORMATION: RNA loop-forming sequence (GAAA)

<400> SEQUENCE: 36

```
gaaa                                                                   4
```

<210> SEQ ID NO 37
<211> LENGTH: 4
<212> TYPE: RNA
<213> ORGANISM: unknown
<220> FEATURE:
<223> OTHER INFORMATION: RNA loop-forming sequence (CAAA)

<400> SEQUENCE: 37

```
caaa                                                                   4
```

<210> SEQ ID NO 38
<211> LENGTH: 4
<212> TYPE: RNA
<213> ORGANISM: unknown
<220> FEATURE:
<223> OTHER INFORMATION: RNA loop-forming sequence (AAAG)

<400> SEQUENCE: 38

```
aaag                                                                   4
```

<210> SEQ ID NO 39
<211> LENGTH: 1434
<212> TYPE: PRT
<213> ORGANISM: artificial sequence
<220> FEATURE:
<223> OTHER INFORMATION: Zebra CPP-Cas9-NLS fusion protein

<400> SEQUENCE: 39

```
Glu Cys Asp Ser Glu Leu Glu Ile Lys Arg Tyr Lys Arg Val Arg Val
1               5                   10                  15

Ala Ser Arg Lys Cys Arg Ala Lys Phe Lys Gln Leu Leu Gln His Tyr
            20                  25                  30

Arg Glu Val Ala Ala Ala Lys Ser Ser Glu Asn Asp Arg Leu Arg Leu
        35                  40                  45

Leu Leu Lys Gln Met Cys Glu Phe Asp Lys Lys Tyr Ser Ile Gly Leu
    50                  55                  60

Asp Ile Gly Thr Asn Ser Val Gly Trp Ala Val Ile Thr Asp Glu Tyr
65                  70                  75                  80

Lys Val Pro Ser Lys Lys Phe Lys Val Leu Gly Asn Thr Asp Arg His
                85                  90                  95

Ser Ile Lys Lys Asn Leu Ile Gly Ala Leu Leu Phe Asp Ser Gly Glu
            100                 105                 110

Thr Ala Glu Ala Thr Arg Leu Lys Arg Thr Ala Arg Arg Arg Tyr Thr
        115                 120                 125

Arg Arg Lys Asn Arg Ile Cys Tyr Leu Gln Glu Ile Phe Ser Asn Glu
    130                 135                 140
```

```
Met Ala Lys Val Asp Asp Ser Phe Phe His Arg Leu Glu Glu Ser Phe
145                 150                 155                 160

Leu Val Glu Glu Asp Lys Lys His Glu Arg His Pro Ile Phe Gly Asn
                165                 170                 175

Ile Val Asp Glu Val Ala Tyr His Glu Lys Tyr Pro Thr Ile Tyr His
            180                 185                 190

Leu Arg Lys Lys Leu Val Asp Ser Thr Asp Lys Ala Asp Leu Arg Leu
                195                 200                 205

Ile Tyr Leu Ala Leu Ala His Met Ile Lys Phe Arg Gly His Phe Leu
210                 215                 220

Ile Glu Gly Asp Leu Asn Pro Asp Asn Ser Asp Val Asp Lys Leu Phe
225                 230                 235                 240

Ile Gln Leu Val Gln Thr Tyr Asn Gln Leu Phe Glu Glu Asn Pro Ile
                245                 250                 255

Asn Ala Ser Gly Val Asp Ala Lys Ala Ile Leu Ser Ala Arg Leu Ser
                260                 265                 270

Lys Ser Arg Arg Leu Glu Asn Leu Ile Ala Gln Leu Pro Gly Glu Lys
        275                 280                 285

Lys Asn Gly Leu Phe Gly Asn Leu Ile Ala Leu Ser Leu Gly Leu Thr
            290                 295                 300

Pro Asn Phe Lys Ser Asn Phe Asp Leu Ala Glu Asp Ala Lys Leu Gln
305                 310                 315                 320

Leu Ser Lys Asp Thr Tyr Asp Asp Asp Leu Asp Asn Leu Leu Ala Gln
                325                 330                 335

Ile Gly Asp Gln Tyr Ala Asp Leu Phe Leu Ala Ala Lys Asn Leu Ser
            340                 345                 350

Asp Ala Ile Leu Leu Ser Asp Ile Leu Arg Val Asn Thr Glu Ile Thr
                355                 360                 365

Lys Ala Pro Leu Ser Ala Ser Met Ile Lys Arg Tyr Asp Glu His His
        370                 375                 380

Gln Asp Leu Thr Leu Leu Lys Ala Leu Val Arg Gln Gln Leu Pro Glu
385                 390                 395                 400

Lys Tyr Lys Glu Ile Phe Phe Asp Gln Ser Lys Asn Gly Tyr Ala Gly
                405                 410                 415

Tyr Ile Asp Gly Gly Ala Ser Gln Glu Glu Phe Tyr Lys Phe Ile Lys
            420                 425                 430

Pro Ile Leu Glu Lys Met Asp Gly Thr Glu Glu Leu Leu Val Lys Leu
        435                 440                 445

Asn Arg Glu Asp Leu Leu Arg Lys Gln Arg Thr Phe Asp Asn Gly Ser
        450                 455                 460

Ile Pro His Gln Ile His Leu Gly Glu Leu His Ala Ile Leu Arg Arg
465                 470                 475                 480

Gln Glu Asp Phe Tyr Pro Phe Leu Lys Asp Asn Arg Glu Lys Ile Glu
                485                 490                 495

Lys Ile Leu Thr Phe Arg Ile Pro Tyr Tyr Val Gly Pro Leu Ala Arg
            500                 505                 510

Gly Asn Ser Arg Phe Ala Trp Met Thr Arg Lys Ser Glu Glu Thr Ile
        515                 520                 525

Thr Pro Trp Asn Phe Glu Glu Val Val Asp Lys Gly Ala Ser Ala Gln
        530                 535                 540

Ser Phe Ile Glu Arg Met Thr Asn Phe Asp Lys Asn Leu Pro Asn Glu
545                 550                 555                 560
```

```
Lys Val Leu Pro Lys His Ser Leu Leu Tyr Glu Tyr Phe Thr Val Tyr
            565                 570                 575

Asn Glu Leu Thr Lys Val Lys Tyr Val Thr Glu Gly Met Arg Lys Pro
            580                 585                 590

Ala Phe Leu Ser Gly Glu Gln Lys Lys Ala Ile Val Asp Leu Leu Phe
            595                 600                 605

Lys Thr Asn Arg Lys Val Thr Val Lys Gln Leu Lys Glu Asp Tyr Phe
            610                 615                 620

Lys Lys Ile Glu Cys Phe Asp Ser Val Glu Ile Ser Gly Val Glu Asp
625                 630                 635                 640

Arg Phe Asn Ala Ser Leu Gly Thr Tyr His Asp Leu Leu Lys Ile Ile
                645                 650                 655

Lys Asp Lys Asp Phe Leu Asp Asn Glu Glu Asn Glu Asp Ile Leu Glu
                660                 665                 670

Asp Ile Val Leu Thr Leu Thr Leu Phe Glu Asp Arg Glu Met Ile Glu
                675                 680                 685

Glu Arg Leu Lys Thr Tyr Ala His Leu Phe Asp Asp Lys Val Met Lys
            690                 695                 700

Gln Leu Lys Arg Arg Arg Tyr Thr Gly Trp Gly Arg Leu Ser Arg Lys
705                 710                 715                 720

Leu Ile Asn Gly Ile Arg Asp Lys Gln Ser Gly Lys Thr Ile Leu Asp
                725                 730                 735

Phe Leu Lys Ser Asp Gly Phe Ala Asn Arg Asn Phe Met Gln Leu Ile
                740                 745                 750

His Asp Asp Ser Leu Thr Phe Lys Glu Asp Ile Gln Lys Ala Gln Val
                755                 760                 765

Ser Gly Gln Gly Asp Ser Leu His Glu His Ile Ala Asn Leu Ala Gly
            770                 775                 780

Ser Pro Ala Ile Lys Lys Gly Ile Leu Gln Thr Val Lys Val Val Asp
785                 790                 795                 800

Glu Leu Val Lys Val Met Gly Arg His Lys Pro Glu Asn Ile Val Ile
                805                 810                 815

Glu Met Ala Arg Glu Asn Gln Thr Thr Gln Lys Gly Gln Lys Asn Ser
                820                 825                 830

Arg Glu Arg Met Lys Arg Ile Glu Glu Gly Ile Lys Glu Leu Gly Ser
            835                 840                 845

Gln Ile Leu Lys Glu His Pro Val Glu Asn Thr Gln Leu Gln Asn Glu
            850                 855                 860

Lys Leu Tyr Leu Tyr Tyr Leu Gln Asn Gly Arg Asp Met Tyr Val Asp
865                 870                 875                 880

Gln Glu Leu Asp Ile Asn Arg Leu Ser Asp Tyr Asp Val Asp His Ile
                885                 890                 895

Val Pro Gln Ser Phe Leu Lys Asp Asp Ser Ile Asp Asn Lys Val Leu
            900                 905                 910

Thr Arg Ser Asp Lys Asn Arg Gly Lys Ser Asp Asn Val Pro Ser Glu
            915                 920                 925

Glu Val Val Lys Lys Met Lys Asn Tyr Trp Arg Gln Leu Leu Asn Ala
            930                 935                 940

Lys Leu Ile Thr Gln Arg Lys Phe Asp Asn Leu Thr Lys Ala Glu Arg
945                 950                 955                 960

Gly Gly Leu Ser Glu Leu Asp Lys Ala Gly Phe Ile Lys Arg Gln Leu
                965                 970                 975

Val Glu Thr Arg Gln Ile Thr Lys His Val Ala Gln Ile Leu Asp Ser
```

```
                980             985             990
Arg Met Asn Thr Lys Tyr Asp Glu Asn Asp Lys Leu Ile Arg Glu Val
                    995             1000            1005
Lys Val Ile Thr Leu Lys Ser Lys Leu Val Ser Asp Phe Arg Lys
    1010            1015            1020
Asp Phe Gln Phe Tyr Lys Val Arg Glu Ile Asn Asn Tyr His His
    1025            1030            1035
Ala His Asp Ala Tyr Leu Asn Ala Val Val Gly Thr Ala Leu Ile
    1040            1045            1050
Lys Lys Tyr Pro Lys Leu Glu Ser Glu Phe Val Tyr Gly Asp Tyr
    1055            1060            1065
Lys Val Tyr Asp Val Arg Lys Met Ile Ala Lys Ser Glu Gln Glu
    1070            1075            1080
Ile Gly Lys Ala Thr Ala Lys Tyr Phe Phe Tyr Ser Asn Ile Met
    1085            1090            1095
Asn Phe Phe Lys Thr Glu Ile Thr Leu Ala Asn Gly Glu Ile Arg
    1100            1105            1110
Lys Arg Pro Leu Ile Glu Thr Asn Gly Glu Thr Gly Glu Ile Val
    1115            1120            1125
Trp Asp Lys Gly Arg Asp Phe Ala Thr Val Arg Lys Val Leu Ser
    1130            1135            1140
Met Pro Gln Val Asn Ile Val Lys Lys Thr Glu Val Gln Thr Gly
    1145            1150            1155
Gly Phe Ser Lys Glu Ser Ile Leu Pro Lys Arg Asn Ser Asp Lys
    1160            1165            1170
Leu Ile Ala Arg Lys Lys Asp Trp Asp Pro Lys Lys Tyr Gly Gly
    1175            1180            1185
Phe Asp Ser Pro Thr Val Ala Tyr Ser Val Leu Val Val Ala Lys
    1190            1195            1200
Val Glu Lys Gly Lys Ser Lys Lys Leu Lys Ser Val Lys Glu Leu
    1205            1210            1215
Leu Gly Ile Thr Ile Met Glu Arg Ser Ser Phe Glu Lys Asn Pro
    1220            1225            1230
Ile Asp Phe Leu Glu Ala Lys Gly Tyr Lys Glu Val Lys Lys Asp
    1235            1240            1245
Leu Ile Ile Lys Leu Pro Lys Tyr Ser Leu Phe Glu Leu Glu Asn
    1250            1255            1260
Gly Arg Lys Arg Met Leu Ala Ser Ala Gly Glu Leu Gln Lys Gly
    1265            1270            1275
Asn Glu Leu Ala Leu Pro Ser Lys Tyr Val Asn Phe Leu Tyr Leu
    1280            1285            1290
Ala Ser His Tyr Glu Lys Leu Lys Gly Ser Pro Glu Asp Asn Glu
    1295            1300            1305
Gln Lys Gln Leu Phe Val Glu Gln His Lys His Tyr Leu Asp Glu
    1310            1315            1320
Ile Ile Glu Gln Ile Ser Glu Phe Ser Lys Arg Val Ile Leu Ala
    1325            1330            1335
Asp Ala Asn Leu Asp Lys Val Leu Ser Ala Tyr Asn Lys His Arg
    1340            1345            1350
Asp Lys Pro Ile Arg Glu Gln Ala Glu Asn Ile Ile His Leu Phe
    1355            1360            1365
Thr Leu Thr Asn Leu Gly Ala Pro Ala Ala Phe Lys Tyr Phe Asp
    1370            1375            1380
```

```
<210> SEQ ID NO 40
<211> LENGTH: 1397
<212> TYPE: PRT
<213> ORGANISM: artificial sequence
<220> FEATURE:
<223> OTHER INFORMATION: PolyR CPP-Cas9-NLS fusion protein

<400> SEQUENCE: 40
```

| | | | | | | | | | | | | | | |
|---|---|---|---|---|---|---|---|---|---|---|---|---|---|---|
| Thr | Thr | Ile | Asp | Arg | Lys | Arg | Tyr | Thr | Ser | Thr | Lys | Glu | Val | Leu |
| | | 1385 | | | | 1390 | | | | 1395 | | | | |
| Asp | Ala | Thr | Leu | Ile | His | Gln | Ser | Ile | Thr | Gly | Leu | Tyr | Glu | Thr |
| 1400 | | | | | 1405 | | | | | 1410 | | | | |
| Arg | Ile | Asp | Leu | Ser | Gln | Leu | Gly | Gly | Asp | Ser | Arg | Ala | Asp | Pro |
| | 1415 | | | | | 1420 | | | | | 1425 | | | |
| Lys | Lys | Lys | Arg | Lys | Val | | | | | | | | | |
| | 1430 | | | | | | | | | | | | | |

Gly Gly Gly Gly Arg Arg Arg Arg Arg Arg Arg Arg Leu Leu Leu
1                5                    10                   15

Leu Glu Phe Asp Lys Lys Tyr Ser Ile Gly Leu Asp Ile Gly Thr Asn
            20                  25                  30

Ser Val Gly Trp Ala Val Ile Thr Asp Glu Tyr Lys Val Pro Ser Lys
        35                  40                  45

Lys Phe Lys Val Leu Gly Asn Thr Asp Arg His Ser Ile Lys Lys Asn
    50                  55                  60

Leu Ile Gly Ala Leu Leu Phe Asp Ser Gly Glu Thr Ala Glu Ala Thr
65                  70                  75                  80

Arg Leu Lys Arg Thr Ala Arg Arg Tyr Thr Arg Arg Lys Asn Arg
                85                  90                  95

Ile Cys Tyr Leu Gln Glu Ile Phe Ser Asn Glu Met Ala Lys Val Asp
            100                 105                 110

Asp Ser Phe Phe His Arg Leu Glu Glu Ser Phe Leu Val Glu Glu Asp
            115                 120                 125

Lys Lys His Glu Arg His Pro Ile Phe Gly Asn Ile Val Asp Glu Val
        130                 135                 140

Ala Tyr His Glu Lys Tyr Pro Thr Ile Tyr His Leu Arg Lys Lys Leu
145                 150                 155                 160

Val Asp Ser Thr Asp Lys Ala Asp Leu Arg Leu Ile Tyr Leu Ala Leu
                165                 170                 175

Ala His Met Ile Lys Phe Arg Gly His Phe Leu Ile Glu Gly Asp Leu
            180                 185                 190

Asn Pro Asp Asn Ser Asp Val Asp Lys Leu Phe Ile Gln Leu Val Gln
        195                 200                 205

Thr Tyr Asn Gln Leu Phe Glu Glu Asn Pro Ile Asn Ala Ser Gly Val
    210                 215                 220

Asp Ala Lys Ala Ile Leu Ser Ala Arg Leu Ser Lys Ser Arg Arg Leu
225                 230                 235                 240

Glu Asn Leu Ile Ala Gln Leu Pro Gly Glu Lys Lys Asn Gly Leu Phe
                245                 250                 255

Gly Asn Leu Ile Ala Leu Ser Leu Gly Leu Thr Pro Asn Phe Lys Ser
            260                 265                 270

Asn Phe Asp Leu Ala Glu Asp Ala Lys Leu Gln Leu Ser Lys Asp Thr
        275                 280                 285

Tyr Asp Asp Asp Leu Asp Asn Leu Leu Ala Gln Ile Gly Asp Gln Tyr
    290                 295                 300

```
Ala Asp Leu Phe Leu Ala Ala Lys Asn Leu Ser Asp Ala Ile Leu Leu
305                 310                 315                 320

Ser Asp Ile Leu Arg Val Asn Thr Glu Ile Thr Lys Ala Pro Leu Ser
            325                 330                 335

Ala Ser Met Ile Lys Arg Tyr Asp Glu His His Gln Asp Leu Thr Leu
        340                 345                 350

Leu Lys Ala Leu Val Arg Gln Gln Leu Pro Glu Lys Tyr Lys Glu Ile
                355                 360                 365

Phe Phe Asp Gln Ser Lys Asn Gly Tyr Ala Gly Tyr Ile Asp Gly Gly
370                 375                 380

Ala Ser Gln Glu Glu Phe Tyr Lys Phe Ile Lys Pro Ile Leu Glu Lys
385                 390                 395                 400

Met Asp Gly Thr Glu Glu Leu Leu Val Lys Leu Asn Arg Glu Asp Leu
            405                 410                 415

Leu Arg Lys Gln Arg Thr Phe Asp Asn Gly Ser Ile Pro His Gln Ile
        420                 425                 430

His Leu Gly Glu Leu His Ala Ile Leu Arg Arg Gln Glu Asp Phe Tyr
                435                 440                 445

Pro Phe Leu Lys Asp Asn Arg Glu Lys Ile Glu Lys Ile Leu Thr Phe
450                 455                 460

Arg Ile Pro Tyr Tyr Val Gly Pro Leu Ala Arg Gly Asn Ser Arg Phe
465                 470                 475                 480

Ala Trp Met Thr Arg Lys Ser Glu Glu Thr Ile Thr Pro Trp Asn Phe
            485                 490                 495

Glu Glu Val Val Asp Lys Gly Ala Ser Ala Gln Ser Phe Ile Glu Arg
        500                 505                 510

Met Thr Asn Phe Asp Lys Asn Leu Pro Asn Glu Lys Val Leu Pro Lys
                515                 520                 525

His Ser Leu Leu Tyr Glu Tyr Phe Thr Val Tyr Asn Glu Leu Thr Lys
530                 535                 540

Val Lys Tyr Val Thr Glu Gly Met Arg Lys Pro Ala Phe Leu Ser Gly
545                 550                 555                 560

Glu Gln Lys Lys Ala Ile Val Asp Leu Leu Phe Lys Thr Asn Arg Lys
            565                 570                 575

Val Thr Val Lys Gln Leu Lys Glu Asp Tyr Phe Lys Lys Ile Glu Cys
        580                 585                 590

Phe Asp Ser Val Glu Ile Ser Gly Val Glu Asp Arg Phe Asn Ala Ser
                595                 600                 605

Leu Gly Thr Tyr His Asp Leu Leu Lys Ile Ile Lys Asp Lys Asp Phe
610                 615                 620

Leu Asp Asn Glu Glu Asn Glu Asp Ile Leu Glu Asp Ile Val Leu Thr
625                 630                 635                 640

Leu Thr Leu Phe Glu Asp Arg Glu Met Ile Glu Glu Arg Leu Lys Thr
            645                 650                 655

Tyr Ala His Leu Phe Asp Asp Lys Val Met Lys Gln Leu Lys Arg Arg
        660                 665                 670

Arg Tyr Thr Gly Trp Gly Arg Leu Ser Arg Lys Leu Ile Asn Gly Ile
                675                 680                 685

Arg Asp Lys Gln Ser Gly Lys Thr Ile Leu Asp Phe Leu Lys Ser Asp
690                 695                 700

Gly Phe Ala Asn Arg Asn Phe Met Gln Leu Ile His Asp Asp Ser Leu
705                 710                 715                 720
```

-continued

```
Thr Phe Lys Glu Asp Ile Gln Lys Ala Gln Val Ser Gly Gln Gly Asp
            725                 730                 735

Ser Leu His Glu His Ile Ala Asn Leu Ala Gly Ser Pro Ala Ile Lys
        740                 745                 750

Lys Gly Ile Leu Gln Thr Val Lys Val Val Asp Glu Leu Val Lys Val
    755                 760                 765

Met Gly Arg His Lys Pro Glu Asn Ile Val Ile Glu Met Ala Arg Glu
770                 775                 780

Asn Gln Thr Thr Gln Lys Gly Gln Lys Asn Ser Arg Glu Arg Met Lys
785                 790                 795                 800

Arg Ile Glu Glu Gly Ile Lys Glu Leu Gly Ser Gln Ile Leu Lys Glu
                805                 810                 815

His Pro Val Glu Asn Thr Gln Leu Gln Asn Glu Lys Leu Tyr Leu Tyr
            820                 825                 830

Tyr Leu Gln Asn Gly Arg Asp Met Tyr Val Asp Gln Glu Leu Asp Ile
        835                 840                 845

Asn Arg Leu Ser Asp Tyr Asp Val Asp His Ile Val Pro Gln Ser Phe
    850                 855                 860

Leu Lys Asp Asp Ser Ile Asp Asn Lys Val Leu Thr Arg Ser Asp Lys
865                 870                 875                 880

Asn Arg Gly Lys Ser Asp Asn Val Pro Ser Glu Glu Val Val Lys Lys
                885                 890                 895

Met Lys Asn Tyr Trp Arg Gln Leu Leu Asn Ala Lys Leu Ile Thr Gln
            900                 905                 910

Arg Lys Phe Asp Asn Leu Thr Lys Ala Glu Arg Gly Gly Leu Ser Glu
        915                 920                 925

Leu Asp Lys Ala Gly Phe Ile Lys Arg Gln Leu Val Glu Thr Arg Gln
    930                 935                 940

Ile Thr Lys His Val Ala Gln Ile Leu Asp Ser Arg Met Asn Thr Lys
945                 950                 955                 960

Tyr Asp Glu Asn Asp Lys Leu Ile Arg Glu Val Lys Val Ile Thr Leu
                965                 970                 975

Lys Ser Lys Leu Val Ser Asp Phe Arg Lys Asp Phe Gln Phe Tyr Lys
            980                 985                 990

Val Arg Glu Ile Asn Asn Tyr His His Ala His Asp Ala Tyr Leu Asn
        995                 1000                1005

Ala Val Val Gly Thr Ala Leu Ile Lys Lys Tyr Pro Lys Leu Glu
    1010                1015                1020

Ser Glu Phe Val Tyr Gly Asp Tyr Lys Val Tyr Asp Val Arg Lys
    1025                1030                1035

Met Ile Ala Lys Ser Glu Gln Glu Ile Gly Lys Ala Thr Ala Lys
    1040                1045                1050

Tyr Phe Phe Tyr Ser Asn Ile Met Asn Phe Phe Lys Thr Glu Ile
    1055                1060                1065

Thr Leu Ala Asn Gly Glu Ile Arg Lys Arg Pro Leu Ile Glu Thr
    1070                1075                1080

Asn Gly Glu Thr Gly Glu Ile Val Trp Asp Lys Gly Arg Asp Phe
    1085                1090                1095

Ala Thr Val Arg Lys Val Leu Ser Met Pro Gln Val Asn Ile Val
    1100                1105                1110

Lys Lys Thr Glu Val Gln Thr Gly Gly Phe Ser Lys Glu Ser Ile
    1115                1120                1125

Leu Pro Lys Arg Asn Ser Asp Lys Leu Ile Ala Arg Lys Lys Asp
```

```
                     1130                1135                1140

Trp Asp Pro Lys Lys Tyr Gly Gly Phe Asp Ser Pro Thr Val Ala
        1145                1150                1155

Tyr Ser Val Leu Val Val Ala Lys Val Glu Lys Gly Lys Ser Lys
        1160                1165                1170

Lys Leu Lys Ser Val Lys Glu Leu Leu Gly Ile Thr Ile Met Glu
        1175                1180                1185

Arg Ser Ser Phe Glu Lys Asn Pro Ile Asp Phe Leu Glu Ala Lys
        1190                1195                1200

Gly Tyr Lys Glu Val Lys Lys Asp Leu Ile Ile Lys Leu Pro Lys
        1205                1210                1215

Tyr Ser Leu Phe Glu Leu Glu Asn Gly Arg Lys Arg Met Leu Ala
        1220                1225                1230

Ser Ala Gly Glu Leu Gln Lys Gly Asn Glu Leu Ala Leu Pro Ser
        1235                1240                1245

Lys Tyr Val Asn Phe Leu Tyr Leu Ala Ser His Tyr Glu Lys Leu
        1250                1255                1260

Lys Gly Ser Pro Glu Asp Asn Glu Gln Lys Gln Leu Phe Val Glu
        1265                1270                1275

Gln His Lys His Tyr Leu Asp Glu Ile Ile Glu Gln Ile Ser Glu
        1280                1285                1290

Phe Ser Lys Arg Val Ile Leu Ala Asp Ala Asn Leu Asp Lys Val
        1295                1300                1305

Leu Ser Ala Tyr Asn Lys His Arg Asp Lys Pro Ile Arg Glu Gln
        1310                1315                1320

Ala Glu Asn Ile Ile His Leu Phe Thr Leu Thr Asn Leu Gly Ala
        1325                1330                1335

Pro Ala Ala Phe Lys Tyr Phe Asp Thr Thr Ile Asp Arg Lys Arg
        1340                1345                1350

Tyr Thr Ser Thr Lys Glu Val Leu Asp Ala Thr Leu Ile His Gln
        1355                1360                1365

Ser Ile Thr Gly Leu Tyr Glu Thr Arg Ile Asp Leu Ser Gln Leu
        1370                1375                1380

Gly Gly Asp Ser Arg Ala Asp Pro Lys Lys Arg Lys Val
        1385                1390                1395

<210> SEQ ID NO 41
<211> LENGTH: 1401
<212> TYPE: PRT
<213> ORGANISM: artificial sequence
<220> FEATURE:
<223> OTHER INFORMATION: TP10 CPP-Cas9-NLS fusion protein

<400> SEQUENCE: 41

Ala Gly Tyr Leu Leu Gly Lys Ile Asn Leu Lys Ala Cys Ala Ala Cys
1               5                  10                   15

Ala Lys Lys Ile Leu Glu Phe Asp Lys Lys Tyr Ser Ile Gly Leu Asp
                20                  25                  30

Ile Gly Thr Asn Ser Val Gly Trp Ala Val Ile Thr Asp Glu Tyr Lys
        35                  40                  45

Val Pro Ser Lys Lys Phe Lys Val Leu Gly Asn Thr Asp Arg His Ser
    50                  55                  60

Ile Lys Lys Asn Leu Ile Gly Ala Leu Leu Phe Asp Ser Gly Glu Thr
65                  70                  75                  80

Ala Glu Ala Thr Arg Leu Lys Arg Thr Ala Arg Arg Arg Tyr Thr Arg
```

```
                    85                  90                  95
Arg Lys Asn Arg Ile Cys Tyr Leu Gln Glu Ile Phe Ser Asn Glu Met
                100                 105                 110

Ala Lys Val Asp Asp Ser Phe Phe His Arg Leu Glu Glu Ser Phe Leu
                115                 120                 125

Val Glu Glu Asp Lys Lys His Glu Arg His Pro Ile Phe Gly Asn Ile
130                 135                 140

Val Asp Glu Val Ala Tyr His Glu Lys Tyr Pro Thr Ile Tyr His Leu
145                 150                 155                 160

Arg Lys Lys Leu Val Asp Ser Thr Asp Lys Ala Asp Leu Arg Leu Ile
                165                 170                 175

Tyr Leu Ala Leu Ala His Met Ile Lys Phe Arg Gly His Phe Leu Ile
                180                 185                 190

Glu Gly Asp Leu Asn Pro Asp Asn Ser Asp Val Asp Lys Leu Phe Ile
                195                 200                 205

Gln Leu Val Gln Thr Tyr Asn Gln Leu Phe Glu Glu Asn Pro Ile Asn
                210                 215                 220

Ala Ser Gly Val Asp Ala Lys Ala Ile Leu Ser Ala Arg Leu Ser Lys
225                 230                 235                 240

Ser Arg Arg Leu Glu Asn Leu Ile Ala Gln Leu Pro Gly Glu Lys Lys
                245                 250                 255

Asn Gly Leu Phe Gly Asn Leu Ile Ala Leu Ser Leu Gly Leu Thr Pro
                260                 265                 270

Asn Phe Lys Ser Asn Phe Asp Leu Ala Glu Asp Ala Lys Leu Gln Leu
                275                 280                 285

Ser Lys Asp Thr Tyr Asp Asp Asp Leu Asp Asn Leu Leu Ala Gln Ile
                290                 295                 300

Gly Asp Gln Tyr Ala Asp Leu Phe Leu Ala Ala Lys Asn Leu Ser Asp
305                 310                 315                 320

Ala Ile Leu Leu Ser Asp Ile Leu Arg Val Asn Thr Glu Ile Thr Lys
                325                 330                 335

Ala Pro Leu Ser Ala Ser Met Ile Lys Arg Tyr Asp Glu His His Gln
                340                 345                 350

Asp Leu Thr Leu Leu Lys Ala Leu Val Arg Gln Gln Leu Pro Glu Lys
                355                 360                 365

Tyr Lys Glu Ile Phe Phe Asp Gln Ser Lys Asn Gly Tyr Ala Gly Tyr
                370                 375                 380

Ile Asp Gly Gly Ala Ser Gln Glu Glu Phe Tyr Lys Phe Ile Lys Pro
385                 390                 395                 400

Ile Leu Glu Lys Met Asp Gly Thr Glu Glu Leu Leu Val Lys Leu Asn
                405                 410                 415

Arg Glu Asp Leu Leu Arg Lys Gln Arg Thr Phe Asp Asn Gly Ser Ile
                420                 425                 430

Pro His Gln Ile His Leu Gly Glu Leu His Ala Ile Leu Arg Arg Gln
                435                 440                 445

Glu Asp Phe Tyr Pro Phe Leu Lys Asp Asn Arg Glu Lys Ile Glu Lys
                450                 455                 460

Ile Leu Thr Phe Arg Ile Pro Tyr Tyr Val Gly Pro Leu Ala Arg Gly
465                 470                 475                 480

Asn Ser Arg Phe Ala Trp Met Thr Arg Lys Ser Glu Glu Thr Ile Thr
                485                 490                 495

Pro Trp Asn Phe Glu Glu Val Val Asp Lys Gly Ala Ser Ala Gln Ser
                500                 505                 510
```

```
Phe Ile Glu Arg Met Thr Asn Phe Asp Lys Asn Leu Pro Asn Glu Lys
            515                 520                 525

Val Leu Pro Lys His Ser Leu Leu Tyr Glu Tyr Phe Thr Val Tyr Asn
530                 535                 540

Glu Leu Thr Lys Val Lys Tyr Val Thr Glu Gly Met Arg Lys Pro Ala
545                 550                 555                 560

Phe Leu Ser Gly Glu Gln Lys Lys Ala Ile Val Asp Leu Leu Phe Lys
                565                 570                 575

Thr Asn Arg Lys Val Thr Val Lys Gln Leu Lys Glu Asp Tyr Phe Lys
            580                 585                 590

Lys Ile Glu Cys Phe Asp Ser Val Glu Ile Ser Gly Val Glu Asp Arg
        595                 600                 605

Phe Asn Ala Ser Leu Gly Thr Tyr His Asp Leu Leu Lys Ile Ile Lys
    610                 615                 620

Asp Lys Asp Phe Leu Asp Asn Glu Glu Asn Glu Asp Ile Leu Glu Asp
625                 630                 635                 640

Ile Val Leu Thr Leu Thr Leu Phe Glu Asp Arg Glu Met Ile Glu Glu
                645                 650                 655

Arg Leu Lys Thr Tyr Ala His Leu Phe Asp Asp Lys Val Met Lys Gln
            660                 665                 670

Leu Lys Arg Arg Arg Tyr Thr Gly Trp Gly Arg Leu Ser Arg Lys Leu
        675                 680                 685

Ile Asn Gly Ile Arg Asp Lys Gln Ser Gly Lys Thr Ile Leu Asp Phe
    690                 695                 700

Leu Lys Ser Asp Gly Phe Ala Asn Arg Asn Phe Met Gln Leu Ile His
705                 710                 715                 720

Asp Asp Ser Leu Thr Phe Lys Glu Asp Ile Gln Lys Ala Gln Val Ser
                725                 730                 735

Gly Gln Gly Asp Ser Leu His Glu His Ile Ala Asn Leu Ala Gly Ser
            740                 745                 750

Pro Ala Ile Lys Lys Gly Ile Leu Gln Thr Val Lys Val Val Asp Glu
        755                 760                 765

Leu Val Lys Val Met Gly Arg His Lys Pro Glu Asn Ile Val Ile Glu
    770                 775                 780

Met Ala Arg Glu Asn Gln Thr Thr Gln Lys Gly Gln Lys Asn Ser Arg
785                 790                 795                 800

Glu Arg Met Lys Arg Ile Glu Glu Gly Ile Lys Glu Leu Gly Ser Gln
                805                 810                 815

Ile Leu Lys Glu His Pro Val Glu Asn Thr Gln Leu Gln Asn Glu Lys
            820                 825                 830

Leu Tyr Leu Tyr Tyr Leu Gln Asn Gly Arg Asp Met Tyr Val Asp Gln
        835                 840                 845

Glu Leu Asp Ile Asn Arg Leu Ser Asp Tyr Asp Val Asp His Ile Val
    850                 855                 860

Pro Gln Ser Phe Leu Lys Asp Asp Ser Ile Asp Asn Lys Val Leu Thr
865                 870                 875                 880

Arg Ser Asp Lys Asn Arg Gly Lys Ser Asp Asn Val Pro Ser Glu Glu
                885                 890                 895

Val Val Lys Lys Met Lys Asn Tyr Trp Arg Gln Leu Leu Asn Ala Lys
            900                 905                 910

Leu Ile Thr Gln Arg Lys Phe Asp Asn Leu Thr Lys Ala Glu Arg Gly
        915                 920                 925
```

```
Gly Leu Ser Glu Leu Asp Lys Ala Gly Phe Ile Lys Arg Gln Leu Val
930                 935                 940
Glu Thr Arg Gln Ile Thr Lys His Val Ala Gln Ile Leu Asp Ser Arg
945                 950                 955                 960
Met Asn Thr Lys Tyr Asp Glu Asn Asp Lys Leu Ile Arg Glu Val Lys
                965                 970                 975
Val Ile Thr Leu Lys Ser Lys Leu Val Ser Asp Phe Arg Lys Asp Phe
                980                 985                 990
Gln Phe Tyr Lys Val Arg Glu Ile Asn Asn Tyr His His Ala His Asp
                995                 1000                1005
Ala Tyr Leu Asn Ala Val Val Gly Thr Ala Leu Ile Lys Lys Tyr
    1010                1015                1020
Pro Lys Leu Glu Ser Glu Phe Val Tyr Gly Asp Tyr Lys Val Tyr
    1025                1030                1035
Asp Val Arg Lys Met Ile Ala Lys Ser Glu Gln Glu Ile Gly Lys
    1040                1045                1050
Ala Thr Ala Lys Tyr Phe Phe Tyr Ser Asn Ile Met Asn Phe Phe
    1055                1060                1065
Lys Thr Glu Ile Thr Leu Ala Asn Gly Glu Ile Arg Lys Arg Pro
    1070                1075                1080
Leu Ile Glu Thr Asn Gly Glu Thr Gly Glu Ile Val Trp Asp Lys
    1085                1090                1095
Gly Arg Asp Phe Ala Thr Val Arg Lys Val Leu Ser Met Pro Gln
    1100                1105                1110
Val Asn Ile Val Lys Lys Thr Glu Val Gln Thr Gly Gly Phe Ser
    1115                1120                1125
Lys Glu Ser Ile Leu Pro Lys Arg Asn Ser Asp Lys Leu Ile Ala
    1130                1135                1140
Arg Lys Lys Asp Trp Asp Pro Lys Lys Tyr Gly Gly Phe Asp Ser
    1145                1150                1155
Pro Thr Val Ala Tyr Ser Val Leu Val Val Ala Lys Val Glu Lys
    1160                1165                1170
Gly Lys Ser Lys Lys Leu Lys Ser Val Lys Glu Leu Leu Gly Ile
    1175                1180                1185
Thr Ile Met Glu Arg Ser Ser Phe Glu Lys Asn Pro Ile Asp Phe
    1190                1195                1200
Leu Glu Ala Lys Gly Tyr Lys Glu Val Lys Lys Asp Leu Ile Ile
    1205                1210                1215
Lys Leu Pro Lys Tyr Ser Leu Phe Glu Leu Glu Asn Gly Arg Lys
    1220                1225                1230
Arg Met Leu Ala Ser Ala Gly Glu Leu Gln Lys Gly Asn Glu Leu
    1235                1240                1245
Ala Leu Pro Ser Lys Tyr Val Asn Phe Leu Tyr Leu Ala Ser His
    1250                1255                1260
Tyr Glu Lys Leu Lys Gly Ser Pro Glu Asp Asn Glu Gln Lys Gln
    1265                1270                1275
Leu Phe Val Glu Gln His Lys His Tyr Leu Asp Glu Ile Ile Glu
    1280                1285                1290
Gln Ile Ser Glu Phe Ser Lys Arg Val Ile Leu Ala Asp Ala Asn
    1295                1300                1305
Leu Asp Lys Val Leu Ser Ala Tyr Asn Lys His Arg Asp Lys Pro
    1310                1315                1320
Ile Arg Glu Gln Ala Glu Asn Ile Ile His Leu Phe Thr Leu Thr
```

```
            1325                1330                1335

Asn Leu Gly Ala Pro Ala Ala Phe Lys Tyr Phe Asp Thr Thr Ile
        1340                1345                1350

Asp Arg Lys Arg Tyr Thr Ser Thr Lys Glu Val Leu Asp Ala Thr
        1355                1360                1365

Leu Ile His Gln Ser Ile Thr Gly Leu Tyr Glu Thr Arg Ile Asp
        1370                1375                1380

Leu Ser Gln Leu Gly Gly Asp Ser Arg Ala Asp Pro Lys Lys Lys
        1385                1390                1395

Arg Lys Val
        1400

<210> SEQ ID NO 42
<211> LENGTH: 1398
<212> TYPE: PRT
<213> ORGANISM: artificial sequence
<220> FEATURE:
<223> OTHER INFORMATION: pVEC CPP-Cas9-NLS fusion protein

<400> SEQUENCE: 42

Leu Leu Ile Ile Leu Arg Arg Arg Ile Arg Lys Gln Ala His Ala His
1               5                   10                  15

Ser Lys Glu Phe Asp Lys Lys Tyr Ser Ile Gly Leu Asp Ile Gly Thr
                20                  25                  30

Asn Ser Val Gly Trp Ala Val Ile Thr Asp Glu Tyr Lys Val Pro Ser
            35                  40                  45

Lys Lys Phe Lys Val Leu Gly Asn Thr Asp Arg His Ser Ile Lys Lys
    50                  55                  60

Asn Leu Ile Gly Ala Leu Leu Phe Asp Ser Gly Glu Thr Ala Glu Ala
65                  70                  75                  80

Thr Arg Leu Lys Arg Thr Ala Arg Arg Arg Tyr Thr Arg Arg Lys Asn
                85                  90                  95

Arg Ile Cys Tyr Leu Gln Glu Ile Phe Ser Asn Glu Met Ala Lys Val
            100                 105                 110

Asp Asp Ser Phe Phe His Arg Leu Glu Glu Ser Phe Leu Val Glu Glu
        115                 120                 125

Asp Lys Lys His Glu Arg His Pro Ile Phe Gly Asn Ile Val Asp Glu
    130                 135                 140

Val Ala Tyr His Glu Lys Tyr Pro Thr Ile Tyr His Leu Arg Lys Lys
145                 150                 155                 160

Leu Val Asp Ser Thr Asp Lys Ala Asp Leu Arg Leu Ile Tyr Leu Ala
                165                 170                 175

Leu Ala His Met Ile Lys Phe Arg Gly His Phe Leu Ile Glu Gly Asp
            180                 185                 190

Leu Asn Pro Asp Asn Ser Asp Val Asp Lys Leu Phe Ile Gln Leu Val
        195                 200                 205

Gln Thr Tyr Asn Gln Leu Phe Glu Glu Asn Pro Ile Asn Ala Ser Gly
    210                 215                 220

Val Asp Ala Lys Ala Ile Leu Ser Ala Arg Leu Ser Lys Ser Arg Arg
225                 230                 235                 240

Leu Glu Asn Leu Ile Ala Gln Leu Pro Gly Glu Lys Lys Asn Gly Leu
                245                 250                 255

Phe Gly Asn Leu Ile Ala Leu Ser Leu Gly Leu Thr Pro Asn Phe Lys
            260                 265                 270

Ser Asn Phe Asp Leu Ala Glu Asp Ala Lys Leu Gln Leu Ser Lys Asp
```

```
            275                 280                 285
Thr Tyr Asp Asp Asp Leu Asp Asn Leu Leu Ala Gln Ile Gly Asp Gln
        290                 295                 300
Tyr Ala Asp Leu Phe Leu Ala Ala Lys Asn Leu Ser Asp Ala Ile Leu
305                 310                 315                 320
Leu Ser Asp Ile Leu Arg Val Asn Thr Glu Ile Thr Lys Ala Pro Leu
                325                 330                 335
Ser Ala Ser Met Ile Lys Arg Tyr Asp Glu His His Gln Asp Leu Thr
            340                 345                 350
Leu Leu Lys Ala Leu Val Arg Gln Gln Leu Pro Glu Lys Tyr Lys Glu
        355                 360                 365
Ile Phe Phe Asp Gln Ser Lys Asn Gly Tyr Ala Gly Tyr Ile Asp Gly
    370                 375                 380
Gly Ala Ser Gln Glu Glu Phe Tyr Lys Phe Ile Lys Pro Ile Leu Glu
385                 390                 395                 400
Lys Met Asp Gly Thr Glu Glu Leu Leu Val Lys Leu Asn Arg Glu Asp
                405                 410                 415
Leu Leu Arg Lys Gln Arg Thr Phe Asp Asn Gly Ser Ile Pro His Gln
            420                 425                 430
Ile His Leu Gly Glu Leu His Ala Ile Leu Arg Arg Gln Glu Asp Phe
        435                 440                 445
Tyr Pro Phe Leu Lys Asp Asn Arg Glu Lys Ile Glu Lys Ile Leu Thr
    450                 455                 460
Phe Arg Ile Pro Tyr Tyr Val Gly Pro Leu Ala Arg Gly Asn Ser Arg
465                 470                 475                 480
Phe Ala Trp Met Thr Arg Lys Ser Glu Glu Thr Ile Thr Pro Trp Asn
                485                 490                 495
Phe Glu Glu Val Val Asp Lys Gly Ala Ser Ala Gln Ser Phe Ile Glu
            500                 505                 510
Arg Met Thr Asn Phe Asp Lys Asn Leu Pro Asn Glu Lys Val Leu Pro
        515                 520                 525
Lys His Ser Leu Leu Tyr Glu Tyr Phe Thr Val Tyr Asn Glu Leu Thr
    530                 535                 540
Lys Val Lys Tyr Val Thr Glu Gly Met Arg Lys Pro Ala Phe Leu Ser
545                 550                 555                 560
Gly Glu Gln Lys Lys Ala Ile Val Asp Leu Leu Phe Lys Thr Asn Arg
                565                 570                 575
Lys Val Thr Val Lys Gln Leu Lys Glu Asp Tyr Phe Lys Lys Ile Glu
            580                 585                 590
Cys Phe Asp Ser Val Glu Ile Ser Gly Val Glu Asp Arg Phe Asn Ala
        595                 600                 605
Ser Leu Gly Thr Tyr His Asp Leu Leu Lys Ile Ile Lys Asp Lys Asp
    610                 615                 620
Phe Leu Asp Asn Glu Glu Asn Glu Asp Ile Leu Glu Asp Ile Val Leu
625                 630                 635                 640
Thr Leu Thr Leu Phe Glu Asp Arg Glu Met Ile Glu Glu Arg Leu Lys
                645                 650                 655
Thr Tyr Ala His Leu Phe Asp Asp Lys Val Met Lys Gln Leu Lys Arg
            660                 665                 670
Arg Arg Tyr Thr Gly Trp Gly Arg Leu Ser Arg Lys Leu Ile Asn Gly
        675                 680                 685
Ile Arg Asp Lys Gln Ser Gly Lys Thr Ile Leu Asp Phe Leu Lys Ser
    690                 695                 700
```

```
Asp Gly Phe Ala Asn Arg Asn Phe Met Gln Leu Ile His Asp Asp Ser
705                 710                 715                 720

Leu Thr Phe Lys Glu Asp Ile Gln Lys Ala Gln Val Ser Gly Gln Gly
            725                 730                 735

Asp Ser Leu His Glu His Ile Ala Asn Leu Ala Gly Ser Pro Ala Ile
            740                 745                 750

Lys Lys Gly Ile Leu Gln Thr Val Lys Val Asp Glu Leu Val Lys
            755                 760                 765

Val Met Gly Arg His Lys Pro Glu Asn Ile Val Ile Glu Met Ala Arg
770                 775                 780

Glu Asn Gln Thr Thr Gln Lys Gly Gln Lys Asn Ser Arg Glu Arg Met
785                 790                 795                 800

Lys Arg Ile Glu Glu Gly Ile Lys Glu Leu Gly Ser Gln Ile Leu Lys
            805                 810                 815

Glu His Pro Val Glu Asn Thr Gln Leu Gln Asn Glu Lys Leu Tyr Leu
            820                 825                 830

Tyr Tyr Leu Gln Asn Gly Arg Asp Met Tyr Val Asp Gln Glu Leu Asp
            835                 840                 845

Ile Asn Arg Leu Ser Asp Tyr Asp Val Asp His Ile Val Pro Gln Ser
850                 855                 860

Phe Leu Lys Asp Asp Ser Ile Asp Asn Lys Val Leu Thr Arg Ser Asp
865                 870                 875                 880

Lys Asn Arg Gly Lys Ser Asp Asn Val Pro Ser Glu Glu Val Val Lys
            885                 890                 895

Lys Met Lys Asn Tyr Trp Arg Gln Leu Leu Asn Ala Lys Leu Ile Thr
            900                 905                 910

Gln Arg Lys Phe Asp Asn Leu Thr Lys Ala Glu Arg Gly Gly Leu Ser
            915                 920                 925

Glu Leu Asp Lys Ala Gly Phe Ile Lys Arg Gln Leu Val Glu Thr Arg
930                 935                 940

Gln Ile Thr Lys His Val Ala Gln Ile Leu Asp Ser Arg Met Asn Thr
945                 950                 955                 960

Lys Tyr Asp Glu Asn Asp Lys Leu Ile Arg Glu Val Lys Val Ile Thr
            965                 970                 975

Leu Lys Ser Lys Leu Val Ser Asp Phe Arg Lys Asp Phe Gln Phe Tyr
            980                 985                 990

Lys Val Arg Glu Ile Asn Asn Tyr His His Ala His Asp Ala Tyr Leu
            995                 1000                1005

Asn Ala Val Val Gly Thr Ala Leu Ile Lys Lys Tyr Pro Lys Leu
    1010                1015                1020

Glu Ser Glu Phe Val Tyr Gly Asp Tyr Lys Val Tyr Asp Val Arg
    1025                1030                1035

Lys Met Ile Ala Lys Ser Glu Gln Glu Ile Gly Lys Ala Thr Ala
    1040                1045                1050

Lys Tyr Phe Phe Tyr Ser Asn Ile Met Asn Phe Phe Lys Thr Glu
    1055                1060                1065

Ile Thr Leu Ala Asn Gly Glu Ile Arg Lys Arg Pro Leu Ile Glu
    1070                1075                1080

Thr Asn Gly Glu Thr Gly Glu Ile Val Trp Asp Lys Gly Arg Asp
    1085                1090                1095

Phe Ala Thr Val Arg Lys Val Leu Ser Met Pro Gln Val Asn Ile
    1100                1105                1110
```

-continued

```
Val Lys Lys Thr Glu Val Gln Thr Gly Gly Phe Ser Lys Glu Ser
1115                1120                1125

Ile Leu Pro Lys Arg Asn Ser Asp Lys Leu Ile Ala Arg Lys Lys
    1130                1135                1140

Asp Trp Asp Pro Lys Lys Tyr Gly Gly Phe Asp Ser Pro Thr Val
    1145                1150                1155

Ala Tyr Ser Val Leu Val Val Ala Lys Val Glu Lys Gly Lys Ser
    1160                1165                1170

Lys Lys Leu Lys Ser Val Lys Glu Leu Leu Gly Ile Thr Ile Met
    1175                1180                1185

Glu Arg Ser Ser Phe Glu Lys Asn Pro Ile Asp Phe Leu Glu Ala
    1190                1195                1200

Lys Gly Tyr Lys Glu Val Lys Lys Asp Leu Ile Ile Lys Leu Pro
    1205                1210                1215

Lys Tyr Ser Leu Phe Glu Leu Glu Asn Gly Arg Lys Arg Met Leu
    1220                1225                1230

Ala Ser Ala Gly Glu Leu Gln Lys Gly Asn Glu Leu Ala Leu Pro
    1235                1240                1245

Ser Lys Tyr Val Asn Phe Leu Tyr Leu Ala Ser His Tyr Glu Lys
    1250                1255                1260

Leu Lys Gly Ser Pro Glu Asp Asn Glu Gln Lys Gln Leu Phe Val
    1265                1270                1275

Glu Gln His Lys His Tyr Leu Asp Glu Ile Ile Glu Gln Ile Ser
    1280                1285                1290

Glu Phe Ser Lys Arg Val Ile Leu Ala Asp Ala Asn Leu Asp Lys
    1295                1300                1305

Val Leu Ser Ala Tyr Asn Lys His Arg Asp Lys Pro Ile Arg Glu
    1310                1315                1320

Gln Ala Glu Asn Ile Ile His Leu Phe Thr Leu Thr Asn Leu Gly
    1325                1330                1335

Ala Pro Ala Ala Phe Lys Tyr Phe Asp Thr Thr Ile Asp Arg Lys
    1340                1345                1350

Arg Tyr Thr Ser Thr Lys Glu Val Leu Asp Ala Thr Leu Ile His
    1355                1360                1365

Gln Ser Ile Thr Gly Leu Tyr Glu Thr Arg Ile Asp Leu Ser Gln
    1370                1375                1380

Leu Gly Gly Asp Ser Arg Ala Asp Pro Lys Lys Lys Arg Lys Val
    1385                1390                1395

<210> SEQ ID NO 43
<211> LENGTH: 23
<212> TYPE: DNA
<213> ORGANISM: unknown
<220> FEATURE:
<223> OTHER INFORMATION: Example of a Cas9 target site:PAM sequence
<220> FEATURE:
<221> NAME/KEY: misc_feature
<222> LOCATION: (1)..(20)
<223> OTHER INFORMATION: n = A, C, T, or G
<220> FEATURE:
<221> NAME/KEY: misc_feature
<222> LOCATION: (21)..(21)
<223> OTHER INFORMATION: n = A, C, T, or G (indicated as an "X" in
      Specification)

<400> SEQUENCE: 43
nnnnnnnnnn nnnnnnnnnn ngg                                              23
```

```
<210> SEQ ID NO 44
<211> LENGTH: 3
<212> TYPE: DNA
<213> ORGANISM: unknown
<220> FEATURE:
<223> OTHER INFORMATION: PAM sequence NGG
<220> FEATURE:
<221> NAME/KEY: misc_feature
<222> LOCATION: (1)..(1)
<223> OTHER INFORMATION: n = A, C, T, or G

<400> SEQUENCE: 44 ngg                                                                       3

<210> SEQ ID NO 45
<211> LENGTH: 6
<212> TYPE: DNA
<213> ORGANISM: unknown
<220> FEATURE:
<223> OTHER INFORMATION: PAM sequence NNAGAA
<220> FEATURE:
<221> NAME/KEY: misc_feature
<222> LOCATION: (1)..(2)
<223> OTHER INFORMATION: n = A, C, T, or G

<400> SEQUENCE: 45 nnagaa                                                                    6

<210> SEQ ID NO 46
<211> LENGTH: 7
<212> TYPE: DNA
<213> ORGANISM: unknown
<220> FEATURE:
<223> OTHER INFORMATION: PAM sequence NNAGAAW
<220> FEATURE:
<221> NAME/KEY: misc_feature
<222> LOCATION: (1)..(2)
<223> OTHER INFORMATION: n = A, C, T, or G
<220> FEATURE:
<221> NAME/KEY: misc_feature
<222> LOCATION: (7)..(7)
<223> OTHER INFORMATION: w = A or T

<400> SEQUENCE: 46 nnagaaw                                                                   7

<210> SEQ ID NO 47
<211> LENGTH: 5
<212> TYPE: DNA
<213> ORGANISM: unknown
<220> FEATURE:
<223> OTHER INFORMATION: PAM sequence NGGNG
<220> FEATURE:
<221> NAME/KEY: misc_feature
<222> LOCATION: (1)..(1)
<223> OTHER INFORMATION: n = A, C, T, or G
<220> FEATURE:
<221> NAME/KEY: misc_feature
<222> LOCATION: (4)..(4)
<223> OTHER INFORMATION: n = A, C, T, or G

<400> SEQUENCE: 47 nggng                                                                     5

<210> SEQ ID NO 48
<211> LENGTH: 8
<212> TYPE: DNA
<213> ORGANISM: unknown
<220> FEATURE:
<223> OTHER INFORMATION: PAM sequence NNNNGATT
<220> FEATURE:
```

-continued

```
<221> NAME/KEY: misc_feature
<222> LOCATION: (1)..(4)
<223> OTHER INFORMATION: n = A, C, T, or G

<400> SEQUENCE: 48 nnnngatt                                                                  8

<210> SEQ ID NO 49
<211> LENGTH: 6
<212> TYPE: DNA
<213> ORGANISM: unknown
<220> FEATURE:
<223> OTHER INFORMATION: PAM sequence NAAAAC
<220> FEATURE:
<221> NAME/KEY: misc_feature
<222> LOCATION: (1)..(1)
<223> OTHER INFORMATION: n = A, C, T, or G

<400> SEQUENCE: 49 naaaac                                                                    6

<210> SEQ ID NO 50
<211> LENGTH: 2
<212> TYPE: DNA
<213> ORGANISM: unknown
<220> FEATURE:
<223> OTHER INFORMATION: PAM sequence NG
<220> FEATURE:
<221> NAME/KEY: misc_feature
<222> LOCATION: (1)..(1)
<223> OTHER INFORMATION: n = A, C, T, or G

<400> SEQUENCE: 50 ng                                                                        2

<210> SEQ ID NO 51
<211> LENGTH: 22
<212> TYPE: RNA
<213> ORGANISM: unknown
<220> FEATURE:
<223> OTHER INFORMATION: TracrRNA mate sequence example 1

<400> SEQUENCE: 51
guuuuuguac ucucaagauu ua                                                 22

<210> SEQ ID NO 52
<211> LENGTH: 15
<212> TYPE: RNA
<213> ORGANISM: unknown
<220> FEATURE:
<223> OTHER INFORMATION: TracrRNA mate sequence example 2

<400> SEQUENCE: 52
guuuuuguac ucuca                                                         15

<210> SEQ ID NO 53
<211> LENGTH: 12
<212> TYPE: RNA
<213> ORGANISM: unknown
<220> FEATURE:
<223> OTHER INFORMATION: TracrRNA mate sequence example 3

<400> SEQUENCE: 53
guuuuagagc ua                                                            12

<210> SEQ ID NO 54
<211> LENGTH: 13
```

```
<212> TYPE: RNA
<213> ORGANISM: unknown
<220> FEATURE:
<223> OTHER INFORMATION: TracrRNA mate sequence example 4

<400> SEQUENCE: 54
guuuuagagc uag                                                          13

<210> SEQ ID NO 55
<211> LENGTH: 60
<212> TYPE: RNA
<213> ORGANISM: Streptococcus pyogenes

<400> SEQUENCE: 55
uagcaaguua aaauaaggcu aguccguuau caacuugaaa aaguggcacc gagucggugc        60

<210> SEQ ID NO 56
<211> LENGTH: 45
<212> TYPE: RNA
<213> ORGANISM: Streptococcus pyogenes

<400> SEQUENCE: 56
uagcaaguua aaauaaggcu aguccguuau caacuugaaa aagug                       45

<210> SEQ ID NO 57
<211> LENGTH: 32
<212> TYPE: RNA
<213> ORGANISM: Streptococcus pyogenes

<400> SEQUENCE: 57
uagcaaguua aaauaaggcu aguccguuau ca                                     32

<210> SEQ ID NO 58
<211> LENGTH: 85
<212> TYPE: RNA
<213> ORGANISM: Streptococcus thermophilus

<400> SEQUENCE: 58
uaaaucuugc agaagcuaca aagauaaggc uucaugccga aaucaacacc cugucauuuu        60
auggcagggu guuucguua uuuaa                                              85

<210> SEQ ID NO 59
<211> LENGTH: 77
<212> TYPE: RNA
<213> ORGANISM: Streptococcus thermophilus

<400> SEQUENCE: 59
ugcagaagcu acaaagauaa ggcuucaugc cgaaaucaac acccugucau uuuauggcag        60 gguguuucg uuauuua                                                       77

<210> SEQ ID NO 60
<211> LENGTH: 65
<212> TYPE: RNA
<213> ORGANISM: Streptococcus thermophilus

<400> SEQUENCE: 60
ugcagaagcu acaaagauaa ggcuucaugc cgaaaucaac acccugucau uuuauggcag        60
ggugu                                                                   65

<210> SEQ ID NO 61
<211> LENGTH: 131
<212> TYPE: RNA
```

```
<213> ORGANISM: artificial sequence
<220> FEATURE:
<223> OTHER INFORMATION: gRNA example 1
<220> FEATURE:
<221> NAME/KEY: misc_feature
<222> LOCATION: (1)..(20)
<223> OTHER INFORMATION: n = A, C, U, or G

<400> SEQUENCE: 61
nnnnnnnnnn nnnnnnnnnn guuuuguac ucucaagauu uagaaauaaa ucuugcagaa      60
gcuacaaaga uaaggcuuca ugccgaaauc aacacccugu cauuuuaugg cagggguguuu   120 ucguuauuua a                                                         131

<210> SEQ ID NO 62
<211> LENGTH: 117
<212> TYPE: RNA
<213> ORGANISM: artificial sequence
<220> FEATURE:
<223> OTHER INFORMATION: gRNA example 2
<220> FEATURE:
<221> NAME/KEY: misc_feature
<222> LOCATION: (1)..(20)
<223> OTHER INFORMATION: n = A, C, U, or G

<400> SEQUENCE: 62
nnnnnnnnnn nnnnnnnnnn guuuuguac ucucagaaau gcagaagcua caaagauaag     60
gcuucaugcc gaaaucaaca cccugucauu uuauggcagg guguuucgu uauuaa         117

<210> SEQ ID NO 63
<211> LENGTH: 104
<212> TYPE: RNA
<213> ORGANISM: artificial sequence
<220> FEATURE:
<223> OTHER INFORMATION: gRNA example 3
<220> FEATURE:
<221> NAME/KEY: misc_feature
<222> LOCATION: (1)..(20)
<223> OTHER INFORMATION: n = A, C, U, or G

<400> SEQUENCE: 63
nnnnnnnnnn nnnnnnnnnn guuuuguac ucucagaaau gcagaagcua caaagauaag     60
gcuucaugcc gaaaucaaca cccugucauu uuauggcagg gugu                     104

<210> SEQ ID NO 64
<211> LENGTH: 99
<212> TYPE: RNA
<213> ORGANISM: artificial sequence
<220> FEATURE:
<223> OTHER INFORMATION: gRNA example 4
<220> FEATURE:
<221> NAME/KEY: misc_feature
<222> LOCATION: (1)..(20)
<223> OTHER INFORMATION: n = A, C, U, or G

<400> SEQUENCE: 64
nnnnnnnnnn nnnnnnnnnn guuuuguac ucucagaaau agcaaguuaa aauaaggcua     60
guccguuauc aacuugaaaa aguggcaccg agucggugc                           99

<210> SEQ ID NO 65
<211> LENGTH: 81
<212> TYPE: RNA
<213> ORGANISM: artificial sequence
<220> FEATURE:
<223> OTHER INFORMATION: gRNA example 5
<220> FEATURE:
<221> NAME/KEY: misc_feature
```

```
<222> LOCATION: (1)..(20)
<223> OTHER INFORMATION: n = A, C, U, or G

<400> SEQUENCE: 65
nnnnnnnnnn nnnnnnnnnn guuuuagagc uagaaauagc aaguuaaaau aaggcuaguc    60
cguuaucaac uugaaaaagu g                                              81

<210> SEQ ID NO 66
<211> LENGTH: 68
<212> TYPE: RNA
<213> ORGANISM: artificial sequence
<220> FEATURE:
<223> OTHER INFORMATION: gRNA example 6
<220> FEATURE:
<221> NAME/KEY: misc_feature
<222> LOCATION: (1)..(20)
<223> OTHER INFORMATION: n = A, C, U, or G

<400> SEQUENCE: 66
nnnnnnnnnn nnnnnnnnnn guuuuagagc uagaaauagc aaguuaaaau aaggcuaguc    60
cguuauca                                                             68

<210> SEQ ID NO 67
<211> LENGTH: 100
<212> TYPE: RNA
<213> ORGANISM: artificial sequence
<220> FEATURE:
<223> OTHER INFORMATION: gRNA example 7
<220> FEATURE:
<221> NAME/KEY: misc_feature
<222> LOCATION: (1)..(20)
<223> OTHER INFORMATION: n = A, C, U, or G

<400> SEQUENCE: 67
nnnnnnnnnn nnnnnnnnnn guuuuagagc uagaaauagc aaguuaaaau aaggcuaguc    60
cguuaucaac uugaaaaagu ggcaccgagu cggugcuuuu                         100

<210> SEQ ID NO 68
<211> LENGTH: 10
<212> TYPE: PRT
<213> ORGANISM: Human immunodeficiency virus

<400> SEQUENCE: 68

Gly Arg Lys Lys Arg Arg Gln Arg Arg Arg
1               5                   10

<210> SEQ ID NO 69
<211> LENGTH: 9
<212> TYPE: PRT
<213> ORGANISM: Human immunodeficiency virus

<400> SEQUENCE: 69

Arg Lys Lys Arg Arg Gln Arg Arg Arg
1               5

<210> SEQ ID NO 70
<211> LENGTH: 8
<212> TYPE: PRT
<213> ORGANISM: Human immunodeficiency virus

<400> SEQUENCE: 70

Arg Lys Lys Arg Arg Gln Arg Arg
1               5
```

```
<210> SEQ ID NO 71
<211> LENGTH: 16
<212> TYPE: PRT
<213> ORGANISM: Drosophila melanogaster

<400> SEQUENCE: 71

Arg Gln Ile Lys Ile Trp Phe Gln Asn Arg Arg Met Lys Trp Lys Lys
1               5                   10                  15

<210> SEQ ID NO 72
<211> LENGTH: 11
<212> TYPE: PRT
<213> ORGANISM: artificial sequence
<220> FEATURE:
<223> OTHER INFORMATION: polyarginine CPP example 2

<400> SEQUENCE: 72

Thr His Arg Leu Pro Arg Arg Arg Arg Arg Arg
1               5                   10

<210> SEQ ID NO 73
<211> LENGTH: 11
<212> TYPE: PRT
<213> ORGANISM: artificial sequence
<220> FEATURE:
<223> OTHER INFORMATION: polyarginine CPP example 3

<400> SEQUENCE: 73

Gly Gly Arg Arg Ala Arg Arg Arg Arg Arg Arg
1               5                   10

<210> SEQ ID NO 74
<211> LENGTH: 17
<212> TYPE: PRT
<213> ORGANISM: mus musculus

<400> SEQUENCE: 74

Leu Ile Ile Leu Arg Arg Arg Ile Arg Lys Gln Ala His Ala His Ser
1               5                   10                  15

Lys

<210> SEQ ID NO 75
<211> LENGTH: 10
<212> TYPE: PRT
<213> ORGANISM: artificial sequence
<220> FEATURE:
<223> OTHER INFORMATION: (KFF)3K CPP

<400> SEQUENCE: 75

Lys Phe Phe Lys Phe Phe Lys Phe Phe Lys
1               5                   10

<210> SEQ ID NO 76
<211> LENGTH: 18
<212> TYPE: PRT
<213> ORGANISM: artificial sequence
<220> FEATURE:
<223> OTHER INFORMATION: MAP peptide CPP

<400> SEQUENCE: 76

Lys Leu Ala Leu Lys Leu Ala Leu Lys Ala Leu Lys Ala Ala Leu Lys
1               5                   10                  15

Leu Ala

<210> SEQ ID NO 77
```

```
<211> LENGTH: 12
<212> TYPE: PRT
<213> ORGANISM: artificial sequence
<220> FEATURE:
<223> OTHER INFORMATION: CPP (RRQRRTSKLMKR)

<400> SEQUENCE: 77

Arg Arg Gln Arg Arg Thr Ser Lys Leu Met Lys Arg
1               5                   10

<210> SEQ ID NO 78
<211> LENGTH: 33
<212> TYPE: PRT
<213> ORGANISM: artificial sequence
<220> FEATURE:
<223> OTHER INFORMATION: CPP (KALAWEAKLAKALAKALAKHLAKALAKALKCEA)

<400> SEQUENCE: 78

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
                20                  25                  30

Ala

<210> SEQ ID NO 79
<211> LENGTH: 6
<212> TYPE: PRT
<213> ORGANISM: artificial sequence
<220> FEATURE:
<223> OTHER INFORMATION: Proline-rich CPP repeat example 1

<400> SEQUENCE: 79

Val His Leu Pro Pro Pro
1               5

<210> SEQ ID NO 80
<211> LENGTH: 6
<212> TYPE: PRT
<213> ORGANISM: artificial sequence
<220> FEATURE:
<223> OTHER INFORMATION: Proline-rich CPP repeat example 2

<400> SEQUENCE: 80

Val His Arg Pro Pro Pro
1               5

<210> SEQ ID NO 81
<211> LENGTH: 27
<212> TYPE: PRT
<213> ORGANISM: artificial sequence
<220> FEATURE:
<223> OTHER INFORMATION: MPG peptide CPP

<400> SEQUENCE: 81

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
                20                  25

<210> SEQ ID NO 82
<211> LENGTH: 21
<212> TYPE: PRT
<213> ORGANISM: artificial sequence
<220> FEATURE:
<223> OTHER INFORMATION: Pep-1 peptide CPP
```

<400> SEQUENCE: 82

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 83
<211> LENGTH: 24
<212> TYPE: PRT
<213> ORGANISM: Homo sapiens

<400> SEQUENCE: 83

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 84
<211> LENGTH: 18
<212> TYPE: PRT
<213> ORGANISM: Homo sapiens

<400> SEQUENCE: 84

Cys Gly Asn Leu Ser Thr Cys Met Leu Gly Thr Tyr Thr Gln Asp Phe
1               5                   10                  15

Asn Lys

<210> SEQ ID NO 85
<211> LENGTH: 240
<212> TYPE: PRT
<213> ORGANISM: Artificial sequence
<220> FEATURE:
<223> OTHER INFORMATION: his tagged dsRED

<400> SEQUENCE: 85

Met Gly Ser Ser His His His His His His Glu Phe Gly Gly Gly Gly
1               5                   10                  15

Ala Ser Ser Glu Asp Val Ile Lys Glu Phe Met Arg Phe Lys Val Arg
            20                  25                  30

Met Glu Gly Ser Val Asn Gly His Glu Phe Glu Ile Glu Gly Glu Gly
        35                  40                  45

Glu Gly Arg Pro Tyr Glu Gly Thr Gln Thr Ala Lys Leu Lys Val Thr
    50                  55                  60

Lys Gly Gly Pro Leu Pro Phe Ala Trp Asp Ile Leu Ser Pro Gln Phe
65                  70                  75                  80

Gln Tyr Gly Ser Lys Val Tyr Val Lys His Pro Ala Asp Ile Pro Asp
                85                  90                  95

Tyr Lys Lys Leu Ser Phe Pro Glu Gly Phe Lys Trp Glu Arg Val Met
            100                 105                 110

Asn Phe Glu Asp Gly Gly Val Val Thr Val Thr Gln Asp Ser Ser Leu
        115                 120                 125

Gln Asp Gly Ser Phe Ile Tyr Lys Val Lys Phe Ile Gly Val Asn Phe
    130                 135                 140

Pro Ser Asp Gly Pro Val Met Gln Lys Lys Thr Met Gly Trp Glu Ala
145                 150                 155                 160

Ser Thr Glu Arg Leu Tyr Pro Arg Asp Gly Val Leu Lys Gly Glu Ile
                165                 170                 175

His Lys Ala Leu Lys Leu Lys Asp Gly Gly His Tyr Leu Val Glu Phe

```
                180              185                190
Lys Ser Ile Tyr Met Ala Lys Lys Pro Val Gln Leu Pro Gly Tyr Tyr
                    195                  200                205

Tyr Val Asp Ser Lys Leu Asp Ile Thr Ser His Asn Glu Asp Tyr Thr
        210                  215                  220

Ile Val Glu Gln Tyr Glu Arg Ala Glu Gly Arg His His Leu Phe Leu
225                  230                  235                240

<210> SEQ ID NO 86
<211> LENGTH: 731
<212> TYPE: DNA
<213> ORGANISM: Artificial sequence
<220> FEATURE:
<223> OTHER INFORMATION: E. coli codon optimized dsRED

<400> SEQUENCE: 86
ccatgggctc cagccatcat catcaccatc atgaattcgg aggtggcggt gcatcctcgg    60
aggatgtgat taaagaattt atgcggttta agtacgtat ggaaggatcg gtgaatggcc   120
atgaatttga gattgagggt gaaggcgaag ccgcccgta cgaaggaact caaacagcga   180
aattaaaagt tacaaaagga ggtcctctgc cgtttgcctg gacatcttg agcccgcaat   240 tccagtacgg ttccaaagtg tatgtaaaac accctgcgga tattccggat tataaaaaac   300
tgagttttcc cgagggttt aaatgggaac gggtgatgaa ttttgaggat ggtgagttg    360 tcaccgtgac ccaggactct agcttacaag acggtagttt catctacaaa gtaaaattta   420
tcggcgtaaa cttcccatcg gacggccccg tcatgcagaa aaagacgatg gctgggaag    480 ccagcaccga acgtttgtac ccacgggacg gcgttttgaa aggggaaatc cataaggccc   540
ttaaactgaa agacggtggt cactatctcg tggagtttaa atcgattat atggctaaaa    600 aaccagtaca gcttccgggt tattattacg ttgactccaa attggacatc acatcgcata   660
atgaagatta cacgattgtt gaacagtacg agcgcgccga gggccggcac catctgttc    720 tgtaaaagct t                                                      731

<210> SEQ ID NO 87
<211> LENGTH: 4092
<212> TYPE: DNA
<213> ORGANISM: Artificial sequence
<220> FEATURE:
<223> OTHER INFORMATION: pBAD/HisB

<400> SEQUENCE: 87
aagaaaccaa ttgtccatat tgcatcagac attgccgtca ctgcgtcttt tactggctct    60
tctcgctaac caaaccggta accccgctta ttaaaagcat tctgtaacaa agcgggacca   120
aagccatgac aaaaacgcgt aacaaaagtg tctataatca cggcagaaaa gtccacattg   180
attatttgca cggcgtcaca ctttgctatg ccatagcatt tttatccata agattagcgg   240
atcctacctg acgcttttta tcgcaactct ctactgtttc tccatacccg ttttttgggc   300
taacaggagg aattaaccat ggggggttct catcatcatc atcatcatgg tatggctagc   360
atgactggtg gacagcaaat gggtcgggat ctgtacgacg atgacgataa ggatccgagc   420
tcgagatctg cagctggtac catatgggaa ttcgaagctt ggctgttttg gcggatgaga   480
gaagattttc agcctgatac agattaaatc agaacgcaga gcggtctga taaaacagaa   540 tttgcctggc ggcagtagcg cggtggtccc acctgacccc atgccgaact cagaagtgaa   600
acgccgtagc gccgatggta gtgtggggtc tccccatgcg agagtaggga actgccaggc   660
```

```
atcaaataaa acgaaaggct cagtcgaaag actgggcctt tcgttttatc tgttgtttgt    720
cggtgaacgc tctcctgagt aggacaaatc cgccgggagc ggatttgaac gttgcgaagc    780
aacggcccgg agggtggcgg gcaggacgcc cgccataaac tgccaggcat caaattaagc    840
agaaggccat cctgacggat ggcctttttg cgtttctaca aactcttttg tttattttc     900
taaatacatt caaatatgta tccgctcatg agacaataac cctgataaat gcttcaataa    960
tattgaaaaa ggaagagtat gagtattcaa catttccgtg tcgcccttat tcccttttt    1020
gcggcatttt gccttcctgt ttttgctcac ccagaaacgc tggtgaaagt aaaagatgct   1080
gaagatcagt tgggtgcacg agtgggttac atcgaactgg atctcaacag cggtaagatc   1140
cttgagagtt ttcgccccga agaacgtttt ccaatgatga gcactttaa agttctgcta   1200
tgtggcgcgg tattatcccg tgttgacgcc gggcaagagc aactcggtcg ccgcatacac   1260
tattctcaga atgacttggt tgagtactca ccagtcacag aaaagcatct tacggatggc   1320
atgacagtaa gagaattatg cagtgctgcc ataaccatga gtgataacac tgcggccaac   1380
ttacttctga caacgatcgg aggaccgaag gagctaaccg cttttttgca acaacatggg   1440
gatcatgtaa ctcgccttga tcgttgggaa ccggagctga atgaagccat accaaacgac   1500
gagcgtgaca ccacgatgcc tgtagcaatg gcaacaacgt tgcgcaaact attaactggc   1560
gaactactta ctctagcttc ccggcaacaa ttaatagact ggatggaggc ggataaagtt   1620
gcaggaccac ttctgcgctc ggcccttccg gctggctggt ttattgctga taaatctgga   1680
gccggtgagc gtgggtctcg cggtatcatt gcagcactgg ggccagatgg taagccctcc   1740
cgtatcgtag ttatctacac gacggggagt caggcaacta tggatgaacg aaatagacag   1800
atcgctgaga taggtgcctc actgattaag cattggtaac tgtcagacca gtttactca   1860
tatatacttt agattgattt aaaacttcat ttttaattta aaaggatcta ggtgaagatc   1920
cttttttgata atctcatgac caaaatccct taacgtgagt tttcgttcca ctgagcgtca   1980
gaccccgtag aaaagatcaa aggatcttct tgagatcctt ttttttctgcg cgtaatctgc   2040
tgcttgcaaa caaaaaaacc accgctacca gcggtggttt gtttgccgga tcaagagcta   2100
ccaactcttt ttccgaaggt aactggcttc agcagagcgc agataccaaa tactgtcctt   2160
ctagtgtagc cgtagttagg ccaccacttc aagaactctg tagcaccgcc tacatacctc   2220
gctctgctaa tcctgttacc agtggctgct gccagtggcg ataagtcgtg tcttaccggg   2280
ttggactcaa gacgatagtt accggataag gcgcagcggt cgggctgaac ggggggttcg   2340
tgcacacagc ccagcttgga gcgaacgacc tacaccgaac tgagatacct acagcgtgag   2400
ctatgagaaa gcgccacgct tcccgaaggg agaaaggcgg acaggtatcc ggtaagcggc   2460
agggtcggaa caggagagcg cacgagggag cttccagggg gaaacgcctg gtatctttat   2520
agtcctgtcg ggtttcgcca cctctgactt gagcgtcgat ttttgtgatg ctcgtcaggg   2580
gggcggagcc tatggaaaaa cgccagcaac gcggcctttt tacggttcct ggccttttgc   2640
tggccttttg ctcacatgtt ctttcctgcg ttatcccctg attctgtgga taaccgtatt   2700
accgcctttg agtgagctga taccgctcgc cgcagccgaa cgaccgagcg cagcgagtca   2760
gtgagcgagg aagcggaaga gcgcctgatg cggtattttc tccttacgca tctgtgcggt   2820
atttcacacc gcatatggtg cactctcagt acaatctgct ctgatgccgc atagttaagc   2880
cagtatacac tccgctatcg ctacgtgact gggtcatggc tgcgcccga cacccgccaa   2940
cacccgctga cgcgccctga cgggcttgtc tgctcccggc atccgcttac agacaagctg   3000
tgaccgtctc cgggagctgc atgtgtcaga ggttttcacc gtcatcaccg aaacgcgcga   3060
```

```
ggcagcagat caattcgcgc gcgaaggcga agcggcatgc ataatgtgcc tgtcaaatgg     3120
acgaagcagg gattctgcaa accctatgct actccgtcaa gccgtcaatt gtctgattcg     3180
ttaccaatta tgacaacttg acggctacat cattcacttt ttcttcacaa ccggcacgga     3240
actcgctcgg gctggccccg gtgcattttt taaatacccg cgagaaatag agttgatcgt     3300 caaaccaac attgcgaccg acggtggcga taggcatccg ggtggtgctc aaaagcagct     3360
tcgcctggct gatacgttgg tcctcgcgcc agcttaagac gctaatccct aactgctggc     3420
ggaaaagatg tgacagacgc gacggcgaca agcaaacatg ctgtgcgacg ctggcgatat     3480
caaaattgct gtctgccagg tgatcgctga tgtactgaca agcctcgcgt acccgattat     3540
ccatcggtgg atggagcgac tcgttaatcg cttccatgcg ccgcagtaac aattgctcaa     3600
gcagatttat cgccagcagc tccgaatagc gcccttcccc ttgcccggcg ttaatgattt     3660
gcccaaacag gtcgctgaaa tgcggctggt gcgcttcatc cgggcgaaag aaccccgtat     3720
tggcaaatat tgacgccag ttaagccatt catgccagta ggcgcgcgga cgaaagtaaa     3780
cccactggtg ataccattcg cgagcctccg gatgacgacc gtagtgatga atctctcctg     3840
gcgggaacag caaaatatca cccggtcggc aaacaaattc tcgtccctga tttttcacca     3900 cccccctgacc gcgaatggtg agattgagaa tataaccttt cattcccagc ggtcggtcga     3960
taaaaaaatc gagataaccg ttggcctcaa tcggcgttaa acccgccacc agatgggcat     4020
taaacgagta tcccggcagc aggggatcat tttgcgcttc agccatactt ttcatactcc     4080
cgccattcag ag                                                         4092
```

<210> SEQ ID NO 88
<211> LENGTH: 4679
<212> TYPE: DNA
<213> ORGANISM: Artificial sequence
<220> FEATURE:
<223> OTHER INFORMATION: pRF161

<400> SEQUENCE: 88

```
catgggctcc agccatcatc atcaccatca tgaattcgga ggtggcggtg catcctcgga      60
ggatgtgatt aaagaattta tgcggtttaa agtacgtatg gaaggatcgg tgaatggcca     120
tgaatttgag attgagggtg aaggcgaagg ccgcccgtac gaaggaactc aaacagcgaa     180
attaaaagtt acaaaaggag gtcctctgcc gtttgcctgg gacatcttga gcccgcaatt     240
ccagtacggt tccaaagtgt atgtaaaaca ccctgcggat attccggatt ataaaaaact     300
gagttttccc gaggggttta atgggaacg ggtgatgaat tttgaggatg gtggagttgt     360
caccgtgacc caggactcta gcttacaaga cggtagtttc atctacaaag taaaatttat     420
cggcgtaaac ttcccatcgg acggcccgt catgcagaaa aagacgatgg gctgggaagc     480
cagcaccgaa cgtttgtacc cacgggacgg cgttttgaaa ggggaaatcc ataaggccct     540
taaactgaaa gacggtggtc actatctcgt ggagtttaaa tcgatttata tggctaaaaa     600
accagtacag cttccgggtt attattacgt tgactccaaa ttggacatca catcgcataa     660
tgaagattac acgattgttg aacagtacga gcgcgccgag ggccggcacc atctgttctct     720 gtaaaagctt ggctgttttg gcggatgaga gaagattttc agcctgatac agattaaatc     780
agaacgcaga gcggtctga taaaacagaa tttgcctggc ggcagtagcg cggtggtccc     840
acctgacccc atgccgaact cagaagtgaa acgccgtagc gccgatggta gtgtggggtc     900
tccccatgcg agagtaggga actgccaggc atcaaataaa acgaaaggct cagtcgaaag     960
```

```
actgggcctt tcgttttatc tgttgtttgt cggtgaacgc tctcctgagt aggacaaatc    1020
cgccgggagc ggatttgaac gttgcgaagc aacggcccgg agggtggcgg gcaggacgcc    1080
cgccataaac tgccaggcat caaattaagc agaaggccat cctgacggat ggcctttttg    1140
cgtttctaca aactcttttg tttatttttc taaatacatt caaatatgta tccgctcatg    1200
agacaataac cctgataaat gcttcaataa tattgaaaaa ggaagagtat gagtattcaa    1260
catttccgtg tcgcccttat tccctttttt gcggcatttt gccttcctgt ttttgctcac    1320
ccagaaacgc tggtgaaagt aaaagatgct gaagatcagt tgggtgcacg agtgggttac    1380
atcgaactgg atctcaacag cggtaagatc cttgagagtt ttcgccccga agaacgtttt    1440
ccaatgatga gcacttttaa agttctgcta tgtggcgcgg tattatcccg tgttgacgcc    1500
gggcaagagc aactcggtcg ccgcatacac tattctcaga atgacttggt tgagtactca    1560
ccagtcacag aaaagcatct tacggatggc atgacagtaa gagaattatg cagtgctgcc    1620
ataaccatga gtgataacac tgcggccaac ttacttctga caacgatcgg aggaccgaag    1680
gagctaaccg cttttttgca caacatgggg gatcatgtaa ctcgccttga tcgttgggaa    1740
ccggagctga atgaagccat accaaacgac gagcgtgaca ccacgatgcc tgtagcaatg    1800
gcaacaacgt tgcgcaaact attaactggc gaactactta ctctagcttc ccggcaacaa    1860
ttaatagact ggatggaggc ggataaagtt gcaggaccac ttctgcgctc ggcccttccg    1920
gctggctggt ttattgctga taaatctgga gccggtgagc gtgggtctcg cggtatcatt    1980
gcagcactgg ggccagatgg taagccctcc cgtatcgtag ttatctacac gacggggagt    2040
caggcaacta tggatgaacg aaatagacag atcgctgaga taggtgcctc actgattaag    2100
cattggtaac tgtcagacca agtttactca tatatacttt agattgattt aaaacttcat    2160
ttttaattta aaaggatcta ggtgaagatc ctttttgata atctcatgac caaaatccct    2220
taacgtgagt tttcgttcca ctgagcgtca gaccccgtag aaaagatcaa aggatcttct    2280
tgagatcctt ttttctgcg cgtaatctgc tgcttgcaaa caaaaaaacc accgctacca    2340
gcggtggttt gtttgccgga tcaagagcta ccaactcttt ttccgaaggt aactggcttc    2400
agcagagcgc agataccaaa tactgtcctt ctagtgtagc cgtagttagg ccaccacttc    2460
aagaactctg tagcaccgcc tacatacctc gctctgctaa tcctgttacc agtggctgct    2520
gccagtggcg ataagtcgtg tcttaccggg ttggactcaa gacgatagtt accggataag    2580
gcgcagcggt cgggctgaac ggggggttcg tgcacacagc ccagcttgga gcgaacgacc    2640
tacaccgaac tgagatacct acagcgtgag ctatgagaaa gcgccacgct tcccgaaggg    2700
agaaaggcgg acaggtatcc ggtaagcggc agggtcggaa caggagagcg cacgagggag    2760
cttccagggg gaaacgcctg gtatctttat agtcctgtcg gtttcgcca cctctgactt    2820
gagcgtcgat ttttgtgatg ctcgtcaggg gggcggagcc tatggaaaaa cgccagcaac    2880
gcggcctttt tacggttcct ggccttttgc tggccttttg ctcacatgtt ctttcctgcg    2940
ttatcccctg attctgtgga taaccgtatt accgcctttg agtgagctga taccgctcgc    3000
cgcagccgaa cgaccgagcg cagcgagtca gtgagcgagg aagcggaaga gcgcctgatg    3060
cggtattttc tccttacgca tctgtgcggt atttcacacc gcatatggtg cactctcagt    3120
acaatctgct ctgatgccgc atagttaagc cagtatacac tccgctatcg ctacgtgact    3180
gggtcatggc tgcgccccga cacccgccaa cacccgctga cgcgccctga cgggcttgtc    3240
tgctcccggc atccgcttac agacaagctg tgaccgtctc cgggagctgc atgtgtcaga    3300
ggttttcacc gtcatcaccg aaacgcgcga ggcagcagat caattcgcgc gcgaaggcga    3360
```

```
agcggcatgc ataatgtgcc tgtcaaatgg acgaagcagg gattctgcaa accctatgct    3420
actccgtcaa gccgtcaatt gtctgattcg ttaccaatta tgacaacttg acggctacat    3480
cattcacttt ttcttcacaa ccggcacgga actcgctcgg gctggcccg gtgcattttt     3540 taaatacccg cgagaaatag agttgatcgt caaaaccaac attgcgaccg acggtggcga    3600
taggcatccg ggtggtgctc aaaagcagct tcgcctggct gatacgttgg tcctcgcgcc    3660
agcttaagac gctaatccct aactgctggc ggaaaagatg tgacagacgc gacggcgaca    3720
agcaaacatg ctgtgcgacg ctggcgatat caaaattgct gtctgccagg tgatcgctga    3780
tgtactgaca agcctcgcgt acccgattat ccatcggtgg atggagcgac tcgttaatcg    3840
cttccatgcg ccgcagtaac aattgctcaa gcagatttat cgccagcagc tccgaatagc    3900
gcccttcccc ttgcccggcg ttaatgattt gcccaaacag gtcgctgaaa tgcggctggt    3960
gcgcttcatc cgggcgaaag aaccccgtat tggcaaatat tgacggccag ttaagccatt    4020
catgccagta ggcgcgcgga cgaaagtaaa cccactggtg ataccattcg cgagcctccg    4080
gatgacgacc gtagtgatga atctctcctg gcgggaacag caaaatatca cccggtcggc    4140
aaacaaattc tcgtccctga ttttcacca ccccctgacc gcgaatggtg agattgagaa     4200
tataaccttt cattcccagc ggtcggtcga taaaaaaatc gagataaccg ttggcctcaa    4260
tcggcgttaa acccgccacc agatgggcat taaacgagta tcccggcagc aggggatcat    4320
tttgcgcttc agccatactt ttcatactcc cgccattcag agaagaaacc aattgtccat    4380
attgcatcag acattgccgt cactgcgtct tttactggct cttctcgcta accaaaccgg    4440 taacccgct tattaaaagc attctgtaac aaagcgggac caaagccatg acaaaaacgc     4500
gtaacaaaag tgtctataat cacggcagaa aagtccacat tgattatttg cacggcgtca    4560
cactttgcta tgccatagca tttttatcca taagattagc ggatcctacc tgacgctttt    4620
tatcgcaact ctctactgtt tctccatacc cgttttttgg gctaacagga ggaattaac    4679
```

<210> SEQ ID NO 89
<211> LENGTH: 20
<212> TYPE: PRT
<213> ORGANISM: Artificial sequence
<220> FEATURE:
<223> OTHER INFORMATION: TAT
<400> SEQUENCE: 89

Gly Arg Lys Lys Arg Arg Gln Arg Arg Pro Pro Gln Pro Lys Lys
1               5                   10                  15

Lys Arg Lys Val
            20

<210> SEQ ID NO 90
<211> LENGTH: 18
<212> TYPE: PRT
<213> ORGANISM: Artificial sequence
<220> FEATURE:
<223> OTHER INFORMATION: TLM
<400> SEQUENCE: 90

Pro Leu Ser Ser Ile Phe Ser Arg Ile Gly Asp Pro Lys Lys Lys Arg
1               5                   10                  15

Lys Val

<210> SEQ ID NO 91
<211> LENGTH: 23

-continued

```
<212> TYPE: PRT
<213> ORGANISM: Artificial sequence
<220> FEATURE:
<223> OTHER INFORMATION: MPG1

<400> SEQUENCE: 91

Ala Leu Phe Leu Gly Gln Leu Gly Ala Ala Gly Ser Thr Met Gly Ala
1               5                   10                  15

Pro Lys Lys Lys Arg Lys Val
            20

<210> SEQ ID NO 92
<211> LENGTH: 21
<212> TYPE: PRT
<213> ORGANISM: Artificial sequence
<220> FEATURE:
<223> OTHER INFORMATION: pep1

<400> SEQUENCE: 92

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 93
<211> LENGTH: 7
<212> TYPE: PRT
<213> ORGANISM: Artificial sequence
<220> FEATURE:
<223> OTHER INFORMATION: CFFKDEL

<400> SEQUENCE: 93

Cys Phe Phe Lys Asp Glu Leu
1               5

<210> SEQ ID NO 94
<211> LENGTH: 98
<212> TYPE: DNA
<213> ORGANISM: Artificial sequence
<220> FEATURE:
<223> OTHER INFORMATION: his-TAT E.coli optimized

<400> SEQUENCE: 94
ccatggggca tcaccatcat catcacggcc gcaaaaaacg tcgtcagcgc cggcgtccgc    60
cccagccgaa aaacggaaa gtgggcggcg gcgaattc                            98

<210> SEQ ID NO 95
<211> LENGTH: 89
<212> TYPE: DNA
<213> ORGANISM: Artificial sequence
<220> FEATURE:
<223> OTHER INFORMATION: his-TLM E.coli optimized

<400> SEQUENCE: 95
ccatggggca tcaccatcat catcatccgt taagctcgat cttttctcgt atcggtgatc    60
cgccaaaaaa gaaacgcaaa gtagaattc                                     89

<210> SEQ ID NO 96
<211> LENGTH: 104
<212> TYPE: DNA
<213> ORGANISM: Artificial sequence
<220> FEATURE:
<223> OTHER INFORMATION: his-MPG1 E. coli optimized

<400> SEQUENCE: 96
```

```
ccatggggca tcatcatcac catcacggcg ccctgttctt aggccagctg ggcgccgcgg    60
gatccacgat gggtgcgccg aagaaaaagc gcaaagttga attc                    104
```

<210> SEQ ID NO 97
<211> LENGTH: 95
<212> TYPE: DNA
<213> ORGANISM: Artificial sequence
<220> FEATURE:
<223> OTHER INFORMATION: his-pep1 E. coli optimized

<400> SEQUENCE: 97

```
ccatggggca ccatcaccat caccataaag aaacttggtg ggagacttgg tggaccgaat    60
ggtcccagcc gaagaaaaaa cgcaaggttg aattc                              95
```

<210> SEQ ID NO 98
<211> LENGTH: 51
<212> TYPE: DNA
<213> ORGANISM: Artificial sequence
<220> FEATURE:
<223> OTHER INFORMATION: his-CFFKDEL E. coli optimized

<400> SEQUENCE: 98

```
ccatggggca tcaccatcac caccattgtt ttttcaaaga cgaactggaa t             51
```

<210> SEQ ID NO 99
<211> LENGTH: 4739
<212> TYPE: DNA
<213> ORGANISM: Artificial sequence
<220> FEATURE:
<223> OTHER INFORMATION: pRF224;

<400> SEQUENCE: 99

```
catgggcat caccatcatc atcacggccg caaaaaacgt cgtcagcgcc ggcgtccgcc     60
ccagccgaaa aaacggaaag tgggcggcgg cgaattcgga ggtggcggtg catcctcgga   120
ggatgtgatt aaagaattta tgcggtttaa agtacgtatg gaaggatcgg tgaatggcca   180
tgaatttgag attgagggtg aaggcgaagg ccgcccgtac gaaggaactc aaacagcgaa   240
attaaaagtt acaaaaggag gtcctctgcc gtttgcctgg gacatcttga gcccgcaatt   300
ccagtacggt tccaaagtgt atgtaaaaca ccctgcggat attccggatt ataaaaaact   360
gagttttccc gaggggttta atgggaacgg ggtgatgaat tttgaggatg gtggagttgt   420
caccgtgacc caggactcta gcttacaaga cggtagtttc atctacaaag taaaattat   480 cggcgtaaac ttcccatcgg acggcccgcg catgcagaaa aagacgatgg gctgggaagc   540
cagcaccgaa cgtttgtacc cacgggacgg cgttttgaaa ggggaaatcc ataaggccct   600
taaactgaaa gacggtggtc actatctcgt ggagtttaaa tcgatttata tggctaaaaa   660
accagtacag cttccgggtt attattacgt tgactccaaa ttggacatca catcgcataa   720
tgaagattac acgattgttg aacagtacga gcgcgccgag ggccggcacc atctgttttct   780 gtaaaagctt ggctgttttg gcggatgaga aagattttc agcctgatac agattaaatc   840
agaacgcaga agcggtctga taaaacagaa tttgcctggc ggcagtagcg cggtggtccc   900 acctgaccccc atgccgaact cagaagtgaa acgccgtagc gccgatggta gtgtgggtc   960 tccccatgcg agagtaggga actgccaggc atcaaataaa acgaaaggct cagtcgaaag   1020
actgggcctt tcgttttatc tgttgtttgt cggtgaacgc tctcctgagt aggacaaatc   1080
cgccgggagc ggatttgaac gttgcgaagc aacggcccgg agggtggcgg gcaggacgcc   1140
```

```
cgccataaac tgccaggcat caaattaagc agaaggccat cctgacggat ggccttttg    1200
cgtttctaca aactcttttg tttattttc taaatacatt caaatatgta tccgctcatg    1260
agacaataac cctgataaat gcttcaataa tattgaaaaa ggaagagtat gagtattcaa    1320
catttccgtg tcgcccttat tccctttttt gcggcatttt gccttcctgt ttttgctcac    1380
ccagaaacgc tggtgaaagt aaaagatgct gaagatcagt tgggtgcacg agtgggttac    1440
atcgaactgg atctcaacag cggtaagatc cttgagagtt ttcgccccga gaacgttttt    1500
ccaatgatga gcacttttaa agttctgcta tgtggcgcgg tattatcccg tgttgacgcc    1560
gggcaagagc aactcggtcg ccgcatacac tattctcaga atgacttggt tgagtactca    1620
ccagtcacag aaaagcatct tacggatggc atgacagtaa gagaattatg cagtgctgcc    1680
ataaccatga gtgataacac tgcggccaac ttacttctga caacgatcgg aggaccgaag    1740
gagctaaccg cttttttgca caacatgggg gatcatgtaa ctcgccttga tcgttgggaa    1800
ccggagctga atgaagccat accaaacgac gagcgtgaca ccacgatgcc tgtagcaatg    1860
gcaacaacgt tgcgcaaact attaactggc gaactactta ctctagcttc ccggcaacaa    1920
ttaatagact ggatggaggc ggataaagtt gcaggaccac ttctgcgctc ggcccttccg    1980
gctggctggt ttattgctga taaatctgga gccggtgagc gtgggtctcg cggtatcatt    2040
gcagcactgg ggccagatgg taagccctcc cgtatcgtag ttatctacac gacggggagt    2100
caggcaacta tggatgaacg aaatagacag atcgctgaga taggtgcctc actgattaag    2160
cattggtaac tgtcagacca agtttactca tatatacttt agattgattt aaaacttcat    2220
ttttaattta aaaggatcta ggtgaagatc ctttttgata atctcatgac caaaatccct    2280
taacgtgagt tttcgttcca ctgagcgtca gaccccgtag aaaagatcaa aggatcttct    2340
tgagatcctt tttttctgcg cgtaatctgc tgcttgcaaa caaaaaaacc accgctacca    2400
gcggtggttt gtttgccgga tcaagagcta ccaactcttt ttccgaaggt aactggcttc    2460
agcagagcgc agataccaaa tactgtcctt ctagtgtagc cgtagttagg ccaccacttc    2520
aagaactctg tagcaccgcc tacatacctc gctctgctaa tcctgttacc agtggctgct    2580
gccagtggcg ataagtcgtg tcttaccggg ttggactcaa gacgatagtt accggataag    2640
gcgcagcggt cgggctgaac ggggggttcg tgcacacagc ccagcttgga gcgaacgacc    2700
tacaccgaac tgagatacct acagcgtgag ctatgagaaa gcgccacgct tcccgaaggg    2760
agaaaggcgg acaggtatcc ggtaagcggc agggtcggaa caggagagcg cacgagggag    2820
cttccagggg gaaacgcctg gtatctttat agtcctgtcg ggtttcgcca cctctgactt    2880
gagcgtcgat ttttgtgatg ctcgtcaggg gggcggagcc tatggaaaaa cgccagcaac    2940
gcggcctttt tacggttcct ggccttttgc tggccttttg ctcacatgtt ctttcctgcg    3000
ttatcccctg attctgtgga taaccgtatt accgcctttg agtgagctga taccgctcgc    3060
cgcagccgaa cgaccgagcg cagcgagtca gtgagcgagg aagcggaaga gcgcctgatg    3120
cggtattttc tccttacgca tctgtgcggt atttcacacc gcatatggtg cactctcagt    3180
acaatctgct ctgatgccgc atagttaagc cagtatacac tccgctatcg ctacgtgact    3240
gggtcatggc tgcgccccga cacccgccaa cacccgctga cgcgccctga cgggcttgtc    3300
tgctcccggc atccgcttac agacaagctg tgaccgtctc cgggagctgc atgtgtcaga    3360
ggttttcacc gtcatcaccg aaacgcgcga ggcagcagat caattcgcgc gcgaaggcga    3420
agcggcatgc ataatgtgcc tgtcaaatgg acgaagcagg gattctgcaa acccctatgct   3480
actccgtcaa gccgtcaatt gtctgattcg ttaccaatta tgacaacttg acggctacat    3540
```

-continued

| | |
|---|---|
| cattcacttt ttcttcacaa ccggcacgga actcgctcgg gctggcccg gtgcattttt | 3600 |
| taaatacccg cgagaaatag agttgatcgt caaaaccaac attgcgaccg acggtggcga | 3660 |
| taggcatccg ggtggtgctc aaaagcagct tcgcctggct gatacgttgg tcctcgcgcc | 3720 |
| agcttaagac gctaatccct aactgctggc ggaaaagatg tgacagacgc gacggcgaca | 3780 |
| agcaaacatg ctgtgcgacg ctggcgatat caaaattgct gtctgccagg tgatcgctga | 3840 |
| tgtactgaca agcctcgcgt acccgattat ccatcggtgg atggagcgac tcgttaatcg | 3900 |
| cttccatgcg ccgcagtaac aattgctcaa gcagatttat cgccagcagc tccgaatagc | 3960 |
| gcccttcccc ttgcccggcg ttaatgattt gcccaaacag gtcgctgaaa tgcggctggt | 4020 |
| gcgcttcatc cgggcgaaag aaccccgtat tggcaaatat tgacggccag ttaagccatt | 4080 |
| catgccagta ggcgcgcgga cgaaagtaaa cccactggtg ataccattcg cgagcctccg | 4140 |
| gatgacgacc gtagtgatga atctctcctg gcgggaacag caaaatatca cccggtcggc | 4200 |
| aaacaaattc tcgtccctga ttttcacca ccccctgacc gcgaatggtg agattgagaa | 4260 |
| tataaccttt cattcccagc ggtcggtcga taaaaaaatc gagataaccg ttggcctcaa | 4320 |
| tcggcgttaa acccgccacc agatgggcat taaacgagta tcccggcagc aggggatcat | 4380 |
| tttgcgcttc agccatactt ttcatactcc cgccattcag agaagaaacc aattgtccat | 4440 |
| attgcatcag acattgccgt cactgcgtct tttactggct cttctcgcta accaaaccgg | 4500 |
| taacccgct tattaaaagc attctgtaac aaagcgggac caaagccatg acaaaaacgc | 4560 |
| gtaacaaaag tgtctataat cacggcagaa aagtccacat tgattatttg cacggcgtca | 4620 |
| cactttgcta tgccatagca tttttatcca taagattagc ggatcctacc tgacgctttt | 4680 |
| tatcgcaact ctctactgtt tctccatacc cgtttttgg gctaacagga ggaattaac | 4739 |

<210> SEQ ID NO 100
<211> LENGTH: 4730
<212> TYPE: DNA
<213> ORGANISM: Artificial sequence
<220> FEATURE:
<223> OTHER INFORMATION: pRF214

<400> SEQUENCE: 100

| | |
|---|---|
| catgggcat caccatcatc atcatccgtt aagctcgatc tttctcgta tcggtgatcc | 60 |
| gccaaaaaag aaacgcaaag tagaattcgg aggtggcggt gcatcctcgg aggatgtgat | 120 |
| taaagaattt atgcggttta agtacgtat ggaaggatcg gtgaatggcc atgaatttga | 180 |
| gattgagggt gaaggcgaag gccgcccgta cgaaggaact caaacagcga aattaaaagt | 240 |
| tacaaaagga ggtcctctgc cgtttgcctg ggacatcttg agcccgcaat tccagtacgg | 300 |
| ttccaaagtg tatgtaaaac accctgcgga tattccggat tataaaaaac tgagttttcc | 360 |
| cgaggggttt aaatgggaac gggtgatgaa ttttgaggat ggtggagttg tcaccgtgac | 420 |
| ccaggactct agcttacaag acggtagttt catctacaaa gtaaaattta tcggcgtaaa | 480 |
| cttcccatcg gacggccccg tcatgcagaa aaagacgatg ggctgggaag ccagcaccga | 540 |
| acgtttgtac ccacgggacg gcgttttgaa aggggaaatc cataaggccc ttaaactgaa | 600 |
| agacggtggt cactatctcg tggagtttaa atcgattat atggctaaaa aaccagtaca | 660 |
| gcttccgggt tattattacg ttgactccaa attggacatc acatcgcata tgaagatta | 720 |
| cacgattgtt gaacagtacg agcgcgccga gggccggcac catctgtttc tgtaaaagct | 780 |
| tggctgtttt ggcggatgag agaagatttt cagcctgata cagattaaat cagaacgcag | 840 |

```
aagcggtctg ataaaacaga atttgcctgg cggcagtagc gcggtggtcc cacctgaccc      900
catgccgaac tcagaagtga aacgccgtag cgccgatggt agtgtggggt ctccccatgc      960
gagagtaggg aactgccagg catcaaataa acgaaaggc tcagtcgaaa gactgggcct     1020
ttcgttttat ctgttgtttg tcggtgaacg ctctcctgag taggacaaat ccgccgggag     1080
cggatttgaa cgttgcgaag caacggcccg gagggtggcg ggcaggacgc ccgccataaa     1140
ctgccaggca tcaaattaag cagaaggcca tcctgacgga tggccttttt gcgtttctac     1200
aaactctttt gtttattttt ctaaatacat tcaaatatgt atccgctcat gagacaataa     1260
ccctgataaa tgcttcaata atattgaaaa aggaagagta tgagtattca acatttccgt     1320 gtcgcccta ttcccttttt tgcggcattt tgccttcctg ttttgctca cccagaaacg     1380 ctggtgaaag taaaagatgc tgaagatcag ttgggtgcac gagtgggtta catcgaactg     1440
gatctcaaca gcggtaagat ccttgagagt tttcgccccg aagaacgttt tccaatgatg     1500
agcactttta agttctgct atgtggcgcg gtattatccc gtgttgacgc cgggcaagag     1560
caactcggtc gccgcataca ctattctcag aatgacttgg ttgagtactc accagtcaca     1620
gaaaagcatc ttacggatgg catgacagta agagaattat gcagtgctgc cataaccatg     1680
agtgataaca ctgcggccaa cttacttctg acaacgatcg gaggaccgaa ggagctaacc     1740 gctttttgc acaacatggg ggatcatgta actcgccttg atcgttggga accggagctg     1800
aatgaagcca taccaaacga cgagcgtgac accacgatgc ctgtagcaat ggcaacaacg     1860
ttgcgcaaac tattaactgg cgaactactt actctagctt cccggcaaca attaatagac     1920
tggatggagg cggataaagt tgcaggacca cttctgcgct cggccttcc ggctggctgg     1980 tttattgctg ataaatctgg agccggtgag cgtgggtctc gcggtatcat tgcagcactg     2040
gggccagatg gtaagccctc ccgtatcgta gttatctaca cgacggggag tcaggcaact     2100
atggatgaac gaaatagaca gatcgctgag ataggtgcct cactgattaa gcattggtaa     2160
ctgtcagacc aagtttactc atatatactt tagattgatt taaaacttca ttttttaattt     2220 aaaaggatct aggtgaagat cctttttgat aatctcatga ccaaaatccc ttaacgtgag     2280
ttttcgttcc actgagcgtc agaccccgta gaaaagatca aggatcttc ttgagatcct     2340 ttttttctgc gcgtaatctg ctgcttgcaa acaaaaaaac caccgctacc agcggtggtt     2400
tgtttgccgg atcaagagct accaactctt tttccgaagg taactggctt cagcagagcg     2460
cagataccaa atactgtcct tctagtgtag ccgtagttag gccaccactt caagaactct     2520
gtagcaccgc ctacatacct cgctctgcta atcctgttac cagtggctgc tgccagtggc     2580
gataagtcgt gtcttaccgg gttggactca agacgatagt taccggataa ggcgcagcgg     2640
tcgggctgaa cggggggttc gtgcacacag cccagcttgg agcgaacgac ctacaccgaa     2700
ctgagatacc tacagcgtga gctatgagaa agcgccacgc ttcccgaagg gagaaaggcg     2760
gacaggtatc cggtaagcgg cagggtcgga acaggagagc gcacgaggga gcttccaggg     2820
ggaaacgcct ggtatcttta tagtcctgtc gggtttcgcc acctctgact tgagcgtcga     2880
tttttgtgat gctcgtcagg gggcggagc ctatggaaaa acgccagcaa cgcggccttt     2940
ttacggttcc tggccttttg ctggccttt gctcacatgt tctttcctgc gttatccct     3000 gattctgtgg ataaccgtat taccgccttt gagtgagctg ataccgctcg ccgcagccga     3060
acgaccgagc gcagcgagtc agtgagcgag gaagcggaag agcgcctgat gcggtatttt     3120
ctccttacgc atctgtgcgg tatttcacac cgcatatggt gcactctcag tacaatctgc     3180
tctgatgccg catagttaag ccagtataca ctccgctatc gctacgtgac tgggtcatgg     3240
```

```
ctgcgcccg acacccgcca acacccgctg acgcgccctg acgggcttgt ctgctcccgg      3300
catccgctta cagacaagct gtgaccgtct ccgggagctg catgtgtcag aggttttcac      3360
cgtcatcacc gaaacgcgcg aggcagcaga tcaattcgcg cgcgaaggcg aagcggcatg      3420
cataatgtgc ctgtcaaatg gacgaagcag ggattctgca aaccctatgc tactccgtca      3480
agccgtcaat tgtctgattc gttaccaatt atgacaactt gacggctaca tcattcactt      3540
tttcttcaca accggcacgg aactcgctcg gctggcccc ggtgcatttt ttaaataccc       3600
gcgagaaata gagttgatcg tcaaaaccaa cattgcgacc gacggtggcg ataggcatcc      3660
gggtggtgct caaaagcagc ttcgcctggc tgatacgttg gtcctcgcgc agcttaaga      3720 cgctaatccc taactgctgg cggaaaagat gtgacagacg cgacggcgac aagcaaacat      3780
gctgtgcgac gctggcgata tcaaaattgc tgtctgccag gtgatcgctg atgtactgac      3840
aagcctcgcg tacccgatta tccatcggtg gatggagcga ctcgttaatc gcttccatgc      3900
gccgcagtaa caattgctca agcagattta tcgccagcag ctccgaatag cgccctttccc     3960 cttgcccggc gttaatgatt tgcccaaaca ggtcgctgaa atgcggctgg tgcgcttcat      4020
ccgggcgaaa gaaccccgta ttggcaaata ttgacggcca gttaagccat tcatgccagt      4080
aggcgcgcgg acgaaagtaa acccactggt gataccattc gcgagcctcc ggatgacgac      4140
cgtagtgatg aatctctcct ggcgggaaca gcaaaatatc acccggtcgg caaacaaatt      4200
ctcgtccctg attttttcacc acccctgac cgcgaatggt gagattgaga atataaccctt    4260 tcattcccag cggtcggtcg ataaaaaaat cgagataacc gttggcctca atcggcgtta     4320
aacccgccac cagatgggca ttaaacgagt atccggcag caggggatca ttttgcgctt      4380
cagccatact tttcatactc ccgccattca gagaagaaac caattgtcca tattgcatca     4440
gacattgccg tcactgcgtc ttttactggc tcttctcgct aaccaaaccg gtaacccccgc    4500 ttattaaaag cattctgtaa caaagcggga ccaaagccat gacaaaaacg cgtaacaaaa     4560
gtgtctataa tcacggcaga aaagtccaca ttgattattt gcacggcgtc acactttgct     4620
atgccatagc atttttatcc ataagattag cggatcctac ctgacgcttt ttatcgcaac    4680
tctctactgt ttctccatac ccgtttttg ggctaacagg aggaattaac                 4730
```

<210> SEQ ID NO 101
<211> LENGTH: 4745
<212> TYPE: DNA
<213> ORGANISM: Artificial sequence
<220> FEATURE:
<223> OTHER INFORMATION: pRF213

<400> SEQUENCE: 101

```
catgggcat catcatcacc atcacggcgc cctgttctta ggccagctgg cgccgcggg        60 atccacgatg ggtgcgccga agaaaaagcg caaagttgaa ttcggaggtg gcggtgcatc     120
ctcggaggat gtgattaaag aatttatgcg gtttaaagta cgtatggaag atcggtgaa    180 tggccatgaa tttgagattg agggtgaagg cgaaggccgc ccgtacgaag aactcaaac     240 agcgaaatta aaagttacaa aaggaggtcc tctgccgttt gcctgggaca tcttgagccc    300
gcaattccag tacggttcca agtgtatgt aaaacaccct gcggatattc cggattataa    360
aaaactgagt tttcccgagg ggtttaaatg gaacgggtg atgaattttg aggatggtgg    420
agttgtcacc gtgacccagg actctagctt acaagacgtt agtttcatct acaaagtaaa   480
atttatcggc gtaaacttcc catcggacgg ccccgtcatg cagaaaaaga cgatgggctg   540
```

```
ggaagccagc accgaacgtt tgtacccacg ggacggcgtt ttgaaagggg aaatccataa    600
ggcccttaaa ctgaaagacg gtggtcacta tctcgtggag tttaaatcga tttatatggc    660
taaaaaacca gtacagcttc cgggttatta ttacgttgac tccaaattgg acatcacatc    720
gcataatgaa gattacacga ttgttgaaca gtacgagcgc gccgagggcc ggcaccatct    780
gtttctgtaa aagcttggct gttttggcgg atgagagaag attttcagcc tgatacagat    840
taaatcagaa cgcagaagcg gtctgataaa acagaatttg cctggcggca gtagcgcggt    900
ggtcccacct gaccccatgc cgaactcaga agtgaaacgc cgtagcgccg atggtagtgt    960
ggggtctccc catgcgagag tagggaactg ccaggcatca aataaaacga aaggctcagt   1020
cgaaagactg ggcctttcgt tttatctgtt gtttgtcggt gaacgctctc ctgagtagga   1080
caaatccgcc gggagcggat ttgaacgttg cgaagcaacg gcccggaggg tggcgggcag   1140
gacgcccgcc ataaactgcc aggcatcaaa ttaagcagaa ggccatcctg acggatggcc   1200 ttttgcgtt tctacaaact cttttgttta tttttctaaa tacattcaaa tatgtatccg   1260
ctcatgagac aataaccctg ataaatgctt caataatatt gaaaaaggaa gagtatgagt   1320
attcaacatt tccgtgtcgc ccttattccc ttttttgcgg cattttgcct tcctgttttt   1380
gctcacccag aaacgctggt gaaagtaaaa gatgctgaag atcagttggg tgcacgagtg   1440
ggttacatcg aactggatct caacagcggt aagatccttg agagttttcg ccccgaagaa   1500
cgttttccaa tgatgagcac ttttaaagtt ctgctatgtg gcgcggtatt atcccgtgtt   1560
gacgccgggc aagagcaact cggtcgccgc atacactatt ctcagaatga cttggttgag   1620
tactcaccag tcacagaaaa gcatcttacg gatggcatga cagtaagaga attatgcagt   1680
gctgccataa ccatgagtga taacactgcg gccaacttac ttctgacaac gatcggagga   1740
ccgaaggagc taaccgcttt tttgcacaac atgggggatc atgtaactcg ccttgatcgt   1800
tgggaaccgg agctgaatga agccatacca aacgacgagc gtgacaccac gatgcctgta   1860
gcaatggcaa caacgttgcg caaactatta actggcgaac tacttactct agcttcccgg   1920
caacaattaa tagactggat ggaggcggat aaagttgcag gaccacttct gcgctcggcc   1980
cttccggctg gctggtttat tgctgataaa tctggagccg gtgagcgtgg gtctcgcggt   2040
atcattgcag cactggggcc agatggtaag ccctcccgta tcgtagttat ctacacgacg   2100
gggagtcagg caactatgga tgaacgaaat agacagatcg ctgagatagg tgcctcactg   2160
attaagcatt ggtaactgtc agaccaagtt tactcatata ctttagat tgatttaaaa   2220 cttcattttt aatttaaaag gatctaggtg aagatccttt ttgataatct catgaccaaa   2280
atcccttaac gtgagttttc gttccactga gcgtcagacc ccgtagaaaa gatcaaagga   2340
tcttcttgag atcctttttt tctgcgcgta atctgctgct tgcaaacaaa aaaaccaccg   2400
ctaccagcgg tggtttgttt gccggatcaa gagctaccaa ctctttttcc gaaggtaact   2460
ggcttcagca gagcgcagat accaaatact gtccttctag tgtagccgta gttaggccac   2520
cacttcaaga actctgtagc accgcctaca tacctcgctc tgctaatcct gttaccagtg   2580
gctgctgcca gtggcgataa gtcgtgtctt accgggttgg actcaagacg atagttaccg   2640
gataaggcgc agcggtcggg ctgaacgggg gttcgtgca cacagcccag cttggagcga   2700
acgacctaca ccgaactgag atacctacag cgtgagctat gagaaagcgc cacgcttccc   2760
gaagggagaa aggcggacag gtatccggta agcggcaggg tcggaacagg agagcgcacg   2820
agggagcttc caggggggaaa cgcctggtat ctttatagtc ctgtcgggtt tcgccacctc   2880
tgacttgagc gtcgattttt gtgatgctcg tcagggggc ggagcctatg gaaaaacgcc   2940
```

```
agcaacgcgg cctttttacg gttcctggcc ttttgctggc cttttgctca catgttcttt      3000
cctgcgttat cccctgattc tgtggataac cgtattaccg cctttgagtg agctgatacc      3060
gctcgccgca gccgaacgac cgagcgcagc gagtcagtga gcgaggaagc ggaagagcgc      3120
ctgatgcggt attttctcct tacgcatctg tgcggtattt cacaccgcat atggtgcact      3180
ctcagtacaa tctgctctga tgccgcatag ttaagccagt atacactccg ctatcgctac      3240
gtgactgggt catggctgcg ccccgacacc cgccaacacc cgctgacgcg ccctgacggg      3300
cttgtctgct cccggcatcc gcttacagac aagctgtgac cgtctccggg agctgcatgt      3360
gtcagaggtt ttcaccgtca tcaccgaaac gcgcgaggca gcagatcaat cgcgcgcga      3420 aggcgaagcg gcatgcataa tgtgcctgtc aaatggacga agcaggatt ctgcaaaccc      3480 tatgctactc cgtcaagccg tcaattgtct gattcgttac caattatgac aacttgacgg      3540
ctacatcatt cacttttct tcacaaccgg cacggaactc gctcgggctg ccccggtgc       3600 attttttaaa tacccgcgag aaatagagtt gatcgtcaaa accaacattg cgaccgacgg      3660
tggcgatagg catccgggtg gtgctcaaaa gcagcttcgc ctggctgata cgttggtcct      3720
cgcgccagct taagacgcta atccctaact gctggcggaa aagatgtgac agacgcgacg      3780
gcgacaagca acatgctgt gcgacgctgg cgatatcaaa attgctgtct gccaggtgat      3840
cgctgatgta ctgacaagcc tcgcgtaccc gattatccat cggtggatgg agcgactcgt      3900
taatcgcttc catgcgccgc agtaacaatt gctcaagcag atttatcgcc agcagctccg      3960
aatagcgccc ttcccttgc ccggcgttaa tgatttgccc aaacaggtcg ctgaaatgcg      4020
gctggtgcgc ttcatccggg cgaaagaacc ccgtattggc aaatattgac ggccagttaa      4080
gccattcatg ccagtaggcg cgcggacgaa agtaaaccca ctggtgatac cattcgcgag      4140
cctccggatg acgaccgtag tgatgaatct ctcctggcgg gaacagcaaa atatcacccg      4200
gtcggcaaac aaattctcgt ccctgatttt tcaccacccc ctgaccgcga atggtgagat      4260
tgagaatata acctttcatt cccagcggtc ggtcgataaa aaaatcgaga taaccgttgg      4320
cctcaatcgg cgttaaaccc gccaccagat gggcattaaa cgagtatccc ggcagcaggg      4380
gatcattttg cgcttcagcc atactttca tactcccgcc attcagagaa gaaaccaatt      4440
gtccatattg catcagacat tgccgtcact gcgtctttta ctggctcttc tcgctaacca      4500
aaccggtaac cccgcttatt aaaagcattc tgtaacaaag cgggaccaaa gccatgacaa      4560
aaacgcgtaa caaaagtgtc tataatcacg gcagaaaagt ccacattgat tatttgcacg      4620
gcgtcacact ttgctatgcc atagcatttt tatccataag attagcggat cctacctgac      4680 gcttttatc gcaactctct actgtttctc catacccgtt ttttgggcta acaggaggaa      4740
ttaac                                                                 4745
```

<210> SEQ ID NO 102
<211> LENGTH: 4736
<212> TYPE: DNA
<213> ORGANISM: Artificial sequence
<220> FEATURE:
<223> OTHER INFORMATION: pRF217

<400> SEQUENCE: 102

```
catgggcac catcaccatc accataaaga aacttggtgg gagacttggt ggaccgaatg       60
gtcccagccg aagaaaaaac gcaaggttga attcggaggt ggcggtgcat cctcggagga      120
tgtgattaaa gaatttatgc ggtttaaagt acgtatggaa ggatcggtga atggccatga      180
```

```
atttgagatt gagggtgaag gcgaaggccg cccgtacgaa ggaactcaaa cagcgaaatt     240
aaaagttaca aaaggaggtc ctctgccgtt tgcctgggac atcttgagcc cgcaattcca     300
gtacggttcc aaagtgtatg taaaacaccc tgcggatatt ccggattata aaaaactgag     360
ttttcccgag gggtttaaat gggaacgggt gatgaatttt gaggatggtg gagttgtcac     420
cgtgacccag gactctagct tacaagacgg tagtttcatc tacaaagtaa aatttatcgg     480
cgtaaacttc ccatcggacg gccccgtcat gcagaaaaag acgatgggct gggaagccag     540
caccgaacgt ttgtacccac gggacggcgt tttgaaaggg gaaatccata aggcccttaa     600
actgaaagac ggtggtcact atctcgtgga gtttaaatcg atttatatgg ctaaaaaacc     660
agtacagctt ccgggttatt attacgttga ctccaaattg gacatcacat cgcataatga     720
agattacacg attgttgaac agtacgagcg cgccgagggc cggcaccatc tgtttctgta     780
aaagcttggc tgttttggcg gatgagagaa gattttcagc ctgatacaga ttaaatcaga     840
acgcagaagc ggtctgataa aacagaattt gcctggcggc agtagcgcgg tggtcccacc     900
tgaccccatg ccgaactcag aagtgaaacg ccgtagcgcc gatggtagtg tggggtctcc     960
ccatgcgaga gtagggaact gccaggcatc aaataaaacg aaaggctcag tcgaaagact    1020
gggcctttcg ttttatctgt tgtttgtcgg tgaacgctct cctgagtagg acaaatccgc    1080
cgggagcgga tttgaacgtt gcgaagcaac ggcccggagg gtggcgggca ggacgcccgc    1140
cataaactgc caggcatcaa attaagcaga aggccatcct gacggatggc cttttgcgt    1200 ttctacaaac tcttttgttt attttttctaa atacattcaa atatgtatcc gctcatgaga    1260
caataaccct gataaatgct tcaataatat tgaaaaagga gagtatgag tattcaacat     1320 ttccgtgtcg cccttattcc ctttttttgcg gcatttttgcc ttcctgtttt tgctcaccca    1380
gaaacgctgt gaaagtaaa agatgctgaa gatcagttgg gtgcacgagt gggttacatc     1440
gaactggatc tcaacagcgg taagatcctt gagagttttc gccccgaaga acgttttcca     1500
atgatgagca cttttaaagt tctgctatgt ggcgcggtat tatcccgtgt tgacgccggg     1560
caagagcaac tcggtcgccg catacactat tctcagaatg acttggttga gtactcacca     1620
gtcacagaaa agcatcttac ggatggcatg acagtaagag aattatgcag tgctgccata     1680
accatgagtg ataacactgc ggccaactta cttctgacaa cgatcggagg accgaaggag     1740
ctaaccgctt ttttgcacaa catgggggat catgtaactc gccttgatcg ttgggaaccg     1800
gagctgaatg aagccatacc aaacgacgag cgtgacacca cgatgcctgt agcaatggca    1860
acaacgttgc gcaaactatt aactggcgaa ctacttactc tagcttcccg gcaacaatta    1920
atagactgga tggaggcgga taaagttgca ggaccacttc tgcgctcggc ccttccggct    1980
ggctggttta ttgctgataa atctggagcc ggtgagcgtg gtctcgcgg tatcattgca     2040 gcactggggc cagatggtaa gccctcccgt atcgtagtta tctacacgac ggggagtcag    2100
gcaactatgg atgaacgaaa tagacagatc gctgagatag gtgcctcact gattaagcat    2160
tggtaactgt cagaccaagt ttactcatat atactttaga ttgatttaaa acttcatttt    2220
taatttaaaa ggatctaggt gaagatcctt tttgataatc tcatgaccaa atcccttaa     2280 cgtgagtttt cgttccactg agcgtcagac cccgtagaaa agatcaaagg atcttcttga    2340
gatccttttt ttctgcgcgt aatctgctgc ttgcaaacaa aaaaaccacc gctaccagcg    2400
gtggtttgtt tgccggatca agagctacca actctttttc cgaaggtaac tggcttcagc    2460
agagcgcaga taccaaatac tgtccttcta gtgtagccgt agttaggcca ccacttcaag    2520
aactctgtag caccgcctac atacctcgct ctgctaatcc tgttaccagt ggctgctgcc    2580
```

```
agtggcgata agtcgtgtct taccggttg gactcaagac gatagttacc ggataaggcg      2640
cagcggtcgg gctgaacggg gggttcgtgc acacagccca gcttggagcg aacgacctac     2700
accgaactga gatacctaca gcgtgagcta tgagaaagcg ccacgcttcc cgaagggaga     2760
aaggcggaca ggtatccggt aagcggcagg gtcggaacag gagagcgcac gagggagctt     2820 ccaggggggaa acgcctggta tctttatagt cctgtcgggt ttcgccacct ctgacttgag    2880
cgtcgatttt tgtgatgctc gtcagggggg cggagcctat ggaaaaacgc cagcaacgcg     2940 gccttttttac ggttcctggc cttttgctgg ccttttgctc acatgttctt cctgcgtta    3000 tcccctgatt ctgtggataa ccgtattacc gcctttgagt gagctgatac cgctcgccgc    3060
agccgaacga ccgagcgcag cgagtcagtg agcgaggaag cggaagagcg cctgatgcgg    3120
tattttctcc ttacgcatct gtgcggtatt tcacaccgca tatggtgcac tctcagtaca    3180
atctgctctg atgccgcata gttaagccag tatacactcc gctatcgcta cgtgactggg    3240
tcatggctgc gccccgacac ccgccaacac ccgctgacgc gccctgacgg gcttgtctgc    3300
tcccggcatc cgcttacaga caagctgtga ccgtctccgg gagctgcatg tgtcagaggt    3360
tttcaccgtc atcaccgaaa cgcgcgaggc agcagatcaa ttcgcgcgcg aaggcgaagc    3420
ggcatgcata atgtgcctgt caaatggacg aagcagggat tctgcaaacc ctatgctact    3480
ccgtcaagcc gtcaattgtc tgattcgtta ccaattatga caacttgacg ctacatcat    3540 tcacttttttc ttcacaaccg gcacggaact cgctcgggct ggccccggtg cattttttaa   3600
atacccgcga gaatagagt tgatcgtcaa accaacatt gcgaccgacg gtggcgatag    3660
gcatccgggt ggtgctcaaa agcagcttcg cctggctgat acgttggtcc tcgcgccagc    3720
ttaagacgct aatccctaac tgctggcgga aagatgtga cagacgcgac ggcgacaagc    3780
aaacatgctg tgcgacgctg gcgatatcaa aattgctgtc tgccaggtga tcgctgatgt    3840
actgacaagc ctcgcgtacc cgattatcca tcggtggatg gagcgactcg ttaatcgctt   3900
ccatgcgccg cagtaacaat tgctcaagca gatttatcgc cagcagctcc gaatagcgcc   3960 cttcccctg cccggcgtta atgatttgcc caaacaggtc gctgaaatgc ggctggtgcg    4020
cttcatccgg gcgaaagaac cccgtattgg caaatattga cggccagtta agccattcat    4080
gccagtaggc gcgcggacga agtaaaccc actggtgata ccattcgcga gcctccggat    4140
gacgaccgta gtgatgaatc tctcctggcg ggaacagcaa aatatcaccc ggtcggcaaa    4200
caaattctcg tccctgattt ttcaccaccc cctgaccgcg aatggtgaga ttgagaatat    4260
aacctttcat tcccagcggt cggtcgataa aaaaatcgag ataaccgttg gcctcaatcg    4320
gcgttaaacc cgccaccaga tgggcattaa acgagtatcc cggcagcagg ggatcatttt    4380
gcgcttcagc catactttttc atactcccgc cattcagaga agaaaccaat tgtccatatt    4440
gcatcagaca ttgccgtcac tgcgtctttt actggctctt ctcgctaacc aaaccggtaa    4500
ccccgcttat taaagcatt ctgtaacaaa gcgggaccaa agccatgaca aaaacgcgta    4560
acaaaagtgt ctataatcac ggcagaaaag tccacattga ttatttgcac ggcgtcacac    4620
tttgctatgc catagcattt ttatccataa gattagcgga tcctacctga cgcttttttat   4680 cgcaactctc tactgtttct ccatacccgt tttttgggct aacaggagga attaac         4736
```

<210> SEQ ID NO 103
<211> LENGTH: 4694
<212> TYPE: DNA
<213> ORGANISM: Artificial sequence
<220> FEATURE:

<223> OTHER INFORMATION: pRF216

<400> SEQUENCE: 103

```
catgggcat caccatcacc accattgttt tttcaaagac gaactggaat tcggaggtgg      60
cggtgcatcc tcggaggatg tgattaaaga atttatgcgg tttaaagtac gtatggaagg    120
atcggtgaat ggccatgaat tgagattga gggtgaaggc gaaggccgcc cgtacgaagg    180
aactcaaaca gcgaaattaa aagttacaaa aggaggtcct ctgccgtttg cctgggacat    240
cttgagcccg caattccagt acggttccaa agtgtatgta aaacaccctg cggatattcc    300
ggattataaa aaactgagtt tccccgaggg gtttaaatgg gaacgggtga tgaattttga    360
ggatggtgga gttgtcaccg tgacccagga ctctagctta caagacggta gtttcatcta    420
caaagtaaaa tttatcggcg taaacttccc atcggacggc cccgtcatgc agaaaaagac    480
gatgggctgg gaagccagca ccgaacgttt gtacccacgg gacggcgttt tgaaagggga    540
aatccataag gcccttaaac tgaaagacgt tggtcactat ctcgtggagt ttaaatcgat    600
ttatatggct aaaaaaccag tacagcttcc gggttattat tacgttgact ccaaattgga    660
catcacatcg cataatgaag attacacgat tgttgaacag tacgagcgcg ccgagggccg    720
gcaccatctg tttctgtaaa agcttggctg ttttggcgga tgagagaaga ttttcagcct    780
gatacagatt aaatcagaac gcagaagcgg tctgataaaa cagaatttgc ctggcggcag    840
tagcgcggtg gtcccacctg accccatgcc gaactcagaa gtgaaacgcc gtagcgccga    900
tggtagtgtg gggtctcccc atgcgagagt agggaactgc caggcatcaa ataaaacgaa    960
aggctcagtc gaaagactgg gcctttcgtt ttatctgttg tttgtcggtg aacgctctcc   1020
tgagtaggac aaatccgccg ggagcggatt tgaacgttgc gaagcaacgg cccggagggt   1080
ggcgggcagg acgcccgcca taaactgcca ggcatcaaat taagcagaag gccatcctga   1140
cggatggcct ttttgcgttt ctacaaactc ttttgtttat ttttctaaat acattcaaat   1200
atgtatccgc tcatgagaca ataaccctga taaatgcttc aataatattg aaaaaggaag   1260
agtatgagta ttcaacattt ccgtgtcgcc cttattccct ttttttgcggc attttgcctt   1320
cctgtttttg ctcacccaga aacgctggtg aaagtaaaag atgctgaaga tcagttgggt   1380
gcacgagtgg gttacatcga actggatctc aacagcggta agatccttga gttttcgc    1440
cccgaagaac gttttccaat gatgagcact tttaaagttc tgctatgtgg cgcggtatta   1500
tcccgtgttg acgccgggca agagcaactc ggtcgccgca tacactattc tcagaatgac   1560
ttggttgagt actcaccagt cacagaaaag catcttacgg atggcatgac agtaagagaa   1620
ttatgcagtg ctgccataac catgagtgat aacactgcgg ccaacttact tctgacaacg   1680
atcggaggac cgaaggagct aaccgctttt ttgcacaaca tgggggatca tgtaactcgc   1740
cttgatcgtt gggaaccgga gctgaatgaa gccataccaa acgacgagcg tgacaccacg   1800
atgcctgtag caatggcaac aacgttgcgc aaactattaa ctggcgaact acttactcta   1860
gcttcccggc aacaattaat agactggatg gaggcggata agttgcagg accacttctg    1920
cgctcggccc ttccggctgg ctggtttatt gctgataaat ctggagccgg tgagcgtggg   1980
tctcgcggta tcattgcagc actggggcca gatggtaagc cctcccgtat cgtagttatc   2040
tacacgacgg ggagtcaggc aactatggat gaacgaaata gacagatcgc tgagataggt   2100
gcctcactga ttaagcattg gtaactgtca gaccaagttt actcatatat actttagatt   2160
gatttaaaac ttcatttttta atttaaaagg atctaggtga agatcctttt tgataatctc   2220
atgaccaaaa tcccttaacg tgagttttcg ttccactgag cgtcagaccc cgtagaaaag   2280
```

```
atcaaaggat cttcttgaga tccttttttt ctgcgcgtaa tctgctgctt gcaaacaaaa    2340
aaaccaccgc taccagcggt ggtttgtttg ccggatcaag agctaccaac tcttttttccg   2400
aaggtaactg gcttcagcag agcgcagata ccaaatactg tccttctagt gtagccgtag    2460
ttaggccacc acttcaagaa ctctgtagca ccgcctacat acctcgctct gctaatcctg    2520
ttaccagtgg ctgctgccag tggcgataag tcgtgtctta ccgggttgga ctcaagacga    2580
tagttaccgg ataaggcgca gcggtcgggc tgaacggggg gttcgtgcac acagcccagc    2640
ttggagcgaa cgacctacac cgaactgaga tacctacagc gtgagctatg agaaagcgcc    2700
acgcttcccg aagggagaaa ggcggacagg tatccggtaa cgcggcaggt cggaacagga    2760
gagcgcacga gggagcttcc agggggaaac gcctggtatc tttatagtcc tgtcgggttt    2820
cgccacctct gacttgagcg tcgatttttg tgatgctcgt caggggggcg agcctatgg     2880
aaaaacgcca gcaacgcggc cttttttacgg ttcctggcct tttgctggcc ttttgctcac   2940
atgttctttc ctgcgttatc ccctgattct gtggataacc gtattaccgc ctttgagtga    3000
gctgataccg ctcgccgcag ccgaacgacc gagcgcagcg agtcagtgag cgaggaagcg    3060
gaagagcgcc tgatgcggta ttttctcctt acgcatctgt gcggtatttc acaccgcata    3120
tggtgcactc tcagtacaat ctgctctgat gccgcatagt taagccagta tacactccgc    3180
tatcgctacg tgactgggtc atggctgcgc cccgacaccc gccaacaccc gctgacgcgc    3240
cctgacgggc ttgtctgctc ccggcatccg cttacagaca agctgtgacc gtctccggga    3300
gctgcatgtg tcagaggttt tcaccgtcat caccgaaacg cgcgaggcag cagatcaatt    3360
cgcgcgcgaa ggcgaagcgg catgcataat gtgcctgtca aatggacgaa gcagggattc    3420
tgcaaaccct atgctactcc gtcaagccgt caattgtctg attcgttacc aattatgaca    3480
acttgacggc tacatcattc acttttttctt cacaaccggc acggaactcg ctcgggctgg   3540
ccccggtgca ttttttaaat acccgcgaga aatagagttg atcgtcaaaa ccaacattgc    3600
gaccgacggt ggcgataggc atccgggtgg tgctcaaaag cagcttcgcc tggctgatac    3660
gttggtcctc gcgccagctt aagacgctaa tccctaactg ctggcggaaa agatgtgaca    3720
gacgcgacgg cgacaagcaa acatgctgtg cgacgctggc gatatcaaaa ttgctgtctg    3780
ccaggtgatc gctgatgtac tgacaagcct cgcgtacccg attatccatc ggtggatgga    3840
gcgactcgtt aatcgcttcc atgcgccgca gtaacaattg ctcaagcaga tttatcgcca    3900
gcagctccga atagcgccct tccccttgcc cggcgttaat gatttgccca acaggtcgc    3960
tgaaatgcgc ctggtgcgct tcatccgggc gaaagaaccc cgtattggca aatattgacg    4020
gccagttaag ccattcatgc cagtaggcgc gcggacgaaa gtaaacccac tggtgatacc    4080
attcgcgagc ctccgatga cgaccgtagt gatgaatctc tcctggcggg aacagcaaaa     4140
tatcacccgg tcggcaaaca aattctcgtc cctgatttt caccacccc tgaccgcgaa      4200
tggtgagatt gagaatataa cctttcattc ccagcggtcg gtcgataaaa aaatcgagat    4260
aaccgttggc ctcaatcggc gttaaacccg ccaccagatg ggcattaaac gagtatcccg    4320
gcagcagggg atcattttgc gcttcagcca tactttttcat actccgcca ttcagagaag    4380
aaaccaattg tccatattgc atcagacatt gccgtcactg cgtctttttac tggctcttct   4440
cgctaaccaa accggtaacc ccgcttatta aaagcattct gtaacaaagc gggaccaaag    4500
ccatgacaaa aacgcgtaac aaaagtgtct ataatcacgg cagaaaagtc cacattgatt    4560
atttgcacgg cgtcacactt tgctatgcca tagcattttt atccataaga ttagcggatc    4620
```
ctacctgacg cttttatcg caactctcta ctgtttctcc atacccgttt tttgggctaa     4680
caggaggaat taac                                                      4694

<210> SEQ ID NO 104
<211> LENGTH: 23
<212> TYPE: DNA
<213> ORGANISM: Artificial sequence
<220> FEATURE:
<223> OTHER INFORMATION: oligo 36

<400> SEQUENCE: 104
ccataagatt agcggatcct acc                                              23

<210> SEQ ID NO 105
<211> LENGTH: 331
<212> TYPE: DNA
<213> ORGANISM: Artificial sequence
<220> FEATURE:
<223> OTHER INFORMATION: His-Zebra PCR

<400> SEQUENCE: 105
ccataagatt agcggatcct acctgacgct ttttatcgca actctctact gtttctccat     60
acccgttttt tgggctaaca ggaggaatta accatggggc atcaccacca tcaccacgaa    120
tgcgactcag aactggaaat caaacgctat aaacgtgtgc gtgtggcatc ccgtaaatgt    180
cgcgcaaagt ttaaacagct gctgaacat tatcgtgaag tagcggctgc gaaaagctcc    240
gaaaacgacc gtttacgcct cctcctgaag caaatgtgcg aattcgacaa gaaatactcc    300
atcggcctgg acattggaac caactctgtc g                                   331

<210> SEQ ID NO 106
<211> LENGTH: 232
<212> TYPE: DNA
<213> ORGANISM: Artificial sequence
<220> FEATURE:
<223> OTHER INFORMATION: His-tp10 PCR

<400> SEQUENCE: 106
ccataagatt agcggatcct acctgacgct ttttatcgca actctctact gtttctccat     60
acccgttttt tgggctaaca ggaggaatta accatggggc atcaccacca tcaccacgcg    120
ggttacctgc tggcaagat taatcttaaa gcctgcgccg cgtgtgctaa gaaaattttg    180
gaattcgaca agaaatactc catcggcctg gacattggaa ccaactctgt cg           232

<210> SEQ ID NO 107
<211> LENGTH: 223
<212> TYPE: DNA
<213> ORGANISM: artificial sequence
<220> FEATURE:
<223> OTHER INFORMATION: His-pVEC PCR

<400> SEQUENCE: 107
ccataagatt agcggatcct acctgacgct ttttatcgca actctctact gtttctccat     60
acccgttttt tgggctaaca ggaggaatta accatggggc atcaccacca tcaccactta    120
ttgattatct tgcgtcgtcg catccgcaaa caggcgcacg cacatagcaa ggaattcgac    180
aagaaatact ccatcggcct ggacattgga accaactctg tcg                     223

<210> SEQ ID NO 108
<211> LENGTH: 8294
<212> TYPE: DNA
<213> ORGANISM: Artificial sequence
<220> FEATURE:
<223> OTHER INFORMATION: pRF144

<400> SEQUENCE: 108

```
ccatggggca tcaccaccat caccacgaat gcgactcaga actggaaatc aaacgctata      60
aacgtgtgcg tgtggcatcc cgtaaatgtc gcgcaaagtt taaacagctg ctgcaacatt     120
atcgtgaagt agcggctgcg aaaagctccg aaaacgaccg tttacgcctc ctcctgaagc     180
aaatgtgcga attcgacaag aaatactcca tcggcctgga cattggaacc aactctgtcg     240
gctgggctgt catcaccgac gagtacaagg tgccctccaa gaaattcaag gtcctcggaa     300
acaccgatcg acactccatc aagaaaaacc tcattggtgc cctgttgttc gattctggcg     360
agactgccga agctaccaga ctcaagcgaa ctgctcggcg acgttacacc cgacggaaga     420
accgaatctg ctacctgcag gagatctttt ccaacgagat ggccaaggtg gacgattcgt     480
tctttcatcg actggaggaa tccttcctcg tcgaggaaga caagaaacac gagcgtcatc     540
ccatctttgg caacattgtg gacgaggttg cttaccacga agtatcct accatctacc       600
acctgcgaaa gaaactcgtc gattccaccg acaaggcgga tctcagactt atctacctcg     660
ctctggcaca catgatcaag tttcgaggtc atttcctcat cgagggcgat ctcaatcccg     720
acaacagcga tgtggacaag ctgttcattc agctcgttca gacctacaac cagctgttcg     780
aggaaaaccc catcaatgcc tccggagtcg atgcaaaggc catcttgtct gctcgactct     840
cgaagagcag acgactggag aacctcattg cccaacttcc tggcgagaaa agaacggac     900
tgtttggcaa cctcattgcc ctttctcttg gtctcacacc caacttcaag tccaacttcg     960
atctggcgga ggacgccaag ctccagctgt ccaaggacac ctacgacgat gacctcgaca    1020
acctgcttgc acagattggc gatcagtacg ccgacctgtt tctcgctgcc aagaaccttt    1080
cggatgctat tctcttgtct gacattctgc gagtcaacac cgagatcaca aaggctcccc    1140
tttctgcctc catgatcaag cgatacgacg agcaccatca ggatctcaca ctgctcaagg    1200
ctcttgtccg acagcaactg cccgagaagt acaaggagat cttttttcgat cagtcgaaga    1260
acggctacgc tggatacatc gacggcggag cctctcagga agagttctac aagttcatca    1320
agccaattct cgagaagatg gacggaaccg aggaactgct tgtcaagctc aatcgagagg    1380
atctgcttcg gaagcaacga accttcgaca acggcagcat tcctcatcag atccacctcg    1440
gtgagctgca cgccattctt cgacgtcagg aagacttcta ccccttttctc aaggacaacc    1500
gagagaagat cgagaagatt cttacctttc gaatcccccta ctatgttggt cctcttgcca    1560
gaggaaactc tcgatttgct tggatgactc gaaagtccga ggaaaccatc actccctgga    1620
acttcgagga agtcgtggac aagggtgcct ctgcacagtc cttcatcgag cgaatgacca    1680
acttcgacaa gaatctgccc aacgagaagg ttcttcccaa gcattcgctg ctctacgagt    1740
actttacagt ctacaacgaa ctcaccaaag tcaagtacgt taccgaggga atgcgaaagc    1800
ctgccttctt gtctggcgaa cagaagaaag ccattgtcga tctcctgttc aagaccaacc    1860
gaaaggtcac tgttaagcag ctcaaggagg actacttcaa gaaaatcgag tgtttcgaca    1920
gcgtcgagat ttccggagtt gaggaccgat tcaacgcctc tttgggcacc atcacgatc     1980
tgctcaagat tatcaaggac aaggattttc tcgacaacga ggaaaacgag gacattctgg    2040
aggacatcgt gctcactctt accctgttcg aagatcggga gatgatcgag gaacgactca    2100
agacatacgc tcacctgttc gacgacaagg tcatgaaaca actcaagcga cgtagataca    2160
ccggctgggg aagactttcg cgaaagctca tcaacggcat cagagacaag cagtccggaa    2220
```

```
agaccattct ggactttctc aagtccgatg gctttgccaa ccgaaacttc atgcagctca    2280
ttcacgacga ttctcttacc ttcaaggagg acatccagaa ggcacaagtg tccggtcagg    2340
gcgacagctt gcacgaacat attgccaacc tggctggttc gccagccatc aagaaaggca    2400
ttctccagac tgtcaaggtt gtcgacgagc tggtgaaggt catgggacgt cacaagcccg    2460
agaacattgt gatcgagatg gccagagaga accagacaac tcaaaagggt cagaaaaact    2520
cgcgagagcg gatgaagcga atcgaggaag gcatcaagga gctgggatcc cagattctca    2580
aggagcatcc cgtcgagaac actcaactgc agaacgagaa gctgtatctc tactatctgc    2640
agaatggtcg agacatgtac gtggatcagg aactggacat caatcgtctc agcgactacg    2700
atgtggacca cattgtccct caatcctttc tcaaggacga ttctatcgac aacaaggtcc    2760
ttacacgatc cgacaagaac agaggcaagt cggacaacgt tcccagcgaa gaggtggtca    2820 aaagatgaa gaactactgg cgacagctgc tcaacgccaa gctcattacc cagcgaaagt    2880
tcgacaatct taccaaggcc gagcgaggcg gtctgtccga gctcgacaag gctggcttca    2940
tcaagcgtca actcgtcgag accagacaga tcacaaagca cgtcgcacag attctcgatt    3000
ctcggatgaa caccaagtac gacgagaacg acaagctcat ccgagaggtc aaggtgatta    3060
ctctcaagtc caaactggtc tccgatttcc gaaaggactt tcagttctac aaggtgcgag    3120
agatcaacaa ttaccaccat gcccacgatg cttacctcaa cgccgtcgtt ggcactgcgc    3180
tcatcaagaa atacccaag ctcgaaagcg agttcgttta cggcgattac aaggtctacg    3240
acgttcgaaa gatgattgcc aagtccgaac aggagattgg caaggctact gccaagtact    3300
tcttttactc caacatcatg aacttttca agaccgagat caccttggcc aacgagaga    3360 ttcgaaagag accacttatc gagaccaacg gcgaaactgg agagatcgtg tgggacaagg    3420
gtcgagactt gcaaccgtg cgaaaggttc tgtcgatgcc tcaggtcaac atcgtcaaga    3480
aaaccgaggt tcagactggc ggattctcca aggagtcgat tctgcccaag cgaaactccg    3540
acaagctcat cgctcgaaag aaagactggg atcccaagaa atacgtggc ttcgattctc    3600 ctaccgtcgc ctattccgtg cttgtcgttg cgaaggtcga gaagggcaag tccaaaaagc    3660
tcaagtccgt caaggagctg ctcggaatta ccatcatgga gcgatcgagc ttcgagaaga    3720
atcccatcga cttcttggaa gccaagggtt acaaggaggt caagaaagac ctcattatca    3780
agctgcccaa gtactctctg ttcgaactgg agaacggtcg aaagcgtatg ctcgcctccg    3840
ctggcgagct gcagaaggga acgagcttg ccttgccttc gaagtacgtc aactttctct    3900
atctggcttc tcactacgag aagctcaagg gttctcccga ggacaacgaa cagaagcaac    3960
tcttcgttga gcagcacaaa cattacctcg acgagattat cgagcagatt tccgagtttt    4020
cgaagcgagt catcctggct gatgccaact tggacaaggt gctctctgcc tacaacaagc    4080
atcgggacaa acccattcga gaacaggcgg agaacatcat tcacctgttt actcttacca    4140
acctgggtgc tcctgcagct ttcaagtact tcgataccac tatcgaccga agcggtaca    4200 catccaccaa ggaggttctc gatgccaccc tgattcacca gtccatcact ggcctgtacg    4260
agacccgaat cgacctgtct cagcttggtg gcgactccag agccgatccc aagaaaaagc    4320
gaaaggtcta gcggccgct aagcttggct gttttggcgg atgagagaag attttcagcc    4380
tgatacagat taaatcagaa cgcagaagcg gtctgataaa acagaatttg cctggcggca    4440
gtagcgcggt ggtcccacct gaccccatgc cgaactcaga agtgaaacgc cgtagcgccg    4500
atggtagtgt ggggtctccc catgcgagag tagggaactg ccaggcatca aataaaacga    4560
aaggctcagt cgaaagactg ggcctttcgt tttatctgtt gtttgtcggt gaacgctctc    4620
```

```
ctgagtagga caaatccgcc gggagcggat ttgaacgttg cgaagcaacg gcccggaggg    4680
tggcgggcag gacgcccgcc ataaactgcc aggcatcaaa ttaagcagaa ggccatcctg    4740
acggatggcc ttttttgcgtt tctacaaact cttttgttta tttttctaaa tacattcaaa   4800
tatgtatccg ctcatgagac aataaccctg ataaatgctt caataatatt gaaaaaggaa    4860
gagtatgagt attcaacatt tccgtgtcgc ccttattccc ttttttgcgg cattttgcct    4920
tcctgttttt gctcacccag aaacgctggt gaaagtaaaa gatgctgaag atcagttggg    4980
tgcacgagtg ggttacatcg aactggatct caacagcggt aagatccttg agagttttcg    5040
ccccgaagaa cgttttccaa tgatgagcac ttttaaagtt ctgctatgtg gcgcggtatt    5100
atcccgtgtt gacgccgggc aagagcaact cggtcgccgc atacactatt ctcagaatga    5160
cttggttgag tactcaccag tcacagaaaa gcatcttacg gatggcatga cagtaagaga    5220
attatgcagt gctgccataa ccatgagtga taacactgcg gccaacttac ttctgacaac    5280
gatcggagga ccgaaggagc taaccgcttt tttgcacaac atgggggatc atgtaactcg    5340
ccttgatcgt tgggaaccgg agctgaatga agccatacca aacgacgagc gtgacaccac    5400
gatgcctgta gcaatggcaa caacgttgcg caaactatta actggcgaac tacttactct    5460
agcttcccgg caacaattaa tagactggat ggaggcggat aaagttgcag gaccacttct    5520
gcgctcggcc cttccggctg gctggtttat tgctgataaa tctggagccg gtgagcgtgg    5580
gtctcgcggt atcattgcag cactggggcc agatggtaag ccctcccgta tcgtagttat    5640
ctacacgacg gggagtcagg caactatgga tgaacgaaat agacagatcg ctgagatagg    5700
tgcctcactg attaagcatt ggtaactgtc agaccaagtt tactcatata ctttttagat    5760
tgatttaaaa cttcatttttt aatttaaaag gatctaggtg aagatccttt ttgataatct    5820
catgaccaaa atcccttaac gtgagttttc gttccactga gcgtcagacc ccgtagaaaa    5880
gatcaaagga tcttcttgag atccttttttt tctgcgcgta atctgctgct tgcaaacaaa    5940
aaaaccaccg ctaccagcgg tggtttgttt gccggatcaa gagctaccaa ctcttttttcc    6000 gaaggtaact ggcttcagca gagcgcagat accaaatact gtccttctag tgtagccgta    6060
gttaggccac cacttcaaga actctgtagc accgcctaca tacctcgctc tgctaatcct    6120
gttaccagtg gctgctgcca gtggcgataa gtcgtgtctt accgggttgg actcaagacg    6180
atagttaccg gataaggcgc agcggtcggg ctgaacgggg ggttcgtgca cacagcccag    6240
cttggagcga acgacctaca ccgaactgag atacctacag cgtgagctat gagaaagcgc    6300
cacgcttccc gaagggagaa aggcggacag gtatccggta agcggcaggg tcggaacagg    6360
agagcgcacg agggagcttc caggggggaaa cgcctggtat ctttatagtc ctgtcgggtt    6420
tcgccacctc tgacttgagc gtcgatttttt gtgatgctcg tcaggggggc ggagcctatg    6480
gaaaaacgcc agcaacgcgg ccttttttacg gttcctggcc ttttgctggc cttttgctca    6540
catgttcttt cctgcgttat cccctgattc tgtggataac cgtattaccg cctttgagtg    6600
agctgatacc gctcgccgca gccgaacgac cgagcgcagc gagtcagtga gcgaggaagc    6660
ggaagagcgc ctgatgcggt attttctcct tacgcatctg tgcggtattt cacaccgcat    6720
atggtgcact ctcagtacaa tctgctctga tgccgcatag ttaagccagt atacactccg    6780
ctatcgctac gtgactgggt catggctgcg ccccgacacc cgccaacacc cgctgacgcg    6840
ccctgacggg cttgtctgct cccggcatcc gcttacagac aagctgtgac cgtctccggg    6900
agctgcatgt gtcagaggtt ttcaccgtca tcaccgaaac gcgcgaggca gcagatcaat    6960
```

```
tcgcgcgcga aggcgaagcg gcatgcataa tgtgcctgtc aaatggacga agcagggatt    7020
ctgcaaaccc tatgctactc cgtcaagccg tcaattgtct gattcgttac caattatgac    7080
aacttgacgg ctacatcatt cacttttctt tcacaaccgg cacggaactc gctcgggctg    7140
gccccggtgc atttttaaa tacccgcgag aaatagagtt gatcgtcaaa accaacattg    7200
cgaccgacgg tggcgatagg catccgggtg gtgctcaaaa gcagcttcgc ctggctgata    7260
cgttggtcct cgcgccagct taagacgcta atccctaact gctggcggaa agatgtgac    7320
agacgcgacg gcgacaagca aacatgctgt gcgacgctgg cgatatcaaa attgctgtct    7380
gccaggtgat cgctgatgta ctgacaagcc tcgcgtaccc gattatccat cggtggatgg    7440
agcgactcgt taatcgcttc catgcgccgc agtaacaatt gctcaagcag atttatcgcc    7500
agcagctccg aatagcgccc ttccccttgc ccggcgttaa tgatttgccc aaacaggtcg    7560
ctgaaatgcg gctggtgcgc ttcatccggg cgaaagaacc ccgtattggc aaatattgac    7620
ggccagttaa gccattcatg ccagtaggcg cgcggacgaa agtaaaccca ctggtgatac    7680
cattcgcgag cctccggatg acgaccgtag tgatgaatct ctcctggcgg aacagcaaa    7740
atatcacccg gtcggcaaac aaattctcgt ccctgatttt tcaccacccc ctgaccgcga    7800
atggtgagat tgagaatata acctttcatt cccagcggtc ggtcgataaa aaaatcgaga    7860
taaccgttgg cctcaatcgg cgttaaaccc gccaccagat gggcattaaa cgagtatccc    7920
ggcagcaggg gatcattttg cgcttcagcc atacttttca tactcccgcc attcagagaa    7980
gaaaccaatt gtccatattg catcagacat tgccgtcact gcgtctttta ctggctcttc    8040
tcgctaacca aaccggtaac cccgcttatt aaaagcattc tgtaacaaag cgggaccaaa    8100
gccatgacaa aaacgcgtaa caaaagtgtc tataatcacg gcagaaaagt ccacattgat    8160
tatttgcacg gcgtcacact ttgctatgcc atagcatttt tatccataag attagcggat    8220
cctacctgac gctttttatc gcaactctct actgtttctc catacccgtt ttttgggcta    8280
acaggaggaa ttaa                                                      8294
```

<210> SEQ ID NO 109
<211> LENGTH: 8195
<212> TYPE: DNA
<213> ORGANISM: Artificial sequence
<220> FEATURE:
<223> OTHER INFORMATION: pRF162

<400> SEQUENCE: 109

```
aattcgacaa gaaatactcc atcggcctgg acattggaac caactctgtc ggctgggctg     60
tcatcaccga cgagtacaag gtgccctcca agaaattcaa ggtcctcgga acaccgatc    120
gacactccat caagaaaaac ctcattggtg ccctgttgtt cgattctggc gagactgccg    180
aagctaccag actcaagcga actgctcggc gacgttacac ccgacggaag aaccgaatct    240
gctacctgca ggagatcttt tccaacgaga tggccaaggt ggacgattcg ttctttcatc    300
gactggagga atccttcctc gtcgaggaag acaagaaaca cgagcgtcat ccatctttg    360
gcaacattgt ggacgaggtt gcttaccacg agaagtatcc taccatctac cacctgcgaa    420
agaaactcgt cgattccacc gacaaggcgg atctcagact tatctacctc gctctggcac    480
acatgatcaa gtttcgaggt catttcctca tcgagggcga tctcaatccc gacaacagcg    540
atgtggacaa gctgttcatt cagctcgttc agacctacaa ccagctgttc gaggaaaacc    600
ccatcaatgc ctccgagtc gatgcaaagg ccatcttgtc tgctcgactc tcgaagagca    660
gacgactgga gaacctcatt gcccaacttc ctggcgagaa aaagaacgga ctgtttggca    720
```

-continued

```
acctcattgc cctttctctt ggtctcacac ccaacttcaa gtccaacttc gatctggcgg      780
aggacgccaa gctccagctg tccaaggaca cctacgacga tgacctcgac aacctgcttg      840
cacagattgg cgatcagtac gccgacctgt ttctcgctgc caagaacctt tcggatgcta      900
ttctcttgtc tgacattctg cgagtcaaca ccgagtcaca aaaggctccc ctttctgcct      960
ccatgatcaa gcgatacgac gagcaccatc aggatctcac actgctcaag gctcttgtcc     1020
gacagcaact gcccgagaag tacaaggaga tcttttttcga tcagtcgaag aacggctacg     1080
ctggatacat cgacggcgga gcctctcagg aagagttcta caagttcatc aagccaattc     1140
tcgagaagat ggacggaacc gaggaactgc ttgtcaagct caatcgagag gatctgcttc     1200
ggaagcaacg aaccttcgac aacggcagca ttcctcatca gatccacctc ggtgagctgc     1260
acgccattct tcgacgtcag gaagacttct accccttct caaggacaac cgagagaaga     1320
tcgagaagat tcttaccttt cgaatcccct actatgttgg tcctcttgcc agaggaaact     1380
ctcgatttgc ttggatgact cgaaagtccg aggaaaccat cactccctgg aacttcgagg     1440
aagtcgtgga caagggtgcc tctgcacagt ccttcatcga gcgaatgacc aacttcgaca     1500
agaatctgcc caacgagaag gttcttccca agcattcgct gctctacgag tactttacag     1560
tctacaacga actcaccaaa gtcaagtacg ttaccgaggg aatgcgaaag cctgccttct     1620
tgtctggcga acagaagaaa gccattgtcg atctcctgtt caagaccaac cgaaaggtca     1680
ctgttaagca gctcaaggag gactacttca agaaaatcga gtgtttcgac agcgtcgaga     1740
tttccggagt tgaggaccga ttcaacgcct ctttgggcac ctatcacgat ctgctcaaga     1800
ttatcaagga caaggatttt ctcgacaacg aggaaaacga ggacattctg gaggacatcg     1860
tgctcactct taccctgttc gaagatcggg agatgatcga ggaacgactc aagacatacg     1920
ctcacctgtt cgacgacaag gtcatgaaac aactcaagcg acgtagatac accggctggg     1980
gaagactttc gcgaaagctc atcaacggca tcagagacaa gcagtccgga agaccattc     2040 tggactttct caagtccgat ggctttgcca accgaaactt catgcagctc attcacgacg     2100
attctcttac cttcaaggag gacatccaga aggcacaagt gtccggtcag ggcgacagct     2160
tgcacgaaca tattgccaac ctggctggtt cgccagccat caagaaaggc attctccaga     2220
ctgtcaaggt tgtcgacgag ctggtgaagg tcatgggacg tcacaagccc gagaacattg     2280
tgatcgagat ggccagagag aaccagacaa ctcaaaaggg tcagaaaaac tcgcgagagc     2340
ggatgaagcg aatcgaggaa ggcatcaagg agctgggatc ccagattctc aaggagcatc     2400
ccgtcgagaa cactcaactg cagaacgaga agctgtatct ctactatctg cagaatggtc     2460
gagacatgta cgtggatcag gaactggaca tcaatcgtct cagcgactac gatgtggacc     2520
acattgtccc tcaatccttt ctcaaggacg attctatcga caacaaggtc cttacacgat     2580
ccgacaagaa cagaggcaag tcggacaacg ttcccagcga agaggtggtc aaaaagatga     2640
agaactactg gcgacagctg ctcaacgcca agctcattac ccagcgaaag ttcgacaatc     2700
ttaccaaggc cgagcgaggc ggtctgtccg agctcgacaa ggctggcttc atcaagcgtc     2760
aactcgtcga gaccagacag atcacaaagc acgtcgcaca gattctcgat tctcggatga     2820
acaccaagta cgacgagaac gacaagctca tccgagaggt caaggtgatt actctcaagt     2880
ccaaactggt ctccgatttc cgaaaggact ttcagttcta caaggtgcga gagatcaaca     2940
attaccacca tgcccacgat gcttacctca acgccgtcgt tggcactgcg ctcatcaaga     3000
aataccccaa gctcgaaagc gagttcgttt acggcgatta caaggtctac gacgttcgaa     3060
```

```
agatgattgc caagtccgaa caggagattg gcaaggctac tgccaagtac ttctttttact    3120
ccaacatcat gaacttttttc aagaccgaga tcaccttggc caacggagag attcgaaaga    3180
gaccacttat cgagaccaac ggcgaaactg gagagatcgt gtgggacaag ggtcgagact    3240
ttgcaaccgt gcgaaaggtt ctgtcgatgc ctcaggtcaa catcgtcaag aaaaccgagg    3300
ttcagactgg cggattctcc aaggagtcga ttctgcccaa gcgaaactcc gacaagctca    3360
tcgctcgaaa gaaagactgg gatcccaaga aatacggtgg cttcgattct cctaccgtcg    3420
cctattccgt gcttgtcgtt gcgaaggtcg agaagggcaa gtccaaaaag ctcaagtccg    3480
tcaaggagct gctcggaatt accatcatgg agcgatcgag cttcgagaag aatcccatcg    3540
acttcttgga agccaagggt tacaaggagg tcaagaaaga cctcattatc aagctgccca    3600
agtactctct gttcgaactg gagaacggtc gaaagcgtat gctcgcctcc gctggcgagc    3660
tgcagaaggg aaacgagctt gccttgcctt cgaagtacgt caactttctc tatctggctt    3720
ctcactacga gaagctcaag ggttctcccg aggacaacga acagaagcaa ctcttcgttg    3780
agcagcacaa acattacctc gacgagatta tcgagcagat ttccgagttt tcgaagcgag    3840
tcatcctggc tgatgccaac ttggacaagg tgctctctgc ctacaacaag catcgggaca    3900
aacccattcg agaacaggcg gagaacatca ttcacctgtt tactcttacc aacctgggtg    3960
ctcctgcagc tttcaagtac ttcgatacca ctatcgaccg aaagcggtac acatccacca    4020
aggaggttct cgatgccacc ctgattcacc agtccatcac tggcctgtac gagacccgaa    4080
tcgacctgtc tcagcttggt ggcgactcca gagccgatcc caagaaaaag cgaaaggtct    4140
aagcggccgc taagcttggc tgttttggcg gatgagagaa gattttcagc ctgatacaga    4200
ttaaatcaga acgcagaagc ggtctgataa acagaatttt gcctggcggc agtagcgcgg    4260
tggtcccacc tgacccccatg ccgaactcag aagtgaaacg ccgtagcgcc gatggtagtg    4320
tggggtctcc ccatgcgaga gtagggaact gccaggcatc aaataaaacg aaaggctcag    4380
tcgaaagact gggcctttcg ttttatctgt tgtttgtcgg tgaacgctct cctgagtagg    4440
acaaatccgc cgggagcgga tttgaacgtt gcgaagcaac ggcccggagg gtggcgggca    4500
ggacgcccgc cataaactgc caggcatcaa attaagcaga aggccatcct gacggatggc    4560
ctttttgcgt ttctacaaac tcttttgttt attttttctaa atacattcaa atatgtatcc    4620
gctcatgaga caataaccct gataaatgct tcaataatat tgaaaaagga agagtatgag    4680
tattcaacat ttccgtgtcg cccttattcc cttttttgcg gcattttgcc ttcctgtttt    4740
tgctcaccca gaaacgctgg tgaaagtaaa agatgctgaa gatcagttgg gtgcacgagt    4800
gggttacatc gaactggatc tcaacagcgg taagatcctt gagagttttc gccccgaaga    4860
acgttttcca atgatgagca cttttaaagt tctgctatgt ggcgcggtat tatcccgtgt    4920
tgacgccggg caagagcaac tcggtcgccg catacactat tctcagaatg acttggttga    4980
gtactcacca gtcacagaaa agcatcttac ggatggcatg acagtaagag aattatgcag    5040
tgctgccata accatgagtg ataacactgc ggccaactta cttctgacaa cgatcggagg    5100
accgaaggag ctaaccgctt ttttgcacaa catgggggat catgtaactc gccttgatcg    5160
ttgggaaccg gagctgaatg aagccatacc aaacgacgag cgtgacacca cgatgcctgt    5220
agcaatggca acaacgttgc gcaaactatt aactggcgaa ctacttactc tagcttcccg    5280
gcaacaatta atagactgga tggaggcgga taaagttgca ggaccacttc tgcgctcggc    5340
ccttccggct ggctggttta ttgctgataa atctggagcc ggtgagcgtg ggtctcgcgg    5400
tatcattgca gcactggggc cagatggtaa gccctcccgt atcgtagtta tctacacgac    5460
```

```
gggggagtcag gcaactatgg atgaacgaaa tagacagatc gctgagatag gtgcctcact    5520
gattaagcat tggtaactgt cagaccaagt ttactcatat atactttaga ttgatttaaa    5580
acttcatttt taatttaaaa ggatctaggt gaagatcctt tttgataatc tcatgaccaa    5640
aatcccttaa cgtgagtttt cgttccactg agcgtcagac cccgtagaaa agatcaaagg    5700
atcttcttga tccttttttt ttctgcgcgt aatctgctgc ttgcaaacaa aaaaaccacc    5760
gctaccagcg gtggtttgtt tgccggatca agagctacca actcttttcc gaaggtaac     5820 tggcttcagc agagcgcaga taccaaatac tgtccttcta gtgtagccgt agttaggcca    5880
ccacttcaag aactctgtag caccgcctac atacctcgct ctgctaatcc tgttaccagt    5940
ggctgctgcc agtggcgata agtcgtgtct taccggggttg gactcaagac gatagttacc    6000
ggataaggcg cagcggtcgg gctgaacggg gggttcgtgc acacagccca gcttggagcg    6060
aacgacctac accgaactga gatacctaca gcgtgagcta tgagaaagcg ccacgcttcc    6120
cgaagggaga aaggcggaca ggtatccggt aagcggcagg gtcggaacag gagagcgcac    6180
gagggagctt ccagggggaa acgcctggta tctttatagt cctgtcgggt ttcgccacct    6240
ctgacttgag cgtcgatttt tgtgatgctc gtcaggggg cggagcctat ggaaaaacgc     6300
cagcaacgcg gcctttttac ggttcctggc cttttgctgg ccttttgctc acatgttctt    6360
tcctgcgtta tcccctgatt ctgtggataa ccgtattacc gcctttgagt gagctgatac    6420
cgctcgccgc agccgaacga ccgagcgcag cgagtcagtg agcgaggaag cggaagagcg    6480
cctgatgcgg tattttctcc ttacgcatct gtgcggtatt tcacaccgca tatggtgcac    6540
tctcagtaca atctgctctg atgccgcata gttaagccag tatacactcc gctatcgcta    6600
cgtgactggg tcatggctgc gccccgacac ccgccaacac ccgctgacgc gccctgacgg    6660
gcttgtctgc tcccggcatc cgcttacaga caagctgtga ccgtctccgg gagctgcatg    6720
tgtcagaggt tttcaccgtc atcaccgaaa cgcgcgaggc agcagatcaa ttcgcgcgcg    6780
aaggcgaagc ggcatgcata atgtgcctgt caaatggacg aagcagggat tctgcaaacc    6840
ctatgctact ccgtcaagcc gtcaattgtc tgattcgtta ccaattatga caacttgacg    6900
gctacatcat tcactttttc ttcacaaccg gcacggaact cgctcgggct ggccccggtg    6960 catttttta ataccecgcga gaaatagagt tgatcgtcaa aaccaacatt gcgaccgacg    7020
gtggcgatag gcatccgggt ggtgctcaaa agcagcttcg cctggctgat acgttggtcc    7080
tcgcgccagc ttaagacgct aatccctaac tgctggcgga aaagatgtga cagacgcgac    7140
ggcgacaagc aaacatgctg tgcgacgctg gcgatatcaa aattgctgtc tgccaggtga    7200
tcgctgatgt actgacaagc ctcgcgtacc cgattatcca tcggtggatg gagcgactcg    7260
ttaatcgctt ccatgcgccg cagtaacaat tgctcaagca gatttatcgc cagcagctcc    7320
gaatagcgcc cttccccttg cccggcgtta atgatttgcc caaacaggtc gctgaaatgc    7380
ggctggtgcg cttcatccgg gcgaaagaac ccgtattgg caaatattga cggccagtta    7440
agccattcat gccagtaggc gcgcggacga agtaaaccc actggtgata ccattcgcga    7500
gcctccggat gacgaccgta gtgatgaatc tctcctggcg ggaacagcaa aatatcaccc    7560
ggtcggcaaa caaattctcg tccctgattt ttcaccaccc cctgaccgcg aatggtgaga    7620
ttgagaatat aacctttcat tcccagcggt cggtcgataa aaaatcgag ataaccgttg     7680 gcctcaatcg cgcgttaaacc cgccaccaga tgggcattaa acgagtatcc cggcagcagg    7740
ggatcatttt gcgcttcagc catacttttc atactcccgc cattcagaga agaaaccaat    7800
```

| | |
|---|---:|
| tgtccatatt gcatcagaca ttgccgtcac tgcgtcttttt actggctctt ctcgctaacc | 7860 |
| aaaccggtaa ccccgcttat taaaagcatt ctgtaacaaa gcgggaccaa agccatgaca | 7920 |
| aaaacgcgta acaaaagtgt ctataatcac ggcagaaaag tccacattga ttatttgcac | 7980 |
| ggcgtcacac tttgctatgc catagcattt ttatccataa gattagcgga tcctacctga | 8040 |
| cgctttttat cgcaactctc tactgtttct ccatacccgt tttttgggct aacaggagga | 8100 |
| attaaccatg gggcatcacc accatcacca cgcgggttac ctgctgggca agattaatct | 8160 |
| taaagcctgc gccgcgtgtg ctaagaaaat tttgg | 8195 |

<210> SEQ ID NO 110
<211> LENGTH: 8186
<212> TYPE: DNA
<213> ORGANISM: Artificial Sequence
<220> FEATURE:
<223> OTHER INFORMATION: pRF146

<400> SEQUENCE: 110

| | |
|---|---:|
| aattcgacaa gaaatactcc atcggcctgg acattggaac caactctgtc ggctgggctg | 60 |
| tcatcaccga cgagtacaag gtgccctcca agaaattcaa ggtcctcgga acaccgatc | 120 |
| gacactccat caagaaaaac ctcattggtg ccctgttgtt cgattctggc gagactgccg | 180 |
| aagctaccag actcaagcga actgctcggc gacgttacac ccgacggaag aaccgaatct | 240 |
| gctacctgca ggagatcttt ccaacgaga tggccaaggt ggacgattcg ttctttcatc | 300 |
| gactggagga atccttcctc gtcgaggaag acaagaaaca cgagcgtcat cccatctttg | 360 |
| gcaacattgt ggacgaggtt gcttaccacg agaagtatcc taccatctac cacctgcgaa | 420 |
| agaaactcgt cgattccacc gacaaggcgg atctcagact tatctacctc gctctggcac | 480 |
| acatgatcaa gtttcgaggt catttcctca tcgagggcga tctcaatccc gacaacagcg | 540 |
| atgtggacaa gctgttcatt cagctcgttc agacctacaa ccagctgttc gaggaaaaacc | 600 |
| ccatcaatgc ctccggagtc gatgcaaagg ccatcttgtc tgctcgactc tcgaagagca | 660 |
| gacgactgga gaacctcatt gcccaacttc ctggcgagaa aaagaacgga ctgtttggca | 720 |
| acctcattgc cctttctctt ggtctcacac ccaacttcaa gtccaacttc gatctggcgg | 780 |
| aggacgccaa gctccagctg tccaaggaca cctacgacga tgacctcgac aacctgcttg | 840 |
| cacagattgg cgatcagtac gccgacctgt ttctcgctgc caagaacctt tcggatgcta | 900 |
| ttctcttgtc tgacattctg cgagtcaaca ccgagatcac aaaggctccc ctttctgcct | 960 |
| ccatgatcaa gcgatacgac gagcaccatc aggatctcac actgctcaag gctcttgtcc | 1020 |
| gacagcaact gcccgagaag tacaaggaga tctttttcga tcagtcgaag aacggctacg | 1080 |
| ctggatacat cgacggcgga gcctctcagg aagagttcta caagttcatc aagccaattc | 1140 |
| tcgagaagat ggacggaacc gaggaactgc ttgtcaagct caatcgagag atctgcttc | 1200 |
| ggaagcaacg aaccttcgac aacgcagca ttcctcatca gatccacctc ggtgagctgc | 1260 |
| acgccattct tcgacgtcag gaagacttct accccttct caaggacaac cgagagaaga | 1320 |
| tcgagaagat tcttaccttt cgaatcccct actatgttgg tcctcttgcc agaggaaact | 1380 |
| ctcgatttgc ttggatgact cgaaagtccg aggaaaccat cactccctgg aacttcgagg | 1440 |
| aagtcgtgga caagggtgcc tctgcacagt ccttcatcga gcgaatgacc aacttcgaca | 1500 |
| agaatctgcc caacgagaag gttcttccca gcattcgct gctctacgag tactttacag | 1560 |
| tctacaacga actcaccaaa gtcaagtacg ttaccgaggg aatgcgaaag cctgccttct | 1620 |
| tgtctggcga acagaagaaa gccattgtcg atctcctgtt caagaccaac cgaaaggtca | 1680 |

```
ctgttaagca gctcaaggag gactacttca agaaaatcga gtgtttcgac agcgtcgaga    1740
tttccggagt tgaggaccga ttcaacgcct ctttgggcac ctatcacgat ctgctcaaga    1800
ttatcaagga caaggatttt ctcgacaacg aggaaaacga ggacattctg gaggacatcg    1860
tgctcactct taccctgttc gaagatcggg agatgatcga ggaacgactc aagacatacg    1920
ctcacctgtt cgacgacaag gtcatgaaac aactcaagcg acgtagatac accggctggg    1980
gaagactttc gcgaaagctc atcaacggca tcagagacaa gcagtccgga agaccattc     2040
tggactttct caagtccgat ggctttgcca accgaaactt catgcagctc attcacgacg    2100
attctcttac cttcaaggag gacatccaga aggcacaagt gtccggtcag gcgacagct     2160
tgcacgaaca tattgccaac ctggctggtt cgccagccat caagaaaggc attctccaga    2220
ctgtcaaggt tgtcgacgag ctggtgaagg tcatgggacg tcacaagccc gagaacattg    2280
tgatcgagat ggccagagag aaccagacaa ctcaaaaggg tcagaaaaac tcgcgagagc    2340
ggatgaagcg aatcgaggaa ggcatcaagg agctgggatc ccagattctc aaggagcatc    2400
ccgtcgagaa cactcaactg cagaacgaga gctgtatct ctactatctg cagaatggtc      2460
gagacatgta cgtggatcag gaactggaca tcaatcgtct cagcgactac gatgtggacc    2520
acattgtccc tcaatccttt ctcaaggacg attctatcga caacaaggtc cttacacgat    2580
ccgacaagaa cagaggcaag tcggacaacg ttcccagcga agaggtggtc aaaaagatga    2640
agaactactg gcgacagctg ctcaacgcca agctcattac ccagcgaaag ttcgacaatc    2700
ttaccaaggc cgagcgaggc ggtctgtccg agctcgacaa ggctggcttc atcaagcgtc    2760
aactcgtcga gaccagacag atcacaaagc acgtcgcaca gattctcgat tctcggatga    2820
acaccaagta cgacgagaac gacaagctca tccgagaggt caaggtgatt actctcaagt    2880
ccaaactggt ctccgatttc cgaaaggact tcagttcta caaggtgcga gagatcaaca      2940
attaccacca tgcccacgat gcttacctca acgccgtcgt tggcactgcg ctcatcaaga    3000
aataccccaa gctcgaaagc gagttcgttt acggcgatta caaggtctac gacgttcgaa    3060
agatgattgc caagtccgaa caggagattg caaggctac tgccaagtac ttctttttact      3120
ccaacatcat gaacttttc aagaccgaga tcaccttggc caacgagag attcgaaaga       3180
gaccacttat cgagaccaac ggcgaaactg gagagatcgt gtgggacaag ggtcgagact    3240
ttgcaaccgt gcgaaaggtt ctgtcgatgc ctcaggtcaa catcgtcaag aaaaccgagg    3300
ttcagactgg cggattctcc aaggagtcga ttctgcccaa gcgaaactcc gacaagctca    3360
tcgctcgaaa gaaagactgg gatcccaaga aatacggtgg cttcgattct cctaccgtcg    3420
cctattccgt gcttgtcgtt gcgaaggtcg agaagggcaa gtccaaaaag ctcaagtccg    3480
tcaaggagct gctcggaatt accatcatgg agcgatcgag cttcgagaag aatcccatcg    3540
acttcttgga agccaagggt tacaaggagg tcaagaaaga cctcattatc aagctgccca    3600
agtactctct gttcgaactg gagaacggtc gaaagcgtat gctcgcctcc gctggcgagc    3660
tgcagaaggg aaacgagctt gccttgcctt cgaagtacgt caactttctc tatctggctt    3720
ctcactacga gaagctcaag ggttctcccg aggacaacga acagaagcaa ctcttcgttg    3780
agcagcacaa acattacctc gacgagatta tcgagcagat ttccgagttt tcgaagcgag    3840
tcatcctggc tgatgccaac ttggacaagg tgctctctgc ctacaacaag catcgggaca    3900
aacccattcg agaacaggcg gagaaacatc aatccacctgtt tactcttacc aacctgggtg    3960
ctcctgcagc tttcaagtac ttcgatacca ctatcgaccg aaagcggtac acatccacca    4020
```

```
aggaggttct cgatgccacc ctgattcacc agtccatcac tggcctgtac gagacccgaa   4080
tcgacctgtc tcagcttggt ggcgactcca gagccgatcc caagaaaaag cgaaaggtct   4140
aagcggccgc taagcttggc tgttttggcg gatgagagaa gattttcagc ctgatacaga   4200
ttaaatcaga acgcagaagc ggtctgataa aacagaattt gcctggcggc agtagcgcgg   4260
tggtcccacc tgaccccatg ccgaactcag aagtgaaacg ccgtagcgcc gatggtagtg   4320
tggggtctcc ccatgcgaga gtagggaact gccaggcatc aaataaaacg aaaggctcag   4380
tcgaaagact gggcctttcg ttttatctgt tgtttgtcgg tgaacgctct cctgagtagg   4440
acaaatccgc cgggagcgga tttgaacgtt gcgaagcaac ggcccggagg gtggcgggca   4500
ggacgcccgc cataaactgc caggcatcaa attaagcaga aggccatcct gacggatggc   4560 cttttttgcgt ttctacaaac tcttttgttt attttttctaa atacattcaa atatgtatcc   4620
gctcatgaga caataacccct gataaatgct tcaataatat tgaaaaagga gagtatgag   4680 tattcaacat ttccgtgtcg cccttattcc cttttttgcg gcattttgcc ttcctgtttt   4740
tgctcaccca gaaacgctgg tgaaagtaaa agatgctgaa gatcagttgg gtgcacgagt   4800
gggttacatc gaactggatc tcaacagcgg taagatcctt gagagttttc gccccgaaga   4860
acgttttcca atgatgagca cttttaaagt tctgctatgt ggcgcggtat tatcccgtgt   4920
tgacgccggg caagagcaac tcggtcgccg catacactat tctcagaatg acttggttga   4980
gtactcacca gtcacagaaa agcatcttac ggatggcatg acagtaagag aattatgcag   5040
tgctgccata accatgagtg ataacactgc ggccaactta cttctgacaa cgatcggagg   5100
accgaaggag ctaaccgctt ttttgcacaa catgggggat catgtaactc gccttgatcg   5160
ttgggaaccg gagctgaatg aagccatacc aaacgacgag cgtgacacca cgatgcctgt   5220
agcaatggca acaacgttgc gcaaactatt aactggcgaa ctacttactc tagcttcccg   5280
gcaacaatta atagactgga tggaggcgga taaagttgca ggaccacttc tgcgctcggc   5340
ccttccggct ggctggttta ttgctgataa atctggagcc ggtgagcgtg gtctcgcgg    5400 tatcattgca gcactggggc cagatggtaa gccctcccgt atcgtagtta tctacacgac   5460
ggggagtcag gcaactatgg atgaacgaaa tagacagatc gctgagatag gtgcctcact   5520
gattaagcat tggtaactgt cagaccaagt ttactcatat atactttaga ttgatttaaa   5580 acttcattt taatttaaaa ggatctaggt gaagatcctt tttgataatc tcatgaccaa   5640
aatcccttaa cgtgagtttt cgttccactg agcgtcagac cccgtagaaa agatcaaagg   5700
atcttcttga tccttttttt ttctgcgcgt aatctgctgc ttgcaaacaa aaaaaccacc   5760
gctaccagcg gtggtttgtt tgccggatca agagctacca actctttttc cgaaggtaac   5820
tggcttcagc agagcgcaga taccaaatac tgtccttcta gtgtagccgt agttaggcca   5880
ccacttcaag aactctgtag caccgcctac atacctcgct ctgctaatcc tgttaccagt   5940
ggctgctgcc agtggcgata gtcgtgtct taccggggttg gactcaagac gatagttacc   6000
ggataaggcg cagcggtcgg gctgaacggg gggttcgtgc acacagccca gcttggagcg   6060
aacgacctac accgaactga gatacctaca gcgtgagcta tgagaaagcg ccacgcttcc   6120
cgaagggaga aaggcggaca ggtatccggt aagcggcagg gtcggaacag gagagcgcac   6180
gagggagctt ccagggggaa acgcctggta tctttatagt cctgtcgggt ttcgccacct   6240
ctgacttgag cgtcgatttt tgtgatgctc gtcaggggg cggagcctat ggaaaaacgc    6300
cagcaacgcg gccttttta cggttcctgg cttttgctgg ccttttgctc acatgttctt   6360
tcctgcgtta tccctgatt ctgtggataa ccgtattacc gcctttgagt gagctgatac   6420
```

```
cgctcgccgc agccgaacga ccgagcgcag cgagtcagtg agcgaggaag cggaagagcg   6480
cctgatgcgg tattttctcc ttacgcatct gtgcggtatt tcacaccgca tatggtgcac   6540
tctcagtaca atctgctctg atgccgcata gttaagccag tatacactcc gctatcgcta   6600
cgtgactggg tcatggctgc gccccgcacac ccgccaacac ccgctgacgc gccctgacgg   6660
gcttgtctgc tcccggcatc cgcttacaga caagctgtga ccgtctccgg gagctgcatg   6720
tgtcagaggt tttcaccgtc atcaccgaaa cgcgcgaggc agcagatcaa ttcgcgcgcg   6780
aaggcgaagc ggcatgcata atgtgcctgt caaatggacg aagcagggat tctgcaaacc   6840
ctatgctact ccgtcaagcc gtcaattgtc tgattcgtta ccaattatga caacttgacg   6900
gctacatcat tcactttttc ttcacaaccg gcacggaact cgctcgggct ggccccggtg   6960
cattttttaa atacccgcga gaaatagagt tgatcgtcaa aaccaacatt gcgaccgacg   7020
gtggcgatag gcatccgggt ggtgctcaaa agcagcttcg cctggctgat acgttggtcc   7080
tcgcgccagc ttaagacgct aatccctaac tgctggcgga aaagatgtga cagacgcgac   7140
ggcgacaagc aaacatgctg tgcgacgctg gcgatatcaa aattgctgtc tgccaggtga   7200
tcgctgatgt actgacaagc ctcgcgtacc cgattatcca tcggtggatg gagcgactcg   7260
ttaatcgctt ccatgcgccg cagtaacaat tgctcaagca gatttatcgc cagcagctcc   7320
gaatagcgcc cttccccttg cccggcgtta atgatttgcc caaacaggtc gctgaaatgc   7380
ggctggtgcg cttcatccgg gcgaaagaac cccgtattgg caaatattga cggccagtta   7440
agccattcat gccagtaggc gcgcggacga aagtaaaccc actggtgata ccattcgcga   7500
gcctccggat gacgaccgta gtgatgaatc tctcctggcg ggaacagcaa aatatcaccc   7560
ggtcggcaaa caaattctcg tccctgattt ttcaccaccc cctgaccgcg aatggtgaga   7620
ttgagaatat aacctttcat tcccagcggt cggtcgataa aaaaatcgag ataaccgttg   7680
gcctcaatcg gcgttaaacc cgccaccaga tgggcattaa acgagtatcc cggcagcagg   7740
ggatcatttt gcgcttcagc catacttttc atactcccgc cattcagaga agaaaccaat   7800
tgtccatatt gcatcagaca ttgccgtcac tgcgtctttt actggctctt ctcgctaacc   7860
aaaccggtaa ccccgcttat taaaagcatt ctgtaacaaa gcgggaccaa agccatgaca   7920
aaaacgcgta acaaaagtgt ctataatcac ggcagaaaag tccacattga ttatttgcac   7980
ggcgtcacac tttgctatgc catagcattt ttatccataa gattagcgga tcctacctga   8040
cgctttttat cgcaactctc tactgtttct ccatacccgt tttttgggct aacaggagga   8100
attaaccatg gggcatcacc accatcacca cttattgatt atcttgcgtc gtcgcatccg   8160
caaacaggcg cacgcacata gcaagg                                        8186
```

<210> SEQ ID NO 111
<211> LENGTH: 20
<212> TYPE: DNA
<213> ORGANISM: Artificial sequencE
<220> FEATURE:
<223> OTHER INFORMATION: oligo 153

<400> SEQUENCE: 111
cgacagagtt ggttccaatg                                               20

<210> SEQ ID NO 112
<211> LENGTH: 4835
<212> TYPE: DNA
<213> ORGANISM: Artificial sequence
<220> FEATURE:

<223> OTHER INFORMATION: pRF186

<400> SEQUENCE: 112

```
catgggcat caccaccatc accacgaatg cgactcagaa ctggaaatca aacgctataa      60
acgtgtgcgt gtggcatccc gtaaatgtcg cgcaaagttt aaacagctgc tgcaacatta    120
tcgtgaagta gcggctgcga aaagctccga aaacgaccgt ttacgcctcc tcctgaagca    180
aatgtgcgaa ttcggaggtg gcggtgcatc ctcggaggat gtgattaaag aatttatgcg    240
gtttaaagta cgtatggaag gatcggtgaa tggccatgaa tttgagattg agggtgaagg    300
cgaaggccgc ccgtacgaag gaactcaaac agcgaaatta aaagttacaa aaggaggtcc    360
tctgccgttt gcctgggaca tcttgagccc gcaattccag tacggttcca aagtgtatgt    420
aaaacaccct gcggatattc cggattataa aaaactgagt tttcccgagg ggtttaaatg    480
ggaacgggtg atgaattttg aggatggtgg agttgtcacc gtgacccagg actctagctt    540
acaagacggt agtttcatct acaaagtaaa atttatcggc gtaaacttcc catcggacgg    600
ccccgtcatg cagaaaaaga cgatgggctg gaagccagc accgaacgtt tgtacccacg    660
ggacggcgtt ttgaaagggg aaatccataa ggcccttaaa ctgaaagacg gtggtcacta    720
tctcgtggag tttaaatcga tttatatggc taaaaaacca gtacagcttc cgggttatta    780
ttacgttgac tccaaattgg acatcacatc gcataatgaa gattacacga ttgttgaaca    840
gtacgagcgc gccgagggcc ggcaccatct gtttctgtaa aagcttggct gttttggcgg    900
atgagagaag attttcagcc tgatacagat aaatcagaa cgcagaagcg gtctgataaa    960
acagaatttg cctggcggca gtagcgcggt ggtcccacct gaccccatgc cgaactcaga   1020
agtgaaacgc cgtagcgccg atggtagtgt ggggtctccc catgcgagag tagggaactg   1080
ccaggcatca aataaaacga aaggctcagt cgaaagactg gcctttcgt tttatctgtt   1140
gtttgtcggt gaacgctctc ctgagtagga caaatccgcc gggagcggat ttgaacgttg   1200
cgaagcaacg gcccggaggg tggcgggcag acgcccgcc ataaactgcc aggcatcaaa   1260
ttaagcagaa ggccatcctg acggatggcc ttttgcgtt tctacaaact cttttgttta   1320
tttttctaaa tacattcaaa tatgtatccg ctcatgagac aataaccctg ataaatgctt   1380
caataatatt gaaaaaggaa gagtatgagt attcaacatt tccgtgtcgc ccttattccc   1440
ttttttgcgg catttttgcct tcctgttttt gctcacccag aaacgctggt gaaagtaaaa   1500
gatgctgaag atcagttggg tgcacgagtg ggttacatcg aactggatct caacagcggt   1560
aagatccttg agagttttcg ccccgaagaa cgttttccaa tgatgagcac ttttaaagtt   1620
ctgctatgtg gcgcggtatt atcccgtgtt gacgccgggc aagagcaact cggtcgccgc   1680
atacactatt ctcagaatga cttggttgag tactcaccag tcacagaaaa gcatcttacg   1740
gatggcatga cagtaagaga attatgcagt gctgccataa ccatgagtga taacactgcg   1800
gccaacttac ttctgacaac gatcggagga ccgaaggagc taaccgcttt tttgcacaac   1860
atgggggatc atgtaactcg ccttgatcgt tgggaaccgg agctgaatga agccatacca   1920
aacgacgagc gtgacaccac gatgcctgta gcaatggcaa caacgttgcg caaactatta   1980
actggcgaac tacttactct agcttcccgg caacaattaa tagactggat ggaggcggat   2040
aaagttgcag gaccacttct gcgctcggcc cttccggctg gctggtttat tgctgataaa   2100
tctggagccg gtgagcgtgg gtctcgcggt atcattgcag cactggggcc agatggtaag   2160
ccctcccgta tcgtagttat ctacacgacg gggagtcagg caactatgga tgaacgaaat   2220
agacagatcg ctgagatagg tgcctcactg attaagcatt ggtaactgtc agaccaagtt   2280
```

```
tactcatata tactttagat tgatttaaaa cttcattttt aatttaaaag gatctaggtg    2340
aagatccttt ttgataatct catgaccaaa atcccttaac gtgagttttc gttccactga    2400
gcgtcagacc ccgtagaaaa gatcaaagga tcttcttgag atccttttt tctgcgcgta    2460 atctgctgct tgcaaacaaa aaaccaccg ctaccagcgg tggtttgttt gccggatcaa    2520
gagctaccaa ctcttttcc gaaggtaact ggcttcagca gagcgcagat accaaatact    2580
gtccttctag tgtagccgta gttaggccac cacttcaaga actctgtagc accgcctaca    2640
tacctcgctc tgctaatcct gttaccagtg gctgctgcca gtggcgataa gtcgtgtctt    2700
accgggttgg actcaagacg atagttaccg gataaggcgc agcggtcggg ctgaacgggg    2760
ggttcgtgca cacagcccag cttggagcga acgacctaca ccgaactgag atacctacag    2820
cgtgagctat gagaaagcgc cacgcttccc gaagggagaa aggcggacag gtatccggta    2880
agcggcaggg tcggaacagg agagcgcacg agggagcttc caggggggaaa cgcctggtat    2940 ctttatagtc ctgtcgggtt tcgccacctc tgacttgagc gtcgattttt gtgatgctcg    3000
tcaggggggc ggagcctatg gaaaaacgcc agcaacgcgg ccttttacg gttcctggcc    3060 ttttgctggc cttttgctca catgttcttt cctgcgttat cccctgattc tgtggataac    3120
cgtattaccg cctttgagtg agctgatacc gctcgccgca gccgaacgac cgagcgcagc    3180
gagtcagtga gcgaggaagc ggaagagcgc ctgatgcggt attttctcct tacgcatctg    3240
tgcggtattt cacaccgcat atggtgcact ctcagtacaa tctgctctga tgccgcatag    3300
ttaagccagt atacactccg ctatcgctac gtgactgggt catggctgcg ccccgacacc    3360
cgccaacacc cgctgacgcg ccctgacggg cttgtctgct cccggcatcc gcttacagac    3420
aagctgtgac cgtctccggg agctgcatgt gtcagaggtt ttcaccgtca tcaccgaaac    3480
gcgcgaggca gcagatcaat tcgcgcgcga aggcgaagcg gcatgcataa tgtgcctgtc    3540
aaatggacga agcagggatt ctgcaaaccc tatgctactc cgtcaagccg tcaattgtct    3600
gattcgttac caattatgac aacttgacgg ctacatcatt cacttttct tcacaaccgg    3660 cacggaactc gctcgggctg gccccggtgc attttttaaa tacccgcgag aaatagagtt    3720
gatcgtcaaa accaacattg cgaccgacgg tggcgatagg catccgggtg gtgctcaaaa    3780
gcagcttcgc ctggctgata cgttggtcct cgcgccagct taagacgcta atccctaact    3840
gctggcggaa aagatgtgac agacgcgacg gcgacaagca acatgctgt gcgacgctgg    3900 cgatatcaaa attgctgtct gccaggtgat cgctgatgta ctgacaagcc tcgcgtaccc    3960
gattatccat cggtggatgg agcgactcgt taatcgcttc catgcgccgc agtaacaatt    4020
gctcaagcag atttatcgcc agcagctccg aatagcgccc ttcccttgc ccggcgttaa    4080 tgatttgccc aaacaggtcg ctgaaatgcg gctggtgcgc ttcatccggg cgaaagaacc    4140
ccgtattggc aaatattgac ggccagttaa gccattcatg ccagtaggcg cgcggacgaa    4200
agtaaaccca ctggtgatac cattcgcgag cctccggatg acgaccgtag tgatgaatct    4260
ctcctggcgg gaacagcaaa atatcacccg gtcggcaaac aaattctcgt ccctgatttt    4320
tcaccacccc ctgaccgcga atggtgagat tgagaatata acctttcatt cccagcggtc    4380
ggtcgataaa aaaatcgaga taaccgttgg cctcaatcgg cgttaaaccc gccaccagat    4440
gggcattaaa cgagtatccc ggcagcaggg gatcattttg cgcttcagcc atacttttca    4500
tactcccgcc attcagagaa gaaaccaatt gtccatattg catcagacat tgccgtcact    4560
gcgtctttta ctggctcttc tcgctaacca aaccggtaac cccgcttatt aaaagcattc    4620
```

| | |
|---|---|
| tgtaacaaag cgggaccaaa gccatgacaa aaacgcgtaa caaaagtgtc tataatcacg | 4680 |
| gcagaaaagt ccacattgat tatttgcacg gcgtcacact ttgctatgcc atagcatttt | 4740 |
| tatccataag attagcggat cctacctgac gcttttatc gcaactctct actgtttctc | 4800 |
| catacccgtt ttttgggcta acaggaggaa ttaac | 4835 |

```
<210> SEQ ID NO 113
<211> LENGTH: 4736
<212> TYPE: DNA
<213> ORGANISM: Artificial sequence
<220> FEATURE:
<223> OTHER INFORMATION: pRF192

<400> SEQUENCE: 113
```

| | |
|---|---|
| aattcggagg tggcggtgca tcctcggagg atgtgattaa agaatttatg cggtttaaag | 60 |
| tacgtatgga aggatcggtg aatggccatg aatttgagat tgagggtgaa ggcgaaggcc | 120 |
| gcccgtacga aggaactcaa acagcgaaat taaaagttac aaaaggaggt cctctgccgt | 180 |
| ttgcctggga catcttgagc ccgcaattcc agtacggttc caaagtgtat gtaaaacacc | 240 |
| ctgcggatat tccggattat aaaaaactga gttttcccga ggggtttaaa tgggaacggg | 300 |
| tgatgaattt tgaggatggt ggagttgtca ccgtgaccca ggactctagc ttacaagacg | 360 |
| gtagtttcat ctacaaagta aaatttatcg gcgtaaactt cccatcggac ggccccgtca | 420 |
| tgcagaaaaa gacgatgggc tgggaagcca gcaccgaacg tttgtaccca cgggacggcg | 480 |
| ttttgaaagg ggaaatccat aaggccctta aactgaaaga cggtggtcac tatctcgtgg | 540 |
| agtttaaatc gatttatatg gctaaaaaac cagtacagct tccgggttat tattacgttg | 600 |
| actccaaatt ggacatcaca tcgcataatg aagattacac gattgttgaa cagtacgagc | 660 |
| gcgccgaggg ccggcaccat ctgtttctgt aaaagcttgg ctgttttggc ggatgagaga | 720 |
| agattttcag cctgatacag attaaatcag aacgcagaag cggtctgata aaacagaatt | 780 |
| tgcctggcgg cagtagcgcg tggtcccac ctgaccccat gccgaactca gaagtgaaac | 840 |
| gccgtagcgc cgatggtagt gtggggtctc cccatgcgag agtagggaac tgccaggcat | 900 |
| caaataaaac gaaaggctca gtcgaaagac tgggcctttc gttttatctg ttgtttgtcg | 960 |
| gtgaacgctc tcctgagtag acaaatccg ccgggagcgg atttgaacgt tgcgaagcaa | 1020 |
| cggcccggag ggtggcgggc aggacgcccg ccataaactg ccaggcatca aattaagcag | 1080 |
| aaggccatcc tgacggatgg cctttttgcg tttctacaaa ctcttttgtt tatttttcta | 1140 |
| aatacattca aatatgtatc cgctcatgag acaataaccc tgataaatgc ttcaataata | 1200 |
| ttgaaaaagg aagagtatga gtattcaaca tttccgtgtc gcccttattc cctttttgc | 1260 |
| ggcattttgc cttcctgttt ttgctcaccc agaaacgctg tgaaagtaa agatgctga | 1320 |
| agatcagttg ggtgcacgag tgggttacat cgaactggat ctcaacagcg gtaagatcct | 1380 |
| tgagagtttt cgccccgaag aacgttttcc aatgatgagc acttttaaag ttctgctatg | 1440 |
| tggcgcggta ttatcccgtg ttgacgccgg gcaagagcaa ctcggtcgcc gcatacacta | 1500 |
| ttctcagaat gacttggttg agtactcacc agtcacagaa aagcatctta cggatggcat | 1560 |
| gacagtaaga gaattatgca gtgctgccat aaccatgagt gataacactg cggccaactt | 1620 |
| acttctgaca acgatcggag gaccgaagga gctaaccgct tttttgcaca acatggggga | 1680 |
| tcatgtaact cgccttgatc gttgggaacc ggagctgaat gaagccatac caaacgacga | 1740 |
| gcgtgacacc acgatgcctg tagcaatggc aacaacgttg cgcaaactat taactggcga | 1800 |
| actacttact ctagcttccc ggcaacaatt aatagactgg atggaggcgg ataaagttgc | 1860 |

-continued

```
aggaccactt ctgcgctcgg cccttccggc tggctggttt attgctgata aatctggagc    1920
cggtgagcgt gggtctcgcg gtatcattgc agcactgggg ccagatggta agccctcccg    1980
tatcgtagtt atctacacga cggggagtca ggcaactatg gatgaacgaa atagacagat    2040
cgctgagata ggtgcctcac tgattaagca ttggtaactg tcagaccaag tttactcata    2100
tatactttag attgatttaa aacttcattt ttaatttaaa aggatctagg tgaagatcct    2160
ttttgataat ctcatgacca aaatccctta acgtgagttt cgttccact gagcgtcaga    2220 ccccgtagaa aagatcaaag gatcttcttg agatcctttt tttctgcgcg taatctgctg    2280
cttgcaaaca aaaaaaccac cgctaccagc ggtggtttgt ttgccggatc aagagctacc    2340
aactcttttt ccgaaggtaa ctggcttcag cagagcgcag ataccaaata ctgtccttct    2400
agtgtagccg tagttaggcc accacttcaa gaactctgta gcaccgccta catacctcgc    2460
tctgctaatc ctgttaccag tggctgctgc cagtggcgat aagtcgtgtc ttaccgggtt    2520
ggactcaaga cgatagttac cggataaggc gcagcggtcg ggctgaacgg ggggttcgtg    2580
cacacagccc agcttggagc gaacgaccta caccgaactg agatacctac agcgtgagct    2640
atgagaaagc gccacgcttc ccgaagggag aaaggcggac aggtatccgg taagcggcag    2700
ggtcggaaca ggagagcgca cgagggagct tccagggga aacgcctggt atctttatag    2760
tcctgtcggg tttcgccacc tctgacttga gcgtcgattt tgtgatgct cgtcaggggg    2820 gcggagccta tggaaaaacg ccagcaacgc ggccttttta cggttcctgg ccttttgctg    2880
gccttttgct cacatgttct ttcctgcgtt atccctgat tctgtggata accgtattac    2940
cgcctttgag tgagctgata ccgctcgccg cagccgaacg accgagcgca gcgagtcagt    3000
gagcgaggaa gcggaagagc gcctgatgcg gtattttctc cttacgcatc tgtgcggtat    3060
ttcacaccgc atatggtgca ctctcagtac aatctgctct gatgccgcat agttaagcca    3120
gtatacactc cgctatcgct acgtgactgg gtcatggctg cgccccgaca cccgccaaca    3180
cccgctgacg cgccctgacg ggcttgtctg ctcccggcat ccgcttacag acaagctgtg    3240
accgtctccg ggagctgcat gtgtcagagg ttttcaccgt catcaccgaa acgcgcgagg    3300
cagcagatca attcgcgcgc gaaggcgaag cggcatgcat aatgtgcctg tcaaatggac    3360
gaagcaggga ttctgcaaac cctatgctac tccgtcaagc cgtcaattgt ctgattcgtt    3420
accaattatg acaacttgac ggctacatca ttcacttttt cttcacaacc ggcacggaac    3480
tcgctcgggc tggccccggt gcattttta aatacccgcg agaaatagag ttgatcgtca    3540
aaaccaacat tgcgaccgac ggtggcgata ggcatccggg tggtgctcaa aagcagcttc    3600
gcctggctga tacgttggtc ctcgcgccag cttaagacgc taatccctaa ctgctggcgg    3660
aaaagatgtg acagacgcga cggcgacaag caaacatgct gtgcgacgct ggcgatatca    3720
aaattgctgt ctgccaggtg atcgctgatg tactgacaag cctcgcgtac ccgattatcc    3780
atcggtggat ggagcgactc gttaatcgct tccatgcgcc gcagtaacaa ttgctcaagc    3840
agatttatcg ccagcagctc cgaatagcgc ccttcccctt gcccggcgtt aatgatttgc    3900
ccaaacaggt cgctgaaatg cggctggtgc gcttcatccg ggcgaaagaa cccgtattg    3960 gcaaatattg acgccagtt aagccattca tgccagtagg cgcgcggacg aaagtaaacc    4020
cactggtgat accattcgcg agcctccgga tgacgaccgt agtgatgaat ctctcctggc    4080
gggaacagca aaatatcacc cggtcggcaa acaaattctc gtccctgatt tttcaccacc    4140
ccctgaccgc gaatggtgag attgagaata taaccttttca ttcccagcgg tcggtcgata    4200
```

| | |
|---|---|
| aaaaaatcga gataaccgtt ggcctcaatc ggcgttaaac ccgccaccag atgggcatta | 4260 |
| aacgagtatc ccggcagcag gggatcattt tgcgcttcag ccatactttt catactcccg | 4320 |
| ccattcagag aagaaaccaa ttgtccatat tgcatcagac attgccgtca ctgcgtcttt | 4380 |
| tactggctct tctcgctaac caaaccggta accccgctta ttaaaagcat tctgtaacaa | 4440 |
| agcgggacca aagccatgac aaaaacgcgt aacaaaagtg tctataatca cggcagaaaa | 4500 |
| gtccacattg attatttgca cggcgtcaca ctttgctatg ccatagcatt tttatccata | 4560 |
| agattagcgg atcctacctg acgctttta tcgcaactct ctactgtttc tccatacccg | 4620 |
| tttttttggc taacaggagg aattaaccat ggggcatcac caccatcacc acgcgggtta | 4680 |
| cctgctgggc aagattaatc ttaaagcctg cgccgcgtgt gctaagaaaa ttttgg | 4736 |

<210> SEQ ID NO 114
<211> LENGTH: 4727
<212> TYPE: DNA
<213> ORGANISM: Artificial sequence
<220> FEATURE:
<223> OTHER INFORMATION: pRF190

<400> SEQUENCE: 114

| | |
|---|---|
| aattcggagg tggcggtgca tcctcggagg atgtgattaa agaatttatg cggtttaaag | 60 |
| tacgtatgga aggatcggtg aatggccatg aatttgagat tgagggtgaa ggcgaaggcc | 120 |
| gcccgtacga aggaactcaa acagcgaaat taaaagttac aaaaggaggt cctctgccgt | 180 |
| ttgcctggga catcttgagc ccgcaattcc agtacggttc caaagtgtat gtaaaacacc | 240 |
| ctgcggatat tccggattat aaaaaactga gttttcccga ggggtttaaa tgggaacggg | 300 |
| tgatgaattt tgaggatggt ggagttgtca ccgtgaccca ggactctagc ttacaagacg | 360 |
| gtagtttcat ctacaaagta aaatttatcg gcgtaaactt cccatcggac ggccccgtca | 420 |
| tgcagaaaaa gacgatgggc tgggaagcca gcaccgaacg tttgtaccca cgggacggcg | 480 |
| ttttgaaagg ggaaatccat aaggcccctta aactgaaaga cggtggtcac tatctcgtgg | 540 |
| agtttaaatc gatttatatg gctaaaaaac cagtacagct tccgggttat tattacgttg | 600 |
| actccaaatt ggacatcaca tcgcataatg aagattacac gattgttgaa cagtacgagc | 660 |
| gcgccgaggg ccggcaccat ctgtttctgt aaaagcttgg ctgttttggc ggatgagaga | 720 |
| agattttcag cctgatacag attaaatcag aacgcagaag cggtctgata aaacagaatt | 780 |
| tgcctggcgg cagtagcgcg gtggtcccac ctgaccccat gccgaactca gaagtgaaac | 840 |
| gccgtagcgc cgatggtagt gtggggtctc cccatgcgag agtagggaac tgccaggcat | 900 |
| caaataaaac gaaaggctca gtcgaaagac tgggcctttc gttttatctg ttgtttgtcg | 960 |
| gtgaacgctc tcctgagtag gacaaatccg ccgggagcgg atttgaacgt tgcgaagcaa | 1020 |
| cggcccggag ggtggcgggc aggacgcccg ccataaactg ccaggcatca attaagcag | 1080 |
| aaggccatcc tgacgatgg cctttttgcg tttctacaaa ctcttttgtt tatttttcta | 1140 |
| aatacattca aatatgtatc cgctcatgag acaataaccc tgataaatgc ttcaataata | 1200 |
| ttgaaaaagg aagagtatga gtattcaaca tttccgtgtc gcccttattc cctttttgc | 1260 |
| ggcattttgc cttcctgttt ttgctcaccc agaaacgctg tgaaagtaa agatgctga | 1320 |
| agatcagttg ggtgcacgag tgggttacat cgaactggat ctcaacagcg gtaagatcct | 1380 |
| tgagagtttt cgccccgaag aacgttttcc aatgatgagc acttttaaag ttctgctatg | 1440 |
| tggcgcggta ttatcccgtg ttgacgccgg gcaagagcaa ctcggtcgcc gcatacacta | 1500 |
| ttctcagaat gacttggttg agtactcacc agtcacagaa aagcatctta cggatggcat | 1560 |

```
gacagtaaga gaattatgca gtgctgccat aaccatgagt gataacactg cggccaactt    1620
acttctgaca acgatcggag gaccgaagga gctaaccgct tttttgcaca acatgggga     1680 tcatgtaact cgccttgatc gttgggaacc ggagctgaat gaagccatac caaacgacga    1740
gcgtgacacc acgatgcctg tagcaatggc aacaacgttg cgcaaactat taactggcga    1800
actacttact ctagcttccc ggcaacaatt aatagactgg atggaggcgg ataaagttgc    1860
aggaccactt ctgcgctcgg cccttccggc tggctggttt attgctgata aatctggagc    1920
cggtgagcgt gggtctcgcg gtatcattgc agcactgggg ccagatggta agccctcccg    1980
tatcgtagtt atctacacga cggggagtca ggcaactatg gatgaacgaa atagacagat    2040
cgctgagata ggtgcctcac tgattaagca ttggtaactg tcagaccaag tttactcata    2100
tatactttag attgatttaa aacttcattt ttaatttaaa aggatctagg tgaagatcct    2160
ttttgataat ctcatgacca aaatccctta acgtgagttt tcgttccact gagcgtcaga    2220
ccccgtagaa aagatcaaag gatcttcttg agatcctttt tttctgcgcg taatctgctg    2280
cttgcaaaca aaaaaaccac cgctaccagc ggtggtttgt ttgccggatc aagagctacc    2340
aactcttttt ccgaaggtaa ctggcttcag cagagcgcag ataccaaata ctgtccttct    2400
agtgtagccg tagttaggcc accacttcaa gaactctgta gcaccgccta catacctcgc    2460
tctgctaatc ctgttaccag tggctgctgc cagtggcgat aagtcgtgtc ttaccgggtt    2520
ggactcaaga cgatagttac cggataaggc gcagcggtcg ggctgaacgg ggggttcgtg    2580
cacacagccc agcttggagc gaacgaccta caccgaactg agatacctac agcgtgagct    2640
atgagaaagc gccacgcttc ccgaagggag aaaggcggac aggtatccgg taagcggcag    2700
ggtcggaaca ggagagcgca cgagggagct tccaggggga aacgcctggt atctttatag    2760
tcctgtcggg tttcgccacc tctgacttga gcgtcgattt ttgtgatgct cgtcaggggg    2820
gcggagccta tggaaaaacg ccagcaacgc ggcctttta cggttcctgg ccttttgctg    2880
gccttttgct cacatgttct ttcctgcgtt atccctgat tctgtggata accgtattac    2940
cgcctttgag tgagctgata ccgctcgccg cagccgaacg accgagcgca gcgagtcagt    3000
gagcgaggaa gcggaagagc gcctgatgcg gtattttctc cttacgcatc tgtgcggtat    3060
ttcacaccgc atatggtgca ctctcagtac aatctgctct gatgccgcat agttaagcca    3120
gtatacactc cgctatcgct acgtgactgg gtcatggctg cgccccgaca cccgccaaca    3180
cccgctgacg cgccctgacg ggcttgtctg ctcccggcat ccgcttacag acaagctgtg    3240
accgtctccg ggagctgcat gtgtcagagg ttttcaccgt catcaccgaa acgcgcgagg    3300
cagcagatca attcgcgcgc gaaggcgaag cggcatgcat aatgtgcctg tcaaatggac    3360
gaagcaggga ttctgcaaac cctatgctac tccgtcaagc cgtcaattgt ctgattcgtt    3420
accaattatg acaacttgac ggctacatca ttcacttttt cttcacaacc ggcacggaac    3480
tcgctcgggc tggccccggt gcatttttta aatacccgcg agaaatagag ttgatcgtca    3540
aaaccaacat tgcgaccgac ggtggcgata ggcatccggg tggtgctcaa aagcagcttc    3600
gcctggctga tacgttggtc ctcgcgccag cttaagacgc taatccctaa ctgctggcgg    3660
aaaagatgtg acagacgcga cggcgacaag caaacatgct gtgcgacgct ggcgatatca    3720
aaattgctgt ctgccaggtg atcgctgatg tactgacaag cctcgcgtac ccgattatcc    3780
atcggtggat ggagcgactc gttaatcgct tccatgcgcc gcagtaacaa ttgctcaagc    3840
agatttatcg ccagcagctc cgaatagcgc ccttccccct tgcccggcgtt aatgatttgc   3900
```

-continued

```
ccaaacaggt cgctgaaatg cggctggtgc gcttcatccg ggcgaaagaa ccccgtattg    3960
gcaaatattg acggccagtt aagccattca tgccagtagg cgcgcggacg aaagtaaacc    4020
cactggtgat accattcgcg agcctccgga tgacgaccgt agtgatgaat ctctcctggc    4080
gggaacagca aaatatcacc cggtcggcaa acaaattctc gtccctgatt tttcaccacc    4140
ccctgaccgc gaatggtgag attgagaata taacctttca ttcccagcgg tcggtcgata    4200
aaaaaatcga gataaccgtt ggcctcaatc ggcgttaaac ccgccaccag atgggcatta    4260
aacgagtatc ccggcagcag gggatcattt tgcgcttcag ccatactttt catactcccg    4320
ccattcagag aagaaaccaa ttgtccatat tgcatcagac attgccgtca ctgcgtcttt    4380
tactggctct tctcgctaac caaaccggta accccgctta ttaaaagcat tctgtaacaa    4440
agcgggacca aagccatgac aaaaacgcgt aacaaaagtg tctataatca cggcagaaaa    4500
gtccacattg attatttgca cggcgtcaca ctttgctatg ccatagcatt tttatccata    4560
agattagcgg atcctacctg acgcttttta tcgcaactct ctactgtttc tccatacccg    4620
tttttggggc taacaggagg aattaaccat ggggcatcac caccatcacc acttattgat    4680
tatcttgcgt cgtcgcatcc gcaaacaggc gcacgcacat agcaagg                 4727
```

<210> SEQ ID NO 115
<211> LENGTH: 1395
<212> TYPE: PRT
<213> ORGANISM: artificial sequence
<220> FEATURE:
<223> OTHER INFORMATION: his-CFFKDEL-Cas9

<400> SEQUENCE: 115

```
Met Gly His His His His His His Cys Phe Phe Lys Asp Glu Leu Glu
1               5                   10                  15

Phe Asp Lys Lys Tyr Ser Ile Gly Leu Asp Ile Gly Thr Asn Ser Val
            20                  25                  30

Gly Trp Ala Val Ile Thr Asp Glu Tyr Lys Val Pro Ser Lys Lys Phe
        35                  40                  45

Lys Val Leu Gly Asn Thr Asp Arg His Ser Ile Lys Lys Asn Leu Ile
    50                  55                  60

Gly Ala Leu Leu Phe Asp Ser Gly Glu Thr Ala Glu Ala Thr Arg Leu
65                  70                  75                  80

Lys Arg Thr Ala Arg Arg Arg Tyr Thr Arg Arg Lys Asn Arg Ile Cys
                85                  90                  95

Tyr Leu Gln Glu Ile Phe Ser Asn Glu Met Ala Lys Val Asp Asp Ser
            100                 105                 110

Phe Phe His Arg Leu Glu Glu Ser Phe Leu Val Glu Glu Asp Lys Lys
        115                 120                 125

His Glu Arg His Pro Ile Phe Gly Asn Ile Val Asp Glu Val Ala Tyr
    130                 135                 140

His Glu Lys Tyr Pro Thr Ile Tyr His Leu Arg Lys Lys Leu Val Asp
145                 150                 155                 160

Ser Thr Asp Lys Ala Asp Leu Arg Leu Ile Tyr Leu Ala Leu Ala His
                165                 170                 175

Met Ile Lys Phe Arg Gly His Phe Leu Ile Glu Gly Leu Asn Pro
            180                 185                 190

Asp Asn Ser Asp Val Asp Lys Leu Phe Ile Gln Leu Val Gln Thr Tyr
        195                 200                 205

Asn Gln Leu Phe Glu Glu Asn Pro Ile Asn Ala Ser Gly Val Asp Ala
    210                 215                 220
```

```
Lys Ala Ile Leu Ser Ala Arg Leu Ser Lys Ser Arg Arg Leu Glu Asn
225                 230                 235                 240

Leu Ile Ala Gln Leu Pro Gly Glu Lys Lys Asn Gly Leu Phe Gly Asn
                245                 250                 255

Leu Ile Ala Leu Ser Leu Gly Leu Thr Pro Asn Phe Lys Ser Asn Phe
            260                 265                 270

Asp Leu Ala Glu Asp Ala Lys Leu Gln Leu Ser Lys Asp Thr Tyr Asp
        275                 280                 285

Asp Asp Leu Asp Asn Leu Leu Ala Gln Ile Gly Asp Gln Tyr Ala Asp
    290                 295                 300

Leu Phe Leu Ala Ala Lys Asn Leu Ser Asp Ala Ile Leu Leu Ser Asp
305                 310                 315                 320

Ile Leu Arg Val Asn Thr Glu Ile Thr Lys Ala Pro Leu Ser Ala Ser
                325                 330                 335

Met Ile Lys Arg Tyr Asp Glu His His Gln Asp Leu Thr Leu Leu Lys
            340                 345                 350

Ala Leu Val Arg Gln Gln Leu Pro Glu Lys Tyr Lys Glu Ile Phe Phe
        355                 360                 365

Asp Gln Ser Lys Asn Gly Tyr Ala Gly Tyr Ile Asp Gly Gly Ala Ser
    370                 375                 380

Gln Glu Glu Phe Tyr Lys Phe Ile Lys Pro Ile Leu Glu Lys Met Asp
385                 390                 395                 400

Gly Thr Glu Glu Leu Leu Val Lys Leu Asn Arg Glu Asp Leu Leu Arg
                405                 410                 415

Lys Gln Arg Thr Phe Asp Asn Gly Ser Ile Pro His Gln Ile His Leu
            420                 425                 430

Gly Glu Leu His Ala Ile Leu Arg Arg Gln Glu Asp Phe Tyr Pro Phe
        435                 440                 445

Leu Lys Asp Asn Arg Glu Lys Ile Glu Lys Ile Leu Thr Phe Arg Ile
    450                 455                 460

Pro Tyr Tyr Val Gly Pro Leu Ala Arg Gly Asn Ser Arg Phe Ala Trp
465                 470                 475                 480

Met Thr Arg Lys Ser Glu Glu Thr Ile Thr Pro Trp Asn Phe Glu Glu
                485                 490                 495

Val Val Asp Lys Gly Ala Ser Ala Gln Ser Phe Ile Glu Arg Met Thr
            500                 505                 510

Asn Phe Asp Lys Asn Leu Pro Asn Glu Lys Val Leu Pro Lys His Ser
        515                 520                 525

Leu Leu Tyr Glu Tyr Phe Thr Val Tyr Asn Glu Leu Thr Lys Val Lys
    530                 535                 540

Tyr Val Thr Glu Gly Met Arg Lys Pro Ala Phe Leu Ser Gly Glu Gln
545                 550                 555                 560

Lys Lys Ala Ile Val Asp Leu Leu Phe Lys Thr Asn Arg Lys Val Thr
                565                 570                 575

Val Lys Gln Leu Lys Glu Asp Tyr Phe Lys Lys Ile Glu Cys Phe Asp
            580                 585                 590

Ser Val Glu Ile Ser Gly Val Glu Asp Arg Phe Asn Ala Ser Leu Gly
        595                 600                 605

Thr Tyr His Asp Leu Leu Lys Ile Ile Lys Asp Lys Asp Phe Leu Asp
    610                 615                 620

Asn Glu Glu Asn Glu Asp Ile Leu Glu Asp Ile Val Leu Thr Leu Thr
625                 630                 635                 640
```

```
Leu Phe Glu Asp Arg Glu Met Ile Glu Glu Arg Leu Lys Thr Tyr Ala
                645                 650                 655

His Leu Phe Asp Asp Lys Val Met Lys Gln Leu Lys Arg Arg Arg Tyr
                660                 665                 670

Thr Gly Trp Gly Arg Leu Ser Arg Lys Leu Ile Asn Gly Ile Arg Asp
            675                 680                 685

Lys Gln Ser Gly Lys Thr Ile Leu Asp Phe Leu Lys Ser Asp Gly Phe
        690                 695                 700

Ala Asn Arg Asn Phe Met Gln Leu Ile His Asp Asp Ser Leu Thr Phe
705                 710                 715                 720

Lys Glu Asp Ile Gln Lys Ala Gln Val Ser Gly Gln Gly Asp Ser Leu
                725                 730                 735

His Glu His Ile Ala Asn Leu Ala Gly Ser Pro Ala Ile Lys Lys Gly
                740                 745                 750

Ile Leu Gln Thr Val Lys Val Val Asp Glu Leu Val Lys Val Met Gly
                755                 760                 765

Arg His Lys Pro Glu Asn Ile Val Ile Glu Met Ala Arg Glu Asn Gln
                770                 775                 780

Thr Thr Gln Lys Gly Gln Lys Asn Ser Arg Glu Arg Met Lys Arg Ile
785                 790                 795                 800

Glu Glu Gly Ile Lys Glu Leu Gly Ser Gln Ile Leu Lys Glu His Pro
                805                 810                 815

Val Glu Asn Thr Gln Leu Gln Asn Glu Lys Leu Tyr Leu Tyr Tyr Leu
                820                 825                 830

Gln Asn Gly Arg Asp Met Tyr Val Asp Gln Glu Leu Asp Ile Asn Arg
                835                 840                 845

Leu Ser Asp Tyr Asp Val Asp His Ile Val Pro Gln Ser Phe Leu Lys
850                 855                 860

Asp Asp Ser Ile Asp Asn Lys Val Leu Thr Arg Ser Asp Lys Asn Arg
865                 870                 875                 880

Gly Lys Ser Asp Asn Val Pro Ser Glu Glu Val Val Lys Lys Met Lys
                885                 890                 895

Asn Tyr Trp Arg Gln Leu Leu Asn Ala Lys Leu Ile Thr Gln Arg Lys
                900                 905                 910

Phe Asp Asn Leu Thr Lys Ala Glu Arg Gly Gly Leu Ser Glu Leu Asp
            915                 920                 925

Lys Ala Gly Phe Ile Lys Arg Gln Leu Val Glu Thr Arg Gln Ile Thr
                930                 935                 940

Lys His Val Ala Gln Ile Leu Asp Ser Arg Met Asn Thr Lys Tyr Asp
945                 950                 955                 960

Glu Asn Asp Lys Leu Ile Arg Glu Val Lys Val Ile Thr Leu Lys Ser
                965                 970                 975

Lys Leu Val Ser Asp Phe Arg Lys Asp Phe Gln Phe Tyr Lys Val Arg
                980                 985                 990

Glu Ile Asn Asn Tyr His His Ala His Asp Ala Tyr Leu Asn Ala Val
                995                 1000                1005

Val Gly Thr Ala Leu Ile Lys Lys Tyr Pro Lys Leu Glu Ser Glu
    1010                1015                1020

Phe Val Tyr Gly Asp Tyr Lys Val Tyr Asp Val Arg Lys Met Ile
    1025                1030                1035

Ala Lys Ser Glu Gln Glu Ile Gly Lys Ala Thr Ala Lys Tyr Phe
    1040                1045                1050

Phe Tyr Ser Asn Ile Met Asn Phe Phe Lys Thr Glu Ile Thr Leu
```

```
                    1055                1060                1065

Ala  Asn  Gly  Glu  Ile  Arg  Lys  Arg  Pro  Leu  Ile  Glu  Thr  Asn  Gly
         1070                1075                1080

Glu  Thr  Gly  Glu  Ile  Val  Trp  Asp  Lys  Gly  Arg  Asp  Phe  Ala  Thr
    1085                1090                1095

Val  Arg  Lys  Val  Leu  Ser  Met  Pro  Gln  Val  Asn  Ile  Val  Lys  Lys
    1100                1105                1110

Thr  Glu  Val  Gln  Thr  Gly  Gly  Phe  Ser  Lys  Glu  Ser  Ile  Leu  Pro
    1115                1120                1125

Lys  Arg  Asn  Ser  Asp  Lys  Leu  Ile  Ala  Arg  Lys  Lys  Asp  Trp  Asp
    1130                1135                1140

Pro  Lys  Lys  Tyr  Gly  Gly  Phe  Asp  Ser  Pro  Thr  Val  Ala  Tyr  Ser
    1145                1150                1155

Val  Leu  Val  Val  Ala  Lys  Val  Glu  Lys  Gly  Lys  Ser  Lys  Lys  Leu
    1160                1165                1170

Lys  Ser  Val  Lys  Glu  Leu  Leu  Gly  Ile  Thr  Ile  Met  Glu  Arg  Ser
    1175                1180                1185

Ser  Phe  Glu  Lys  Asn  Pro  Ile  Asp  Phe  Leu  Glu  Ala  Lys  Gly  Tyr
    1190                1195                1200

Lys  Glu  Val  Lys  Lys  Asp  Leu  Ile  Ile  Lys  Leu  Pro  Lys  Tyr  Ser
    1205                1210                1215

Leu  Phe  Glu  Leu  Glu  Asn  Gly  Arg  Lys  Arg  Met  Leu  Ala  Ser  Ala
    1220                1225                1230

Gly  Glu  Leu  Gln  Lys  Gly  Asn  Glu  Leu  Ala  Leu  Pro  Ser  Lys  Tyr
    1235                1240                1245

Val  Asn  Phe  Leu  Tyr  Leu  Ala  Ser  His  Tyr  Glu  Lys  Leu  Lys  Gly
    1250                1255                1260

Ser  Pro  Glu  Asp  Asn  Glu  Gln  Lys  Gln  Leu  Phe  Val  Glu  Gln  His
    1265                1270                1275

Lys  His  Tyr  Leu  Asp  Glu  Ile  Ile  Glu  Gln  Ile  Ser  Glu  Phe  Ser
    1280                1285                1290

Lys  Arg  Val  Ile  Leu  Ala  Asp  Ala  Asn  Leu  Asp  Lys  Val  Leu  Ser
    1295                1300                1305

Ala  Tyr  Asn  Lys  His  Arg  Asp  Lys  Pro  Ile  Arg  Glu  Gln  Ala  Glu
    1310                1315                1320

Asn  Ile  Ile  His  Leu  Phe  Thr  Leu  Thr  Asn  Leu  Gly  Ala  Pro  Ala
    1325                1330                1335

Ala  Phe  Lys  Tyr  Phe  Asp  Thr  Thr  Ile  Asp  Arg  Lys  Arg  Tyr  Thr
    1340                1345                1350

Ser  Thr  Lys  Glu  Val  Leu  Asp  Ala  Thr  Leu  Ile  His  Gln  Ser  Ile
    1355                1360                1365

Thr  Gly  Leu  Tyr  Glu  Thr  Arg  Ile  Asp  Leu  Ser  Gln  Leu  Gly  Gly
    1370                1375                1380

Asp  Ser  Arg  Ala  Asp  Pro  Lys  Lys  Lys  Arg  Lys  Val
    1385                1390                1395

<210> SEQ ID NO 116
<211> LENGTH: 1412
<212> TYPE: PRT
<213> ORGANISM: Artificial sequence
<220> FEATURE:
<223> OTHER INFORMATION: his-MPG1-Cas9

<400> SEQUENCE: 116

Met Gly His His His His His His Gly Ala Leu Phe Leu Gly Gln Leu
```

```
  1               5                   10                  15
Gly Ala Ala Gly Ser Thr Met Gly Ala Pro Lys Lys Arg Lys Val
                20                  25                  30
Glu Phe Asp Lys Lys Tyr Ser Ile Gly Leu Asp Ile Gly Thr Asn Ser
                35                  40                  45
Val Gly Trp Ala Val Ile Thr Asp Glu Tyr Lys Val Pro Ser Lys Lys
 50                  55                  60
Phe Lys Val Leu Gly Asn Thr Asp Arg His Ser Ile Lys Lys Asn Leu
 65                  70                  75                  80
Ile Gly Ala Leu Leu Phe Asp Ser Gly Glu Thr Ala Glu Ala Thr Arg
                85                  90                  95
Leu Lys Arg Thr Ala Arg Arg Arg Tyr Thr Arg Arg Lys Asn Arg Ile
                100                 105                 110
Cys Tyr Leu Gln Glu Ile Phe Ser Asn Glu Met Ala Lys Val Asp Asp
                115                 120                 125
Ser Phe Phe His Arg Leu Glu Glu Ser Phe Leu Val Glu Glu Asp Lys
                130                 135                 140
Lys His Glu Arg His Pro Ile Phe Gly Asn Ile Val Asp Glu Val Ala
145                 150                 155                 160
Tyr His Glu Lys Tyr Pro Thr Ile Tyr His Leu Arg Lys Lys Leu Val
                165                 170                 175
Asp Ser Thr Asp Lys Ala Asp Leu Arg Leu Ile Tyr Leu Ala Leu Ala
                180                 185                 190
His Met Ile Lys Phe Arg Gly His Phe Leu Ile Glu Gly Asp Leu Asn
                195                 200                 205
Pro Asp Asn Ser Asp Val Asp Lys Leu Phe Ile Gln Leu Val Gln Thr
                210                 215                 220
Tyr Asn Gln Leu Phe Glu Glu Asn Pro Ile Asn Ala Ser Gly Val Asp
225                 230                 235                 240
Ala Lys Ala Ile Leu Ser Ala Arg Leu Ser Lys Ser Arg Arg Leu Glu
                245                 250                 255
Asn Leu Ile Ala Gln Leu Pro Gly Glu Lys Lys Asn Gly Leu Phe Gly
                260                 265                 270
Asn Leu Ile Ala Leu Ser Leu Gly Leu Thr Pro Asn Phe Lys Ser Asn
                275                 280                 285
Phe Asp Leu Ala Glu Asp Ala Lys Leu Gln Leu Ser Lys Asp Thr Tyr
                290                 295                 300
Asp Asp Asp Leu Asp Asn Leu Leu Ala Gln Ile Gly Asp Gln Tyr Ala
305                 310                 315                 320
Asp Leu Phe Leu Ala Ala Lys Asn Leu Ser Asp Ala Ile Leu Leu Ser
                325                 330                 335
Asp Ile Leu Arg Val Asn Thr Glu Ile Thr Lys Ala Pro Leu Ser Ala
                340                 345                 350
Ser Met Ile Lys Arg Tyr Asp Glu His His Gln Asp Leu Thr Leu Leu
                355                 360                 365
Lys Ala Leu Val Arg Gln Gln Leu Pro Glu Lys Tyr Lys Glu Ile Phe
                370                 375                 380
Phe Asp Gln Ser Lys Asn Gly Tyr Ala Gly Tyr Ile Asp Gly Gly Ala
385                 390                 395                 400
Ser Gln Glu Glu Phe Tyr Lys Phe Ile Lys Pro Ile Leu Glu Lys Met
                405                 410                 415
Asp Gly Thr Glu Glu Leu Leu Val Lys Leu Asn Arg Glu Asp Leu Leu
                420                 425                 430
```

Arg Lys Gln Arg Thr Phe Asp Asn Gly Ser Ile Pro His Gln Ile His
435                     440                     445

Leu Gly Glu Leu His Ala Ile Leu Arg Arg Gln Glu Asp Phe Tyr Pro
450                     455                     460

Phe Leu Lys Asp Asn Arg Glu Lys Ile Glu Lys Ile Leu Thr Phe Arg
465                     470                     475                 480

Ile Pro Tyr Tyr Val Gly Pro Leu Ala Arg Gly Asn Ser Arg Phe Ala
                485                     490                     495

Trp Met Thr Arg Lys Ser Glu Glu Thr Ile Thr Pro Trp Asn Phe Glu
                500                     505                     510

Glu Val Val Asp Lys Gly Ala Ser Ala Gln Ser Phe Ile Glu Arg Met
                515                     520                     525

Thr Asn Phe Asp Lys Asn Leu Pro Asn Glu Lys Val Leu Pro Lys His
                530                     535                     540

Ser Leu Leu Tyr Glu Tyr Phe Thr Val Tyr Asn Glu Leu Thr Lys Val
545                     550                     555                 560

Lys Tyr Val Thr Glu Gly Met Arg Lys Pro Ala Phe Leu Ser Gly Glu
                565                     570                     575

Gln Lys Lys Ala Ile Val Asp Leu Leu Phe Lys Thr Asn Arg Lys Val
                580                     585                     590

Thr Val Lys Gln Leu Lys Glu Asp Tyr Phe Lys Lys Ile Glu Cys Phe
                595                     600                     605

Asp Ser Val Glu Ile Ser Gly Val Glu Asp Arg Phe Asn Ala Ser Leu
                610                     615                     620

Gly Thr Tyr His Asp Leu Leu Lys Ile Ile Lys Asp Lys Asp Phe Leu
625                     630                     635                 640

Asp Asn Glu Glu Asn Glu Asp Ile Leu Glu Asp Ile Val Leu Thr Leu
                645                     650                     655

Thr Leu Phe Glu Asp Arg Glu Met Ile Glu Glu Arg Leu Lys Thr Tyr
                660                     665                     670

Ala His Leu Phe Asp Asp Lys Val Met Lys Gln Leu Lys Arg Arg Arg
                675                     680                     685

Tyr Thr Gly Trp Gly Arg Leu Ser Arg Lys Leu Ile Asn Gly Ile Arg
                690                     695                     700

Asp Lys Gln Ser Gly Lys Thr Ile Leu Asp Phe Leu Lys Ser Asp Gly
705                     710                     715                 720

Phe Ala Asn Arg Asn Phe Met Gln Leu Ile His Asp Asp Ser Leu Thr
                725                     730                     735

Phe Lys Glu Asp Ile Gln Lys Ala Gln Val Ser Gly Gln Gly Asp Ser
                740                     745                     750

Leu His Glu His Ile Ala Asn Leu Ala Gly Ser Pro Ala Ile Lys Lys
                755                     760                     765

Gly Ile Leu Gln Thr Val Lys Val Val Asp Glu Leu Val Lys Val Met
                770                     775                     780

Gly Arg His Lys Pro Glu Asn Ile Val Ile Glu Met Ala Arg Glu Asn
785                     790                     795                 800

Gln Thr Thr Gln Lys Gly Gln Lys Asn Ser Arg Glu Arg Met Lys Arg
                805                     810                     815

Ile Glu Glu Gly Ile Lys Glu Leu Gly Ser Gln Ile Leu Lys Glu His
                820                     825                     830

Pro Val Glu Asn Thr Gln Leu Gln Asn Glu Lys Leu Tyr Leu Tyr Tyr
                835                     840                     845

-continued

```
Leu Gln Asn Gly Arg Asp Met Tyr Val Asp Gln Glu Leu Asp Ile Asn
850                 855                 860

Arg Leu Ser Asp Tyr Asp Val Asp His Ile Val Pro Gln Ser Phe Leu
865                 870                 875                 880

Lys Asp Asp Ser Ile Asp Asn Lys Val Leu Thr Arg Ser Asp Lys Asn
                885                 890                 895

Arg Gly Lys Ser Asp Asn Val Pro Ser Glu Val Val Lys Lys Met
                900                 905                 910

Lys Asn Tyr Trp Arg Gln Leu Leu Asn Ala Lys Leu Ile Thr Gln Arg
            915                 920                 925

Lys Phe Asp Asn Leu Thr Lys Ala Glu Arg Gly Gly Leu Ser Glu Leu
    930                 935                 940

Asp Lys Ala Gly Phe Ile Lys Arg Gln Leu Val Glu Thr Arg Gln Ile
945                 950                 955                 960

Thr Lys His Val Ala Gln Ile Leu Asp Ser Arg Met Asn Thr Lys Tyr
                965                 970                 975

Asp Glu Asn Asp Lys Leu Ile Arg Glu Val Lys Val Ile Thr Leu Lys
                980                 985                 990

Ser Lys Leu Val Ser Asp Phe Arg Lys Asp Phe Gln Phe Tyr Lys Val
            995                 1000                1005

Arg Glu Ile Asn Asn Tyr His His Ala His Asp Ala Tyr Leu Asn
    1010                1015                1020

Ala Val Val Gly Thr Ala Leu Ile Lys Lys Tyr Pro Lys Leu Glu
    1025                1030                1035

Ser Glu Phe Val Tyr Gly Asp Tyr Lys Val Tyr Asp Val Arg Lys
    1040                1045                1050

Met Ile Ala Lys Ser Glu Gln Glu Ile Gly Lys Ala Thr Ala Lys
    1055                1060                1065

Tyr Phe Phe Tyr Ser Asn Ile Met Asn Phe Phe Lys Thr Glu Ile
    1070                1075                1080

Thr Leu Ala Asn Gly Glu Ile Arg Lys Arg Pro Leu Ile Glu Thr
    1085                1090                1095

Asn Gly Glu Thr Gly Glu Ile Val Trp Asp Lys Gly Arg Asp Phe
    1100                1105                1110

Ala Thr Val Arg Lys Val Leu Ser Met Pro Gln Val Asn Ile Val
    1115                1120                1125

Lys Lys Thr Glu Val Gln Thr Gly Gly Phe Ser Lys Glu Ser Ile
    1130                1135                1140

Leu Pro Lys Arg Asn Ser Asp Lys Leu Ile Ala Arg Lys Lys Asp
    1145                1150                1155

Trp Asp Pro Lys Lys Tyr Gly Gly Phe Asp Ser Pro Thr Val Ala
    1160                1165                1170

Tyr Ser Val Leu Val Val Ala Lys Val Glu Lys Gly Lys Ser Lys
    1175                1180                1185

Lys Leu Lys Ser Val Lys Glu Leu Leu Gly Ile Thr Ile Met Glu
    1190                1195                1200

Arg Ser Ser Phe Glu Lys Asn Pro Ile Asp Phe Leu Glu Ala Lys
    1205                1210                1215

Gly Tyr Lys Glu Val Lys Lys Asp Leu Ile Ile Lys Leu Pro Lys
    1220                1225                1230

Tyr Ser Leu Phe Glu Leu Glu Asn Gly Arg Lys Arg Met Leu Ala
    1235                1240                1245

Ser Ala Gly Glu Leu Gln Lys Gly Asn Glu Leu Ala Leu Pro Ser
```

```
                  1250                1255                1260
Lys  Tyr  Val  Asn  Phe  Leu  Tyr  Leu  Ala  Ser  His  Tyr  Glu  Lys  Leu
           1265                1270                1275
Lys  Gly  Ser  Pro  Glu  Asp  Asn  Glu  Gln  Lys  Gln  Leu  Phe  Val  Glu
           1280                1285                1290
Gln  His  Lys  His  Tyr  Leu  Asp  Glu  Ile  Ile  Glu  Gln  Ile  Ser  Glu
           1295                1300                1305
Phe  Ser  Lys  Arg  Val  Ile  Leu  Ala  Asp  Ala  Asn  Leu  Asp  Lys  Val
           1310                1315                1320
Leu  Ser  Ala  Tyr  Asn  Lys  His  Arg  Asp  Lys  Pro  Ile  Arg  Glu  Gln
           1325                1330                1335
Ala  Glu  Asn  Ile  Ile  His  Leu  Phe  Thr  Leu  Thr  Asn  Leu  Gly  Ala
           1340                1345                1350
Pro  Ala  Ala  Phe  Lys  Tyr  Phe  Asp  Thr  Thr  Ile  Asp  Arg  Lys  Arg
           1355                1360                1365
Tyr  Thr  Ser  Thr  Lys  Glu  Val  Leu  Asp  Ala  Thr  Leu  Ile  His  Gln
           1370                1375                1380
Ser  Ile  Thr  Gly  Leu  Tyr  Glu  Thr  Arg  Ile  Asp  Leu  Ser  Gln  Leu
           1385                1390                1395
Gly  Gly  Asp  Ser  Arg  Ala  Asp  Pro  Lys  Lys  Lys  Arg  Lys  Val
           1400                1405                1410
```

<210> SEQ ID NO 117
<211> LENGTH: 8237
<212> TYPE: DNA
<213> ORGANISM: Artificial sequence
<220> FEATURE:
<223> OTHER INFORMATION: pRF48

<400> SEQUENCE: 117

```
aattcgacaa gaaatactcc atcggcctgg acattggaac caactctgtc ggctgggctg      60
tcatcaccga cgagtacaag gtgccctcca agaaattcaa ggtcctcgga aacaccgatc     120
gacactccat caagaaaaac ctcattggtg ccctgttgtt cgattctggc gagactgccg     180
aagctaccag actcaagcga actgctcggc gacgttacac ccgacggaag aaccgaatct     240
gctacctgca ggagatcttt tccaacgaga tggccaaggt ggacgattcg ttctttcatc     300
gactggagga atccttcctc gtcgaggaag acaagaaaca cgagcgtcat cccatctttg     360
gcaacattgt ggacgaggtt gcttaccacg agaagtatcc taccatctac cacctgcgaa     420
agaaactcgt cgattccacc gacaaggcgg atctcagact tatctacctc gctctggcac     480
acatgatcaa gtttcgaggt catttcctca tcgagggcga tctcaatccc gacaacagcg     540
atgtggacaa gctgttcatt cagctcgttc agacctacaa ccagctgttc gaggaaaacc     600
ccatcaatgc ctccggagtc gatgcaaagg ccatcttgtc tgctcgactc tcgaagagca     660
gacgactgga gaacctcatt gcccaacttc ctggcgagaa aaagaacgga ctgtttggca     720
acctcattgc cctttctctt ggtctcacac ccaacttcaa gtccaacttc gatctggcgg     780
aggacgccaa gctccagctg tccaaggaca cctacgacga tgacctcgac aacctgcttg     840
cacagattgg cgatcagtac gccgaccgtg ttctcgctgc caagaacctt cggatgcta     900
ttctcttgtc tgacattctg cgagtcaaca ccgagatcac aaaggctccc ctttctgcct     960
ccatgatcaa gcgatacgac gagcaccatc aggatctcac actgctcaag gctcttgtcc    1020
gacagcaact gcccgagaag tacaaggaga tcttttttcga tcagtcgaag aacggctacg    1080
ctggatacat cgacggcgga gcctctcagg aagagttcta caagttcatc aagccaattc    1140
```

```
tcgagaagat ggacggaacc gaggaactgc ttgtcaagct caatcgagag gatctgcttc    1200
ggaagcaacg aaccttcgac aacggcagca ttcctcatca gatccacctc ggtgagctgc    1260
acgccattct tcgacgtcag gaagacttct accccttttct caaggacaac cgagagaaga    1320
tcgagaagat tcttaccttt cgaatcccct actatgttgg tcctcttgcc agaggaaact    1380
ctcgatttgc ttggatgact cgaaagtccg aggaaaccat cactccctgg aacttcgagg    1440
aagtcgtgga caagggtgcc tctgcacagt ccttcatcga gcgaatgacc aacttcgaca    1500
agaatctgcc caacgagaag gttcttccca agcattcgct gctctacgag tactttacag    1560
tctacaacga actcaccaaa gtcaagtacg ttaccgaggg aatgcgaaag cctgccttct    1620
tgtctggcga acagaagaaa gccattgtcg atctcctgtt caagaccaac cgaaaggtca    1680
ctgttaagca gctcaaggag gactacttca agaaaatcga gtgtttcgac agcgtcgaga    1740
tttccggagt tgaggaccga ttcaacgcct ctttgggcac ctatcacgat ctgctcaaga    1800
ttatcaagga caaggatttt tcgacaacga aggaaaacga ggacattctg gaggacatcg    1860
tgctcactct tacccctgttc gaagatcggg agatgatcga ggaacgactc aagacatacg    1920
ctcacctgtt cgacgacaag gtcatgaaac aactcaagcg acgtagatac accggctggg    1980
gaagactttc gcgaaagctc atcaacggca tcagagacaa gcagtccgga aagaccattc    2040 tggacttttct caagtccgat ggctttgcca accgaaactt catgcagctc attcacgacg    2100
attctcttac cttcaaggag gacatccaga aggcacaagt gtccggtcag ggcgacagct    2160
tgcacgaaca tattgccaac ctggctggtt cgccagccat caagaaaggc attctccaga    2220
ctgtcaaggt tgtcgacgag ctggtgaagg tcatgggacg tcacaagccc gagaacattg    2280
tgatcgagat ggccagagag aaccagacaa ctcaaaaggg tcagaaaaac tcgcgagagc    2340
ggatgaagcg aatcgaggaa ggcatcaagg agctgggatc ccagattctc aaggagcatc    2400
ccgtcgagaa cactcaactg cagaacgaga agctgtatct ctactatctg cagaatggtc    2460
gagacatgta cgtggatcag gaactggaca tcaatcgtct cagcgactac gatgtggacc    2520
acattgtccc tcaatccttt ctcaaggacg attctatcga caacaaggtc cttacacgat    2580
ccgacaagaa cagaggcaag tcggacaacg ttcccagcga agaggtggtc aaaaagatga    2640
agaactactg gcgacagctg ctcaacgcca agctcattac ccagcgaaag ttcgacaatc    2700
ttaccaaggc cgagcgaggc ggtctgtccg agctcgacaa ggctggcttc atcaagcgtc    2760
aactcgtcga gaccagacag atcacaaagc acgtcgcaca gattctcgat tctcggatga    2820
acaccaagta cgacgagaac gacaagctca tccgagaggt caaggtgatt actctcaagt    2880
ccaaactggt ctccgatttc cgaaaggact ttcagttcta caaggtgcga gagatcaaca    2940
attaccacca tgcccacgat gcttacctca acgccgtcgt tggcactgcg ctcatcaaga    3000
aataccccaa gctcgaaagc gagttcgttt acggcgatta caaggtctac gacgttcgaa    3060
agatgattgc caagtccgaa caggagattg caaggctac tgccaagtac ttcttttact    3120
ccaacatcat gaacttttc aagaccgaga tcaccttggc caacggagag attcgaaaga    3180
gaccacttat cgagaccaac ggcgaaactg gagagatcgt gtgggacaag ggtcgagact    3240 tgcaaccgt gcgaaaggtt ctgtcgatgc ctcaggtcaa catcgtcaag aaaaccgagg    3300
ttcagactgg cggattctcc aaggagtcga ttctgcccaa gcgaaactcc gacaagctca    3360
tcgctcgaaa gaaagactgg gatcccaaga aatacggtgg cttcgattct cctaccgtcg    3420
cctattccgt gcttgtcgtt gcgaaggtcg agaagggcaa gtccaaaaag ctcaagtccg    3480
```

```
tcaaggagct gctcggaatt accatcatgg agcgatcgag cttcgagaag aatcccatcg   3540
acttcttgga agccaagggt tacaaggagg tcaagaaaga cctcattatc aagctgccca   3600
agtactctct gttcgaactg agaacggtc gaaagcgtat gctcgcctcc gctggcgagc    3660
tgcagaaggg aaacgagctt gccttgcctt cgaagtacgt caactttctc tatctggctt   3720
ctcactacga gaagctcaag ggttctcccg aggacaacga acagaagcaa ctcttcgttg   3780
agcagcacaa acattacctc gacgagatta tcgagcagat ttccgagttt tcgaagcgag   3840
tcatcctggc tgatgccaac ttggacaagg tgctctctgc ctacaacaag catcgggaca   3900
aacccattcg agaacaggcg gagaacatca ttcacctgtt tactcttacc aacctgggtg   3960
ctcctgcagc tttcaagtac ttcgatacca ctatcgaccg aaagcggtac acatccacca   4020
aggaggttct cgatgccacc ctgattcacc agtccatcac tggcctgtac gagacccgaa   4080
tcgacctgtc tcagcttggt ggcgactcca gagccgatcc caagaaaaag cgaaaggtct   4140
aagcggccgc taagcttggc tgttttggcg gatgagagaa gattttcagc ctgatacaga   4200
ttaaatcaga acgcagaagc ggtctgataa aacagaattt gcctggcggc agtagcgcgg   4260
tggtcccacc tgaccccatg ccgaactcag aagtgaaacg ccgtagcgcc gatggtagtg   4320
tggggtctcc ccatgcgaga gtagggaact gccaggcatc aaataaaacg aaaggctcag   4380
tcgaaagact gggcctttcg ttttatctgt tgtttgtcgg tgaacgctct cctgagtagg   4440
acaaatccgc cgggagcgga tttgaacgtt gcgaagcaac ggcccggagg gtggcgggca   4500
ggacgcccgc cataaactgc caggcatcaa attaagcaga aggccatcct gacggatggc   4560
ctttttgcgt ttctacaaac tctttttgttt atttttctaa atacattcaa atatgtatcc   4620
gctcatgaga caataaccct gataaatgct tcaataatat tgaaaaagga agagtatgag   4680
tattcaacat ttccgtgtcg cccttattcc cttttttgcg cattttgcc ttcctgtttt    4740
tgctcaccca gaaacgctgg tgaaagtaaa agatgctgaa gatcagttgg gtgcacgagt   4800
gggttacatc gaactggatc tcaacagcgg taagatcctt gagagttttc gccccgaaga   4860
acgttttcca atgatgagca cttttaaagt tctgctatgt ggcgcggtat tatcccgtgt    4920
tgacgccggg caagagcaac tcggtcgccg catacactat tctcagaatg acttggttga   4980
gtactcacca gtcacagaaa agcatcttac ggatggcatg acagtaagag aattatgcag   5040
tgctgccata accatgagtg ataacactgc ggccaactta cttctgacaa cgatcggagg   5100
accgaaggag ctaaccgctt ttttgcacaa catgggggat catgtaactc gccttgatcg   5160
ttgggaaccg gagctgaatg aagccatacc aaacgacgag cgtgacacca cgatgcctgt   5220
agcaatggca acaacgttgc gcaaactatt aactggcgaa ctacttactc tagcttcccg   5280
gcaacaatta atagactgga tggaggcgga taaagttgca ggaccacttc tgcgctcggc   5340
ccttccggct ggctggttta ttgctgataa atctggagcc ggtgagcgtg gtctcgcgg    5400
tatcattgca gcactggggc cagatggtaa gccctcccgt atcgtagtta tctacacgac   5460
ggggagtcag gcaactatgg atgaacgaaa tagacagatc gctgagatag gtgcctcact   5520
gattaagcat tggtaactgt cagaccaagt ttactcatat atactttaga ttgatttaaa   5580
acttcatttt taatttaaaa ggatctaggt gaagatcctt tttgataatc tcatgaccaa   5640
aatcccttaa cgtgagtttt cgttccactg agcgtcagac cccgtagaaa agatcaaagg   5700
atcttcttga tccttttttt ttctgcgcgt aatctgctgc ttgcaaacaa aaaaaccacc   5760
gctaccagcg gtggtttgtt tgccggatca agagctacca actctttttc cgaaggtaac   5820
tggcttcagc agagcgcaga taccaaatac tgtccttcta gtgtagccgt agttaggcca   5880
```

```
ccacttcaag aactctgtag caccgcctac atacctcgct ctgctaatcc tgttaccagt   5940
ggctgctgcc agtggcgata agtcgtgtct taccgggttg gactcaagac gatagttacc   6000
ggataaggcg cagcggtcgg gctgaacggg gggttcgtgc acacagccca gcttggagcg   6060
aacgacctac accgaactga gatacctaca gcgtgagcta tgagaaagcg ccacgcttcc   6120
cgaagggaga aaggcggaca ggtatccggt aagcggcagg gtcggaacag gagagcgcac   6180
gagggagctt ccaggggaaa acgcctggta tctttatagt cctgtcgggt ttcgccacct   6240
ctgacttgag cgtcgatttt tgtgatgctc gtcaggggg cggagcctat ggaaaaacgc    6300
cagcaacgcg gcctttttac ggttcctggc cttttgctgg ccttttgctc acatgttctt   6360
tcctgcgtta tcccctgatt ctgtggataa ccgtattacc gcctttgagt gagctgatac   6420
cgctcgccgc agccgaacga ccgagcgcag cgagtcagtg agcgaggaag cggaagagcg   6480
cctgatgcgg tattttctcc ttacgcatct gtgcggtatt tcacaccgca tatggtgcac   6540
tctcagtaca atctgctctg atgccgcata gttaagccag tatacactcc gctatcgcta   6600
cgtgactggg tcatggctgc gccccgacac ccgccaacac ccgctgacgc gccctgacgg   6660
gcttgtctgc tcccggcatc cgcttacaga caagctgtga ccgtctccgg agctgcatg    6720
tgtcagaggt tttcaccgtc atcaccgaaa cgcgcgaggc agcagatcaa ttcgcgcgcg   6780
aaggcgaagc ggcatgcata atgtgcctgt caaatggacg aagcagggat tctgcaaacc   6840
ctatgctact ccgtcaagcc gtcaattgtc tgattcgtta ccaattatga caacttgacg   6900
gctacatcat tcacttttc ttcacaaccg gcacggaact cgctcgggct ggccccggtg    6960
catttttttaa atacccgcga gaaatagagt tgatcgtcaa accaacatt gcgaccgacg    7020
gtggcgatag gcatccgggt ggtgctcaaa agcagcttcg cctggctgat acgttggtcc   7080
tcgcgccagc ttaagacgct aatccctaac tgctggcgga aaagatgtga cagacgcgac   7140
ggcgacaagc aaacatgctg tgcgacgctg gcgatatcaa aattgctgtc tgccaggtga   7200
tcgctgatgt actgacaagc ctcgcgtacc cgattatcca tcggtggatg gagcgactcg   7260
ttaatcgctt ccatgcgccg cagtaacaat tgctcaagca gatttatcgc cagcagctcc   7320
gaatagcgcc cttccccttg cccggcgtta atgatttgcc caaacaggtc gctgaaatgc   7380
ggctggtgcg cttcatccgg gcgaaagaac ccgtattgg caaatattga cggccagtta    7440
agccattcat gccagtaggc gcgcggacga aagtaaaccc actggtgata ccattcgcga   7500
gcctccggat gacgaccgta gtgatgaatc tctcctggcg gaacagcaa aatatcaccc    7560
ggtcggcaaa caaattctcg tccctgattt ttcaccaccc cctgaccgcg aatggtgaga   7620
ttgagaatat aacctttcat tcccagcggt cggtcgataa aaaatcgag ataaccgttg    7680
gcctcaatcg gcgttaaacc cgccaccaga tgggcattaa acgagtatcc cggcagcagg   7740
ggatcatttt gcgcttcagc catactttc atactcccgc cattcagaga agaaaccaat    7800
tgtccatatt gcatcagaca ttgccgtcac tgcgtctttt actggctctt ctcgctaacc   7860
aaaccggtaa ccccgcttat taaaagcatt ctgtaacaaa gcgggaccaa agccatgaca   7920
aaaacgcgta acaaaagtgt ctataatcac ggcagaaaag tccacattga ttatttgcac   7980
ggcgtcacac tttgctatgc catagcattt ttatccataa gattagcgga tcctacctga   8040
cgctttttat cgcaactctc tactgtttct ccatacccgt ttttgggct aacaggagga    8100
attaaccatg ggggttctc atcatcatca tcatcatggt atggctagca tgactggtgg   8160
acagcaaatg ggtcgggatc tgtacgacga tgacgataag gatccgagct cgagatctgc   8220
```

-continued

```
agctggtacc atatggg                                                 8237
```

<210> SEQ ID NO 118
<211> LENGTH: 8153
<212> TYPE: DNA
<213> ORGANISM: Artificial sequence
<220> FEATURE:
<223> OTHER INFORMATION: pRF243

<400> SEQUENCE: 118

```
catgggcat caccatcacc accattgttt tttcaaagac gaactggaat tcgacaagaa      60
atactccatc ggcctggaca ttggaaccaa ctctgtcggc tgggctgtca tcaccgacga    120
gtacaaggtg ccctccaaga aattcaaggt cctcggaaac accgatcgac actccatcaa    180
gaaaaacctc attggtgccc tgttgttcga ttctggcgag actgccgaag ctaccagact    240
caagcgaact gctcggcgac gttacacccg acggaagaac cgaatctgct acctgcagga    300
gatcttttcc aacgagatgg ccaaggtgga cgattcgttc tttcatcgac tggaggaatc    360
cttcctcgtc gaggaagaca agaaacacga gcgtcatccc atctttggca acattgtgga    420
cgaggttgct taccacgaga agtatcctac catctaccac ctgcgaaaga aactcgtcga    480
ttccaccgac aaggcggatc tcagacttat ctacctcgct ctggcacaca tgatcaagtt    540
tcgaggtcat ttcctcatcg agggcgatct caatcccgac aacagcgatg tggacaagct    600
gttcattcag ctcgttcaga cctacaacca gctgttcgag aaaaccccca tcaatgcctc    660
cggagtcgat gcaaaggcca tcttgtctgc tcgactctcg aagagcagac gactggagaa    720
cctcattgcc caacttcctg gcgagaaaaa gaacggactg tttggcaacc tcattgccct    780
ttctcttggt ctcacaccca acttcaagtc caacttcgat ctggcggagg acgccaagct    840
ccagctgtcc aaggacacct acgacgatga cctcgacaac ctgcttgcac agattggcga    900
tcagtacgcc gacctgtttc tcgctgccaa gaacctttcg gatgctattc tcttgtctga    960
cattctgcga gtcaacaccg agatcacaaa ggctcccctt tctgcctcca tgatcaagcg   1020
atacgacgag caccatcagg atctcacact gctcaaggct cttgtccgac agcaactgcc   1080
cgagaagtac aaggagatct ttttcgatca gtcgaagaac ggctacgctg atacatcga    1140
cggcggagcc tctcaggaag agttctacaa gttcatcaag ccaattctcg agaagatgga   1200
cggaaccgag gaactgcttg tcaagctcaa tcgagaggat ctgcttcgga agcaacgaac   1260
cttcgacaac ggcagcattc ctcatcagat ccacctcggt gagctgcacg ccattcttcg   1320
acgtcaggaa gacttctacc cctttctcaa ggacaaccga gagaagatcg agaagattct   1380
taccttttcga atccctact atgttggtcc tcttgccaga ggaaactctc gatttgcttg   1440
gatgactcga aagtccgagg aaaccatcac tccctggaac ttcgaggaag tcgtggacaa   1500
gggtgcctct gcacagtcct tcatcgagcg aatgaccaac ttcgacaaga atctgcccaa   1560
cgagaaggtt cttcccaagc attcgctgct ctacgagtac tttacagtct acaacgaact   1620
caccaaagtc aagtacgtta ccgagggaat gcgaaagcct gccttcttgt ctggcgaaca   1680
gaagaaagcc attgtcgatc tcctgttcaa gaccaaccga aggtcactg ttaagcagct   1740
caaggaggac tacttcaaga aaatcgagtg tttcgacagc gtcgagattt ccggagttga   1800
ggaccgattc aacgcctctt tgggcaccta tcacgatctg ctcaagatta tcaaggacaa   1860
ggattttctc gacaacgagg aaaacgagga cattctggag gacatcgtgc tcactcttac   1920
cctgttcgaa gatcgggaga tgatcgagga acgactcaag acatacgctc acctgttcga   1980
cgacaaggtc atgaaacaac tcaagcgacg tagatacacc ggctggggaa gactttcgcg   2040
```

```
aaagctcatc aacggcatca gagacaagca gtccggaaag accattctgg actttctcaa    2100
gtccgatggc tttgccaacc gaaacttcat gcagctcatt cacgacgatt ctcttacctt    2160
caaggaggac atccgaagg cacaagtgtc cggtcagggc gacagcttgc acgaacatat    2220
tgccaacctg gctggttcgc cagccatcaa gaaaggcatt ctccagactg tcaaggttgt    2280
cgacgagctg gtgaaggtca tgggacgtca caagcccgag aacattgtga tcgagatggc    2340
cagagagaac cagacaactc aaaagggtca gaaaaactcg cgagagcgga tgaagcgaat    2400
cgaggaaggc atcaaggagc tgggatccca gattctcaag gagcatcccg tcgagaacac    2460
tcaactgcag aacgagaagc tgtatctcta ctatctgcag aatggtcgag acatgtacgt    2520
ggatcaggaa ctggacatca atcgtctcag cgactacgat gtggaccaca ttgtccctca    2580
atcctttctc aaggacgatt ctatcgacaa caaggtcctt acacgatccg acaagaacag    2640
aggcaagtcg acaacgttc ccagcgaaga ggtggtcaaa aagatgaaga actactggcg    2700
acagctgctc aacgccaagc tcattaccca gcgaaagttc gacaatctta ccaaggccga    2760
gcgaggcggt ctgtccgagc tcgacaaggc tggcttcatc aagcgtcaac tcgtcgagac    2820
cagacagatc acaaagcacg tcgcacagat tctcgattct cggatgaaca ccaagtacga    2880
cgagaacgac aagctcatcc gagaggtcaa ggtgattact ctcaagtcca aactggtctc    2940
cgatttccga aaggactttc agttctacaa ggtgcgagag atcaacaatt accaccatgc    3000
ccacgatgct tacctcaacg ccgtcgttgg cactgcgctc atcaagaaat accccaagct    3060
cgaaagcgag ttcgtttacg gcgattacaa ggtctacgac gttcgaaaga tgattgccaa    3120
gtccgaacag gagattggca aggctactgc caagtacttc ttttactcca acatcatgaa    3180
cttttcaag accagatca ccttggccaa cggagagatt cgaaagagac cacttatcga    3240
gaccaacggc gaaactggag agatcgtgtg ggacaagggt cgagactttg caaccgtgcg    3300
aaaggttctg tcgatgcctc aggtcaacat cgtcaagaaa accgaggttc agactggcgg    3360
attctccaag gagtcgattc tgcccaagcg aaactccgac aagctcatcg ctcgaaagaa    3420
agactgggat cccaagaaat acggtggctt cgattctcct accgtcgcct attccgtgct    3480
tgtcgttgcg aaggtcgaga agggcaagtc caaaaagctc aagtccgtca aggagctgct    3540
cggaattacc atcatggagc gatcgagctt cgagaagaat cccatcgact tcttggaagc    3600
caagggttac aaggaggtca gaaagacct cattatcaag ctgcccaagt actctctgtt    3660
cgaactggag aacggtcgaa agcgtatgct cgcctccgct ggcgagctgc agaagggaaa    3720
cgagcttgcc ttgccttcga agtacgtcaa ctttctctat ctggcttctc actacgagaa    3780
gctcaagggt ctcccgagg acaacgaaca gaagcaactc ttcgttgagc agcacaaaca    3840
ttacctcgac gagattatcg agcagatttc cgagttttcg aagcgagtca tcctggctga    3900
tgccaacttg gacaaggtgc tctctgccta caacaagcat cgggacaaac ccattcgaga    3960
acaggcggaa aacatcattc acctgtttac tcttaccaac ctgggtgctc ctgcagcttt    4020
caagtacttc gataccacta tcgaccgaaa gcggtacaca tccaccaagg aggttctcga    4080
tgccaccctg attcaccagt ccatcactgg cctgtacgag acccgaatcg acctgtctca    4140
gcttggtggc gactccagag ccgatcccaa gaaaaagcga aaggtctaag cggccgctaa    4200
gcttggctgt tttggcggat gagagaagat tttcagcctg atacagatta aatcagaacg    4260
cagaagcggt ctgataaaac agaatttgcc tggcggcagt agcgcggtgg tcccacctga    4320
ccccatgccg aactcagaag tgaaacgccg tagcgccgat ggtagtgtgg ggtctcccca    4380
```

```
tgcgagagta gggaactgcc aggcatcaaa taaaacgaaa ggctcagtcg aaagactggg      4440
cctttcgttt tatctgttgt ttgtcggtga acgctctcct gagtaggaca aatccgccgg      4500
gagcggattt gaacgttgcg aagcaacggc ccggagggtg gcgggcagga cgcccgccat      4560
aaactgccag gcatcaaatt aagcagaagg ccatcctgac ggatggcctt tttgcgtttc      4620
tacaaactct tttgtttatt tttctaaata cattcaaata tgtatccgct catgagacaa      4680
taaccctgat aaatgcttca ataatattga aaaggaaga gtatgagtat tcaacatttc      4740
cgtgtcgccc ttattccctt ttttgcggca ttttgccttc ctgttttgc tcacccagaa      4800 acgctggtga agtaaaaga tgctgaagat cagttgggtg cacgagtggg ttacatcgaa      4860
ctggatctca acagcggtaa gatccttgag agttttcgcc ccgaagaacg ttttccaatg      4920
atgagcactt ttaaagttct gctatgtggc gcggtattat cccgtgttga cgccgggcaa      4980
gagcaactcg gtcgccgcat acactattct cagaatgact tggttgagta ctcaccagtc      5040
acagaaaagc atcttacgga tggcatgaca gtaagagaat tatgcagtgc tgccataacc      5100
atgagtgata acactgcggc caacttactt ctgacaacga tcggaggacc gaaggagcta      5160
accgcttttt tgcacaacat gggggatcat gtaactcgcc ttgatcgttg ggaaccggag      5220
ctgaatgaag ccataccaaa cgacgagcgt gacaccacga tgcctgtagc aatggcaaca      5280
acgttgcgca aactattaac tggcgaacta cttactctag cttcccggca acaattaata      5340
gactggatgg aggcggataa agttgcagga ccacttctgc gctcggccct tccggctggc      5400
tggtttattg ctgataaatc tggagccggt gagcgtgggt ctcgcggtat cattgcagca      5460
ctggggccag atggtaagcc ctcccgtatc gtagttatct acacgacggg gagtcaggca      5520
actatggatg aacgaaatag acagatcgct gagataggtg cctcactgat taagcattgg      5580
taactgtcag accaagttta ctcatatata ctttagattg atttaaaact tcatttttaa      5640
tttaaaagga tctaggtgaa gatcctttt gataatctca tgaccaaaat cccttaacgt      5700
gagttttcgt tccactgagc gtcagacccc gtagaaaaga tcaaaggatc ttcttgagat      5760 ccttttttc tgcgcgtaat ctgctgcttg caaacaaaaa aaccaccgct accagcggtg      5820
gtttgtttgc cggatcaaga gctaccaact cttttttccga aggtaactgg cttcagcaga      5880
gcgcagatac caaatactgt ccttctagtg tagccgtagt taggccacca cttcaagaac      5940
tctgtagcac cgcctacata cctcgctctg ctaatcctgt taccagtggc tgctgccagt      6000
ggcgataagt cgtgtcttac cgggttggac tcaagacgat agttaccgga taaggcgcag      6060
cggtcgggct gaacggggg ttcgtgcaca cagcccagct tggagcgaac gacctacacc      6120
gaactgagat acctacagcg tgagctatga gaaagcgcca cgcttcccga agggagaaag      6180
gcggacaggt atccggtaag cggcagggtc ggaacaggag agcgcacgag ggagcttcca      6240
gggggaaacg cctggtatct ttatagtcct gtcgggtttc gccacctctg acttgagcgt      6300
cgatttttgt gatgctcgtc agggggggcgg agcctatgga aaaacgccag caacgcggcc      6360 ttttttacggt tcctggcctt ttgctggcct tttgctcaca tgttctttcc tgcgttatcc      6420
cctgattctg tggataaccg tattaccgcc tttgagtgag ctgataccgc tcgccgcagc      6480
cgaacgaccg agcgcagcga gtcagtgagc gaggaagcgg aagagcgcct gatgcggtat      6540
tttctcctta cgcatctgtg cggtatttca caccgcatat ggtgcactct cagtacaatc      6600
tgctctgatg ccgcatagtt aagccagtat acactccgct atcgctacgt gactgggtca      6660
tggctgcgcc ccgacacccg ccaacacccg ctgacgcgcc ctgacgggct tgtctgctcc      6720
cggcatccgc ttacagacaa gctgtgaccg tctccgggag ctgcatgtgt cagaggtttt      6780
```

| | |
|---|---:|
| caccgtcatc accgaaacgc gcgaggcagc agatcaattc gcgcgcgaag gcgaagcggc | 6840 |
| atgcataatg tgcctgtcaa atggacgaag cagggattct gcaaacccta tgctactccg | 6900 |
| tcaagccgtc aattgtctga ttcgttacca attatgacaa cttgacggct acatcattca | 6960 |
| cttttcttc acaaccggca cggaactcgc tcgggctggc cccggtgcat ttttaaata | 7020 |
| cccgcgagaa atagagttga tcgtcaaaac caacattgcg accgacggtg gcgataggca | 7080 |
| tccgggtggt gctcaaaagc agcttcgcct ggctgatacg ttggtcctcg cgccagctta | 7140 |
| agacgctaat ccctaactgc tggcggaaaa gatgtgacag acgcgacggc gacaagcaaa | 7200 |
| catgctgtgc gacgctggcg atatcaaaat tgctgtctgc caggtgatcg ctgatgtact | 7260 |
| gacaagcctc gcgtacccga ttatccatcg gtggatggag cgactcgtta atcgcttcca | 7320 |
| tgcgccgcag taacaattgc tcaagcagat ttatcgccag cagctccgaa tagcgccctt | 7380 |
| ccccttgccc ggcgttaatg atttgcccaa acaggtcgct gaaatgcggc tggtgcgctt | 7440 |
| catccgggcg aaagaacccc gtattggcaa atattgacgg ccagttaagc cattcatgcc | 7500 |
| agtaggcgcg cggacgaaag taaacccact ggtgatacca ttcgcgagcc tccggatgac | 7560 |
| gaccgtagtg atgaatctct cctgcggga acagcaaaat atcacccggt cggcaaacaa | 7620 |
| attctcgtcc ctgatttttc accaccccct gaccgcgaat ggtgagattg agaatataac | 7680 |
| ctttcattcc cagcggtcgg tcgataaaaa aatcgagata accgttggcc tcaatcggcg | 7740 |
| ttaaacccgc caccagatgg gcattaaacg agtatcccgg cagcagggga tcattttgcg | 7800 |
| cttcagccat acttttcata ctcccgccat tcagagaaga aaccaattgt ccatattgca | 7860 |
| tcagacattg ccgtcactgc gtcttttact ggctcttctc gctaaccaaa ccggtaaccc | 7920 |
| cgcttattaa aagcattctg taacaaagcg ggaccaaagc catgacaaaa acgcgtaaca | 7980 |
| aaagtgtcta taatcacggc agaaaagtcc acattgatta tttgcacggc gtcacacttt | 8040 |
| gctatgccat agcattttta tccataagat tagcggatcc tacctgacgc tttttatcgc | 8100 |
| aactctctac tgtttctcca tacccgtttt ttgggctaac aggaggaatt aac | 8153 |

<210> SEQ ID NO 119
<211> LENGTH: 8204
<212> TYPE: DNA
<213> ORGANISM: Artificial sequence
<220> FEATURE:
<223> OTHER INFORMATION: pRF238

<400> SEQUENCE: 119

| | |
|---|---:|
| catggggcat catcatcacc atcacggcgc cctgttctta ggccagctgg gcgccgcggg | 60 |
| atccacgatg ggtgcgccga agaaaaagcg caaagttgaa ttcgacaaga aatactccat | 120 |
| cggcctggac attggaacca actctgtcgg ctgggctgtc atcaccgacg agtacaaggt | 180 |
| gccctccaag aaattcaagg tcctcggaaa caccgatcga cactccatca gaaaaaacct | 240 |
| cattggtgcc ctgttgttcg attctggcga gactgccgaa gctaccagac tcaagcgaac | 300 |
| tgctcggcga cgttacaccc cgacggaagaa ccgaatctgc tacctgcagg atctttttc | 360 |
| caacgagatg gccaaggtgg acgattcgtt ctttcatcga ctggaggaat ccttcctcgt | 420 |
| cgaggaagac aagaaacacg agcgtcatcc catctttggc aacattgtgg acgaggttgc | 480 |
| ttaccacgag aagtatccta ccatctacca cctgcgaaag aaactcgtcg attccaccga | 540 |
| caaggcggat ctcagactta tctacctcgc tctggcacac atgatcaagt tcgaggtca | 600 |
| tttcctcatc gagggcgatc tcaatcccga caacagcgat gtggacaagc tgttcattca | 660 |

```
gctcgttcag acctacaacc agctgttcga ggaaaacccc atcaatgcct ccggagtcga    720
tgcaaaggcc atcttgtctg ctcgactctc gaagagcaga cgactggaga acctcattgc    780
ccaacttcct ggcgagaaaa agaacggact gtttggcaac ctcattgccc tttctcttgg    840
tctcacaccc aacttcaagt ccaacttcga tctggcggag gacgccaagc tccagctgtc    900
caaggacacc tacgacgatg acctcgacaa cctgcttgca cagattggcg atcagtacgc    960
cgacctgttt ctcgctgcca agaacctttc ggatgctatt ctcttgtctg acattctgcg   1020
agtcaacacc gagatcacaa aggctcccct ttctgcctcc atgatcaagc gatacgacga   1080
gcaccatcag gatctcacac tgctcaaggc tcttgtccga cagcaactgc ccgagaagta   1140
caaggagatc ttttttcgatc agtcgaagaa cggctacgct ggatacatcg acggcggagc   1200
ctctcaggaa gagttctaca agttcatcaa gccaattctc gagaagatgg acggaaccga   1260
ggaactgctt gtcaagctca atcgagagga tctgcttcgg aagcaacgaa ccttcgacaa   1320
cggcagcatt cctcatcaga tccacctcgg tgagctgcac gccattcttc gacgtcagga   1380
agacttctac ccctttctca aggacaaccg agagaagatc gagaagattc ttacctttcg   1440
aatcccctac tatgttggtc ctcttgccag aggaaactct cgatttgctt ggatgactcg   1500
aaagtccgag gaaaccatca ctccctggaa cttcgaggaa gtcgtggaca agggtgcctc   1560
tgcacagtcc ttcatcgagc gaatgaccaa cttcgacaag aatctgccca cgagaaggt   1620
tcttcccaag cattgctgc tctacgagta ctttacagtc tacaacgaac tcaccaaagt   1680
caagtacgtt accgagggaa tgcgaaagcc tgccttcttg tctggcgaac agaagaaagc   1740
cattgtcgat ctcctgttca agaccaaccg aaaggtcact gttaagcagc tcaaggagga   1800
ctacttcaag aaaatcgagt gtttcgacag cgtcgagatt ccggagttg aggaccgatt   1860
caacgcctct ttgggcacct atcacgatct gctcaagatt atcaaggaca aggattttct   1920
cgacaacgag gaaaacgagg acattctgga ggacatcgtg ctcactctta ccctgttcga   1980
agatcgggag atgatcgagg aacgactcaa gacatacgct cacctgttcg acgacaaggt   2040
catgaaacaa ctcaagcgac gtagatacac cggctgggga agactttcgc gaaagctcat   2100
caacggcatc agagacaagc agtccggaaa gaccattctg gactttctca gtccgatgg   2160
ctttgccaac cgaaacttca tgcagctcat tcacgacgat tctcttacct tcaaggagga   2220
catccagaag gcacaagtgt ccggtcaggg cgacagcttg cacgaacata ttgccaacct   2280
ggctggttcg ccagccatca gaaaaggcat tctccagact gtcaaggttg tcgacgagct   2340
ggtgaaggtc atgggacgtc acaagcccga gaacattgtg atcgagatgg ccagagagaa   2400
ccagacaact caaaagggtc agaaaaactc gcgagagcgg atgaagcgaa tcgaggaagg   2460
catcaaggag ctgggatccc agattctcaa ggagcatccc gtcgagaaca ctcaactgca   2520
gaacgagaag ctgtatctct actatctgca gaatggtcga gacatgtacg tggatcagga   2580
actggacatc aatcgtctca gcgactacga tgtggaccac attgtccctc aatcctttct   2640
caaggacgat tctatcgaca caaggtcct tacacgatcc gacaagaaca gaggcaagtc   2700
ggacaacgtt cccagcgaag aggtggtcaa aaagatgaag aactactggc gacagctgct   2760
caacgccaag ctcattaccc agcgaaagtt cgacaatctt accaaggccg agcgaggcgg   2820
tctgtccgag ctcgacaagg ctggcttcat caagcgtcaa ctcgtcgaga ccagacagat   2880
cacaaagcac gtcgcacaga ttctcgattc tcggatgaac accaagtacg acgaaacga   2940
caagctcatc cgagaggtca aggtgattac tctcaagtcc aaactggtct ccgatttccg   3000
aaaggacttt cagttctaca aggtgcgaga gatcaacaat taccaccatg cccacgatgc   3060
```

```
ttacctcaac gccgtcgttg gcactgcgct catcaagaaa tacccccaagc tcgaaagcga    3120 gttcgtttac ggcgattaca aggtctacga cgttcgaaag atgattgcca agtccgaaca    3180
ggagattggc aaggctactg ccaagtactt cttttactcc aacatcatga acttttcaa    3240 gaccgagatc accttggcca acggagagat tcgaaagaga ccacttatcg agaccaacgg    3300
cgaaactgga gagatcgtgt gggacaaggg tcgagacttt gcaaccgtgc gaaaggttct    3360
gtcgatgcct caggtcaaca tcgtcaagaa aaccgaggtt cagactggcg gattctccaa    3420
ggagtcgatt ctgcccaagc gaaactccga caagctcatc gctcgaaaga aagactggga    3480
tcccaagaaa tacggtggct tcgattctcc taccgtcgcc tattccgtgc ttgtcgttgc    3540
gaaggtcgag aagggcaagt ccaaaaagct caagtccgtc aaggagctgc tcggaattac    3600
catcatggag cgatcgagct tcgagaagaa tcccatcgac ttcttggaag ccaagggtta    3660
caaggaggtc aagaaagacc tcattatcaa gctgcccaag tactctctgt cgaactgga    3720 gaacggtcga aagcgtatgc tcgcctccgc tggcgagctg cagaagggaa acgagcttgc    3780
cttgccttcg aagtacgtca actttctcta tctggcttct cactacgaga agctcaaggg    3840
ttctcccgag gacaacgaac agaagcaact cttcgttgag cagcacaaac attacctcga    3900
cgagattatc gagcagattt ccgagttttc gaagcgagtc atcctggctg atgccaactt    3960
ggacaaggtc ctctctgcct acaacaagca tcgggacaaa cccattcgag aacaggcgga    4020
gaacatcatt cacctgttta ctcttaccaa cctgggtgct cctgcagctt tcaagtactt    4080
cgataccact atcgaccgaa agcggtacac atccaccaag gaggttctcg atgccaccct    4140
gattcaccag tccatcactg gcctgtacga gacccgaatc gacctgtctc agcttggtgg    4200
cgactccaga gccgatccca agaaaaagcg aaaggtctaa gcggccgcta agcttggctg    4260
ttttggcgga tgagagaaga ttttcagcct gatacagatt aaatcagaac gcagaagcgg    4320
tctgataaaa cagaatttgc ctggcggcag tagcgcggtg gtcccacctg acccatgcc    4380 gaactcagaa gtgaaacgcc gtagcgccga tggtagtgtg gggtctcccc atgcgagagt    4440
agggaactgc caggcatcaa ataaaacgaa aggctcagtc gaaagactgg gcctttcgtt    4500
ttatctgttg tttgtcggtg aacgctctcc tgagtaggac aaatccgccg ggagcggatt    4560
tgaacgttgc gaagcaacgg cccggagggt ggcgggcagg acgcccgcca taaactgcca    4620
ggcatcaaat taagcagaag gccatcctga cggatggcct ttttgcgttt ctacaaactc    4680
ttttgtttat ttttctaaat acattcaaat atgtatccgc tcatgagaca ataacccctga    4740 taaatgcttc aataatattg aaaaaggaag agtatgagta ttcaacattt ccgtgtcgcc    4800
cttattccct ttttgcggc attttgcctt cctgttttg ctcacccaga aacgctggtg    4860
aaagtaaaag atgctgaaga tcagttgggt gcacgagtgg gttacatcga actggatctc    4920
aacagcggta agatccttga gttttcgc cccgaagaac gttttccaat gatgagcact    4980
tttaaagttc tgctatgtgg cgcggtatta cccgtgttg acgccgggca agagcaactc    5040
ggtcgccgca tacactattc tcagaatgac ttggttgagt actcaccagt cacagaaaag    5100
catcttacgg atggcatgac agtaagagaa ttatgcagtg ctgccataac catgagtgat    5160
aacactgcgg ccaacttact tctgacaacg atcggaggac cgaaggagct aaccgctttt    5220
ttgcacaaca tgggggatca tgtaactcgc cttgatcgtt gggaaccgga gctgaatgaa    5280
gccataccaa acgacgagcg tgacaccacg atgcctgtag caatggcaac aacgttgcgc    5340
aaactattaa ctggcgaact acttactcta gcttcccggc aacaattaat agactggatg    5400
```

```
gaggcggata aagttgcagg accacttctg cgctcggccc ttccggctgg ctggtttatt   5460
gctgataaat ctggagccgg tgagcgtggg tctcgcggta tcattgcagc actggggcca   5520
gatggtaagc cctcccgtat cgtagttatc tacacgacgg ggagtcaggc aactatggat   5580
gaacgaaata gacagatcgc tgagataggt gcctcactga ttaagcattg gtaactgtca   5640
gaccaagttt actcatatat actttagatt gatttaaaac ttcattttta atttaaaagg   5700
atctaggtga agatcctttt tgataatctc atgaccaaaa tccccttaacg tgagttttcg   5760 ttccactgag cgtcagaccc cgtagaaaag atcaaaggat cttcttgaga tcctttttt   5820 ctgcgcgtaa tctgctgctt gcaaacaaaa aaccaccgc taccagcggt ggtttgtttg   5880
ccggatcaag agctaccaac tcttttccg aaggtaactg gcttcagcag agcgcagata   5940
ccaaatactg tccttctagt gtagccgtag ttaggccacc acttcaagaa ctctgtagca   6000
ccgcctacat acctcgctct gctaatcctg ttaccagtgg ctgctgccag tggcgataag   6060
tcgtgtctta ccgggttgga ctcaagacga tagttaccgg ataaggcgca gcggtcgggc   6120
tgaacggggg gttcgtgcac acagcccagc ttggagcgaa cgacctacac cgaactgaga   6180
tacctacagc gtgagctatg agaaagcgcc acgcttcccg aagggagaaa ggcggacagg   6240
tatccggtaa cgcgcaggt cggaacagga gagcgcacga gggagcttcc agggggaaac   6300
gcctggtatc tttatagtcc tgtcgggttt cgccacctct gacttgagcg tcgatttttg   6360
tgatgctcgt cagggggggcg agcctatgg aaaaacgcca gcaacgcggc cttttacgg   6420 ttcctggcct tttgctggcc ttttgctcac atgttctttc ctgcgttatc ccctgattct   6480
gtggataacc gtattaccgc ctttgagtga gctgataccg ctcgccgcag ccgaacgacc   6540
gagcgcagcg agtcagtgag cgaggaagcg gaagagcgcc tgatgcggta ttttctcctt   6600
acgcatctgt gcggtatttc acaccgcata tggtgcactc tcagtacaat ctgctctgat   6660
gccgcatagt taagccagta tacactccgc tatcgctacg tgactgggtc atggctgcgc   6720
cccgacaccc gccaacaccc gctgacgcgc cctgacgggg ttgtctgctc ccggcatccg   6780
cttacagaca agctgtgacc gtctccggga gctgcatgtg tcagaggttt tcaccgtcat   6840
caccgaaacg cgcgaggcag cagatcaatt cgcgcgcgaa ggcgaagcgg catgcataat   6900
gtgcctgtca aatggacgaa gcagggattc tgcaaaccct atgctactcc gtcaagccgt   6960
caattgtctg attcgttacc aattatgaca acttgacggc tacatcattc actttttctt   7020
cacaaccggc acgaactcg ctcgggctgg ccccggtgca ttttttaaat acccgcgaga   7080
aatagagttg atcgtcaaaa ccaacattgc gaccgacggt ggcgataggc atccgggtgg   7140
tgctcaaaag cagcttcgcc tggctgatac gttggtcctc gcgccagctt aagacgctaa   7200
tccctaactg ctggcggaaa agatgtgaca gacgcgacgg cgacaagcaa acatgctgtg   7260
cgacgctggc gatatcaaaa ttgctgtctg ccaggtgatc gctgatgtac tgacaagcct   7320
cgcgtacccg attatccatc ggtggatgga gcgactcgtt aatcgcttcc atgcgccgca   7380
gtaacaattg ctcaagcaga tttatcgcca gcagctccga atagcgccct tccccttgcc   7440
cggcgttaat gatttgccca acaggtcgc tgaaatgcgg ctggtgcgct tcatccgggc   7500
gaaagaaccc cgtattggca aatattgacg gccagttaag ccattcatgc cagtaggcgc   7560
gcggacgaaa gtaaacccac tggtgatacc attcgcgagc ctccggatga cgaccgtagt   7620
gatgaatctc tcctggcggg aacagcaaaa tatcacccgg tcggcaaaca aattctcgtc   7680
cctgattttt caccacccc tgaccgcgaa tggtgagatt gagaatataa cctttcattc   7740
ccagcggtcg gtcgataaaa aaatcgagat aaccgttggc ctcaatcggc gttaaacccg   7800
```

```
ccaccagatg ggcattaaac gagtatcccg gcagcagggg atcattttgc gcttcagcca    7860 tactttcat actcccgcca ttcagagaag aaaccaattg tccatattgc atcagacatt    7920
gccgtcactg cgtcttttac tggctcttct cgctaaccaa accggtaacc ccgcttatta    7980
aaagcattct gtaacaaagc gggaccaaag ccatgacaaa aacgcgtaac aaaagtgtct    8040
ataatcacgg cagaaaagtc cacattgatt atttgcacgg cgtcacactt tgctatgcca    8100
tagcattttt atccataaga ttagcggatc ctacctgacg cttttttatcg caactctcta    8160 ctgtttctcc atacccgttt tttgggctaa caggaggaat taac                    8204
```

<210> SEQ ID NO 120
<211> LENGTH: 1149
<212> TYPE: DNA
<213> ORGANISM: Escherichia coli
<220> FEATURE:
<221> NAME/KEY: misc_feature
<222> LOCATION: (1)..(1149)
<223> OTHER INFORMATION: galK gene

<400> SEQUENCE: 120

```
atgagtctga aagaaaaaac acaatctctg tttgccaacg catttggcta ccctgccact      60
cacaccattc aggcgcctgg ccgcgtgaat ttgattggtg aacacaccga ctacaacgac     120
ggtttcgttc tgccctgcgc gattgattat caaaccgtga tcagttgtgc accacgcgat     180
gaccgtaaag ttcgcgtgat ggcagccgat tatgaaaatc agctcgacga gttttccctc     240
gatgcgccca ttgtcgcaca tgaaaactat caatgggcta actacgttcg tggcgtggtg     300
aaacatctgc aactgcgtaa caacagcttc ggcggcgtgg acatggtgat cagcggcaat     360
gtgccgcagg gtgccgggtt aagttcttcc gcttcactgg aagtcgcggt cggaaccgta     420
ttgcagcagc tttatcatct gccgctggac ggcgcacaaa tcgcgcttaa cggtcaggaa     480
gcagaaaacc agtttgtagg ctgtaactgc gggatcatgg atcagctaat ttccgcgctc     540
ggcaagaaag atcatgcctt gctgatcgat tgccgctcac tggggaccaa agcagtttcc     600
atgcccaaag gtgtggctgt cgtcatcatc aacagtaact tcaaacgtac cctggttggc     660
agcgaataca cacccgtcg tgaacagtgc gaaaccggtg cgcgtttctt ccagcagcca     720
gccctgcgtg atgtcaccat tgaagagttc aacgctgttg cgcatgaact ggacccgatc     780
gtggcaaaac gcgtgcgtca tatactgact gaaaacgccc gcaccgttga agctgccagc     840
gcgctggagc aaggcgacct gaaacgtatg ggcgagttga tggcggagtc tcatgcctct     900
atgcgcgatg atttcgaaat caccgtgccg caaattgaca ctctggtaga aatcgtcaaa     960
gctgtgattg cgacaaaggg tggcgtacgc atgaccggcg gcggatttgg cggctgtatc    1020
gtcgcgctga tcccggaaga gctggtgcct gccgtacagc aagctgtcgc tgaacaatat    1080
gaagcaaaaa caggtattaa agagacttttt acgtttgta aaccatcaca aggagcagga    1140
cagtgctga                                                           1149
```

<210> SEQ ID NO 121
<211> LENGTH: 1017
<212> TYPE: DNA
<213> ORGANISM: Escherichia coli

<400> SEQUENCE: 121

```
atgagagttc tggttaccgg tggtagcggt tacattggaa gtcatacctg tgtgcaatta     60
ctgcaaaacg gtcatgatgt catcattctt gataacctct gtaacagtaa gcgcagcgta    120
```

```
ctgcctgtta tcgagcgttt aggcggcaaa catccaacgt tgttgaagg cgatattcgt      180 aacgaagcgt tgatgaccga gatcctgcac gatcacgcta tcgacaccgt gatccacttc     240
gccgggctga agccgtggg cgaatcggta caaaaaccgc tggaatatta cgacaacaat      300
gtcaacggca ctctgcgcct gattagcgcc atgcgcgccg ctaacgtcaa aaactttatt    360
tttagctcct ccgccaccgt ttatggcgat cagcccaaaa ttccatacgt tgaaagcttc    420
ccgaccggca caccgcaaag cccttacggc aaaagcaagc tgatggtgga acagatcctc    480
accgatctgc aaaaagccca gccggactgg agcattgccc tgctgcgcta cttcaacccg    540
gttggcgcgc atccgtcggg cgatatgggc gaagatccgc aaggcattcc gaataacctg    600
atgccataca tcgcccaggt tgctgtaggc cgtcgcgact cgctggcgat ttttggtaac    660
gattatccga ccgaagatgg tactggcgta cgcgattaca tccacgtaat ggatctggcg    720
gacggtcacg tcgtggcgat ggaaaaactg gcgaacaagc caggcgtaca catctacaac    780
ctcggcgctg gcgtaggcaa cagcgtgctg gacgtggtta atgccttcag caaagcctgc    840
ggcaaaccgg ttaattatca ttttgcaccg cgtcgcgagg gcgaccttcc ggcctactgg    900
gcggacgcca gcaaagccga ccgtgaactg aactggcgcg taacgcgcac actcgatgaa    960
atggcgcagg acacctggca ctggcagtca cgccatccac agggatatcc cgattaa     1017

<210> SEQ ID NO 122
<211> LENGTH: 1047
<212> TYPE: DNA
<213> ORGANISM: Escherichia coli

<400> SEQUENCE: 122
atgacgcaat ttaatcccgt tgatcatcca catcgccgct acaacccgct caccgggcaa      60
tggattctgg tttcaccgca ccgcgctaag cgccctgc aggggggcgca ggaaacgcca     120 gccaaacagg tgttacctgc gcacgatcca gattgcttcc tctgcgcagg taatgtgcgg    180
gtgacaggcg ataaaaaccc cgattacacc gggacttacg ttttcactaa tgactttgcg    240
gctttgatgt ctgacacgcc agatgcgcca gaaagtcacg atccgctgat gcgttgccag    300
agcgcgcgcg gcaccagccg ggtgatctgc ttttcaccgg atcacagtaa acgctgcca    360 gagctcagcg ttgcagcatt gacggaaatc gtcaaaacct ggcaggagca aaccgcagaa    420
ctggggaaaa cgtacccatg ggtgcaggtt tttgaaaaca aaggcgcggc gatgggctgc    480
tctaacccgc atccgcacgg tcagatttgg gcaaatagct tcctgcctaa cgaagctgag    540
cgcgaagacc gcctgcaaaa agaatatttt gccgaacaga atcaccaat gctggtggat    600 tatgttcagc gcgagctggc agacggtagc cgtaccgttg tcgaaaccga acactggtta    660
gccgtcgtgc cttactgggc tgcctggccg ttcgaaacgc tactgctgcc caaagcccac    720
gttttacgga tcaccgattt gaccgacgcc cagcgcagcg atctggcgct ggcgttgaaa    780
aagctgacca gtcgttatga caacctcttc cagtgctcct tcccctactc tatgggctgg    840
cacggcgcgc catttaatgg cgaagagaat caacactgga gctgcacgc gcacttttat    900 ccgcctctgc tgcgctccgc caccgtacgt aaatttatgg ttggttatga aatgctggca    960
gagacccagc gagacctgac cgcagaacag gcagcagagc gtttgcgcgc agtcagcgat   1020
atccattttc gcgaatccgg agtgtaa                                     1047

<210> SEQ ID NO 123
<211> LENGTH: 76
<212> TYPE: RNA
<213> ORGANISM: Artificial sequence
```

<220> FEATURE:
<223> OTHER INFORMATION: CER domain1

<400> SEQUENCE: 123
guuuuagagc uagaaauagc aaguuaaaau aaggcuaguc cguuaucaac uugaaaaagu    60
ggcaccgagu cggugc                                                    76

<210> SEQ ID NO 124
<211> LENGTH: 76
<212> TYPE: DNA
<213> ORGANISM: Artificial sequence
<220> FEATURE:
<223> OTHER INFORMATION: CER encoding DNA PCR

<400> SEQUENCE: 124
gttttagagc tagaaatagc aagttaaaat aaggctagtc cgttatcaac ttgaaaaagt    60
ggcaccgagt cggtgc                                                    76

<210> SEQ ID NO 125
<211> LENGTH: 11714
<212> TYPE: DNA
<213> ORGANISM: Artificial sequence
<220> FEATURE:
<223> OTHER INFORMATION: pRF291

<400> SEQUENCE: 125
cgataaaaaa caaaaaaaaa agcaccgact cggtgccact ttttcaagtt gataacggac    60
tagccttatt ttaacttgct atttctagct ctaaaacgca ggtgtaaaaa taaaaggcc    120 tgcgattacc agcaggcctg ttattaacct aagccttagg acgcttcacg ccatacttgg    180
aacgagcctg cttacggtct ttaacgccgg agcagtcaag cgcaccacgt acggtgtggt    240
aacgaacacc cgggaggtct ttaacacgac cgccacggat caggatcacg gagtgctcct    300
gcaggttgtg accttcacca ccgatgtagg aagtcacttc gaaaccgtta gtcagacgaa    360
cacggcatac tttacgcagc gcggagttcg gttttttagg agtggtagta tatacacgag    420
tacatacgcc acgttttgc gggcatgctt ccagcgcagg cacgttgctt ttcgcaactt    480
tgcgagcacg tggtttgcgt accagctggt taactgttgc cattaaatag ctcctggttt    540
tagcttttgc ttcgtaaaca cgtaataaaa cgtcctcaca caatatgagg acgccgaatt    600
tagggcgatg ccgaaaaggt gtcaagaaat atacaacgat cccgccatca cctgcgtccc    660
attcgccatg ccgaagcatg ttgcccagcc ggcgccagcg aggaggctgg gaccatgccg    720
gccattattt tgcgttaagt ttctaatcat cacgaaatta tctatcaaaa ataactaggt    780
cccaccgaga ttcgaactcg ggaccttaag atttgcaatc tcacgcgcta ccgctgtgcc    840
ataggaccga agttaaaatt tggccaaaga aggacctggg caccctggac tgtgggttag    900
ggtaatattc cttatggaga caatgggcta gggtaaatta cctaaaatgg gtcgataaag    960
aggggtgttc ccagttggga agtgtaattg aagacgggt caaaaagaa aatcaaaaaa    1020 aatttaatta agtcatacac aagtcagctt tcttcgagcc tcatataagt ataagtagtt    1080
caacgtatta gcactgtacc cagcatctcc gtatcgagaa acacaacaac atgccccatt    1140
ggacagatca tgcggataca caggttgtgc agtatcatac atactcgatc agacaggtcg    1200
tctgaccatc atacaagctg aacaagcgct ccatacttgc acgctctcta tatacacagt    1260
taaattacat atccatagtc taacctctaa cagttaatct tctggtaagc ctcccagcca    1320
gccttctggt atcgcttggc ctcctcaata ggatctcggt tctggccgta cagacctcgg    1380

```
ccgacaatta tgatatccgt tccggtagac atgacatcct caacagttcg gtactgctgt    1440
ccgagagcgt ctcccttgtc gtcaagaccc accccggggg tcagaataag ccagtcctca    1500
gagtcgccct taggtcggtt ctgggcaatg aagccaacca caaactcggg gtcggatcgg    1560
gcaagctcaa tggtctgctt ggagtactcg ccagtggcca gagagccctt gcaagacagc    1620
tcggccagca tgagcagacc tctggccagc ttctcgttgg gagaggggac taggaactcc    1680
ttgtactggg agttctcgta gtcagagacg tcctccttct tctgttcaga gacagtttcc    1740
tcggcaccag ctcgcaggcc agcaatgatt ccggttccgg gtacaccgtg ggcgttggtg    1800
atatcggacc actcggcgat tcggtgacac cggtactggt gcttgacagt gttgccaata    1860
tctgcgaact ttctgtcctc gaacaggaag aaaccgtgct taagagcaag ttccttgagg    1920
gggagcacag tgccggcgta ggtgaagtcg tcaatgatgt cgatatgggt tttgatcatg    1980
cacacataag gtccgacctt atcggcaagc tcaatgagct ccttggtggt ggtaacatcc    2040
agagaagcac acaggttggt tttcttggct gccacgagct tgagcactcg agcggcaaag    2100
gcggacttgt ggacgttagc tcgagcttcg taggagggca ttttggtggt gaagaggaga    2160
ctgaaataaa tttagtctgc agaacttttt atcggaacct tatctggggc agtgaagtat    2220
atgttatggt aatagttacg agttagttga acttatagat agactggact atacggctat    2280
cggtccaaat tagaaagaac gtcaatggct ctctgggcgt cgcctttgcc gacaaaaatg    2340
tgatcatgat gaaagccagc aatgacgttg cagctgatat tgttgtcggc caaccgcgcc    2400
gaaaacgcag ctgtcagacc cacagcctcc aacgaagaat gtatcgtcaa agtgatccaa    2460
gcacactcat agttggagtc gtactccaaa ggcggcaatg acgagtcaga cagatactcg    2520
tcgacgttta aaccatcatc taagggcctc aaaactacct cggaactgct gcgctgatct    2580
ggacaccaca gaggttccga gcactttagg ttgcaccaaa tgtcccacca ggtgcaggca    2640
gaaaacgctg aacagcgtg tacagtttgt cttaacaaaa agtgagggcg ctgaggtcga    2700
gcagggtggt gtgacttgtt atagccttta gagctgcgaa agcgcgtatg gatttggctc    2760
atcaggccag attgagggtc tgtggacaca tgtcatgtta gtgtacttca atcgccccct    2820
ggatatagcc ccgacaatag gccgtggcct catttttttg ccttccgcac atttccattg    2880
ctcggtaccc acaccttgct tctcctgcac ttgccaacct taatactggt ttacattgac    2940
caacatctta caagcggggg gcttgtctag ggtatatata aacagtggct ctcccaatcg    3000
gttgccagtc tcttttttcc tttctttccc cacagattcg aaatctaaac tacacatcac    3060
accatggaca agaaatactc catcggcctg acattggaa ccaactctgt cggctgggct    3120
gtcatcaccg acgagtacaa ggtgccctcc aagaaattca aggtcctcgg aaacaccgat    3180
cgacactcca tcaagaaaaa cctcattggt gccctgttgt tcgattctgg cgagactgcc    3240
gaagctacca gactcaagcg aactgctcgg cgacgttaca cccgacggaa gaaccgaatc    3300
tgctacctgc aggagatctt ttccaacgag atggccaagg tggacgattc gttctttcat    3360
cgactggagg aatccttcct cgtcgaggaa gacaagaaac acgagcgtca tcccatcttt    3420
ggcaacattg tggacgaggt tgcttaccac gagaagtatc ctaccatcta ccatctccga    3480
aagaaactcg tcgattccac cgacaaggcg atctcagac ttatctacct cgctctggca    3540
cacatgatca agtttcgagg tcatttcctc atcgagggcg atctcaatcc cgacaacagc    3600
gatgtggaca agctgttcat tcagctcgtt cagacctaca accagctgtt cgaggaaaac    3660
cccatcaatg cctccggagt cgatgcaaag gccatcttgt ctgctcgact ctcgaagagc    3720
agacgactgg agaacctcat tgcccaactt cctggcgaga aaagaacgg actgtttggc    3780
```

```
aacctcattg ccctttctct tggtctcaca cccaacttca agtccaactt cgatctggcg    3840
gaggacgcca agctccagct gtccaaggac acctacgacg atgacctcga caacctgctt    3900
gcacagattg gcgatcagta cgccgacctg tttctcgctg ccaagaacct ttcggatgct    3960
attctcttgt ctgacattct gcgagtcaac accgagatca caaaggctcc cctttctgcc    4020
tccatgatca agcgatacga cgagcaccat caggatctca cactgctcaa ggctcttgtc    4080
cgacagcaac tgcccgagaa gtacaaggag atcttttcg atcagtcgaa gaacggctac    4140
gctggataca tcgacggcgg agcctctcag gaagagttct acaagttcat caagccaatt    4200
ctcgagaaga tggacggaac cgaggaactg cttgtcaagc tcaatcgaga ggatctgctt    4260
cggaagcaac gaaccttcga caacggcagc attcctcatc agatccacct cggtgagctg    4320
cacgccattc ttcgacgtca ggaagacttc taccccttc tcaaggacaa ccgagagaag    4380
atcgagaaga ttcttacctt tcgaatcccc tactatgttg gtcctcttgc cagaggaaac    4440
tctcgatttg cttggatgac tcgaaagtcc gaggaaacca tcactccctg gaacttcgag    4500
gaagtcgtgg acaagggtgc ctctgcacag tccttcatcg agcgaatgac caacttcgac    4560
aagaatctgc ccaacgagaa ggttcttccc aagcattcgc tgctctacga gtactttaca    4620
gtctacaacg aactcaccaa agtcaagtac gttaccgagg gaatgcgaaa gcctgccttc    4680
ttgtctggcg aacagaagaa agccattgtc gatctcctgt tcaagaccaa ccgaaaggtc    4740
actgttaagc agctcaagga ggactacttc aagaaaatcg agtgtttcga cagcgtcgag    4800
atttccggag ttgaggaccg attcaacgcc tctttgggca cctatcacga tctgctcaag    4860
attatcaagg acaaggattt tctcgacaac gaggaaaacg aggacattct ggaggacatc    4920
gtgctcactc ttaccctgtt cgaagatcgg gagatgatcg aggaacgact caagacatac    4980
gctcacctgt tcgacgacaa ggtcatgaaa caactcaagc gacgtagata caccggctgg    5040
ggaagacttt cgcgaaagct catcaacggc atcagagaca agcagtccgg aaagaccatt    5100
ctggactttc tcaagtccga tggctttgcc aaccgaaact tcatgcagct cattcacgac    5160
gattctctta ccttcaagga ggacatccag aaggcacaag tgtccggtca gggcgacagc    5220
ttgcacgaac atattgccaa cctggctggt tcgccagcca tcaagaaagg cattctccag    5280
actgtcaagg ttgtcgacga gctggtgaag gtcatggac gtcacaagcc cgagaacatt    5340
gtgatcgaga tggccagaga gaaccagaca actcaaaagg gtcagaaaaa ctcgcgagag    5400
cggatgaagc gaatcgagga aggcatcaag gagctgggat cccagattct caaggagcat    5460
cccgtcgaga cactcaact gcagaacgag aagctgtatc tctactatct gcagaatggt    5520
cgagacatgt acgtggatca ggaactggac atcaatcgtc tcagcgacta cgatgtggac    5580
cacattgtcc ctcaatcctt tctcaaggac gattctatcg acaacaaggt ccttacacga    5640
tccgacaaga acagaggcaa gtcggacaac gttcccagcg aagaggtggt caaaaagatg    5700
aagaactact ggcgacagct gctcaacgcc aagctcatta cccagcgaaa gttcgacaat    5760
cttaccaagg ccgagcgagg cggtctgtcc gagctcgaca aggctggctt catcaagcgt    5820
caactcgtcg agaccagaca gatcacaaag cacgtcgcac agattctcga ttctcggatg    5880
aacaccaagt acgacgagaa cgacaagctc atccgagagg tcaaggtgat tactctcaag    5940
tccaaactgg tctccgattt ccgaaaggac tttcagttct acaaggtgcg agagatcaac    6000
aattaccacc atgcccacga tgcttacctc aacgccgtcg ttggcactgc gctcatcaag    6060 aaataccccca agctcgaaag cgagttcgtt tacggcgatt acaaggtcta cgacgttcga    6120
```

```
aagatgattg ccaagtccga acaggagatt ggcaaggcta ctgccaagta cttcttttac    6180
tccaacatca tgaactttt caagaccgag atcaccttgg ccaacggaga gattcgaaag     6240
agaccactta tcgagaccaa cggcgaaact ggagagatcg tgtgggacaa gggtcgagac    6300
tttgcaaccg tgcgaaaggt tctgtcgatg cctcaggtca acatcgtcaa gaaaaccgag    6360
gttcagactg gcggattctc caaggagtcg attctgccca agcgaaactc cgacaagctc    6420
atcgctcgaa agaaagactg ggatcccaag aaatacggtg gcttcgattc tcctaccgtc    6480
gcctattccg tgcttgtcgt tgcgaaggtc gagaagggca agtccaaaaa gctcaagtcc    6540
gtcaaggagc tgctcggaat taccatcatg gagcgatcga gcttcgagaa gaatcccatc    6600
gacttcttgg aagccaaggg ttacaaggag gtcaagaaag acctcattat caagctgccc    6660
aagtactctc tgttcgaact ggagaacggt cgaaagcgta tgctcgcctc cgctggcgag    6720
ctgcagaagg gaaacgagct tgccttgcct tcgaagtacg tcaactttct ctatctggct    6780
tctcactacg agaagctcaa gggttctccc gaggacaacg aacagaagca actcttcgtt    6840
gagcagcaca acattaccct cgacgagatt atcgagcaga tttccgagtt ttcgaagcga    6900
gtcatcctgg ctgatgccaa cttggacaag gtgctctctg cctacaacaa gcatcgggac    6960
aaacccattc gagaacaggc ggagaacatc attcacctgt ttactcttac caacctgggt    7020
gctcctgcag cttcaagta cttcgatacc actatcgacc gaaagcggta cacatccacc     7080
aaggaggttc tcgatgccac cctgattcac cagtccatca ctggcctgta cgagacccga    7140
atcgacctgt ctcagcttgg tggcgactcc agagccgatc ccaagaaaaa gcgaaaggtc    7200
taagcggccg caagtgtgga tggggaagtg agtgcccggt tctgtgtgca caattggcaa    7260
tccaagatgg atggattcaa cacagggata tagcgagcta cgtggtggtg cgaggatata    7320 gcaacgata tttatgtttg acacttgaga atgtacgata caagcactgt ccaagtacaa      7380
tactaaacat actgtacata ctcatactcg tacccgggca acggtttcac ttgagtgcag    7440
tggctagtgc tcttactcgt acagtgtgca atactgcgta tcatagtctt tgatgtatat    7500
cgtattcatt catgttagtt gcgtacgagc cggaagcata aagtgtaaag cctggggtgc    7560
ctaatgagtg agctaactca cattaattgc gttgcgctca ctgcccgctt tccagtcggg    7620
aaacctgtcg tgccagctgc attaatgaat cggccaacgc gcgggagag gcggtttgcg      7680 tattgggcgc tcttccgctt cctcgctcac tgactcgctg cgctcggtcg ttcggctgcg    7740
gcgagcggta tcagctcact caaaggcggt aatacggtta ccacagaat cagggataa      7800 cgcaggaaag aacatgtgag caaaaggcca gcaaaaggcc aggaaccgta aaaaggccgc    7860
gttgctggcg ttttccata ggctccgccc ccctgacgag catcacaaaa atcgacgctc      7920
aagtcagagg tggcgaaacc cgacaggact ataaagatac caggcgtttc ccctggaag    7980 ctccctcgtg cgctctcctg ttccgaccct gccgcttacc ggatacctgt ccgcctttct    8040
cccttcggga agcgtggcgc tttctcatag ctcacgctgt aggtatctca gttcggtgta    8100
ggtcgttcgc tccaagctgg gctgtgtgca cgaaccccc gttcagcccg accgctgcgc      8160
cttatccggt aactatcgtc ttgagtccaa cccggtaaga cacgacttat cgccactggc    8220
agcagccact ggtaacagga ttagcagagc gaggtatgta ggcggtgcta cagagttctt    8280
gaagtggtgg cctaactacg gctacactag aaggacagta tttggtatct gcgctctgct    8340
gaagccagtt accttcggaa aaagagttgg tagctcttga tccggcaaac aaaccaccgc    8400
tggtagcggg ggtttttttg tttgcaagca gcagattacg cgcagaaaaa aaggatctca    8460
agaagatcct ttgatctttt ctacggggtc tgacgctcag tggaacgaaa actcacgtta    8520
```

```
agggattttg gtcatgagat tatcaaaaag gatcttcacc tagatccttt taaattaaaa   8580
atgaagtttt aaatcaatct aaagtatata tgagtaaact tggtctgaca gttaccaatg   8640
cttaatcagt gaggcaccta tctcagcgat ctgtctattt cgttcatcca tagttgcctg   8700 actcccccgtc gtgtagataa ctacgatacg ggagggctta ccatctggcc ccagtgctgc   8760
aatgataccg cgagacccac gctcaccggc tccagattta tcagcaataa accagccagc   8820
cggaagggcc gagcgcagaa gtggtcctgc aactttatcc gcctccatcc agtctattaa   8880
ttgttgccgg gaagctagag taagtagttc gccagttaat agtttgcgca acgttgttgc   8940
cattgctaca ggcatcgtgg tgtcacgctc gtcgtttggt atggcttcat tcagctccgg   9000
ttcccaacga tcaaggcgag ttacatgatc ccccatgttg tgcaaaaaag cggttagctc   9060
cttcggtcct ccgatcgttg tcagaagtaa gttggccgca gtgttatcac tcatggttat   9120
ggcagcactg cataattctc ttactgtcat gccatccgta agatgctttt ctgtgactgg   9180
tgagtactca accaagtcat tctgagaata gtgtatgcgg cgaccgagtt gctcttgccc   9240
ggcgtcaata cgggataata ccgcgccaca tagcagaact ttaaaagtgc tcatcattgg   9300
aaaacgttct cgggggcgaa aactctcaag gatcttaccg ctgttgagat ccagttcgat   9360
gtaacccact cgtgcaccca actgatcttc agcatctttt actttcacca gcgtttctgg   9420
gtgagcaaaa acaggaaggc aaaatgccgc aaaaaaggga ataagggcga cacggaaatg   9480
ttgaatactc atactcttcc ttttttcaata ttattgaagc atttatcagg gttattgtct   9540
catgagcgga tacatatttg aatgtattta gaaaaataaa caaatagggg ttccgcgcac   9600
atttccccga aaagtgccac ctgacgcgcc ctgtagcggc gcattaagcg cggcgggtgt   9660
ggtggttacg cgcagcgtga ccgctacact tgccagcgcc ctagcgcccg ctcctttcgc   9720
tttcttccct tcctttctcg ccacgttcgc cggctttccc cgtcaagctc taaatcgggg   9780
gctcccttta gggttccgat ttagtgcttt acggcacctc gaccccaaaa aacttgatta   9840
gggtgatggt tcacgtagtg gccatcgccc tgatagacg gttttttcgcc ctttgacgtt   9900 ggagtccacg ttctttaata gtggactctt gttccaaact ggaacaacac tcaaccctat   9960
ctcggtctat tcttttgatt tataagggat tttgccgatt tcggcctatt ggttaaaaaa  10020
tgagctgatt taacaaaaat ttaacgcgaa ttttaacaaa atattaacgc ttacaatttc  10080
cattcgccat tcaggctgcg caactgttgg gaagggcgat cggtgcgggc ctcttcgcta  10140
ttacgccagc tggcgaaagg gggatgtgct gcaaggcgat taagttgggt aacgccaggg  10200
ttttcccagt cacgacgttg taaaacgacg gccagtgaat tgtaatacga ctcactatag  10260
ggcgaattgg gtaccgggcc ccccctcgag gtcgatggtg tcgataagct tgatatcgaa  10320
ttcatgtcac acaaaccgat cttcgcctca aggaaaccta attctacatc cgagagactg  10380
ccgagatcca gtctacactg attaattttc gggccaataa tttaaaaaaa tcgtgttata  10440
taatattata tgtattatat atatacatca tgatgatact gacagtcatg tcccattgct  10500
aaatagacag actccatctg ccgcctccaa ctgatgttct caatatttaa ggggtcatct  10560
cgcattgttt aataataaac agactccatc taccgcctcc aaatgatgtt ctcaaaatat  10620
attgtatgaa cttattttta ttacttagta ttattagaca acttacttgc tttatgaaaa  10680
acacttccta tttaggaaac aatttataat ggcagttcgt tcatttaaca atttatgtag  10740
aataaatgtt ataaatgcgt atgggaaatc ttaaatatgg atagcataaa tgatatctgc  10800
attgcctaat tcgaaatcaa cagcaacgaa aaaaatccct tgtacaacat aaatagtcat  10860
```

```
cgagaaatat caactatcaa agaacagcta ttcacacgtt actattgaga ttattattgg    10920
acgagaatca cacactcaac tgtctttctc tcttctagaa atacaggtac aagtatgtac    10980
tattctcatt gttcatactt ctagtcattt catcccacat attccttgga tttctctcca    11040
atgaatgaca ttctatcttg caaattcaac aattataata agatatacca aagtagcggt    11100
atagtggcaa tcaaaaagct tctctggtgt gcttctcgta tttatttta ttctaatgat      11160 ccattaaagg tatatattta tttcttgtta tataatcctt ttgtttatta catgggctgg    11220
atacataaag gtattttgat ttaattttt gcttaaattc aatccccct cgttcagtgt        11280 caactgtaat ggtaggaaat taccatactt ttgaagaagc aaaaaaatg aaagaaaaaa      11340 aaaatcgtat ttccaggtta gacgttccgc agaatctaga atgcggtatg cggtacattg    11400
ttcttcgaac gtaaaagttg cgctccctga gatattgtac atttttgctt ttacaagtac    11460
aagtacatcg tacaactatg tactactgtt gatgcatcca caacagtttg ttttgttttt    11520
ttttgttttt tttttttcta atgattcatt accgctatgt ataccactt gtacttgtag      11580 taagccgggt tattggcgtt caattaatca tagacttatg aatctgcacg gtgtgcgctg    11640
cgagttactt ttagcttatg catgctactt gggtgtaata ttgggatctg ttcggaaatc    11700
aacggatgct caat                                                      11714

<210> SEQ ID NO 126
<211> LENGTH: 20
<212> TYPE: DNA
<213> ORGANISM: Artificial sequence
<220> FEATURE:
<223> OTHER INFORMATION: CER forward

<400> SEQUENCE: 126
gttttagagc tagaaatagc                                                 20

<210> SEQ ID NO 127
<211> LENGTH: 20
<212> TYPE: DNA
<213> ORGANISM: Artificial sequence
<220> FEATURE:
<223> OTHER INFORMATION: univeral reverse

<400> SEQUENCE: 127
gcaccgactc ggtgccactt                                                 20

<210> SEQ ID NO 128
<211> LENGTH: 18
<212> TYPE: DNA
<213> ORGANISM: Artificial sequence
<220> FEATURE:
<223> OTHER INFORMATION: universal forward T7 primer

<400> SEQUENCE: 128
taatacgact cactatag                                                   18

<210> SEQ ID NO 129
<211> LENGTH: 34
<212> TYPE: DNA
<213> ORGANISM: Artificial sequence
<220> FEATURE:
<223> OTHER INFORMATION: galK2-1 forward primer

<400> SEQUENCE: 129
taatacgact cactatagat cagcggcaat gtgc                                 34
```

```
<210> SEQ ID NO 130
<211> LENGTH: 34
<212> TYPE: DNA
<213> ORGANISM: Artificial sequence
<220> FEATURE:
<223> OTHER INFORMATION: galK2-1 reverse primer

<400> SEQUENCE: 130
ttctagctct aaaactgcgg cacattgccg ctga                              34

<210> SEQ ID NO 131
<211> LENGTH: 114
<212> TYPE: DNA
<213> ORGANISM: Artificial Sequence
<220> FEATURE:
<223> OTHER INFORMATION: galK2-1 sgRNA in vitro transcription template

<400> SEQUENCE: 131
taatacgact cactatagat cagcggcaat gtgccgcagt tttagagcta gaaatagcaa    60
gttaaaataa ggctagtccg ttatcaactt gaaaaagtgg caccgagtcg gtgc         114

<210> SEQ ID NO 132
<211> LENGTH: 18
<212> TYPE: DNA
<213> ORGANISM: T7 phage

<400> SEQUENCE: 132
taatacgact cactatag                                                18

<210> SEQ ID NO 133
<211> LENGTH: 20
<212> TYPE: DNA
<213> ORGANISM: Escherichia coli

<400> SEQUENCE: 133
atcagcggca atgtgccgca                                              20

<210> SEQ ID NO 134
<211> LENGTH: 23
<212> TYPE: DNA
<213> ORGANISM: Escherichia coli

<400> SEQUENCE: 134
atcagcggca atgtgccgca ggg                                          23

<210> SEQ ID NO 135
<211> LENGTH: 96
<212> TYPE: RNA
<213> ORGANISM: Artificial sequence
<220> FEATURE:
<223> OTHER INFORMATION: galK2-1 sgRNA

<400> SEQUENCE: 135
aucagcggca augugccgca guuuuagagc uagaaauagc aaguuaaaau aaggcuaguc    60
cguuaucaac uugaaaaagu ggcaccgagu cggugc                             96

<210> SEQ ID NO 136
<211> LENGTH: 262
<212> TYPE: PRT
<213> ORGANISM: Artificial sequence
<220> FEATURE:
<223> OTHER INFORMATION: his-MPG1-dsREDexpress

<400> SEQUENCE: 136
```

Met Gly His His His His His Gly Ala Leu Phe Leu Gly Gln Leu
1               5                   10                  15

Gly Ala Ala Gly Ser Thr Met Gly Ala Pro Lys Lys Lys Arg Lys Val
                20                  25                  30

Glu Phe Gly Gly Gly Gly Ala Ser Ser Glu Asp Val Ile Lys Glu Phe
        35                  40                  45

Met Arg Phe Lys Val Arg Met Glu Gly Ser Val Asn Gly His Glu Phe
50                  55                  60

Glu Ile Glu Gly Glu Gly Glu Gly Arg Pro Tyr Glu Gly Thr Gln Thr
65                  70                  75                  80

Ala Lys Leu Lys Val Thr Lys Gly Gly Pro Leu Pro Phe Ala Trp Asp
                85                  90                  95

Ile Leu Ser Pro Gln Phe Gln Tyr Gly Ser Lys Val Tyr Val Lys His
                100                 105                 110

Pro Ala Asp Ile Pro Asp Tyr Lys Lys Leu Ser Phe Pro Glu Gly Phe
            115                 120                 125

Lys Trp Glu Arg Val Met Asn Phe Glu Asp Gly Gly Val Val Thr Val
130                 135                 140

Thr Gln Asp Ser Ser Leu Gln Asp Gly Ser Phe Ile Tyr Lys Val Lys
145                 150                 155                 160

Phe Ile Gly Val Asn Phe Pro Ser Asp Gly Pro Val Met Gln Lys Lys
                165                 170                 175

Thr Met Gly Trp Glu Ala Ser Thr Glu Arg Leu Tyr Pro Arg Asp Gly
            180                 185                 190

Val Leu Lys Gly Glu Ile His Lys Ala Leu Lys Leu Lys Asp Gly Gly
            195                 200                 205

His Tyr Leu Val Glu Phe Lys Ser Ile Tyr Met Ala Lys Lys Pro Val
210                 215                 220

Gln Leu Pro Gly Tyr Tyr Tyr Val Asp Ser Lys Leu Asp Ile Thr Ser
225                 230                 235                 240

His Asn Glu Asp Tyr Thr Ile Val Glu Gln Tyr Glu Arg Ala Glu Gly
                245                 250                 255

Arg His His Leu Phe Leu
            260

<210> SEQ ID NO 137
<211> LENGTH: 256
<212> TYPE: PRT
<213> ORGANISM: Artificial sequence
<220> FEATURE:
<223> OTHER INFORMATION: pVEC-dsREDexpress

<400> SEQUENCE: 137

Met Gly His His His His His Leu Leu Ile Ile Leu Arg Arg Arg
1               5                   10                  15

Ile Arg Lys Gln Ala His Ala His Ser Lys Glu Phe Gly Gly Gly Gly
                20                  25                  30

Ala Ser Ser Glu Asp Val Ile Lys Glu Phe Met Arg Phe Lys Val Arg
        35                  40                  45

Met Glu Gly Ser Val Asn Gly His Glu Phe Ile Glu Gly Glu Gly
50                  55                  60

Glu Gly Arg Pro Tyr Glu Gly Thr Gln Thr Ala Lys Leu Lys Val Thr
65                  70                  75                  80

Lys Gly Gly Pro Leu Pro Phe Ala Trp Asp Ile Leu Ser Pro Gln Phe
                85                  90                  95

Gln Tyr Gly Ser Lys Val Tyr Val Lys His Pro Ala Asp Ile Pro Asp
            100                 105                 110

Tyr Lys Lys Leu Ser Phe Pro Glu Gly Phe Lys Trp Glu Arg Val Met
        115                 120                 125

Asn Phe Glu Asp Gly Gly Val Val Thr Val Thr Gln Asp Ser Ser Leu
    130                 135                 140

Gln Asp Gly Ser Phe Ile Tyr Lys Val Lys Phe Ile Gly Val Asn Phe
145                 150                 155                 160

Pro Ser Asp Gly Pro Val Met Gln Lys Thr Met Gly Trp Glu Ala
                165                 170                 175

Ser Thr Glu Arg Leu Tyr Pro Arg Asp Gly Val Leu Lys Gly Glu Ile
            180                 185                 190

His Lys Ala Leu Lys Leu Lys Asp Gly Gly His Tyr Leu Val Glu Phe
        195                 200                 205

Lys Ser Ile Tyr Met Ala Lys Lys Pro Val Gln Leu Pro Gly Tyr Tyr
    210                 215                 220

Tyr Val Asp Ser Lys Leu Asp Ile Thr Ser His Asn Glu Asp Tyr Thr
225                 230                 235                 240

Ile Val Glu Gln Tyr Glu Arg Ala Glu Gly Arg His His Leu Phe Leu
                245                 250                 255

<210> SEQ ID NO 138
<211> LENGTH: 245
<212> TYPE: PRT
<213> ORGANISM: Artificial sequence
<220> FEATURE:
<223> OTHER INFORMATION: CFFKDEL-dsREDexpress

<400> SEQUENCE: 138

Met Gly His His His His His His Cys Phe Phe Lys Asp Glu Leu Glu
1               5                   10                  15

Phe Gly Gly Gly Gly Ala Ser Ser Glu Asp Val Ile Lys Glu Phe Met
            20                  25                  30

Arg Phe Lys Val Arg Met Glu Gly Ser Val Asn Gly His Glu Phe Glu
        35                  40                  45

Ile Glu Gly Glu Gly Glu Gly Arg Pro Tyr Glu Gly Thr Gln Thr Ala
    50                  55                  60

Lys Leu Lys Val Thr Lys Gly Gly Pro Leu Pro Phe Ala Trp Asp Ile
65                  70                  75                  80

Leu Ser Pro Gln Phe Gln Tyr Gly Ser Lys Val Tyr Val Lys His Pro
                85                  90                  95

Ala Asp Ile Pro Asp Tyr Lys Lys Leu Ser Phe Pro Glu Gly Phe Lys
            100                 105                 110

Trp Glu Arg Val Met Asn Phe Glu Asp Gly Gly Val Val Thr Val Thr
        115                 120                 125

Gln Asp Ser Ser Leu Gln Asp Gly Ser Phe Ile Tyr Lys Val Lys Phe
    130                 135                 140

Ile Gly Val Asn Phe Pro Ser Asp Gly Pro Val Met Gln Lys Lys Thr
145                 150                 155                 160

Met Gly Trp Glu Ala Ser Thr Glu Arg Leu Tyr Pro Arg Asp Gly Val
                165                 170                 175

Leu Lys Gly Glu Ile His Lys Ala Leu Lys Leu Lys Asp Gly Gly His
            180                 185                 190

Tyr Leu Val Glu Phe Lys Ser Ile Tyr Met Ala Lys Lys Pro Val Gln
        195                 200                 205

Leu Pro Gly Tyr Tyr Tyr Val Asp Ser Lys Leu Asp Ile Thr Ser His
210                 215                 220

Asn Glu Asp Tyr Thr Ile Val Glu Gln Tyr Glu Arg Ala Glu Gly Arg
225                 230                 235                 240

His His Leu Phe Leu
            245

<210> SEQ ID NO 139
<211> LENGTH: 257
<212> TYPE: PRT
<213> ORGANISM: Artificial Sequence
<220> FEATURE:
<223> OTHER INFORMATION: TLM-dsREDexpress

<400> SEQUENCE: 139

Met Gly His His His His His Pro Leu Ser Ser Ile Phe Ser Arg
1               5                   10                  15

Ile Gly Asp Pro Pro Lys Lys Arg Lys Val Glu Phe Gly Gly Gly
                20                  25                  30

Gly Ala Ser Ser Glu Asp Val Ile Lys Glu Phe Met Arg Phe Lys Val
            35                  40                  45

Arg Met Glu Gly Ser Val Asn Gly His Glu Phe Glu Ile Glu Gly Glu
50                  55                  60

Gly Glu Gly Arg Pro Tyr Glu Gly Thr Gln Thr Ala Lys Leu Lys Val
65                  70                  75                  80

Thr Lys Gly Gly Pro Leu Pro Phe Ala Trp Asp Ile Leu Ser Pro Gln
                85                  90                  95

Phe Gln Tyr Gly Ser Lys Val Tyr Val Lys His Pro Ala Asp Ile Pro
            100                 105                 110

Asp Tyr Lys Lys Leu Ser Phe Pro Glu Gly Phe Lys Trp Glu Arg Val
            115                 120                 125

Met Asn Phe Glu Asp Gly Gly Val Val Thr Val Thr Gln Asp Ser Ser
130                 135                 140

Leu Gln Asp Gly Ser Phe Ile Tyr Lys Val Lys Phe Ile Gly Val Asn
145                 150                 155                 160

Phe Pro Ser Asp Gly Pro Val Met Gln Lys Lys Thr Met Gly Trp Glu
                165                 170                 175

Ala Ser Thr Glu Arg Leu Tyr Pro Arg Asp Gly Val Leu Lys Gly Glu
            180                 185                 190

Ile His Lys Ala Leu Lys Leu Lys Asp Gly Gly His Tyr Leu Val Glu
        195                 200                 205

Phe Lys Ser Ile Tyr Met Ala Lys Lys Pro Val Gln Leu Pro Gly Tyr
    210                 215                 220

Tyr Tyr Val Asp Ser Lys Leu Asp Ile Thr Ser His Asn Glu Asp Tyr
225                 230                 235                 240

Thr Ile Val Glu Gln Tyr Glu Arg Ala Glu Gly Arg His His Leu Phe
                245                 250                 255

Leu

<210> SEQ ID NO 140
<211> LENGTH: 292
<212> TYPE: PRT
<213> ORGANISM: Artificial sequence
<220> FEATURE:
<223> OTHER INFORMATION: Zebra-dsREDexpress

<400> SEQUENCE: 140

Met Gly His His His His His Glu Cys Asp Ser Glu Leu Glu Ile
1               5                   10                  15

Lys Arg Tyr Lys Arg Val Arg Val Ala Ser Arg Lys Cys Arg Ala Lys
                20                  25                  30

Phe Lys Gln Leu Leu Gln His Tyr Arg Glu Val Ala Ala Ala Lys Ser
            35                  40                  45

Ser Glu Asn Asp Arg Leu Arg Leu Leu Leu Lys Gln Met Cys Glu Phe
50                  55                  60

Gly Gly Gly Gly Ala Ser Ser Glu Asp Val Ile Lys Glu Phe Met Arg
65                  70                  75                  80

Phe Lys Val Arg Met Glu Gly Ser Val Asn Gly His Glu Phe Glu Ile
                85                  90                  95

Glu Gly Glu Gly Glu Gly Arg Pro Tyr Glu Gly Thr Gln Thr Ala Lys
                100                 105                 110

Leu Lys Val Thr Lys Gly Gly Pro Leu Pro Phe Ala Trp Asp Ile Leu
            115                 120                 125

Ser Pro Gln Phe Gln Tyr Gly Ser Lys Val Tyr Val Lys His Pro Ala
130                 135                 140

Asp Ile Pro Asp Tyr Lys Lys Leu Ser Phe Pro Glu Gly Phe Lys Trp
145                 150                 155                 160

Glu Arg Val Met Asn Phe Glu Asp Gly Gly Val Val Thr Val Thr Gln
                165                 170                 175

Asp Ser Ser Leu Gln Asp Gly Ser Phe Ile Tyr Lys Val Lys Phe Ile
            180                 185                 190

Gly Val Asn Phe Pro Ser Asp Gly Pro Val Met Gln Lys Lys Thr Met
            195                 200                 205

Gly Trp Glu Ala Ser Thr Glu Arg Leu Tyr Pro Arg Asp Gly Val Leu
210                 215                 220

Lys Gly Glu Ile His Lys Ala Leu Lys Leu Lys Asp Gly Gly His Tyr
225                 230                 235                 240

Leu Val Glu Phe Lys Ser Ile Tyr Met Ala Lys Lys Pro Val Gln Leu
                245                 250                 255

Pro Gly Tyr Tyr Tyr Val Asp Ser Lys Leu Asp Ile Thr Ser His Asn
                260                 265                 270

Glu Asp Tyr Thr Ile Val Glu Gln Tyr Glu Arg Ala Glu Gly Arg His
            275                 280                 285

His Leu Phe Leu
    290

<210> SEQ ID NO 141
<211> LENGTH: 259
<212> TYPE: PRT
<213> ORGANISM: Artificial sequence
<220> FEATURE:
<223> OTHER INFORMATION: pep1-dsREDexpress

<400> SEQUENCE: 141

Met Gly His His His His His Lys Glu Thr Trp Trp Glu Thr Trp
1               5                   10                  15

Trp Thr Glu Trp Ser Gln Pro Lys Lys Lys Arg Lys Val Glu Phe Gly
                20                  25                  30

Gly Gly Gly Ala Ser Ser Glu Asp Val Ile Lys Glu Phe Met Arg Phe
            35                  40                  45

Lys Val Arg Met Glu Gly Ser Val Asn Gly His Glu Phe Glu Ile Glu
50                  55                  60

```
Gly Glu Gly Glu Gly Arg Pro Tyr Glu Gly Thr Gln Thr Ala Lys Leu
 65                  70                  75                  80

Lys Val Thr Lys Gly Gly Pro Leu Pro Phe Ala Trp Asp Ile Leu Ser
                 85                  90                  95

Pro Gln Phe Gln Tyr Gly Ser Lys Val Tyr Val Lys His Pro Ala Asp
            100                 105                 110

Ile Pro Asp Tyr Lys Lys Leu Ser Phe Pro Glu Gly Phe Lys Trp Glu
        115                 120                 125

Arg Val Met Asn Phe Glu Asp Gly Gly Val Val Thr Val Thr Gln Asp
    130                 135                 140

Ser Ser Leu Gln Asp Gly Ser Phe Ile Tyr Lys Val Lys Phe Ile Gly
145                 150                 155                 160

Val Asn Phe Pro Ser Asp Gly Pro Val Met Gln Lys Lys Thr Met Gly
                165                 170                 175

Trp Glu Ala Ser Thr Glu Arg Leu Tyr Pro Arg Asp Gly Val Leu Lys
            180                 185                 190

Gly Glu Ile His Lys Ala Leu Lys Leu Lys Asp Gly Gly His Tyr Leu
        195                 200                 205

Val Glu Phe Lys Ser Ile Tyr Met Ala Lys Lys Pro Val Gln Leu Pro
    210                 215                 220

Gly Tyr Tyr Tyr Val Asp Ser Lys Leu Asp Ile Thr Ser His Asn Glu
225                 230                 235                 240

Asp Tyr Thr Ile Val Glu Gln Tyr Glu Arg Ala Glu Gly Arg His His
                245                 250                 255

Leu Phe Leu

<210> SEQ ID NO 142
<211> LENGTH: 259
<212> TYPE: PRT
<213> ORGANISM: Artificial sequence
<220> FEATURE:
<223> OTHER INFORMATION: tp10-dsREDexpress

<400> SEQUENCE: 142

Met Gly His His His His His His Ala Gly Tyr Leu Leu Gly Lys Ile
 1               5                  10                  15

Asn Leu Lys Ala Cys Ala Ala Cys Ala Lys Lys Ile Leu Glu Phe Gly
                 20                  25                  30

Gly Gly Gly Ala Ser Ser Glu Asp Val Ile Lys Glu Phe Met Arg Phe
            35                  40                  45

Lys Val Arg Met Glu Gly Ser Val Asn Gly His Glu Phe Glu Ile Glu
 50                  55                  60

Gly Glu Gly Glu Gly Arg Pro Tyr Glu Gly Thr Gln Thr Ala Lys Leu
 65                  70                  75                  80

Lys Val Thr Lys Gly Gly Pro Leu Pro Phe Ala Trp Asp Ile Leu Ser
                 85                  90                  95

Pro Gln Phe Gln Tyr Gly Ser Lys Val Tyr Val Lys His Pro Ala Asp
            100                 105                 110

Ile Pro Asp Tyr Lys Lys Leu Ser Phe Pro Glu Gly Phe Lys Trp Glu
        115                 120                 125

Arg Val Met Asn Phe Glu Asp Gly Gly Val Val Thr Val Thr Gln Asp
    130                 135                 140

Ser Ser Leu Gln Asp Gly Ser Phe Ile Tyr Lys Val Lys Phe Ile Gly
145                 150                 155                 160

Val Asn Phe Pro Ser Asp Gly Pro Val Met Gln Lys Lys Thr Met Gly
```

```
                    165                 170                 175
Trp Glu Ala Ser Thr Glu Arg Leu Tyr Pro Arg Asp Gly Val Leu Lys
                180                 185                 190

Gly Glu Ile His Lys Ala Leu Lys Leu Lys Asp Gly Gly His Tyr Leu
            195                 200                 205

Val Glu Phe Lys Ser Ile Tyr Met Ala Lys Lys Pro Val Gln Leu Pro
        210                 215                 220

Gly Tyr Tyr Tyr Val Asp Ser Lys Leu Asp Ile Thr Ser His Asn Glu
225                 230                 235                 240

Asp Tyr Thr Ile Val Glu Gln Tyr Glu Arg Ala Glu Gly Arg His His
                245                 250                 255

Leu Phe Leu

<210> SEQ ID NO 143
<211> LENGTH: 1442
<212> TYPE: PRT
<213> ORGANISM: Artificial sequence
<220> FEATURE:
<223> OTHER INFORMATION: Zebra-Cas9

<400> SEQUENCE: 143

Met Gly His His His His His His Glu Cys Asp Ser Glu Leu Glu Ile
1               5                   10                  15

Lys Arg Tyr Lys Arg Val Arg Val Ala Ser Arg Lys Cys Arg Ala Lys
                20                  25                  30

Phe Lys Gln Leu Leu Gln His Tyr Arg Glu Val Ala Ala Ala Lys Ser
            35                  40                  45

Ser Glu Asn Asp Arg Leu Arg Leu Leu Leu Lys Gln Met Cys Glu Phe
        50                  55                  60

Asp Lys Lys Tyr Ser Ile Gly Leu Asp Ile Gly Thr Asn Ser Val Gly
65                  70                  75                  80

Trp Ala Val Ile Thr Asp Glu Tyr Lys Val Pro Ser Lys Lys Phe Lys
                85                  90                  95

Val Leu Gly Asn Thr Asp Arg His Ser Ile Lys Lys Asn Leu Ile Gly
            100                 105                 110

Ala Leu Leu Phe Asp Ser Gly Glu Thr Ala Glu Ala Thr Arg Leu Lys
        115                 120                 125

Arg Thr Ala Arg Arg Arg Tyr Thr Arg Arg Lys Asn Arg Ile Cys Tyr
    130                 135                 140

Leu Gln Glu Ile Phe Ser Asn Glu Met Ala Lys Val Asp Asp Ser Phe
145                 150                 155                 160

Phe His Arg Leu Glu Glu Ser Phe Leu Val Glu Glu Asp Lys Lys His
                165                 170                 175

Glu Arg His Pro Ile Phe Gly Asn Ile Val Asp Glu Val Ala Tyr His
            180                 185                 190

Glu Lys Tyr Pro Thr Ile Tyr His Leu Arg Lys Lys Leu Val Asp Ser
        195                 200                 205

Thr Asp Lys Ala Asp Leu Arg Leu Ile Tyr Leu Ala Leu Ala His Met
    210                 215                 220

Ile Lys Phe Arg Gly His Phe Leu Ile Glu Gly Asp Leu Asn Pro Asp
225                 230                 235                 240

Asn Ser Asp Val Asp Lys Leu Phe Ile Gln Leu Val Gln Thr Tyr Asn
                245                 250                 255

Gln Leu Phe Glu Glu Asn Pro Ile Asn Ala Ser Gly Val Asp Ala Lys
            260                 265                 270
```

-continued

```
Ala Ile Leu Ser Ala Arg Leu Ser Lys Ser Arg Arg Leu Glu Asn Leu
            275                 280                 285
Ile Ala Gln Leu Pro Gly Glu Lys Lys Asn Gly Leu Phe Gly Asn Leu
290                 295                 300
Ile Ala Leu Ser Leu Gly Leu Thr Pro Asn Phe Lys Ser Asn Phe Asp
305                 310                 315                 320
Leu Ala Glu Asp Ala Lys Leu Gln Leu Ser Lys Asp Thr Tyr Asp Asp
                325                 330                 335
Asp Leu Asp Asn Leu Leu Ala Gln Ile Gly Asp Gln Tyr Ala Asp Leu
            340                 345                 350
Phe Leu Ala Ala Lys Asn Leu Ser Asp Ala Ile Leu Leu Ser Asp Ile
            355                 360                 365
Leu Arg Val Asn Thr Glu Ile Thr Lys Ala Pro Leu Ser Ala Ser Met
        370                 375                 380
Ile Lys Arg Tyr Asp Glu His His Gln Asp Leu Thr Leu Leu Lys Ala
385                 390                 395                 400
Leu Val Arg Gln Gln Leu Pro Glu Lys Tyr Lys Glu Ile Phe Phe Asp
                405                 410                 415
Gln Ser Lys Asn Gly Tyr Ala Gly Tyr Ile Asp Gly Gly Ala Ser Gln
            420                 425                 430
Glu Glu Phe Tyr Lys Phe Ile Lys Pro Ile Leu Glu Lys Met Asp Gly
        435                 440                 445
Thr Glu Glu Leu Leu Val Lys Leu Asn Arg Glu Asp Leu Leu Arg Lys
    450                 455                 460
Gln Arg Thr Phe Asp Asn Gly Ser Ile Pro His Gln Ile His Leu Gly
465                 470                 475                 480
Glu Leu His Ala Ile Leu Arg Arg Gln Glu Asp Phe Tyr Pro Phe Leu
                485                 490                 495
Lys Asp Asn Arg Glu Lys Ile Glu Lys Ile Leu Thr Phe Arg Ile Pro
            500                 505                 510
Tyr Tyr Val Gly Pro Leu Ala Arg Gly Asn Ser Arg Phe Ala Trp Met
        515                 520                 525
Thr Arg Lys Ser Glu Glu Thr Ile Thr Pro Trp Asn Phe Glu Glu Val
    530                 535                 540
Val Asp Lys Gly Ala Ser Ala Gln Ser Phe Ile Glu Arg Met Thr Asn
545                 550                 555                 560
Phe Asp Lys Asn Leu Pro Asn Glu Lys Val Leu Pro Lys His Ser Leu
                565                 570                 575
Leu Tyr Glu Tyr Phe Thr Val Tyr Asn Glu Leu Thr Lys Val Lys Tyr
            580                 585                 590
Val Thr Glu Gly Met Arg Lys Pro Ala Phe Leu Ser Gly Glu Gln Lys
        595                 600                 605
Lys Ala Ile Val Asp Leu Leu Phe Lys Thr Asn Arg Lys Val Thr Val
    610                 615                 620
Lys Gln Leu Lys Glu Asp Tyr Phe Lys Lys Ile Glu Cys Phe Asp Ser
625                 630                 635                 640
Val Glu Ile Ser Gly Val Glu Asp Arg Phe Asn Ala Ser Leu Gly Thr
                645                 650                 655
Tyr His Asp Leu Leu Lys Ile Ile Lys Asp Lys Asp Phe Leu Asp Asn
            660                 665                 670
Glu Glu Asn Glu Asp Ile Leu Glu Asp Ile Val Leu Thr Leu Thr Leu
        675                 680                 685
```

```
Phe Glu Asp Arg Glu Met Ile Glu Arg Leu Lys Thr Tyr Ala His
    690             695             700
Leu Phe Asp Asp Lys Val Met Lys Gln Leu Lys Arg Arg Tyr Thr
705             710             715             720
Gly Trp Gly Arg Leu Ser Arg Lys Leu Ile Asn Gly Ile Arg Asp Lys
                725             730             735
Gln Ser Gly Lys Thr Ile Leu Asp Phe Leu Lys Ser Asp Gly Phe Ala
            740             745             750
Asn Arg Asn Phe Met Gln Leu Ile His Asp Asp Ser Leu Thr Phe Lys
            755             760             765
Glu Asp Ile Gln Lys Ala Gln Val Ser Gly Gln Gly Asp Ser Leu His
770             775             780
Glu His Ile Ala Asn Leu Ala Gly Ser Pro Ala Ile Lys Lys Gly Ile
785             790             795             800
Leu Gln Thr Val Lys Val Val Asp Glu Leu Val Lys Val Met Gly Arg
                805             810             815
His Lys Pro Glu Asn Ile Val Ile Glu Met Ala Arg Glu Asn Gln Thr
                820             825             830
Thr Gln Lys Gly Gln Lys Asn Ser Arg Glu Arg Met Lys Arg Ile Glu
            835             840             845
Glu Gly Ile Lys Glu Leu Gly Ser Gln Ile Leu Lys Glu His Pro Val
850             855             860
Glu Asn Thr Gln Leu Gln Asn Glu Lys Leu Tyr Leu Tyr Tyr Leu Gln
865             870             875             880
Asn Gly Arg Asp Met Tyr Val Asp Gln Glu Leu Asp Ile Asn Arg Leu
            885             890             895
Ser Asp Tyr Asp Val Asp His Ile Val Pro Gln Ser Phe Leu Lys Asp
            900             905             910
Asp Ser Ile Asp Asn Lys Val Leu Thr Arg Ser Asp Lys Asn Arg Gly
            915             920             925
Lys Ser Asp Asn Val Pro Ser Glu Glu Val Val Lys Lys Met Lys Asn
930             935             940
Tyr Trp Arg Gln Leu Leu Asn Ala Lys Leu Ile Thr Gln Arg Lys Phe
945             950             955             960
Asp Asn Leu Thr Lys Ala Glu Arg Gly Gly Leu Ser Glu Leu Asp Lys
            965             970             975
Ala Gly Phe Ile Lys Arg Gln Leu Val Glu Thr Arg Gln Ile Thr Lys
            980             985             990
His Val Ala Gln Ile Leu Asp Ser Arg Met Asn Thr Lys Tyr Asp Glu
            995             1000            1005
Asn Asp Lys Leu Ile Arg Glu Val Lys Val Ile Thr Leu Lys Ser
    1010            1015            1020
Lys Leu Val Ser Asp Phe Arg Lys Asp Phe Gln Phe Tyr Lys Val
    1025            1030            1035
Arg Glu Ile Asn Asn Tyr His His Ala His Asp Ala Tyr Leu Asn
    1040            1045            1050
Ala Val Val Gly Thr Ala Leu Ile Lys Lys Tyr Pro Lys Leu Glu
    1055            1060            1065
Ser Glu Phe Val Tyr Gly Asp Tyr Lys Val Tyr Asp Val Arg Lys
    1070            1075            1080
Met Ile Ala Lys Ser Glu Gln Glu Ile Gly Lys Ala Thr Ala Lys
    1085            1090            1095
Tyr Phe Phe Tyr Ser Asn Ile Met Asn Phe Phe Lys Thr Glu Ile
```

1100                1105                1110

Thr Leu Ala Asn Gly Glu Ile Arg Lys Arg Pro Leu Ile Glu Thr
            1115                1120                1125

Asn Gly Glu Thr Gly Glu Ile Val Trp Asp Lys Gly Arg Asp Phe
        1130                1135                1140

Ala Thr Val Arg Lys Val Leu Ser Met Pro Gln Val Asn Ile Val
        1145                1150                1155

Lys Lys Thr Glu Val Gln Thr Gly Gly Phe Ser Lys Glu Ser Ile
        1160                1165                1170

Leu Pro Lys Arg Asn Ser Asp Lys Leu Ile Ala Arg Lys Lys Asp
        1175                1180                1185

Trp Asp Pro Lys Lys Tyr Gly Gly Phe Asp Ser Pro Thr Val Ala
        1190                1195                1200

Tyr Ser Val Leu Val Val Ala Lys Val Glu Lys Gly Lys Ser Lys
        1205                1210                1215

Lys Leu Lys Ser Val Lys Glu Leu Leu Gly Ile Thr Ile Met Glu
        1220                1225                1230

Arg Ser Ser Phe Glu Lys Asn Pro Ile Asp Phe Leu Glu Ala Lys
        1235                1240                1245

Gly Tyr Lys Glu Val Lys Lys Asp Leu Ile Ile Lys Leu Pro Lys
        1250                1255                1260

Tyr Ser Leu Phe Glu Leu Glu Asn Gly Arg Lys Arg Met Leu Ala
        1265                1270                1275

Ser Ala Gly Glu Leu Gln Lys Gly Asn Glu Leu Ala Leu Pro Ser
        1280                1285                1290

Lys Tyr Val Asn Phe Leu Tyr Leu Ala Ser His Tyr Glu Lys Leu
        1295                1300                1305

Lys Gly Ser Pro Glu Asp Asn Glu Gln Lys Gln Leu Phe Val Glu
        1310                1315                1320

Gln His Lys His Tyr Leu Asp Glu Ile Ile Glu Gln Ile Ser Glu
        1325                1330                1335

Phe Ser Lys Arg Val Ile Leu Ala Asp Ala Asn Leu Asp Lys Val
        1340                1345                1350

Leu Ser Ala Tyr Asn Lys His Arg Asp Lys Pro Ile Arg Glu Gln
        1355                1360                1365

Ala Glu Asn Ile Ile His Leu Phe Thr Leu Thr Asn Leu Gly Ala
        1370                1375                1380

Pro Ala Ala Phe Lys Tyr Phe Asp Thr Thr Ile Asp Arg Lys Arg
        1385                1390                1395

Tyr Thr Ser Thr Lys Glu Val Leu Asp Ala Thr Leu Ile His Gln
        1400                1405                1410

Ser Ile Thr Gly Leu Tyr Glu Thr Arg Ile Asp Leu Ser Gln Leu
        1415                1420                1425

Gly Gly Asp Ser Arg Ala Asp Pro Lys Lys Lys Arg Lys Val
        1430                1435                1440

<210> SEQ ID NO 144
<211> LENGTH: 1406
<212> TYPE: PRT
<213> ORGANISM: Artificial sequence
<220> FEATURE:
<223> OTHER INFORMATION: pVEC-Cas9

<400> SEQUENCE: 144

Met Gly His His His His His His Leu Leu Ile Ile Leu Arg Arg Arg

-continued

```
  1               5                  10                 15
Ile Arg Lys Gln Ala His Ala His Ser Lys Glu Phe Asp Lys Tyr
            20                  25                 30
Ser Ile Gly Leu Asp Ile Gly Thr Asn Ser Val Gly Trp Ala Val Ile
            35                  40                 45
Thr Asp Glu Tyr Lys Val Pro Ser Lys Lys Phe Lys Val Leu Gly Asn
            50                  55                 60
Thr Asp Arg His Ser Ile Lys Lys Asn Leu Ile Gly Ala Leu Leu Phe
 65                  70                 75                  80
Asp Ser Gly Glu Thr Ala Glu Ala Thr Arg Leu Lys Arg Thr Ala Arg
                 85                  90                 95
Arg Arg Tyr Thr Arg Arg Lys Asn Arg Ile Cys Tyr Leu Gln Glu Ile
                100                 105                110
Phe Ser Asn Glu Met Ala Lys Val Asp Asp Ser Phe Phe His Arg Leu
                115                 120                125
Glu Glu Ser Phe Leu Val Glu Glu Asp Lys Lys His Glu Arg His Pro
                130                 135                140
Ile Phe Gly Asn Ile Val Asp Glu Val Ala Tyr His Glu Lys Tyr Pro
145                 150                 155                160
Thr Ile Tyr His Leu Arg Lys Lys Leu Val Asp Ser Thr Asp Lys Ala
                165                 170                175
Asp Leu Arg Leu Ile Tyr Leu Ala Leu Ala His Met Ile Lys Phe Arg
                180                 185                190
Gly His Phe Leu Ile Glu Gly Asp Leu Asn Pro Asp Asn Ser Asp Val
                195                 200                205
Asp Lys Leu Phe Ile Gln Leu Val Gln Thr Tyr Asn Gln Leu Phe Glu
                210                 215                220
Glu Asn Pro Ile Asn Ala Ser Gly Val Asp Ala Lys Ala Ile Leu Ser
225                 230                 235                240
Ala Arg Leu Ser Lys Ser Arg Arg Leu Glu Asn Leu Ile Ala Gln Leu
                245                 250                255
Pro Gly Glu Lys Lys Asn Gly Leu Phe Gly Asn Leu Ile Ala Leu Ser
                260                 265                270
Leu Gly Leu Thr Pro Asn Phe Lys Ser Asn Phe Asp Leu Ala Glu Asp
                275                 280                285
Ala Lys Leu Gln Leu Ser Lys Asp Thr Tyr Asp Asp Asp Leu Asp Asn
                290                 295                300
Leu Leu Ala Gln Ile Gly Asp Gln Tyr Ala Asp Leu Phe Leu Ala Ala
305                 310                 315                320
Lys Asn Leu Ser Asp Ala Ile Leu Leu Ser Asp Ile Leu Arg Val Asn
                325                 330                335
Thr Glu Ile Thr Lys Ala Pro Leu Ser Ala Ser Met Ile Lys Arg Tyr
                340                 345                350
Asp Glu His His Gln Asp Leu Thr Leu Leu Lys Ala Leu Val Arg Gln
                355                 360                365
Gln Leu Pro Glu Lys Tyr Lys Glu Ile Phe Phe Asp Gln Ser Lys Asn
                370                 375                380
Gly Tyr Ala Gly Tyr Ile Asp Gly Gly Ala Ser Gln Glu Glu Phe Tyr
385                 390                 395                400
Lys Phe Ile Lys Pro Ile Leu Glu Lys Met Asp Gly Thr Glu Glu Leu
                405                 410                415
Leu Val Lys Leu Asn Arg Glu Asp Leu Leu Arg Lys Gln Arg Thr Phe
                420                 425                430
```

```
Asp Asn Gly Ser Ile Pro His Gln Ile His Leu Gly Glu Leu His Ala
        435                 440                 445

Ile Leu Arg Arg Gln Glu Asp Phe Tyr Pro Phe Leu Lys Asp Asn Arg
450                 455                 460

Glu Lys Ile Glu Lys Ile Leu Thr Phe Arg Ile Pro Tyr Tyr Val Gly
465                 470                 475                 480

Pro Leu Ala Arg Gly Asn Ser Arg Phe Ala Trp Met Thr Arg Lys Ser
                485                 490                 495

Glu Glu Thr Ile Thr Pro Trp Asn Phe Glu Val Val Asp Lys Gly
                500                 505                 510

Ala Ser Ala Gln Ser Phe Ile Glu Arg Met Thr Asn Phe Asp Lys Asn
            515                 520                 525

Leu Pro Asn Glu Lys Val Leu Pro Lys His Ser Leu Leu Tyr Glu Tyr
            530                 535                 540

Phe Thr Val Tyr Asn Glu Leu Thr Lys Val Lys Tyr Val Thr Glu Gly
545                 550                 555                 560

Met Arg Lys Pro Ala Phe Leu Ser Gly Glu Gln Lys Lys Ala Ile Val
                565                 570                 575

Asp Leu Leu Phe Lys Thr Asn Arg Lys Val Thr Val Lys Gln Leu Lys
            580                 585                 590

Glu Asp Tyr Phe Lys Lys Ile Glu Cys Phe Asp Ser Val Glu Ile Ser
            595                 600                 605

Gly Val Glu Asp Arg Phe Asn Ala Ser Leu Gly Thr Tyr His Asp Leu
610                 615                 620

Leu Lys Ile Ile Lys Asp Lys Asp Phe Leu Asp Asn Glu Glu Asn Glu
625                 630                 635                 640

Asp Ile Leu Glu Asp Ile Val Leu Thr Leu Thr Leu Phe Glu Asp Arg
                645                 650                 655

Glu Met Ile Glu Glu Arg Leu Lys Thr Tyr Ala His Leu Phe Asp Asp
                660                 665                 670

Lys Val Met Lys Gln Leu Lys Arg Arg Arg Tyr Thr Gly Trp Gly Arg
            675                 680                 685

Leu Ser Arg Lys Leu Ile Asn Gly Ile Arg Asp Lys Gln Ser Gly Lys
            690                 695                 700

Thr Ile Leu Asp Phe Leu Lys Ser Asp Gly Phe Ala Asn Arg Asn Phe
705                 710                 715                 720

Met Gln Leu Ile His Asp Asp Ser Leu Thr Phe Lys Glu Asp Ile Gln
                725                 730                 735

Lys Ala Gln Val Ser Gly Gln Gly Asp Ser Leu His Glu His Ile Ala
                740                 745                 750

Asn Leu Ala Gly Ser Pro Ala Ile Lys Lys Gly Ile Leu Gln Thr Val
            755                 760                 765

Lys Val Val Asp Glu Leu Val Lys Val Met Gly Arg His Lys Pro Glu
770                 775                 780

Asn Ile Val Ile Glu Met Ala Arg Glu Asn Gln Thr Thr Gln Lys Gly
785                 790                 795                 800

Gln Lys Asn Ser Arg Glu Arg Met Lys Arg Ile Glu Glu Gly Ile Lys
                805                 810                 815

Glu Leu Gly Ser Gln Ile Leu Lys Glu His Pro Val Glu Asn Thr Gln
                820                 825                 830

Leu Gln Asn Glu Lys Leu Tyr Leu Tyr Tyr Leu Gln Asn Gly Arg Asp
            835                 840                 845
```

```
Met Tyr Val Asp Gln Glu Leu Asp Ile Asn Arg Leu Ser Asp Tyr Asp
850                 855                 860
Val Asp His Ile Val Pro Gln Ser Phe Leu Lys Asp Asp Ser Ile Asp
865                 870                 875                 880
Asn Lys Val Leu Thr Arg Ser Asp Lys Asn Arg Gly Lys Ser Asp Asn
            885                 890                 895
Val Pro Ser Glu Glu Val Val Lys Lys Met Lys Asn Tyr Trp Arg Gln
                900                 905                 910
Leu Leu Asn Ala Lys Leu Ile Thr Gln Arg Lys Phe Asp Asn Leu Thr
                915                 920                 925
Lys Ala Glu Arg Gly Gly Leu Ser Glu Leu Asp Lys Ala Gly Phe Ile
930                 935                 940
Lys Arg Gln Leu Val Glu Thr Arg Gln Ile Thr Lys His Val Ala Gln
945                 950                 955                 960
Ile Leu Asp Ser Arg Met Asn Thr Lys Tyr Asp Glu Asn Asp Lys Leu
                965                 970                 975
Ile Arg Glu Val Lys Val Ile Thr Leu Lys Ser Lys Leu Val Ser Asp
                980                 985                 990
Phe Arg Lys Asp Phe Gln Phe Tyr Lys Val Arg Glu Ile Asn Asn Tyr
            995                 1000                1005
His His Ala His Asp Ala Tyr Leu Asn Ala Val Val Gly Thr Ala
    1010                1015                1020
Leu Ile Lys Lys Tyr Pro Lys Leu Glu Ser Glu Phe Val Tyr Gly
    1025                1030                1035
Asp Tyr Lys Val Tyr Asp Val Arg Lys Met Ile Ala Lys Ser Glu
    1040                1045                1050
Gln Glu Ile Gly Lys Ala Thr Ala Lys Tyr Phe Phe Tyr Ser Asn
    1055                1060                1065
Ile Met Asn Phe Phe Lys Thr Glu Ile Thr Leu Ala Asn Gly Glu
    1070                1075                1080
Ile Arg Lys Arg Pro Leu Ile Glu Thr Asn Gly Glu Thr Gly Glu
    1085                1090                1095
Ile Val Trp Asp Lys Gly Arg Asp Phe Ala Thr Val Arg Lys Val
    1100                1105                1110
Leu Ser Met Pro Gln Val Asn Ile Val Lys Lys Thr Glu Val Gln
    1115                1120                1125
Thr Gly Gly Phe Ser Lys Glu Ser Ile Leu Pro Lys Arg Asn Ser
    1130                1135                1140
Asp Lys Leu Ile Ala Arg Lys Lys Asp Trp Asp Pro Lys Lys Tyr
    1145                1150                1155
Gly Gly Phe Asp Ser Pro Thr Val Ala Tyr Ser Val Leu Val Val
    1160                1165                1170
Ala Lys Val Glu Lys Gly Lys Ser Lys Lys Leu Lys Ser Val Lys
    1175                1180                1185
Glu Leu Leu Gly Ile Thr Ile Met Glu Arg Ser Ser Phe Glu Lys
    1190                1195                1200
Asn Pro Ile Asp Phe Leu Glu Ala Lys Gly Tyr Lys Glu Val Lys
    1205                1210                1215
Lys Asp Leu Ile Ile Lys Leu Pro Lys Tyr Ser Leu Phe Glu Leu
    1220                1225                1230
Glu Asn Gly Arg Lys Arg Met Leu Ala Ser Ala Gly Glu Leu Gln
    1235                1240                1245
Lys Gly Asn Glu Leu Ala Leu Pro Ser Lys Tyr Val Asn Phe Leu
```

-continued

```
            1250                    1255                    1260
Tyr Leu Ala Ser His Tyr Glu Lys Leu Lys Gly Ser Pro Glu Asp
            1265                    1270                    1275

Asn Glu Gln Lys Gln Leu Phe Val Glu Gln His Lys His Tyr Leu
            1280                    1285                    1290

Asp Glu Ile Ile Glu Gln Ile Ser Glu Phe Ser Lys Arg Val Ile
            1295                    1300                    1305

Leu Ala Asp Ala Asn Leu Asp Lys Val Leu Ser Ala Tyr Asn Lys
            1310                    1315                    1320

His Arg Asp Lys Pro Ile Arg Glu Gln Ala Glu Asn Ile Ile His
            1325                    1330                    1335

Leu Phe Thr Leu Thr Asn Leu Gly Ala Pro Ala Ala Phe Lys Tyr
            1340                    1345                    1350

Phe Asp Thr Thr Ile Asp Arg Lys Arg Tyr Thr Ser Thr Lys Glu
            1355                    1360                    1365

Val Leu Asp Ala Thr Leu Ile His Gln Ser Ile Thr Gly Leu Tyr
            1370                    1375                    1380

Glu Thr Arg Ile Asp Leu Ser Gln Leu Gly Gly Asp Ser Arg Ala
            1385                    1390                    1395

Asp Pro Lys Lys Lys Arg Lys Val
            1400                    1405
```

PEPTIDE-MEDIATED DELIVERY OF RNA-GUIDED ENDONUCLEASE INTO CELLS

This application claims the benefit of U.S. Provisional Application No. 62/075,999 filed Nov. 6, 2014, incorporated herein in its entirety by reference.

FIELD OF INVENTION

The invention is in the field of molecular biology. Specifically, this invention pertains to delivery of protein components of RNA-guided endonucleases into cells using cell-penetrating peptides.

REFERENCE TO SEQUENCE LISTING SUBMITTED ELECTRONICALLY

The official copy of the sequence listing is submitted electronically via EFS-Web as an ASCII formatted sequence listing with a file named 20151013_CL6273PCT_SequenceListing_ST25.txt created Oct. 13, 2015, and having a size of 384 kilobytes and is filed concurrently with the specification. The sequence listing contained in this ASCII-formatted document is part of the specification and is herein incorporated by reference in its entirety.

BACKGROUND

A way to understand the function of a gene within an organism is to inhibit its expression. Inhibition of gene expression can be accomplished, for example, by interrupting or deleting the DNA sequence of the gene, resulting in "knock-out" of the gene (Austin et al., *Nat. Genetics* 36:921-924). Gene knock-outs mostly have been carried out through homologous recombination (HR), a technique applicable across a wide array of organisms from bacteria to mammals. Another way for studying gene function can be through genetic "knock-in", which is also usually performed by HR. HR for purposes of gene targeting (knock-out or knock-in) can employ the presence of an exogenously supplied DNA having homology with the target site ("donor DNA").

HR for gene targeting has been shown to be enhanced when the targeted DNA site contains a double-strand break (Rudin et al., *Genetics* 122:519-534; Smih et al., *Nucl. Acids Res.* 23:5012-5019). Strategies for introducing double-strand breaks to facilitate HR-mediated DNA targeting have therefore been developed. For example, zinc finger nucleases have been engineered to cleave specific DNA sites leading to enhanced levels of HR at the site when a donor DNA was present (Bibikova et al., *Science* 300:764; Bibikova et al., *Mol. Cell. Biol.* 21:289-297). Similarly, artificial meganucleases (homing endonucleases) and transcription activator-like effector (TALE) nucleases have also been developed for use in HR-mediated DNA targeting (Epinat et al., *Nucleic Acids Res.* 31: 2952-2962; Miller et al., *Nat. Biotech.* 29:143-148).

Loci encoding CRISPR (clustered regularly interspaced short palindromic repeats) DNA cleavage systems have been found exclusively in about 40% of bacterial genomes and most archaeal genomes (Horvath and Barrangou, *Science* 327:167-170; Karginov and Hannon, *Mol. Cell* 37:7-19). In particular, the CRISPR-associated (Cas) RNA-guided endonuclease (RGEN), Cas9, of the type II CRIPSR system has been developed as a means for introducing site-specific DNA strand breaks that stimulate HR with donor DNA (WO2015/026883, published Feb. 26, 2015. The sequence of the RNA component of Cas9 can be designed such that Cas9 recognizes and cleaves DNA containing (i) sequence complementary to a portion of the RNA component and (ii) a protospacer adjacent motif (PAM) sequence.

Native Cas9/RNA complexes comprise two RNA sequences, a CRISPR RNA (crRNA) and a trans-activating CRISPR RNA (tracrRNA). A crRNA contains, in the 5'-to-3' direction, a unique sequence complementary to a target DNA site and a portion of a sequence encoded by a repeat region of the CRISPR locus from which the crRNA was derived. A tracrRNA contains, in the 5'-to-3' direction, a sequence that anneals with the repeat region of crRNA and a stem loop-containing portion. Recent work has led to the development of guide RNAs (gRNA), which are chimeric sequences containing, in the 5'-to-3' direction, a crRNA linked to a tracrRNA (WO2015/026883, published Feb. 26, 2015.

Protein and RNA components for performing Cas9-mediated DNA targeting in a cell have been provided in some studies through recombinant DNA expression strategies. For example, Cas9 protein has been expressed in cells using nucleic acid-based expression systems. Methods of expressing RNA components such as gRNA in certain cell types have included using RNA polymerase III (Pol III) promoters, which allow for transcription of RNA with precisely defined, unmodified, 5'- and 3'-ends (DiCarlo et al., *Nucleic Acids Res.* 41: 4336-4343; Ma et al., *Mol. Ther. Nucleic Acids* 3:e161). These protein and RNA expression techniques have been applied in cells of several different species including maize and soybean (WO2015/026883, published Feb. 26, 2015, as well as humans, mouse, zebrafish, *Trichoderma* and *Saccharomyces cerevisiae*.

Despite these advances, other means of providing protein and RNA components in a cell, such as a microbial cell, to mediate Cas9-mediated DNA targeting are of interest.

SUMMARY OF INVENTION

In one embodiment, the invention concerns a composition comprising at least one protein component of an RNA-guided endonuclease (RGEN) and at least one cell-penetrating peptide (CPP), wherein the protein component and CPP are covalently, or non-covalently, linked to each other in an RGEN protein-CPP complex, and wherein the RGEN protein-CPP complex can traverse (i) a cell membrane, or (ii) a cell wall and cell membrane, of a microbial cell.

In a second embodiment, the protein component of the RGEN is associated with at least one RNA component that comprises a sequence complementary to a target site sequence on a chromosome or episome in the microbial cell, wherein the RGEN can bind to the target site sequence, and optionally cleave one or both DNA strands at the target site sequence. In a third embodiment, the RNA component comprises a guide RNA (gRNA) comprising a CRISPR RNA (crRNA) operably linked to a trans-activating CRISPR RNA (tracrRNA). In a fourth embodiment, the RGEN can cleave one or both DNA strands at the target site sequence.

In a fifth embodiment, the RGEN comprises a CRISPR-associated (Cas) protein-9 (Cas9) amino acid sequence.

In a sixth embodiment, the RGEN protein component and CPP are covalently linked.

In a seventh embodiment, the RGEN protein component and CPP are non-covalently linked.

In an eighth embodiment, the CPP is cationic or amphipathic.

In a ninth embodiment, the CPP comprises (i) a CPP from an Epstein-Barr virus Zebra trans-activator protein, (ii) a CPP having 6 or more contiguous arginine residues, (iii) a transportan-10 (TP10) CPP, or (iv) a CPP from a vascular endothelium cadherin protein.

In a tenth embodiment, the RGEN protein-CPP complex can traverse a cell wall and cell membrane of a microbial cell.

An eleventh embodiment concerns a microbial cell comprising a composition disclosed herein.

A twelfth embodiment concerns a method of delivering a protein component of an RNA-guided endonuclease (RGEN) into a microbial cell. This method comprises contacting a microbial cell with a composition comprising the RGEN protein component and at least one cell-penetrating peptide (CPP), wherein the RGEN protein component and CPP are covalently, or non-covalently, linked to each other in an RGEN protein-CPP complex. As a result of this contacting step, the RGEN protein-CPP complex can traverse (i) a cell membrane, or (ii) a cell wall and cell membrane, of the microbial cell, and thereby gain entry to the microbial cell.

In a thirteenth embodiment, with respect to the method, (i) the composition further comprises at least one RNA component that is associated with the protein component of the RGEN, or (ii) the microbial cell comprises the RNA component, wherein the RNA component associates with the protein component of the RGEN after the RGEN protein-CPP complex enters the microbial cell; wherein the RNA component in (i) or (ii) comprises a sequence complementary to a target site sequence on a chromosome or episome in the microbial cell, and wherein the RGEN can bind to the target site sequence, and optionally cleave one or both DNA strands at the target site sequence. In a fourteenth embodiment, the RGEN can cleave one or both DNA strands at the target site sequence. In a fifteenth embodiment, the microbial cell further comprises a donor polynucleotide comprising at least one sequence homologous to a sequence at or near the target site sequence, wherein the donor polynucleotide integrates at or near the target site sequence by homologous recombination.

A sixteenth embodiment concerns a polynucleotide sequence comprising a nucleotide sequence encoding an RGEN protein-CPP fusion protein that comprises a protein component of an RNA-guided endonuclease (RGEN) and at least one cell-penetrating peptide (CPP), wherein optionally, the nucleotide sequence is operably linked to a promoter sequence.

A seventeenth embodiment concerns a method of producing an RGEN protein-CPP fusion protein. This method comprises: (a) providing a polynucleotide sequence comprising a nucleotide sequence encoding an RGEN protein-CPP fusion protein that comprises a protein component of an RNA-guided endonuclease (RGEN) and at least one cell-penetrating peptide (CPP), wherein optionally, the nucleotide sequence is operably linked to a promoter sequence; (b) expressing the RGEN protein-CPP fusion protein from the polynucleotide sequence, thereby producing the RGEN protein-CPP fusion protein, wherein the expressing is optionally performed in a microbial cell; and (c) optionally, isolating the RGEN protein-CPP fusion protein produced in step (b).

An eighteenth embodiment concerns a composition comprising at least one protein component of a guide polynucleotide/Cas endonuclease complex and at least one cell-penetrating peptide (CPP), wherein the protein component and CPP are covalently, or non-covalently, linked to each other in a guide polynucleotide/Cas endonuclease-CPP complex, wherein the guide polynucleotide/Cas endonuclease-CPP complex can traverse (i) a cell membrane, or (ii) a cell wall and cell membrane, of a microbial cell.

A nineteenth embodiment concerns a method for modifying a target site in the genome of a microbial cell. This method comprises providing a guide polynucleotide, a cell-penetrating peptide (CPP) and a Cas endonuclease to a microbial cell, wherein the guide polynucleotide, Cas endonuclease and CPP are covalently, or non-covalently, linked to each other in a guide polynucleotide/Cas endonuclease-CPP complex, and wherein the guide polynucleotide/Cas endonuclease-CPP complex can traverse (i) a cell membrane, or (ii) a cell wall and cell membrane, of the microbial cell

BRIEF DESCRIPTION OF THE DRAWINGS AND SEQUENCES

FIG. 1: pZUFCas9 plasmid (SEQ ID NO:6) contains the *Yarrowia* codon-optimized Cas9 expression cassette set forth in SEQ ID NO:5. Origins of replication (ARS 18, f1 ori, ColE1) are in cross-hatch, and selectable markers (Ura3, Amp) are in grey. Refer to Example 1.

Figure 2B:
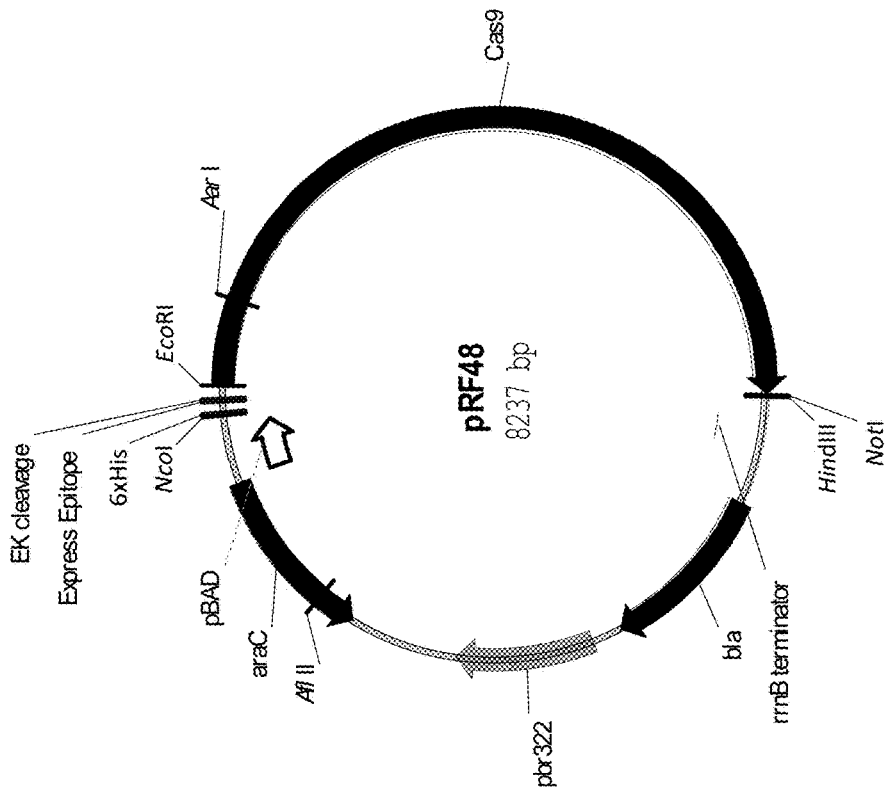
Figure 2A:
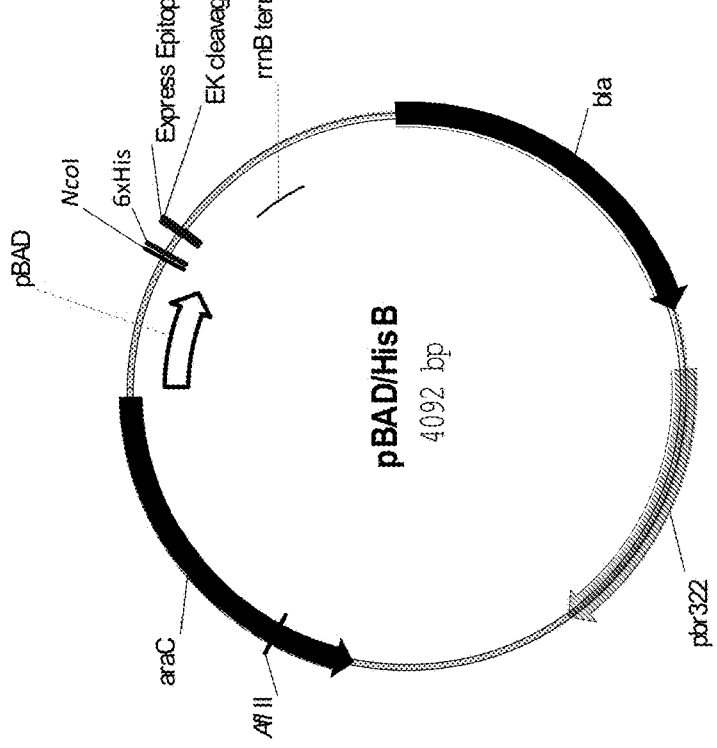

FIG. 2A: pBAD/HisB plasmid (SEQ ID NO:10) for expressing heterologous proteins in *E. coli*. pBAD promoter is in white. Origin of replication is in cross-hatch. Refer to Example 1.

FIG. 2B: pRF48 plasmid (SEQ ID NO:11) for expressing Cas9-NLS ("Cas9" in figure) in *E. coli*. Origin of replication is in cross-hatch. Refer to Example 1.

Figure 3B:
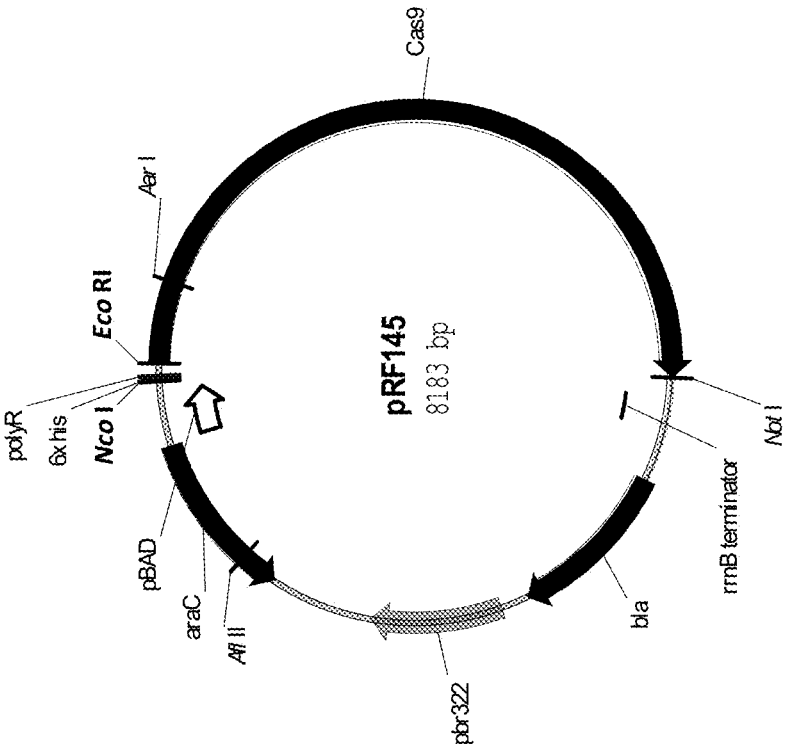
Figure 3A:
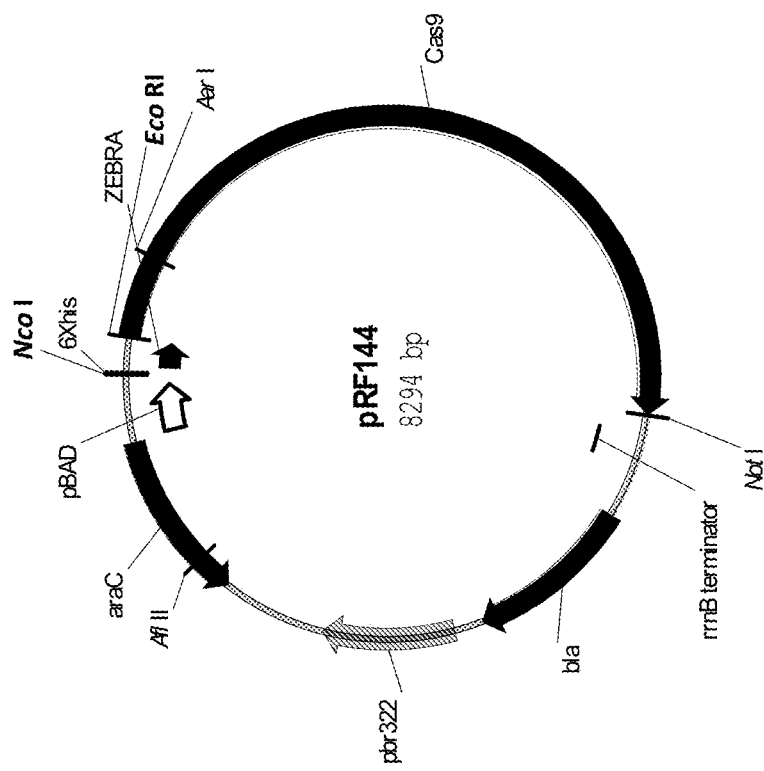

FIG. 3A: pRF144 plasmid (SEQ ID NO:20) for expressing 6xHis-Zebra CPP-Cas9-NLS fusion in *E. coli*. Origin of replication is in cross-hatch. Refer to Example 1.

FIG. 3B: pRF145 plasmid (SEQ ID NO:21) for expressing 6xHis-PolyR CPP-Cas9-NLS fusion in *E. coli*. Origin of replication is in cross-hatch. Refer to Example 1.

FIG. 3C: pRF146 plasmid (SEQ ID NO:22) for expressing 6xHis-TP10 CPP-Cas9-NLS fusion in *E. coli*. Origin of replication is in cross-hatch. Refer to Example 1.

FIG. 3D: pRF162 plasmid (SEQ ID NO:23) for expressing 6xHis-pVEC CPP-Cas9-NLS fusion in *E. coli*. Origin of replication is in cross-hatch. Refer to Example 1.

Figure 4:
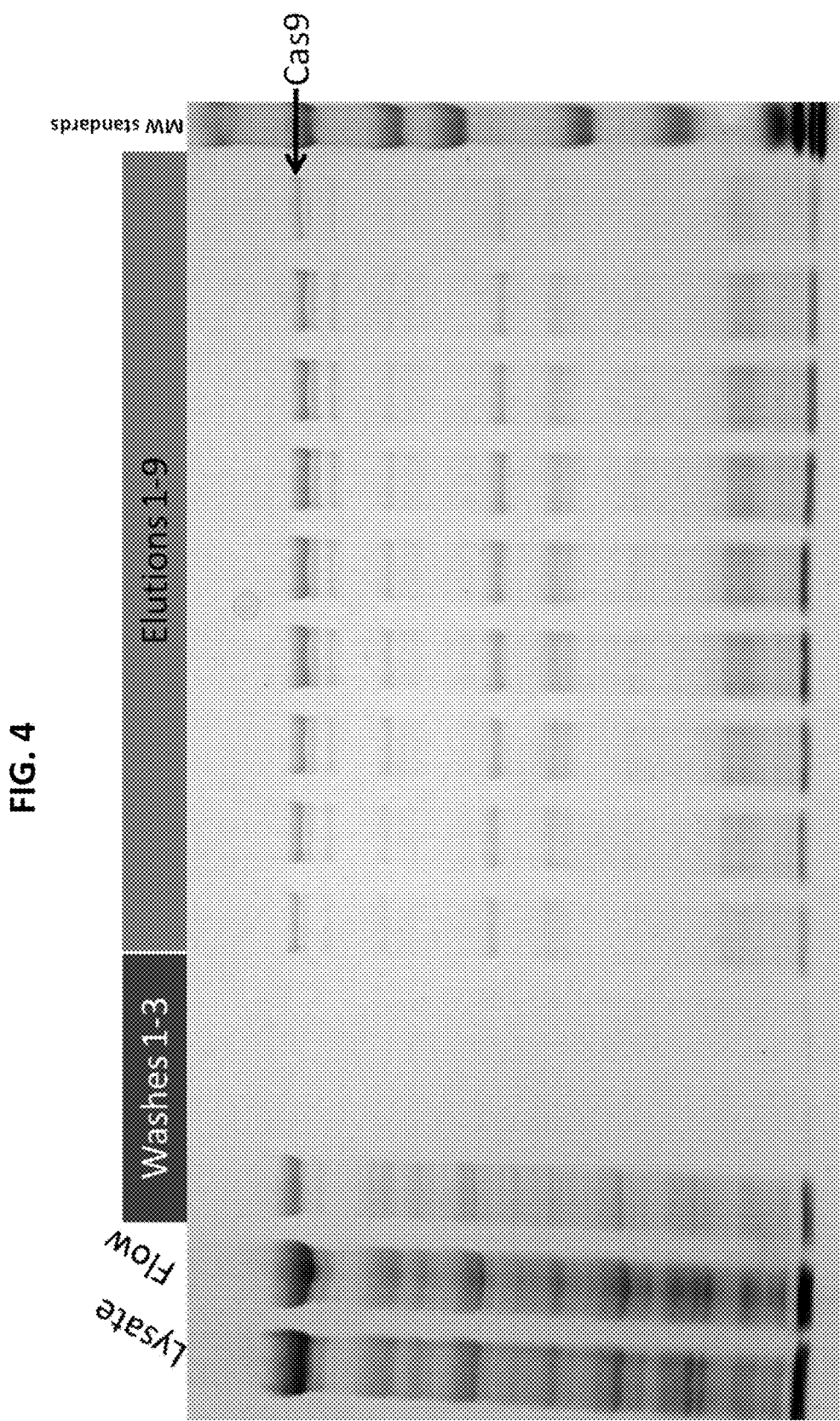

FIG. 4: SDS-PAGE separation of purification fractions of 6xHis-Zebra-Cas9-NLS. Lysates, washes, elution fractions, and molecular weight standards are indicated. Refer to Example 1.

Figure 5:
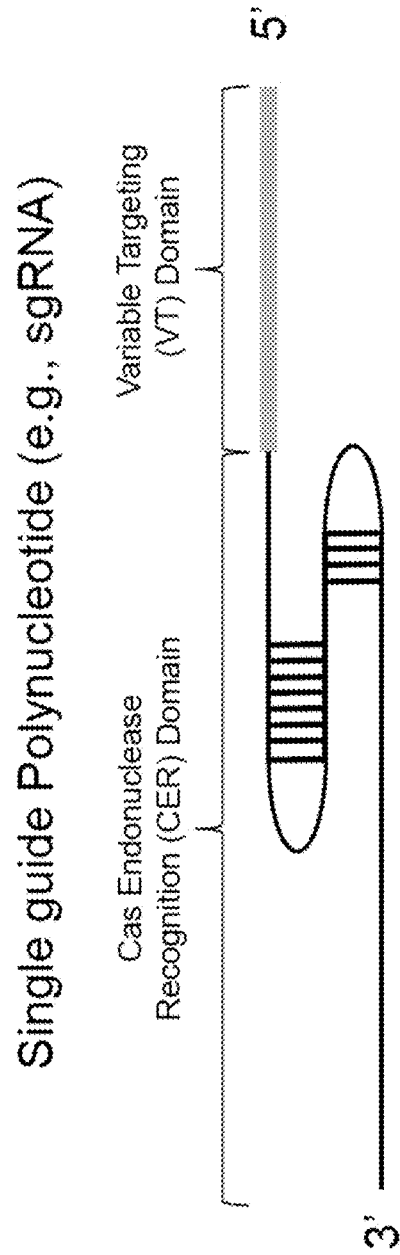

FIG. 5: A structural model of a single guide polynucleotide such as a single guide RNA (sgRNA). A variable targeting (VT) domain is shown in gray. A Cas9 endonuclease recognition (CER) domain is shown in black.

Figure 6:
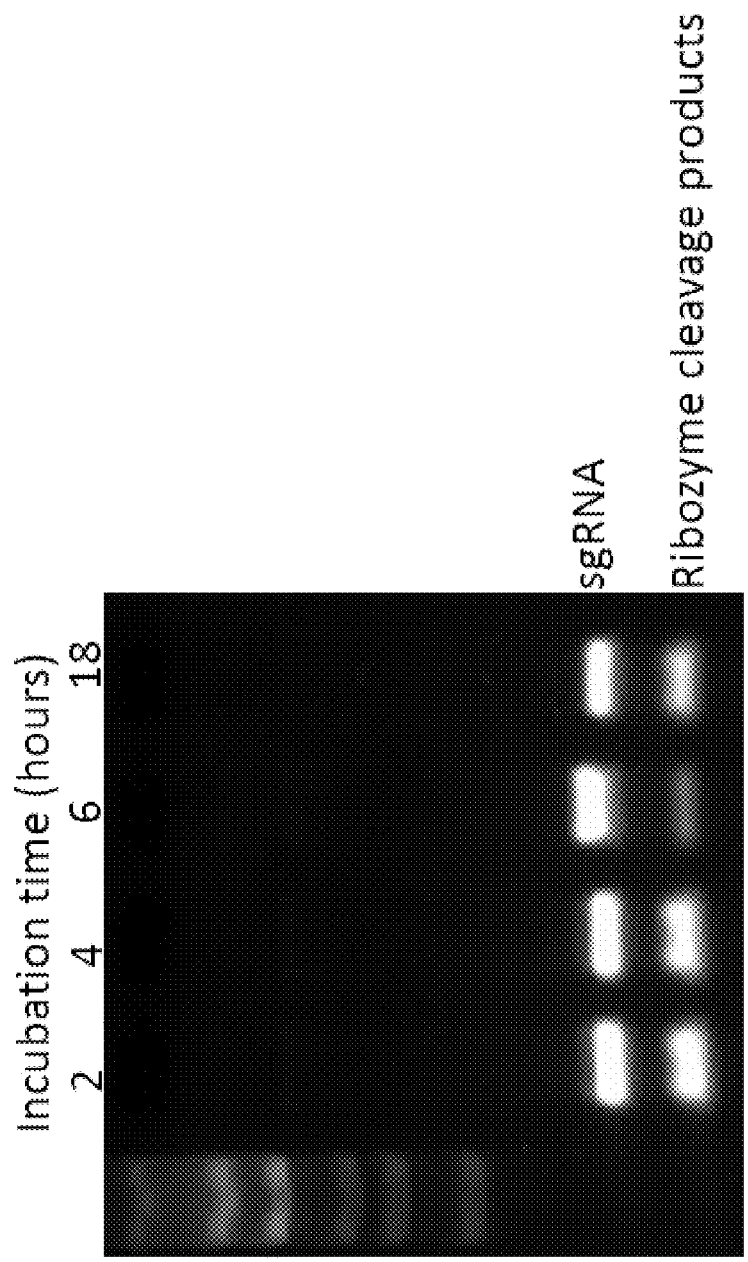

FIG. 6: In vitro transcription of RGR sgRNA (targeting Can1-1 locus) off of template derived from plasmid pRF46 (SEQ ID NO:30). In vitro transcription reactions incubated for 2, 4, 6 and 18 hours produced similar levels of sgRNA. Ribozyme autocatalytic cleavage products were also produced. Refer to Example 2.

Figure 7:
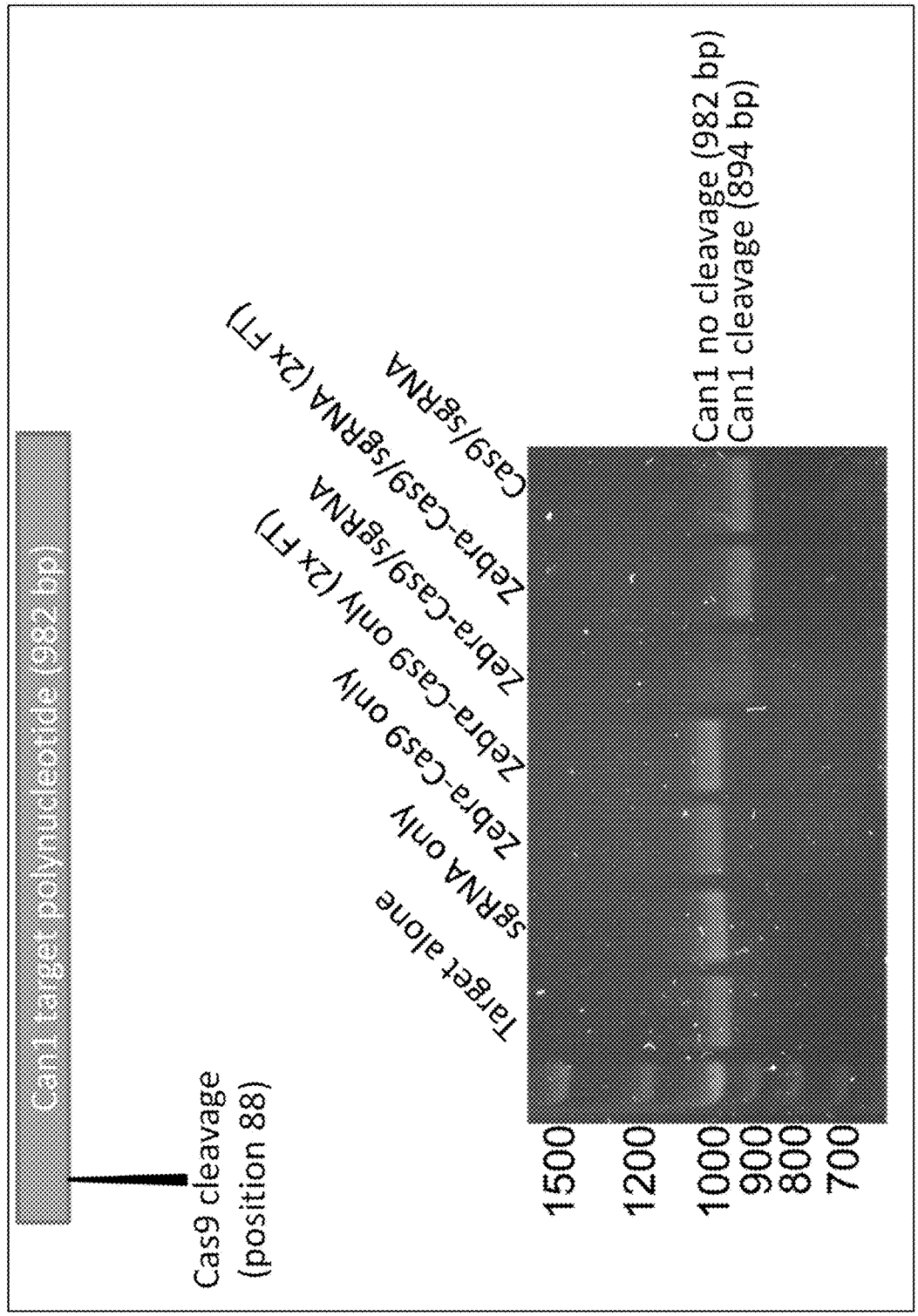

FIG. 7: In vitro cleavage assay using Zebra CPP-Cas9 complexed with sgRNA specific for Can1-1 target site. A DNA polynucleotide (982 bp) containing the Can1-1 target site was included in each reaction. Each reaction was electrophoretically resolved on a 1.2% gel. "Target only", "sgRNA only", "Zebra-Cas9 only", and "Zebra-Cas9 only (2xFT)" (FT, freeze-thaw) reactions did not cleave the target polynucleotide. "Zebra-Cas9/sgRNA", "Zebra-Cas9/sgRNA (2xFT)", and "Cas9/sgRNA" (wild type Cas9) reactions cleaved the target polynucleotide in a specific manner as indicated by the resulting cleavage products. Refer to Example 3.

Figure 8:
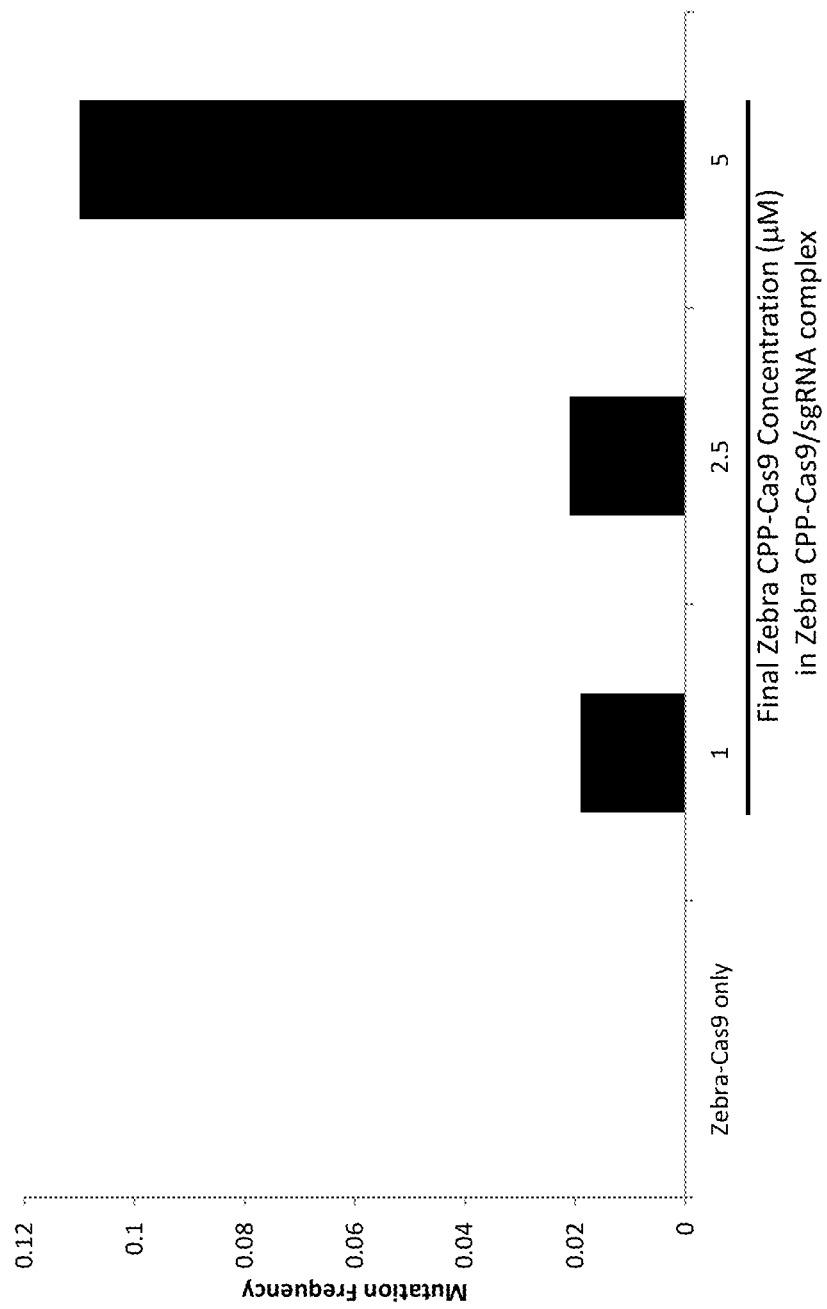

FIG. 8: Measuring the genome-targeting efficiency of Zebra CPP-Cas9 (not associated with sgRNA) and Zebra CPP-Cas9/gRNA complexes after contact thereof with *Yarrowia lipolytica* cells. The final concentration of Zebra-Cas9 used alone was 5 μM, while different final concentrations (1-5 μM) of Zebra CPP-Cas9 were used in the sgRNA complexes. Mutation frequency is reported as the proportion of yeast colonies (grown on non-selective medium after contacting cells with either Zebra CPP-Cas9 or Zebra CPP-Cas9/gRNA) that scored as resistant to canavanine upon transfer to canavanine-containing medium. Refer to Example 4.

Figure 9:
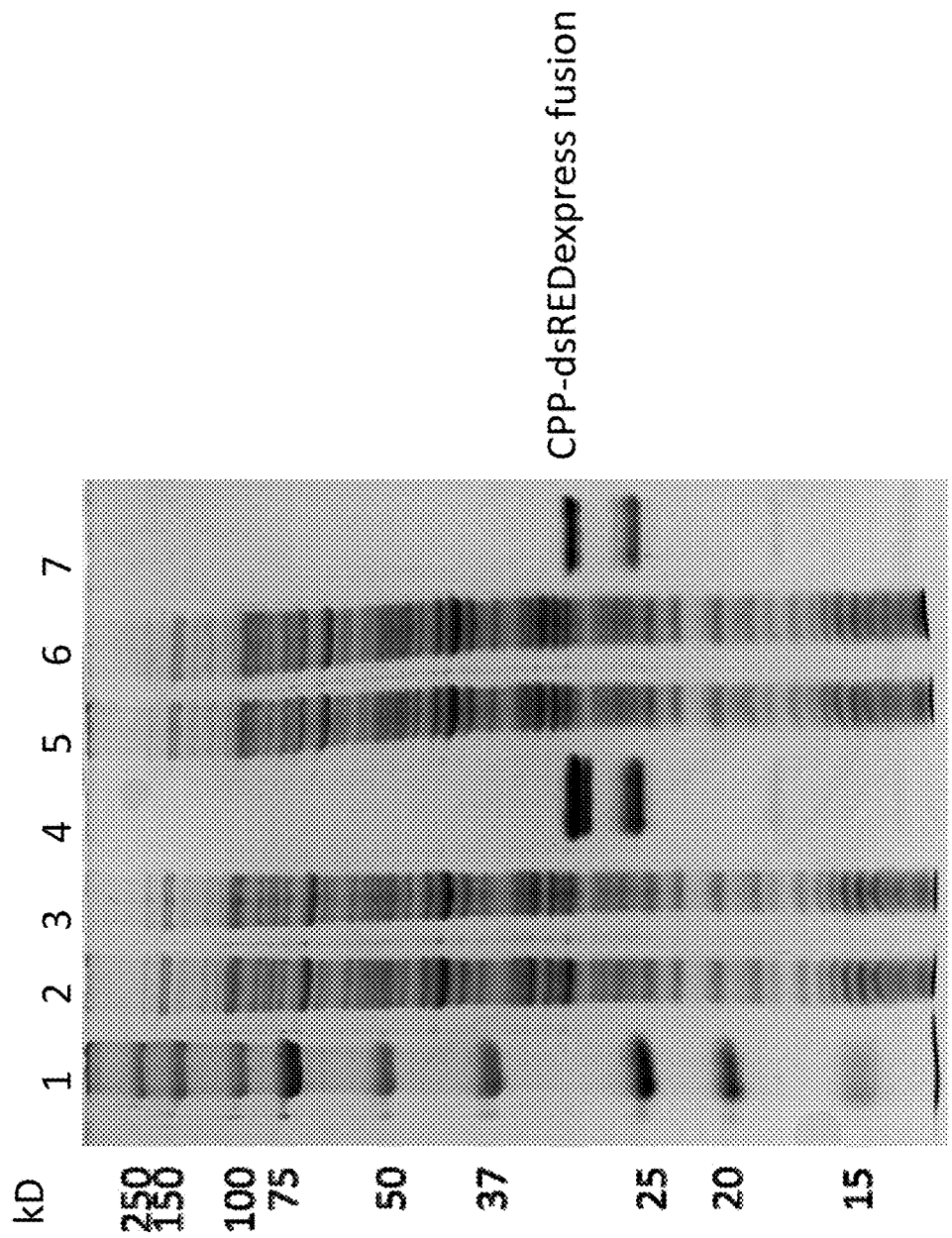

FIG. 9: Example of PAGE gel analysis of CPP-dsRED purification. 12.5% PAGE gel stained with Simply blue stain. Lane 1: Molecular weight standard, Lane 2: clarified cell extract tp10-dsREDexpress, Lane 3: clarified-cell extract post bead treatment tp10-dsREDexpress, lane 4: final protein solution tp10-dsREDexpress, Lane 5 clarified cell extract MPG-dsREDexpress, Lane 3: clarified-cell extract post bead treatment MPG-dsREDexpress, lane 4: final protein solution MPG-dsREDexpress.

TABLE 1

Summary of Nucleic Acid and Protein SEQ ID Numbers

| Description | Nucleic acid SEQ ID NO. | Protein SEQ ID NO. |
| --- | --- | --- |
| *Streptococcus pyogenes* Cas9 open reading frame codon-optimized for expression in *Y. lipolytica*. | 1 (4107 bases) | |
| *Streptococcus pyogenes* Cas9 including C-terminal linker and SV40 NLS ("Cas9-NLS"); open reading frame codon-optimized for expression in *Y. lipolytica*. | 2 (4140 bases) | 3 (1379 aa) |
| *Y. lipolytica* FBA1 promoter. | 4 (543 bases) | |
| Cas9-NLS expression cassette (FBA1 promoter and Cas9-NLS open reading frame). | 5 (4683 bases) | |
| pZUFCas9 plasmid. | 6 (10706 bases) | |
| Cas9-NLS forward PCR primer. | 7 (35 bases) | |
| Cas9-NLS reverse PCR primer. | 8 (31 bases) | |
| EcoRI-Cas9-NLS-HinDIII PCR product | 9 (4166 bases) | |
| pBAD/HisB plasmid | 10 (4092 bases) | |
| pRF48 plasmid | 11 (8237 bases) | |
| Zebra cell-penetrating peptide (CPP), from Epstein-Barr virus Zebra trans-activator protein | | 12 (54 aa) |
| pVEC CPP, from murine endothelial cadherin protein | | 13 (18 aa) |
| TP10 CPP, from neuropeptide galanin protein | | 14 (21 aa) |
| Poly-arginine (PolyR) CPP | | 15 (17 aa) |
| Ncol-6xHis-Zebra CPP-EcoRI | 16 (194 bases) | |
| Ncol-6xHis-pVEC CPP-EcoRI | 17 (86 bases) | |
| Ncol-6xHis-TP10 CPP-EcoRI | 18 (95 bases) | |
| Ncol-6xHis-PolyR CPP-EcoRI | 19 (83 bases) | |
| pRF144 plasmid, encoding Zebra CPP-Cas9 fusion protein | 20 (8294 bases) | |
| pRF145 plasmid, encoding PolyR CPP-Cas9 fusion protein | 21 (8183 bases) | |
| pRF146 plasmid, encoding TP10 CPP-Cas9 fusion protein | 22 (8195 bases) | |
| pRF162 plasmid, encoding pVEC CPP-Cas9 fusion protein | 23 (8186 bases) | |
| Cas9 endonuclease recognition (CER) domain of a gRNA. | 24 (80 bases) | |
| *Y. lipolytica* Can1-1 target site, or alternatively, DNA encoding Can1-1 variable target domain of a gRNA. | 25 (20 bases) | |
| Hammerhead (HH) ribozyme. | 26 (43 bases) | |
| HDV ribozyme. | 27 (68 bases) | |
| HH-sgRNA-HDV (RGR) pre-sgRNA expression cassette, or alternatively, "RGR" expression cassette (for targeting Can1-1 locus) | 28 (211 bases) | |

TABLE 1-continued

Summary of Nucleic Acid and Protein SEQ ID Numbers

| Description | Nucleic acid SEQ ID NO. | Protein SEQ ID NO. |
|---|---|---|
| T7 RNA polymerase promoter | 29 (20 bases) | |
| pRF46 plasmid | 30 (2875 bases) | |
| T7 forward primer | 31 (20 bases) | |
| gRNArev1 reverse primer | 32 (20 bases) | |
| IV-up primer | 33 (21 bases) | |
| IV-down primer | 34 (20 bases) | |
| Can1 cleavage assay DNA sequence | 35 (982 bases) | |
| RNA loop-forming sequence (GAAA). | 36 (4 bases) | |
| RNA loop-forming sequence (CAAA). | 37 (4 bases) | |
| RNA loop-forming sequence (AAAG). | 38 (4 bases) | |
| Zebra CPP-Cas9-NLS fusion protein | | 39 (1434 aa) |
| PolyR CPP-Cas9-NLS fusion protein | | 40 (1397 aa) |
| TP10 CPP-Cas9-NLS fusion protein | | 41 (1401 aa) |
| pVEC CPP-Cas9-NLS fusion protein | | 42 (1398 aa) |
| Example of a Cas9 target site: PAM sequence. | 43 (23 bases) | |
| PAM sequence NGG. | 44 (3 bases) | |
| PAM sequence NNAGAA. | 45 (6 bases) | |
| PAM sequence NNAGAAW. | 46 (7 bases) | |
| PAM sequence NGGNG. | 47 (5 bases) | |
| PAM sequence NNNNGATT. | 48 (8 bases) | |
| PAM sequence NAAAAC. | 49 (6 bases) | |
| PAM sequence NG. | 50 (2 bases) | |
| TracrRNA mate sequence example 1. | 51 (22 bases) | |
| TracrRNA mate sequence example 2. | 52 (15 bases) | |
| TracrRNA mate sequence example 3. | 53 (12 bases) | |
| TracrRNA mate sequence example 4. | 54 (13 bases) | |
| TracrRNA example 1. | 55 (60 bases) | |
| TracrRNA example 2. | 56 (45 bases) | |
| TracrRNA example 3. | 57 (32 bases) | |
| TracrRNA example 4. | 58 (85 bases) | |
| TracrRNA example 5. | 59 (77 bases) | |
| TracrRNA example 6. | 60 (65 bases) | |
| gRNA example 1. | 61 (131 bases) | |
| gRNA example 2. | 62 (117 bases) | |
| gRNA example 3. | 63 (104 bases) | |
| gRNA example 4. | 64 (99 bases) | |
| gRNA example 5. | 65 (81 bases) | |

TABLE 1-continued

Summary of Nucleic Acid and Protein SEQ ID Numbers

| Description | Nucleic acid SEQ ID NO. | Protein SEQ ID NO. |
| --- | --- | --- |
| gRNA example 6. | 66 (68 bases) | |
| gRNA example 7. | 67 (100 bases) | |
| Tat-derived CPP (GRKKRRQRRR) | | 68 (10 aa) |
| Tat-derived CPP (RKKRRQRRR) | | 69 (9 aa) |
| Tat-derived CPP (RKKRRQRR) | | 70 (8 aa) |
| Penetratin CPP (RQIKIWFQNRRMKWKK) | | 71 (16 aa) |
| Polyarginine CPP (THRLPRRRRRR) | | 72 (11 aa) |
| Polyarginine CPP (GGRRARRRRRR) | | 73 (11 aa) |
| pVEC CPP (shorter version), from murine endothelial cadherin protein | | 74 (17 aa) |
| CPP comprising (KFF)$_3$K | | 75 (10 aa) |
| MAP peptide CPP | | 76 (18 aa) |
| CPP (RRQRRTSKLMKR) | | 77 (12 aa) |
| CPP (KALAWEAKLAKALAKALAKHLAKALAKALKCEA) | | 78 (33 aa) |
| Proline-rich CPP repeat VHLPPP | | 79 (6 aa) |
| Proline-rich CPP repeat VHRPPP | | 80 (6 aa) |
| MPG peptide CPP | | 81 (27 aa) |
| Pep-1 peptide CPP | | 82 (21 aa) |
| hCT CPP example 1 | | 83 (24 aa) |
| hCT CPP example 2 | | 84 (18 aa) |
| his tagged dsRED | | 85 |
| E. coli codon optimized dsRED | 86 | |
| pBAD/HisB | 87 | |
| pRF161 | 88 | |
| TAT | | 89 |
| TLM | | 90 |
| MPG1 | | 91 |
| pep1 | | 92 |
| CFFKDEL | | 93 |
| his-TAT E. coli optimized | 94 | |
| his-TLM E. coli optimized | 95 | |
| his-MPG1 E. coli optimized | 96 | |
| his-pep1 E. coli optimized | 97 | |
| his-CFFKDEL E. coli optimized | 98 | |
| pRF224 | 99 | |
| pRF214 | 100 | |
| pRF213 | 101 | |
| pRF217 | 102 | |
| pRF216 | 103 | |
| oligo 36 | 104 | |
| His-Zebra PCR | 105 | |
| His-tp10 PCR | 106 | |
| His-pVEC PCR | 107 | |
| pRF144 | 108 | |
| pRF162 | 109 | |
| pRF146 | 110 | |
| oligo 153 | 111 | |
| pRF186 | 112 | |
| pRF192 | 113 | |
| pRF190 | 114 | |
| his-CFFKDEL-Cas9 | | 115 |
| his-MPG1-Cas9 | | 116 |
| pRF48 | 117 | |
| pRF243 | 118 | |
| pRF238 | 119 | |

TABLE 1-continued

Summary of Nucleic Acid and Protein SEQ ID Numbers

| Description | Nucleic acid SEQ ID NO. | Protein SEQ ID NO. |
|---|---|---|
| galK gene | 120 | |
| galE gene | | 121 |
| galT gene | | 122 |
| CER domain I | 123 | |
| CER encoding DNA PCR | 124 | |
| pRF291 | 125 | |
| CER forward | 126 | |
| universal reverse | 127 | |
| universal forward T7 primer | 128 | |
| galK2-1 forward primer | 129 | |
| galK2-1 reverse primer | 130 | |
| galK2-1 sgRNA in vitro transcription template | 131 | |
| T7 promoter | 132 | |
| DNA encoding galK2-1 variable targeting domain | 133 | |
| galK2-1 target site | 134 | |
| galK2-1 sgRNA | 135 | |
| his-MPG1-dsREDexpress; | | 136 |
| pVEC-dsREDexpress | | 137 |
| CFFKDEL-dsREDexpress | | 138 |
| TLM-dsREDexpress | | 139 |
| Zebra-dsREDexpress | | 140 |
| pep1-dsREDexpress | | 141 |
| tp10-dsREDexpress | | 142 |
| Zebra-Cas9 | | 143 |
| pVEC-Cas9 | | 144 |

DETAILED DESCRIPTION OF THE INVENTION

The disclosures of all cited patent and non-patent literature are incorporated herein by reference in their entirety.

As used herein, the term "invention" or "disclosed invention" is not meant to be limiting, but applies generally to any of the inventions defined in the claims or described herein. These terms are used interchangeably herein.

The term "cell" herein refers to any type of cell such as a prokaryotic or eukaryotic cell. A eukaryotic cell has a nucleus and other membrane-enclosed structures (organelles), whereas a prokaryotic cell lacks a nucleus. A cell in certain embodiments can be a mammalian cell or non-mammalian cell. Non-mammalian cells can be eukaryotic or prokaryotic. For example, a non-mammalian cell herein can refer to a microbial cell or cell of a non-mammalian multicellular organism such as a plant, insect, nematode, avian species, amphibian, reptile, or fish.

A microbial cell herein can refer to a fungal cell (e.g., yeast cell), prokaryotic cell, protist cell (e.g., algal cell), euglenoid cell, stramenopile cell, or oomycete cell, for example. A prokaryotic cell herein can refer to a bacterial cell or archaeal cell, for example. Fungal cells (e.g., yeast cells), protist cells (e.g., algal cells), euglenoid cells, stramenopile cells, and oomycete cells represent examples of eukaryotic microbial cells. A eukaryotic microbial cell has a nucleus and other membrane-enclosed structures (organelles), whereas a prokaryotic cell lacks a nucleus.

The term "yeast" herein refers to fungal species that predominantly exist in unicellular form. Yeast can alternatively be referred to as "yeast cells". A yeast herein can be characterized as either a conventional yeast or non-conventional yeast, for example.

The term "conventional yeast" ("model yeast") herein generally refers to *Saccharomyces* or *Schizosaccharomyces* yeast species. Conventional yeast in certain embodiments are yeast that favor homologous recombination (HR) DNA repair processes over repair processes mediated by non-homologous end-joining (NHEJ).

The term "non-conventional yeast" herein refers to any yeast that is not a *Saccharomyces* or *Schizosaccharomyces* yeast species. Non-conventional yeast are described in *Non-Conventional Yeasts in Genetics, Biochemistry and Biotechnology: Practical Protocols* (K. Wolf, K. D. Breunig, G. Barth, Eds., Springer-Verlag, Berlin, Germany, 2003) and Spencer et al. (Appl. Microbiol. Biotechnol. 58:147-156), which are incorporated herein by reference. Non-conventional yeast in certain embodiments may additionally (or alternatively) be yeast that favor NHEJ DNA repair processes over repair processes mediated by HR. Definition of a non-conventional yeast along these lines—preference of NHEJ over HR—is further disclosed by Chen et al. (*PLoS ONE* 8:e57952), which is incorporated herein by reference. Preferred non-conventional yeast herein are those of the genus *Yarrowia* (e.g., *Yarrowia lipolytica*).

The term "plant" herein refers to whole plants, plant organs, plant tissues, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores. Plant parts include differentiated and undifferentiated tissues including, but not limited to roots, stems, shoots, leaves, pollens, seeds, tumor tissue and various forms of cells and culture (e.g., single cells, protoplasts, embryos, and callus tissue). The plant tissue may be in plant or in a plant organ, tissue or cell culture. The term "plant organ" refers to plant tissue or a group of tissues that constitute a morphologically and functionally distinct part of a plant. The term "genome" refers to the entire complement of genetic material (genes and non-coding sequences) that is present in each cell of an organism, or virus or organelle; and/or a complete set of chromosomes inherited as a (haploid) unit from one parent. "Progeny" comprises any subsequent generation of a plant.

A transgenic plant includes, for example, a plant which comprises within its genome a heterologous polynucleotide introduced by a transformation step. The heterologous polynucleotide can be stably integrated within the genome such that the polynucleotide is passed on to successive generations. The heterologous polynucleotide may be integrated into the genome alone or as part of a recombinant DNA construct. A transgenic plant can also comprise more than one heterologous polynucleotide within its genome. Each heterologous polynucleotide may confer a different trait to the transgenic plant. A heterologous polynucleotide can include a sequence that originates from a foreign species, or, if from the same species, can be substantially modified from its native form. Transgenic plant material can include any cell, cell line, callus, tissue, plant part or plant, the genotype of which has been altered by the presence of heterologous nucleic acid including those transgenics initially so altered as well as those created by sexual crosses or asexual propagation from the initial transgenic. The alterations of a plant genome (chromosomal or extra-chromosomal) by conventional plant breeding methods, by a genome editing procedure described herein that does not result in an insertion of a foreign polynucleotide, or by naturally occurring events such as random cross-fertilization, non-recombinant viral infection, non-recombinant bacterial transformation, non-recombinant transposition, or spontaneous mutation are not intended to be regarded as transgenic.

A fertile plant is a plant that produces viable male and female gametes and is self-fertile. Such a self-fertile plant can produce a progeny plant without the contribution from any other plant of a gamete and the genetic material contained therein. Male-sterile plants include plants that do not produce male gametes that are viable or otherwise capable of fertilization. Female-sterile plants include plants that do not produce female gametes that are viable or otherwise capable of fertilization. It is recognized that male-sterile and female-sterile plants can be female-fertile and male-fertile, respectively. It is further recognized that a male-fertile (but female-sterile) plant can produce viable progeny when crossed with a female-fertile plant and that a female-fertile (but male-sterile) plant can produce viable progeny when crossed with a male-fertile plant.

The term "RNA-guided endonuclease" (RGEN) herein refers to a complex comprising at least one CRISPR (clustered regularly interspaced short palindromic repeats)-associated (Cas) protein and at least one RNA component. The terms "protein component of an RGEN" and "RGEN protein component" are used interchangeably herein and refer to a Cas protein, which is, or forms part of, the endonuclease component of an RGEN. A protein component in certain embodiments can be a complete endonuclease (e.g., Cas9); such a protein component can alternatively be referred to as "the endonuclease component" of an RGEN. An RGEN herein typically has specific DNA targeting activity, given its association with at least one RNA component.

Briefly, an RNA component of an RGEN contains sequence that is complementary to a DNA sequence in a target site sequence. Based on this complementarity, an RGEN can specifically recognize and cleave a particular DNA target site sequence. An RGEN herein can comprise Cas protein(s) and suitable RNA component(s) of any of the four known CRISPR systems (Horvath and Barrangou, Science 327:167-170) such as a type I, II, or III CRISPR system. An RGEN in preferred embodiments comprises a Cas9 endonuclease (CRISPR II system) and at least one RNA component (e.g., a crRNA and tracrRNA, or a gRNA).

The term "CRISPR" (clustered regularly interspaced short palindromic repeats) refers to certain genetic loci encoding factors of class I, II, or III DNA cleavage systems, for example, used by bacterial and archaeal cells to destroy foreign DNA (Horvath and Barrangou, Science 327:167-170). Components of CRISPR systems are taken advantage of herein in a heterologous manner for DNA targeting in cells.

The terms "type II CRISPR system" and "type II CRISPR-Cas system" are used interchangeably herein and refer to a DNA cleavage system utilizing a Cas9 endonuclease in complex with at least one RNA component. For example, a Cas9 can be in complex with a CRISPR RNA (crRNA) and a trans-activating CRISPR RNA (tracrRNA). In another example, a Cas9 can be in complex with a guide RNA. Thus, crRNA, tracrRNA, and guide RNA are non-limiting examples of RNA components herein.

The term CRISPR-associated ("Cas") endonuclease herein refers to a Cas protein encoded by a Cas gene. A Cas endonuclease, when in complex with a suitable RNA component, is capable of cleaving all or part of a specific DNA target sequence in certain embodiments. For example, it is can be capable of introducing a single- or double-strand break in a specific DNA target sequence; it can alternatively be characterized as being able to cleave one or both strands of a specific DNA target sequence. A Cas endonuclease can unwind the DNA duplex at the target sequence and cleaves at least one DNA strand, as mediated by recognition of the target sequence by a crRNA or guide RNA that is in complex with the Cas. Such recognition and cutting of a target sequence by a Cas endonuclease typically occurs if the correct protospacer-adjacent motif (PAM) is located at or adjacent to the 3' end of the DNA target sequence. Alternatively, a Cas protein herein may lack DNA cleavage or nicking activity, but can still specifically bind to a DNA target sequence when complexed with a suitable RNA component. A preferred Cas protein herein is Cas9.

Any guided endonuclease can be used in the methods disclosed herein. Such endonucleases include, but are not limited to Cas9 and Cpf1 endonucleases. Many endonucleases have been described to date that can recognize specific PAM sequences (see for example WO2016/186953, published on Nov. 14, 2016 and WO2016/186946 published on Nov. 14, 2016, and Zetsche B et al. 2015. Cell 163, 1013) and cleave the target DNA at a specific position. It is understood that based on the methods and embodiments described herein utilizing a guided Cas system, one can now tailor these methods such that they can utilize any guided endonuclease system.

"Cas9" (formerly referred to as Cas5, Csn1, or Csx12) herein refers to a Cas endonuclease of a type II CRISPR system that forms a complex with crRNA and tracrRNA, or with a guide RNA, for specifically recognizing and cleaving all or part of a DNA target sequence. Cas9 protein comprises an RuvC nuclease domain and an HNH (H-N-H) nuclease domain, each of which cleaves a single DNA strand at a target sequence (the concerted action of both domains leads to DNA double-strand cleavage, whereas activity of one domain leads to a nick). In general, the RuvC domain comprises subdomains I, II and III, where domain I is located near the N-terminus of Cas9 and subdomains II and III are located in the middle of the protein, flanking the HNH domain (Hsu et al, Cell 157:1262-1278). "Apo-Cas9" refers to Cas9 that is not complexed with an RNA component. Apo-Cas9 can bind DNA, but does so in a non-specific manner, and cannot cleave DNA (Sternberg et al., Nature 507:62-67).

The term "RNA component" herein refers to an RNA component of an RGEN containing a ribonucleic acid sequence that is complementary to a strand of a DNA target sequence. This complementary sequence is referred to herein as a "guide sequence" or "variable targeting domain" sequence (FIG. 5). Examples of suitable RNA components herein include crRNA and guide RNA. RNA components in certain embodiments (e.g., guide RNA alone, crRNA+tracrRNA) can render an RGEN competent for specific DNA targeting.

The term "CRISPR RNA" (crRNA) herein refers to an RNA sequence that can form a complex with one or more Cas proteins (e.g., Cas9) and provides DNA binding specificity to the complex. A crRNA provides DNA binding specificity since it contains "guide sequence" ("variable targeting domain" [VT]) that is complementary to a strand of a DNA target sequence. A crRNA further comprises a "repeat sequence" ("tracr RNA mate sequence") encoded by a repeat region of the CRISPR locus from which the crRNA was derived. A repeat sequence of a crRNA can anneal to sequence at the 5'-end of a tracrRNA. crRNA in native CRISPR systems is derived from a "pre-crRNA" transcribed from a CRISPR locus. A pre-crRNA comprises spacer regions and repeat regions; spacer regions contain unique sequence complementary to a DNA target site sequence. Pre-crRNA in native systems is processed to multiple different crRNAs, each with a guide sequence along with a portion of repeat sequence. CRISPR systems utilize crRNA, for example, for DNA targeting specificity.

The term "trans-activating CRISPR RNA" (tracrRNA) herein refers to a non-coding RNA used in type II CRISPR systems, and contains, in the 5'-to-3' direction, (i) a sequence that anneals with the repeat region of CRISPR type II crRNA and (ii) a stem loop-containing portion (Deltcheva et al., *Nature* 471:602-607).

The terms "guide RNA" (gRNA) and "single guide RNA" (sgRNA) are used interchangeably herein. A gRNA herein can refer to a chimeric sequence containing a crRNA operably linked to a tracrRNA. Alternatively, a gRNA can refer to a synthetic fusion of a crRNA and a tracrRNA, for example. A gRNA can also be characterized in terms of having a guide sequence (variable targeting domain) followed by a Cas endonuclease recognition (CER) domain. A CER domain can comprise a tracrRNA mate sequence followed by a tracrRNA sequence.

A "CRISPR DNA" (crDNA) can optionally be used instead of an RNA component. A crDNA has a DNA sequence corresponding to the sequence of a crRNA as disclosed herein. A crDNA can be used with a tracrRNA in a crDNA/tracrRNA complex, which in turn can be associated with an RGEN protein component. U.S. Appl. No. 61/953,090 discloses crDNA and the methods of its use in RGEN-mediated DNA targeting. It is contemplated that any disclosure herein regarding a crRNA can similarly apply to using a crDNA, accordingly. Thus, in embodiments herein incorporating a crDNA, an "RNA-guided endonuclease" (RGEN) could instead be referred to as a complex comprising at least one Cas protein and at least one crDNA.

As used herein, the term "guide polynucleotide", relates to a polynucleotide sequence that can form a complex with a Cas endonuclease and enables the Cas endonuclease to recognize and optionally cleave a DNA target site. The guide polynucleotide can be a single molecule or a double molecule. The guide polynucleotide sequence can be a RNA sequence, a DNA sequence, or a combination thereof (an RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, Phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA".

The guide polynucleotide can be a double molecule (also referred to as duplex guide polynucleotide) comprising a first nucleotide sequence domain (referred to as Variable Targeting domain or VT domain) that is complementary to a nucleotide sequence in a target DNA and a second nucleotide sequence domain (referred to as Cas endonuclease recognition domain or CER domain) that interacts with a Cas endonuclease polypeptide. The CER domain of the double molecule guide polynucleotide comprises two separate molecules that are hybridized along a region of complementarity. The two separate molecules can be RNA, DNA, and/or RNA-DNA-combination sequences. In some embodiments, the first molecule of the duplex guide polynucleotide comprising a VT domain linked to a CER domain ("crNucleotide") is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). In some embodiments the second molecule of the duplex guide polynucleotide comprising a CER domain is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides).

The guide polynucleotide can also be a single molecule comprising a first nucleotide sequence domain (referred to as Variable Targeting domain or VT domain) that is complementary to a nucleotide sequence in a target DNA and a second nucleotide domain (referred to as Cas endonuclease recognition domain or CER domain) that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise an RNA sequence, a DNA sequence, or a, RNA-DNA-combination sequence. In some embodiments the single guide polynucleotide comprises a crNucleotide (comprising a VT domain linked to a CER domain) linked to a tracrNucleotide (comprising a CER domain), wherein the linkage is a nucleotide sequence comprising an RNA sequence, a DNA sequence, or an RNA-DNA combination sequence. The single guide polynucleotide being comprised of sequences from the crNucleotide and tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides).

Thus, a guide polynucleotide and a type II Cas endonuclease in certain embodiments can form a complex with each other (referred to as a "guide polynucleotide/Cas endonuclease complex" or also referred to as "guide polynucleotide/Cas endonuclease system"), wherein the guide polynucleotide/Cas endonuclease complex can direct the Cas endonuclease to target a genomic target site in a cell (e.g., plant cell), optionally enabling the Cas endonuclease to introduce a single- or double-strand break into the genomic target site. A guide polynucleotide/Cas endonuclease complex can be linked to at least one CPP, wherein such complex is capable of binding to, and optionally creating a single- or double-strand break to, a target site of a cell (e.g., a plant cell).

The term "variable targeting domain" or "VT domain" is used interchangeably herein and refers to a nucleotide sequence that is complementary to one strand (nucleotide sequence) of a double strand DNA target site. The percent complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, an RNA sequence, a modified DNA sequence, a modified RNA sequence (see, e.g., modifications described herein), or any combination thereof.

The term "Cas endonuclease recognition domain" or "CER domain" of a guide polynucleotide is used interchangeably herein and relates to a nucleotide sequence (such as a second nucleotide sequence domain of a guide polynucleotide), that interacts with a Cas endonuclease polypeptide. A CER domain can be composed of a DNA sequence, an RNA sequence, a modified DNA sequence, a modified RNA sequence (see, e.g., modifications described herein), or any combination thereof.

The terms "target site", "target sequence", "target DNA", "DNA target sequence", "target locus", "protospacer" and the like are used interchangeably herein. A target site sequence refers to a polynucleotide sequence on a chromosome, episome, or any other DNA molecule in the genome of a cell to which an RGEN herein can recognize, bind to, and optionally nick or cleave. A target site can be (i) an endogenous/native site in the cell, (ii) heterologous to the cell and therefore not be naturally occurring in the genome, or (iii) found in a heterologous genomic location compared to where it natively occurs.

A target site sequence herein is at least 13 nucleotides in length and has a strand with sufficient complementarity to a guide sequence (of a crRNA or gRNA) to be capable of hybridizing with the guide sequence and direct sequence-specific binding of a Cas protein or Cas protein complex to the target sequence (if a suitable PAM is adjacent to the target sequence in certain embodiments). A cleavage/nick site (applicable with a endonucleolytic or nicking Cas) can be within the target sequence (e.g., using a Cas9) or a cleavage/nick site could be outside of the target sequence (e.g., using a Cas9 fused to a heterologous endonuclease domain such as one derived from a FokI enzyme). It is also possible for a target site sequence to be bound by an RGEN lacking cleavage or nicking activity.

An "artificial target site" or "artificial target sequence" herein refers to a target sequence that has been introduced into the genome of a cell. An artificial target sequence in some embodiments can be identical in sequence to a native target sequence in the genome of the cell, but be located at a different position (a heterologous position) in the genome, or it can different from the native target sequence if located at the same position in the genome of the cell.

An "episome" herein refers to a DNA molecule that can exist in a cell autonomously (can replicate and pass on to daughter cells) apart from the chromosomes of the cell. Episomal DNA can be either native or heterologous to a cell. Examples of native episomes herein include mitochondrial DNA (mtDNA) and chloroplast DNA. Examples of heterologous episomes herein include plasmids and yeast artificial chromosomes (YACs).

A "protospacer adjacent motif" (PAM) herein refers to a short sequence that is recognized by an RGEN herein. The sequence and length of a PAM herein can differ depending on the Cas protein or Cas protein complex used, but are typically 2, 3, 4, 5, 6, 7, or 8 nucleotides long, for example.

The terms "5'-cap" and "7-methylguanylate ($m^7G$) cap" are used interchangeably herein. A 7-methylguanylate residue is located on the 5' terminus of RNA transcribed by RNA polymerase II (Pol II) in eukaryotes. A capped RNA herein has a 5'-cap, whereas an uncapped RNA does not have such a cap.

The terminology "uncapped", "not having a 5'-cap", and the like are used interchangeably herein to refer to RNA lacking a 5'-cap and optionally having, for example, a 5'-hydroxyl group instead of a 5'-cap. Uncapped RNA can better accumulate in the nucleus following transcription, since 5'-capped RNA is subject to nuclear export.

The terms "ribozyme", "ribonucleic acid enzyme" and "self-cleaving ribozyme" are used interchangeably herein. A ribozyme refers to one or more RNA sequences that form secondary, tertiary, and/or quaternary structure(s) that can cleave RNA at a specific site, particularly at a cis-site relative to the ribozyme sequence (i.e., auto-catalytic, or self-cleaving). The general nature of ribozyme nucleolytic activity has been described (e.g., Lilley, *Biochem. Soc. Trans.* 39:641-646). A "hammerhead ribozyme" (HHR) herein may comprise a small catalytic RNA motif made up of three base-paired stems and a core of highly conserved, non-complementary nucleotides that are involved in catalysis. Pley et al. (*Nature* 372:68-74) and Hammann et al. (*RNA* 18:871-885), which are incorporated herein by reference, disclose hammerhead ribozyme structure and activity. A hammerhead ribozyme herein may comprise a "minimal hammerhead" sequence as disclosed by Scott et al. (*Cell* 81:991-1002, incorporated herein by reference), for example.

The terms "targeting", "gene targeting", "DNA targeting", "editing", "gene editing" and "DNA editing" are used interchangeably herein. DNA targeting herein may be the specific introduction of an indel, knock-out, or knock-in at a particular DNA sequence, such as in a chromosome or episome of a cell. In general, DNA targeting can be performed herein by cleaving one or both strands at a specific DNA sequence in a cell with a Cas protein associated with a suitable RNA component. Such DNA cleavage, if a double-strand break (DSB), can prompt NHEJ processes which can lead to indel formation at the target site. Also, regardless of whether the cleavage is a single-strand break (SSB) or DSB, HR processes can be prompted if a suitable donor DNA polynucleotide is provided at the DNA nick or cleavage site. Such an HR process can be used to introduce a knock-out or knock-in at the target site, depending on the sequence of the donor DNA polynucleotide. Alternatively, DNA targeting herein can refer to specific association of a Cas/RNA component complex herein to a target DNA sequence, where the Cas protein does or does not cut a DNA strand (depending on the status of the Cas protein's endonucleolytic domains).

The term "indel" herein refers to an insertion or deletion of a nucleotide base or bases in a target DNA sequence in a chromosome or episome. Such an insertion or deletion may be of 1, 2, 3, 4, 5, 6, 7, 8, 9, 10, or more bases, for example. An indel in certain embodiments can be even larger, at least about 20, 30, 40, 50, 60, 70, 80, 90, or 100 bases. If an indel is introduced within an open reading frame (ORF) of a gene, oftentimes the indel disrupts wild type expression of protein encoded by the ORF by creating a frameshift mutation.

The terms "knock-out", "gene knock-out" and "genetic knock-out" are used interchangeably herein. A knock-out represents a DNA sequence of a cell herein that has been rendered partially or completely inoperative by targeting with a Cas protein; such a DNA sequence prior to knock-out could have encoded an amino acid sequence, or could have had a regulatory function (e.g., promoter), for example. A knock-out may be produced by an indel (by NHEJ, prompted by Cas-mediated cleavage), or by specific removal of sequence (by HR, prompted by Cas-mediated cleavage or nicking, when a suitable donor DNA polynucleotide is also used), that reduces or completely destroys the function of sequence at, adjoining, or near the targeting site. A knocked out DNA polynucleotide sequence herein can alternatively be characterized as being partially or totally disrupted or downregulated, for example.

The terms "knock-in", "gene knock-in" and "genetic knock-in" are used interchangeably herein. A knock-in represents the replacement or insertion of a DNA sequence at a specific DNA sequence in a cell by targeting with a Cas protein (by HR, prompted by Cas-mediated cleavage or nicking, when a suitable donor DNA polynucleotide is also used). Examples of knock-ins are a specific insertion of a heterologous amino acid coding sequence in a coding region of a gene, or a specific insertion of a transcriptional regulatory element in a genetic locus.

The terms "donor polynucleotide", "donor DNA", "targeting polynucleotide" and "targeting DNA" are used interchangeably herein. A donor polynucleotide refers to a DNA sequence that comprises at least one sequence that is homologous to a sequence at or near a DNA target site (e.g., a sequence specifically targeted by a Cas protein herein). A suitable donor polynucleotide is able to undergo HR with a DNA target site if the target site contains a SSB or DSB (such as can be introduced using certain Cas proteins herein associated with an appropriate RNA component). A "homologous sequence" within a donor polynucleotide herein can, for example, comprise or consist of a sequence of at least about 25 nucleotides, for example, having 100% identity with a sequence at or near a target site, or at least about 90%, 91%, 92%, 93%, 94%, 95%, 96%, 97%, 98%, or 99% identity with a sequence at or near a target site.

In certain embodiments, a donor DNA polynucleotide can have two homologous sequences separated by a sequence (or base pair) that is heterologous to sequence at a target site. These two homologous sequences of such a donor polynucleotide can be referred to as "homology arms", which flank the heterologous sequence. HR between a target site and a donor polynucleotide with two homology arms typically results in the replacement of a sequence at the target site with the heterologous sequence of the donor polynucleotide (target site sequence located between DNA sequences homologous to the homology arms of the donor polynucleotide is replaced by the heterologous sequence of the donor polynucleotide). In a donor polynucleotide with two homology arms, the arms can be separated by 1 or more nucleotides (i.e., the heterologous sequence in the donor polynucleotide can be at least 1 nucleotide in length). Various HR procedures that can be performed in a cell herein are disclosed, for example, in DNA *Recombination: Methods and Protocols: 1st Edition* (H. Tsubouchi, Ed., Springer-Verlag, New York, 2011), which is incorporated herein by reference.

The terms "cell-penetrating peptide" (CPP) and "protein transduction domain" (PTD) are used interchangeably herein. A CPP refers to a peptide, typically of about 5-60 amino acid residues in length, that can facilitate cellular uptake of molecular cargo, particularly one or more RGEN protein components herein (e.g., Cas9 protein). Such protein cargo can be associated with one or more CPPs through covalent or non-covalent linkage. A CPP can also be characterized in certain embodiments as being able to facilitate the movement or traversal of molecular cargo across/through one or more of a lipid bilayer, micelle, cell membrane, organelle membrane, vesicle membrane, or cell wall. A CPP herein can be cationic, amphipathic, or hydrophobic in certain embodiments. Examples of CPPs useful herein, and further description of CPPs in general, are disclosed in Schmidt et al. (*FEBS Lett.* 584:1806-1813), Holm et al. (*Nature Protocols* 1:1001-1005), Yandek et al. (*Biophys. J.* 92:2434-2444), Morris et al. (*Nat. Biotechnol.* 19:1173-1176), and U.S. Patent Appl. Publ. No. 2014/0068797, which are all incorporated herein by reference.

A "cationic", or "polycationic", CPP herein refers to a CPP having a high relative abundance (at least 60%) of positively charged amino acids such as lysine (K), arginine (R), and/or histidine (H).

An "amphipathic", or "amphiphilic", CPP herein refers to a CPP with an amino acid sequence containing an alternating pattern of polar/charged residues and non-polar, hydrophobic residues. An amphipathic CPP can alternatively be characterized as possessing both hydrophilic and lipophilic properties.

A "hydrophobic", or "lipophilic", CPP herein contains mostly, or only, non-polar residues with low net charge and/or hydrophobic amino acid groups.

The terms "covalently linked", "covalently attached", "covalently associated", "covalent linkage", "covalent interaction" and the like are used interchangeably herein. A covalent linkage herein can be via a peptide bond(s) or chemical crosslink(s), for example. A covalent linkage can be direct, for example, where there is a covalent link directly between (directly linking) an RGEN protein component and a CPP (e.g., there is a chemical bond [sharing of electrons] between an atom of an RGEN protein component and an atom of a CPP). A covalent linkage can alternatively be indirect, for example, where an RGEN protein component and a CPP are linked to each other through at least one intermediary factor. Such an intermediary factor, or group of intermediary factors that are themselves covalently linked together, is covalently linked to the RGEN protein component and CPP. Thus, an intermediary factor or group thereof can be characterized as being a bridge between an RGEN protein component and a CPP.

The terms "fusion protein", "protein fusion", "chimeric protein" and the like are used interchangeably herein. A fusion protein herein contains at least two different (heterologous) amino acid sequences linked together within a single polypeptide. Fusion proteins are typically produced by genetic engineering processes in which DNA sequences encoding different amino acid sequences are joined together to encode a single protein containing the different amino acid sequences. Examples of fusion proteins herein include RGEN protein-CPP fusions (RGEN protein amino acid sequence fused to one or more CPP amino acid sequences).

The terms "non-covalently linked", "non-covalently attached", "non-covalently associated", "non-covalent linkage", "non-covalent interaction" and the like are used interchangeably herein. A non-covalent linkage herein refers to an interaction between atoms in which electrons are not shared. This type of interaction is weaker than a covalent linkage. Hydrophobic interactions represent an example of a non-covalent linkage that may occur between an RGEN protein component and one or more CPPs. Other examples of non-covalent linkages that may apply herein include electrostatic forces (e.g., ionic, hydrogen bonding) and Van der Waals forces (London Dispersion forces).

An "RGEN protein-CPP complex" as used herein refers to a complex between a protein component of an RGEN and at least one CPP, where the RGEN and CPP interact via covalent or non-covalent linkage. Both RGEN and CPP components in this complex typically retain all of, or some of (e.g., at least 50%), their respective activity/function as disclosed herein. For example, in embodiment in which the RGEN protein component is Cas9, the Cas9 in a Cas9-CPP complex is capable of associating with a suitable RNA component (e.g., gRNA) and targeting the Cas9-CPP complex to a DNA target site in a cell.

The terms "traverse", "travel through", "cross through", "goes across" and the like are used interchangeably herein.

The terms "cell membrane", "plasma membrane", and "cytoplasmic membrane" are used interchangeably herein and refer to a biological membrane that separates the interior of a cell from its exterior. A cell membrane typically comprises a phospholipid bilayer with proteins embedded therein. Among several other functions, a cell membrane can serve as an attachment surface for extracellular structures such as cell wall or glycocalyx structures. Detailed information regarding cell membrane lipid bilayers is provided in *Molecular Biology of the Cell. 4th Edition* (B. Alberts et al., Eds., Garland Science, New York, 2002), which is incorporated herein by reference.

The term "cell wall" herein refers to a tough, flexible (but sometimes fairly rigid) layer that surrounds some types of non-mammalian cells (e.g., bacteria, plants, algae, fungi such as yeast). It is located outside the cell membrane and provides structural support and protection to cells. A major function of a cell wall in certain embodiments is to help maintain cell osmotic pressure. Fungal cell (e.g., yeast cell) walls generally comprise chitin, and algal cells walls generally comprise glycoproteins and polysaccharides. Plant cell walls generally comprise mostly polysaccharides with lesser amounts of other components (e.g., phenolic esters, structural proteins). "Primary cell wall" and/or "secondary cell wall" may be used to characterize a plant cell wall, where the secondary wall is located inside the primary wall. Lignin is a major component of secondary walls. Bacterial cell walls generally comprise peptidoglycan as the main constituent. In certain aspects, such as in bacteria, a cell wall can further comprise at its outer layer a glycocalyx, which is generally a coat of polysaccharides.

The term "leucine zipper domain" herein refers to a dimerization domain characterized by the presence of a leucine residue every seventh residue in a stretch of approximately 35 residues. Leucine zipper domains form dimers held together by an alpha-helical coiled coil. A coiled coil has 3.5 residues per turn, which means that every seventh residue occupies an equivalent position with respect to the helix axis. The regular array of leucines inside the coiled coil stabilizes the structure by hydrophobic and Van der Waals interactions.

The terms "percent by volume", "volume percent", "vol %" and "v/v %" are used interchangeably herein. The percent by volume of a solute in a solution can be determined using the formula: [(volume of solute)/(volume of solution)]×100%.

The terms "percent by weight", "weight percentage (wt %)" and "weight-weight percentage (% w/w)" are used interchangeably herein. Percent by weight refers to the percentage of a material on a mass basis as it is comprised in a composition, mixture, or solution.

The terms "polynucleotide", "polynucleotide sequence", and "nucleic acid sequence" are used interchangeably herein. These terms encompass nucleotide sequences and the like. A polynucleotide may be a polymer of DNA or RNA that is single- or double-stranded, that optionally contains synthetic, non-natural or altered nucleotide bases. A polynucleotide may be comprised of one or more segments of cDNA, genomic DNA, synthetic DNA, or mixtures thereof. Nucleotides (ribonucleotides or deoxyribonucleotides) can be referred to by a single letter designation as follows: "A" for adenylate or deoxyadenylate (for RNA or DNA, respectively), "C" for cytidylate or deoxycytidylate (for RNA or DNA, respectively), "G" for guanylate or deoxyguanylate (for RNA or DNA, respectively), "U" for uridylate (for RNA), "T" for deoxythymidylate (for DNA), "R" for purines (A or G), "Y" for pyrimidines (C or T), "K" for G or T, "H" for A or C or T, "I" for inosine, "W" for A or T, and "N" for any nucleotide (e.g., N can be A, C, T, or G, if referring to a DNA sequence; N can be A, C, U, or G, if referring to an RNA sequence). Any RNA sequence (e.g., crRNA, tracrRNA, gRNA) disclosed herein may be encoded by a suitable DNA sequence.

The term "isolated" as used herein refers to a polynucleotide or polypeptide molecule that has been completely or partially purified from its native source. In some instances, the isolated polynucleotide or polypeptide molecule is part of a greater composition, buffer system or reagent mix. For example, the isolated polynucleotide or polypeptide molecule can be comprised within a cell or organism in a heterologous manner. Compositions herein comprising a protein component of an RGEN and a cell-penetrating peptide can be considered isolated compositions. These compositions contain heterologous components and do not occur in nature.

The term "gene" as used herein refers to a DNA polynucleotide sequence that expresses an RNA (RNA is transcribed from the DNA polynucleotide sequence) from a coding region, which RNA can be a messenger RNA (encoding a protein) or a non-protein-coding RNA (e.g., a crRNA, tracrRNA, or gRNA herein). A gene may refer to the coding region alone, or may include regulatory sequences upstream and/or downstream to the coding region (e.g., promoters, 5'-untranslated regions, 3'-transcription terminator regions). A coding region encoding a protein can alternatively be referred to herein as an "open reading frame" (ORF). A gene that is "native" or "endogenous" refers to a gene as found in nature with its own regulatory sequences; such a gene is located in its natural location in the genome of a host cell. A "chimeric" gene refers to any gene that is not a native gene, comprising regulatory and coding sequences that are not found together in nature (i.e., the regulatory and coding regions are heterologous with each other). Accordingly, a chimeric gene may comprise regulatory sequences and coding sequences that are derived from different sources, or regulatory sequences and coding sequences derived from the same source, but arranged in a manner different than that found in nature. A "foreign" or "heterologous" gene refers to a gene that is introduced into the host organism by gene transfer. Foreign/heterologous genes can comprise native genes inserted into a non-native organism, native genes introduced into a new location within the native host, or chimeric genes. The polynucleotide sequences in certain embodiments disclosed herein are heterologous. A "transgene" is a gene that has been introduced into the genome by a gene delivery procedure (e.g., transformation). A "codon-optimized" open reading frame has its frequency of codon usage designed to mimic the frequency of preferred codon usage of the host cell.

A "mutated gene" is a gene that has been altered through human intervention. Such a "mutated gene" has a sequence that differs from the sequence of the corresponding non-mutated gene by at least one nucleotide addition, deletion, or substitution. In certain embodiments of the disclosure, the mutated gene comprises an alteration that is made by using a guide polynucleotide/Cas endonuclease system as disclosed herein. A mutated plant is a plant comprising at least one mutated gene.

A "non-native" amino acid sequence or polynucleotide sequence comprised in a cell or organism herein does not occur in a native (natural) counterpart of such cell or organism.

"Regulatory sequences" as used herein refer to nucleotide sequences located upstream of a gene's transcription start site (e.g., promoter), 5' untranslated regions, and 3' non-coding regions, and which may influence the transcription, processing or stability, or translation of an RNA transcribed from the gene. Regulatory sequences herein may include promoters, enhancers, silencers, 5' untranslated leader sequences, introns, polyadenylation recognition sequences, RNA processing sites, effector binding sites, stem-loop structures, and other elements involved in regulation of gene expression. One or more regulatory elements herein may be heterologous to a coding region herein.

A "promoter" as used herein refers to a DNA sequence capable of controlling the transcription of RNA from a gene. In general, a promoter sequence is upstream of the transcription start site of a gene. Promoters may be derived in their entirety from a native gene, or be composed of different elements derived from different promoters found in nature, or even comprise synthetic DNA segments. Promoters that cause a gene to be expressed in a cell at most times under all circumstances are commonly referred to as "constitutive promoters". One or more promoters herein may be heterologous to a coding region herein.

A "strong promoter" as used herein refers to a promoter that can direct a relatively large number of productive initiations per unit time, and/or is a promoter driving a higher level of gene transcription than the average transcription level of the genes in a cell.

A plant promoter is a promoter capable of initiating transcription in a plant cell; for a review of plant promoters, see Potenza et al., (2004) *In Vitro Cell Dev Biol* 40:1-22. Constitutive promoters include, for example, the core promoter of the Rsyn7 promoter and other constitutive promoters disclosed in WO99/43838 and U.S. Pat. No. 6,072,050; the core CaMV 35S promoter (Odell et al., (1985) *Nature* 313:810-2); rice actin (McElroy et al., (1990) *Plant Cell* 2:163-71); ubiquitin (Christensen et al., (1989) *Plant Mol Biol* 12:619-32; Christensen et al., (1992) *Plant Mol Biol* 18:675-89); pEMU (Last et al., (1991) *Theor Appl Genet* 81:581-8); MAS (Velten et al., (1984) *EMBO J* 3:2723-30); ALS promoter (U.S. Pat. No. 5,659,026), and the like. Other constitutive promoters are described in, for example, U.S. Pat. Nos. 5,608,149; 5,608,144; 5,604,121; 5,569,597; 5,466,785; 5,399,680; 5,268,463; 5,608,142 and 6,177,611. In some examples, an inducible promoter may be used.

Pathogen-inducible promoters induced following infection by a pathogen include, but are not limited to those regulating expression of PR proteins, SAR proteins, beta-1,3-glucanase, chitinase, etc.

Chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. Chemical-inducible promoters include, but are not limited to, the maize In2-2 promoter, activated by benzene sulfonamide herbicide safeners (De Veylder et al., (1997) *Plant Cell Physiol* 38:568-77), the maize GST promoter (GST-II-27, WO93/01294), activated by hydrophobic electrophilic compounds used as pre-emergent herbicides, and the tobacco PR-1a promoter (Ono et al., (2004) *Biosci Biotechnol Biochem* 68:803-7) activated by salicylic acid. Other chemical-regulated promoters include steroid-responsive promoters (see, for example, the glucocorticoid-inducible promoter (Schena et al., (1991) *Proc. Natl. Acad. Sci. USA* 88:10421-5; McNellis et al., (1998) *Plant J* 14:247-257); tetracycline-inducible and tetracycline-repressible promoters (Gatz et al., (1991) *Mol Gen Genet* 227:229-37; U.S. Pat. Nos. 5,814,618 and 5,789,156).

Tissue-preferred promoters can be utilized to target enhanced expression within a particular plant tissue. Tissue-preferred promoters include, for example, Kawamata et al., (1997) *Plant Cell Physiol* 38:792-803; Hansen et al., (1997) *Mol Gen Genet* 254:337-43; Russell et al., (1997) *Transgenic Res* 6:157-68; Rinehart et al., (1996) *Plant Physiol* 112:1331-41; Van Camp et al., (1996) *Plant Physiol* 112:525-35; Canevascini et al., (1996) *Plant Physiol* 112:513-524; Lam, (1994) *Results Probl Cell Differ* 20:181-96; and Guevara-Garcia et al., (1993) *Plant J* 4:495-505. Leaf-preferred promoters include, for example, Yamamoto et al., (1997) *Plant J* 12:255-65; Kwon et al., (1994) *Plant Physiol* 105:357-67; Yamamoto et al., (1994) *Plant Cell Physiol* 35:773-8; Gotor et al., (1993) *Plant J* 3:509-18; Orozco et al., (1993) *Plant Mol Biol* 23:1129-38; Matsuoka et al., (1993) *Proc. Natl. Acad. Sci. USA* 90:9586-90; Simpson et al., (1958) *EMBO J* 4:2723-9, Timko et al., (1988) *Nature* 318:57-8. Root-preferred promoters include, for example, Hire et al., (1992) *Plant Mol Biol* 20:207-18 (soybean root-specific glutamine synthase gene); Miao et al., (1991) *Plant Cell* 3:11-22 (cytosolic glutamine synthase (GS)); Keller and Baumgartner, (1991) *Plant Cell* 3:1051-61 (root-specific control element in the GRP 1.8 gene of French bean); Sanger et al., (1990) *Plant Mol Biol* 14:433-43 (root-specific promoter of *A. tumefaciens* mannopine synthase (MAS)); Bogusz et al., (1990) *Plant Cell* 2:633-41 (root-specific promoters isolated from *Parasponia andersonii* and *Trema tomentosa*); Leach and Aoyagi, (1991) *Plant Sci* 79:69-76 (*A. rhizogenes* rolC and rolD root-inducing genes); Teeri et al., (1989) *EMBO J* 8:343-50 (*Agrobacterium* wound-induced TR1' and TR2' genes); VfENOD-GRP3 gene promoter (Kuster et al., (1995) *Plant Mol Biol* 29:759-72); and rolB promoter (Capana et al., (1994) *Plant Mol Biol* 25:681-91; phaseolin gene (Murai et al., (1983) *Science* 23:476-82; Sengopta-Gopalen et al., (1988) *Proc. Natl. Acad. Sci. USA* 82:3320-4). See also, U.S. Pat. Nos. 5,837,876; 5,750,386; 5,633,363; 5,459,252; 5,401,836; 5,110,732 and 5,023,179.

Seed-preferred promoters include both seed-specific promoters active during seed development, as well as seed-germinating promoters active during seed germination. See, Thompson et al., (1989) *BioEssays* 10:108. Seed-preferred promoters include, but are not limited to, Cim1 (cytokinin-induced message); cZ19B1 (maize 19 kDa zein); and milps (myo-inositol-1-phosphate synthase); (WO00/11177; and U.S. Pat. No. 6,225,529). For dicots, seed-preferred promoters include, but are not limited to, bean beta-phaseolin, napin, beta-conglycinin, soybean lectin, cruciferin, and the like. For monocots, seed-preferred promoters include, but are not limited to, maize 15 kDa zein, 22 kDa zein, 27 kDa gamma zein, waxy, shrunken 1, shrunken 2, globulin 1, oleosin, and nuc1. See also, WO00/12733, where seed-preferred promoters from END1 and END2 genes are disclosed.

The terms "3' non-coding sequence", "transcription terminator" and "terminator" as used herein refer to DNA sequences located downstream of a coding sequence. This includes polyadenylation recognition sequences and other sequences encoding regulatory signals capable of affecting mRNA processing or gene expression.

The term "cassette" as used herein refers to a promoter operably linked to a DNA sequence encoding a protein-coding RNA or non-protein-coding RNA. A cassette may optionally be operably linked to a 3' non-coding sequence.

The terms "upstream" and "downstream" as used herein with respect to polynucleotides refer to "5' of" and "3' of", respectively.

The term "expression" as used herein refers to (i) transcription of RNA (e.g., mRNA or a non-protein coding RNA such as crRNA, tracrRNA, or gRNA) from a coding region, or (ii) translation of a polypeptide from mRNA.

When used to describe the expression of a gene or polynucleotide sequence, the terms "down-regulation", "disruption", "inhibition", "inactivation", and "silencing" are used interchangeably herein to refer to instances when the transcription of the polynucleotide sequence is reduced or eliminated. This results in the reduction or elimination of RNA transcripts from the polynucleotide sequence, which results in a reduction or elimination of protein expression derived from the polynucleotide sequence (if the gene comprised an ORF). Alternatively, down-regulation can refer to instances where protein translation from transcripts produced by the polynucleotide sequence is reduced or eliminated. Alternatively still, down-regulation can refer to instances where a protein expressed by the polynucleotide sequence has reduced activity. The reduction in any of the above processes (transcription, translation, protein activity) in a cell can be by about 20%, 30%, 40%, 50%, 60%, 70%, 80%, 90%, 95%, or 100% relative to the transcription, translation, or protein activity of a suitable control cell. Down-regulation can be the result of a targeting event as disclosed herein (e.g., indel, knock-out), for example.

The terms "control cell" and "suitable control cell" are used interchangeably herein and may be referenced with respect to a cell in which a particular modification (e.g., over-expression of a polynucleotide, down-regulation of a polynucleotide) has been made (i.e., an "experimental cell"). A control cell may be any cell that does not have or does not express the particular modification of the experimental cell. Thus, a control cell may be an untransformed wild type cell or may be genetically transformed but does not express the genetic transformation. For example, a control cell may be a direct parent of the experimental cell, which direct parent cell does not have the particular modification that is in the experimental cell. Alternatively, a control cell may be a parent of the experimental cell that is removed by one or more generations. Alternatively still, a control cell may be a sibling of the experimental cell, which sibling does not comprise the particular modification that is present in the experimental cell.

The term "increased" as used herein may refer to a quantity or activity that is at least about 1%, 2%, 3%, 4%, 5%, 6%, 7%, 8%, 9%, 10%, 11%, 12%, 13%, 14%, 15%, 16%, 17%, 18%, 19%, 20%, 50%, 100%, or 200% more than the quantity or activity for which the increased quantity or activity is being compared. The terms "increased", "elevated", "enhanced", "greater than", and "improved" are used interchangeably herein. The term "increased" can be used to characterize the expression of a polynucleotide encoding a protein, for example, where "increased expression" can also mean "over-expression".

The term "operably linked" as used herein refers to the association of two or more nucleic acid sequences such that that the function of one is affected by the other. For example, a promoter is operably linked with a coding sequence when it is capable of affecting the expression of that coding sequence. That is, the coding sequence is under the transcriptional control of the promoter. Coding sequences can be operably linked to regulatory sequences, for example. Also, for example, a crRNA can be operably linked (fused to) a tracrRNA herein such that the tracrRNA mate sequence of the crRNA anneals with 5' sequence of the tracrRNA. Such operable linkage may comprise a suitable loop-forming sequence such as GAAA (SEQ ID NO:36), CAAA (SEQ ID NO:37), or AAAG (SEQ ID NO:38). Also, for example, an RGEN can be operably linked (fused to) one or more CPPs.

The term "recombinant" as used herein refers to an artificial combination of two otherwise separated segments of sequence, e.g., by chemical synthesis or by the manipulation of isolated segments of nucleic acids by genetic engineering techniques.

Methods for preparing recombinant constructs/vectors herein (e.g., a DNA polynucleotide encoding an RNA component cassette herein, or a DNA polynucleotide encoding a Cas protein or Cas-CPP fusion protein herein) can follow standard recombinant DNA and molecular cloning techniques as described by J. Sambrook and D. Russell (*Molecular Cloning: A Laboratory Manual*, 3rd Edition, Cold Spring Harbor Laboratory Press, Cold Spring Harbor, N.Y., 2001); T. J. Silhavy et al. (*Experiments with Gene Fusions*, Cold Spring Harbor Laboratory Press, Cold Spring Harbor, N Y, 1984); and F. M. Ausubel et al. (*Short Protocols in Molecular Biology*, 5th Ed. Current Protocols, John Wiley and Sons, Inc., NY, 2002), for example.

The term "transformation" as used herein refers to the transfer of a nucleic acid molecule into a host organism or host cell by any method. A nucleic acid molecule that has been transformed into an organism/cell may be one that replicates autonomously in the organism/cell, or that integrates into the genome of the organism/cell, or that exists transiently in the cell without replicating or integrating. Non-limiting examples of nucleic acid molecules suitable for transformation are disclosed herein, such as plasmids and linear DNA molecules.

A "transgenic plant" herein includes, for example, a plant which comprises within its genome a heterologous polynucleotide introduced by a transformation step. The heterologous polynucleotide can be stably integrated within the genome such that the polynucleotide is passed on to successive generations. The heterologous polynucleotide may be integrated into the genome alone or as part of a recombinant DNA construct. A transgenic plant can also comprise more than one heterologous polynucleotide within its genome. Each heterologous polynucleotide may confer a different trait to the transgenic plant. Transgenic plant material can include any cell, cell line, callus, tissue, plant part or plant, the genotype of which has been altered by the presence of heterologous nucleic acid including those transgenics initially so altered as well as those created by sexual crosses or asexual propagation from the initial transgenic. The alterations of the genome (chromosomal or extra-chromosomal) by conventional plant breeding methods, by genome editing procedures that does not result in an insertion of a foreign polynucleotide, or by naturally occurring events such as random cross-fertilization, non-recombinant viral infection, non-recombinant bacterial transformation, non-recombinant transposition, or spontaneous mutation are not intended to be regarded as transgenic.

A "phenotypic marker" is a screenable or selectable marker that includes visual markers and selectable markers whether it is a positive or negative selectable marker. Any phenotypic marker can be used. Specifically, a selectable or screenable marker comprises a DNA segment that allows one to identify, or select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products which provide resistance against otherwise toxic compounds including antibiotics, such as, spectinomycin, ampicillin, kanamycin, tetracycline, Basta, neomycin phosphotransferase II (NEO) and hygromycin phosphotransferase (HPT); DNA segments that encode products which are otherwise lacking in the recipient cell (e.g., tRNA genes, auxotrophic markers); DNA segments that encode products which can be readily identified (e.g., phenotypic markers such as beta-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Additional selectable markers include genes that confer resistance to herbicidal compounds, such as glufosinate ammonium, bromoxynil, imidazolinones, and 2,4-dichloro-phenoxyacetate (2,4-D). See for example, Yarranton, (1992) *Curr Opin Biotech* 3:506-11; Christopherson et al., (1992) *Proc. Natl. Acad. Sci. USA* 89:6314-8; Yao et al., (1992) *Cell* 71:63-72; Reznikoff, (1992) *Mol Microbiol* 6:2419-22; Hu et al., (1987) *Cell* 48:555-66; Brown et al., (1987) *Cell* 49:603-12; Figge et al., (1988) *Cell* 52:713-22; Deuschle et al., (1989) *Proc. Natl. Acad. Sci. USA* 86:5400-4; Fuerst et al., (1989) *Proc. Natl. Acad. Sci. USA* 86:2549-53; Deuschle et al., (1990) *Science* 248:480-3; Gossen, (1993) Ph.D. Thesis, University of Heidelberg; Reines et al., (1993) *Proc. Natl. Acad. Sci. USA* 90:1917-21; Labow et al., (1990) *Mol Cell Biol* 10:3343-56; Zambretti et al., (1992) *Proc. Natl. Acad. Sci. USA* 89:3952-6; Baim et al., (1991) *Proc. Natl. Acad. Sci. USA* 88:5072-6; Wyborski et al., (1991) *Nucleic Acids Res* 19:4647-53; Hillen and Wissman, (1989) *Topics Mol Struc Biol* 10:143-62; Degenkolb et al., (1991) *Antimicrob Agents Chemother* 35:1591-5; Kleinschnidt et al., (1988) *Biochemistry* 27:1094-104; Bonin, (1993) Ph.D. Thesis, University of Heidelberg; Gossen et al., (1992) *Proc. Natl. Acad. Sci. USA* 89:5547-51; Oliva et al., (1992) *Antimicrob Agents Chemother* 36:913-9; Hlavka et al., (1985) *Handbook of Experimental Pharmacology*, Vol. 78 (Springer-Verlag, Berlin); Gill et al., (1988) *Nature* 334:721-4.

The terms "sequence identity" or "identity" as used herein with respect to polynucleotide or polypeptide sequences refer to the nucleic acid residues or amino acid residues in two sequences that are the same when aligned for maximum correspondence over a specified comparison window. Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. It would be understood that, when calculating sequence identity between a DNA sequence and an RNA sequence, T residues of the DNA sequence align with, and can be considered "identical" with, U residues of the RNA sequence. For purposes of determining percent complementarity of first and second polynucleotides, one can obtain this by determining (i) the percent identity between the first polynucleotide and the complement sequence of the second polynucleotide (or vice versa), for example, and/or (ii) the percentage of bases between the first and second polynucleotides that would create canonical Watson and Crick base pairs.

The Basic Local Alignment Search Tool (BLAST) algorithm, which is available online at the National Center for Biotechnology Information (NCBI) website, may be used, for example, to measure percent identity between or among two or more of the polynucleotide sequences (BLASTN algorithm) or polypeptide sequences (BLASTP algorithm) disclosed herein. Alternatively, percent identity between sequences may be performed using a Clustal algorithm (e.g., ClustalW or ClustalV). For multiple alignments using a Clustal method of alignment, the default values may correspond to GAP PENALTY=10 and GAP LENGTH PENALTY=10. Default parameters for pairwise alignments and calculation of percent identity of protein sequences using a Clustal method may be KTUPLE=1, GAP PENALTY=3, WINDOW=5 and DIAGONALS SAVED=5. For nucleic acids, these parameters may be KTUPLE=2, GAP PENALTY=5, WINDOW=4 and DIAGONALS SAVED=4. Alternatively still, percent identity between sequences may be performed using an EMBOSS algorithm (e.g., needle) with parameters such as GAP OPEN=10, GAP EXTEND=0.5, END GAP PENALTY=false, END GAP OPEN=10, END GAP EXTEND=0.5 using a BLOSUM matrix (e.g., BLOSUM62).

Herein, a first sequence that is "complementary" to a second sequence can alternatively be referred to as being in the "antisense" orientation with the second sequence.

Various polypeptide amino acid sequences and polynucleotide sequences are disclosed herein as features of certain embodiments of the disclosed invention. Variants of these sequences that are at least about 70-85%, 85-90%, or 90%-95% identical to the sequences disclosed herein can be used. Alternatively, a variant amino acid sequence or polynucleotide sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence has the same function/activity of the disclosed sequence, or at least about 80%, 81%, 82%, 83%, 84%, 85%, 86%, 87%, 88%, 89%, 90%, 91%, 92%, 93%, 94%, 95%, 96%, 97%, 98%, or 99% of the function/activity of the disclosed sequence.

All the amino acid residues disclosed herein at each amino acid position of Cas9 proteins herein are examples. Given that certain amino acids share similar structural and/or charge features with each other (i.e., conserved), the amino acid at each position in a Cas9 can be as provided in the disclosed sequences or substituted with a conserved amino acid residue ("conservative amino acid substitution") as follows:

1. The following small aliphatic, nonpolar or slightly polar residues can substitute for each other: Ala (A), Ser (S), Thr (T), Pro (P), Gly (G);
2. The following polar, negatively charged residues and their amides can substitute for each other: Asp (D), Asn (N), Glu (E), Gln (Q);
3. The following polar, positively charged residues can substitute for each other: His (H), Arg (R), Lys (K);
4. The following aliphatic, nonpolar residues can substitute for each other: Ala (A), Leu (L), Ile (I), Val (V), Cys (C), Met (M); and
5. The following large aromatic residues can substitute for each other: Phe (F), Tyr (Y), Trp (W).

Advances have been made in expressing protein and RNA components in cells for performing RGEN-mediated DNA targeting therein (e.g., WO2015/026883, published Feb. 26, 2015 and WO2016/025131, published Feb. 18, 2016). Such strategies typically have entailed recombinant DNA expression in the target cells. Additional means of providing protein and RNA components in a cell to mediate RGEN-mediated DNA targeting are of interest.

Embodiments of the disclosed invention concern a composition comprising at least one protein component of an RNA-guided endonuclease (RGEN) and at least one cell-penetrating peptide (CPP), wherein the RGEN protein component and CPP are covalently or non-covalently linked to each other in an RGEN protein-CPP complex. The RGEN protein-CPP complex can traverse (i) a cell membrane, or (ii) a cell wall and cell membrane, of a cell.

Significantly, certain embodiments of the disclosed invention can be used to deliver an RGEN already associated (pre-associated) with an RNA component into a cell. Such embodiments may avoid the need to deliver a DNA construct into cells for expressing an RGEN RNA component, thus averting any potentially unwanted effects of introducing exogenous DNA into cells. The disclosed invention is flexible, however, since in certain other embodiments an RNA component can be provided (e.g., expressed) in a cell into which an RGEN protein-CPP complex is being delivered. An RNA component provided in this manner can associate with an RGEN protein component after delivery/entry of the RGEN protein-CPP complex into the cell. Regardless of the mode of RNA component delivery, an RGEN protein-CPP complex herein is able to associate with an RNA component, forming an RGEN-CPP complex that can target a specific DNA sequence in the cell. Thus, the disclosed invention offers substantial flexibility for providing an RGEN in cells to perform RGEN-mediated DNA targeting.

Compositions disclosed in certain embodiments comprise at least one protein component of an RGEN. An RGEN herein refers to a complex comprising at least one Cas protein and at least one RNA component. Thus, an RGEN protein component can refer to a Cas protein such as Cas9. Examples of suitable Cas proteins include one or more Cas endonucleases of type I, II, or III CRISPR systems (Bhaya et al., *Annu. Rev. Genet.* 45:273-297, incorporated herein by reference). A type I CRISPR Cas protein can be a Cas3 or Cas4 protein, for example. A type II CRISPR Cas protein can be a Cas9 protein, for example. A type III CRISPR Cas protein can be a Cas10 protein, for example. A Cas9 protein is used in certain preferred embodiments. A Cas protein in certain embodiments may be a bacterial or archaeal protein. Type I-III CRISPR Cas proteins herein are typically prokaryotic in origin; type I and III Cas proteins can be derived from bacterial or archaeal species, whereas type II Cas proteins (i.e., a Cas9) can be derived from bacterial species, for example. In other embodiments, suitable Cas proteins include one or more of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof.

In other aspects of the disclosed invention, a Cas protein herein can be from any of the following genera: *Aeropyrum, Pyrobaculum, Sulfolobus, Archaeoglobus, Haloarcula, Methanobacteriumn, Methanococcus, Methanosarcina, Methanopyrus, Pyrococcus, Picrophilus, Thernioplasnia, Corynebacterium, Mycobacterium, Streptomyces, Aquifrx, Porphyromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myrococcus, Campylobacter, Wolinella, Acinetobacter, Erwinia, Escherichia, Legionella, Methylococcus, Pasteurella, Photobacterium, Salmonella, Xanthomonas, Yersinia, Streptococcus, Treponema, Francisella,* or *Thermotoga*. Alternatively, a Cas protein herein can be encoded, for example, by any of SEQ ID NOs:462-465, 467-472, 474-477, 479-487, 489-492, 494-497, 499-503, 505-508, 510-516, or 517-521 as disclosed in U.S. Appl. Publ. No. 2010/0093617, which is incorporated herein by reference.

An RGEN protein component can comprise a Cas9 amino acid sequence, for example. An RGEN comprising this type of protein component typically can be characterized as having Cas9 as the endonuclease component of the RGEN. The amino acid sequence of a Cas9 protein herein, as well as certain other Cas proteins herein, may be derived from a *Streptococcus* (e.g., *S. pyogenes, S. pneumoniae, S. thermophilus, S. agalactiae, S. parasanguinis, S. oralis, S. salivarius, S. macacae, S. dysgalactiae, S. anginosus, S. constellatus, S. pseudoporcinus, S. mutans*), *Listeria* (e.g., *L. innocua*), *Spiroplasma* (e.g., *S. apis, S. syrphidicola*), *Peptostreptococcaceae, Atopobium, Porphyromonas* (e.g., *P. catoniae*), *Prevotella* (e.g., *P. intermedia*), *Veillonella, Treponema* (e.g., *T. socranskii, T. denticola*), *Capnocytophaga, Finegoldia* (e.g., *F. magna*), Coriobacteriaceae (e.g., *C. bacterium*), *Olsenella* (e.g., *O. profusa*), *Haemophilus* (e.g., *H. sputorum, H. pittmaniae*), *Pasteurella* (e.g., *P. bettyae*), *Olivibacter* (e.g., *O. sitiensis*), *Epilithonimonas* (e.g., *E. tenax*), *Mesonia* (e.g., *M. mobilis*), *Lactobacillus, Bacillus* (e.g., *B. cereus*), *Aquimarina* (e.g., *A. muellen*), *Chryseobacterium* (e.g., *C. palustre*), *Bacteroides* (e.g., *B. graminisolvens*), *Neisseria* (e.g., *N. meningitidis*), *Franci-* sella (e.g., *F. novicida*), or *Flavobacterium* (e.g., *F. frigidarium, F. soli*) species, for example. An *S. pyogenes* Cas9 is preferred in certain aspects herein. As another example, a Cas9 protein can be any of the Cas9 proteins disclosed in Chylinski et al. (*RNA Biology* 10:726-737), which is incorporated herein by reference.

Accordingly, the sequence of a Cas9 protein herein can comprise, for example, any of the Cas9 amino acid sequences disclosed in GenBank Accession Nos. G3ECR1 (*S. thermophilus*), WP_026709422, WP_027202655, WP_027318179, WP_027347504, WP_027376815, WP_027414302, WP_027821588, WP_027886314, WP_027963583, WP_028123848, WP_028298935, Q03JI6 (*S. thermophilus*), EGP66723, EGS38969, EGV05092, EHI65578 (*S. pseudoporcinus*), EIC75614 (*S. oralis*), EID22027 (*S. constellatus*), EIJ69711, EJP22331 (*S. oralis*), EJP26004 (*S. anginosus*), EJP30321, EPZ44001 (*S. pyogenes*), EPZ46028 (*S. pyogenes*), EQL78043 (*S. pyogenes*), EQL78548 (*S. pyogenes*), ERL10511, ERL12345, ERL19088 (*S. pyogenes*), ESA57807 (*S. pyogenes*), ESA59254 (*S. pyogenes*), ESU85303 (*S. pyogenes*), ETS96804, UC75522, EGR87316 (*S. dysgalactiae*), EGS33732, EGV01468 (*S. oralis*), EHJ52063 (*S. macacae*), EID26207 (*S. oralis*), EID33364, EIG27013 (*S. parasanguinis*), EJF37476, EJO19166 (*Streptococcus* sp. BS35b), EJU16049, EJU32481, YP_006298249, ERF61304, ERK04546, ETJ95568 (*S. agalactiae*), TS89875, ETS90967 (*Streptococcus* sp. SR4), ETS92439, EUB27844 (*Streptococcus* sp. BS21), AFJ08616, EUC82735 (*Streptococcus* sp. CM6), EWC92088, EWC94390, EJP25691, YP_008027038, YP_008868573, AGM26527, AHK22391, AHB36273, Q927P4, G3ECR1, or Q99ZW2 (*S. pyogenes*), which are incorporated by reference. A variant of any of these Cas9 protein sequences may be used, but should have specific binding activity, and optionally cleavage or nicking activity, toward DNA when associated with an RNA component herein. Such a variant may comprise an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of the reference Cas9.

Alternatively, a Cas9 protein herein can be encoded by any of SEQ ID NOs:462 (*S. thermophilus*), 474 (*S. thermophilus*), 489 (*S. agalactiae*), 494 (*S. agalactiae*), 499 (*S. mutans*), 505 (*S. pyogenes*), or 518 (*S. pyogenes*) as disclosed in U.S. Appl. Publ. No. 2010/0093617 (incorporated herein by reference), for example. Alternatively still, a Cas9 protein herein can comprise the amino acid sequence of SEQ ID NO:3, or residues 1-1368, 2-1368, or 2-1379, of SEQ ID NO:3, for example. Alternatively still, a Cas9 protein may comprise an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to any of the foregoing amino acid sequences, for example. Such a variant Cas9 protein should have specific binding activity, and optionally cleavage or nicking activity, toward DNA when associated with an RNA component herein.

The origin of a Cas protein used herein (e.g., Cas9) may be from the same species from which the RNA component(s) is derived, or it can be from a different species. For example, an RGEN comprising a Cas9 protein derived from a *Streptococcus* species (e.g., *S. pyogenes* or *S. thermophilus*) may be complexed with at least one RNA component having a sequence (e.g., crRNA repeat sequence, tracrRNA sequence) derived from the same *Streptococcus* species. Alternatively, the origin of a Cas protein used herein (e.g., Cas9) may be from a different species from which the RNA component(s) is derived (the Cas protein and RNA component(s) may be heterologous to each other); such heterologous Cas/RNA component RGENs should have DNA targeting activity.

Determining binding activity and/or endonucleolytic activity of a Cas protein herein toward a specific target DNA sequence may be assessed by any suitable assay known in the art, such as disclosed in U.S. Pat. No. 8,697,359, which is disclosed herein by reference. A determination can be made, for example, by expressing a Cas protein and suitable RNA component in a cell, and then examining the predicted DNA target site for the presence of an indel (a Cas protein in this particular assay would typically have complete endonucleolytic activity [double-strand cleaving activity]). Examining for the presence of an alteration/modification (e.g., indel) at the predicted target site could be done via a DNA sequencing method or by inferring alteration/modification formation by assaying for loss of function of the target sequence, for example. In another example, Cas protein activity can be determined by expressing a Cas protein and suitable RNA component in a cell that has been provided a donor DNA comprising a sequence homologous to a sequence in at or near the target site. The presence of donor DNA sequence at the target site (such as would be predicted by successful HR between the donor and target sequences) would indicate that targeting occurred. In still another example, Cas protein activity can be determined using an in vitro assay in which a Cas protein and suitable RNA component are mixed together along with a DNA polynucleotide containing a suitable target sequence. This assay can be used to detect binding (e.g., gel-shift) by Cas proteins lacking cleavage activity, or cleavage by Cas proteins that are endonucleolytically competent.

A Cas protein herein such as a Cas9 can further comprise a heterologous nuclear localization sequence (NLS) in certain aspects. A heterologous NLS amino acid sequence herein may be of sufficient strength to drive accumulation of a Cas protein, or Cas protein-CPP complex, in a detectable amount in the nucleus of a cell herein, for example. An NLS may comprise one (monopartite) or more (e.g., bipartite) short sequences (e.g., 2 to 20 residues) of basic, positively charged residues (e.g., lysine and/or arginine), and can be located anywhere in a Cas amino acid sequence but such that it is exposed on the protein surface. An NLS may be operably linked to the N-terminus or C-terminus of a Cas protein herein, for example. Two or more NLS sequences can be linked to a Cas protein, for example, such as on both the N- and C-termini of a Cas protein. Non-limiting examples of suitable NLS sequences herein include those disclosed in U.S. Pat. Nos. 6,660,830 and 7,309,576 (e.g., Table 1 therein), which are both incorporated herein by reference. Another example of an NLS useful herein includes amino acid residues 1373-1379 of SEQ ID NO:3. A Cas protein as disclosed herein can be fused with a CPP (an example of a Cas protein covalently linked to a CPP), for example. It would be understood that such a Cas-CPP fusion protein can also comprise an NLS as described above. It would also be understood that, in embodiments in which a Cas protein is fused with an amino acid sequence targeting a different organelle (e.g., mitochondria), such a Cas protein typically would not contain an NLS.

In certain embodiments, a Cas protein and its respective RNA component (e.g., crRNA) that directs DNA-specific targeting by the Cas protein can be heterologous to a cell, in particular a non-prokaryotic cell. The heterologous nature of these RGEN components is due to that Cas proteins and their respective RNA components are only known to exist in prokaryotes (bacteria and archaea).

In some embodiments, a Cas protein is part of a fusion protein comprising one or more heterologous protein domains (e.g., 1, 2, 3, or more domains in addition to the Cas protein). These embodiments can encompass a Cas protein that is covalently linked to a CPP and one or more additional heterologous amino acid sequences, for example. Other embodiments can encompass a Cas protein that is covalently linked to one or more additional heterologous amino acid sequences not including a CPP, for example (a CPP would be non-covalently linked to a Cas fusion protein in such embodiments). A fusion protein comprising a Cas protein may comprise any additional protein sequence, and optionally a linker sequence between any two domains, such as between Cas and a first heterologous domain. Examples of protein domains that may be fused to a Cas protein herein include, without limitation, epitope tags (e.g., histidine [His, poly-histidine], V5, FLAG, influenza hemagglutinin [HA], myc, VSV-G, thioredoxin [Trx]), reporters (e.g., glutathione-5-transferase [GST], horseradish peroxidase [HRP], chloramphenicol acetyltransferase [CAT], beta-galactosidase, beta-glucuronidase [GUS], luciferase, green fluorescent protein [GFP], HcRed, DsRed, cyan fluorescent protein [CFP], yellow fluorescent protein [YFP], blue fluorescent protein [BFP]), and domains having one or more of the following activities: methylase activity, demethylase activity, transcription activation activity (e.g., VP16 or VP64), transcription repression activity, transcription release factor activity, histone modification activity, RNA cleavage activity and nucleic acid binding activity. A Cas protein in other embodiments may be in fusion with a protein that binds DNA molecules or other molecules, such as maltose binding protein (MBP), S-tag, Lex A DNA binding domain (DBD), GAL4A DNA binding domain, and herpes simplex virus (HSV) VP16. Additional domains that may be part of a fusion protein comprising a Cas protein herein are disclosed in U.S. Patent Appl. Publ. No. 2011/0059502, which is incorporated herein by reference. In certain embodiments in which a Cas protein is fused to a heterologous protein (e.g., a transcription factor), the Cas protein has DNA recognition and binding activity (when in complex with a suitable RNA component herein), but no DNA nicking or cleavage activity. A Cas protein as disclosed herein can be fused with a CPP (an example of a Cas protein covalently linked to a CPP), for example. It would be understood that such a Cas-CPP fusion protein can also be fused with one or more heterologous domains as described above, if desired.

Other examples of heterologous domains that can be linked to a Cas protein herein include amino acid sequences targeting the protein to a particular organelle (i.e., localization signal). Examples of organelles that can be targeted include mitochondria and chloroplasts. Typically, such targeting domains are used instead of an NLS when targeting extra-nuclear DNA sites. A mitochondrial targeting sequence (MTS) can be situated at or near the N-terminus of a Cas protein, for example. MTS examples are disclosed in U.S. Patent Appl. Publ. Nos. 2007/0011759 and 2014/0135275, which are incorporated herein by reference. A chloroplast targeting sequence can be as disclosed in U.S. Patent Appl. Publ. No. 2010/0192262 or 2012/0042412, for example, which are incorporated herein by reference.

The protein component of an RGEN can be associated with at least one RNA component (thereby constituting a complete RGEN) that comprises a sequence complementary to a target site sequence on a chromosome or episome in a cell, for example. The RGEN in such embodiments can bind to the target site sequence, and optionally cleave one or both DNA strands at the target site sequence. An RGEN can cleave one or both strands of a DNA target sequence, for example. An RGEN can cleave both strands of a DNA target sequence in another example. It would be understood that in all these embodiments, an RGEN protein component can be covalently or non-covalently linked to at least one CPP in an RGEN protein-CPP complex. The association of an RGEN protein-CPP complex with an RNA component herein can be characterized as forming an RGEN-CPP complex. Any disclosure herein regarding an RGEN can likewise apply to the RGEN component of an RGEN-CPP complex, unless otherwise noted.

An RGEN herein that can cleave both strands of a DNA target sequence typically comprises a Cas protein that has all of its endonuclease domains in a functional state (e.g., wild type endonuclease domains or variants thereof retaining some or all activity in each endonuclease domain). Thus, a wild type Cas protein (e.g., a Cas9 protein disclosed herein), or a variant thereof retaining some or all activity in each endonuclease domain of the Cas protein, is a suitable example of an RGEN that can cleave both strands of a DNA target sequence. A Cas9 protein comprising functional RuvC and HNH nuclease domains is an example of a Cas protein that can cleave both strands of a DNA target sequence. An RGEN herein that can cleave both strands of a DNA target sequence typically cuts both strands at the same position such that blunt-ends (i.e., no nucleotide overhangs) are formed at the cut site.

An RGEN herein that can cleave one strand of a DNA target sequence can be characterized herein as having nickase activity (e.g., partial cleaving capability). A Cas nickase (e.g., Cas9 nickase) herein typically comprises one functional endonuclease domain that allows the Cas to cleave only one strand (i.e., make a nick) of a DNA target sequence. For example, a Cas9 nickase may comprise (i) a mutant, dysfunctional RuvC domain and (ii) a functional HNH domain (e.g., wild type HNH domain). As another example, a Cas9 nickase may comprise (i) a functional RuvC domain (e.g., wild type RuvC domain) and (ii) a mutant, dysfunctional HNH domain.

Non-limiting examples of Cas9 nickases suitable for use herein are disclosed by Gasiunas et al. (*Proc. Natl. Acad. Sci. U.S.A.* 109:E2579-E2586), Jinek et al. (*Science* 337:816-821), Sapranauskas et al. (*Nucleic Acids Res.* 39:9275-9282) and in U.S. Patent Appl. Publ. No. 2014/0189896, which are incorporated herein by reference. For example, a Cas9 nickase herein can comprise an *S. thermophilus* Cas9 having an Asp-31 substitution (e.g., Asp-31-Ala) (an example of a mutant RuvC domain), or a His-865 substitution (e.g., His-865-Ala), Asn-882 substitution (e.g., Asn-882-Ala), or Asn-891 substitution (e.g., Asn-891-Ala) (examples of mutant HNH domains). Also for example, a Cas9 nickase herein can comprise an *S. pyogenes* Cas9 having an Asp-10 substitution (e.g., Asp-10-Ala), Glu-762 substitution (e.g., Glu-762-Ala), or Asp-986 substitution (e.g., Asp-986-Ala) (examples of mutant RuvC domains), or a His-840 substitution (e.g., His-840-Ala), Asn-854 substitution (e.g., Asn-854-Ala), or Asn-863 substitution (e.g., Asn-863-Ala) (examples of mutant HNH domains). Regarding *S. pyogenes* Cas9, the three RuvC subdomains are generally located at amino acid residues 1-59, 718-769 and 909-1098, respectively, and the HNH domain is located at amino acid residues 775-908 (Nishimasu et al., *Cell* 156:935-949).

A Cas9 nickase herein can be used for various purposes in cells, if desired. For example, a Cas9 nickase can be used to stimulate HR at or near a DNA target site sequence with a suitable donor polynucleotide. Since nicked DNA is not a substrate for NHEJ processes, but is recognized by HR processes, nicking DNA at a specific target site should render the site more receptive to HR with a suitable donor polynucleotide.

As another example, a pair of Cas9 nickases can be used to increase the specificity of DNA targeting. In general, this can be done by providing two Cas9 nickases that, by virtue of being associated with RNA components with different guide sequences, target and nick nearby DNA sequences on opposite strands in the region for desired targeting. Such nearby cleavage of each DNA strand creates a DSB (i.e., a DSB with single-stranded overhangs), which is then recognized as a substrate for NHEJ (leading to indel formation) or HR (leading to recombination with a suitable donor polynucleotide, if provided). Each nick in these embodiments can be at least about 5, 10, 15, 20, 30, 40, 50, 60, 70, 80, 90, or 100 (or any integer between 5 and 100) bases apart from each other, for example. One or two Cas9 nickase proteins herein can be used in a Cas9 nickase pair as described above. For example, a Cas9 nickase with a mutant RuvC domain, but functioning HNH domain (i.e., Cas9 HNH$^+$/RuvC$^-$), could be used (e.g., *S. pyogenes* Cas9 HNH$^+$/RuvC$^-$). Each Cas9 nickase (e.g., Cas9 HNH$^+$/RuvC$^-$) would be directed to specific DNA sites nearby each other (up to 100 base pairs apart) by using suitable RNA components herein with guide RNA sequences targeting each nickase to each specific DNA site.

An RGEN in certain embodiments can bind to a DNA target site sequence, but does not cleave any strand at the target site sequence. Such an RGEN may comprise a Cas protein in which all of its nuclease domains are mutant, dysfunctional. For example, a Cas9 protein herein that can bind to a DNA target site sequence, but does not cleave any strand at the target site sequence, may comprise both a mutant, dysfunctional RuvC domain and a mutant, dysfunctional HNH domain. Non-limiting examples of such a Cas9 protein comprise any of the RuvC and HNH nuclease domain mutations disclosed above (e.g., an *S. pyogenes* Cas9 with an Asp-10 substitution such as Asp-10-Ala and a His-840 substitution such as His-840-Ala). A Cas protein herein that binds, but does not cleave, a target DNA sequence can be used to modulate gene expression, for example, in which case the Cas protein could be fused with a transcription factor (or portion thereof) (e.g., a repressor or activator, such as any of those disclosed herein). For example, a Cas9 comprising an *S. pyogenes* Cas9 with an Asp-10 substitution (e.g., Asp-10-Ala) and a His-840 substitution (e.g., His-840-Ala) can be fused to a VP16 or VP64 transcriptional activator domain. The guide sequence used in the RNA component of such an RGEN would be complementary to a DNA sequence in a gene promoter or other regulatory element (e.g., intron), for example.

An RGEN herein can bind to a target site sequence, and optionally cleave one or both strands of the target site sequence, in a chromosome, episome, or any other DNA molecule in the genome of a cell. This recognition and binding of a target sequence is specific, given that an RNA component of the RGEN comprises a sequence (guide sequence) that is complementary to a strand of the target sequence. A target site in certain embodiments can be unique (i.e., there is a single occurrence of the target site sequence in the subject genome).

The length of a target sequence herein can be at least 13, 14, 15, 16, 17, 18, 19, 20, 21, 22, 23, 24, 25, 26, 27, 28, 29, or 30 nucleotides; between 13-30 nucleotides; between 17-25 nucleotides; or between 17-20 nucleotides, for example. This length can include or exclude a PAM sequence. Also, a strand of a target sequence herein has sufficient complementarity with a guide sequence (of a crRNA or gRNA) to hybridize with the guide sequence and direct sequence-specific binding of a Cas protein or Cas protein complex to the target sequence (if a suitable PAM is adjacent to the target sequence, see below). The degree of complementarity between a guide sequence and a strand of its corresponding DNA target sequence is at least about 90%, 91%, 92%, 93%, 94%, 95%, 96%, 97%, 98%, 99%, or 100%, for example. A target site herein may be located in a sequence encoding a gene product (e.g., a protein or an RNA) or a non-coding sequence (e.g., a regulatory sequence or a "junk" sequence), for example.

A PAM (protospacer-adjacent motif) sequence may be adjacent to the target site sequence. A PAM sequence is a short DNA sequence recognized by an RGEN herein. The associated PAM and first 11 nucleotides of a DNA target sequence are likely important to Cas9/gRNA targeting and cleavage (Jiang et al., Nat. Biotech. 31:233-239). The length of a PAM sequence herein can vary depending on the Cas protein or Cas protein complex used, but is typically 2, 3, 4, 5, 6, 7, or 8 nucleotides long, for example. A PAM sequence is immediately downstream from, or within 2, or 3 nucleotides downstream of, a target site sequence that is complementary to the strand in the target site that is in turn complementary to an RNA component guide sequence, for example. In embodiments herein in which an RGEN is an endonucleolytically active Cas9 protein complexed with an RNA component, Cas9 binds to the target sequence as directed by the RNA component and cleaves both strands immediately 5' of the third nucleotide position upstream of the PAM sequence. Consider the following example of a target site:PAM sequence:

(SEQ ID NO: 43)
5'-NNNNNNNNNNNNNNNNNNNN<u>N</u>NN<u>XGG</u>-3'.

N can be A, C, T, or G, and X can be A, C, T, or G in this example sequence (X can also be referred to as $N_{PAM}$). The PAM sequence in this example is XGG (underlined). A suitable Cas9/RNA component complex would cleave this target immediately 5' of the double-underlined N. The string of N's in SEQ ID NO:43) represents target sequence that is at least about 90%, 91%, 92%, 93%, 94%, 95%, 96%, 97%, 98%, 99%, or 100% identical, for example, with a guide sequence in an RNA component herein (where any T's of the DNA target sequence would align with any U's of the RNA guide sequence). A guide sequence of an RNA component of a Cas9 complex, in recognizing and binding at this target sequence (which is representative of target sites herein), would anneal with the complement sequence of the string of N's; the percent complementarity between a guide sequence and the target site complement is at least about 90%, 91%, 92%, 93%, 94%, 95%, 96%, 97%, 98%, 99%, or 100%, for example. If a Cas9 nickase is used to target SEQ ID NO:43) in a genome, the nickase would nick immediately 5' of the double-underlined N or at the same position of the complementary strand, depending on which endonuclease domain in the nickase is dysfunctional. If a Cas9 having no nucleolytic activity (both RuvC and HNH domains dysfuntional) is used to target SEQ ID NO:43 in a genome, it would recognize and bind the target sequence, but not make any cuts to the sequence.

A PAM herein is typically selected in view of the type of RGEN being employed. A PAM sequence herein may be one recognized by an RGEN comprising a Cas, such as Cas9, derived from any of the species disclosed herein from which a Cas can be derived, for example. In certain embodiments, the PAM sequence may be one recognized by an RGEN comprising a Cas9 derived from S. pyogenes, S. thermophilus, S. agalactiae, N. meningitidis, T. denticola, or F. novicida. For example, a suitable Cas9 derived from S. pyogenes could be used to target genomic sequences having a PAM sequence of NGG (SEQ ID NO:44; N can be A, C, T, or G). As other examples, a suitable Cas9 could be derived from any of the following species when targeting DNA sequences having the following PAM sequences: S. thermophilus (NNAGAA [SEQ ID NO:45]), S. agalactiae (NGG [SEQ ID NO:44]), NNAGAAW [SEQ ID NO:46, W is A or T], NGGNG [SEQ ID NO:47]), N. meningitidis (NNNNGATT [SEQ ID NO:48]), T. denticola (NAAAAC [SEQ ID NO:49]), or F. novicida (NG [SEQ ID NO:50]) (where N's in all these particular PAM sequences are A, C, T, or G). Other examples of Cas9/PAMs useful herein include those disclosed in Shah et al. (*RNA Biology* 10:891-899) and Esvelt et al. (*Nature Methods* 10:1116-1121), which are incorporated herein by reference. Examples of target sequences herein follow SEQ ID NO:43, but with the 'XGG' PAM replaced by any one of the foregoing PAMs.

An RNA component herein can comprise a sequence complementary to a target site sequence in a chromosome or episome in a cell. An RGEN can specifically bind to a target site sequence, and optionally cleave one or both strands of the target site sequence, based on this sequence complementary. Thus, the complementary sequence of an RNA component in certain embodiments of the disclosed invention can also be referred to as a guide sequence or variable targeting domain.

The guide sequence of an RNA component (e.g., crRNA or gRNA) herein can be at least 13, 14, 15, 16, 17, 18, 19, 20, 21, 22, 23, 24, 25, 26, 27, 28, 29, or 30 ribonucleotides in length; between 13-30 ribonucleotides in length; between 17-25 ribonucleotides in length; or between 17-20 ribonucleotides in length, for example. In general, a guide sequence herein has sufficient complementarity with a strand of a target DNA sequence to hybridize with the target sequence and direct sequence-specific binding of a Cas protein or Cas protein complex to the target sequence (if a suitable PAM is adjacent to the target sequence). The degree of complementarity between a guide sequence and its corresponding DNA target sequence is at least about 90%, 91%, 92%, 93%, 94%, 95%, 96%, 97%, 98%, 99%, or 100%, for example. The guide sequence can be engineered accordingly to target an RGEN to a DNA target sequence in a cell.

An RNA component herein can comprise a crRNA, for example, which comprises a guide sequence and a repeat (tracrRNA mate) sequence. The guide sequence is typically located at or near (within 1, 2, 3, 4, 5, 6, 7, 8, 9, 10 or more bases) the 5' end of the crRNA. Downstream the guide sequence of a crRNA is a "repeat" or "tracrRNA mate" sequence that is complementary to, and can hybridize with, sequence at the 5' end of a tracrRNA. Guide and tracrRNA mate sequences can be immediately adjacent, or separated by 1, 2, 3, 4 or more bases, for example. A tracrRNA mate sequence has, for example, at least 50%, 60%, 70%, 80%, 90%, 95%, 96%, 97%, 98%, 99%, or 100% sequence complementarity to the 5' end of a tracrRNA. In general, degree of complementarity can be with reference to the optimal alignment of the tracrRNA mate sequence and 5' end of the tracrRNA sequence, along the length of the shorter of the two sequences. The length of a tracrRNA mate sequence herein can be at least 8, 9, 10, 11, 12, 13, 14, 15, 16, 17, or 18 ribonucleotides in length, for example, and hybridizes with sequence of the same or similar length (e.g., plus or minus 1, 2, 3, 4, or 5 bases) at the 5' end of a tracrRNA. Suitable examples of tracrRNA mate sequences herein comprise SEQ ID NO:51 (guuuuguacucucaagauuua), SEQ ID NO:52 (guuuuuguacucuca), SEQ ID NO:53 (guuuuagagcua), or SEQ ID NO:54 (guuuuagagcuag), or variants thereof that (i) have at least about 90%, 91%, 92%, 93%, 94%, 95%, 96%, 97%, 98%, or 99% sequence identity and (ii) can anneal with the 5'-end sequence of a tracrRNA. The length of a crRNA herein can be at least about 18, 20, 22, 24, 26, 28, 30, 32, 34, 36, 38, 40, 42, 44, 46, or 48 ribonucleotides; or about 18-48 ribonucleotides; or about 25-50 ribonucleotides, for example.

A tracrRNA can be included along with a crRNA in embodiments in which a Cas9 protein of a type II CRISPR system is comprised in the RGEN. A tracrRNA herein comprises in 5'-to-3' direction (i) a sequence that anneals with the repeat region (tracrRNA mate sequence) of crRNA and (ii) a stem loop-containing portion. The length of a sequence of (i) can be the same as, or similar with (e.g., plus or minus 1, 2, 3, 4, or 5 bases), any of the tracrRNA mate sequence lengths disclosed above, for example. The total length of a tracrRNA herein (i.e., sequence components [i] and [ii]) can be at least about 30, 35, 40, 45, 50, 55, 60, 65, 70, 75, 80, 85, or 90 (or any integer between 30 and 90) ribonucleotides, for example. A tracrRNA may further include 1, 2, 3, 4, 5, or more uracil residues at the 3'-end, which may be present by virtue of expressing the tracrRNA with a transcription terminator sequence.

A tracrRNA herein can be derived from any of the bacterial species listed above from which a Cas9 sequence can be derived, for example. Examples of suitable tracrRNA sequences include those disclosed in U.S. Pat. No. 8,697,359 and Chylinski et al. (*RNA Biology* 10:726-737), which are incorporated herein by reference. A preferred tracrRNA herein can be derived from a *Streptococcus* species tracrRNA (e.g., *S. pyogenes*, *S. thermophilus*). Other suitable examples of tracrRNAs herein may comprise:

```
SEQ ID NO: 55:
uagcaaguuaaaauaaggcuaguccguuaucaacuugaaaaaguggc
accgagucggugc, SEQ ID NO: 56:
uagcaaguuaaaauaaggcuaguccguuaucaacuugaaaaagug,
or SEQ ID NO: 57:
uagcaaguuaaaauaaggcuaguccguuauca,
which are derived from S. pyogenes tracrRNA.

Other suitable examples of tracrRNAs herein
may comprise:
SEQ ID NO: 58:
uaaaucuugcagaagcuacaaagauaaggcuucaugccgaaaucaac
acccugucauuuuauggcagggguguuuucguuauuuaa, SEQ ID NO: 59:
ugcagaagcuacaaagauaaggcuucaugccgaaaucaacacccugu
cauuuuauggcaggguguuuucguuauuua,
or SEQ ID NO: 60:
ugcagaagcuacaaagauaaggcuucaugccgaaaucaacacccugu
cauuuuauggcagggugu,
``` which are derived from *S. thermophilus* tracrRNA.

Still other examples of tracrRNAs herein are variants of these tracrRNA SEQ ID NOs that (i) have at least about 80%, 85%, 90, 91, 92, 93, 94, 95, 96, 97, 98, or 99% sequence identity therewith and (ii) can function as a tracrRNA (e.g., 5'-end sequence can anneal to tracrRNA mate sequence of a crRNA, sequence downstream from the 5'-end sequence can form one or more hairpins, variant tracrRNA can form complex with a Cas9 protein).

An RNA component of an RGEN disclosed herein (or said another way, an RNA component that may be associated with an RGEN protein component) can comprise, for example, a guide RNA (gRNA) comprising a crRNA operably linked to, or fused to, a tracrRNA. The crRNA component of a gRNA in certain preferred embodiments is upstream of the tracrRNA component (i.e., such a gRNA comprises, in 5'-to-3' direction, a crRNA operably linked to a tracrRNA). Any crRNA and/or tracrRNA (and/or portion thereof, such as a crRNA repeat sequence, tracrRNA mate sequence, or tracrRNA 5'-end sequence) as disclosed herein (e.g., above embodiments) can be comprised in a gRNA, for example.

The tracrRNA mate sequence of the crRNA component of a gRNA herein should be able to anneal with the 5'-end of the tracrRNA component, thereby forming a hairpin structure. Any of the above disclosures regarding lengths of, and percent complementarity between, tracrRNA mate sequences (of crRNA component) and 5'-end sequences (of tracrRNA component) can characterize the crRNA and tracrRNA components of a gRNA, for example. To facilitate this annealing, the operable linkage or fusion of the crRNA and tracrRNA components preferably comprises a suitable loop-forming ribonucleotide sequence (i.e., a loop-forming sequence may link the crRNA and tracrRNA components together, forming the gRNA). Suitable examples of RNA loop-forming sequences include GAAA (SEQ ID NO:36), CAAA (SEQ ID NO:37) and AAAG (SEQ ID NO:38). However, longer or shorter loop sequences may be used, as may alternative loop sequences. A loop sequence preferably comprises a ribonucleotide triplet (e.g., AAA) and an additional ribonucleotide (e.g., C or G) at either end of the triplet.

A gRNA herein forms a hairpin ("first hairpin") with annealing of its tracrRNA mate sequence (of the crRNA component) and tracrRNA 5'-end sequence portions. One or more (e.g., 1, 2, 3, or 4) additional hairpin structures can form downstream from this first hairpin, depending on the sequence of the tracrRNA component of the gRNA. A gRNA may therefore have up to five hairpin structures, for example. A gRNA may further include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more residues following the end of the gRNA sequence, which may be present by virtue of expressing the gRNA with a transcription terminator sequence, for example. These additional residues can be all U residues, or at least 90%, 91%, 92%, 93%, 94%, 95%, 96%, 97%, 98%, or 99% U residues, for example, depending on the choice of terminator sequence.

Non-limiting examples of suitable gRNAs useful in the disclosed invention may comprise:

SEQ ID NO: 61:
<u>NNNNNNNNNNNNNNNNNNNNN</u>guuuuuguacucucaagauuuaGAAA<u>u
aaaucuugcagaagcuacaaaga</u>uaaggcuucaugccgaaaucaaca
cccugucauuuuauggcagggguguuuucguuauuuaa, SEQ ID NO: 62:
<u>NNNNNNNNNNNNNNNNNNNN</u>guuuuuguacucucaGAAA<u>ugcagaag
cuacaaaga</u>uaaggcuucaugccgaaaucaacacccugucauuuuau
ggcaggguguuuucguuauuuaa, SEQ ID NO: 63:
<u>NNNNNNNNNNNNNNNNNNNN</u>guuuuuguacucucaGAAA<u>ugcagaag
cuacaaaga</u>uaaggcuucaugccgaaaucaacacccugucauuuuau
ggcaggguguu, SEQ ID NO: 64:
<u>NNNNNNNNNNNNNNNNNNNN</u>guuuuuguacucucaGAAA<u>uagcaagu
uaaaaua</u>aggcuaguccguuaucaacuugaaaaaguggcaccgaguc
ggugc, SEQ ID NO: 65:
<u>NNNNNNNNNNNNNNNNNNNN</u>guuuuagagcuaGAAA<u>uagcaaguuaa
aa</u>uaaggcuaguccguuaucaacuugaaaaagug, SEQ ID NO: 66:
<u>NNNNNNNNNNNNNNNNNNNN</u>guuuuagagcuaGAAA<u>uagcaaguuaa
aa</u>uaaggcuaguccguuauca,
or SEQ ID NO: 67:
<u>NNNNNNNNNNNNNNNNNNNN</u>guuuuagagcuaGAAA<u>uagcaaguuaa
aa</u>uaaggcuaguccguuaucaacuugaaaaaguggcaccgagucggu
gcuuuu.

In each of SEQ ID NOs:61-67, the single-underlined sequence represents a crRNA portion of the gRNA. Each "N" represents a ribonucleotide base (A, U, G, or C) of a suitable guide sequence. The first block of lower case letters represents tracrRNA mate sequence. The second block of lower case letters represents a tracrRNA portion of the gRNA. The double-underlined sequence approximates that portion of tracrRNA sequence that anneals with the tracrRNA mate sequence to form a first hairpin. A loop sequence (GAAA, SEQ ID NO:36) is shown in capital letters, which operably links the crRNA and tracrRNA portions of each gRNA. Other examples of gRNAs herein include variants of the foregoing gRNAs that (i) have at least about 80%, 85%, 90, 91, 92, 93, 94, 95, 96, 97, 98, or 99% sequence identity (excluding guide sequence in this calculation) with these sequences, and (ii) can function as a gRNA that specifically targets a Cas9 protein to bind with, and optionally nick or cleave, a target DNA sequence.

A gRNA herein can also be characterized in terms of having a guide sequence (VT domain) followed by a Cas endonuclease recognition (CER) domain. A CER domain comprises a tracrRNA mate sequence followed by a tracrRNA sequence. Examples of CER domains useful herein include those comprised in SEQ ID NOs:61-67 above (the CER domain in each is the sequence following the N's of the VT domain). Another suitable example of a CER domain is SEQ ID NO:24 (see Examples), which comprises in 5'-to-3' direction the tracrRNA mate sequence of SEQ ID NO:53, the loop-forming sequence of SEQ ID NO:36 (GAAA), and the tracrRNA sequence of SEQ ID NO:55.

An RNA component of an RGEN optionally does not have a 5'-cap (7-methylguanylate [$m^7G$] cap) (i.e., such an RNA component does not have an $m^7G$ cap at its 5'-terminus). An RNA component herein can have, for example, a 5'-hydroxyl group instead of a 5'-cap. Alternatively, an RNA component herein can have, for example, a 5' phosphate instead of a 5'-cap. It is believed that an RNA component in these embodiments can better accumulate in the nucleus (such as after its transcription in the nucleus, or after its RGEN-mediated import into the nucleus, depending on how the RNA component is provided herein), since 5'-capped RNA (i.e., RNA having 5' $m^7G$ cap) is subject to nuclear export. Preferred examples of uncapped RNA components herein include suitable gRNAs, crRNAs, and/or tracrRNAs. In certain embodiments, an RNA component herein lacks a 5'-cap, and optionally has a 5'-hydroxyl group instead, by virtue of RNA autoprocessing by a ribozyme sequence at the 5'-end of a precursor of the RNA component (i.e., a precursor RNA comprising a ribozyme sequence upstream of an RNA component such as a gRNA undergoes ribozyme-mediated autoprocessing to remove the ribozyme sequence, thereby leaving the downstream RNA component without a 5'-cap). In certain other embodiments, an RNA component herein is not produced by transcription from an RNA polymerase III (Pol III) promoter.

A cell-penetrating peptide (CPP) herein can be about 5-30, 5-25, 5-20, 10-30, 10-25, or 10-20 amino acid residues in length, for example. As other examples, a CPP can be about 5, 6, 7, 8, 9, 10, 11, 12, 13, 14, 15, 16, 17, 18, 19, 20, 21, 22, 23, 24, 25, 26, 27, 28, 29, or 30 amino acid residues in length. Yet in further aspects herein, a CPP can be up to about 35, 40, 45, 50, 55, or 60 amino acid residues in length.

A CPP disclosed herein can be cationic or amphipathic, for example. A cationic CPP herein typically comprises at least about 60% positively charged amino acids such as lysine (K), arginine (R), and/or histidine (H). Alternatively, a cationic CPP can comprise, for example, at least 60%, 65%, 70%, 75%, 80%, 85%, 90%, or 95% positively charged amino acids (e.g., R residues; K residues; K and R residues; K, R and H residues). A cationic CPP can be characterized as being arginine-rich (e.g., comprising at least 70% or 80% R residues) or lysine-rich (e.g., comprising at least 70% or 80% L residues) in certain embodiments. Examples of cationic CPPs useful herein are disclosed in Schmidt et al. (*FEBS Lett.* 584:1806-1813) and Wender et al. (polylysine; *Proc. Natl. Acad. Sci. USA* 97:13003-13008), which are incorporated herein by reference. Other examples of cationic CPPs comprise GRKKRRQRRR (SEQ ID NO:68), RKKRRQRRR (SEQ ID NO:69), or RKKRRQRR (SEQ ID NO:70), which were originally derived from HIV Tat protein, and penetratin (RQIKIWFQNRRMKWKK, SEQ ID NO:71), which was originally derived for the Antennapedia homeodomain protein of *Drosophila*.

Another example of a cationic CPP comprises a polyarginine sequence having a number of contiguous arginines sufficient to direct entry of the CPP and its cargo (e.g., RGEN protein component or RGEN) into a cell. The number of contiguous arginine residues in such a polyarginine sequence can be at least 3, 4, 5, 6, 7, 8, 9, 10, or 10-50 arginines, for instance. In certain aspects herein, a CPP can have 6 or more contiguous arginine residues (e.g., 6-7, 6-8, 6-9, or 6-10 arginine residues). "PolyR" (GGGGR-RRRRRRRRLLLL, SEQ ID NO:15) can be comprised in a polyarginine CPP, if desired. Other polyarginine CPP examples comprise THRLPRRRRRR (SEQ ID NO:72) or GGRRARRRRRR (SEQ ID NO:73). In some embodiments, a CPP is an activatable CPP ("ACPP") (Aguilera et al., *Integr Biol.* (Camb) 1:371-381; incorporated herein by reference). ACPPs typically comprise a polycationic CPP (e.g., nine contiguous arginines) connected via a cleavable linker to a matching polyanion (e.g., nine contiguous glutamates), which reduces the net charge to nearly zero and thereby inhibits CPP adhesion and uptake into cells. Upon cleavage of the linker, the polyanion is released, locally unmasking the polycation portion and its inherent adhesiveness, thereby allowing CPP cell entry. Another example herein is a polylysine CPP; any of the above embodiments of polyarginine, but in which R is replaced with K, are examples of polylysine CPPs herein.

An amphipathic CPP herein comprises an amino acid sequence containing an alternating pattern of polar/charged residues and non-polar, hydrophobic residues. The following CPPs are believed to be amphipathic, and are useful in certain aspects (regardless of whether amphipathic terminology perfectly applies): a CPP comprising transportan-10 (TP10) peptide (e.g., AGYLLGKINLKACAACAKKIL, SEQ ID NO:14); a CPP from a vascular endothelium cadherin protein, such as a CPP comprising a pVEC peptide (e.g., LIILRRRIRKQAHAHSK, SEQ ID NO:74; LLIILR-RRIRKQAHAHSK, SEQ ID NO:13); a CPP from an Epstein-Barr virus Zebra trans-activator protein, such as a CPP comprising a Zebra peptide (e.g., ECD-SELEIKRYKRVRVASRKCRAKFKQLLQHY-REVAAAKSSENDRLRLLLKQMC, SEQ ID NO:12); a CPP comprising a (KFF)₃K peptide (e.g., KFFKFFKFFK, SEQ ID NO:75); a CPP comprising a MAP peptide (KLA-LKLALKALKAALKLA, SEQ ID NO:76); a CPP comprising RRQRRTSKLMKR (SEQ ID NO:77); a CPP comprising KALAWEAKLAKALAKALAKHLAKALAKALKCEA (SEQ ID NO:78). Other amphipathic CPPs suitable herein include proline-rich CPPs, such as those comprising at least 3, 4, 5, 6, 7, or 8 repeats of VHLPPP (SEQ ID NO:79) or VRLPPP (SEQ ID NO:80).

As other examples, a CPP herein may comprise an MPG peptide (e.g., GALFLGFLGAAGSTMGAWSQPKSKRKV, SEQ ID NO:81); a Pep-1 peptide (e.g., KETWWETWW-TEWSQPKKKRKV, SEQ ID NO:82); or a CPP from a human calcitonin protein, such as an hCT peptide (e.g., LGTYTQDFNKFHTFPQTAIGVGAP, SEQ ID NO:83; CGNLSTCMLGTYTQDFNK, SEQ ID NO:84). Still other examples of CPPs herein include those disclosed in Regberg et al. (*Int. J. Pharm.* 464:111-116), which is incorporated herein by reference.

A CPP suitable herein can alternatively comprise an amino acid sequence that is at least 90%, 91%, 92%, 93%, 94%, 95%, 96%, 97%, 98%, or 99% identical to any of the CPP amino acid sequences disclosed herein, for example. Such a variant CPP protein should have CPP activity, such as the ability to mediate cellular uptake of molecular cargo (e.g., an amino acid sequence comprising one or more RGEN protein components [e.g., Cas9], or an amino acid sequence comprising one or more RGEN protein components [e.g., Cas9] associated with an RNA component). Testing the activity of a variant CPP can be done any number of ways, such as by covalently linking it with a fluorescent protein (e.g., GFP) and measuring the degree of fluorescence emitted from a cell contacted with a the CPP-fluorescent protein complex.

A CPP herein can be modified, if desired, to render it even more capable of carrying RGEN protein cargo from outside a cell to inside a cell. For example, a CPP can be modified to have a lipid group at either its N- or C-terminus. Suitable lipid groups herein include acyl groups such as stearyl and myristyl groups. Other examples of lipid groups are acyl groups with 8, 9, 10, 11, 12, 13, 14, 15, 16, 17, or 18 carbons. Conditions for modifying peptides with lipid groups useful herein are disclosed in Regberg et al. (*Int. J. Pharm.* 464:111-116) and Anko et al. (*Biochim. Biophys. Acta—Biomembranes* 1818:915-924) for example, which are incorporated herein by reference.

An RGEN protein component and at least one CPP herein can be covalently linked to each other in an RGEN protein-CPP complex in certain aspects herein. For example, an RGEN protein component and at least one CPP can be fused together in a single amino acid sequence (i.e., an RGEN protein component and at least one CPP can be comprised within a fusion protein). Thus, an example of covalent linkage herein can be via a peptide bond in which the amino acid sequence of an RGEN protein component is fused with the amino acid sequence of a CPP, such that both these amino acid sequences are contained in a single amino acid sequence. Such a fusion protein (or "chimeric protein"), can be characterized as an RGEN protein-CPP fusion herein. In those embodiments in which an RNA component is associated with an RGEN protein component, such a fusion protein can be characterized as an RGEN-CPP fusion.

One or more CPPs can be located at the N-terminus or C-terminus of an RGEN protein-CPP fusion, for example. Alternatively, one or more CPPs can be located at both the N- and C-termini of an RGEN protein-CPP fusion. Alternatively still, one or more CPPs can be located within the amino acid sequence of an RGEN protein-CPP fusion. Embodiments herein comprising more than one CPP can comprise at least 2, 3, 4, 5, 6, 7, 8, 9, 10, 11, 12, 13, 14, 15, 16, 17, 18, 19, or 20 CPPs, or 5-10, 5-20, or 10-20 CPPs. The CPPs fused to the RGEN protein component can be the same or different (e.g., 2, 3, 4, or more different types of CPPs). One or more CPPs can be fused directly to the amino acid sequence of an RGEN protein, and/or can be fused to a heterologous domain(s) (e.g., NLS or other organelle-targeting sequence such as an MTS) that is fused with an RGEN protein.

A fusion between a CPP and an RGEN protein component herein can be direct (i.e., CPP amino acid sequence is directly linked to RGEN amino acid sequence by a peptide bond). Alternatively, a fusion between a CPP and an RGEN protein component can be via an intermediary amino acid sequence (this is an example of a CPP and RGEN protein component being indirectly linked). Examples of an intermediary amino acid sequence include suitable linker sequences comprising at least 1, 2, 3, 4, 5, 6, 7, 8, 9, 10, 11, 12, 13, 14, 15, 16, 17, 18, 19, 20, 30, 40, 50, 60, 70, 80, 90, or 100 amino acid residues such as glycine, serine, alanine and/or proline. Suitable amino acid linkers are disclosed in U.S. Pat. Nos. 8,828,690, 8,580,922 and 5,990,275, for example, which are incorporated herein by reference. Other examples of intermediary amino acid sequences can comprise one or more other types of proteins and/or domains. For example, a marker protein (e.g., a fluorescent protein such as any of those disclosed herein) can be comprised in an intermediary amino acid sequence.

A composition comprising a covalent complex of an RGEN protein component and at least one CPP, such as in a fusion protein, can be used with any cell type disclosed herein. Optionally, however, this composition can be used with non-mammalian cells such as yeast, fungi, and plants, but excludes use on mammalian cells.

Examples of RGEN protein-CPP fusion proteins herein can comprise SEQ ID NO:39 (Zebra CPP-Cas9-NLS fusion protein), 40 (PolyR CPP-Cas9-NLS fusion protein), 41 (TP10 CPP-Cas9-NLS fusion protein), or 42 (pVEC CPP-Cas9-NLS fusion protein). SEQ ID NOs:39-42 are examples of Cas9-CPP fusion proteins. Other examples of RGEN protein-CPP fusion proteins comprise an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to any of SEQ ID NOs:39-42. Such a variant fusion protein should have (i) a CPP domain that can mediate cellular uptake of the fusion protein, and (ii) a Cas9 protein with specific binding activity, and optionally cleavage or nicking activity, toward DNA when associated with an RNA component. SEQ ID NO:39, 40, 41 and 42 comprise Zebra CPP (SEQ ID NO:12), PolyR CPP (SEQ ID NO:15), TP10 CPP (SEQ ID NO:14) and pVEC CPP (SEQ ID NO:13), respectively, operably linked to Cas9 (*S. pyogenes*)-NLS protein (residues 2-1379 of SEQ ID NO:3).

In certain embodiments, the protein component of a guide polynucleotide/Cas endonuclease system can be fused to a CPP, wherein the CPP comprises:
(i) a CPP from an Epstein-Barr virus Zebra trans-activator protein,
(ii) a CPP having 6 or more contiguous arginine residues,
(iii) a transportan-10 (TP10) CPP,
(iv) a CPP from a vascular endothelium cadherin protein, or
(vi) a CPP selected from the group consisting of a synthetic non-arginine CPP, a histidine-rich nona-arginine CPP and a Pas nona-arginine CPP. Examples of synthetic nona-arginine, histidine-rich nona-arginine, and Pas nona-arginine CPPs are disclosed in, for example, Liu et al. (*Advanced Studies in Biology* 5(2):71-88, HIKARI Ltd), which is incorporated herein by reference.

Another example of how an RGEN protein component and at least one CPP can be covalently linked is via crosslinking (chemical crosslinking). Thus, an example of an RGEN protein-CPP complex herein can comprise an RGEN protein crosslinked to at least one CPP. Crosslinking herein refers to a process of chemically joining two or more molecules (an RGEN protein component and at least one CPP, in this case) by a covalent bond(s). Crosslinking can be performed using any number of processes known in the art, such as those disclosed in U.S. Patent Appl. Publ. No. 2011/0190813, U.S. Pat. No. 8,642,744, and *Bioconjugate Techniques, 2nd Edition* (G. T. Hermanson, Academic Press, 2008), which are all incorporated herein by reference.

Typically, a CPP can be modified and/or synthesized to contain a suitable protein linking group at its N-terminus, C-terminus, and/or an amino acid side group, for the purpose of crosslinking the CPP to an RGEN protein component. A "protein linking group" refers to a group that is capable of reacting directly, either spontaneously or after activation (e.g., light), with an accessible side chain functional group of an RGEN protein component under suitable conditions (e.g., aqueous conditions) to produce a covalently link the CPP to the RGEN protein. A protein linking group may react with the side chain functional groups of a Lys, Cys, Ser, Thr, Tyr, His, or Arg amino acid residue in an RGEN protein, for example, to produce a covalent linkage to the protein. Either a homobifunctional (e.g., capable of linking amine to amine) or heterobifunctional (e.g., capable of linking amine to thiol) protein linking group can be used, for example. A protein linking group on a CPP can also react with a terminal group (e.g., N-terminus) of an RGEN protein in certain embodiments. Suitable protein linking groups herein include amino-reactive (e.g., NHS ester or imidoester), thiol (sulfhydryl)-reactive (e.g., a maleimide such as BMOE, BMB, or BMH), hydroxyl-reactive, imidazolyl-reactive, or guanidinyl-reactive groups. Exemplary protein linking groups include active esters (e.g., an amino-reactive NHS ester), and thiol-reactive maleimide or iodoacetamide groups. Further exemplary protein linking groups useful herein and methods of using them are described in *Bioconjugate Techniques, 2nd Edition* (G. T. Hermanson, Academic Press, 2008), for example.

A protein linking group herein typically can produce a link between a CPP and an RGEN protein with a backbone of 20 atoms or less in length. For example, such a link can be between 1 and 20 atoms in length, or about 1, 2, 3, 4, 5, 6, 8, 10, 12, 14, 16, 18 or 20 carbon atoms in length. A link may be linear, branched, cyclic or a single atom in certain embodiments. In certain cases, one, two, three, four or five or more carbon atoms of a linker backbone may be substituted with a sulfur, nitrogen or oxygen heteroatom. The bonds between backbone atoms may be saturated or unsaturated (usually not more than one, two, or three unsaturated bonds in the linker backbone). A linker may include, without limitation, an oligo(ethylene glycol); ether; thioether; tertiary amine; or alkyl group, which may be straight or branched (e.g., methyl, ethyl, n-propyl, iso-propyl, n-butyl, n-pentyl, t-butyl). As other examples, a linker backbone may include a cyclic group such as an aryl, a heterocycle, or a cycloalkyl group, where 2 or more atoms (e.g., 2, 3 or 4 atoms) of the cyclic group are included in the backbone.

More than one type of CPP (e.g., 2, 3, 4, or more different types of CPPs) can be crosslinked to an RGEN protein component in certain embodiments. The ratio (molar ratio) of CPP(s) to RGEN protein that can be used when crosslinking can be at least about 1:1, 2:1, 3:1, 4:1, 5:1, 6:1, 7:1, 8:1, 9:1, 10:1 15:1, 20:1, 30:1, 40:1, or 50:1, for example. In other aspects, the average number of CPPs crosslinked to an RGEN protein may be at least 1, 2, 3, 4, 5, 6, 7, 8, 9, 10, 11, 12, 13, 14, 15, 16, 17, 18, 19, 20, 21, 22, 23, 24, or 25, or at least 5-10, 5-15, 5-20, or 5-25.

An RGEN protein component and at least one CPP can be crosslinked into a complex further comprising one or more other proteins/peptides/domains, if desired. Such other elements can optionally be used to bridge an RGEN protein component with a CPP, and may include any of the intermediary amino acid sequences described above.

An RGEN protein component and at least one CPP herein can be non-covalently linked to each other in an RGEN protein-CPP complex in certain aspects herein. Though not intending to be held to any particular theory or mechanism, it is contemplated that a non-covalent linkage between an RGEN protein component and at least one CPP can be due to electrostatic, Van der Waals, and/or hydrophobic forces. In those embodiments in which an RNA component is associated with an RGEN protein component, such embodiments can be characterized as comprising an RGEN that is non-covalently linked to at least one CPP in an RGEN-CPP complex. A composition comprising an RGEN protein component and CPP that are non-covalently linked can optionally be characterized as a mixture of these components.

In certain embodiments, an RGEN protein component is non-covalently linked to at least one CPP with an amino acid sequence consisting of the CPP amino acid sequence only. Such a CPP, while not having any "non-CPP" amino acid sequence, can optionally comprise a modification such as a lipid group as disclosed herein.

Alternatively, a CPP that is non-covalently linked to an RGEN protein component may be comprised in a fusion protein having both CPP amino acid sequence and one or more heterologous amino acid sequences (non-RGEN protein sequences). A heterologous sequence in such embodiments can be that of a domain or a protein (e.g., a fluorescent protein such as any of those disclosed herein, or any domain/protein listed in the above disclosure regarding Cas fusions). Another example is fusing a dimerization domain to a CPP, which dimerization domain is able to bind to a dimerization domain linked or fused to an RGEN protein component.

Leucine zipper domains are examples of dimerization domains herein. Leucine zipper domains can represent those from natural proteins known to contain such domains (e.g., transcription factors), or can be synthetically designed. A leucine zipper domain linked to a CPP can associate ("zip together") with a leucine zipper domain of an RGEN protein component, thereby linking the CPP and RGEN protein component in a non-covalent complex. A pair of leucine zipper domains for non-covalently linking a CPP and an RGEN protein component can be the same (such a domain pair forms a homodimeric leucine zipper) or different (such a domain pair forms a heterodimeric leucine zipper). Examples of leucine zipper domains include those disclosed in U.S. Patent Appl. Publ. Nos. 2003/0108869 and 2004/0147721. In certain aspects, a homodimeric leucine zipper can be formed using a leucine zipper domain from a GCN4 transcription factor, while in other aspects a heterodimeric leucine zipper can be formed using leucine zipper domains from fos and jun transcription factors, respectively.

A non-covalent complex of an RGEN protein component and at least one CPP can further comprise one or more other proteins/peptides/domains, if desired. Such other elements can optionally be used to bridge an RGEN protein component with a CPP, and may include any of the intermediary amino acid sequences described above.

More than one type of CPP (e.g., 2, 3, 4, or more different types of CPPs) can be non-covalently linked to an RGEN protein component in certain embodiments. The ratio (molar ratio) of CPP(s) to RGEN protein that can be used to prepare such a complex can be at least about 1:1, 2:1, 3:1, 4:1, 5:1, 6:1, 7:1, 8:1, 9:1, 10:1 15:1, 20:1, 30:1, 40:1, or 50:1, for example. In other aspects, the average number of CPPs non-covalently linked to an RGEN protein may be at least 1, 2, 3, 4, 5, 6, 7, 8, 9, 10, 11, 12, 13, 14, 15, 16, 17, 18, 19, 20, 21, 22, 23, 24, or 25, or at least 5-10, 5-15, 5-20, or 5-25.

In certain embodiments, a non-covalent complex of an RGEN protein component and at least one CPP can be prepared by mixing an appropriate amount of each component (e.g., such as to obtain a ratio of CPP to RGEN protein disclosed above) in an aqueous medium. A suitable aqueous medium can comprise a buffer solution such as PBS or a serum-free medium such as DMEM, for example. The mixture can be incubated for about 30, 60, 90, or 120 minutes at a temperature of about 4 to 45° C., for example, to allow formation of a non-covalent RGEN protein-CPP complex. A suitable volume (e.g., a minimum volume that adequately covers/immerses cells being treated) of this solution comprising the complex can be applied to a cell in a cell type-appropriate manner. In embodiments in which an RNA component is associated with an RGEN protein component, such formation of an RGEN can comprise adding an RNA component before, at the same time of, or after incubating a CPP with the RGEN protein component.

A composition comprising a non-covalent complex of an RGEN protein component and at least one CPP can be used with any cell type disclosed herein. Optionally, however, this composition can be used with non-mammalian cells such as yeast, fungi, and plants, but excludes use on mammalian cells.

An RGEN protein-CPP complex, as it may exist in a composition before application to cells can be at least about 30%, 40%, 50%, 60%, 65%, 70%, 75%, 80%, 85%, 90%, 95%, 98%, or 99% pure, for example. Such purity can be on a protein basis in certain embodiments. As an example, if the purity of a complex is at least 80%, this would mean that at least 80% of all the protein in a composition is constituted by the complex. Complex purity alternatively can take into account not only purity on a protein basis, but also in account of other biomolecules (e.g., lipids, saccharides, and/or nucleic acids). As an example, if the purity of a complex is at least 80%, this could mean that at least 80% of all the biomolecules in the composition herein is constituted by the complex. In certain embodiments, compounds such as carbohydrates, salts, and/or lipids and the like do not affect the determination of percent purity herein. All these disclosures regarding purity can also apply to an RGEN- CPP complex (i.e., RGEN protein component of complex is associated with an RNA component).

A composition herein is preferably aqueous, wherein the solvent in which an RGEN protein-CPP complex or RGEN-CPP complex is dissolved is at least about 70, 75, 80, 85, 90, 95, 98, or 99 wt % water. The concentration of a complex in a composition can be at least about 0.5, 1.0, 1.5, 2.0, 2.5, 3.0, 3.5, 4.0, 4.5, 5.0, 6.0, 7.0, 8.0, 9.0 or 10.0 µM, or about 0.5 to 5.0 µM, 0.5 to 2.5 µM, 1.0 to 5.0 µM, 1.0 to 2.5 µM, or 2.5 to 5.0 µM, for example. It would be understood that such compositions can be in a liquid state.

The pH of a composition in certain embodiments can be between about 4.0 to about 10.0. Alternatively, the pH can be about 4.0, 4.5, 5.0, 5.5, 6.0, 6.5, 7.0, 7.5, 8.0, 8.5, 9.0, 9.5 or 10.0. pH can be adjusted or controlled by the addition or incorporation of a suitable buffer, including but not limited to: HEPES, phosphate (e.g., PBS), Tris, Tris-HCl, citrate, or a combination thereof. Buffer concentration in a composition herein can be from 0 mM to about 100 mM, or about 10, 20, or 50 mM, for example. A HEPES buffer (e.g., ~25 mM HEPES, such as 25 mM HEPES/KOH pH 7.5, 200 mM KCl, 20% glycerol, 1 mM DTT) can be used in certain aspects.

A composition herein can optionally comprise other components in addition to an RGEN protein-CPP complex or RGEN-CPP complex. For example, the composition can comprise one or more salts such as a sodium salt (e.g., NaCl, $Na_2SO_4$). Other non-limiting examples of salts include those having (i) an aluminum, ammonium, barium, calcium, chromium (II or III), copper (I or II), iron (II or III), hydrogen, lead (II), lithium, magnesium, manganese (II or III), mercury (I or II), potassium, silver, sodium strontium, tin (II or IV), or zinc cation, and (ii) an acetate, borate, bromate, bromide, carbonate, chlorate, chloride, chlorite, chromate, dichromate, dihydrogen phosphate, ferricyanide, ferrocyanide, fluoride, hydrogen carbonate, hydrogen phosphate, hydrogen sulfate, hydrogen sulfide, hydrogen sulfite, hydride, hydroxide, hypochlorite, iodate, iodide, nitrate, nitride, nitrite, oxalate, oxide, perchlorate, permanganate, peroxide, phosphate, phosphide, phosphite, silicate, stannate, stannite, sulfate, sulfide, sulfite, tartrate, or thiocyanate anion. Thus, any salt having a cation from (i) above and an anion from (ii) above can be in a composition herein, for example. A salt can be present at a wt % of about 0.01 to about 10.00 (or any hundredth increment between 0.01 and 10.00), for example.

An RGEN protein-CPP complex herein can traverse (i) a cell membrane, or (ii) a cell wall and cell membrane, of a cell. In those embodiments in which an RGEN protein component is associated with an RNA component (thereby constituting a complete RGEN), an RGEN-CPP complex similarly has this cell membrane/cell wall-traversing ability. Either an RGEN protein-CPP complex or an RGEN-CPP complex can traverse a cell wall and cell membrane in certain aspects herein.

An RGEN protein-CPP or RGEN-CPP complex herein can optionally traverse a cell wall that comprises a glycocalyx (capsule). These embodiments typically are with regard to prokaryotic cells (e.g., bacteria), some of which may have a glycocalyx depending on species type and growth conditions.

Though not intending to be held to any particular theory or mechanism, it is believed that a CPP herein may deliver an RGEN protein component into a cell via an endocytic process. Examples of such a process might include macropinocytosis, clathrin-mediated endocytosis, caveolae/lipid raft-mediated endocytosis, and/or receptor mediated endocytosis mechanisms (e.g., scavenger receptor-mediated uptake, proteoglycan-mediated uptake).

Once an RGEN protein-CPP or RGEN-CPP complex is inside a cell, it can traverse an organelle membrane such as a nuclear membrane or mitochondrial membrane, for example. This ability depends on, in certain embodiments, the presence of at least one organelle-targeting sequence (e.g., NLS, MTS) being included with the RGEN protein. Still, in other embodiments, the ability to traverse an organelle membrane such as a nuclear membrane or mitochondrial membrane does not depend on the presence of an organelle-targeting sequence (i.e., a CPP[s] in such embodiments may be responsible for allowing RGEN traversal into an organelle such as the nucleus or mitochondria).

A cell herein can be a mammalian cell or a non-mammalian cell, the latter of which is used in certain preferred embodiments. In certain other aspects, a cell herein can be as it exists (i) in an organism/tissue in vivo, (ii) in a tissue or group of cells ex vivo, or (iii) in an in vitro state.

A microbial cell herein can be as it exists in an isolated state (e.g., in vitro cells, cultured cells) or a non-isolated state.

A microbial cell in certain embodiments is a fungal cell such as a yeast cell. A yeast in certain aspects herein can be one that reproduces asexually (anamorphic) or sexually (teleomorphic). While yeast herein typically exist in unicellular form, certain types of these yeast may optionally be able to form pseudohyphae (strings of connected budding cells). In still further aspects, a yeast may be haploid or diploid, and/or may have the ability to exist in either of these ploidy forms.

Examples of yeast herein include conventional yeast and non-conventional yeast. Conventional yeast in certain embodiments are yeast that favor homologous recombination (HR) DNA repair processes over repair processes mediated by non-homologous end-joining (NHEJ). Examples of conventional yeast herein include species of the genera *Saccharomyces* (e.g., *S. cerevisiae*, which is also known as budding yeast, baker's yeast, and/or brewer's yeast; *S. bayanus; S. boulardii; S. bulderi; S. cariocanus; S. cariocus; S. chevalieri; S. dairenensis; S. ellipsoideus; S. eubayanus; S. exiguus; S. florentinus; S. kluyveri; S. martiniae; S. monacensis; S. norbensis; S. paradoxus; S. pastorianus; S. spencerorum; S. turicensis; S. unisporus; S. uvarum; S. zonatus*) and *Schizosaccharomyces* (e.g., *S. pombe*, which is also known as fission yeast; *S. cryophilus; S. japonicus; S. octosporus*).

A non-conventional yeast herein is not a conventional yeast such as a *Saccharomyces* (e.g., *S. cerevisiae*) or *Schizosaccharomyces* (e.g., *S. pombe*) species. Non-conventional yeast in certain embodiments can be yeast that favor NHEJ DNA repair processes over repair processes mediated by HR. Conventional yeasts such as *S. cerevisiae* and *S. pombe* typically exhibit specific integration of donor DNA with short flanking homology arms (30-50 bp) with efficiencies routinely over 70%, whereas non-conventional yeasts such as *Pichia pastoris, Pichia stipitis, Hansenula polymorpha, Yarrowia lipolytica* and *Kluyveromyces lactis* usually show specific integration with similarly structured donor DNA at efficiencies of less than 1% (Chen et al., *PLoS ONE* 8:e57952). Thus, a preference for HR processes can be gauged, for example, by transforming yeast with a suitable donor DNA and determining the degree to which it is specifically recombined with a genomic site predicted to be targeted by the donor DNA. A preference for NHEJ (or low preference for HR), for example, would be manifest if such an assay yielded a high degree of random integration of the donor DNA in the yeast genome. Assays for determining the rate of specific (HR-mediated) and/or random (NHEJ-mediated) integration of DNA in yeast are known in the art (e.g., Ferreira and Cooper, *Genes Dev.* 18:2249-2254; Corrigan et al., *PLoS ONE* 8:e69628; Weaver et al., *Proc. Natl. Acad. Sci. U.S.A.* 78:6354-6358; Keeney and Boeke, *Genetics* 136:849-856).

Given their low level of HR activity, non-conventional yeast herein can (i) exhibit a rate of specific targeting by a suitable donor DNA having 30-50 bp flanking homology arms of less than about 1%, 2%, 3%, 4%, 5%, 6%, 7%, or 8%, for example, and/or (ii) exhibit a rate of random integration of the foregoing donor DNA of more than about 65%, 66%, 67%, 68%, 69%, 70%, 71%, 72%, 73%, 74%, or 75%, for example. These rates of (i) specific targeting and/or (ii) random integration of a suitable donor DNA can characterize a non-conventional yeast as it exists before being provided an RGEN as disclosed herein. An aim for providing an RGEN to a non-conventional yeast in certain embodiments is to create site-specific DNA single-strand breaks (SSB) or double-strand breaks (DSB) for biasing the yeast toward HR at the specific site. Thus, providing a suitable RGEN in a non-conventional yeast typically should allow the yeast to exhibit an increased rate of HR with a particular donor DNA. Such an increased rate can be at least about 2-, 3-, 4-, 5-, 6-, 7-, 8-, 9-, or 10-fold higher than the rate of HR in a suitable control (e.g., same non-conventional yeast transformed with the same donor DNA, but lacking a suitable RGEN).

A non-conventional yeast herein can be cultivated following any means known in the art, such as described in *Non-Conventional Yeasts in Genetics, Biochemistry and Biotechnology: Practical Protocols* (K. Wolf, K. D. Breunig, G. Barth, Eds., Springer-Verlag, Berlin, Germany, 2003), *Yeasts in Natural and Artificial Habitats* (J. F. T. Spencer, D. M. Spencer, Eds., Springer-Verlag, Berlin, Germany, 1997), and/or *Yeast Biotechnology: Diversity and Applications* (T. Satyanarayana, G. Kunze, Eds., Springer, 2009), all of which are incorporated herein by reference.

Non-limiting examples of non-conventional yeast herein include yeasts of the following genera: *Yarrowia*, *Pichia*, *Schwanniomyces*, *Kluyveromyces*, *Arxula*, *Trichosporon*, *Candida*, *Ustilago*, *Torulopsis*, *Zygosaccharomyces*, *Trigonopsis*, *Cryptococcus*, *Rhodotorula*, *Phaffia*, *Sporobolomyces*, *Pachysolen*, and *Moniliella*. A suitable example of a *Yarrowia* species is *Y. lipolytica*. Suitable examples of *Pichia* species include *P. pastoris*, *P. methanolica*, *P. stipitis*, *P. anomala* and *P. angusta*. Suitable examples of *Schwanniomyces* species include *S. castellii*, *S. alluvius*, *S. hominis*, *S. occidentalis*, *S. capriottii*, *S. etchellsii*, *S. polymorphus*, *S. pseudopolymorphus*, *S. vanrijiae* and *S. yamadae*. Suitable examples of *Kluyveromyces* species include *K. lactis*, *K. marxianus*, *K. fragilis*, *K. drosophilarum*, *K. thermotolerans*, *K. phaseolosporus*, *K. vanudenii*, *K. waltii*, *K. africanus* and *K. polysporus*. Suitable examples of Arxula species include *A. adeninivorans* and *A. terrestre*. Suitable examples of *Trichosporon* species include *T. cutaneum*, *T. capitatum*, *T. inkin* and *T. beemeri*. Suitable examples of *Candida* species include *C. albicans*, *C. ascalaphidarum*, *C. amphixiae*, *C. antarctica*, *C. apicola*, *C. argentea*, *C. atlantica*, *C. atmosphaerica*, *C. blattae*, *C. bromeliacearum*, *C. carpophila*, *C. carvajalis*, *C. cerambycidarum*, *C. chauliodes*, *C. corydali*, *C. dosseyi*, *C. dubliniensis*, *C. ergatensis*, *C. fructus*, *C. glabrata*, *C. fermentati*, *C. guilliermondii*, *C. haemulonii*, *C. insectamens*, *C. insectorum*, *C. intermedia*, *C. jeffresii*, *C. kefyr*, *C. keroseneae*, *C. krusei*, *C. lusitaniae*, *C. lyxosophila*, *C. maltosa*, *C. marina*, *C. membranifaciens*, *C. milleri*, *C. mogii*, *C. oleophila*, *C. oregonensis*, *C. parapsilosis*, *C. quercitrusa*, *C. rugosa*, *C. sake*, *C. shehatea*, *C. temnochilae*, *C. tenuis*, *C. theae*, *C. tolerans*, *C. tropicalis*, *C. tsuchiyae*, *C. sinolaborantium*, *C. sojae*, *C. subhashii*, *C. viswanathii*, *C. uti/is*, *C. ubatubensis* and *C. zemplinina*. Suitable examples of *Ustilago* species include *U. avenae*, *U. esculenta*, *U. hordei*, *U. maydis*, *U. nuda* and *U. tritici*. Suitable examples of *Torulopsis* species include *T. geochares*, *T. azyma*, *T. glabrata* and *T. candida*. Suitable examples of *Zygosaccharomyces* species include *Z. bailiff*, *Z. bisporus*, *Z. cidri*, *Z. fermentati*, *Z. florentinus*, *Z. kombuchaensis*, *Z. lentus*, *Z. mellis*, *Z. microellipsoides*, *Z. mrakii*, *Z. pseudorouxii* and *Z. rouxii*. Suitable examples of *Trigonopsis* species include *T. variabilis*. Suitable examples of *Cryptococcus* species include *C. laurentii*, *C. albidus*, *C. neoformans*, *C. gattii*, *C. uniguttulatus*, *C. adeliensis*, *C. aerius*, *C. albidosimilis*, *C. antarcticus*, *C. aquaticus*, *C. ater*, *C. bhutanensis*, *C. consortionis*, *C. curvatus*, *C. phenolicus*, *C. skinneri*, *C. terreus* and *C. vishniacci*. Suitable examples of *Rhodotorula* species include *R. acheniorum*, *R. tula*, *R. acuta*, *R. americana*, *R. araucariae*, *R. arctica*, *R. armeniaca*, *R. aurantiaca*, *R. auriculariae*, *R. bacarum*, *R. benthica*, *R. biourgei*, *R. bogoriensis*, *R. bronchialis*, *R. buffonii*, *R. calyptogenae*, *R. chungnamensis*, *R. cladiensis*, *R. corallina*, *R. cresolica*, *R. crocea*, *R. cycloclastica*, *R. dairenensis*, *R. diffluens*, *R. evergladiensis*, *R. ferulica*, *R. foliorum*, *R. fragaria*, *R. fujisanensis*, *R. futronensis*, *R. gelatinosa*, *R. glacialis*, *R. glutinis*, *R. gracilis*, *R. graminis*, *R. grinbergsii*, *R. himalayensis*, *R. hinnulea*, *R. histolytica*, *R. hylophila*, *R. incarnata*, *R. ingeniosa*, *R. javanica*, *R. koishikawensis*, *R. lactosa*, *R. lamellibrachiae*, *R. laryngis*, *R. lignophila*, *R. lini*, *R. longissima*, *R. ludwigii*, *R. lysinophila*, *R. marina*, *R. martyniae-fragantis*, *R. matritensis*, *R. meli*, *R. minuta*, *R. mucilaginosa*, *R. nitens*, *R. nothofagi*, *R. oryzae*, *R. pacifica*, *R. pallida*, *R. peneaus*, *R. philyla*, *R. phylloplana*, *R. pilatii*, *R. pilimanae*, *R. pinicola*, *R. plicata*, *R. polymorpha*, *R. psychrophenolica*, *R. psychrophila*, *R. pustula*, *R. retinophila*, *R. rosacea*, *R. rosulata*, *R. rubefaciens*, *R. rubella*, *R. rubescens*, *R. rubra*, *R. rubrorugosa*, *R. rufula*, *R. rutila*, *R. sanguinea*, *R. sanniei*, *R. sartoryi*, *R. silvestris*, *R. simplex*, *R. sinensis*, *R. slooffiae*, *R. sonckii*, *R. straminea*, *R. subericola*, *R. suganii*, *R. taiwanensis*, *R. taiwaniana*, *R. terpenoidalis*, *R. terrea*, *R. texensis*, *R. tokyoensis*, *R. ulzamae*, *R. vanillica*, *R. vuilleminii*, *R. yarrowii*, *R. yunnanensis* and *R. zsoltii*. Suitable examples of *Phaffia* species include *P. rhodozyma*. Suitable examples of *Sporobolomyces* species include *S. alborubescens*, *S. bannaensis*, *S. beijingensis*, *S. bischofiae*, *S. clavatus*, *S. coprosmae*, *S. coprosmicola*, *S. corallinus*, *S. dimmenae*, *S. dracophylli*, *S. elongatus*, *S. gracilis*, *S. inositophilus*, *S. johnsonii*, *S. koalae*, *S. magnisporus*, *S. novozealandicus*, *S. odorus*, *S. patagonicus*, *S. productus*, *S. roseus*, *S. sasicola*, *S. shibatanus*, *S. singularis*, *S. subbrunneus*, *S. symmetricus*, *S. syzygii*, *S. taupoensis*, *S. tsugae*, *S. xanthus* and *S. yunnanensis*. Suitable examples of *Pachysolen* and *Moniliella* species include *P. tannophilus* and *M. pollinis*, respectively. Still other examples of non-conventional yeasts herein include *Pseudozyma* species (e.g., *S. antarctica*), *Thodotorula* species (e.g., *T. bogoriensis*), *Wickerhamiella* species (e.g., *W. domercqiae*), and *Starmerella* species (e.g., *S. bombicola*).

*Yarrowia lipolytica* is preferred in certain embodiments disclosed herein. Examples of suitable *Y. lipolytica* include the following isolates available from the American Type Culture Collection (ATCC, Manassas, Va.): strain designations ATCC #20362, #8862, #8661, #8662, #9773, #15586, #16617, #16618, #18942, #18943, #18944, #18945, #20114,

20177, #20182, #20225, #20226, #20228, #20327, #20255, #20287, #20297, #20315, #20320, #20324, #20336, #20341, #20346, #20348, #20363, #20364, #20372, #20373, #20383, #20390, #20400, #20460, #20461, #20462, #20496, #20510, #20628, #20688, #20774, #20775, #20776, #20777, #20778, #20779, #20780, #20781, #20794, #20795, #20875, #20241, #20422, #20423, #32338, #32339, #32340, #32341, #34342, #32343, #32935, #34017, #34018, #34088, #34922, #34922, #38295, #42281, #44601, #46025, #46026, #46027, #46028, #46067, #46068, #46069, #46070, #46330, #46482, #46483, #46484, #46436, #60594, #62385, #64042, #74234, #76598, #76861, #76862, #76982, #90716, #90811, #90812, #90813, #90814, #90903, #90904, #90905, #96028, #201241, #201242, #201243, #201244, #201245, #201246, #201247, #201249, and/or #201847.

A fungal cell herein can be a yeast (e.g., as described above) or of any other fungal type such as a filamentous fungus. For instance, a fungus herein can be a Basidiomycetes, Zygomycetes, Chytridiomycetes, or Ascomycetes fungus. Examples of filamentous fungi herein include those of the genera *Trichoderma, Chrysosporium, Thielavia, Neurospora* (e.g., *N. crassa, N. sitophila*), *Cryphonectria* (e.g., *C. parasitica*), *Aureobasidium* (e.g., *A. pullulans*), *Filibasidium, Piromyces, Cryplococcus, Acremonium, Tolypocladium, Scytalidium, Schizophyllum, Sporotrichum, Penicillium* (e.g., *P. bilaiae, P. camemberti, P. candidum, P. chrysogenum, P. expansum, P. funiculosum, P. glaucum, P. marneffei, P. roqueforti, P. verrucosum, P. viridicatum*), *Gibberella* (e.g., *G. acuminata, G. avenacea, G. baccata, G. circinata, G. cyanogena, G. fujikuroi, G. intricans, G. pulicaris, G. stilboides, G. tricincta, G. zeae*), *Myceliophthora, Mucor* (e.g., *M. rouxii, M. circinelloides*), *Aspergillus* (e.g., *A. niger, A. oryzae, A. nidulans, A. flavus, A. lentulus, A. terreus, A. clavatus, A. fumigatus*), *Fusarium* (e.g., *F. graminearum, F. oxysporum, F. bubigenum, F. solani, F. oxysporum, F. verticillioides, F. proliferatum, F. venenatum*), and *Humicola*, and anamorphs and teleomorphs thereof. The genus and species of fungi herein can be defined, if desired, by morphology as disclosed in Barnett and Hunter (*Illustrated Genera of Imperfect Fungi*, 3rd Edition, Burgess Publishing Company, 1972). A fungus can optionally be characterized as a pest/pathogen of a plant or animal (e.g., human) in certain embodiments.

*Trichoderma* species in certain aspects herein include *T. aggressivum, T. amazonicum, T. asperellum, T. atroviride, T. aureoviride, T. austrokoningii, T. brevicompactum, T. candidum, T. caribbaeum, T. catoptron, T. cremeum, T. ceramicum, T. cerinum, T. chlorosporum, T. chromospermum, T. cinnamomeum, T. citrinoviride, T. crassum, T. cremeum, T. dingleyeae, T. dorotheae, T. effusum, T. erinaceum, T. estonicum, T. fertile, T. gelatinosus, T. ghanense, T. hamatum, T. harzianum, T. helicum, T. intricatum, T. konilangbra, T. koningii, T. koningiopsis, T. longibrachiatum, T. longipile, T. minutisporum, T. oblongisporum, T. ovalisporum, T. petersenii, T. phyllostahydis, T. piluliferum, T. pleuroticola, T. pleurotum, T. poiysporum, T. pseudokoningii, T. pubescens, T. reesei, T. rogersonii, T. rossicum, T. saturnisporum, T. sinensis, T. sinuosum, T. spirale, T. stramineum, T. strigosum, T. stromaticum, T. surrotundum, T. taiwanense, T. thailandicum, T. thelephoricolum, T. theobromicola, T. tomentosum, T. velutinum, T. virens, T. viride and T. viridescens*. A *Trichoderma* species herein can be cultivated and/or manipulated as described in *Trichoderma: Biology and Applications* (P. K. Mukherjee et al., Eds., CABI, Oxfordshire, U K, 2013), for example, which is incorporated herein by reference.

A microbial cell in certain embodiments is an algal cell. For example, an algal cell can be from any of the following: Chlorophyta (green algae), Rhodophyta (red algae), Phaeophyceae (brown algae), Bacillariophycaeae (diatoms), and Dinoflagellata (dinoflagellates). An algal cell can be of a microalgae (e.g., phytoplankton, microphytes, or planktonic algae) or macroalgae (kelp, seaweed) in other aspects. As further examples, an algal cell herein can be a *Porphyra* (purple laver), *Palmaria* species such as *P. palmata* (dulse), *Arthrospira* species such as *A. platensis* (spirulina), *Chlorella* (e.g., *C. protothecoides*), a *Chondrus* species such as *C. crispus* (Irish moss), *Aphanizomenon, Sargassum, Cochayuyo, Botryococcus* (e.g., *B. braunii*), *Dunaliella* (e.g., *D. tertiolecta*), *Gracilaria, Pleurochrysis* (e.g., *P. carteraez*), *Ankistrodesmus, Cyclotella, Hantzschia, Nannochloris, Nannochloropsis, Nitzschia, Phaeodactylum* (e.g., *P. tricornutum*), *Scenedesmus, Stichococcus, Tetraselmis* (e.g., *T. suecica*), *Thalassiosira* (e.g., *T. pseudonana*), *Crypthecodinium* (e.g., *C. cohnii*), *Neochloris* (e.g., *N. oleoabundans*), or *Schiochytrium*. An algal species herein can be cultivated and/or manipulated as described in Thompson (*Algal Cell Culture. Encyclopedia of Life Support System (EOLSS), Biotechnology Vol 1*, available at eolss.net/sample-chapters internet site), for example, which is incorporated herein by reference.

In one embodiment, the method comprises a method of delivering a protein component of an RNA-guided endonuclease (RGEN) into a microbial cell, said method comprising: contacting the microbial cell with a composition comprising the protein component of the RNA-guided endonuclease (RGEN) and at least one cell-penetrating peptide (CPP), wherein said protein component and CPP are covalently, or non-covalently, linked to each other in an RGEN protein-CPP complex, wherein said RGEN protein-CPP complex traverses (i) a cell membrane, or (ii) a cell wall and cell membrane, of the cell, thereby entering the microbial cell. Microbial cells useful for the methods and composition described herein include cells selected from *Phytophtora* species such as *Phytophtora capsici* (Lamour et al. 2012. The oomycete broad-host-range pathogen *Phytophthora capsici*. Mol. Plant Pathol. May 13(4): 329-337), *Zymoseptoria* species such as *Septoria tritici* (Testa et al. 2015. Overview of genomic and bioinformatics resources for *Zymoseptoria tritici*. Fungal Genet. Biol. June 79:13-16) and *Botrytis* species such as *Botrytis cinerea* (Hahn M. 2014. The rising threat of fungicide resistance in plant pathogenic fungi: *Botrytis* as a case study. J. Chem. Biol 7:133-141).

A protist cell herein can be selected from the class Ciliata (e.g., the genera *Tetrahymena, Paramecium, Colpidium, Colpoda, Glaucoma, Platyophrya, Vorticella, Potomacus, Pseudocohnilembus, Euplotes, Engelmanielia*, and *Stylonichia*), the subphylum Mastigophora (flagellates), the class Phytomastigophorea (e.g., the genera *Euglena, Astasia, Haematococcus*, and *Crypthecodinium*), the class Zoomastigophorea, the superclass Rhizopoda, the class Lobosea (e.g., the genus *Amoeba*), and the class Eumycetozoea (e.g., the genera *Dictyostelium* and *Physarum*), for example. Certain protist species herein can be cultivated and/or manipulated as described in *ATCC® Protistology Culture Guide: tips and techniques for propagating protozoa and algae* (2013, available at American Type Culture Collection internet site), for example, which is incorporated herein by reference. A protist can optionally be characterized as a pest/pathogen of a plant or animal (e.g., human) in certain embodiments.

A bacterial cell in certain embodiments can be those in the form of cocci, bacilli, spirochetes, spheroplasts, protoplasts, etc. Other non-limiting examples of bacteria include those that are Gram-negative and Gram-positive. Still other non-limiting examples of bacteria include those of the genera *Salmonella* (e.g., *S. typhi, S. enteritidis*), *Shigella* (e.g., *S. dysenteriae*), *Escherichia* (e.g., *E. coli*), *Enterobacter, Serratia, Proteus, Yersinia, Citrobacter, Edwardsiella, Providencia, Klebsiella, Hafnia, Ewingella, Kluyvera, Morganella, Planococcus, Stomatococcus, Micrococcus, Staphylococcus* (e.g., *S. aureus, S. epidermidis*), *Vibrio* (e.g., *V. cholerae*), *Aeromonas, Plessiomonas, Haemophilus* (e.g., *H. influenzae*), *Actinobacillus, Pasteurella, Mycoplasma* (e.g., *M. pneumonia*), *Ureaplasma, Rickettsia, Coxiella, Rochalimaea, Ehrlichia, Streptococcus* (e.g., *S. pyogenes, S. mutans, S. pneumoniae*), *Enterococcus* (e.g., *E. faecalis*), *Aerococcus, Gemella, Lactococcus* (e.g., *L. lactis*), *Leuconostoc* (e.g., *L. mesenteroides*), *Pedicoccus, Bacillus* (e.g., *B. cereus, B. subtilis, B. thuringiensis*), *Corynebacterium* (e.g., *C. diphtheriae*), *Arcanobacterium, Actinomyces, Rhodococcus, Listeria* (e.g., *L. monocytogenes*), *Erysipelothrix, Gardnerella, Neisseria* (e.g., *N. meningitidis, N. gonorrhoeae*), *Campylobacter, Arcobacter, Wolinella, Helicobacter* (e.g., *H. pylori*), *Achromobacter, Acinetobacter, Agrobacterium* (e.g., *A. tumefaciens*), *Alcaligenes, Chryseomonas, Comamonas, Eikenella, Flavimonas, Flavobacterium, Moraxella, Oligella, Pseudomonas* (e.g., *P. aeruginosa*), *Shewanella, Weeksella, Xanthomonas, Bordetella, Franciesella, Brucella, Legionella, Afipia, Bartonella, Calymmatobacterium, Cardiobacterium, Streptobacillus, Spirillum, Peptostreptococcus, Peptococcus, Sarcinia, Coprococcus, Ruminococcus, Propionibacterium, Mobiluncus, Bifidobacterium, Eubacterium, Lactobacillus* (e.g., *L. lactis, L. acidophilus*), *Rothia, Clostridium* (e.g., *C. botulinum, C. perfringens*), *Bacteroides, Porphyromonas, Prevotella, Fusobacterium, Bilophila, Leptotrichia, Wolinella, Acidaminococcus, Megasphaera, Veilonella, Norcardia, Actinomadura, Norcardiopsis, Streptomyces, Micropolysporas, Thermoactinomycetes, Mycobacterium* (e.g., *M. tuberculosis, M. bovis, M. leprae*), *Treponema, Borrelia* (e.g., *B. burgdorferi*), *Leptospira*, and *Chlamydiae*. A bacteria can optionally be characterized as a pest/pathogen of a plant or animal (e.g., human) in certain embodiments. Bacteria can be comprised in a mixed microbial population (e.g., containing other bacteria, or containing yeast and/or other bacteria) in certain embodiments.

An archaeal cell in certain embodiments can be from any Archaeal phylum, such as Euryarchaeota, Crenarchaeota, Nanoarchaeota, Korarchaeota, Aigarchaeota, or Thaumarchaeota. Archaeal cells herein can be extremophilic (e.g., able to grow and/or thrive in physically or geochemically extreme conditions that are detrimental to most life), for example. Some examples of extremophilic archaea include those that are thermophilic (e.g., can grow at temperatures between 45-122° C.), hyperthermophilic (e.g., can grow at temperatures between 80-122° C.), acidophilic (e.g., can grow at pH levels of 3 or below), alkaliphilic (e.g., can grow at pH levels of 9 or above), and/or halophilic (e.g., can grow in high salt concentrations [e.g., 20-30% NaCl]). Examples of archaeal species include those of the genera *Halobacterium* (e.g., *H. volcanii*), *Sulfolobus* (e.g., *S. solfataricus, S. acidocaldarius*), *Thermococcus* (e.g., *T. alcaliphilus, T. celer, T. chitonophagus, T. gammatolerans, T. hydrothermalis, T. kodakarensis, T. litoralis, T. peptonophilus, T. profundus, T. stetteri*), *Methanocaldococcus* (e.g., *M. thermolithotrophicus, M. jannaschii*), *Methanococcus* (e.g., *M. maripaludis*), *Methanothermobacter* (e.g., *M. marburgensis, M. thermautotrophicus*), *Archaeoglobus* (e.g., *A. fulgidus*), *Nitrosopumilus* (e.g., *N. maritimus*), *Metallosphaera* (e.g., *M. sedula*), *Ferroplasma, Thermoplasma, Methanobrevibacter* (e.g., *M. smithii*), and *Methanosphaera* (e.g., *M. stadtmanae*).

Examples of insect cells herein include *Spodoptera frugiperda* cells, *Trichoplusia ni* cells, *Bombyx mori* cells and the like. *S. frugiperda* cells include Sf9 and Sf21, for instance. *T. ni* ovary cells include HIGH FIVE cells (alias BTI-TN-5B1-4, manufactured by Invitrogen), for example. *B. mori* cells include N4, for example. Certain insect cells herein can be cultivated and/or manipulated as described in *Growth and Maintenance of Insect cell lines* (2010, Invitrogen, Manual part no. 25-0127, MAN0000030), for example, which is incorporated herein by reference. In other aspects, an insect cell can be a cell of a plant pest/pathogen such as an armyworm, black cutworm, corn earworm, corn flea beetle, corn leaf aphid, corn root aphid, European corn borer, fall armyworm, granulate cutworm, Japanese beetle, lesser cornstalk borer, maize billbug, melanotus communis, seedcorn maggot, sod webworms, sorghum midge, sorghum webworm, southern corn billbug, southern corn rootworm, southern cornstalk borer, southern potato wireworm, spider mite, stalk borer, sugarcane beetle, tobacco wireworm, white grub, aphid, boll weevil, bollworm complex, cabbage looper, tarnished plant bug, thrip, two spotted spider mite, yellow striped armyworm, alfalfa weevil, clover leaf weevil, clover root curculio, fall armyworm, grasshopper, meadow spittlebug, pea aphid, potato leafhopper, sod webworm, variegated cutworm, lesser cornstalk borer, tobacco thrip, wireworm, cereal leaf beetle, chinch bug, English grain aphid, greenbug, hessian fly, bean leaf beetle, beet armyworm, blister beetle, grape colaspis, green cloverworm, Mexican bean beetle, soybean looper, soybean stem borer, stink bug, three-cornered alfalfa hopper, velvetbean caterpillar, budworm, cabbage looper, cutworm, green june beetle, green peach aphid, hornworm, potato tuberworm, southern mole cricket, suckfly, tobacco flea beetle, vegetable weevil, or whitefringed beetle. Alternatively, an insect cell can be a cell of a pest/pathogen of an animal (e.g., human).

A nematode cell, for example, can be of a nematode from any of the following genera: *Meloidogyne* (root-knot nematode), *Pratylenchus* (lesion nematode), *Heterodera* (cyst nematode), *Globodera* (cyst nematode), *Ditylenchus* (stem and bulb nematode), *Tylenchulus* (citrus nematode), *Xiphinema* (dagger nematode), *Radopholus* (burrowing nematode), *Rotylenchulus* (reniform nematode), *Helicotylenchus* (spiral nematode), or *Belonolaimus* (sting nematode). A nematode can optionally be characterized as a pest/pathogen of a plant or animal (e.g., human) in certain embodiments. A nematode can be *C. elegans* in other aspects.

A fish cell herein can be any of those as disclosed in U.S. Pat. Nos. 7,408,095 and 7,217,564, and *Tissue Culture of Fish Cell Lines* (T. Ott, NWFHS Laboratory Procedures Manual—Second Edition, Chapter 10, 2004), for example, which are incorporated herein by reference. These references also disclose information regarding cultivating and/or manipulating fish cells. Non-limiting examples of fish cells can be from a teleost such as zebrafish, medaka, Giant rerio, or puffer fish.

A plant cell herein can be, for example, a monocot plant cell or dicot plant cell. Examples of monocot plants herein include corn (*Zea mays*), rice (*Oryza sativa*), rye (*Secale cereale*), sorghum (*Sorghum bicolor, Sorghum vulgare*), millet (e.g., pearl millet, *Pennisetum glaucum*), proso millet (*Panicum miliaceum*), foxtail millet (*Setaria italica*), finger millet (*Eleusine coracana*)), wheat (*Triticum aestivum*), sugarcane (*Saccharum* spp.), oats (*Avena*), barley (*Hordeum*), switchgrass (*Panicum virgatum*), pineapple (*Ananas*

*comosus*), banana (*Musa* spp.), palm, ornamentals, and turfgrasses. Examples of dicot plants herein include soybean (*Glycine max*), canola (*Brassica napus* and *B. campestris*), alfalfa (*Medicago sativa*), tobacco (*Nicotiana tabacum*), *Arabidopsis* (*A. thaliana*), sunflower (*Helianthus annuus*), cotton (*Gossypium arboreum*), peanut (*Arachis hypogaea*), tomato (*Solanum lycopersicum*), and potato (*Solanum tuberosum*). A plant cell may be from any part of a plant and/or from any stage of plant development.

Plant cells herein may be grown or regenerated into plants using conventional conditions, see for example, McCormick et al., (1986) *Plant Cell Rep* 5:81-4. Regenerated plants may then be grown, and either pollinated with the same strain or with a different strain, and resulting progeny having the desired characteristic (e.g., alteration) and/or comprising an introduced polynucleotide or polypeptide identified. Two or more generations may be grown to ensure that an alteration is stably maintained and inherited, and seeds harvested.

Mammalian cells in certain embodiments can be human, non-human primate (e.g., monkey, ape), rodent (e.g., mouse, rat, hamster, guinea pig), rabbit, dog, cat, cow, pig, horse, goat, or sheep cells. Other examples of mammalian cells herein include primary epithelial cells (e.g., keratinocytes, cervical epithelial cells, bronchial epithelial cells, tracheal epithelial cells, kidney epithelial cells, retinal epithelial cells); established cell lines (e.g., 293 embryonic kidney cells, HeLa cervical epithelial cells, PER-C6 retinal cells, MDBK, CRFK, MDCK, CHO, BeWo, Chang cells, Detroit 562, Hep-2, KB, LS 180, LS 174T, NCI-H-548, RPMI 2650, SW-13, T24, WI-28 VA13, 2RA, WISH, BS-C-I, LLC-MK2, Clone M-3, RAG, TCMK-1, LLC-PK1, PK-15, GH1, GH3, L2, LLC-RC 256, MH1C1, XC, MDOK, VSW, TH-1, B1 cells); any epithelial, mesenchymal (e.g., fibroblast), neural, or muscular cell from any tissue or organ (e.g., skin, heart; liver; kidney; colon; intestine; esophagus; stomach; neural tissue such as brain or spinal cord; lung; vascular tissue; lymphoid tissue such as lymph gland, adenoid, tonsil, bone marrow, or blood; spleen); and fibroblast or fibroblast-like cell lines (e.g., TRG-2, IMR-33, Don cells, GHK-21, citrullinemia cells, Dempsey cells, Detroit 551, Detroit 510, Detroit 525, Detroit 529, Detroit 532, Detroit 539, Detroit 548, Detroit 573, HEL 299, IMR-90, MRC-5, WI-38, WI-26, MiCl1, CV-1, COS-1, COS-3, COS-7, Vero, DBS-FrhL-2, BALB/3T3, F9, SV-T2, M-MSV-BALB/3T3, K-BALB, BLO-11, NOR-10, C3H/IOTI/2, HSDM1C3, KLN205, McCoy cells, Mouse L cells, SCC-PSA1, Swiss/3T3 cells, Indian muntjac cells, SIRC, Jensen cells). Methods of culturing and manipulating mammalian cells lines are known in the art.

In certain embodiments, a microbial cell can be of any pathogen and/or pest of an animal or plant. Examples of such pathogens/pests include various types of bacteria, fungi, yeast, protists, nematodes, and insects. Those skilled in the art would recognize examples of such pathogens/pests disclosed above.

As described herein (see Example 10), cell-penetrating peptides were able to deliver cargo to different eukaryotic species including *Phytophthora capsici, Septoria tritici*, and *Botrytis cinerea*.

In one embodiment, the method described herein is a method of delivering a protein component of an RNA-guided endonuclease (RGEN) into a microbial cell selected from the group consisting of *Phytophthora capsici, Septoria tritici*, and *Botrytis cinerea*, said method comprising: contacting the microbial cell with a composition comprising the protein component of the RNA-guided endonuclease (RGEN) and at least one cell-penetrating peptide (CPP), wherein said protein component and CPP are covalently, or non-covalently, linked to each other in an RGEN protein-CPP complex, wherein said RGEN protein-CPP complex traverses (i) a cell membrane, or (ii) a cell wall and cell membrane, of the cell, thereby entering the microbial cell.

A composition in certain embodiments herein can comprise at least one protein component of a guide polynucleotide/Cas endonuclease complex and at least one cell-penetrating peptide (CPP), wherein the protein component and CPP are covalently, or non-covalently, linked to each other in a polynucleotide/endonuclease protein-CPP complex, and wherein the polynucleotide/endonuclease protein-CPP complex can traverse (i) a cell membrane, or (ii) a cell wall and cell membrane, of a cell (such as a microbial cell). The guide polynucleotide and Cas endonuclease are capable of forming a complex, referred to as a "guide polynucleotide/Cas endonuclease complex", that enables the Cas endonuclease to introduce a double-strand break at a DNA target site.

The disclosed invention also concerns a method of delivering a protein component of an RNA-guided endonuclease (RGEN) into a cell (such as a microbial cell). This method comprises contacting a cell with a composition comprising the RGEN protein component and at least one cell-penetrating peptide (CPP), wherein the RGEN protein component and CPP are covalently, or non-covalently, linked to each other in an RGEN protein-CPP complex. As a result of this contacting step, the RGEN protein-CPP complex can traverse (i) a cell membrane, or (ii) a cell wall and cell membrane, of the cell, and thereby gain entry to the cell. In certain embodiments in which an RGEN protein component is associated with an RNA component (thereby forming an RGEN), the disclosed method is directed to delivering an RGEN-CPP complex into a cell. Additionally, since an RGEN can be used in RGEN-mediated DNA targeting in certain embodiments, this method can optionally be characterized as a method of targeting DNA in a cell.

This method can be practiced using any of the above-disclosed embodiments or below Examples regarding each of the method features (e.g., cell type, RGEN protein component, CPP, organelle-targeting sequence, etc.), for example. Thus, any of the features disclosed above or in the Examples, or any combination of these features, can be used appropriately to characterize embodiments of a delivery method herein. The following delivery method features are examples.

Embodiments of a delivery method herein comprise contacting a cell (such as a microbial cell) with a composition comprising an RGEN protein-CPP complex. It is believed that such contacting results in interaction of the complex with the outer surface of the cell (e.g., cell membrane, cell wall), thereby allowing the CPP component of the complex to initiate traversal of the complex across (i) a cell membrane, or (ii) a cell wall and cell membrane.

Contacting a composition comprising an RGEN protein-CPP complex with a cell (such as a microbial cell) can be done at a temperature that allows the complex to enter the cell. Such contacting can be done at any temperature between about 4 and 45° C., for example. The contacting temperature can be about 4, 15, 20, 30, 37, or 42° C. in non-limiting embodiments. The same temperature or temperature range can be maintained during the contacting step, or modified appropriately (e.g., two or more different temperatures).

Contacting a composition comprising an RGEN protein-CPP complex with a cell can be done for an amount of time that is adequate for allowing the complex to enter the cell.

For example, cells can be incubated with an RGEN protein-CPP complex for at least about 15, 30, 45, 60, 75, 90, 105, 120, 135, 150, 165, 180, 240, 300, 360, 420, 480, 540, 600, 660, or 720 minutes.

The milieu (e.g., buffer, water and salt concentrations, pH, purity of RGEN protein-CPP complex) in which the contacting is performed may be any of those conditions disclosed above regarding a composition comprising an RGEN protein-CPP complex. For example, cells can be incubated with a complex in a HEPES buffer (e.g., ~25 mM HEPES, such as 25 mM HEPES/KOH pH 7.5, 200 mM KCl, 20% glycerol, 1 mM DTT) or PBS (e.g., 1×PBS, pH 7).

One or more cells (such as microbial cells) may be contacted with a composition comprising an RGEN protein-CPP complex. A cell herein may be as it exists (i) in an organism/tissue in vivo, (ii) in a tissue or group of cells ex vivo, or (iii) in an in vitro state (e.g., cultured cells).

Entry of an RGEN protein-CPP complex into a cell herein typically refers to when a complex has completely traversed (i) a cell membrane, or (ii) a cell wall and cell membrane, and is comprised within at least the cell cytoplasm. Though not intending to be held to any particular theory or mechanism, it is believed that an RGEN protein-CPP complex held together by non-covalent linkage either remains in a complete or partial complex, or the RGEN protein component separates from the CPP component(s) of the complex, after the RGEN protein-CPP complex gains cell entry. In either case, the RGEN protein component is able to associate with a suitable RNA component herein; such association can occur in the cytoplasm, nucleus, or mitochondria, for example. This capability likewise applies to an RGEN protein-CPP complex held together by covalent linkage.

In certain embodiments of an RGEN protein delivery method, a composition herein further comprises at least one RNA component that is associated with the RGEN protein component of the RGEN protein-CPP complex (i.e., the composition comprises an RGEN-CPP complex). The RNA component in this embodiment can be as disclosed herein, comprising a sequence complementary to a target site sequence on a chromosome or episome in the microbial cell. The RGEN can bind to the target site sequence, and optionally cleave one or both DNA strands at the target site sequence. Such an embodiment can also be characterized as a method of delivering an RGEN-CPP complex into a microbial cell, or alternatively as a method of delivering an RNA into a microbial cell.

An RNA component (e.g., gRNA) for use in this embodiment can be prepared using any number of means known in the art. For example, an in vitro transcription process can be used to prepare an RNA component herein. Bacterial RNA polymerases (e.g., T7, T3, SP6) can be used to transcribe an RNA component from a suitable DNA construct encoding the RNA component in certain non-limiting embodiments. An RNA component may be processed to at least about 70%, 80%, 90%, or 95% purity with respect to other biomolecules (e.g., protein, saccharides, lipids), if desired.

To prepare a composition comprising an RNA component and an RGEN protein-CPP complex, the RNA component can be dissolved in a composition in which an RGEN protein-CPP complex is already dissolved, or vice versa (or these components can be dissolved at the same time). A molar ratio of RNA component to RGEN protein-CPP complex of at least about 0.5:1, 1.0:1, 1.5:1, 2.0:1, 2.5:1, 3.0:1, 3.5:1, or 4.0:1, for example, can be used when mixing these elements together. In certain aspects, the molar ratio of RNA component to RGEN protein-CPP complex can be about 3.0:1, or can range from about 2.5:1 to 3.5:1, 2.75:1 to 3.25:1, or 2.9:1 to 3.1:1. In these and other aspects, the concentration of an RGEN protein-CPP complex with which an RNA component is mixed can be at least about 0.5, 1.0, 1.5, 2.0, 2.5, 3.0, 3.5, 4.0, 4.5, 5.0, 6.0, 7.0, 8.0, 9.0 or 10.0 $\mu$M, or about 0.5 to 5.0 $\mu$M, 0.5 to 2.5 $\mu$M, 1.0 to 5.0 $\mu$M, 1.0 to 2.5 $\mu$M, or 2.5 to 5.0 $\mu$M. The amount of time allowed for RNA association with an RGEN protein-CPP complex to form an RGEN-CPP complex can be at least about 1, 2, 3, 4, 5, 6, 7, 8, 9, 10, 15, 20, 25, 30, 45, or 60 minutes, for example. Other conditions (e.g., temperature, buffer, water and salt concentrations, pH, purity of RGEN protein-CPP complex) in which an RNA component can be associated with an RGEN protein-CPP complex may be any of those conditions disclosed above regarding (i) a composition comprising an RGEN protein-CPP complex, or (ii) contacting an RGEN protein-CPP complex with a cell. For example, an RNA component such as a gRNA can be contacted with an RGEN protein-CPP complex in a HEPES buffer (e.g., ~25 mM HEPES, such as 25 mM HEPES/KOH pH 7.5, 200 mM KCl, 20% glycerol, 1 mM DTT), or PBS (e.g., 1×PBS, pH 7), at room temperature (e.g., about 20-25° C.) for about 15 minutes. In those embodiments in which an RGEN protein-CPP complex is held together by non-covalent linkage, association of an RNA component to an RGEN protein can comprise adding an RNA component before, at the same time of, or after incubating a CPP with the RGEN protein component.

After associating an RNA component with an RGEN protein-CPP complex the resulting composition comprising an RGEN-CPP complex (e.g., CPP-Cas9/gRNA) can be immediately contacted with cells, for example. Contact can be made in the milieu in which the RNA component and RGEN protein-CPP complex were associated (e.g., see above), for example. A composition comprising an RGEN-CPP complex can be stored at about room temperature, 4° C., or frozen (e.g., −20 or −80° C.) for later use, if desired. RGEN-CPP complex stability, and/or ability to enter cells and effect DNA targeting, can remain unchanged, or can have at least about 50%, 60%, 70%, 80%, 90%, or 95% of either respective activity, even if the complex is in a composition that has been through one, two, or more freeze-thaw cycles.

A composition comprising an RGEN protein-CPP complex or RGEN-CPP complex, for contacting with a cell, may optionally comprise one or more volume exclusion agents, which are contemplated to enhance contact points between the cell and complexes. Examples of suitable volume exclusion agents herein include glycerol and polyethylene glycol (PEG). Other examples include anionic polymer such as polyacrylate, polymethylacrylate, or anionic polysaccharidic polymers (e.g., dextran sulfate). Still other examples of volume exclusion agents are disclosed in U.S. Pat. No. 4,886,741, which is incorporated herein by reference.

In certain embodiments of an RGEN protein delivery method, a cell (such as a microbial cell) comprises an RNA component that associates with an RGEN protein component of an RGEN protein-CPP complex after the RGEN protein-CPP complex enters the cell (i.e., thereby forming an RGEN-CPP complex in the cell). The RNA component in this embodiment can be as disclosed herein, comprising a sequence complementary to a target site sequence on a chromosome or episome in the cell. The RGEN can bind to the target site sequence, and optionally cleave one or both DNA strands at the target site sequence.

One or more RNA components herein can be stably or transiently expressed in a cell (such as a microbial cell) to which an RGEN protein-CPP complex is introduced, for example. As examples of transient expression, an RGEN protein-CPP complex can be (i) delivered into a cell that has previously been modified to transiently express an RNA component, (ii) co-delivered into a cell with an RNA component, or (iii) delivered into a cell afterwhich the cell is modified for transient RNA component expression.

A DNA polynucleotide sequence comprising (i) a promoter operably linked to (ii) a nucleotide sequence encoding an RNA component can typically be used for stable and/or transient RNA component expression herein. Such a polynucleotide sequence can be comprised within a plasmid, yeast artificial chromosome (YAC), cosmid, phagemid, bacterial artificial chromosome (BAC), virus, or linear DNA (e.g., linear PCR product), for example, or any other type of vector or construct useful for transferring a polynucleotide sequence into a cell. This polynucleotide sequence can be capable of existing transiently (i.e., not integrated into the genome) or stably (i.e., integrated into the genome) in a cell. Also, this polynucleotide sequence can comprise, or lack, one or more suitable marker sequences (e.g., selection or phenotype marker).

A suitable promoter comprised in a polynucleotide sequence for expressing an RNA component herein can be constitutive or inducible, for example. A promoter in certain aspects can comprise a strong promoter, which is a promoter that can direct a relatively large number of productive initiations per unit time, and/or is a promoter driving a higher transcription level than the average transcription level of the genes in a cell comprising the strong promoter.

Examples of strong promoters useful in certain aspects herein (e.g., fungal and/or yeast cells) herein include those disclosed in U.S. Patent Appl. Publ. Nos. 2012/0252079 (DGAT2), 2012/0252093 (EL1), 2013/0089910 (ALK2), 2013/0089911 (SPS19), 2006/0019297 (GPD and GPM), 2011/0059496 (GPD and GPM), 2005/0130280 (FBA, FBAIN, FBAINm), 2006/0057690 (GPAT) and 2010/0068789 (YAT1), which are incorporated herein by reference. Other examples of strong promoters include those listed in Table 2, which also may be useful in fungal and/or yeast cells, for example.

TABLE 2

Strong Promoters

| Promoter Name | Native Gene | Reference[a] |
|---|---|---|
| XPR2 | alkaline extracellular protease | U.S. Pat. No. 4,937,189; EP220864 |
| TEF | translation elongation factor EF1-α (tef) | U.S. Pat. No. 6,265,185 |
| GPD, GPM | glyceraldehyde-3-phosphate-dehydrogenase (gpd), phosphoglycerate mutase (gpm) | U.S. Pat. Nos. 7,259,255 and 7,459,546 |
| GPDIN | glyceraldehyde-3-phosphate-dehydrogenase (gpd) | U.S. Pat. No. 7,459,546 |
| GPM/FBAIN | chimeric phosphoglycerate mutase (gpm)/fructose-bisphosphate aldolase (fba1) | U.S. Pat. No. 7,202,356 |
| FBA, FBAIN, FBAINm | fructose-bisphosphate aldolase (fba1) | U.S. Pat. No. 7,202,356 |
| GPAT | glycerol-3-phosphate O-acyltransferase (gpat) | U.S. Pat. No. 7,264,949 |
| YAT1 | ammonium transporter enzyme (yat1) | U.S. Pat. Appl. Publ. No. 2006/0094102 |
| EXP1 | export protein | U.S. Pat. No. 7,932,077 |

[a]Each reference in this table is incorporated herein by reference.

Other examples of strong promoters useful in certain embodiments herein include PGK1, ADH1, TDH3, TEF1, PHO5, LEU2, and GAL1 promoters, as well as strong yeast promoters disclosed in Velculescu et al. (Cell 88:243-251), which is incorporated herein by reference.

A promoter for stable and/or transient expression of an RNA component herein can be an RNA polymerase II (Pol II) promoter, for example. It is believed that all the above-listed strong promoters are examples of suitable Pol II promoters. Transcription from a Pol II promoter may involve formation of an RNA polymerase II complex of at least about 12 proteins (e.g., RPB1-RPN12 proteins), for example. RNA transcribed from a Pol II promoter herein typically is 5'-capped (e.g., contains an m$^7$G group at the 5'-end) and/or has a polyadenylate (polyA) tail, for example. Means for removing a 5'-cap and/or polyA tail from an RNA component can be employed, if desired, when expressing an RNA component from a Pol II promoter. Suitable means for effectively removing a 5'-cap and/or polyA tail from a Pol II-transcribed RNA component herein include appropriate use of one or more ribozymes (see below), group 1 self-splicing introns, and group 2 self-splicing introns, for example.

Alternatively, a promoter for stable and/or transient expression of an RNA component herein can be an RNA polymerase III (Pol III) promoter, for example. Such a promoter typically allows for expressing an RNA component with defined 5'- and 3'-ends, since initiation and termination of transcription with an RNA polymerase III can be controlled. Examples of Pol III promoters useful herein include U6 and H1 promoters. Other suitable Pol III promoters are disclosed in U.S. Appl. Publ. No. 2010/0160416, for example, which is incorporated herein by reference.

One or more ribozyme sequences may be used to create defined 5' and/or 3' transcript ends, such as in those embodiments in which a Pol II promoter is used for expressing an RNA component in a cell. For example, a nucleotide sequence herein encoding an RNA component may further encode a ribozyme that is upstream of the sequence encoding the RNA component. Thus, a cell in certain embodiments further comprises a DNA polynucleotide sequence comprising (i) a promoter operably linked to (ii) a nucleotide sequence encoding, in 5'-to-3' direction, a ribozyme and an RNA component. Transcripts expressed from such a polynucleotide sequence autocatalytically remove the ribozyme sequence to yield an RNA with a defined 5'-end (without a 5'-cap) but which comprises the RNA component sequence. This "autoprocessed" RNA can comprise a crRNA or gRNA, for example, and can complex with an RGEN protein component such as a Cas9, thereby forming an RGEN.

A ribozyme herein can be a hammerhead (HH) ribozyme, hepatitis delta virus (HDV) ribozyme, group I intron ribozyme, RnaseP ribozyme, or hairpin ribozyme, for example. Other non-limiting examples of ribozymes herein include Varkud satellite (VS) ribozymes, glucosamine-6-phosphate activated ribozymes (glmS), and CPEB3 ribozymes. Lilley (Biochem. Soc. Trans. 39:641-646) discloses information pertaining to ribozyme structure and activity. Examples of ribozymes that should be suitable for use herein include ribozymes disclosed in EP0707638 and U.S. Pat. Nos. 6,063,566, 5,580,967, 5,616,459, and 5,688,670, which are incorporated herein by reference. Further information regarding using ribozymes to express RNA components with defined 5' and/or 3' ends is disclosed in WO2016/025131, published Feb. 18, 2016.

In certain embodiments, a DNA polynucleotide comprising a cassette for expressing an RNA component comprises a suitable transcription termination sequence downstream of the RNA component sequence. Examples of transcription termination sequences useful herein are disclosed in U.S. Pat. Appl. Publ. No. 2014/0186906, which is herein incorporated by reference. Such embodiments typically comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more residues following the end of the RNA component sequence, depending on the choice of terminator sequence. These additional residues can be all U residues, or at least 90%, 91%, 92%, 93%, 94%, 95%, 96%, 97%, 98%, or 99% U residues, for example, depending on the choice of terminator sequence. Alternatively, a ribozyme sequence (e.g., hammerhead or HDV ribozyme) can be 3' of (e.g., 1, 2, 3, 4, 5, 6, 7, 8, 9, 10 or more nucleotides downstream) the RNA component sequence, for example. A 3' ribozyme sequence can be positioned accordingly such that it cleaves itself from the RNA component sequence; such cleavage would render a transcript ending exactly at the end of the RNA component sequence, or with 1, 2, 3, 4, 5, 6, 7, 8, 9, 10, 11, 12, 13, 14, 15, or more residues following the end of the RNA component sequence, for example.

An RNA component in other examples can be provided in the nucleus and/or cytoplasm of a cell into which an RGEN protein-CPP complex is delivered. For example, an RNA component expressed from a Pol II promoter without use of a 5'-located ribozyme sequence can be expected to exist in both the nucleus and cytoplasm. An RNA component expressed from any type of promoter (e.g. Pol II or III promoter) and using a 5'-located ribozyme sequence can be expected to exist mostly in the nucleus in other embodiments. An RNA component expressed from a Pol III promoter in certain aspects can be expected to exist mostly in the nucleus. In certain aspects, an RNA component is uncapped (e.g., by virtue of being expressed from a Pol III promoter, and/or by ribozyme autoprocessing) and typically is located in the nucleus, while in other aspects is capped and located in nuclear and cytoplasmic locations. In general, the RGEN protein component of an RGEN protein-CPP complex, once delivered into a cell, can associate with an RNA component (thereby forming an RGEN) in the cytoplasm and/or nucleus (depending on RNA component location). Such association in the nucleus is generally due to the ability of an RGEN protein component herein to localize to the nucleus as directed by an NLS.

An RGEN herein is useful for RGEN-mediated DNA targeting. Any of the above embodiments regarding delivering an RGEN protein component into a cell can be applied to a DNA targeting method. For example, an RGEN protein-CPP complex can be contacted with at least one RNA component outside of a microbial cell to form an RGEN-CPP complex for delivery into a cell for DNA targeting therein. As another example, an RGEN protein-CPP complex, after its delivery into a microbial cell, can be contacted with at least one RNA component inside a microbial cell to form an RGEN-CPP complex therein that can then mediate DNA targeting. The following disclosure regarding targeting methods refers to an "RGEN", as opposed to referring to an "RGEN-CPP complex". It would be understood that, depending on whether a covalent or non-covalent RGEN-CPP complex is used in an RGEN delivery method herein (and depending on how strong a non-covalent linkage is in embodiments employing a non-covalent RGEN-CPP complex), reference to an RGEN below refers to such an RGEN-CPP complex, accordingly.

An RGEN herein that can cleave one or both DNA strands of a DNA target sequence can be used in a DNA targeting method, for example. Such DNA targeting methods can involve HR-mediated DNA targeting if a suitable donor DNA is provided in the method. Thus, in certain embodiments, a microbial cell in a targeting method herein can comprise a donor polynucleotide comprising at least one sequence homologous to a sequence at or near a target site sequence (a sequence specifically targeted by an RGEN herein). Such embodiments can optionally be characterized in that the targeting method further comprises a step of providing a suitable donor polynucleotide to the microbial cell.

A donor polynucleotide herein can undergo HR with a sequence at or near a DNA target site if the target site contains a SSB or DSB (such as can be introduced using an RGEN herein). A "homologous sequence" within a donor polynucleotide herein can, for example, comprise or consist of a sequence of at least about 25, 50, 75, 100, 150, 200, 300, 400, 500, 600, 700, 800, 900, 1000, 2000, 3000, 4000, 5000, 6000, 7000, 8000, 9000 or 10000 nucleotides, or about 50-500, 50-550, 50-600, 50-650, or 50-700 nucleotides, that have 100% identity with a sequence at or near the target site sequence, or at least about 90%, 91%, 92%, 93%, 94%, 95%, 96%, 97%, 98%, or 99% identity with a sequence at or near the target site sequence, for example.

A donor polynucleotide herein can have two homologous sequences (homology arms), for example, separated by a sequence that is heterologous to sequence at or near a target site sequence. HR between such a donor polynucleotide and a target site sequence typically results in the replacement of a sequence at the target site with the heterologous sequence of the donor polynucleotide (i.e., a target site sequence located between target site sequences homologous to the homology arms of the donor polynucleotide is replaced by the heterologous sequence of the donor polynucleotide). In a donor polynucleotide with two homology arms, the arms can be separated by at least about 1, 2, 3, 4, 5, 10, 20, 30, 40, 50, 75, 100, 250, 500, 1000, 2500, 5000, 10000, 15000, 20000, 25000, or 30000 nucleotides (i.e., the heterologous sequence in the donor polynucleotide can be at least about 1, 2, 3, 4, 5, 10, 20, 30, 40, 50, 75, 100, 250, 500, 1000, 2500, 5000, 10000, 15000, 20000, 25000, or 30000 nucleotides in length), for example. The length (e.g., any of the lengths disclosed above for a homologous sequence) of each homology arm may be the same or different. The percent identity (e.g., any of the % identities disclosed above for a homologous sequence) of each arm with respective homologous sequences at or near the target site can be the same or different.

A DNA sequence at or near (alternatively, in the locality or proximity of) the target site sequence that is homologous to a corresponding homologous sequence in a donor polynucleotide can be within about 1, 2, 3, 4, 5, 6, 7, 8, 9, 10, 15, 20, 25, 30, 35, 40, 45, 50, 60, 70, 80, 90, 100, 150, 200, 250, 300, 450, 500, 750, 1000, 2000, 3000, 4000, 5000, 6000, 7000, 8000, 9000, 10000, 20000, 30000, 40000, 50000, or 60000 (or any integer between 1 and 60000) nucleotides (e.g., about 1-1000, 100-1000, 500-1000, 1-500, or 100-500 nucleotides), for example, from the predicted RGEN cut site (DSB or nick) in the target sequence. These nucleotide distances can be marked from the cut site to the first nucleotide of the homologous sequence, going either in the upstream or downstream direction from the cut site. For example, a sequence near a target sequence that is homologous to a corresponding sequence in a donor polynucleotide can start at 500 nucleotide base pairs downstream the predicted RGEN cut site in a target sequence. In embodiments herein employing a donor polynucleotide with two homology arms (e.g., first and second homology arms separated by a heterologous sequence), a homologous sequence (corresponding in homology with the first homology arm of a donor) can be upstream the predicted RGEN cut site, and a homologous sequence (corresponding in homology with the second homology arm of a donor) can be downstream the predicted RGEN cut site, for example. The nucleotide distances of each of these upstream and downstream homologous sequences from the predicted cut site can be the same or different, and can be any of the nucleotide distances disclosed above, for example. For instance, the 3' end of a homologous sequence (corresponding in homology with the first homology arm of a donor) may be located 600 nucleotide base pairs upstream a predicted RGEN cut site, and the 5' end of a homologous sequence (corresponding in homology with the second homology arm of a donor) may be located 400 nucleotide base pairs downstream the predicted RGEN cut site.

A donor polynucleotide in various aspects can be delivered into a cell (such as a microbial cell) at or near (e.g., within 1, 2, 3 or more hours) the time when an RGEN protein-CPP complex is delivered into the cell. Such delivery can be via by any means known in the art suitable for the particular type of cell being used. These techniques include transformation (e.g., lithium acetate transformation [*Methods in Enzymology*, 194:186-187]), transfection, biolistic impact, electroporation, and microinjection, for example. As examples, U.S. Pat. Nos. 4,880,741 and 5,071,764, and Chen et al. (*Appl. Microbiol. Biotechnol.* 48:232-235), which are incorporated herein by reference, describe DNA transfer techniques for *Y. lipolytica*. Examples of delivery modes useful in plants include *Agrobacterium*-mediated transformation and biolistic particle bombardment.

An RGEN that cleaves one or both DNA strands of a DNA target sequence can be used to create an indel in other non-limiting embodiments of DNA targeting herein. A method of forming an indel in a cell can be performed as disclosed above for HR-mediated targeting, but without further providing a donor DNA polynucleotide that could undergo HR at or near the target DNA site (i.e., NHEJ is induced in this method). Examples of indels that can be created are disclosed herein. The size of an indel may be 1, 2, 3, 4, 5, 6, 7, 8, 9, 10, or more bases, for example. An indel in certain embodiments can be even larger such as at least about 20, 30, 40, 50, 60, 70, 80, 90, 100, 110, 120, 130, 140, or 150 bases. In still other embodiments, insertions or deletions can be at least about 500, 750, 1000, or 1500 bases. When attempting to create an indel in certain embodiments, a single base substitution may instead be formed in a target site sequence. Thus, a targeting method herein can be performed for the purpose of creating single base substitution, for example.

In certain embodiments of a targeting method herein aimed at indel formation, the frequency of indel formation in a non-conventional yeast (e.g., *Y. lipolytica*) is significantly higher than what would be observed using the same or similar targeting strategy in a conventional yeast such as *S. cerevisiae*. For example, while the frequency of indel formation in a conventional yeast may be about 0.0001 to 0.001 (DiCarlo et al., *Nucleic Acids Res.* 41:4336-4343), the frequency in a non-conventional yeast herein may be at least about 0.05, 0.10, 0.15, 0.20, 0.25, 0.30, 0.35, 0.40, 0.45, 0.50, 0.55, 0.60, 0.65, 0.70, 0.75, or 0.80. Thus, the frequency of indel formation in a non-conventional yeast herein may be at least about 50, 100, 250, 500, 750, 1000, 2000, 4000, or 8000 times higher, for example, than what would be observed using the same or similar RGEN-mediated targeting strategy in a conventional yeast.

A targeting method in certain embodiments can be performed to disrupt one or more DNA polynucleotide sequences encoding a protein or a non-coding RNA. An example of such a sequence that can be targeted for disruption is one encoding a marker (i.e., a marker gene). Non-limiting examples of markers herein include screenable markers and selectable markers. A screenable marker herein can be one that renders a cell visually different under appropriate conditions. Examples of screenable markers include polynucleotides encoding beta-glucuronidase (GUS), beta-galactosidase (lacZ), and fluorescent proteins (e.g., GFP, RFP, YFP, BFP). A selectable marker herein can be one that renders a cell resistant to a selective agent or selective environment. Examples of selectable markers are auxotrophic markers such as HIS3, LEU2, TRP1, MET15, or URA3, which allow cells such as yeast cells to survive in the absence of exogenously provided histidine, leucine, tryptophan, methionine, or uracil, respectively. Other examples of selectable markers are antibiotic- or antifungal-resistance markers such as those rendering a cell resistant to ampicillin, chloramphenicol, hygromycin B, nourseothricin, phleomycin, puromycin, or neomycin (e.g., G418). Examples of these methods can optionally be characterized as marker recycling methods.

At least one purpose for disrupting a marker in certain embodiments can be for marker recycling. Marker recycling is a process, for example, comprising (i) transforming a cell with a marker and heterologous DNA sequence, (ii) selecting a transformed cell comprising the marker and the heterologous DNA sequence (where a marker-selectable cell typically has a higher chance of containing the heterologous DNA sequence), (iii) disrupting the marker, and then repeating steps (i)-(iii) as many times as necessary (using the same [or different] marker, but each cycle using a different heterologous DNA sequence) to transform cells with multiple heterologous DNA sequences. One or more heterologous sequences in this process may comprise the marker itself in the form of a donor polynucleotide(e.g., marker flanked by homology arms for targeting a particular locus). Examples of marker recycling processes herein include those using URA3 as a marker, such as in certain methods employing a yeast (e.g., a non-conventional yeast such as *Y. lipolytica*).

An RGEN herein that can bind to a DNA target site sequence, but does not cleave any strand at the target site sequence, can be used in a DNA targeting method in other embodiments. Any RGEN disclosed herein that has only dysfunctional nuclease domains, but retains specific DNA-binding activity, can be used in this type of targeting method.

In certain embodiments of DNA targeting with an RGEN having no functional nuclease domains, an RGEN can bind to a target site and modulate transcription of a polynucleotide sequence (i.e., gene transcription). Typically, an RGEN is targeted to a regulatory sequence such as a promoter (e.g., within 1-1000, 1-500, 1-250, 1-125, or 1-50 bases upstream a transcription start site), a sequence encoding a 5'-untranslated RNA sequence, or an intron (e.g., first intron) to effect transcriptional modulation of a polynucleotide sequence.

As a non-limiting example, an RGEN linked or fused to a repressor transcription factor or repressor domain thereof can be used to repress, or silence, expression of one or more polynucleotide sequences. An RGEN in certain alternative embodiments can, by itself (without a repressor or domain thereof), inhibit gene expression; such an RGEN can be targeted such that it inhibits binding and/or movement of RNA transcriptional machinery necessary for transcription. A method incorporating any repressing RGEN can optionally be characterized as a gene silencing or transcriptional silencing method. The level of transcriptional down-regulation in a silencing method can be about 100% (gene completely silenced), or at least about 30% (gene moderately silenced), 40%, 50%, 60%, 70%, 80%, 90%, or 95% (gene substantially silenced), for example, compared to the transcription level before application of a repressing RGEN.

An RGEN linked or fused to an activator transcription factor or activator domain thereof can be used to upregulate expression of one or more polynucleotide sequences. A method incorporating such an activating RGEN can optionally be characterized as a transcriptional up-regulation or activation method. The level of transcriptional up-regulation in such a method can be at least about 25%, 50%, 75%, 100%, 250%, 500%, or 1000%, for example, compared to the transcription level before application of an activating RGEN.

In certain embodiment, an RGEN that can bind to a DNA target site sequence, but preferably does not cleave any strand at the target site sequence, can be used as a diagnostic tool (e.g., probe for detecting a DNA sequence). An RGEN protein component in DNA probe can be linked to a reporter agent such as a reporter protein (e.g., fluorescent protein such as GFP), for example. Specific DNA binding of the RGEN-reporter protein, as specified by the RNA component of the RGEN, can be incorporated in a detection system accordingly, taking advantage of the activity of the reporter agent. Flow cytometry (e.g., flow-activated cell sorting [FACS]) and fluorescence in situ hybridization (FISH) are examples of suitable detection systems herein that use a fluorescent reporter.

A targeting method herein can be performed in such a way that two or more DNA target sites are targeted in the method, for example. Such a method can optionally be characterized as a multiplex method. Two, three, four, five, six, seven, eight, nine, ten, or more target sites can be targeted at the same time in certain embodiments. A multiplex method is typically performed by a targeting method herein in which multiple different RNA components are provided, each designed to guide an RGEN to a unique DNA target site. For example, two or more different RNA components can be used to prepare a mix of RGEN-CPP complexes in vitro (e.g., following a procedure disclosed herein for associating an RNA component with an RGEN protein-CPP complex), which mix is then contacted with a cell.

Another aspect of multiplex targeting herein can comprise providing two or more different RNA components in a cell which associate with the RGEN protein components of RGEN protein-CPP complexes that have traversed into the cell. Such a method can comprise, for example, providing to the cell (i) individual DNA polynucleotides, each of which express a particular RNA component that, and/or (ii) at least one DNA polynucleotide encoding two or more RNA components (e.g., see below disclosure regarding tandem ribozyme-RNA component cassettes).

A multiplex method can optionally target DNA sites very close to the same sequence (e.g., a promoter or open reading frame, and/or sites that are distant from each other (e.g., in different genes and/or chromosomes). A multiplex method in other embodiments can be performed with (for HR) or without (for NHEJ leading to indel and/or base substitution) suitable donor DNA polynucleotides, depending on the desired outcome of the targeting (if an endonuclease- or nickase-competent RGEN is used). In still other embodiments, a multiplex method can be performed with a repressing or activating RGEN as disclosed herein. For example, multiple repressing RGENs can be provided that down-regulate a set of genes, such as genes involved in a particular metabolic pathway.

A multiplex method in certain embodiments can comprise providing to a cell a DNA polynucleotide comprising (i) a promoter operably linked to (ii) a sequence comprising more than one ribozyme-RNA component cassettes (i.e., tandem cassettes). A transcript expressed from such a DNA polynucleotide can have, for example, 2, 3, 4, 5, 6, 7, 8, 9, 10, or more cassettes. A 3' ribozyme sequence can optionally be included following all or some RNA component sequences to allow cleavage and separation of the RNA component from downstream transcript sequence (i.e., tandem cassettes may comprise one or more ribozyme-RNA component-ribozyme cassettes). A DNA polynucleotide herein for expressing tandem ribozyme-RNA component-ribozyme cassettes can be designed such that there are about 10, 20, 30, 40, 50, 60, 70, 80, 90, 100, or more nucleotides between each cassette (e.g., non-coding spacer sequence). The distances between each cassette may be the same or different.

Any construct or vector comprising a DNA polynucleotide encoding an RNA component described herein can be introduced into a cell by any means known in the art suitable for the particular type of cell being used. For example, any of the means disclosed above for delivering a donor DNA into a cell can be employed.

Certain embodiments herein concern a method of modifying or altering a target site in the genome of a microbial cell, wherein the method comprises contacting the microbial cell with a guide polynucleotide and Cas endonuclease covalently or non-covalently linked to a CPP, wherein the guide polynucleotide and CPP-Cas endonuclease are capable of forming a complex that enables the Cas endonuclease to introduce a double-strand break at the target site in the genome of the microbial cell. The modification or alteration of the target site can include (i) a replacement of at least one nucleotide, (ii) a deletion of at least one nucleotide, (iii) an insertion of at least one nucleotide, or (iv) any combination of (i)-(iii).

Certain embodiments herein concern a polynucleotide sequence comprising a nucleotide sequence encoding a fusion protein that comprises a protein component of an RNA-guided endonuclease (RGEN) and at least one cell-penetrating peptide (CPP). Any fusion protein as disclosed herein, for example, can be encoded by the nucleotide sequence. The nucleotide sequence may optionally be in operable linkage with a promoter sequence. Certain embodiments include, for example, a polynucleotide (e.g., vector or construct) comprising at least one open reading frame encoding any RGEN protein-CPP fusion disclosed herein. Such a coding region can optionally be operably linked to a promoter sequence suitable for expressing an RGEN protein-CPP fusion in a cell (e.g., bacteria cell; eukaryotic cell such as a yeast, insect, or mammalian cell) or in an in vitro protein expression system, for example. Examples of a vector or construct include circular (e.g., plasmid) and non-circular (e.g., linear DNA such as an amplified DNA sequence) polynucleotide molecules.

Certain embodiments herein concern a method of producing an RGEN protein-CPP fusion protein comprising the steps of: providing a polynucleotide sequence having a nucleotide sequence encoding the RGEN protein-CPP fusion protein, and expressing the RGEN protein-CPP fusion protein from the polynucleotide sequence, thereby producing the RGEN protein-CPP fusion protein. The expression step in such a method can optionally be performed in a cell (e.g., bacteria cell such as *E. coli*; eukaryotic cell such as a yeast [e.g., *S. cerevisiae*], insect, or mammalian cell). Alternatively, expression of an RGEN protein-CPP fusion protein can be performed in an in vitro protein expression system (e.g., cell-free protein expression systems such as those employing rabbit reticulocyte lysate or wheat germ extract). Also, the RGEN protein-CPP fusion protein produced in the expression step can optionally be isolated. Such isolation can be performed in a manner that produces a composition having any of the above-disclosed features (e.g., purity, pH, buffer, and/or salt level), for example.

Non-limiting examples of compositions and methods disclosed herein include:

1. A composition comprising at least one protein component of an RNA-guided endonuclease (RGEN) and at least one cell-penetrating peptide (CPP), wherein the protein component and CPP are covalently, or non-covalently, linked to each other in an RGEN protein-CPP complex, and wherein the RGEN protein-CPP complex can traverse (i) a cell membrane, or (ii) a cell wall and cell membrane, of a cell.
2. The composition of embodiment 1, wherein the protein component of the RGEN is associated with at least one RNA component that comprises a sequence complementary to a target site sequence on a chromosome or episome in the cell, wherein the RGEN can bind to the target site sequence, and optionally cleave one or both DNA strands at the target site sequence.
3. The composition of embodiment 2, wherein the RNA component comprises a guide RNA (gRNA) comprising a CRISPR RNA (crRNA) operably linked to a trans-activating CRISPR RNA (tracrRNA).
4. The composition of embodiment 2, wherein the RGEN can cleave one or both DNA strands at the target site sequence.
5. The composition of embodiment 1, wherein the RGEN comprises a CRISPR-associated (Cas) protein-9 (Cas9) amino acid sequence.
6. The composition of embodiment 1, wherein the RGEN protein component and CPP are covalently linked.
7. The composition of embodiment 1, wherein the RGEN protein component and CPP are non-covalently linked.
8. The composition of embodiment 1, wherein the CPP is cationic or amphipathic.
9. The composition of embodiment 1, wherein the CPP comprises:
   (i) a CPP from an Epstein-Barr virus Zebra trans-activator protein,
   (ii) a CPP having 6 or more contiguous arginine residues,
   (iii) a transportan-10 (TP10) CPP, or
   (iv) a CPP from a vascular endothelium cadherin protein.
10. The composition of embodiment 1, wherein the RGEN protein-CPP complex can traverse a cell wall and cell membrane of a cell.
11. A cell comprising the composition according to embodiment 1.
12. A method of delivering a protein component of an RNA-guided endonuclease (RGEN) into a cell, the method comprising:
    contacting the cell with a composition comprising the protein component of the RNA-guided endonuclease (RGEN) and at least one cell-penetrating peptide (CPP),
    wherein the protein component and CPP are covalently, or non-covalently, linked to each other in an RGEN protein-CPP complex,
    wherein the RGEN protein-CPP complex traverses (i) a cell membrane, or (ii) a cell wall and cell membrane, of the cell, thereby entering the cell.
13. The method of embodiment 12, wherein:
    (i) the composition further comprises at least one RNA component that is associated with the protein component of the RGEN; or
    (ii) the cell comprises the RNA component, wherein the RNA component associates with the protein component of the RGEN after the RGEN protein-CPP complex enters the cell;
    wherein the RNA component comprises a sequence complementary to a target site sequence on a chromosome or episome in the cell, wherein the RGEN can bind to the target site sequence, and optionally cleave one or both DNA strands at the target site sequence.
14. The method of embodiment 13, wherein the RGEN can cleave one or both DNA strands at the target site sequence.
15. The method of embodiment 14, wherein the cell further comprises a donor polynucleotide comprising at least one sequence homologous to a sequence at or near the target site sequence.
16. The method of embodiment 12, wherein the cell is a non-mammalian cell.
17. A composition comprising at least one protein component of a guide polynucleotide/Cas endonuclease complex and at least one cell-penetrating peptide (CPP), wherein the protein component and CPP are covalently, or non-covalently, linked to each other in a guide polynucleotide/Cas endonuclease-CPP complex, and wherein the guide polynucleotide/Cas endonuclease-CPP complex can traverse (i) a cell membrane, or (ii) a cell wall and cell membrane, of a cell, wherein the cell is optionally a plant cell.
18. The composition of embodiment 17, wherein the Cas endonuclease is a plant-optimized Cas9 endonuclease.
19. The composition of embodiment 17, wherein the guide polynucleotide comprises
    (i) a first nucleotide sequence domain that is complementary to a nucleotide sequence in a target DNA, and
    (ii) a second nucleotide sequence domain that interacts with a Cas endonuclease,
    wherein the first nucleotide sequence domain and the second nucleotide sequence domain are composed of deoxyribonucleic acids (DNA), ribonucleic acids (RNA), or a combination thereof.
20. The composition of embodiment 17, wherein the guide polynucleotide/Cas endonuclease-CPP complex can traverse the cell wall of a plant cell.
21. The composition of embodiment 17, wherein the CPP comprises:
    (i) a CPP from an Epstein-Barr virus Zebra trans-activator protein,
    (ii) a CPP having 6 or more contiguous arginine residues,
    (iii) a transportan-10 (TP10) CPP,
    (iv) a CPP from a vascular endothelium cadherin protein, or
    (vi) a CPP selected from the group consisting of a synthetic nona-arginine CPP, a histidine-rich nona-arginine CPP, and a Pas nona-arginine CPP.
22. The composition of embodiment 20, wherein the plant cell is a monocot or a dicot cell.
23. The composition of embodiment 22, wherein the monocot is selected from the group consisting of maize, rice, sorghum, rye, barley, wheat, millet, oats, sugarcane, turfgrass, and switchgrass.

24. The composition of embodiment 22, wherein the dicot is selected from the group consisting of soybean, canola, alfalfa, sunflower, cotton, tobacco, peanut, potato, tobacco, Arabidopsis, and safflower.

25. A method for modifying a target site in the genome of a cell, the method comprising providing a guide polynucleotide, a cell-penetrating peptide (CPP) and a Cas endonuclease to the cell, wherein the guide polynucleotide, Cas endonuclease and CPP are covalently, or non-covalently, linked to each other in a guide polynucleotide/Cas endonuclease-CPP complex, and wherein the guide polynucleotide/Cas endonuclease-CPP complex can traverse (i) a cell membrane, or (ii) a cell wall and cell membrane, of a cell, wherein the cell is optionally a plant cell.

26. The method of embodiment 25, further comprising identifying at least one plant cell that has a modification at the target site, wherein the modification at the target site is selected from the group consisting of (i) a replacement of at least one nucleotide, (ii) a deletion of at least one nucleotide, (iii) an insertion of at least one nucleotide, and (iv) any combination of (i)-(iii).

27. The method of embodiment 25, wherein the plant cell is a monocot or dicot cell.

28. A composition comprising at least one protein component of an RNA-guided endonuclease (RGEN) and at least one cell-penetrating peptide (CPP), wherein the protein component and CPP are covalently, or non-covalently, linked to each other in an RGEN protein-CPP complex, and wherein the RGEN protein-CPP complex can traverse (i) a cell membrane, or (ii) a cell wall and cell membrane, of a microbial cell.

29. The composition of embodiment 28, wherein the protein component of the RGEN is associated with at least one RNA component that comprises a sequence complementary to a target site sequence on a chromosome or episome in the microbial cell, wherein the RGEN can bind to the target site sequence, and optionally cleave one or both DNA strands at the target site sequence.

30. The composition of embodiment 28, wherein the RGEN protein-CPP complex can traverse a cell wall and cell membrane of a microbial cell.

31. A microbial cell comprising the composition according to embodiment 28.

32. A method of delivering a protein component of an RNA-guided endonuclease (RGEN) into a microbial cell, the method comprising:
  contacting the microbial cell with a composition comprising the protein component of the RNA-guided endonuclease (RGEN) and at least one cell-penetrating peptide (CPP),
  wherein the protein component and CPP are covalently, or non-covalently, linked to each other in an RGEN protein-CPP complex,
  wherein the RGEN protein-CPP complex traverses (i) a cell membrane, or (ii) a cell wall and cell membrane, of the microbial cell, thereby entering the microbial cell.

33. The method of embodiment 32, wherein:
  (i) the composition further comprises at least one RNA component that is associated with the protein component of the RGEN; or
  (ii) the microbial cell comprises the RNA component, wherein the RNA component associates with the protein component of the RGEN after the RGEN protein-CPP complex enters the microbial cell;
  wherein the RNA component comprises a sequence complementary to a target site sequence on a chromosome or episome in the microbial cell, wherein the RGEN can bind to the target site sequence, and optionally cleave one or both DNA strands at the target site sequence.

34. The method of embodiment 33, wherein the RGEN can cleave one or both DNA strands at the target site sequence.

34. The method of embodiment 34, wherein the microbial cell further comprises a donor polynucleotide comprising at least one sequence homologous to a sequence at or near the target site sequence.

36. The method of embodiment 32, wherein the microbial cell is a yeast cell.

37. A composition comprising at least one protein component of a guide polynucleotide/Cas endonuclease complex and at least one cell-penetrating peptide (CPP), wherein the protein component and CPP are covalently, or non-covalently, linked to each other in a guide polynucleotide/Cas endonuclease-CPP complex, and wherein the guide polynucleotide/Cas endonuclease-CPP complex can traverse (i) a cell membrane, or (ii) a cell wall and cell membrane, of a microbial cell.

38. The composition of embodiment 37, wherein the guide polynucleotide/Cas endonuclease-CPP complex can traverse the cell wall of the microbial cell.

39. A method for modifying a target site in the genome of a microbial cell, the method comprising providing a guide polynucleotide, a cell-penetrating peptide (CPP) and a Cas endonuclease to the microbial cell, wherein the guide polynucleotide, Cas endonuclease and CPP are covalently, or non-covalently, linked to each other in a guide polynucleotide/Cas endonuclease-CPP complex, and wherein the guide polynucleotide/Cas endonuclease-CPP complex can traverse (i) a cell membrane, or (ii) a cell wall and cell membrane, of a microbial cell.

23. The method of embodiment 39, further comprising identifying at least one microbial cell that has a modification at the target site, wherein the modification at the target site is selected from the group consisting of (i) a replacement of at least one nucleotide, (ii) a deletion of at least one nucleotide, (iii) an insertion of at least one nucleotide, and (iv) any combination of (i)-(iii).

EXAMPLES

The disclosed invention is further defined in the following Examples. It should be understood that these Examples, while indicating certain preferred aspects of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Example 1

Vectors for Expressing a Cas9-CPP (Cell-Penetrating Peptide) Fusion Protein in *E. coli*

In this example, vectors designed for inducible expression of translational fusion proteins comprising Cas9 protein and a cell-penetrating peptide (CPP) were produced and tested for expression in *E. coli*. Cas9-CPP fusion proteins were shown to express in *E. coli* as expected, and subsequently purified.

The open reading frame of the Cas9 gene from *Streptococcus pyogenes* M1 GAS (SF370) was codon-optimized for expression in *Yarrowia* per standard techniques, yielding SEQ ID NO:1. DNA sequence encoding a simian virus 40 (SV40) monopartite nuclear localization signal (NLS) plus a short linker (4 amino acids) was incorporated after the last sense codon of SEQ ID NO:1 to render SEQ ID NO:2. SEQ ID NO:2 encodes the amino acid sequence shown in SEQ ID NO:3. The last seven amino acids of SEQ ID NO:3 encode the added NLS, whereas residues at positions 1369-1372 of SEQ ID NO:3 encode the added linker. The *Yarrowia* codon-optimized Cas9-NLS sequence (SEQ ID NO:2) was linked to a *Yarrowia* constitutive promoter, FBA1 (SEQ ID NO:4), by standard molecular biology techniques. A *Yarrowia* codon-optimized Cas9 expression cassette containing the constitutive FBA1 promoter, *Yarrowia* codon-optimized Cas9, and the SV40 NLS is set forth in SEQ ID NO:5. This Cas9 expression cassette (SEQ ID NO:5) was cloned into the plasmid pZUF rendering construct pZUFCas9 (FIG. 1, SEQ ID NO:6).

The *Yarrowia* codon-optimized Cas9-NLS sequence was PCR-amplified from pZUFCas9 (SEQ ID NO:6) using standard molecular biology techniques. Primers for the PCR reaction were SEQ ID NO:7 (Forward) and SEQ ID NO:8 (Reverse), which added a 5' EcoRI site and 3' HindIII site, respectively, to the amplified DNA product. The added 5' EcoRI site replaced the ATG start codon of the Cas9-NLS open reading frame (ORF) in the amplified product. The amplified product (SEQ ID NO:9) was digested with EcoRI and HindIII, and then purified using Zymoclean™ and concentrator columns (Zymo Research, Irvine, Calif.). The purified DNA fragment was cloned into the EcoRI and HindIII sites of plasmid pBAD/HisB from Life Technologies (Carlsbad, Calif.) (FIG. 2A, SEQ ID NO:10) to create plasmid construct pRF48 (FIG. 2B, SEQ ID NO:11). Plasmid pRF48 is capable of expressing, in *E. coli*, a Cas9-NLS comprising a hexahistidine (6xHis) tag at its N-terminus.

To fuse a cell-penetrating peptide (CPP) sequence to Cas9-NLS, individual DNA polynucleotide sequences were prepared, each codon-optimized for expression in *E. coli* and comprising sequence encoding a 6xHis tag linked to a particular CPP amino acid sequence: Zebra peptide (ECD-SELEIKRYKRVRVASRKCRAKFKQLLQHY-REVAAAKSSENDRLRLLLKQMC, SEQ ID NO:12), from the Epstein-Barr virus Zebra trans-activator protein; pVEC peptide (LLIILRRRIRKQAHAHSK, SEQ ID NO:13), from a murine endothelial cadherin protein; TP10 peptide (AGYLLGKINLKACAACAKKIL, SEQ ID NO:14), from a neuropeptide galanin protein; and synthetic arginine-rich "PolyR" peptide (GGGGRRRRRRRRRLLLL, SEQ ID NO:15). Each DNA polynucleotide sequence included a 5'-end NcoI restriction site and a 3'-end EcoRI site to create cloning sequences structured as follows: NcoI-6xHis-CPP-EcoRI (SEQ ID NOs:16-19). Each of SEQ ID NOs:16-19 was individually cloned into the NcoI and EcoRI sites of pRF48, thereby creating plasmid constructs capable of expressing certain 6xHis-CPP-Cas9-NLS fusion proteins in *E. coli*. In particular, plasmid construct pRF144 (FIG. 3A, SEQ ID NO:20) was prepared for expressing a 6xHis-Zebra CPP-Cas9-NLS fusion; plasmid construct pRF145 (FIG. 3B, SEQ ID NO:21) was prepared for expressing a 6xHis-PolyR CPP-Cas9-NLS fusion; plasmid construct pRF146 (FIG. 3C, SEQ ID NO:22) was prepared for expressing a 6xHis-TP10 CPP-Cas9-NLS fusion, and plasmid construct pRF162 (FIG. 3D, SEQ ID NO:23) was prepared for expressing a 6xHis-pVEC CPP-Cas9-NLS fusion.

Each of plasmids pRF48, pRF144, pRF145, pRF146 and pRF162 was individually transformed into TOP10 competent cells (Life Technologies). Cells were grown overnight at 37° C. with shaking (220 rpm) in L broth (Miller) containing 0.4% (w/v) glucose and 100 µg/mL ampicillin. Each pre-culture was diluted 1:100 in 2xYT medium containing 100 µg/mL ampicillin and further grown at 37° C. with shaking (220 rpm). When cultures reached an $OD_{600}$ of about 0.5, protein expression from each plasmid was induced by adding L-arabinose to a final concentration of 0.2% (w/v). The cultures were grown for an additional 18 hours at 18° C. with shaking (200 rpm). Cells were pelleted at 5000xg for 15 minutes at 4° C. Medium was disposed of and cell pellets were frozen at −80° C. for at least 4 hours. Cell pellets were thawed for 15 minutes on ice and resuspended in 15 mL of lysis buffer (20 mM tris pH 7.5, 500 mM NaCl, 1 mM $MgCl_2$, 10 mM imidazole, 120 units/mL DNaseI, 1 mM PMSF, 1 mM DTT) per liter of original culture. Cells were lysed by passage twice through a large French pressure cell at 16000 psi. Cell debris was pelleted at 20000xg for 30 minutes at 4° C. Supernatants were transferred to a 50-mL conical tubes, to which 2 ml of a 50% slurry of Ni-NTA resin (Qiagen) was added for binding the 6xHis Tag of each expressed fusion protein. Each tube was slowly rotated at 4° C. for 1 hour and then applied to an empty gravity column through which the supernatant was allowed to flow. Flow-through sample (75 µL) was taken, added to 25 µL of 4x-reduced Laemmeli buffer, and stored on ice. The resin was washed four times in each column with 5 ml of wash buffer (20 mM tris pH 7.5, 500 mM NaCl, 10 mM imidazole, 1 mM PMSF, 1 mM DTT). A sample (75 µL) was taken from each wash, added to 25 µL of 4x-reduced Laemmeli buffer, and stored on ice. 1-ml aliquots of elution buffer (20 mM Tris pH 7.5, 500 mM NaCl, 1 mM $MgCl_2$, 500 mM imidazole, 1 mM PMSF, 1 mM DTT) were applied to the resin in each column and allowed to incubate for 10 minutes. Protein elution was monitored by absorbance at 280 nm. A sample (75 µL) was taken from each elution, added to 25 µL of 4x-reduced Laemmeli buffer, and stored on ice. For each plasmid expression experiment, fractions containing eluted protein from the column were combined, loaded into 10000 MWCO dialysis membrane, and dialyzed against dialysis buffer (25 mM HEPES/KOH pH 7.5, 200 mM KCl, 20% glycerol, 1 mM DTT) at 4° C. for at least 14 hours. The protein concentration of each dialysate was determined using the Bradford assay and absorbance at 565 nm. Purified protein was split into two aliquots, one of which was frozen at −80° C. and the other stored on ice at 4° C. Samples taken during the column purification process for each plasmid expression experiment were heated at 95° C. for 5 minutes and loaded onto an 8% (w/v) tris-glycine polyacrylamide resolving gel with a 4% (w/v) stacking gel. Proteins were electrophoretically separated at 200 volts for 30 minutes and stained with Coomassie blue. The gel for the 6xHis-Zebra-Cas9-NLS purification process is shown in FIG. 4 as an example.

Thus, four different CPP-Cas9 fusion proteins were expressed and isolated. These fusion proteins represent examples of RGEN protein-CPP complexes herein.

Example 2

Expressing Short Guide RNA (sgRNA) by In Vitro Transcription

In this example, a DNA sequence was designed that encodes an sgRNA fused to ribozymes at its 5'- and 3'-ends (referred to as "RGR"), respectively. The RGR sequence allowed for in vitro transcription by T7 RNA polymerase of an sgRNA with precisely defined ends.

FIG. 5 illustrates an sgRNA molecule, which is a single RNA molecule containing two regions, a variable targeting domain (VT) (guide sequence) and Cas endonuclease recognition (CER) domain (SEQ ID NO:24 represents an example of a CER). The VT region can be a 20mer of RNA polynucleotide that has identity to a targeted nucleic acid molecule, for example. The VT domain specifies a target site for cleavage in the target site that lies 5' of a PAM motif. The CER domain interacts with Cas9 protein and allows the VT domain to interact and direct the Cas9 protein cleavage (Jinek et al., *Science* 337:816-821). Both VT and CER domains are required for the function of an sgRNA.

The addition of 5' HammerHead (HH) and 3' Hepatitis Delta Virus (HDV) ribozymes to an sgRNA sequence allows expression of the sgRNA from any promoter without consideration for certain transcriptional requirements of some RNA polymerases (e.g., T7 RNA polymerase requires one transcribed G residue directly after initiation of transcription, but works best with three transcribed G residues). When such sgRNA is expressed, the ribozymes present in the pre-sgRNA transcript autocleave, thereby separating from the transcript leaving an unmodified sgRNA.

A DNA sequence encoding an sgRNA that targets the Can1-1 locus (SEQ ID NO:25) in *Yarrowia lipolytica* was prepared; this sgRNA comprises SEQ ID NO:24 as its CER domain. The sgRNA-encoding sequence was linked at its 5'-end to sequence encoding an HH ribozyme (SEQ ID NO:26) and at its 3'-end to a sequence encoding an HDV ribozyme (SEQ ID NO:27), such that the first 6 bases of the HH ribozyme were a reverse compliment to the first 6 bases of the VT region of the sgRNA. This particular RGR sgRNA is encoded by SEQ ID NO:28. The RGR sgRNA of SEQ ID NO:28 was then linked to a T7 RNA polymerase promoter (SEQ ID NO:29) via standard molecular biology techniques to create plasmid pRF46 (SEQ ID NO:30).

T7-RGR sgRNA-encoding sequence was PCR-amplified from plasmid pRF46 (SEQ ID NO:30) using standard techniques. Primers for the PCR reaction were SEQ ID NO:31 (T7 forward primer) and SEQ ID NO:32 (gRNArev1 reverse primer). The PCR product was purified by ethanol precipitation and resuspended in ddH$_2$O; this DNA was used as template in an in vitro transcription reaction. Template DNA was added to a final concentration of 150 nM in 20-µL in vitro transcription reactions (MEGAshortscript™ T7 Kit, Life Technologies). Reactions were allowed to proceed for various times (2 hours, 4 hours, 6 hours, and overnight) to determine suitable conditions for in vitro transcription (FIG. 6). The reactions were then treated with 10 units of DNaseI for 15 minutes at 37° C. to remove template DNA. RNA was precipitated using ethanol and standard protocols. Each 20-µl in vitro transcription reaction produced between 60 and 100 µg of RNA.

Thus, sgRNA with defined 5'- and 3'-ends was synthesized in vitro. As demonstrated in Example 3 below, in vitro transcribed sgRNA can be associated with a Cas9-CPP fusion protein to form an RGEN-CPP complex.

Example 3

Specific In Vitro Cleavage of Target DNA Sequence Using Cas9-CPP Fusion Protein Complexed with sgRNA In this example, the targeting endonuclease function of Zebra CPP-Cas9 fusion protein (comprising SEQ ID NO:39) in complex with an sgRNA was tested to confirm that fusion with a CPP does not hinder Cas9 endonuclease activity.

An in vitro Can1 cleavage assay DNA polynucleotide (SEQ ID NO:35) containing the Can1-1 target sequence of SEQ ID NO:25 was PCR-amplified from *Y. lipolytica* cells (ATCC 20362) and purified using standard techniques. Primers for the PCR reaction were SEQ ID NO:33 (IV-up forward primer) and SEQ ID NO:34 (IV-down reverse primer).

Purified Zebra CPP-Cas9 fusion protein (600 ng, prepared in Example 1), sgRNA targeting the Can1-1 target site (250 ng, prepared in Example 2), NEBuffer 3.1 (New England BioLabs, Ipswich, Mass.), and Can1 cleavage assay DNA (150 ng, SEQ ID NO:35) were mixed in a 10-µL reaction (volume brought up to final volume with ddH$_2$O). As negative controls, reactions lacking either Zebra CPP-Cas9 fusion protein or sgRNA were also prepared. As a positive control, wild type Cas9 protein (PNA Bio, Thousand Oaks, Calif.) was used in a reaction instead of Zebra CPP-Cas9. The reactions were incubated at 37° C. for 60 minutes. RNaseI (4 µg) was then added to each reaction and incubated at 37° C. for 15 minutes to degrade the sgRNA. Stop solution (1 µL; 30% [w/v] glycerol, 1.2% [w/v] SDS, 250 mM EDTA, pH 8.0) was added to terminate the reactions, which were then further incubated for 15 minutes at 37° C. Each reaction was loaded onto a 1.2% FlashGel™ (Lonza, Basel, Switzerland) and electrophoresed for 10 minutes at 200 volts (FIG. 7). The target DNA cleavage pattern rendered by Zebra CPP-Cas9 was consistent with the cleavage pattern rendered by wild type Cas9 (FIG. 7), thereby indicating that Zebra CPP-Cas9 functions normally in vitro. Furthermore, this activity was not inhibited using Zebra CPP-Cas9/sgRNA that had been subjected to two freeze-thaw cycles.

Thus, a CPP-Cas9 fusion protein complexed with a suitable sgRNA (i.e., an example of an RGEN-CPP complex) had specific DNA cleavage activity. This activity was shown to be similar with the activity of a wild type Cas9-sgRNA complex, thereby indicating that CPP fusion does not inhibit Cas9-sgRNA endonucleolytic function. While the CPP-Cas9 fusion protein in this example comprised SEQ ID NO:39 (Zebra CPP-Cas9), it is contemplated that a CPP-Cas9 fusion protein comprising SEQ ID NO:40, 41, or 42, for example, also has cleavage activity when associated with a suitable sgRNA as an RNA component.

Example 4

Delivery of a CPP-Cas9/sgRNA Complex into Yeast Cells and Cleavage of Target DNA Therein In this example, Zebra CPP-Cas9 fusion protein (comprising SEQ ID NO:39) in complex with an sgRNA (Zebra CPP-Cas9/sgRNA) was tested for the ability to enter yeast cells after simple contact with the cells. Zebra CPP-Cas9/sgRNA specific for Can1-1 was able to enter cells and cleave the Can1 gene, thereby rendering cells to be canavanine-resistant.

*Y. lipolytica* yeast cells (ATCC 20362) were grown in YPD (2% glucose, 2% peptone, 1% yeast extract) liquid medium at 30° C. with shaking (220 rpm) to OD$_{600}$=0.5 (approximately 5×10$^6$ cells per mL of culture). Purified Zebra CPP-Cas9 fusion protein (prepared in Example 1) and sgRNA targeting the Can1-1 target site (prepared in Example 2) were mixed in a 1:3 molar ratio, respectively, in the dialysis buffer used in Example 1 and pre-incubated at room temperature for 15 minutes to allow the sgRNA to associate with the Zebra CPP-Cas9. 5×10$^5$ *Y. lipolytica* cells were mixed into the Zebra CPP-Cas9/sgRNA preparation such that the final concentration of Zebra CPP-Cas9 was 1 µM, 2.5 µM, or 5 µM. Cells were also mixed with 5 µM final concentration Zebra CPP-Cas9 alone (no sgRNA as RNA component) as a negative control. All the cell-Cas9 preparations were incubated at 30° C. with shaking (220 rpm) for 2 hours. The cells were then serially diluted 1000- and 10000-fold. Each serial dilution (100 µL) was plated onto complete medium lacking arginine (CM-Arg) and allowed to recover for 48 hours at 30° C.

Colonies of the $10^{-3}$-dilution plates were counted to determine the total number of cells plated. Colonies were transferred to CM-Arg plates with canavanine (60 µg/mL) via replica-plating technique. Colonies were allowed to grow at 30° C. for 48 hours. The number of canavanine-resistant colonies were scored and divided by the total number of colonies (from plates without canavanine) to determine a mutation frequency for each case. Contacting cells with Zebra CPP-Cas9/sgRNA complexes yielded colonies that were resistant to canavanine at frequencies of about 2% to 10% of the total colonies (FIG. 8). This canavanine-resistance is expected to be due to loss of Can1 gene function by indel formation at/near the predicted Cas9 cleavage site in the Can1 gene coding sequence. However, contacting cells with Zebra CPP-Cas9 alone (no sgRNA) did not yield canavanine-resistant colonies (FIG. 8), indicating that canavanine-resistance in the experimental cells was dependent on sgRNA-based specificity given to CPP-Cas9 protein. Given the nature of yeast cells, the CPP-Cas9/sgRNA complexes likely had to traverse both cell wall and cell membrane structures to mediate specific DNA targeting.

Thus, a CPP-Cas9 fusion protein complexed with a suitable sgRNA (i.e., an example of an RGEN-CPP complex) is able to enter yeast cells (traverse cell wall and cell membrane) and target a specific DNA sequence therein. While the CPP-Cas9 fusion protein in this example comprised SEQ ID NO:39 (Zebra CPP-Cas9), it is contemplated that a CPP-Cas9 fusion protein comprising SEQ ID NO: 40, 41, or 42, for example, also has cell-entry activity, and specific DNA targeting activity in cells, when associated with a suitable sgRNA as an RNA component.

Example 5

CPP-Facilitated Cas9/sgRNA Complex Delivery into Plant Cells and Cleavage of Target DNA Therein CPP-facilitated protein delivery into soybean cells can be tested by incubating soybean callus cells with DS-RED fluorescent proteins fused to CPPs. Fluorescent signals are expected in CPP-DS-RED treatments, but not in controls incubated with DS-RED proteins only. Various CPPs can be tested in this manner to help identify the most effective CPPs for plant cell penetration and delivery of protein cargo. Some examples of CPPs that can be tested include:
  (i) a CPP from an Epstein-Barr virus Zebra trans-activator protein,
    (ii) a CPP having 6 or more contiguous arginine residues,
    (iii) a transportan-10 (TP10) CPP,
    (iv) a CPP from a vascular endothelium cadherin protein, or
    (vi) a CPP selected from the group consisting of a synthetic nona-arginine CPP, a histidine-rich nona-arginine CPP and a Pas nona-arginine CPP. Examples of a synthetic nona-arginine CPP, a histidine-rich nona-arginine CPP and a Pas nona-arginine CPP are disclosed in, for example, Liu et al. (*Advanced Studies in Biology* 5(2):71-88, HIKARI Ltd).

In vitro translated Cas9 proteins and synthetic sgRNA can be mixed with CPPs, by themselves or in a fusion (e.g., CPP-DS-RED above), and incubated with soybean callus to test if Cas9/sgRNA can be transported into the cells. Once in the cells, the Cas9/sgRNA complex can recognize a genomic target specified by the sgRNA targeting sequence to make DNA double strand breaks (DSBs). Spontaneous repair of the DSBs by cell machinery can result in mutations through non-homologous end joining (NHEJ), or gene integration through homologous recombination if appropriate donor DNA is present. CPPs can also be covalently linked to Cas9 proteins for potentially better efficiency. The success of CPP-Cas9/sgRNA delivery into soybean cells, and thus the transfer of the CPP-Cas endonuclease complex across a plant cell wall and plant cell membrane, can be verified by the detection of mutations or gene integrations at the specific target site by PCR analysis, for example.

Example 6

Expression and Purification of CPP-dsREDexpress Proteins from *E. coli* Cells

To rapidly assess the ability of a given cell-penetrating peptide to enter a specific cell type CPP fusions to the dsREDexpress protein (SEQ ID NO: 85) were created, expressed in *E. coli* cells, and purified. The CPP-dsREDexpress protein fusions are a tool that allows rapid assessment of cargo delivery into a given cell type by a given CPP. This allows selection of a species, cell type, or strain specific CPP molecule to maximize delivery of cargo in a rapid and high-throughput manner by assessing cellular fluorescence by microscopic or flow cytometric analysis.

An *E. coli* codon optimized dsREDexpress gene (SEQ ID NO: 86) was synthesized (IDT DNA) and cloned into the NcoI/HinDIII sites of pBAD/HisB (SEQ ID NO: 87) creating pRF161 (SEQ ID NO: 88). The *E. coli* codon optimized dsREDexpress contained an internal EcoRI site such that digestion of the plasmid with NcoI/EcoRI would allow replacement of the his tag with various his tag-CPP sequences to create his tag-CPP-dsREDexpress fusion expression plasmids. Various his-tag-CPP fusions; TAT (SEQ ID NO: 89), TLM (SEQ ID NO: 90), MPG1(SEQ ID NO: 91), pep1 (SEQ ID NO: 92), and CFFKDEL (SEQ ID NO: 93); were codon optimized for *E. coli* and flanked with in frame 5' NcoI and 3' EcoRI sites (SEQ ID NO: 94-98 respectively) and cloned using standard techniques into the NcoI/EcoRI sites of pRF161 (SEQ ID NO: 88) replacing the his tag sequence with the corresponding his tag-CPP fusion and generating plasmids pRF224 (his-TAT-dsREDexpress SEQ ID NO: 99), pRF214 (his-TLM-dsREDexpress SEQ ID NO: 100), pRF213 (his-MPG1-dsREDexpress SEQ ID NO: 101), pRF217 (his-pep1-dsREDexpress SEQ ID NO: 102), pRF216 (his-CFFKDEL-dsREDexpress SEQ ID NO: 103). Sequences of the inserted fragments were verified using standard sequencing techniques and oligo 36 (SEQ ID NO: 104).

*E. coli* codon optimized His-Zebra (SEQ ID NO: 105), His-tp10 (SEQ ID NO: 106), and His-pVEC (SEQ ID NO: 107) were PCR amplified from pRF144 (SEQ ID NO 108), pRF162 (SEQ ID NO 109), and pRF146 (SEQ ID NO: 110) respectively using oligo 36 (SEQ ID NO: 104) and oligo 153 (SEQ ID NO: 111) with standard PCR techniques. PCR fragments were cloned into the NcoI/EcoRI sites of pRF161 (SEQ ID NO: 88) creating plasmids pRF186 (his-Zebra-dsREDexpress SEQ ID NO:112), pRF192 (his-tp10-dsRE- Dexpress SEQ ID NO: 113), and pRF190 (his-pVEC-dsRE-Dexpress SEQ ID NO: 114). Sequences were verified using oligo 36 (SEQ ID NO: 104).

His tagged CPP-dsREDexpress fusion proteins were expressed using standard techniques. In brief, cells were precultured in either 10 ml ZYM-505 (1% N-Z amine, 0.5% yeast extract, 5% glycerol, 1.0% dextrose, 25 mM Na$_2$HPO$_4$, 25 mM KH$_2$PO$_4$, 50 mM NH$_4$Cl, 5 mM Na$_2$SO$_4$, 1× trace metals (Teknova), 5×10$^{-5}$% Thiamine, 2 mM MgCl$_2$, 100 μg/ml Ampicillin) or lysogeny broth (1% Tryptone, 0.5% yeast extract, 1% sodium chloride, 100 μg/ml Ampicillin, 0.4% dextrose) in 125 ml flasks for 12-16 hours at 37° C. and 220 RPM. Precultures were diluted 1:1000 (ZYM-505) in 500 ml ZYM-5052 (1% N-Z amine, 0.5% yeast extract, 5% glycerol, 0.5% dextrose, 2% L-arabinose, 25 mM Na$_2$HPO$_4$, 25 mM KH$_2$PO$_4$, 50 mM NH$_4$Cl, 5 mM Na$_2$SO$_4$, 1× trace metals (Teknova), 5×10$^{-5}$% Thiamine, 2 mM MgCl$_2$, 100 μg/ml Ampicillin) or 1:100 (Lysis broth) in 500 ml 2×YT (1.6% Tryptone, 1% Yeast extract, 0.5% NaCl, 100 μg/ml ampicillin) and grown at 37° C. 220 RPM in 2.9 L Fernbach flasks to OD$_{600}$~0.5. L-arabinose was added to a final concentration of 0.1% to 2× YT cultures and all cultures were shifted to 18° C. 220R\PM for 20-30 hours for protein expression. Cells were harvested at 5000 RPM for 10 minutes, spent medium was discarded and cell pellets frozen at −80° C.

Cell pellets were thawed and resuspended in Denaturing lysis buffer (50 mM Tris pH8.0, 150 mM NaCl, 8M Urea, 20 mM Imidazole) and lysed via passage through a French pressure cell at 16,000 PSI twice. Solid precipitates were removed from the supernatant by centrifugation at 10,000 g 4° C. for 15 minutes. 20 μl of clarified extract was mixed with 20 μl of 2× Laemmli buffer (4% SDS, 20% Glycerol, 100 mM DTT, 0.004% bromophenol blue, 125 mM Tris pH 6.8), heated to 95° C. for 5 minutes and frozen at −20° C. to save for analysis. Clarified extract was mixed with 6 ml of 50% (v/v) Nickel-NTA-agarose slurry for 1 hour at room temperature. Beads were pelleted from mixture at 2000 RPM for 5 minutes. Supernatant was removed and a 20 μl sample was taken as for the clarified extract. The pelleted beads were resuspended in 10 ml of denaturing lysis buffer and applied to a gravity flow chromatography column. The liquid was allowed to flow out leaving a bed of packed beads. The bed was washed with a series washes using different ratios of wash buffer 1 (50 mM Tris pH8.0, 150 mM NaCl, 8M Urea, 20 mM Imidazole) and wash buffer 2 (50 mM Tris pH 8.0, 500 mM NaCl, 20 mM Imidazole) to step down the concentration of the denaturant (urea) and step up the concentration of NaCl and allow the protein to refold on the column. In brief the column was washed with (Buffer 1: Buffer 2): 10 ml of 1:0 (8M urea 150 mM NaCl), 10 ml of 7:1 (7M Urea, 194 mM NaCl), 10 ml of 3:1 (6M Urea, 238 mM NaCl) 10 ml of 5:3 (5M Urea, 281 mM NaCl), 10 ml of 1:1 (4M Urea, 325 mM NaCl), 20 ml of 3:5 (3M Urea, 369 mM NaCl), 20 ml of 1:3 (2M Urea, 413 mM NaCl), 20 ml of 3:13 (1.5M Urea, 434 mM NaCl), 20 ml of 1:5 (1M urea, 456 mM NaCl), 20 ml of 1:15 (0.5M Urea, 478 mM NaCl), and 30 ml of 0:1 (0M Urea, 500 mM NaCl). Protein was eluted in native elution buffer (50 mM Tris pH8.0, 500 mM NaCl, 10% Glycerol, 500 mM Imidazole) in 10×1 ml fractions. Fractions containing the eluted dsRED-express or CPP-dsREDexpress protein were red in color. Red fractions were combined and dialyzed in 10,000 MWCO regenerated cellulose dialysis membrane against 1000 volumes of dialysis buffer (50 mM Tris pH 8.0, 10% glycerol) overnight at room temperature. Protein solution was removed from dialysis membrane and filter sterilized using a 0.22 μM Tuffryn® membrane. 20 μl of protein solution was processed as for the clarified cell extract.

Samples taken during the purification in Laemmli buffer were heated to 95° C. for 5 minutes and loaded onto a 12.5% PAGE gel. The gel was run at 200 volts constant for 1 hour and stained using simply blue stain. An example of a representative PAGE gel for the purification of CPP-dsRE-Dexpress tagged proteins is shown in FIG. 9. Total protein concentration for each purified protein was determined using Pierce™ Coomassie Plus assay with bovine serum albumin as a standard. The concentration of each purified CPP-dsREDexpress fusion is given in Table 3.

TABLE 3

Concentration of purified dsREDexpress protein fusions.

| Protein | mg/ml | μM |
|---|---|---|
| dsREDexpress (SEQ ID NO: 700) | 3.8 | 137 |
| MPG1-dsREDexpress (SEQ ID NO: 751) | 0.5 | 17 |
| pVEC-dsREDexpress (SEQ ID NO: 752) | 2.0 | 68 |
| CFFKDEL-dsREDexpress (SEQ ID NO: 753) | 1.5 | 54 |
| TLM-dsREDexpress (SEQ ID NO: 754) | 2.5 | 86 |
| Zebra-dsREDexpress (SEQ ID NO: 755) | 0.5 | 18 |
| pep1-dsREDexpress (SEQ ID NO: 756) | 0.3 | 10 |
| tp10-dsREDexpress (SEQ ID NO: 757) | 0.9 | 33 |

Example 7

Expression and Purification of Additional CPP-Cas9 Proteins from E. coli Cells

The delivery of Cas9 into different cell types may require Cas9 tagged with different CPP molecules. In order to isolate various CPP-Cas9 fusion proteins different CPPs were fused to Cas9 in an E. coli expression vector. These proteins were expressed and purified from E. coli cells for use in CPP mediated delivery of Cas9/sgRNA ribonucleoprotein complex to cells.

In order to make His-CFFKDEL-Cas9 (SEQ ID NO: 115) and His-MPG1-Cas9 (SEQ ID NO: 116) fusion expression cassettes the NcoI/EcoRI fragments of pRF216 (CFFKDEL SEQ ID NO: 103) or pRF213 (MPG1 SEQ ID NO: 101) were cloned into the same sites of the Cas9 protein expression plasmid pRF48 (SEQ ID NO: 117) using standard techniques generating plasmids pRF243 (his-CFFKDEL-Cas9 SEQ ID NO: 118) and pRF238 (his-MPG1-Cas9, SEQ ID NO: 119) respectively. Correct construction of the MPG1-Cas9 or CFFKDEL-Cas9 fusion cassettes was confirmed via Sanger sequencing with oligo 36 (SEQ ID NO: 104).

His tagged CPP-Cas9 fusion proteins were expressed using standard techniques. In brief, cells were precultured in either 10 ml ZYM-505 (1% N-Z amine, 0.5% yeast extract, 5% glycerol, 1.0% dextrose, 25 mM Na$_2$HPO$_4$, 25 mM KH$_2$PO$_4$, 50 mM NH$_4$Cl, 5 mM Na$_2$SO$_4$, 1× trace metals (Teknova), 5×10$^{-5}$% Thiamine, 2 mM MgCl$_2$, 100 μg/ml Ampicillin) or lysogeny broth (1% Tryptone, 0.5% yeast extract, 1% sodium chloride, 100 μg/ml Ampicillin, 0.4% dextrose) in 125 ml flasks for 12-16 hours at 37° C. and 220 RPM. Precultures were diluted 1:1000(ZYM-505) in 500 ml ZYM-5052 (1% N-Z amine, 0.5% yeast extract, 5% glycerol, 0.5% dextrose, 2% L-arabinose, 25 mM Na$_2$HPO$_4$, 25 mM KH$_2$PO$_4$, 50 mM NH$_4$Cl, 5 mM Na$_2$SO$_4$, 1× trace metals (Teknova), 5×10$^{-5}$% Thiamine, 2 mM MgCl$_2$, 100 μg/ml Ampicillin) or 1:100 (Lysis broth) in 500 ml 2×YT (1.6% Tryptone, 1% Yeast extract, 0.5% NaCl, 100 μg/ml ampicillin) and grown at 37° C. 220 RPM in 2.9 L Fernbach flasks to $OD_{600}$~0.5. L-arabinose was added to a final concentration of 0.1% to 2×YT cultures and all cultures were shifted to 18° C. 220R\PM for 20-30 hours for protein expression. Cells were harvested at 5000 RPM for 10 minutes, spent medium was discarded and cell pellets frozen at −80° C. Proteins were purified as described in Example 1. The final concentrations of the purified CPP-Cas9 proteins as determined by Coomasie Plus assay (Pierce™) are listed in Table 4.

TABLE 4

Concentration of purified CPP-Cas9 proteins.

| Protein | mg/ml | µM |
| --- | --- | --- |
| Zebra-Cas9 (SEQ ID NO: 758) | 1.5 | 9 |
| CFFKDEL-Cas9 (SEQ ID NO: 730) | 4.6 | 28 |
| MPG1-Cas9 (SEQ ID NO: 731) | 3.8 | 23 |
| pVEC-Cas9 (SEQ ID NO: 759) | 2.5 | 15 |

Example 8

CPP-Cas9/gRNA Mediated Gene Targeting in E. coli Cells

This example demonstrates the treatment of Escherichia coli cells with CPP-Cas9/sgRNA ribonucleoprotein complexes with sgRNAs targeting the galK gene of E. coli. The entry of the CPP-Cas9/sgRNA into the cell allows targeting and cleavage to occur within the galK gene leading to gene inactivation by error-prone DNA repair mechanisms which can be phenotypically monitored as resistance to galactose. This method depends on delivery of Cas9/sgRNA cargo to the cells via CPP-mediated delivery.

The galK gene of E. coli (SEQ ID NO: 120) is responsible for a galactose sensitive phenotype seen in galE mutants in the presence of the sugar galactose. As galactose enters the cell it is phosphorylated by galactokinase, the product of the galK gene (SEQ ID NO: 120). Galactose phosphate is toxic to the cell. In wild-type cells the galactose phosphate is further metabolized by the products of the galE (SEQ ID NO: 121) and galT (SEQ ID NO: 122) genes and used as a carbon source. In galE or galT loss-of-function mutants galactose phosphate accumulates leading to cell death. Therefore, loss of function mutations in the galK gene can be selected in the background of a galE mutant as allowing colony formation in the presence of galactose.

In order to produce sgRNA (SEQ ID NO: 135) targeting the galK gene (SEQ ID NO: 120) at the galK2-1 target site (SEQ ID NO: 134) an in vitro transcription template (SEQ ID NO: 131) was produced. First a PCR product of the DNA encoding the CER domain (SEQ ID NO: 123) was amplified from pRF291 (SEQ ID NO: 125) using CER forward (SEQ ID NO: 126) and universal reverse primers (SEQ ID NO: 127) in a standard PCR reaction (SEQ ID NO: 124). The CER encoding PCR product (SEQ ID NO: 124) was purified using Zymo™ clean and concentrate 25 columns and eluted in 35 µl of $ddH_2O$. Amplification of the sgRNA in vitro transcription template used a multiplex PCR containing 4 primers, a universal forward primer containing the T7 promoter (SEQ ID NO: 128), a target specific forward primer containing some of the T7 promoter and some of the target site (SEQ ID NO: 129), a target reverse primer containing some of the target site and overlap with the CER domain (SEQ ID NO: 130), and the universal reverse primer (SEQ ID NO: 127). A PCR reaction was run using Phusion flash master mix containing 15 nM CER domain PCR product (SEQ ID NO: 124), 1 µM each the universal forward (SEQ ID NO: 128) and reverse primers (SEQ ID NO: 127) and 300 nM each target forward (SEQ ID NO: 129) and target reverse (SEQ ID NO: 130) primers. The PCR reaction was cycled as for a standard reaction. sgRNA in vitro transcription template (SEQ ID NO: 131) was purified using Zymo clean and concentrate 25 columns and eluted in 35 µl of $ddH_2O$. The sgRNA in vitro transcription template (SEQ ID NO: 131) contained the T7 promoter (SEQ ID NO: 132), the DNA encoding the galK2-1 variable targeting domain (SEQ ID NO: 133), and the DNA encoding the CER domain (SEQ ID NO: 125) The in vitro transcription reaction to create the galK2-1 sgRNA (SEQ ID NO: 135) was performed as described in Example 2.

CPP delivery of Cas9/sgRNA nucleoprotein complexes was performed by growing a strain of E. coli deleted for galE in lysogeny broth (1% Tryptone, 0.5% Yeast Extract, 1% NACl) overnight at 37° C., 220 RPM. The culture was diluted 1:100 in fresh lysogeny broth and grown at 37° C., 220 RPM for 2 hours to obtain cells in exponential growth phase. CPP-Cas9 (pvEC-Cas9 (SEQ ID NO: 144), Zebra-Cas9 (SEQ ID NO: 143), MPG1-Cas9 (SEQ ID NO: 116), CFFKDEL-Cas9 (SEQ ID NO: 115)) were incubated at 10 µM final concentration either in the presence or absence of 10 µM galK2-1 sgRNA (SEQ ID NO: 135) in a 50 µl volume for 30 minutes at room temperature. For the treatment 1.2 ml of cells were pelleted at 3000 RPM for 3 minutes, supernatant was discarded and cells were resuspended in 600 µl of LB containing 2× nuclease buffer (200 mM NaCl, 100 mM Tris-HCl, 20 mM $MgCl_2$, 200 µg/ml BSA pH 7.9). 50 µl of the cell suspension was mixed with each reaction as well as gRNA only control and no treatment. Samples were incubated at 37° C., 220 RPM for 4 hours. 100 µl of $10^{-3}$, $10^{-4}$, and $10^{-5}$ dilutions of the samples were plated on lysogeny broth plates to obtain a viable cell count at the end of the treatment, the remainder of the reaction was plated onto lysogeny broth plates and incubated overnight at 37° C. Viable cells were counted from the $10^{-5}$ dilution to determine the number of viable colony forming units (CFU) plated on the sample lysogeny broth plate. The sample plates were replica plated via standard techniques to minimal A medium (1 g/L $(NH_4)_2SO_4$, 4.5 g/L $KH_2PO_4$, 10.5 g/L $K_2HPO_4$, 0.5 g/L sodium Citrate.$2H_2O$, 1 mM $MgSO_4.7H_2O$, $5\times10^{-5}$% Thiamine) solidified with 1.5% (w/v) Bacto agar containing 0.2% (w/v) glycerol and 0.2% (w/v) galactose as carbon sources. The plates were incubated at 37° C. for 24 hours and then scored for formation of colonies. Each CFU from a galE strain on a plate containing galactose represents a gene inactivation event of the galK gene. The results of the replica plating are shown in Table 5.

TABLE 5

Frequency of galK gene inactivation in galE mutant E. coli cells treated with CPP-Cas9/sgRNA.

| Cas9 protein | sgRNA | CPU on galactose | CPU plated on galactose | Frequency of $Gal^R$ CPU | Fold Frequency $Gal^R$/ untreated $Gal^R$ frequency |
| --- | --- | --- | --- | --- | --- |
| None | None | 21 | $1.65 \times 10^8$ | $1.27 \times 10^{-7}$ | 1.00 |
| pVEC-Cas9 | None | 21 | $1.18 \times 10^8$ | $1.78 \times 10^{-7}$ | 1.39 |
| pVEC-Cas9 | galK2-1 | 15 | $1.23 \times 10^8$ | $1.22 \times 10^{-7}$ | 0.96 |

TABLE 5-continued

Frequency of galK gene inactivation in galE mutant
E. coli cells treated with CPP-Cas9/sgRNA.

| Cas9 protein | sgRNA | CPU on galactose | CPU plated on galactose | Frequency of Gal$^R$ CPU | Fold Frequency Gal$^R$/ untreated Gal$^R$ frequency |
|---|---|---|---|---|---|
| MPG1-Cas9 | None | 22 | $1.34 \times 10^8$ | $1.65 \times 10^{-7}$ | 1.29 |
| MPG1-Cas9 | galK2-1 | 16 | $1.11 \times 10^8$ | $1.44 \times 10^{-7}$ | 1.13 |
| Zebra-Cas9 | None | 29 | $1.89 \times 10^8$ | $1.53 \times 10^{-7}$ | 1.20 |
| Zebra-Cas9 | galK2-1 | 25 | $8.88 \times 10^7$ | $2.82 \times 10^{-7}$ | 2.21 |
| CFFKDEL-Cas9 | None | 29 | $1.24 \times 10^8$ | $2.34 \times 10^{-7}$ | 1.84 |
| CFFKDEL-Cas9 | galK2-1 | 63 | $1.24 \times 10^8$ | $5.10 \times 10^{-7}$ | 4.00 |
| None | galK2-1 | 31 | $1.42 \times 10^8$ | $2.19 \times 10^{-7}$ | 1.72 |

The treatment of E. coli cells with CPP-Cas9/sgRNA ribonucleoprotein complexes in some cases enhanced the frequency of galK inactivation around 4 fold over the background of untreated cells. This enhancement was not seen in cells treated with only CPP-Cas9 or sgRNA only suggesting that the increased inactivation of the galK gene was due to the CPP-Cas9/sgRNA ribonucleoprotein entering the cell and making DNA double-stranded breaks at the galK2-1 target site within the galK gene.

Example 9

Delivery of CPP-dsREDexpress Protein to Archeal Cells

In order to test the delivery of cargo using cell-penetrating peptides to Archeal cells and determine candidate CPPs that cross the archeal cell wall which includes elements that are similar to bacterial and eukaryotic cell walls (eg. phospholipids) and membranes and elements that are distinctly archeal (eg. S-layer) archeal cells were treated with CPP-dsREDexpress protein fusions. The CPPs identified in this screen could be used to deliver other cargo (eg. Cas9/sgRNA ribonucleoprotein complex) to Archeal cells.

The archeon Halobacterium salinarum ATCC19700 was grown on medium 213 (250 g/L NaCl, 10 g/L MgSO$_4$.7H$_2$O, 5 g/L KCl, 0.2 g/L CaCl$_2$.6H$_2$O, 10 g/L Yeast extract, 2.5 g/L Tryptone) solidified with 1.5% Bacto agar at 37° C. until colonies formed (4 days). A single colony was used to inoculate 50 ml of medium 213 in a 250 ml flask. The culture was grown at 37° C. 220 RPM until the OD$_{600}$ reached approximately 0.5 indicating exponential growth phase. 100 µl of cells were mixed with either No protein, 5 µM dsREDexpress (SEQ ID NO: 85), 5 µM MPG1-dsREDexpress (SEQ ID NO: 136), 5 µM pVEC-dsREDexpress (SEQ ID NO: 137), 5 µM CFFKDEL-dsREDexpress (SEQ ID NO: 138), 5 µM TLM-dsREDexpress (SEQ ID NO: 139), 5 µM pep1-dsREDexpress (SEQ ID NO: 141), or 5 µM tp10 dsRED-express (SEQ ID NO: 142) in a 24 well block. Mixtures were incubated for 4 hours at 37° C. 220 RPM. Cells were washed twice with medium 213 lacking tryptone and yeast extract and resusepended in 100 µl of medium 213 lacking tryptone and yeast extract. Cells were analyzed for flourecense in the red channel of an Accuri C5 flow cytometer to determine which CPP tags had delivered the dsREDexpress cargo to H. salinarum cells. The untreated cells were used to create an analysis gate for the flow cytometry data between non-red and red cells such that the gate created a false positive frequency of 0.2% of the untreated cells falling in the red gate (Table 6).

TABLE 6

CPP delivery of dsREDexpress to H. salinarum.

| Treatment | Percent of population in red cell gate ± standard deviation[1] | Fold increase in red population over dsREDexpress alone |
|---|---|---|
| No dsREDexpress | 0.21 ± 0.06 | 0.73 |
| dsREDexpress | 0.29 ± 0.21 | 1.00 |
| MPG1-dsREDexpress | 0.37 ± 0.08 | 1.27 |
| pVEC-dsREDexpress | 16.87 ± 9.90 | 57.50 |
| CFFKDEL-dsREDexpress | 0.33 ± 0.14 | 1.14 |
| TLM-dsREDexpress | 2.03 ± 1.02 | 6.93 |
| pep1-dsREDexpress | 0.36 ± 0.18 | 1.23 |
| tp10-dsREDexpress | 0.91 ± 0.27 | 3.09 |

[1]Data represents three replicates ± standard deviation.

The delivery of the dsREDexpress cargo into archeal cells demonstrates that at least three of the cell-penetrating peptides (pVEC, TLM, tp10) are capable of delivering a protein cargo to the archeal cells with an efficiency as high as more than 50 fold that of the delivery of the dsREDexpress protein alone suggesting that these three CPP motifs can be used to deliver other cargo to archeal cells (eg. Cas9 ribonucleoprotein complex). Additionally the CPP motifs deliver cargo to as much 16% of the entire cell population suggesting that deliver of cargo by CPP to archeal cells is an efficient process.

Example 10

Delivery of CPP-dsREDexpress Protein to Eukaryotic Cells

To test the ability of cell-penetrating peptides to deliver cargo to different eukaryotic species a panel of three species, Phytophthora capsici (Oomycete), Septori tritici (True Fungus), and Botrytis cinerea (True Fungus) was treated with various CPP-dsREDexpress fusions. The delivery of dsREDexpress cargo was monitored for various CPP moieties by FACS analysis to determine the percentage of cells to which the cargo was delivered. CPPs that are capable of delivering the dsREDexpress cargo to these cells which suggests that the CPPs would be capable of delivering other cargos to these classes of eukaryotic cells (eg. Cas9/sgRNA ribonucleoprotein complex).

P. capsici was grown on V8 medium (20% V8 juice, 4.5 g/L CaCO$_3$) solidified with 1.8% Bacto Agar at 23° C. in the dark for 3 days. The plate was then placed in the light at 23° C. for an additional 7 days. Plates were chilled at 4° C. for 30 minutes. Water was placed on the plate to just cover the surface and allowed to incubate for 30 minutes at room temperature. Liquid was removed to harvest zoospores. Zoospores were confirmed via microscopic analysis. An equal volume of 2× encystment medium (40 g/L Tryptone, 10 g/L Yeast extract, 200 ml/L 10×SOC salts [5.84 g/L NaCl, 1.86 g/L KCl, 20.3 g/L MgCl$_2$.6H$_2$O, 24.6 g/L MgSO$_4$.7H$_2$O, 36 g/L Dextrose], 36.4 g/L Sorbitol, 1.47 g/L CaCl$_2$.2H$_2$O) was added to the zoospores and gently mixed. Zoospores in enzystment medium were incubated for 20 minutes at room temperature. Encystment was confirmed microscopically. Spores were pelleted and resuspended in an equal volume of YMA medium (2 g/L Yeast extract, 4 g/L Malt extract) and counted using a hemocytometer. Zoospores were diluted to $3 \times 10^7$ spores/ml in YMA. 100 µl of Zoospores in YMA were mixed with various dsREDexpress fusion proteins (New example 5, table N1) to a final concentration of 5 µM protein. Mixtures were incubated at 25° C. 400 RPM for 2 hours. Cells were washed twice with phosphate buffered saline (PBS) (8 g/L NaCl, 0.2 g/L KCl, 1.44 g/L Na$_2$HPO$_4$.2H$_2$O, 0.24 g/L KH$_2$PO$_4$ pH 6.8) and resuspended in a final volume of 200 µl PBS. Uptake of dsREDexpress fusion proteins was monitored using flow cytometry as for *Halobacterium salinarium* (Example 9). The percent of cells to which the cargo was successfully delivered was determined by drawing an arbitrary gate in the dsREDexpress treated cells such that 0.1% of the population scored as a false positive red event (1:1000 cells). The results of this treatment can be seen in Table 7. pVEC, pep1, and tp10 produce 5.8, 5.5, and 1.8 fold more red cells than the dsREDexpress treated cells alone suggesting that these CPP moieties might be candidates for delivering other cargo to Oomycetes (eg. Cas9/sgRNA ribonucleoprotein complex)

TABLE 7

CPP delivery of dsREDexpress to *Phytophora capsici*.

| Treatment | Percent of population in red cell gate ± standard deviation[1] | Fold increase in red population over dsREDexpress alone |
|---|---|---|
| dsREDexpress | 0.10 ± 0.03 | 1.00 |
| pVEC-dsREDexpress | 0.56 ± 0.16 | 5.79 |
| CFFKDEL-dsREDexpress | 0.01 ± 0.01 | 0.07 |
| TLM-dsREDexpress | 0.00 ± 0.00 | 0.00 |
| pep1-dsREDexpress | 0.53 ± 0.29 | 5.52 |
| Tp10-dsREDexpress | 0.17 ± 0.14 | 1.76 |
| MPG-dsREDexpress | 0.00 ± 0.00 | 0.00 |
| Zebra-dsREDexpress | 0.03 ± 0.05 | 0.34 |

[1]Data represents three biological replicates ± standard deviation

*B. cinerea* was grown on PDA medium (24 g/L potato dextrose broth) solidified with 1.8% Bacto agar in the dark for 5 to 10 days. Conidia were harvested in water with a sterile plastic spreader and filtered through 2 layers of cheesecloth. Conidia were counted on a hemocytometer and diluted to 3×10$^7$ conidia per ml in YMA medium. 100 µl of conidia in YMA were mixed with various dsREDexpress fusion proteins (New example 5, table N1) to a final concentration of 5 µM protein. Mixtures were incubated at 25° C. 400 RPM for 2 hours. Cells were washed twice with phosphate buffered saline (PBS) (8 g/L NaCl, 0.2 g/L KCl, 1.44 g/L Na$_2$HPO$_4$.2H$_2$O, 0.24 g/L KH$_2$PO$_4$ pH 6.8) and resuspended in a final volume of 200 µl PBS. Uptake of dsREDexpress fusion proteins was monitored using flow cytometry as for *Halobacterium* salinarium (Example 8). The percent of cells to which the cargo was successfully delivered was determined by drawing an arbitrary gate in the dsREDexpress treated cells such that 0.1% of the population scored as a false positive red event (1:1000 cells). The results of this treatment can be seen in Table 8.

TABLE 8

CPP delivery of dsREDexpress to *Botrytis cinerea*

| Treatment | Percent of population in red cell gate ± standard deviation[1] | Fold increase in red population over dsREDexpress alone |
|---|---|---|
| dsREDexpress | 0.12 ± 0.04 | 1.00 |
| pVEC-dsREDexpress | 0.08 ± 0.10 | 0.68 |
| CFFKDEL-dsREDexpress | 0.03 ± 0.01 | 0.22 |
| TLM-dsREDexpress | 0.01 ± 0.01 | 0.05 |
| pep1-dsREDexpress | 0.01 ± 0.01 | 0.05 |

TABLE 8-continued

CPP delivery of dsREDexpress to *Botrytis cinerea*

| Treatment | Percent of population in red cell gate ± standard deviation[1] | Fold increase in red population over dsREDexpress alone |
|---|---|---|
| Tp10-dsREDexpress | 0.03 ± 0.02 | 0.24 |
| MPG-dsREDexpress | 0.01 ± 0.02 | 0.11 |
| Zebra-dsREDexpress | 0.01 ± 0.02 | 0.11 |

[1]Data represents three biological replicates ± standard deviation

*S. tritici* was grown on YMA medium solidified with 1.8% Bacto agar at 23° C. in light. Conidia were harvested after 5 to 10 days with a sterile plastic spreader and water. Conidia was counted on a hemocytometer and diluted to 3×10$^7$ conidia in YMA medium. 100 µl of conidia in YMA were mixed with various dsREDexpress fusion proteins (New example 5, table N1) to a final concentration of 5 µM protein. Mixtures were incubated at 25° C. 400 RPM for 2 hours. Cells were washed twice with phosphate buffered saline (PBS) (8 g/L NaCl, 0.2 g/L KCl, 1.44 g/L Na$_2$HPO$_4$.2H$_2$O, 0.24 g/L KH$_2$PO$_4$ pH 6.8) and resuspended in a final volume of 200 µl PBS. Uptake of dsREDexpress fusion proteins was monitored using flow cytometry as for *Halobacterium* salinarium (Example 9). The percent of cells to which the cargo was successfully delivered was determined by drawing an arbitrary gate in the dsREDexpress treated cells such that 0.1% of the population scored as a false positive red event (1:1000 cells). The results of this treatment can be seen in Table 9. pVEC, TLM, pep1, and tp10 increased the delivery of dsREDexpress 25, 4, 3, and 5 fold respectively compared to dsREDexpress alone. This suggests that these CPPs would be good candidates for the delivery of other cargo to True fungi (eg. Cas9/sgRNA ribonucleoprotein complex).

TABLE 9

CPP delivery of dsREDexpress to *Septoria tritici*

| Treatment | Percent of population in red cell gate ± standard deviation[1] | Fold increase in red population over dsREDexpress alone |
|---|---|---|
| dsREDexpress | 0.12 ± 0.03 | 1.00 |
| pVEC-dsREDexpress | 3.02 ± 0.91 | 25.2 |
| CFFKDEL-dsREDexpress | 0.00 ± 0.01 | 0.03 |
| TLM-dsREDexpress | 0.48 ± 0.14 | 4.03 |
| pep1-dsREDexpress | 0.37 ± 0.21 | 3.06 |
| Tp10-dsREDexpress | 0.71 ± 0.69 | 5.94 |
| MPG-dsREDexpress | 0.14 ± 0.05 | 1.17 |
| Zebra-dsREDexpress | 0.00 ± 0.00 | 0.00 |

[1]Data represents three biological replicates ± standard deviation

Example 11

Delivery of Seven CPPs-dsRED and Two CPPs-tagRFP into Seven Gut Bacteria

In this example, the efficiency of CPPs in delivering two cargo proteins, dsRED and tag RFP, into 7 gut bacterial species (whose beneficial effects on host physiology have been demonstrated) was tested.

Bacterial cells were grown in appropriate media (see Table 10) overnight at 37° C. in a rotary shaker at 150 rpm in an anaerobic tent (80% N$_2$, 15% CO$_2$, and 5% H$_2$). For the assay, 1×10$^8$ bacterial cells were mixed with a final concentration of 5 uM of CPPs-dsRED and CPPs-tagRFP proteins in a 96 well plate, followed by two hours outgrowth at 37° C. To measure the dsRED and RFP fluorescence signals in cells, bacterial cells were harvested by centrifugation (3,500×g, 4° C., 20 min) and washed twice in phosphate buffered saline (100 ul per well). Fluorescence intensities were quantitated with Tecan Spark 10M plate reader (Tecan, Männedorf, Switzerland) equipped with 554 nm excitation and 586 nm emission filters with 10 nm bandwidth. Raw fluorescence values were subtracted from that of the untreated cells (background). The fluorescence intensity values of 7000 as a minimum cutoff was taken for delivery of CPPs inside the cells.

TABLE 10

Culture medium of 7 bacterial species

| Bacteria | Phylum | Culture medium |
| --- | --- | --- |
| Bacteroides thetaiotaomicron | Bacteroidetes | Brain and Heart Infusion supplemented with 10% bovine blood (Blood BHI) |
| Eubacterium hallii | Firmicutes | Blood BHI |
| Faecalibacterium prausnitzii | Firmicutes | Blood BHI |
| Blautia hydrogenotrophica | Firmicutes | YCFA |
| Bacteroides fragilis | Bacteroidetes | Blood BHI |
| Prevotella histicola | Bacteroidetes | Blood BHI |
| Clostridium scindens | Firmicutes | YCFA |

As shown in Table 11, these results indicate that five CPPs including MPG, pVEC, TLM, ZEBRA, and pep1 were effectively delivered into the anaerobic gut bacteria belonging to the phyla Firmicutes and Bacteroidetes, thereby indicating that the CPP's can traverse through the cell membrane of these (Table 9).

TABLE 11

Differential delivery efficiencies of CPPs in different bacterial strains as demonstrated by the fluorescence intensity above the cutoff value of 7000

| | MPG-1-dsRED | pVEC-dsRED | TLM-dsRED | ZEBRA-dsRED | pep1-dsRED |
| --- | --- | --- | --- | --- | --- |
| Bacteroides thetaiotaomicron | — | — | — | 10230 | 16657 |
| Eubacterium hallii | 10015 | 17156 | — | 16894 | 7004 |
| Faecalibacterium prausnitzii | — | 40525 | 14998 | 17014 | 12696 |
| Blautia hydrogenotrophica | — | 11770 | 14612 | 9623 | — |
| Bacteroides fragilis | — | 14783 | — | 15026 | — |
| Prevotella histicola | — | — | — | 22416 | — |
| Clostridium scindens | — | 17677 | 32492 | — | — |

What is claimed is:

1. A method of delivering a protein component of an RNA-guided endonuclease (RGEN) into a microbial cell, said method comprising:
    contacting the microbial cell with a composition comprising the protein component of the RNA-guided endonuclease (RGEN) and at least one cell-penetrating peptide (CPP),
    wherein said protein component and CPP are covalently, or non-covalently, linked to each other in an RGEN protein-CPP complex,
    wherein said RGEN protein-CPP complex traverses (i) a cell membrane, or (ii) a cell wall and cell membrane, of the cell, thereby entering the microbial cell.

2. The method of claim 1, wherein:
    (i) the composition further comprises at least one RNA component that is associated with the protein component of the RGEN; or
    (ii) the microbial cell comprises the RNA component, wherein the RNA component associates with the protein component of the RGEN after the RGEN protein-CPP complex enters the microbial cell;
    wherein the RNA component comprises a sequence complementary to a target site sequence on a chromosome or episome in the cell, wherein the RGEN can bind to the target site sequence, and optionally cleave one or both DNA strands at the target site sequence.

3. The method of claim 2, wherein the RGEN can cleave one or both DNA strands at the target site sequence.

4. The method of claim 3, wherein the microbial cell further comprises a donor polynucleotide comprising at least one sequence homologous to a sequence at or near the target site sequence, and wherein the donor polynucleotide integrates at or near the target site sequence by homologous recombination.

* * * * *